(12) United States Patent
Benson et al.

(10) Patent No.: US 12,084,682 B2
(45) Date of Patent: *Sep. 10, 2024

(54) GENE-REGULATING COMPOSITIONS AND METHODS FOR IMPROVED IMMUNOTHERAPY

(71) Applicant: KSQ Therapeutics, Inc., Lexington, MA (US)

(72) Inventors: Micah Benson, Lexington, MA (US); Jason J. Merkin, Lexington, MA (US); Gregory V. Kryukov, Lexington, MA (US); Solomon Martin Shenker, Lexington, MA (US); Michael R. Schlabach, Lexington, MA (US); Noah Jacob Tubo, Lexington, MA (US); James Martin Kaberna, II, Lexington, MA (US)

(73) Assignee: KSQ Therapeutics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/065,580

(22) Filed: Dec. 13, 2022

(65) Prior Publication Data

US 2023/0340411 A1    Oct. 26, 2023

Related U.S. Application Data

(63) Continuation of application No. 17/707,725, filed on Mar. 29, 2022, which is a continuation of application No. 16/951,310, filed on Nov. 18, 2020, now Pat. No. 11,332,713, which is a continuation of application No. 16/354,100, filed on Mar. 14, 2019, now Pat. No. 11,261,428.

(60) Provisional application No. 62/804,261, filed on Feb. 12, 2019, provisional application No. 62/790,192, filed on Jan. 9, 2019, provisional application No. 62/790,179, filed on Jan. 9, 2019, provisional application No. 62/768,441, filed on Nov. 16, 2018, provisional application No. 62/768,428, filed on Nov.

(Continued)

(51) Int. Cl.
| | |
|---|---|
| C12N 5/0783 | (2010.01) |
| A61K 35/17 | (2015.01) |
| A61K 38/00 | (2006.01) |
| A61K 39/00 | (2006.01) |
| A61P 35/00 | (2006.01) |
| A61P 35/04 | (2006.01) |
| C07K 14/705 | (2006.01) |
| C07K 14/725 | (2006.01) |
| C07K 16/28 | (2006.01) |
| C07K 16/32 | (2006.01) |
| C12N 9/22 | (2006.01) |
| C12N 15/11 | (2006.01) |
| C12N 15/113 | (2010.01) |

(52) U.S. Cl.
CPC ............ *C12N 5/0636* (2013.01); *A61K 35/17* (2013.01); *A61P 35/00* (2018.01); *A61P 35/04* (2018.01); *C07K 14/7051* (2013.01); *C07K 14/70517* (2013.01); *C07K 16/2803* (2013.01); *C07K 16/2863* (2013.01); *C07K 16/32* (2013.01); *C12N 9/22* (2013.01); *C12N 15/11* (2013.01); *C12N 15/113* (2013.01); *C12N 15/1135* (2013.01); *A61K 38/00* (2013.01); *A61K 2039/505* (2013.01); *C07K 2317/24* (2013.01); *C07K 2317/622* (2013.01); *C07K 2319/30* (2013.01); *C12N 2310/122* (2013.01); *C12N 2310/14* (2013.01); *C12N 2310/20* (2017.05); *C12N 2310/531* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 5,222,982 A | 6/1993 | Ommaya | |
| 5,356,802 A | 10/1994 | Chandrasegaran | |

(Continued)

FOREIGN PATENT DOCUMENTS

| | | | |
|---|---|---|---|
| JP | 2008-522951 A | 7/2008 | |
| WO | WO 1993/003769 A1 | 3/1993 | |

(Continued)

OTHER PUBLICATIONS

Rohann, et al. (2019, available Nov. 2018) "Adoptive cellular therapies: the current landscape", Virchows Archiv, 474: 449-61. (Year: 2019).*

(Continued)

*Primary Examiner* — Robert M Kelly
(74) *Attorney, Agent, or Firm* — Wolf, Greenfield & Sacks, P.C.

(57) ABSTRACT

The present disclosure provides methods and compositions related to the modification of immune effector cells to increase therapeutic efficacy. In some embodiments, immune effector cells modified to reduce expression of one or more endogenous target genes, or to reduce one or more functions of an endogenous protein to enhance effector functions of the immune cells are provided. In some embodiments, immune effector cells further modified by introduction of transgenes conferring antigen specificity, such as exogenous T cell receptors (TCRs) or chimeric antigen receptors (CARs) are provided. Methods of treating a cell proliferative disorder, such as a cancer, using the modified immune effector cells described herein are also provided.

7 Claims, 24 Drawing Sheets
Specification includes a Sequence Listing.

Related U.S. Application Data 16, 2018, provisional application No. 62/736,185, filed on Sep. 25, 2018, provisional application No. 62/692,010, filed on Jun. 29, 2018, provisional application No. 62/692,016, filed on Jun. 29, 2018, provisional application No. 62/643,584, filed on Mar. 15, 2018, provisional application No. 62/643,578, filed on Mar. 15, 2018.

(56) References Cited

U.S. PATENT DOCUMENTS

| | | |
|---|---|---|
| 5,385,582 A | 1/1995 | Ommaya |
| 5,436,150 A | 7/1995 | Chandrasegaran |
| 5,487,994 A | 1/1996 | Chandrasegaran |
| 5,858,358 A | 1/1999 | June et al. |
| 5,883,223 A | 3/1999 | Gray |
| 6,352,694 B1 | 3/2002 | June et al. |
| 6,453,242 B1 | 9/2002 | Eisenberg et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 6,962,810 B2 | 11/2005 | Fraser et al. |
| 7,067,318 B2 | 6/2006 | June et al. |
| 7,078,387 B1 | 7/2006 | Leiden et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,348,139 B1 | 3/2008 | Herman et al. |
| 8,034,334 B2 | 10/2011 | Dudley et al. |
| 8,324,369 B2 | 12/2012 | Chen |
| 8,383,099 B2 | 2/2013 | Dudley et al. |
| 9,233,125 B2 | 1/2016 | Davila et al. |
| 9,624,279 B2 | 4/2017 | Nonaka et al. |
| 9,782,437 B2 | 10/2017 | Holmes et al. |
| 9,944,931 B2 | 4/2018 | Wucherpfennig et al. |
| 10,016,421 B2 | 7/2018 | Sotomayor et al. |
| 10,603,378 B2 * | 3/2020 | June ............... A61P 37/06 |
| 11,261,428 B2 | 3/2022 | Benson et al. |
| 11,332,713 B2 * | 5/2022 | Benson ............. C07K 16/2863 |
| 11,459,544 B2 | 10/2022 | Benson et al. |
| 2003/0147869 A1 | 8/2003 | Riley et al. |
| 2005/0137251 A1 | 6/2005 | Garzon et al. |
| 2006/0121005 A1 | 6/2006 | Berenson et al. |
| 2007/0254842 A1 | 11/2007 | Bankiewicz |
| 2008/0081064 A1 | 4/2008 | Jelle et al. |
| 2009/0196903 A1 | 8/2009 | Kliman |
| 2010/0240732 A1 | 9/2010 | Gilboa |
| 2013/0287748 A1 | 10/2013 | June et al. |
| 2014/0171492 A1 | 6/2014 | Di Ruscio et al. |
| 2015/0232881 A1 | 8/2015 | Glucksmann et al. |
| 2015/0238631 A1 | 8/2015 | Kim et al. |
| 2015/0291966 A1 | 10/2015 | Zhang et al. |
| 2016/0083449 A1 | 3/2016 | Schmitt et al. |
| 2016/0120905 A1 | 5/2016 | Galetto et al. |
| 2016/0298113 A1 | 10/2016 | Sætrom |
| 2016/0304873 A1 | 10/2016 | Wolfson et al. |
| 2017/0002426 A1 | 1/2017 | Astsaturov et al. |
| 2017/0152478 A1 | 6/2017 | Rosenberg et al. |
| 2017/0356010 A1 | 12/2017 | Frost et al. |
| 2018/0104354 A1 | 4/2018 | Kim et al. |
| 2018/0207201 A1 | 7/2018 | Wardell et al. |
| 2018/0282694 A1 | 10/2018 | Wardell et al. |
| 2018/0327750 A1 | 11/2018 | Wucherpfennig et al. |
| 2019/0106679 A1 | 4/2019 | Regev et al. |
| 2019/0284530 A1 | 9/2019 | Benson et al. |
| 2020/0347386 A1 | 11/2020 | Benson et al. |
| 2021/0071140 A1 | 3/2021 | Benson et al. |
| 2022/0220442 A1 | 7/2022 | Benson et al. |
| 2022/0267727 A1 | 8/2022 | Benson et al. |

FOREIGN PATENT DOCUMENTS

| | | |
|---|---|---|
| WO | WO 1993/009239 A1 | 5/1993 |
| WO | WO 1993/019191 A1 | 9/1993 |
| WO | WO 1994/012649 A2 | 6/1994 |
| WO | WO 1994/028938 A1 | 12/1994 |
| WO | WO 1995/000655 A1 | 1/1995 |
| WO | WO 1995/011984 A2 | 5/1995 |
| WO | WO 2002/088346 A2 | 11/2002 |
| WO | WO 2003/057171 A2 | 7/2003 |
| WO | WO 2006/112869 A2 | 10/2006 |
| WO | WO 2009/091826 A2 | 7/2009 |
| WO | WO 2013/059343 A1 | 4/2013 |
| WO | WO 2014/055657 A1 | 4/2014 |
| WO | WO 2015/071474 A2 | 5/2015 |
| WO | WO 2015/090229 A1 | 6/2015 |
| WO | WO 2015/142675 A2 | 9/2015 |
| WO | WO 2015/161276 A2 | 10/2015 |
| WO | WO 2016/106236 A1 | 6/2016 |
| WO | WO 2017/075465 A1 | 5/2017 |
| WO | WO 2017/079642 A1 | 5/2017 |
| WO | WO 2017/082562 A1 | 5/2017 |
| WO | WO 2017/120996 A1 | 7/2017 |
| WO | WO 2017/120998 A1 | 7/2017 |
| WO | WO 2017/165245 A2 | 9/2017 |
| WO | WO 2018/006880 A1 | 1/2018 |
| WO | WO 2018/009525 A1 | 1/2018 |
| WO | WO 2018/137293 A1 | 8/2018 |
| WO | WO 2018/137295 A1 | 8/2018 |
| WO | WO 2018/148378 A1 | 8/2018 |
| WO | WO 2018/156886 A1 | 8/2018 |
| WO | WO 2019/178422 A1 | 9/2019 |

OTHER PUBLICATIONS

Perica, et al. (2015) "Adoptive T Cell Immunotherapy for Cancer", 6(1): e0004, 9 pages long. (Year: 2015).*
Takeuchi, et al. (2016) "Roles of regulatory T cells in cancer immunity", International Immunity, 28(8): 401-09. (Year: 2016).*
U.S. Appl. No. 16/354,100, filed Mar. 14, 2019, Granted, U.S. Pat. No. 11,261,428.
U.S. Appl. No. 16/951,310, filed Nov. 18, 2020, Granted, U.S. Pat. No. 11,332,713.
U.S. Appl. No. 17/707,725, filed Mar. 29, 2022, Published, 2022-0220442.
U.S. Appl. No. 17/707,789, filed Mar. 29, 2022, Granted, U.S. Pat. No. 11,459,544.
U.S. Appl. No. 16/781,732, filed Feb. 4, 2020, Published, 2020-0347386.
[No Author Listed], Genbank Submission; NIH/NCBI, Accession No. NM_025079.1. Nov. 17, 2006. 2 pages.
Abudayyeh et al., RNA targeting with CRISPR-Cas13. Nature (2017); 550(7675): 280-284. Epub Oct. 4, 2017.
Ahmed et al., Human Epidermal Growth Factor Receptor 2 (HER2)-Specific Chimeric Antigen Receptor-Modified T Cells for the Immunotherapy of HER2-Positive Sarcoma. J Clin Oncol. (2015); 33(15): 1688-1696. Epub Mar. 23, 2015.
Ahmed et al., Immunotherapy for osteosarcoma: genetic modification of T cells overcomes low levels of tumor antigen expression. Mol Ther. (2009); 17(10): 1779-1787. Epub Jun. 16, 2009.
Ali et al., Adena-associated virus gene transfer to mouse retina. Hum Gene Ther. (1998); 9(1): 81-86.
Ali et al., Gene transfer into the mouse retina mediated by an adeno-associated viral vector. Hum Mol Genet. (1996); 5(5): 591-594.
Altschul et al., Basic local alignment search tool. J Mol Biol. (1990); 215 (3): 403-410.
Altschul et al., Gapped BLAST and PSI-BLAST: a new generation of protein database search programs. Nucleic Acids Res. (1997); 25 (17): 3389-3402.
Ashwood-Smith et al., Preservation of mouse bone marrow at −79 degrees C. with dimethyl sulphoxide. Nature (1961); 190: 1204-1205.
Ausubel et al., (eds.), DNA sequencing, Current Protocols in Molecular Biology (2003), Chapter 7, Supplement 47, p. 7.0.1-7.

(56) References Cited

OTHER PUBLICATIONS 7.23; Contributed by Slatko, et al., Current Protocols in Molecular Biology (1999) 7.1.1-7.1.7, 163 pages.
Balazs et al., Liposomes for Use in Gene Delivery. Journal of Drug Delivery (2011); Article ID 326497, 12 pages.
Balciunas et al., Harnessing a High Cargo-Capacity Transposon for Genetic Applications in Vertebrates. PLoS Genet. (Nov. 2006); 2(11): e169. Published online Nov. 10, 2006. Prepublished online Aug. 28, 2006.
Beerli et al., Engineering polydactyl zinc-finger transcription factors. Nat Biotechnol. (2002); 20(2): 135-141.
Belfort et al., Homing endonucleases: keeping the house in order. Nucleic Acids Res. (1997); 25(17): 3379-3788.
Bennett et al., Real-time, noninvasive in vivo assessment of adeno-associated virus-mediated retinal transduction. Invest Ophthalmol Vis Sci. (1997); 38(13): 2857-2863.
Bitinaite et al., Fok1 dimerization is required for DNA cleavage. Proc. Natl. Acad. Sci. U.S.A. (1998); 95(18): 10570-10575.
Bitter et al., Expression and secretion vectors for yeast. Methods Enzymol. (1987); 153 (33): 516-544.
Bondanza et al., Suicide gene therapy of graft-versus-host disease induced by central memory human T lymphocytes. Blood (2006); 107(5): 1828-1836. Epub Nov. 17, 2005.
Bonini et al., HSV-TK gene transfer into donor lymphocytes for control of allogeneic graft-versus-leukemia. Science (1997); 276 (5319): 1719-1724.
Borras et al., Adenoviral reporter gene transfer to the human trabecular meshwork does not alter aqueous humor outflow. Relevance for potential gene therapy of glaucoma. Gene Ther. (1999); 6(4): 515-524.
Brown et al., Bioactivity and Safety of IL13Ra2-Redirected Chimeric Antigen Receptor CD8+ T Cells in Patients with Recurrent Glioblastoma. Clin Cancer Res. (2015); 21(18): 4062-4072. Epub Jun. 9, 2015.
Brudno et al., Chimeric antigen receptor T-cell therapies for lymphoma. Nat Rev Clin Oncol. (2018); 15 (1): 31-46. Epub Aug. 31, 2017.
Caruana et al., Heparanase promotes tumor infiltration and antitumor activity of CAR-redirected T lymphocytes. Nat Med. (2015); 21(5): 524-529. Epub Apr. 13, 2015.
Casucci et al., Suicide Gene Therapy to Increase the Safety of Chimeric Antigen Receptor-Redirected T Lymphocytes. Journal of Cancer (2011); 2: 378-382. Epub Jul. 1, 2011.
Cermak et al., Efficient design and assembly of custom TALEN and other TAL effector-based constructs for DNA targeting. Nucleic Acids Res. (2011); 39(12): e82. Epub Apr. 14, 2011.
Chen et al., Dynamic imaging of genomic loci in living human cells by an optimized CRISPR/Cas system. Cell (2013); 155(7): 1479-1491.
Chikuma et al., Suppressors of cytokine signaling: Potential immune checkpoint molecules for cancer immunotherapy. Cancer Sci. Apr. 2017;108(4):574-580. Epub Apr. 19, 2017.
Choo et al., Advances in zinc finger engineering. Curr. Opin. Struct. Biol. (2000); 10: 411-416.
Chylinski et al., The tracrRNA and Cas9 families of type II CRISPR-Cas immunity systems. RNA Biol. (2013); 10(5): 726-737. Epub Apr. 5, 2013.
Ciceri et al., Antitumor effects of HSV-TK-engineered donor lymphocytes after allogeneic stem-cell transplantation. Blood. (2007); 109 (11): 4698-4707. Epub Feb. 27, 2007.
Cox et al., RNA editing with CRISPR-Cas13. Science (2017); 358(6366): 1019-1027. Epub Oct. 25, 2017.
De Lavallade et al., Tyrosine kinase inhibitors impair B-cell immune responses in CML through off-target inhibition of kinases important for cell signaling. Blood (2013);122: 227-238. Epub May 29, 2013.
Debets et al., TCR-engineered T cells to treat tumors: Seeing but not touching? Semin Immunol. (2016); 28(1): 10-21. Epub Mar. 17, 2016.
Deltcheva et al., CRISPR RNA maturation by trans-encoded small RNA and host factor RNase III. Nature (2011); 471(7340): 602-607.
Deveau et al., Phage response to CRISPR-encoded resistance in *Streptococcus thermophilus*. J Bacterial. (2008); 190(4): 1390-1400. Epub Dec. 7, 2007.
Esvelt et al., A system for the continuous directed evolution of biomolecules. Nature (2011); 472(7344): 499-503. Epub Apr. 10, 2011.
Esvelt et al., Orthogonal Cas9 proteins for RNA-guided gene regulation and editing. Nat. Methods (2013); 10(11): 1116-1121. Epub Sep. 29, 2013.
Fire et al., Potent and specific genetic interference by double-stranded RNA in Caenorhabditis elegans. Nature (Feb. 1998); 391(6669): 806-811.
Flannery et al., Efficient photoreceptor-targeted gene expression in vivo by recombinant adeno-associated virus. Proc Natl Acad Sci U.S.A. (1997); 94(13): 6916-6921.
Flotte et al., Stable in vivo expression of the cystic fibrosis transmembrane conductance regulator with an adeno-associated virus vector. Proc Natl Acad Sci U.S.A. (1993); 90(22): 10613-10617.
Germer et al., RNA aptamers and their therapeutic and diagnostic applications. Int J Biochem Mol Biol (2013); 4(1): 27-40.
Grada et al., TanCAR: A Novel Bispecific Chimeric Antigen Receptor for Cancer Immunotherapy. Mol Ther Nucleic Acids (2013); 2:e105.
Graham et al., Resources for the design of CRISPR gene editing experiments. Genome Biol. Nov. 27, 2015;16:260.
Hanada et al., A Mutant Form of JAB/SOCS1 Augments the Cytokine-induced JAK/STAT Pathway by Accelerating Degradation of Wild-type JAB/CIS Family Proteins through the SOCS-box. The Journal of Biological Chemistry (2001); 276 (44): 40746-40754.
Horvath et al., The immune system of bacteria and archaea. Science (2010); 327(5962): 167-170.
Hou et al., Efficient genome engineering in human pluripotent stem cells using Cas9 from Neisseria meningitidis. PNAS (Sep. 2013); 110(39): 15644-15649.
Huang, et al., Monocyte Chemotactic Protein-induced Protein 1 and 4 Form a Complex but Act Independently in Regulation of Interleukin-6 mRNA Degradation. J Biol Chem. Aug. 21, 2015;290(34):20782-20792. doi: 10.1074/jbc.M114.635870. Epub Jul. 1, 2015.
Introna et al., Genetic modification of human T cells with CD20: a strategy to purify and lyse transduced cells with anti-CD20 antibodies. Hum Gene Ther. (2000); 11(4): 611-620.
Isalan et al., A rapid, generally applicable method to engineer zinc fingers illustrated by targeting the HIV-1 promoter. Nat Biotechnol. (2001); 19(7): 656-660.
Isvak et al., Sleeping Beauty, a wide host-range transposon vector for genetic transformation in vertebrates. J Mol Biol. (2000); 302(1): 93-102.
Ji et al., Abstract PR10: enhancing the efficacy of T cell-based immunotherapies using miR-155 engineered tumor-specific CD8+ T cells. Cancer Immunol Res. Mar. 1, 2017;5(3): Abstract only, 2 pages.
Ji et al., miR-155 augments CD8+ T-cell antitumor activity in lymphoreplete hosts by enhancing responsiveness to homeostatic γc cytokines. PNAS (Jan. 2015); 112(2): 476-481.
Ji et al., miR-155 releases the brakes on antitumor T cells. Oncoimmunology. Jun. 3, 2015;4(8):e1026533.
Johnson et al., Gene therapy with human and mouse T-cell receptors mediates cancer regression and targets normal tissues expressing cognate antigen Blood (2009); 114(3): 535-546. Epub May 18, 2009.
Jomary et al., Rescue of photoreceptor function by AAV-mediated gene transfer in a mouse model of inherited retinal degeneration. Gene Ther. (1997); 4(7): 683-690.
June et al., Chimeric Antigen Receptor Therapy. N Engl J Med (Jul. 2018); 379(1): 64-73.
Katz et al., Phase I Hepatic Immunotherapy for Metastases Study of Intra-Arterial Chimeric Antigen Receptor-Modified T-cell Therapy for CEA+ Liver Metastases. Clin Cancer Res. (2015); 21(14): 3149-3159. Epub Apr. 7, 2015.

(56) References Cited

OTHER PUBLICATIONS

Kawakami et al., Identification of a functional transposase of the Tol2 element, an Ac-like element from the Japanese medaka fish, and its transposition in the zebrafish germ lineage. PNAS (Oct. 2000); 97 (21): 11403-11408.

Kershaw et al., A phase I study on adoptive immunotherapy using gene-modified T cells for ovarian cancer. Clin Cancer Res. (2006); 12 (20 Pt 1): 6106-6115.

Kim et al., Chimeric restriction endonuclease. Proc Natl Acad Sci U.S.A. (1994); 91(3): 883-887.

Kim et al., Insertion and Deletion Mutants of Fok1 Restriction Endonuclease. The Journal of Biological Chemistry (1994); 269(50): 31978-31982.

Kimmel, Identification and characterization of specific clones: strategy for confirming the validity of presumptive clones. Methods Enzymol. (1987); 152: 507-511.

Kobold et al., Selective bispecific T cell recruiting antibody and antitumor activity of adoptive T cell transfer. J Natl Cancer Inst. (2014); 107(1): 364. Print Jan. 2015.

Kochenderfer et al., B-cell depletion and remissions of malignancy along with cytokine-associated toxicity in a clinical trial of anti-CD19 chimeric-antigen-receptor-transduced T cells. Blood (2012); 119 (12): 2709-2720. Epub Dec. 8, 2011.

Konermann et al., Transcriptome Engineering with RNA-Targeting Type VI-D Crispr Effectors. Cell. (2018); 173(3): 665-676.e14 Epub Mar. 15, 2018.

Lamers et al., Treatment of metastatic renal cell carcinoma with CAIX CAR-engineered T cells: clinical evaluation and management of on-target toxicity. Mol Ther. (2013); 21 (4): 904-12. Epub Feb. 19, 2013.

Langer, New methods of drug delivery. Science (1990); 249 (4976): 1527-1533.

Li et al., Alteration of the cleavage distance of Fok I restriction endonuclease by insertion mutagenesis. Proc Natl Acad Sci U.S.A. (1993); 90(7): 2764-2768.

Li et al., Chimeric antigen receptor T cell (CAR-T) immunotherapy for solid tumors: lessons learned and strategies for moving forward. J Hematol Oncol. (2018); 11( 1): 22.

Li et al., Functional domains in Fok I restriction endonuclease. Proc Natl Acad Sci U.S.A. (1992); 89(10): 4275-4279.

Li et al., In vivo transfer of a reporter gene to the retina mediated by an adenoviral vector. Invest Ophthalmol Vis Sci. (1994); 35(5): 2543-2549.

Li et al., Phenotype correction in retinal pigment epithelium in murine mucopolysaccharidosis VII by adenovirus-mediated gene transfer. Proc Natl Acad Sci U.S.A. (1995); 92(17): 07700-07704.

Liu et al., A Chimeric Switch-Receptor Targeting PD1 Augments the Efficacy of Second-Generation CART Cells in Advanced Solid Tumors. Cancer Res. (2016); 76(6): 1578-1590.

Liu et al., Poly(cationic lipid)-mediated in vivo gene delivery to mouse liver. Gene Ther. (2003); 10(2): 180-187.

Liu, et al., Regnase-1 in microglia negatively regulates high mobility group box 1-mediated inflammation and neuronal injury. Scientific Reports (Apr. 5, 2016); 6: 24073, pp. 1-9, and supplementary information.

Loakes et al., 5-Nitroindole as an universal base analogue. Nucleic Acids Res. (1994); 22 (20): 4039-4043.

Louis et al., Antitumor activity and long-term fate of chimeric antigen receptor-positive T cells in patients with neuroblastoma. Blood. (2011); 118(23): 6050-6056. Epub Oct. 7, 2011.

Lovelock et al., Prevention of freezing damage to living cells by dimethyl sulphoxide. Nature (1959); 183 (4672): 1394-1395.

Luo et al., Bifunctional aHER2/CD3 RNA-engineered CART-like human T cells specifically eliminate HER2(+) gastric cancer. Cell Res. (2016); 26(7): 850-853. Epub Jun. 24, 2016.

Mali et al., Church GM. RNA-guided human genome engineering via Cas9. Science. (2013); 339(6121): 823-826. Epub Jan. 3, 2013.

Mendelson et al., Expression and rescue of a nonselected marker from an integrated AAV vector. Virology. (1988); 166(1): 154-165.

Meuer et al., An alternative pathway of T-cell activation: a functional role for the 50 kd T11 sheep erythrocyte receptor protein. Cell (1984); 36(4): 897-906.

Miller et al. Repetitive zinc-binding domains in the protein transcription factor IIIA from Xenopus oocytes. EMBO J. (1985); 4(6):1609-1614.

Mino et al., Regnase-1 and Roquin Regulate a Common Element in Inflammatory mRNAs by Spatiotemporally Distinct Mechanisms, Cell 161, May 21, 2015, pp. 1058-1073.

Miskey et al., The Frog Prince: a reconstructed transposon from Rana pipiens with high transpositional activity in vertebrate cells. Nucleic Acids Res. (2003); 31(23): 6873-6881.

Miyoshi et al., Stable and efficient gene transfer into the retina using an HIV-based lentiviral vector. Proc Natl Acad Sci U.S.A.(1997); 94(19): 10319-10323.

Moon et al., 520. A PD1-CD28 Switch Receptor Is Able to Augment Mesothelin-Directed Chimeric Antigen Receptor T Cell Therapy in a Resistant In Vivo Model of Human Tumor. Cancer-Immunotherapy I Molecular Therapy vol. 22, Supplement 1, May 2014, p. S201.

Moon et al., Blockade of Programmed Death 1 Augments the Ability of Human T Cells Engineered to Target NY-ESO-1 to Control Tumor Growth after AdoptiveTransfer. Clin Cancer Res. (2016); 22(2): 436-447. Epub Aug. 31, 2015.

Moon et al., Expression of a functional CCR2 receptor enhances tumor localization and tumor eradication by retargeted human T cells expressing amesothelin-specific chimeric antibody receptor. Clin Cancer Res. (2011); 17(14): 4719-4730. Epub May 24, 2011.

Morgan et al., Cancer regression and neurological toxicity following anti-MAGE-A3 TCR gene therapy_ J Immunother. (2013); 36(2): 133-151.

Morgan et al., Case report of a serious adverse event following the administration of T cells transduced with a chimeric antigen receptor recognizing ERBB2. Mol Ther. (2010); 18(4): 843-851. Epub Feb. 23, 2010.

Morgan et al., Recognition of glioma stem cells by genetically modified T cells targeting EGFRvlll and development of adoptive cell therapy for glioma. Hum Gene Ther. (2012); 23(10): 1043-1053. Epub Sep. 24, 2012.

Nakazawa et al., PiggyBac-mediated cancer immunotherapy using EBV-specific cytotoxic T-cells expressing HER2-specific chimeric antigen receptor. Mol Ther. (2011); 19(12): 2133-2143. Epub Jul. 19, 2011.

Needleman et al., A general method applicable to the search for similarities in the amino acid sequence of two proteins. J. Mol. Biol. 1970;48(3):443-453.

Nichols et al., A universal nucleoside for use at ambiguous sites in DNA primers. Nature (1994); 369 (6480): 492-4933.

Oda et al., A CD200R-CD28 fusion protein appropriates an inhibitory signal to enhance T-cell function and therapy of murine leukemia. Blood (2017); 130 (22): 2410-2419. Epub Oct. 17, 2017.

Pabo et al., Design and selection of novel Cys2His2 zinc finger proteins. Annu. Rev. Biochem. (2001); 70: 313-340.

Palmer et al., Suppressors of Cytokine Signaling (SOCS) in T cell differentiation, maturation, and function. Trends Immunol. (Dec. 2009); 30(12): 592-602.

Panyam et al., Biodegradable nanoparticles for drug and gene delivery to cells and tissue. Advanced Drug Delivery Reviews (Feb. 2003); 55(3): 329-347.

Park et al., Adoptive transfer of chimeric antigen receptor re-directed cytolytic T lymphocyte clones in patients with neuroblastoma. Mol Ther. (2007); 15(4): 825-833. Epub Feb. 13, 2007.

Parkhurst et al., T cells targeting carcinoembryonic antigen can mediate regression of metastatic colorectal cancer but induce severe transient colitis. Mol Ther. (2011); 19(3): 620-626. Epub Dec. 14, 2010.

Patro et al., Salmon provides fast and bias-aware quantification of transcript expression. Nat Methods (Apr. 2017); 14(4): 417-419. Epub Mar. 6, 2017.

Pearson et al., Improved tools for biological sequence comparison. ProcNatl Acad Sci U.S.A. (1988); 85 (8): 2444-2448.

Portela et al., Epigenetic modifications and human disease. Nat Biotechnol. Oct. 2010;28(10):1057-68.

(56) References Cited

OTHER PUBLICATIONS

Pyzocha et al., Diverse Class 2 CRISPR-Cas Effector Proteins for Genome Engineering Applications. ACS Chem Biol. (2018); 13(2): 347-356. Epub Dec. 5, 2017.

Radvany et al., Specific lymphocyte subsets predict response to adoptive cell therapy using expanded autologous tumor-infiltrating lymphocytes in metastatic melanoma patients. Clin Cancer Res. (2012); 18 (24): 6758-6770. Epub Oct. 2, 2012.

Rapoport et al., NY-ESO-1-specific TCR-engineered T cells mediate sustained antigen-specific antitumor effects in myeloma. Nat Med. (2015); 21(8): 914-921. Epub Jul. 20, 2015.

Rhodes et al., Zinc fingers. Scientific American (1993); 268(2): 56-65, 12 pages.

Rinfret et al., Factors affecting the erythrocyte during rapid freezing and thawing. Ann NY Acad Sci. (1960); 85: 576-594.

Ritchie et al., limma powers differential expression analyses for RNA-sequencing and microarray studies. Nucleic Acids Res. (Apr. 20, 2015); 43(7):e47. Epub Jan. 20, 2015.

Robbins et al, Single and dual amino acid substitutions in TCR CDRs can enhance antigen-specific T cell functions. J Immunol. (2008); 180(9): 6116-6131.

Robbins et al., A pilot trial using lymphocytes genetically engineered with an NY-ESO-1-reactive T-cell receptor: long-term follow-up and correlates with response. Clin Cancer Res. (2015); 21(5): 1019-1027. Epub Dec. 23, 2014.

Robbins et al., Tumor regression in patients with metastatic synovial cell sarcoma and melanoma using genetically engineered lymphocytes reactive with NY-ESO-1. J Clin Oncol. (2011); 29(7): 917-924. Epub Jan. 31, 2011.

Rolling et al., Evaluation of adeno-associated virus-mediated gene transfer into the rat retina by clinical fluorescence photography. Hum Gene Ther. (1999); 10(4): 641-648.

Sakamoto et al., A vitrectomy improves the transfection efficiency of adenoviral vector-mediated gene transfer to Muller cells. Gene Ther. (1998); 5(8): 1088-1097.

Samulski et al., Helper-free stocks of recombinant adeno-associated viruses: normal integration does not require viral gene expression. J Virol. (1989); 63(9): 3822-3828.

Segal et al., Custom DNA-binding proteins come of age: polydactyl zinc-finger proteins. Curr Opin Biotechnol. (2001); 12(6): 632-637.

Serafini et al., Characterization of CD20-transduced T lymphocytes as an alternative suicide gene therapy approach for the treatment of graft-versus-host disease. Hum Gene Ther. (2004); 15(1): 63-76.

Shen et al., Silencing of SOCS1 enhances antigen presentation by dendritic cells and antigen-specific anti-tumor immunity. Nat Biotechnol. Dec. 2004;22(12):1546-53. Epub Nov. 21, 2004.

Sirin et al., Regulating gene expression using self-inactivating lentiviral vectors containing the mifepristone-inducible system. Gene (2003); 323: 67-77.

Sloviter et al., Recovery and transfusion of human erythrocytes after freezing in polyglycol solutions. Nature. (1962); 196: 899-900.

Straathof et al, An inducible caspase 9 safety switch for T-cell therapy. Blood. (2005); 105(11): 4247-4254. Epub Feb. 22, 2005.

Swarts et al., DNA-guided DNA interference by a prokaryotic Argonaute. Nature (2014); 507(7491): 258-261. Epub Feb. 16, 2014.

Takahashi et al., Rescue from Photoreceptor Degeneration in the rd Mouse by Human Immunodeficiency Virus Vector-Mediated Gene Transfer. J Virol. (1999); 73(9): 7812-7816.

Takahashi et al., SOCS1 is essential for regulatory T cell functions by preventing loss of Foxp3 expression as well as IFN-y and IL-17A production. J. Exp. Med. (Sep. 26, 2011); 208(10): 2055-2067. Epub Sep. 5, 2011.

Thomis et al., A Fas-based suicide switch in human T cells for the treatment of graft-versus-host disease. Blood. (2001); 97(5): 1249-1257.

Tsai et al., GUIDE-seq enables genome-wide profiling of off-target cleavage by CRISPR-Cas nucleases. Nat Biotechnol. (Feb. 2015); 33(2): 187-197. Epub Dec. 16, 2014.

Van Den Berg et al., Case Report of a Fatal Serious Adverse Event Upon Administration of T Cells Transduced With a MART-1-specific T-cell Receptor. Mol Ther. (2015); 23(9): 1541-1550. Epub Apr. 21, 2015.

Van Meerten et al., The CD20/alphaCD20'suicide' system: novel vectors with improved safety and expression profiles and efficient elimination of CD20-transgenic T cells. Gene Ther. (2006); 13(9): 789-797.

Vanseggelen et al., T Cells Engineered With Chimeric Antigen Receptors Targeting NKG2D Ligands Display Lethal Toxicity in Mice. Mol Ther. (2015); 23(10): 1600-1610. Epub Jun. 30, 2015.

Wahl et al., Molecular hybridization of immobilized nucleic acids: theoretical concepts and practical considerations. Methods Enzymol. (1987); 152: 399-407.

Wang et al., Targeting fibroblast activation protein in tumor stroma with chimeric antigen receptor Tcells can inhibit tumor growth and augment host immunity without severe toxicity. Cancer Immunol Res. (2014); 2(2): 154-166. Epub Nov. 12, 2013.

Warren, Clinical Studies of regional and systemic gene therapy with autologous CC49-s modified T cells in colorectal cancer metastatic to the liver. 7th International Conference on Gene Therapy of Cancer, San Diego, California, USA. Nov. 19-21, 1998. Abstracts. Cancer Gene Ther. Nov.-Dec. 1998;5(6Suppl):S1-35, 37 pages.

Watkins et al., Nearest-neighbor thermodynamics of deoxyinosine pairs in DNA duplexes. Nucleic Acids Res. (2005); 33 (19): 6258-6267.

Wherry, T cell exhaustion. Nature Immunology (Jun. 2011); 12(6): 492-499. Epub May 18, 2011.

Wilkie et al., Dual targeting of ErbB2 and MUC1 in breast cancer using chimeric antigen receptors engineered to provide complementary signaling. J Clin Immunol. (2012); 32(5): 1059-1070. Epub Apr. 17, 2012.

Wong et al., 204 KSQ-004: Unbiased pair-wise discovery of SOCS1 and Regnase-1 as the top CRISPR/Cas9 dual-edit combination enhancing in vivo TIL potency against solid tumors. Journal for Immuno Therapy of Cancer. 2021;9(2)A215:doi: 10.1136/jitc-2021-SITC2021.204. Abstract only, 1 page.

Yan et al., Therapeutic Composition for treating glioblastoma. China Patents Full Text—Dialog. Translation document by machine, created May 20, 2021. 14 pages.

Yang et al., A common pathway for T lymphocyte activation involving both the CD3-Ti complex and CO2 sheep erythrocyte receptor determinants. J Immunol. (1986); 137(4): 1097-1100.

Yong et al, CART-cell therapy of solid tumors. Immunol Cell Biol. (2017); 95 (4): 356-363. Epub Dec. 22, 2016.

Zhang et al., Characterization of Transcriptional Regulatory Domains of Ankyrin Repeat Cofactor-1. Biochem Biophys Res Commun. (Jul. 13, 2007); 358(4): 1034-1040. Published online May 11, 2007.

Zhang et al., Structural Basis for the RNA-Guided Ribonuclease Activity of CRISPR-Cas13d. Cell (2018); 175(1): 212-223.e17.

U.S. Appl. No. 17/707,725, filed Mar. 29, 2022, Benson et al.

U.S. Appl. No. 16/781,732, filed Feb. 4, 2020, Benson et al.

Drake et al., Blocking the regulatory T cell molecule LAG-3 augments in vivo anti-tumor immunity in an autochthonous model of prostate cancer. Journal of Clinical Oncology. Jun. 20, 2006;24(18_suppl):2573. Abstract.

Foppen et al., Tumor-infiltrating lymphocytes for the treatment of metastatic cancer. Molecular oncology. Dec. 1, 2015;9(10):1918-35.

Liu et al., PD-1/PD-L1 Checkpoint Inhibitors in Tumor Immunotherapy. Front Pharmacol. Sep. 1, 2021;12:731798. doi: 10.3389/fphar.2021. 731798. 8 pages.

Wang et al., CRISPR/Cas9 in Genome Editing and Beyond. Annu Rev Biochem. Jun. 2, 2016;85:227-64. doi: 10.1146/annurev-biochem-060815-014607. Epub Apr. 25, 2016.

\* cited by examiner

Fig. 1A

| | Ikzf1 | Ikzf3 | Gata3 | Bcl3 | Tnip1 | Tnfaip3 | Nfkbia | Smad2 | Tgfbr1 | Tgfbr2 | Tank | Foxp3 | Ikzf2 | Rc3h1 | Traf6 |
|---|---|---|---|---|---|---|---|---|---|---|---|---|---|---|---|
| Ikzf1 | | 25 | 49 | 73 | 97 | 121 | 145 | 169 | 193 | 217 | 241 | 265 | 289 | 313 | 337 |
| Ikzf3 | 1 | | 50 | 74 | 98 | 122 | 146 | 170 | 194 | 218 | 242 | 266 | 290 | 314 | 338 |
| Gata3 | 2 | 26 | | 75 | 99 | 123 | 147 | 171 | 195 | 219 | 243 | 267 | 291 | 315 | 339 |
| Bcl3 | 3 | 27 | 51 | | 100 | 124 | 148 | 172 | 196 | 220 | 244 | 268 | 292 | 316 | 340 |
| Tnip1 | 4 | 28 | 52 | 76 | | 125 | 149 | 173 | 197 | 221 | 245 | 269 | 293 | 317 | 341 |
| Tnfaip3 | 5 | 29 | 53 | 77 | 101 | | 150 | 174 | 198 | 222 | 246 | 270 | 294 | 318 | 342 |
| Nfkbia | 6 | 30 | 54 | 78 | 102 | 126 | | 175 | 199 | 223 | 247 | 271 | 295 | 319 | 343 |
| Smad2 | 7 | 31 | 55 | 79 | 103 | 127 | 151 | | 200 | 224 | 248 | 272 | 296 | 320 | 344 |
| Tgfbr1 | 8 | 32 | 56 | 80 | 104 | 128 | 152 | 176 | | 225 | 249 | 273 | 297 | 321 | 345 |
| Tgfbr2 | 9 | 33 | 57 | 81 | 105 | 129 | 153 | 177 | 201 | | 250 | 274 | 298 | 322 | 346 |
| Tank | 10 | 34 | 58 | 82 | 106 | 130 | 154 | 178 | 202 | 226 | | 275 | 299 | 323 | 347 |
| Foxp3 | 11 | 35 | 59 | 83 | 107 | 131 | 155 | 179 | 203 | 227 | 251 | | 300 | 324 | 348 |
| Ikzf2 | 12 | 36 | 60 | 84 | 108 | 132 | 156 | 180 | 204 | 228 | 252 | 276 | | 325 | 349 |
| Rc3h1 | 13 | 37 | 61 | 85 | 109 | 133 | 157 | 181 | 205 | 229 | 253 | 277 | 301 | | 350 |
| Traf6 | 14 | 38 | 62 | 86 | 110 | 134 | 158 | 182 | 206 | 230 | 254 | 278 | 302 | 326 | |
| Cblb | 15 | 39 | 63 | 87 | 111 | 135 | 159 | 183 | 207 | 231 | 255 | 279 | 303 | 327 | 351 |
| Ppp2r2d | 16 | 40 | 64 | 88 | 112 | 136 | 160 | 184 | 208 | 232 | 256 | 280 | 304 | 328 | 352 |
| Nrp1 | 17 | 41 | 65 | 89 | 113 | 137 | 161 | 185 | 209 | 233 | 257 | 281 | 305 | 329 | 353 |
| Havcr2 | 18 | 42 | 66 | 90 | 114 | 138 | 162 | 186 | 210 | 234 | 258 | 282 | 306 | 330 | 354 |
| Lag3 | 19 | 43 | 67 | 91 | 115 | 139 | 163 | 187 | 211 | 235 | 259 | 283 | 307 | 331 | 355 |
| Tigit | 20 | 44 | 68 | 92 | 116 | 140 | 164 | 188 | 212 | 236 | 260 | 284 | 308 | 332 | 356 |
| Ctla4 | 21 | 45 | 69 | 93 | 117 | 141 | 165 | 189 | 213 | 237 | 261 | 285 | 309 | 333 | 357 |
| Ptpn6 | 22 | 46 | 70 | 94 | 118 | 142 | 166 | 190 | 214 | 238 | 262 | 286 | 310 | 334 | 358 |
| Pdcd1 | 23 | 47 | 71 | 95 | 119 | 143 | 167 | 191 | 215 | 239 | 263 | 287 | 311 | 335 | 359 |
| Bcor | 24 | 48 | 72 | 96 | 120 | 144 | 168 | 192 | 216 | 240 | 264 | 288 | 312 | 336 | 360 |

Fig. 1B

| | Cblb | Ppp2r2d | Nrp1 | Havcr2 | Lag3 | Tigit | Ctla4 | Ptpn6 | Pdcd1 | Bcor |
|---|---|---|---|---|---|---|---|---|---|---|
| Ikzf1 | 361 | 385 | 409 | 433 | 457 | 481 | 505 | 529 | 553 | 577 |
| Ikzf3 | 362 | 386 | 410 | 434 | 458 | 482 | 506 | 530 | 554 | 578 |
| Gata3 | 363 | 387 | 411 | 435 | 459 | 483 | 507 | 531 | 555 | 579 |
| Bcl3 | 364 | 388 | 412 | 436 | 460 | 484 | 508 | 532 | 556 | 580 |
| Tnip1 | 365 | 389 | 413 | 437 | 461 | 485 | 509 | 533 | 557 | 581 |
| Tnfaip3 | 366 | 390 | 414 | 438 | 462 | 486 | 510 | 534 | 558 | 582 |
| Nfkbia | 367 | 391 | 415 | 439 | 463 | 487 | 511 | 535 | 559 | 583 |
| Smad2 | 368 | 392 | 416 | 440 | 464 | 488 | 512 | 536 | 560 | 584 |
| Tgfbr1 | 369 | 393 | 417 | 441 | 465 | 489 | 513 | 537 | 561 | 585 |
| Tgfbr2 | 370 | 394 | 418 | 442 | 466 | 490 | 514 | 538 | 562 | 586 |
| TANK | 371 | 395 | 419 | 443 | 467 | 491 | 515 | 539 | 563 | 587 |
| FOXP3 | 372 | 396 | 420 | 444 | 468 | 492 | 516 | 540 | 564 | 588 |
| IKZF2 | 373 | 397 | 421 | 445 | 469 | 493 | 517 | 541 | 565 | 589 |
| Rc3h1 | 374 | 398 | 422 | 446 | 470 | 494 | 518 | 542 | 566 | 590 |
| Traf6 | 375 | 399 | 423 | 447 | 471 | 495 | 519 | 543 | 567 | 591 |
| Cblb | | 400 | 424 | 448 | 472 | 496 | 520 | 544 | 568 | 592 |
| Ppp2r2d | 376 | | 425 | 449 | 473 | 497 | 521 | 545 | 569 | 593 |
| Nrp1 | 377 | 401 | | 450 | 474 | 498 | 522 | 546 | 570 | 594 |
| Havcr2 | 378 | 402 | 426 | | 475 | 499 | 523 | 547 | 571 | 595 |
| Lag3 | 379 | 403 | 427 | 451 | | 500 | 524 | 548 | 572 | 596 |
| Tigit | 380 | 404 | 428 | 452 | 476 | | 525 | 549 | 573 | 597 |
| Ctla4 | 381 | 405 | 429 | 453 | 477 | 501 | | 550 | 574 | 598 |
| Ptpn6 | 382 | 406 | 430 | 454 | 478 | 502 | 526 | | 575 | 599 |
| Pdcd1 | 383 | 407 | 431 | 455 | 479 | 503 | 527 | 551 | | 600 |
| Bcor | 384 | 408 | 432 | 456 | 480 | 504 | 528 | 552 | 576 | |

Fig. 2A

|  | Bcl2l11 | Fli1 | Calm2 | Dhodh | Umps | Rbm39 | Sema7A | Chic2 | Pcbp1 | Pbrm1 | Wdr6 | E2f8 | Serpina3 | Gnas |
|---|---|---|---|---|---|---|---|---|---|---|---|---|---|---|
| Ikzf1 | 601 | 626 | 651 | 676 | 701 | 726 | 751 | 776 | 801 | 826 | 851 | 876 | 901 | 926 |
| Ikzf3 | 602 | 627 | 652 | 677 | 702 | 727 | 752 | 777 | 802 | 827 | 852 | 877 | 902 | 927 |
| Gata3 | 603 | 628 | 653 | 678 | 703 | 728 | 753 | 778 | 803 | 828 | 853 | 878 | 903 | 928 |
| Bcl3 | 604 | 629 | 654 | 679 | 704 | 729 | 754 | 779 | 804 | 829 | 854 | 879 | 904 | 929 |
| Tnip1 | 605 | 630 | 655 | 680 | 705 | 730 | 755 | 780 | 805 | 830 | 855 | 880 | 905 | 930 |
| Tnfaip3 | 606 | 631 | 656 | 681 | 706 | 731 | 756 | 781 | 806 | 831 | 856 | 881 | 906 | 931 |
| Nfkbia | 607 | 632 | 657 | 682 | 707 | 732 | 757 | 782 | 807 | 832 | 857 | 882 | 907 | 932 |
| Smad2 | 608 | 633 | 658 | 683 | 708 | 733 | 758 | 783 | 808 | 833 | 858 | 883 | 908 | 933 |
| Tgfbr1 | 609 | 634 | 659 | 684 | 709 | 734 | 759 | 784 | 809 | 834 | 859 | 884 | 909 | 934 |
| Tgfbr2 | 610 | 635 | 660 | 685 | 710 | 735 | 760 | 785 | 810 | 835 | 860 | 885 | 910 | 935 |
| Tank | 611 | 636 | 661 | 686 | 711 | 736 | 761 | 786 | 811 | 836 | 861 | 886 | 911 | 936 |
| Foxp3 | 612 | 637 | 662 | 687 | 712 | 737 | 762 | 787 | 812 | 837 | 862 | 887 | 912 | 937 |
| Ikzf2 | 613 | 638 | 663 | 688 | 713 | 738 | 763 | 788 | 813 | 838 | 863 | 888 | 913 | 938 |
| Rc3h1 | 614 | 639 | 664 | 689 | 714 | 739 | 764 | 789 | 814 | 839 | 864 | 889 | 914 | 939 |
| Traf6 | 615 | 640 | 665 | 690 | 715 | 740 | 765 | 790 | 815 | 840 | 865 | 890 | 915 | 940 |
| Cblb | 616 | 641 | 666 | 691 | 716 | 741 | 766 | 791 | 816 | 841 | 866 | 891 | 916 | 941 |
| Ppp2r2d | 617 | 642 | 667 | 692 | 717 | 742 | 767 | 792 | 817 | 842 | 867 | 892 | 917 | 942 |
| Nrp1 | 618 | 643 | 668 | 693 | 718 | 743 | 768 | 793 | 818 | 843 | 868 | 893 | 918 | 943 |
| Havcr2 | 619 | 644 | 669 | 694 | 719 | 744 | 769 | 794 | 819 | 844 | 869 | 894 | 919 | 944 |
| Lag3 | 620 | 645 | 670 | 695 | 720 | 745 | 770 | 795 | 820 | 845 | 870 | 895 | 920 | 945 |
| Tigit | 621 | 646 | 671 | 696 | 721 | 746 | 771 | 796 | 821 | 846 | 871 | 896 | 921 | 946 |
| Ctla4 | 622 | 647 | 672 | 697 | 722 | 747 | 772 | 797 | 822 | 847 | 872 | 897 | 922 | 947 |
| Ptpn6 | 623 | 648 | 673 | 698 | 723 | 748 | 773 | 798 | 823 | 848 | 873 | 898 | 923 | 948 |
| Pdcd1 | 624 | 649 | 674 | 699 | 724 | 749 | 774 | 799 | 824 | 849 | 874 | 899 | 924 | 949 |
| Bcor | 625 | 650 | 675 | 700 | 725 | 750 | 775 | 800 | 825 | 850 | 875 | 900 | 925 | 950 |

*Fig. 2B*

|  | Ankrd11 | Socs1 |
|---|---|---|
| Ikzf1 | 951 | 976 |
| Ikzf3 | 952 | 977 |
| Gata3 | 953 | 978 |
| Bcl3 | 954 | 979 |
| Tnip1 | 955 | 980 |
| Tnfaip3 | 956 | 981 |
| Nfkbia | 957 | 982 |
| Smad2 | 958 | 983 |
| Tgfbr1 | 959 | 984 |
| Tgfbr2 | 960 | 985 |
| Tank | 961 | 986 |
| Foxp3 | 962 | 987 |
| Ikzf2 | 963 | 988 |
| Rc3h1 | 964 | 989 |
| Traf6 | 965 | 990 |
| Cblb | 966 | 991 |
| Ppp2r2d | 967 | 992 |
| Nrp1 | 968 | 993 |
| Havcr2 | 969 | 994 |
| Lag3 | 970 | 995 |
| Tigit | 971 | 996 |
| Ctla4 | 972 | 997 |
| Ptpn6 | 973 | 998 |
| Pdcd1 | 974 | 999 |
| Bcor | 975 | 1000 |

*Fig. 3A*

|  | Bcl2l11 | Fli1 | Calm2 | Dhodh | Umps | Rbm39 | Sema7A | Chic2 | Pcbp1 | Pbrm1 | Wdr6 | E2f8 | Serpina3 | Gnas |
|---|---|---|---|---|---|---|---|---|---|---|---|---|---|---|
| Bcl2l11 |  | 1016 | 1031 | 1046 | 1061 | 1076 | 1091 | 1106 | 1121 | 1136 | 1151 | 1166 | 1181 | 1196 |
| Fli1 | 1001 |  | 1032 | 1047 | 1062 | 1077 | 1092 | 1107 | 1122 | 1137 | 1152 | 1167 | 1182 | 1197 |
| Calm2 | 1002 | 1017 |  | 1048 | 1063 | 1078 | 1093 | 1108 | 1123 | 1138 | 1153 | 1168 | 1183 | 1198 |
| Dhodh | 1003 | 1018 | 1033 |  | 1064 | 1079 | 1094 | 1109 | 1124 | 1139 | 1154 | 1169 | 1184 | 1199 |
| Umps | 1004 | 1019 | 1034 | 1049 |  | 1080 | 1095 | 1110 | 1125 | 1140 | 1155 | 1170 | 1185 | 1200 |
| Rbm39 | 1005 | 1020 | 1035 | 1050 | 1065 |  | 1096 | 1111 | 1126 | 1141 | 1156 | 1171 | 1186 | 1201 |
| Sema7A | 1006 | 1021 | 1036 | 1051 | 1066 | 1081 |  | 1112 | 1127 | 1142 | 1157 | 1172 | 1187 | 1202 |
| Chic2 | 1007 | 1022 | 1037 | 1052 | 1067 | 1082 | 1097 |  | 1128 | 1143 | 1158 | 1173 | 1188 | 1203 |
| Pcbp1 | 1008 | 1023 | 1038 | 1053 | 1068 | 1083 | 1098 | 1113 |  | 1144 | 1159 | 1174 | 1189 | 1204 |
| Pbrm1 | 1009 | 1024 | 1039 | 1054 | 1069 | 1084 | 1099 | 1114 | 1129 |  | 1160 | 1175 | 1190 | 1205 |
| Wdr6 | 1010 | 1025 | 1040 | 1055 | 1070 | 1085 | 1100 | 1115 | 1130 | 1145 |  | 1176 | 1191 | 1206 |
| E2f8 | 1011 | 1026 | 1041 | 1056 | 1071 | 1086 | 1101 | 1116 | 1131 | 1146 | 1161 |  | 1192 | 1207 |
| Serpina3 | 1012 | 1027 | 1042 | 1057 | 1072 | 1087 | 1102 | 1117 | 1132 | 1147 | 1162 | 1177 |  | 1208 |
| Gnas | 1013 | 1028 | 1043 | 1058 | 1073 | 1088 | 1103 | 1118 | 1133 | 1148 | 1163 | 1178 | 1193 |  |
| Ankrd11 | 1014 | 1029 | 1044 | 1059 | 1074 | 1089 | 1104 | 1119 | 1134 | 1149 | 1164 | 1179 | 1194 | 1209 |
| Socs1 | 1015 | 1030 | 1045 | 1060 | 1075 | 1090 | 1105 | 1120 | 1135 | 1150 | 1165 | 1180 | 1195 | 1210 |

*Fig. 3B*

|        | Ankrd11 | Socs1 |
|-------:|:-------:|:-----:|
| Bcl2l11 | 1211 | 1226 |
| Fli1 | 1212 | 1227 |
| Calm2 | 1213 | 1228 |
| Dhodh | 1214 | 1229 |
| Umps | 1215 | 1230 |
| Rbm39 | 1216 | 1231 |
| Sema7A | 1217 | 1232 |
| Chic2 | 1218 | 1233 |
| Pcbp1 | 1219 | 1234 |
| Pbrm1 | 1220 | 1235 |
| Wdr6 | 1221 | 1236 |
| E2f8 | 1222 | 1237 |
| Serpina3 | 1223 | 1238 |
| Gnas | 1224 | 1239 |
| Ankrd11 |  | 1240 |
| Socs1 | 1225 |  |

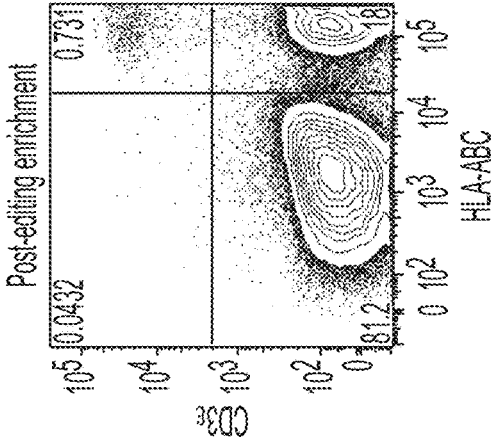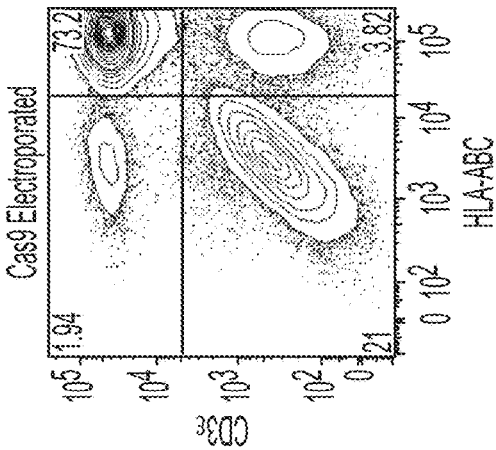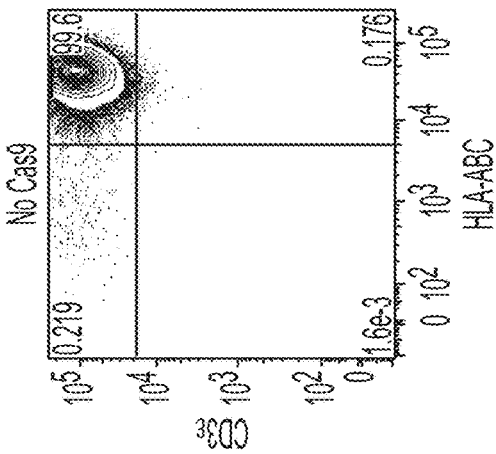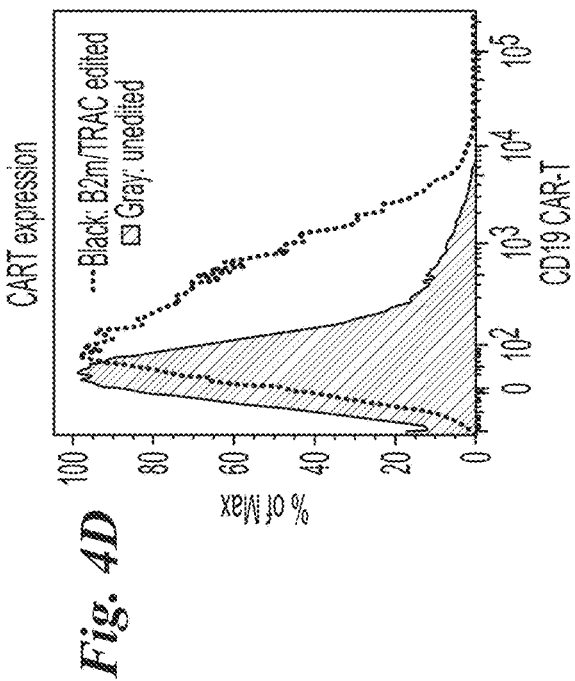

GENE-REGULATING COMPOSITIONS AND METHODS FOR IMPROVED IMMUNOTHERAPY

CROSS-REFERENCE TO RELATED APPLICATIONS

This application is a continuation of U.S. application Ser. No. 17/707,725, filed Mar. 29, 2022, which is a continuation of U.S. patent application Ser. No. 16/951,310, now U.S. Pat. No. 11,332,713, filed Nov. 18, 2020, which is a continuation of U.S. patent application Ser. No. 16/354,100, now U.S. Pat. No. 11,261,428, filed Mar. 14, 2019, which claims priority to U.S. Provisional Application No. 62/643,578, filed Mar. 15, 2018, U.S. Provisional Application No. 62/692,010, filed Jun. 29, 2018, U.S. Provisional Application No. 62/768,428, filed Nov. 16, 2018, U.S. Provisional Application No. 62/643,584, filed Mar. 15, 2018, U.S. Provisional Application No. 62/692,016, filed Jun. 29, 2018, U.S. Provisional Application No. 62/768,441, filed Nov. 16, 2018, U.S. Provisional Application No. 62/790,179, filed Jan. 9, 2019, U.S. Provisional Application No. 62/804,261, filed Feb. 12, 2019, U.S. Provisional Application No. 62/736,185, filed Sep. 25, 2018, and U.S. Provisional Application No. 62/790,192, filed Jan. 9, 2019, which are hereby incorporated by reference in their entireties.

REFERENCE TO AN ELECTRONIC SEQUENCE LISTING

The contents of the electronic sequence listing (K071370002US09-SEQ-HJD.xml; Size: 1,187,559 bytes; and Date of Creation: Dec. 13, 2022) is herein incorporated by reference in its entirety.

FIELD

The disclosure relates to methods, compositions, and components for editing a target nucleic acid sequence, or modulating expression of a target nucleic acid sequence, and applications thereof in connection with immunotherapy, including use with receptor-engineered immune effector cells, in the treatment of cell proliferative diseases, inflammatory diseases, and/or infectious diseases.

BACKGROUND

Adoptive cell transfer utilizing genetically modified T cells, in particular CAR-T cells has entered clinical testing as a therapeutic for solid and hematologic malignancies. Results to date have been mixed. In hematologic malignancies (especially lymphoma, CLL and ALL), the majority of patients in several Phase 1 and 2 trials exhibited at least a partial response, with some exhibiting complete responses (Kochenderfer et al., 2012 Blood 119, 2709-2720). In 2017, the FDA approved two CAR-T therapies, Kymriah™ and Yescarta™, both for the treatment of hematological cancers. However, in most tumor types (including melanoma, renal cell carcinoma and colorectal cancer), fewer responses have been observed (Johnson et al., 2009 Blood 114, 535-546; Lamers et al., 2013 Mol. Ther. 21, 904-912; Warren et al., 1998 Cancer Gene Ther. 5, S1-S2). As such, there is considerable room for improvement with adoptive T cell therapies, as success has largely been limited to CAR-T cells approaches targeting hematological malignancies of the B cell lineage.

SUMMARY

There exists a need to improve the efficacy of adoptive transfer of modified immune cells in cancer treatment, in particular increasing the efficacy of adoptive cell therapies against solid malignancies, as reduced responses have been observed in these tumor types (melanoma, renal cell carcinoma and colorectal cancer; Yong, 2017, Imm Cell Biol., 95:356-363). In addition, even in hematological malignancies where a benefit of adoptive transfer has been observed, not all patients respond and relapses occur with a greater than desired frequency, likely as a result of diminished function of the adoptively transferred T cells.

Factors limiting the efficacy of genetically modified immune cells as cancer therapeutics include (1) cell proliferation, e.g., limited proliferation of T cells following adoptive transfer; (2) cell survival, e.g., induction of T cell apoptosis by factors in the tumor environment; and (3) cell function, e.g., inhibition of cytotoxic T cell function by inhibitory factors secreted by host immune cells and cancer cells and exhaustion of immune cells during manufacturing processes and/or after transfer.

Particular features thought to increase the anti-tumor effects of an immune cell include a cell's ability to 1) proliferate in the host following adoptive transfer; 2) infiltrate a tumor; 3) persist in the host and/or exhibit resistance to immune cell exhaustion; and 4) function in a manner capable of killing tumor cells. The present disclosure provides immune cells comprising decreased expression and/or function of one or more endogenous target genes wherein the modified immune cells demonstrate an enhancement of one or more effector functions including increased proliferation, increased infiltration into tumors, persistence of the immune cells in a subject, and/or increased resistance to immune cell exhaustion. The present disclosure also provides methods and compositions for modification of immune effector cells to elicit enhanced immune cell activity towards a tumor cell, as well as methods and compositions suitable for use in the context of adoptive immune cell transfer therapy.

In some embodiments, the present disclosure provides a modified immune effector cell comprising a gene-regulating system capable of reducing expression and/or function of one or more endogenous target genes selected from: (a) the group consisting of BCL2L11, FL11, CALM2, DHODH, UMPS, RBM39, SEMA7A, CHIC2, PCBP1, PBRM1, WDR6, E2F8, SERPINA3, and GNAS; or (b) the group consisting of SOCS1 and ANKRD11; wherein the reduced expression and/or function of the one or more endogenous genes enhances an effector function of the immune effector cell. In some embodiments, the gene-regulating system is capable of reducing the expression and/or function of two or more of endogenous target genes selected from: (a) the group consisting of BCL2L11, FL11, CALM2, DHODH, UMPS, RBM39, SEMA7A, CHIC2, PCBP1, PBRM1, WDR6, E2F8, SERPINA3, and GNAS; (b) the group consisting of SOCS1 and ANKRD11.

In some embodiments, the present disclosure provides a modified immune effector cell comprising a gene-regulating system capable of reducing the expression and/or function of one or more endogenous target genes selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, wherein the reduced expression and/or function of the one or more endogenous genes enhances an effector function of the immune effector cell. In some embodiments, the gene-regulating system is capable of reducing the expression and/or function of two or more of endogenous target genes selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2 and at least one of the endogenous target genes is selected from the group consisting of CBLB, PPP2R2D, NRP1, HAVCR2, LAG3, TIGIT, CTLA4, PTPN6, PDCD1, and BCOR.

In some embodiments, the present disclosure provides a modified immune effector cell comprising a gene-regulating system capable of reducing expression and/or function of one or more endogenous target genes selected from: (a) the group consisting of BCL2L11, FL11, CALM2, DHODH, UMPS, RBM39, SEMA7A, CHIC2, PCBP1, PBRM1, WDR6, E2F8, SERPINA3, and GNAS; or (b) the group consisting of SOCS1 and ANKRD11 and one or more endogenous target genes selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the gene-regulating system is capable of reducing the expression and/or function of at least one endogenous target gene selected from the group consisting of BCL2L11, FL11, CALM2, DHODH, UMPS, RBM39, SEMA7A, CHIC2, PCBP1, PBRM1, WDR6, E2F8, SERPINA3, and GNAS and at least one endogenous target gene selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the gene-regulating system is capable of reducing the expression and/or function of at least one endogenous target gene selected from the group consisting of SOCS1 and ANKRD11 and at least one endogenous target gene selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR.

In some embodiments, the gene-regulating system is capable of reducing the expression and/or function of SOCS1 and CBLB. In some embodiments, the gene-regulating system is capable of reducing the expression and/or function of SOCS1 and BCOR. In some embodiments, the gene-regulating system is capable of reducing the expression and/or function of SOCS1 and TNFAIP3. In some embodiments, the gene-regulating system is capable of reducing the expression and/or function of ANKRD11 and CBLB. In some embodiments, the gene-regulating system is capable of reducing the expression and/or function of ANKRD11 and BCOR. In some embodiments, the gene-regulating system is capable of reducing the expression and/or function of ANKRD11 and TNFAIP3. In some embodiments, the gene-regulating system is capable of reducing the expression and/or function of ANKRD11 and SOCS1.

In some embodiments, the gene-regulating system comprises (i) one or more nucleic acid molecules; (ii) one or more enzymatic proteins; or (iii) one or more guide nucleic acid molecules and an enzymatic protein. In some embodiments, the one or more nucleic acid molecules are selected from an siRNA, an shRNA, a microRNA (miR), an antagomiR, or an antisense RNA. In some embodiments, the gene-regulating system comprises an siRNA or an shRNA nucleic acid molecule.

In some embodiments, the one or more endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR and wherein the siRNA or shRNA molecule comprises about 19-30 nucleotides that bind to an RNA sequence encoded by a DNA sequence defined by a set of genome coordinates shown in Table 5A and Table 5B. In some embodiments, the siRNA or shRNA comprises about 19-30 nucleotides that bind to an RNA sequence encoded by a DNA sequence selected from the group consisting of SEQ ID NOs: 154-813.

In some embodiments, the one or more endogenous target genes is selected from the group consisting of BCL2L11, FL11, CALM2, DHODH, UMPS, RBM39, SEMA7A, CHIC2, PCBP1, PBRM1, WDR6, E2F8, SERPINA3, and GNAS, and wherein the siRNA or shRNA molecule comprises about 19-30 nucleotides that bind to an RNA sequence encoded by a DNA sequence defined by a set of genome coordinates shown in Table 6A and Table 6B. In some embodiments, the siRNA or shRNA comprises about 19-30 nucleotides that bind to an RNA sequence encoded by a DNA sequence selected from the group consisting of SEQ ID NOs: 814-1064.

In some embodiments, the one or more endogenous target genes is SOCS1, and wherein the siRNA or shRNA molecule comprises about 19-30 nucleotides that bind to an RNA sequence encoded by a DNA sequence defined by a set of genome coordinates shown in Table 6C and Table 6D. In some embodiments, the siRNA or shRNA comprises about 19-30 nucleotides that bind to an RNA sequence encoded by a DNA sequence selected from the group consisting of SEQ ID NOs: 1088-1232. In some embodiments, the one or more endogenous target genes is ANKRD11, and wherein the siRNA or shRNA molecule comprises about 19-30 nucleotides that bind to an RNA sequence encoded by a DNA sequence defined by a set of genome coordinates shown in Table 6E and Table 6F. In some embodiments, the siRNA or shRNA comprises about 19-30 nucleotides that bind to an RNA sequence encoded by a DNA sequence selected from the group consisting of SEQ ID NOs: 1065-1087.

In some embodiments, the gene-regulating system comprises a plurality of siRNA or shRNA molecules and is capable of reducing the expression and/or function of two or more endogenous target genes.

In some embodiments, at least one of the endogenous target genes is selected from the group consisting of BCL2L11, FL11, CALM2, DHODH, UMPS, RBM39, SEMA7A, CHIC2, PCBP1, PBRM1, WDR6, E2F8, SERPINA3, and GNAS and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6A and Table 6B and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 814-1064 and at least one of the plurality of siRNA or shRNA molecules comprises about 19-30 nucleotides that bind to an RNA sequence encoded by a DNA sequence selected from the group consisting of SEQ ID NOs: 154-813.

In some embodiments, at least one of the endogenous target genes is selected from the group consisting of BCL2L11, FL11, CALM2, DHODH, UMPS, RBM39, SEMA7A, CHIC2, PCBP1, PBRM1, WDR6, E2F8, SERPINA3, and GNAS and at least one of the endogenous target genes is CBLB. In some embodiments, at least one of the plurality of siRNA or shRNA molecules comprises about 19-30 nucleotides that bind to an RNA sequence encoded by a DNA sequence selected from the group consisting of SEQ ID NOs: 814-1064 and at least one of the plurality of siRNA or shRNA molecules comprises about 19-30 nucleotides that bind to an RNA sequence encoded by a DNA sequence selected from the group consisting of SEQ ID NOs: 499-524. In some embodiments, at least one of the endogenous target genes is selected from the group consisting of BCL2L11, FL11, CALM2, DHODH, UMPS, RBM39, SEMA7A, CHIC2, PCBP1, PBRM1, WDR6, E2F8, SERPINA3, and GNAS and at least one of the endogenous target genes is CBLB, TNFAIP3, or BCOR.

In some embodiments, at least one of the endogenous target genes is SOCS1 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6C and Table 6D and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 1088-1232 and at least one of the plurality of siRNA or shRNA molecules comprises about 19-30 nucleotides that bind to an RNA sequence encoded by a DNA sequence selected from the group consisting of SEQ ID NOs: 154-813.

In some embodiments, at least one of the endogenous target genes is SOCS1 and at least one of the endogenous target genes is CBLB. In some embodiments, at least one of the plurality of siRNA or shRNA molecules comprises about 19-30 nucleotides that bind to an RNA sequence encoded by a DNA sequence selected from the group consisting of SEQ ID NOs: 1088-1232 and at least one of the plurality of siRNA or shRNA molecules comprises about 19-30 nucleotides that bind to an RNA sequence encoded by a DNA sequence selected from the group consisting of SEQ ID NOs: 499-524. In some embodiments, at least one of the endogenous target genes is SOCS1 and at least one of the endogenous target genes is CBLB, TNFAIP3, or BCOR.

In some embodiments, at least one of the endogenous target genes is ANKRD11 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6E and Table 6F and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 1065-1087 and at least one of the plurality of siRNA or shRNA molecules comprises about 19-30 nucleotides that bind to an RNA sequence encoded by a DNA sequence selected from the group consisting of SEQ ID NOs: 154-813.

In some embodiments, at least one of the endogenous target genes is ANKRD11 and at least one of the endogenous target genes is CBLB. In some embodiments, at least one of the plurality of siRNA or shRNA molecules comprises about 19-30 nucleotides that bind to an RNA sequence encoded by a DNA sequence selected from the group consisting of SEQ ID NOs: 1065-1087 and at least one of the plurality of siRNA or shRNA molecules comprises about 19-30 nucleotides that bind to an RNA sequence encoded by a DNA sequence selected from the group consisting of SEQ ID NOs: 499-524. In some embodiments, at least one of the endogenous target genes is ANKRD11 and at least one of the endogenous target genes is CBLB, TNFAIP3, or BCOR.

In some embodiments, at least one of the endogenous target genes is SOCS1 and at least one of the endogenous target genes is ANKRD11. In some embodiments, at least one of the plurality of siRNA or shRNA molecules comprises about 19-30 nucleotides that bind to an RNA sequence encoded by a DNA sequence defined by a set of genome coordinates shown in Table 6C and Table 6D and at least one of the plurality of siRNA or shRNA molecules comprises about 19-30 nucleotides that bind to an RNA sequence encoded by a DNA sequence defined by a set of genome coordinates shown in Table 6E and Table 6F. In some embodiments, at least one of the plurality of siRNA or shRNA molecules comprises about 19-30 nucleotides that bind to an RNA sequence encoded by a DNA sequence selected from the group consisting of SEQ ID NOs: 1065-1087 and at least one of the plurality of siRNA or shRNA molecules comprises about 19-30 nucleotides that bind to an RNA sequence encoded by a DNA sequence selected from the group consisting of SEQ ID NOs: 1088-1232.

In some embodiments, the gene-regulating system comprises an enzymatic protein, and wherein the enzymatic protein has been engineered to specifically bind to a target sequence in one or more of the endogenous genes. In some embodiments, the protein is a Transcription activator-like effector nuclease (TALEN), a zinc-finger nuclease, or a meganuclease.

In some embodiments, the gene-regulating system comprises a guide nucleic acid molecule and an enzymatic protein, wherein the nucleic acid molecule is a guide RNA (gRNA) molecule and the enzymatic protein is a Cas protein or Cas ortholog.

In some embodiments, the one or more endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, and wherein the gRNA molecule comprises a targeting domain sequence that binds to a nucleic acid sequence defined by a set of genome coordinates shown in Table 5A and Table 5B. In some embodiments, the gRNA molecule comprises a targeting domain sequence that binds to a target DNA sequence selected from the group consisting of SEQ ID NOs: 154-813. In some embodiments, the gRNA molecule comprises a targeting domain sequence encoded by a nucleic acid sequence selected from the group consisting of SEQ ID NOs: 154-813.

In some embodiments, the one or more endogenous target genes selected from the group consisting of BCL2L11, FL11, CALM2, DHODH, UMPS, RBM39, SEMA7A, CHIC2, PCBP1, PBRM1, WDR6, E2F8, SERPINA3, and GNAS, and wherein the gRNA molecule comprises a targeting domain sequence that binds to a nucleic acid sequence defined by a set of genome coordinates shown in Table 6A and Table 6B. In some embodiments, the gRNA molecule comprises a targeting domain sequence that binds to a target DNA sequence selected from the group consisting of SEQ ID NOs: 814-1064. In some embodiments, the gRNA molecule comprises a targeting domain sequence encoded by a nucleic acid sequence selected from the group consisting of SEQ ID NOs: 814-1064.

In some embodiments, the one or more endogenous target genes is SOCS1, and wherein the gRNA molecule comprises a targeting domain sequence that binds to a nucleic acid sequence defined by a set of genome coordinates shown in Tables 6C and 6D. In some embodiments, the gRNA molecule comprises a targeting domain sequence that binds to a target DNA sequence selected from the group consisting of SEQ ID NOs: 1088-1232. In some embodiments, the gRNA molecule comprises a targeting domain sequence encoded by a nucleic acid sequence selected from the group consisting of SEQ ID NOs: 1088-1232.

In some embodiments, the one or more endogenous target genes is ANKRD11, and wherein the gRNA molecule comprises a targeting domain sequence that binds to a nucleic acid sequence defined by a set of genome coordinates shown in Tables 6E and 6F. In some embodiments, the gRNA molecule comprises a targeting domain sequence that binds to a target DNA sequence selected from the group consisting of SEQ ID NOs: 1065-1087. In some embodiments, the gRNA molecule comprises a targeting domain sequence encoded by a nucleic acid sequence selected from the group consisting of SEQ ID NOs: 1065-1087.

In some embodiments, the gene-regulating system comprises a plurality of gRNA molecules and is capable of reducing the expression and/or function of two or more endogenous target genes.

In some embodiments, at least one of the endogenous target genes selected from the group consisting of BCL2L11, FL11, CALM2, DHODH, UMPS, RBM39, SEMA7A, CHIC2, PCBP1, PBRM1, WDR6, E2F8, SERPINA3, and GNAS and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNA molecules comprises a targeting domain sequence that binds to a nucleic acid sequence defined by a set of genome coordinates shown in Table 6A and Table 6B and at least one of the plurality of gRNA molecule comprises a targeting domain sequence that binds to a nucleic acid sequence defined by a set of genome coordinates shown in Table 5A and Table 5B. In some embodiments, at least one of the plurality of gRNA molecules comprises a targeting domain sequence that binds to a target DNA sequence selected from the group consisting of SEQ ID NOs: 814-1064 and at least one of the plurality of gRNA molecules comprises a targeting domain sequence that binds to a target DNA sequence selected from the group consisting of SEQ ID NOs: 154-813. In some embodiments, at least one of the plurality of gRNA molecules comprises a targeting domain sequence encoded by a nucleic acid sequence selected from the group consisting of SEQ ID NOs: 814-1064 and at least one of the plurality of gRNA molecules comprises a targeting domain sequence encoded by a nucleic acid sequence selected from the group consisting of SEQ ID NOs: 154-813.

In some embodiments, at least one of the endogenous target genes is selected from the group consisting of BCL2L11, FL11, CALM2, DHODH, UMPS, RBM39, SEMA7A, CHIC2, PCBP1, PBRM1, WDR6, E2F8, SERPINA3, and GNAS and at least one of the endogenous target genes is CBLB. In some embodiments, at least one of the plurality of gRNA molecules comprises a targeting domain sequence that binds to a target DNA sequence selected from the group consisting of SEQ ID NOs: 814-1064 and at least one of the plurality of gRNA molecules comprises a targeting domain sequence that binds to a target DNA sequence selected from the group consisting of SEQ ID NOs: 499-524. In some embodiments, at least one of the plurality of gRNA molecules comprises a targeting domain sequence encoded by a nucleic acid sequence selected from the group consisting of SEQ ID NOs: 814-1064 and at least one of the plurality of gRNA molecules comprises a targeting domain sequence encoded by a nucleic acid sequence selected from the group consisting of SEQ ID NOs: 499-524. In some embodiments, n at least one of the endogenous target genes is selected from the group consisting of BCL2L11, FL11, CALM2, DHODH, UMPS, RBM39, SEMA7A, CHIC2, PCBP1, PBRM1, WDR6, E2F8, SERPINA3, and GNAS and at least one of the endogenous target genes is CBLB, TNFAIP3, or BCOR.

In some embodiments, at least one of the endogenous target genes is SOCS1 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNA molecules comprises a targeting domain sequence that binds to a nucleic acid sequence defined by a set of genome coordinates shown in Table 6C and Table 6D and at least one of the plurality of gRNA molecule comprises a targeting domain sequence that binds to a nucleic acid sequence defined by a set of genome coordinates shown in Table 5A and Table 5B. In some embodiments, at least one of the plurality of gRNA molecules comprises a targeting domain sequence that binds to a target DNA sequence selected from the group consisting of SEQ ID NOs: 1088-1232 and at least one of the plurality of gRNA molecules comprises a targeting domain sequence that binds to a target DNA sequence selected from the group consisting of SEQ ID NOs: 154-813. In some embodiments, at least one of the plurality of gRNA molecules comprises a targeting domain sequence encoded by a nucleic acid sequence selected from the group consisting of SEQ ID NOs: 1088-1232 and at least one of the plurality of gRNA molecules comprises a targeting domain sequence encoded by a nucleic acid sequence selected from the group consisting of SEQ ID NOs: 154-813.

In some embodiments, at least one of the endogenous target genes is SOCS1 and at least one of the endogenous target genes is CBLB. In some embodiments, at least one of the plurality of gRNA molecules comprises a targeting domain sequence that binds to a target DNA sequence selected from the group consisting of SEQ ID NOs: 1088-1232 and at least one of the plurality of gRNA molecules comprises a targeting domain sequence that In some embodiments, at least one of the plurality of gRNA molecules comprises a targeting domain sequence encoded by a nucleic acid sequence selected from the group consisting of SEQ ID NOs: 1088-1232 and at least one of the plurality of gRNA molecules comprises a targeting domain sequence encoded by a nucleic acid sequence selected from the group consisting of SEQ ID NOs: 499-524. In some embodiments, at least one of the endogenous target genes is SOCS1 and at least one of the endogenous target genes is CBLB, TNFAIP3, or BCOR.

In some embodiments, at least one of the endogenous target genes is ANKRD11 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNA molecules comprises a targeting domain sequence that binds to a nucleic acid sequence defined by a set of genome coordinates shown in Table 6E and Table 6F and at least one of the plurality of gRNA molecule comprises a targeting domain sequence that binds to a nucleic acid sequence defined by a set of genome coordinates shown in Table 5A and Table 5B. In some embodiments, at least one of the plurality of gRNA molecules comprises a targeting domain sequence that binds to a target DNA sequence selected from the group consisting of SEQ ID NOs: 1065-1087 and at least one of the plurality of gRNA molecules comprises a targeting domain sequence that binds to a target DNA sequence selected from the group consisting of SEQ ID NOs: 154-813. In some embodiments, at least one of the plurality of gRNA molecules comprises a targeting domain sequence encoded by a nucleic acid sequence selected from the group consisting of SEQ ID NOs: 1065-1087 and at least one of the plurality of gRNA molecules comprises a targeting domain sequence that binds to a target DNA sequence selected from the group consisting of SEQ ID NOs: 154-813.

In some embodiments, at least one of the endogenous target genes is ANKRD11 and at least one of the endogenous target genes is CBLB. In some embodiments, at least one of the plurality of gRNA molecules comprises a targeting domain sequence that binds to a target DNA sequence selected from the group consisting of SEQ ID NOs: 1065-1087 and at least one of the plurality of gRNA molecules comprises a targeting domain sequence that binds to a target DNA sequence selected from the group consisting of SEQ ID NOs: 499-524. In some embodiments, at least one of the plurality of gRNA molecules comprises a targeting domain sequence encoded by a nucleic acid sequence selected from the group consisting of SEQ ID NOs: 1065-1087 and at least one of the plurality of gRNA molecules comprises a targeting domain sequence encoded by a nucleic acid sequence selected from the group consisting of SEQ ID NOs: 499-524. In some embodiments, at least one of the endogenous target genes is ANKRD11 and at least one of the endogenous target genes is CBLB, TNFAIP3, or BCOR.

In some embodiments, at least one of the endogenous target genes is SOCS1 and at least one of the endogenous target genes is ANKRD11. In some embodiments, at least one of the plurality of gRNA molecules comprises a targeting domain sequence that binds to a nucleic acid sequence defined by a set of genome coordinates shown in Table 6E and Table 6F and at least one of the plurality of gRNA molecule comprises a targeting domain sequence that binds to a nucleic acid sequence defined by a set of genome coordinates shown in Table 6C and Table 6D. In some embodiments, at least one of the plurality of gRNA molecules comprises a targeting domain sequence that binds to a target DNA sequence selected from the group consisting of SEQ ID NOs: 1065-1087 and at least one of the plurality of gRNA molecules comprises a targeting domain sequence that binds to a target DNA sequence selected from the group consisting of SEQ ID NOs: 1088-1232. In some embodiments, at least one of the plurality of gRNA molecules comprises a targeting domain sequence encoded by a DNA sequence selected from the group consisting of SEQ ID NOs: 1065-1087 and at least one of the plurality of gRNA molecules comprises a targeting domain sequence encoded by a DNA sequence selected from the group consisting of SEQ ID NOs: 1088-1232.

In some embodiments, the modified immune effector cell comprises a Cas protein wherein: the Cas protein is a wild-type Cas protein comprising two enzymatically active domains, and capable of inducing double stranded DNA breaks; the Cas protein is a Cas nickase mutant comprising one enzymatically active domain and capable of inducing single stranded DNA breaks; or the Cas protein is a deactivated Cas protein (dCas) and is associated with a heterologous protein capable of modulating the expression of the one or more endogenous target genes. In some embodiments, the Cas protein is a Cas9 protein. In some embodiments, the heterologous protein is selected from the group consisting of MAX-interacting protein 1 (MXI1), Krippel-associated box (KRAB) domain, methyl-CpG binding protein 2 (MECP2), and four concatenated mSin3 domains (SID4X).

In some embodiments, the gene regulating system introduces an inactivating mutation into the one or more endogenous target genes. In some embodiments, the inactivating mutation comprises a deletion, substitution, or insertion of one or more nucleotides in the genomic sequences of the two or more endogenous genes. In some embodiments, the deletion is a partial or complete deletion of the two or more endogenous target genes. In some embodiments, the inactivating mutation is a frame shift mutation. In some embodiments, the inactivating mutation reduces the expression and/or function of the two or more endogenous target genes.

In some embodiments, the gene-regulating system is introduced to the immune effector cell by transfection, transduction, electroporation, or physical disruption of the cell membrane by a microfluidics device. In some embodiments, the gene-regulating system is introduced as a polynucleotide encoding one or more components of the system, a protein, or a ribonucleoprotein (RNP) complex.

In some embodiments, the present disclosure provides a modified immune effector cell comprising reduced expression and/or function of one or more endogenous genes selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, wherein the reduced expression and/or function of the one or more endogenous genes enhances an effector function of the immune effector cell In some embodiments, the present disclosure provides a modified immune effector cell comprising reduced expression and/or function of one or more endogenous genes selected from (a) the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2; or (b) the group consisting of CBLB, PPP2R2D, NRP1, HAVCR2, LAG3, TIGIT, CTLA4, PTPN6, PDCD1, and BCOR, wherein the reduced expression and/or function of the one or more endogenous genes enhances an effector function of the immune effector cell.

In some embodiments, the present disclosure provides a modified immune effector cell comprising reduced expression and/or function of one or more endogenous genes selected from: (a) the group consisting of BCL2L11, FL11, CALM2, DHODH, UMPS, RBM39, SEMA7A, CHIC2, PCBP1, PBRM1, WDR6, E2F8, SERPINA3, and GNAS; (b) SOCS1; or (c) ANKRD11; wherein the reduced expression and/or function of the one or more endogenous genes enhances an effector function of the modified immune effector cell. In some embodiments, the modified immune effector cell comprises reduced expression and/or function of SOCS and ANKRD11.

In some embodiments, the present disclosure provides a modified immune effector cell comprising reduced expression and/or function of two or more target genes selected from Ikzf1, Ikzf3, GATA3, Bcl3, Tnip1, Tnfaip3, NFKBIA, SMAD2, Tgfbr1, Tgfbr2, TANK, FOXP3, RC3H1, TRAF6, IKZF2, Cblb, Ppp2r2d, Nrp1, Havcr2, Lag3, Tigit, Ctla4, Ptpn6, Pdcd1, and BCOR, wherein the reduced expression and/or function of the two or more endogenous genes enhances an effector function of the modified immune effector cell. In some embodiments, the modified immune effector cell comprises reduced expression and/or function of CBLB and BCOR.

In some embodiments, the present disclosure provides a modified immune effector cell comprising reduced expression and/or function of two or more target genes, wherein at least one target gene is selected from the group consisting of BCL2L11, FL11, CALM2, DHODH, UMPS, RBM39, SEMA 7A, CHIC2, PCBP1, PBRM1, WDR6, E2F8, SERPINA3, and GNAS, and wherein at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, wherein the reduced expression and/or function of the two or more endogenous genes enhances an effector function of the modified immune effector cell.

In some embodiments, the present disclosure provides a modified immune effector cell comprising reduced expression and/or function of two or more target genes, wherein at least one target gene is selected from the group consisting of BCL2L11, FL11, CALM2, DHODH, UMPS, RBM39, SEMA7A, CHIC2, PCBP1, PBRM1, WDR6, E2F8, SERPINA3, and GNAS, and wherein at least one target gene is CBLB.

In some embodiments, the present disclosure provides a modified immune effector cell comprising reduced expression and/or function of two or more target genes, wherein at least one target gene is SOCS1, and wherein at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, wherein the reduced expression and/or function of the two or more endogenous genes enhances an effector function of the modified immune effector cell. In some embodiments, the modified immune effector cell comprises reduced expression and/or function of SOCS1 and CBLB. In some embodiments, the modified immune effector cell comprises reduced expression and/or function of SOCS1 and TNFAIP3. In some embodiments, the modified immune effector cell comprises reduced expression and/or function of SOCS1 and BCOR.

In some embodiments, the present disclosure provides a modified immune effector cell comprising reduced expression and/or function of two or more target genes, wherein at least one target gene is ANKRD11, and wherein at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, wherein the reduced expression and/or function of the two or more endogenous genes enhances an effector function of the modified immune effector cell. In some embodiments, the modified immune effector cell comprises reduced expression and/or function of ANKRD11 and CBLB. In some embodiments, the modified immune effector cell comprises reduced expression and/or function of ANKRD11 and TNFAIP3. In some embodiments, the modified immune effector cell comprises reduced expression and/or function of ANKRD11 and BCOR.

In some embodiments, the present disclosure provides a modified immune effector cell comprising an inactivating mutation in one or more endogenous genes selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR.

In some embodiments, the present disclosure provides a modified immune effector cell comprising an inactivating mutation in one or more endogenous genes selected from: (a) the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2; or (b) the group consisting of CBLB, PPP2R2D, NRP1, HAVCR2, LAG3, TIGIT, CTLA4, PTPN6, PDCD1, and BCOR.

In some embodiments, the present disclosure provides a modified immune effector cell comprising an inactivating mutation in one or more endogenous genes selected from: (a) the group consisting of BCL2L11, FL11, CALM2, DHODH, UMPS, RBM39, SEMA7A, CHIC2, PCBP1, PBRM1, WDR6, E2F8, SERPINA3, and GNAS; or (b) SOCS1; or (c) ANKRD11. In some embodiments, the modified immune effector cell comprises an inactivating mutation in SOCS1 and ANKRD11.

A modified immune effector cell comprising an inactivating mutation in two or more target genes selected from Ikzf1, Ikzf3, GATA3, Bcl3, Tnip1, Tnfaip3, NFKBIA, SMAD2, Tgfbr1, Tgfbr2, TANK, FOXP3, RC3H1, TRAF6, IKZF2, Cblb, Ppp2r2d, Nrp1, Havcr2, Lag3, Tigit, Ctla4, Ptpn6, Pdcd1, and BCOR. In some embodiments, the modified immune effector cell comprises an inactivating mutation in the CBLB and BCOR genes.

In some embodiments, the present disclosure provides a modified immune effector cell comprising an inactivating mutation in two or more target genes, wherein at least one target gene is selected from the group consisting of BCL2L11, FL11, CALM2, DHODH, UMPS, RBM39, SEMA7A, CHIC2, PCBP1, PBRM1, WDR6, E2F8, SERPINA3, and GNAS, and at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR.

In some embodiments, the present disclosure provides a modified immune effector cell comprising an inactivating mutation in two or more target genes, wherein at least one target gene is selected from the group consisting of BCL2L11, FL11, CALM2, DHODH, UMPS, RBM39, SEMA7A, CHIC2, PCBP1, PBRM1, WDR6, E2F8, SERPINA3, and GNAS, and at least one target gene is CBLB.

In some embodiments, the present disclosure provides a modified immune effector cell comprising an inactivating mutation in two or more target genes, wherein at least one target gene is SOCS1 and at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the modified immune effector cell comprises an inactivating mutation in the SOCS1 and TNFAIP3 genes. In some embodiments, the modified immune effector cell comprises an inactivating mutation in the SOCS1 and BCOR genes. In some embodiments, the modified immune effector cell comprises an inactivating mutation in the SOCS1 and CBLB genes.

In some embodiments, the present disclosure provides a modified immune effector cell comprising an inactivating mutation in two or more target genes, wherein at least one target gene is ANKRD11 and at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the modified immune effector cell comprises an inactivating mutation in the ANKRD11 and TNFAIP3 genes. In some embodiments, the modified immune effector cell comprises an inactivating mutation in the ANKRD11 and BCOR genes. In some embodiments, the modified immune effector cell comprises an inactivating mutation in the ANKRD11 and CBLB genes.

In some embodiments, the inactivating mutation comprises a deletion, substitution, or insertion of one or more nucleotides in the genomic sequences of the two or more endogenous genes. In some embodiments, the deletion is a partial or complete deletion of the two or more endogenous target genes. In some embodiments, the inactivating mutation is a frame shift mutation. In some embodiments, the inactivating mutation reduces the expression and/or function of the two or more endogenous target genes. In some embodiments, the expression of the one or more endogenous target genes is reduced by at least 50%, at least 60%, at least 70%, at least 80%, or at least 90% compared to an un-modified or control immune effector cell. In some embodiments, the function of the one or more endogenous target genes is reduced by at least 50%, at least 60%, at least 70%, at least 80%, or at least 90% compared to an un-modified or control immune effector cell.

In some embodiments, the modified immune effector cell further comprises an engineered immune receptor displayed on the cell surface. In some embodiments, the engineered immune receptor is a CAR comprising an antigen-binding domain, a transmembrane domain, and an intracellular signaling domain. In some embodiments, the engineered immune receptor is an engineered TCR. In some embodiments, the engineered immune receptor specifically binds to an antigen expressed on a target cell, wherein the antigen is a tumor-associated antigen.

In some embodiments, the modified immune effector cell further comprises an exogenous transgene expressing an immune activating molecule. In some embodiments, the immune activating molecule is selected from the group consisting of a cytokine, a chemokine, a co-stimulatory molecule, an activating peptide, an antibody, or an antigen-binding fragment thereof. In some embodiments, the antibody or binding fragment thereof specifically binds to and inhibits the function of the protein encoded by NRP1, HAVCR2, LAG3, TIGIT, CTLA4, or PDCD1.

In some embodiments, the lymphocyte is a tumor infiltrating lymphocyte (TIL).

In some embodiments, the effector function is selected from cell proliferation, cell viability, tumor infiltration, cytotoxicity, anti-tumor immune responses, and/or resistance to exhaustion.

In some embodiments, the present disclosure provides a composition comprising the modified immune effector cells described herein. In some embodiments, the composition further comprises a pharmaceutically acceptable carrier or diluent. In some embodiments, the composition comprises at least $1\times10^4$, $1\times10^5$, or $1\times10^6$ modified immune effector cells. In some embodiments, the composition is suitable for administration to a subject in need thereof. In some embodiments, the composition comprises autologous immune effector cells derived from the subject in need thereof. In some embodiments, the composition comprises allogeneic immune effector cells derived from a donor subject.

In some embodiments, the present disclosure provides a gene-regulating system capable of reducing expression and/or function of one or more endogenous target genes in a cell selected from: (a) the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2; or (b) the group consisting of CBLB, PPP2R2D, NRP1, HAVCR2, LAG3, TIGIT, CTLA4, PTPN6, PDCD1, and BCOR, wherein the system comprises (i) a nucleic acid molecule; (ii) an enzymatic; or (iii) a guide nucleic acid molecule and an enzymatic protein In some embodiments, the present disclosure provides a gene-regulating system capable of reducing expression of one or more endogenous target genes in a cell selected from: (a) the group consisting of BCL2L11, FL11, CALM2, DHODH, UMPS, RBM39, SEMA7A, CHIC2, PCBP1, PBRM1, WDR6, E2F8, SERPINA3, and GNAS; (b) SOCS1; or (b) ANKRD11, wherein the system comprises (i) a nucleic acid molecule; (ii) an enzymatic; or (iii) a guide nucleic acid molecule and an enzymatic protein.

In some embodiments, the system comprises a guide RNA (gRNA) nucleic acid molecule and a Cas endonuclease.

In some embodiments, the one or more endogenous target genes are selected from IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2 or is selected from CBLB, PPP2R2D, NRP1, HAVCR2, LAG3, TIGIT, CTLA4, PTPN6, PDCD1, and BCOR and wherein the gRNA molecule comprises a targeting domain sequence that is complementary to a target DNA sequence defined by a set of genomic coordinates shown in Table 5A and Table 5B. In some embodiments, the one or more endogenous target genes are selected from IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2 and wherein the gRNA molecule comprises a targeting domain sequence that binds to a target DNA sequence selected from the group consisting of SEQ ID NOs: 154-498. In some embodiments, the gRNA molecule comprises a targeting domain sequence encoded by a nucleic acid sequence selected from the group consisting of SEQ ID NOs: 154-498.

In some embodiments, the one or more endogenous target genes are selected from CBLB, PPP2R2D, NRP1, HAVCR2, LAG3, TIGIT, CTLA4, PTPN6, PDCD1, and BCOR and wherein the gRNA molecule comprises a targeting domain sequence that binds to a target DNA sequence selected from the group consisting of SEQ ID NOs: 499-813. In some embodiments, the gRNA molecule comprises a targeting domain sequence encoded by a nucleic acid sequence selected from the group consisting of SEQ ID NOs: 499-813.

In some embodiments, the one or more endogenous target genes are selected from BCL2L11, FL11, CALM2, DHODH, UMPS, RBM39, SEMA7A, CHIC2, PCBP1, PBRM1, WDR6, E2F8, SERPINA3, and GNAS and wherein the gRNA molecule comprises a targeting domain sequence that binds to a target DNA sequence defined by a set of genomic coordinates shown in Table 6A and Table 6B. In some embodiments, the gRNA molecule comprises a targeting domain sequence that binds to a target DNA sequence selected from the group consisting of SEQ ID NOs: 814-1064. In some embodiments, the gRNA molecule comprises a targeting domain sequence encoded by a nucleic acid sequence selected from the group consisting of SEQ ID NOs: 814-1064.

T In some embodiments, the one or more endogenous target genes comprises SOCS1 and wherein the gRNA molecule comprises a targeting domain sequence that binds to a target DNA sequence defined by a set of genomic coordinates shown in Table 6C and Table 6D. In some embodiments, the gRNA molecule comprises a targeting domain sequence that binds to a target DNA sequence selected from the group consisting of SEQ ID NOs: 1088-1232. In some embodiments, the gRNA molecule comprises a targeting domain sequence encoded by a nucleic acid sequence selected from the group consisting of SEQ ID NOs: 1088-1232.

In some embodiments, the one or more endogenous target genes comprises ANKRD11 and wherein the gRNA molecule comprises a targeting domain sequence that binds to a target DNA sequence defined by a set of genomic coordinates shown in Table 6E and Table 6F. In some embodiments, the gRNA molecule comprises a targeting domain sequence that binds to a target DNA sequence selected from the group consisting of SEQ ID NOs: 1065-1087. In some embodiments, the gRNA molecule comprises a targeting domain sequence encoded by a nucleic acid sequence selected from the group consisting of SEQ ID NOs: 1065-1087.

In some embodiments, the gene-regulating system comprises an siRNA or an shRNA nucleic acid molecule. In some embodiments, the one or more endogenous target genes are selected from IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2 or is selected from CBLB, PPP2R2D, NRP1, HAVCR2, LAG3, TIGIT, CTLA4, PTPN6, PDCD1, and BCOR and wherein the siRNA or shRNA molecule comprises about 19-30 nucleotides that bind to an RNA sequence encoded by a DNA sequence defined by a set of genome coordinates shown in Table 5A and Table 5B. In some embodiments, the one or more endogenous target genes are selected from IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2 and wherein the siRNA or shRNA molecule comprises about 19-30 nucleotides that bind to an RNA sequence encoded by a DNA sequence selected from SEQ ID NOs: 154-498. In some embodiments, the one or more endogenous target genes are selected from CBLB, PPP2R2D, NRP1, HAVCR2, LAG3, TIGIT, CTLA4, PTPN6, PDCD1, and BCOR and wherein the siRNA or shRNA molecule comprises about 19-30 nucleotides that bind to an RNA sequence encoded by a DNA sequence selected from SEQ ID NOs: 499-813.

In some embodiments, the one or more endogenous target genes are selected from BCL2L11, FL11, CALM2, DHODH, UMPS, RBM39, SEMA7A, CHIC2, PCBP1, PBRM1, WDR6, E2F8, SERPINA3, and GNAS and wherein the siRNA or shRNA molecule comprises about 19-30 nucleotides that bind to an RNA sequence encoded by a DNA sequence defined by a set of genome coordinates shown in Table 6A and Table 6B. In some embodiments, the siRNA or shRNA molecule comprises about 19-30 nucleotides that bind to an RNA sequence encoded by a DNA sequence selected from SEQ ID NOs: 814-1064.

In some embodiments, the one or more endogenous target genes comprises SOCS1 and wherein the siRNA or shRNA molecule comprises about 19-30 nucleotides that bind to an RNA sequence encoded by a DNA sequence defined by a set of genome coordinates shown in Table 6C and Table 6D. In some embodiments, the siRNA or shRNA molecule comprises about 19-30 nucleotides that bind to an RNA sequence encoded by a DNA sequence selected from SEQ ID NOs: 1088-1232. In some embodiments, the one or more endogenous target genes comprises ANKRD11 and wherein the siRNA or shRNA molecule comprises about 19-30 nucleotides that bind to an RNA sequence encoded by a DNA sequence defined by a set of genome coordinates shown in Table 6E and Table 6F. In some embodiments, the siRNA or shRNA molecule comprises about 19-30 nucleotides that bind to an RNA sequence encoded by a DNA sequence selected from SEQ ID NOs: 1065-1087.

In some embodiments, the present disclosure provides a gene-regulating system capable of reducing the expression and/or function of two or more endogenous target genes in a cell, wherein at least one of the endogenous target genes is selected from: (a) the group consisting of BCL2L11, FL11, CALM2, DHODH, UMPS, RBM39, SEMA7A, CHIC2, PCBP1, PBRM1, WDR6, E2F8, SERPINA3, and GNAS; (b) SOCS1; or (b) ANKRD11; and wherein at least one of the endogenous target genes is selected from: (a) group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2; or (b) the group consisting of CBLB, PPP2R2D, NRP1, HAVCR2, LAG3, TIGIL CTLA4, PTPN6, PDCD1, and BCOR, wherein the system comprises (i) a nucleic acid molecule; (ii) an enzymatic; or (iii) a guide nucleic acid molecule and an enzymatic protein In some embodiments, the system comprises a plurality of guide RNA (gRNA) nucleic acid molecules and a Cas endonuclease.

In some embodiments, at least one of the endogenous target genes is selected from the group consisting of BCL2L11, FL11, CALM2, DHODH, UMPS, RBM39, SEMA7A, CHIC2, PCBP1, PBRM1, WDR6, E2F8, SERPINA3, and GNAS and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNAs binds to a target DNA sequence defined by a set of genomic coordinates shown in Table 6A and Table 6B, and wherein at least one of the plurality of gRNAs binds to a target DNA sequence defined by a set of genomic coordinates shown in Table 5A and Table 5B. In some embodiments, at least one of the plurality of gRNA molecules comprises a targeting domain sequence that binds to a target DNA sequence selected from the group consisting of SEQ ID NOs: 814-1064 and wherein at least one of the plurality of gRNA molecules comprises a targeting domain sequence that binds to a target DNA sequence selected from the group consisting of SEQ ID NOs: 154-498 or SEQ ID NOs: 499-813. In some embodiments, at least one of the plurality of gRNA molecules comprises a targeting domain sequence encoded by a nucleic acid sequence selected from the group consisting of SEQ ID NOs: 814-1064 and wherein at least one of the plurality of gRNA molecules comprises a targeting domain sequence encoded by a nucleic acid sequence selected from SEQ ID NOs: 154-498 or SEQ ID NOs: 499-813.

In some embodiments, at least one of the endogenous target genes is selected from the group consisting of BCL2L11, FL11, CALM2, DHODH, UMPS, RBM39, SEMA7A, CHIC2, PCBP1, PBRM1, WDR6, E2F8, SERPINA3, and GNAS and at least one of the endogenous target genes is CBLB. In some embodiments, at least one of the plurality of gRNA molecules comprises a targeting domain sequence that binds to a target DNA sequence selected from the group consisting of SEQ ID NOs: 814-1064 and wherein at least one of the plurality of gRNA molecules comprises a targeting domain sequence that binds to a target DNA sequence selected from the group consisting of SEQ ID NOs: 499-524. In some embodiments, at least one of the plurality of gRNA molecules comprises a targeting domain sequence encoded by a nucleic acid sequence selected from the group consisting of SEQ ID NOs: 814-1064 and wherein at least one of the plurality of gRNA molecules comprises a targeting domain sequence encoded by a nucleic acid sequence selected from SEQ ID NOs: 499-524.

In some embodiments, at least one of the endogenous target genes is SOCS1 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNAs binds to a target DNA sequence defined by a set of genomic coordinates shown in Table 6C and Table 6D, and wherein at least one of the plurality of gRNAs binds to a target DNA sequence defined by a set of genomic coordinates shown in Table 5A and Table 5B. In some embodiments, at least one of the plurality of gRNA molecules comprises a targeting domain sequence that binds to a target DNA sequence selected from the group consisting of SEQ ID NOs: 1088-1232 and wherein at least one of the plurality of gRNA molecules comprises a targeting domain sequence that binds to a target DNA sequence selected from the group consisting of SEQ ID NOs: 154-498 or SEQ ID NOs: 499-813. In some embodiments, at least one of the plurality of gRNA molecules comprises a targeting domain sequence encoded by a DNA sequence selected from the group consisting of SEQ ID NOs: 1088-1232 and wherein at least one of the plurality of gRNA molecules comprises a targeting domain sequence encoded by a DNA sequence selected from the group consisting of SEQ ID NOs: 154-498 or SEQ ID NOs: 499-813. In some embodiments, at least one of the endogenous target genes is SOCS1 and at least one of the endogenous target genes is CBLB. In some embodiments, at least one of the endogenous target genes is SOCS1 and at least one of the endogenous target genes is TNFAIP3. In some embodiments, at least one of the endogenous target genes is SOCS1 and at least one of the endogenous target genes is BCOR. In some embodiments, at least one of the plurality of gRNA molecules comprises a targeting domain sequence that binds to a target nucleic acid sequence selected from the group consisting of SEQ ID NOs: 1088-1232 and wherein at least one of the plurality of gRNA molecules comprises a targeting domain sequence that binds to a target nucleic acid sequence selected from SEQ ID NOs: 499-524. In some embodiments, at least one of the plurality of gRNA molecules comprises a targeting domain sequence encoded by a nucleic acid sequence selected from the group consisting of SEQ ID NOs: 1088-1232 and wherein at least one of the plurality of gRNA molecules comprises a targeting domain sequence encoded by a nucleic acid sequence selected from SEQ ID NOs: 499-524.

In some embodiments, at least one of the endogenous target genes is ANKRD11 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNAs binds to a target DNA sequence defined by a set of genomic coordinates shown in Table 6E and Table 6F, and wherein at least one of the plurality of gRNAs binds to a target DNA sequence defined by a set of genomic coordinates shown in Table 5A and Table 5B. In some embodiments, at least one of the plurality of gRNA molecules comprises a targeting domain sequence that binds to a target DNA sequence selected from the group consisting of SEQ ID NOs: 1065-1087 and wherein at least one of the plurality of gRNA molecules comprises a targeting domain sequence that binds to a target DNA sequence selected from the group consisting of SEQ ID NOs: 154-498 or SEQ ID NOs: 499-813. In some embodiments, at least one of the plurality of gRNA molecules comprises a targeting domain sequence encoded by a DNA sequence selected from the group consisting of SEQ ID NOs: 1065-1087 and wherein at least one of the plurality of gRNA molecules comprises a targeting domain sequence encoded by a DNA sequence selected from the group consisting of SEQ ID NOs: 154-498 or SEQ ID NOs: 499-813. In some embodiments, at least one of the endogenous target genes is ANKRD11 and at least one of the endogenous target genes is CBLB. In some embodiments, at least one of the endogenous target genes is ANKRD11 and at least one of the endogenous target genes is TNFAIP3. In some embodiments, at least one of the endogenous target genes is ANKRD11 and at least one of the endogenous target genes is BCOR. In some embodiments, at least one of the plurality of gRNA molecules comprises a targeting domain sequence that binds to a target nucleic acid sequence selected from the group consisting of SEQ ID NOs: 1065-1087 and wherein at least one of the plurality of gRNA molecules comprises a targeting domain sequence that binds to a target nucleic acid sequence selected from SEQ ID NOs: 499-524. In some embodiments, at least one of the plurality of gRNA molecules comprises a targeting domain sequence encoded by a nucleic acid sequence selected from the group consisting of SEQ ID NOs: 1065-1087 and wherein at least one of the plurality of gRNA molecules comprises a targeting domain sequence encoded by a nucleic acid sequence selected from SEQ ID NOs: 499-524.

In some embodiments, at least one of the endogenous target genes is ANKRD11 and at least one of the endogenous target genes is SOCS1. In some embodiments, at least one of the plurality of gRNAs binds to a target DNA sequence defined by a set of genomic coordinates shown in Table 6E and Table 6F, and wherein at least one of the plurality of gRNAs binds to a target DNA sequence defined by a set of genomic coordinates shown in Table 6C and Table 6D. In some embodiments, at least one of the plurality of gRNA molecules comprises a targeting domain sequence binds to a target nucleic acid sequence selected from the group consisting of SEQ ID NOs: 1065-1087 and wherein at least one of the plurality of gRNA molecules comprises a targeting domain sequence that binds to a target nucleic acid sequence selected from SEQ ID NOs: 1088-1232. In some embodiments, at least one of the plurality of gRNA molecules comprises a targeting domain sequence encoded by a DNA sequence selected from the group consisting of SEQ ID NOs: 1065-1087 and wherein at least one of the plurality of gRNA molecules comprises a targeting domain sequence encoded by a DNA sequence selected from SEQ ID NOs: 1088-1232.

In some embodiments, the Cas protein is: a wild-type Cas protein comprising two enzymatically active domains, and capable of inducing double stranded DNA breaks; a Cas nickase mutant comprising one enzymatically active domain and capable of inducing single stranded DNA breaks; a deactivated Cas protein (dCas) and is associated with a heterologous protein capable of modulating the expression of the one or more endogenous target genes. In some embodiments, the heterologous protein is selected from the group consisting of MAX-interacting protein 1 (MX11), Kruppel-associated box (KRAB) domain, and four concatenated mSin3 domains (SID4X). In some embodiments, the Cas protein is a Cas9 protein.

In some embodiments, the system comprises a nucleic acid molecule and wherein the nucleic acid molecule is an siRNA, an shRNA, a microRNA (miR), an antagomiR, or an antisense RNA. In some embodiments, the system comprises a plurality of shRNA or siRNA molecules.

In some embodiments, at least one of the endogenous target genes is selected from the group consisting of BCL2L11, FL11, CALM2, DHODH, UMPS, RBM39, SEMA7A, CHIC2, PCBP1, PBRM1, WDR6, E2F8, SERPINA3, and GNAS and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6A and Table 6B and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 814-1064 and wherein at least one of the plurality of siRNA or shRNA molecules comprises about 19-30 nucleotides that bind to an RNA sequence encoded by a DNA sequence selected from the group consisting of SEQ ID NOs: 154-498 or SEQ ID NOs: 499-813.

In some embodiments, at least one of the endogenous target genes is selected from the group consisting of BCL2L11, FL11, CALM2, DHODH, UMPS, RBM39, SEMA7A, CHIC2, PCBP1, PBRM1, WDR6, E2F8, SERPINA3, and GNAS and at least one of the endogenous target genes is CBLB. In some embodiments, at least one of the plurality of siRNA or shRNA molecules comprises about 19-30 nucleotides that bind to an RNA sequence encoded by a DNA sequence selected from the group consisting of SEQ ID NOs: 814-1064 and wherein at least one of the plurality of siRNA or shRNA molecules comprises about 19-30 nucleotides that bind to an RNA sequence encoded by a DNA sequence selected from the group consisting of SEQ ID NOs: 499-524.

In some embodiments, at least one of the endogenous target genes is SOCS1 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6C and Table 6D and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 1088-1232 and at least one of the plurality of siRNA or shRNA molecules comprises about 19-30 nucleotides that bind to an RNA sequence encoded by a DNA sequence selected from the group consisting of SEQ ID NOs: 154-498 or SEQ ID NOs: 499-813. In some embodiments, at least one of the endogenous target genes is SOCS1 and at least one of the endogenous target genes is CBLB. In some embodiments, at least one of the plurality of siRNA or shRNA molecules comprises about 19-30 nucleotides that bind to an RNA sequence encoded by a DNA sequence selected from the group consisting of SEQ ID NOs: 1088-1232 and at least one of the plurality of siRNA or shRNA molecules comprises about 19-30 nucleotides that bind to an RNA sequence encoded by a DNA sequence selected from the group consisting of SEQ ID NOs: 499-524.

In some embodiments, at least one of the endogenous target genes is ANKRD11 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6E and Table 6F and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 1065-1087 and at least one of the plurality of siRNA or shRNA molecules comprises about 19-30 nucleotides that bind to an RNA sequence encoded by a DNA sequence selected from the group consisting of SEQ ID NOs: 154-498 or SEQ ID NOs: 499-813.

In some embodiments, at least one of the endogenous target genes is ANKRD11 and at least one of the endogenous target genes is CBLB. In some embodiments, at least one of the plurality of siRNA or shRNA molecules comprises about 19-30 nucleotides that bind to an RNA sequence encoded by a DNA sequence selected from the group consisting of SEQ ID NOs: 1065-1087 and at least one of the plurality of siRNA or shRNA molecules comprises about 19-30 nucleotides that bind to an RNA sequence encoded by a DNA sequence selected from the group consisting of SEQ ID NOs: 499-524.

In some embodiments, at least one of the endogenous target genes is ANKRD11 and at least one of the endogenous target genes is SOCS1. In some embodiments, at least one of the plurality of siRNA or shRNA molecules comprises about 19-30 nucleotides that bind to an RNA sequence encoded by a set of genome coordinates shown in Table 6C and Table 6D and at least one of the plurality of siRNA or shRNA molecules comprises about 19-30 nucleotides that bind to an RNA sequence encoded by a DNA sequence defined by a set of genome coordinates shown in Table 6E and Table 6F. In some embodiments, at least one of the plurality of siRNA or shRNA molecules comprises about 19-30 nucleotides that bind to an RNA sequence encoded by a DNA sequence selected from the group consisting of SEQ ID NOs: 1088-1232 and at least one of the plurality of siRNA or shRNA molecules comprises about 19-30 nucleotides that bind to an RNA sequence encoded by a DNA sequence selected from the group consisting of SEQ ID NOs: 1065-1087.

In some embodiments, the system comprises a protein comprising a DNA binding domain and an enzymatic domain and is selected from a zinc finger nuclease and a transcription-activator-like effector nuclease (TALEN).

In some embodiments, the present disclosure provides a gene-regulating system comprising a vector encoding one or more gRNAs and a vector encoding a Cas endonuclease protein, wherein the one or more gRNAs comprise a targeting domain sequence encoded by a nucleic acid sequence selected from: SEQ ID NOs: 814-1064, SEQ ID NOs: 1065-1087, SEQ ID NOs: 1088-1232, SEQ ID NOs: 154-498, or SEQ ID NOs: 499-813.

In some embodiments, the present disclosure provides a gene-regulating system comprising a vector encoding a plurality of gRNAs and a vector encoding a Cas endonuclease protein, wherein at least one of the plurality of gRNA comprises a targeting domain sequence encoded by a nucleic acid sequence selected from: SEQ ID NOs: 814-1064, SEQ ID NOs: 1065-1087, and SEQ ID NOs: 1088-1232, and wherein at least one of the plurality of gRNA comprises a targeting domain sequence encoded by a nucleic acid sequence selected from: SEQ ID NOs: 154-498 or SEQ ID NOs: 499-813.

In some embodiments, the present disclosure provides a gene-regulating system comprising a vector encoding one or more gRNAs and an mRNA molecule encoding a Cas endonuclease protein, wherein the one or more gRNAs comprise a targeting domain sequence encoded by a nucleic acid sequence selected from SEQ ID NOs: 814-1064, SEQ ID NOs: 1065-1087, SEQ ID NOs: 1088-1232, SEQ ID NOs: 154-498, or SEQ ID NOs: 499-813.

In some embodiments, the present disclosure provides a gene-regulating system comprising a vector encoding a plurality of gRNAs and an mRNA molecule encoding a Cas endonuclease protein, wherein at least one of the plurality of gRNA comprises a targeting domain sequence encoded by a nucleic acid sequence selected from: SEQ ID NOs: 814-1064, SEQ ID NOs: 1065-1087, and SEQ ID NOs: 1088-1232, and wherein at least one of the plurality of gRNA comprises a targeting domain sequence encoded by a nucleic acid sequence selected from: SEQ ID NOs: 154-498 or SEQ ID NOs: 499-813.

In some embodiments, the present disclosure provides a gene-regulating system comprising one or more gRNAs and a Cas endonuclease protein, wherein the one or more gRNAs comprise a targeting domain sequence encoded by a nucleic acid sequence selected from: SEQ ID NOs: 814-1064, SEQ ID NOs: 1065-1087, SEQ ID NOs: 1088-1232, SEQ ID NOs: 154-498, or SEQ ID NOs: 499-813, and wherein the one or more gRNAs and the Cas endonuclease protein are complexed to form a ribonucleoprotein (RNP) complex.

In some embodiments, the present disclosure provides a gene-regulating system comprising a plurality of gRNAs and a Cas endonuclease protein: wherein at least one of the plurality of gRNA comprises a targeting domain sequence encoded by a nucleic acid sequence selected from: SEQ ID NOs: 814-1064, SEQ ID NOs: 1065-1087, and SEQ ID NOs: 1088-1232, wherein at least one of the plurality of gRNA comprises a targeting domain sequence encoded by a nucleic acid sequence selected from: SEQ ID NOs: 154-498 or SEQ ID NOs: 499-813, and wherein the one or more gRNAs and the Cas endonuclease protein are complexed to form a ribonucleoprotein (RNP) complex.

In some embodiments, the present disclosure provides a kit comprising a gene-regulating system described herein.

In some embodiments, the present disclosure provides a gRNA nucleic acid molecule comprising a targeting domain nucleic acid sequence that is complementary to a target sequence in an endogenous target gene selected from: (a) the group consisting of BCL2L11, FL11, CALM2, DHODH, UMPS, RBM39, SEMA7A, CHIC2, PCBP1, PBRM1, WDR6, E2F8, SERPINA3, and GNAS; (b) SOCS1; (c) ANKRD11; (d) the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2; or (e) the group consisting of CBLB, PPP2R2D, NRP1, HAVCR2, LAG3, TIGIT, CTLA4, PTPN6, PDCD1, and BCOR.

In some embodiments, the endogenous gene is selected from the group consisting of BCL2L11, FL11, CALM2, DHODH, UMPS, RBM39, SEMA7A, CHIC2, PCBP1, PBRM1, WDR6, E2F8, SERPINA3, and GNAS and the gRNA comprises a targeting domain sequence that is complementary to a target DNA sequence located at genomic coordinates selected from those shown in Tables 6A and 6B; the endogenous gene is SOCS1 and the gRNA comprises a targeting domain sequence that is complementary to a target DNA sequence located at genomic coordinates selected from those shown in Table 6C and Table 6D; the endogenous gene is ANKRD11 and the gRNA comprises a targeting domain sequence that is complementary to a target DNA sequence located at genomic coordinates selected from those shown in Table 6E and Table 6F; the endogenous gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2 and the gRNA comprises a targeting domain sequence that is complementary to a target DNA sequence located at genomic coordinates selected from those shown in Table 5A and Table 5B; or the endogenous gene is selected from the group consisting of CBLB, PPP2R2D, NRP1, HAVCR2, LAG3, TIGIT, CTLA4, PTPN6, PDCD1, and BCOR and the gRNA comprises a targeting domain sequence that is complementary to a target DNA sequence located at genomic coordinates selected from those shown in Table 5A and Table 5B.

In some embodiments, the gRNA comprises a targeting domain sequence that binds to a target DNA sequence selected from SEQ ID NOs: 814-1064, SEQ ID NOs: 1088-1232, SEQ ID NOs: 1065-1087, SEQ ID NOs: 154-498, or SEQ ID NOs: 499-813. In some embodiments, the gRNA comprises a targeting domain sequence encoded by a sequence selected from SEQ ID NOs: 814-1064, SEQ ID NOs: 1088-1232, SEQ ID NOs: 1065-1087, SEQ ID NOs: 154-498, or SEQ ID NOs: 499-813. In some embodiments, the target sequence comprises a PAM sequence.

In some embodiments, the gRNA is a modular gRNA molecule. In some embodiments, the gRNA is a dual gRNA molecule. In some embodiments, the targeting domain is 16, 17, 18, 19, 20, 21, 22, 23, 24, 25, 26 or more nucleotides in length. In some embodiments, the gRNA comprises a modification at or near its 5' end (e.g., within 1-10, 1-5, or 1-2 nucleotides of its 5' end) and/or a modification at or near its 3' end (e.g., within 1-10, 1-5, or 1-2 nucleotides of its 3' end). In some embodiments, the modified gRNA exhibits increased stability towards nucleases when introduced into a T cell. In some embodiments, the modified gRNA exhibits a reduced innate immune response when introduced into a T cell.

In some embodiments, the present disclosure provides a polynucleotide molecule encoding a gRNA molecule described herein. In some embodiments, the present disclosure provides a composition comprising one or more gRNA molecules described herein or a polynucleotide encoding the same. In some embodiments, the present disclosure provides a kit comprising a gRNA molecules described herein or a polynucleotide encoding the same.

In some embodiments, the present disclosure provides a method of producing a modified immune effector cell comprising: obtaining an immune effector cell from a subject; introducing the gene-regulating described herein into the immune effector cell; and culturing the immune effector cell such that the expression and/or function of one or more endogenous target genes is reduced compared to an immune effector cell that has not been modified.

In some embodiments, the present disclosure provides a method of producing a modified immune effector cell comprising introducing the gene-regulating system of any one of claims described herein into the immune effector cell. In some embodiments, the method further comprises introducing a polynucleotide sequence encoding an engineered immune receptor selected from a CAR and a TCR. In some embodiments, the gene-regulating system and/or the polynucleotide encoding the engineered immune receptor are introduced to the immune effector cell by transfection, transduction, electroporation, or physical disruption of the cell membrane by a microfluidics device. In some embodiments, the gene-regulating system is introduced as a polynucleotide sequence encoding one or more components of the system, as a protein, or as an ribonucleoprotein (RNP) complex.

In some embodiments, the present disclosure provides a method of producing a modified immune effector cell comprising: expanding a population of immune effector cells in culture; and introducing a gene-regulating system described herein into the population of immune effector cells. In some embodiments, the method further comprises obtaining the population of immune effector cells from a subject. In some embodiments, the gene-regulating system is introduced to the population of immune effector cells before, during, or after expansion. In some embodiments, the expansion of the population of immune effector cells comprises a first round expansion and a second round of expansion. In some embodiments, the gene-regulating system is introduced to the population of immune effector cells before, during, or after the first round of expansion. In some embodiments, the gene-regulating system is introduced to the population of immune effector cells before, during, or after the second round of expansion. In some embodiments, the gene-regulating system is introduced to the population of immune effector cells before the first and second rounds of expansion. In some embodiments, the gene-regulating system is introduced to the population of immune effector cells after the first and second rounds of expansion. In some embodiments, the gene-regulating system is introduced to the population of immune effector cells after the first round of expansion and before the second round of expansion.

In some embodiments, the present disclosure provides a method of treating a disease or disorder in a subject in need thereof comprising administering an effective amount of a modified immune effector cell described herein, or a composition thereof. In some embodiments, the disease or disorder is a cell proliferative disorder, an inflammatory disorder, or an infectious disease. In some embodiments, the disease or disorder is a cancer or a viral infection. In some embodiments, cancer is selected from a leukemia, a lymphoma, or a solid tumor. In some embodiments, the solid tumor is a melanoma, a pancreatic tumor, a bladder tumor, a lung tumor or metastasis, a colorectal cancer, or a head and neck cancer. In some embodiments,the cancer is a PD1 resistant or insensitive cancer. In some embodiments, the subject has previously been treated with a PD1 inhibitor or a PDL1 inhibitor. In some embodiments, the method further comprises administering to the subject an antibody or binding fragment thereof that specifically binds to and inhibits the function of the protein encoded by NRP1, HAVCR2, LAG3, TIGIT, CTLA4, or PDCD1.

In some embodiments, the modified immune effector cells are autologous to the subject. In some embodiments, the modified immune effector cells are allogenic to the subject. In some embodiments, the subject has not undergone lymphodepletion prior to administration of the modified immune effector cells or compositions thereof. In some embodiments, the subject does not receive high-dose IL-2 treatment with or after the administration of the modified immune effector cells or compositions thereof. In some embodiments, the subject receives low-dose IL-2 treatment with or after the administration of the modified immune effector cells or compositions thereof. In some embodiments, the subject does not receive IL-2 treatment with or after the administration of the modified immune effector cells or compositions thereof.

In some embodiments, the present disclosure provides a method of killing a cancerous cell comprising exposing the cancerous cell to a modified immune effector cell described herein or a composition thereof. In some embodiments, the exposure is in vitro, in vivo, or ex vivo.

In some embodiments, the present disclosure provides a method of enhancing one or more effector functions of an immune effector cell comprising introducing a gene-regulating system described herein into the immune effector cell. In some embodiments, the present disclosure provides a method of enhancing one or more effector functions of an immune effector cell comprising introducing a gene-regulating system described herein into the immune effector cell, wherein the modified immune effector cell demonstrates one or more enhanced effector functions compared to the immune effector cell that has not been modified. In some embodiments, the one or more effector functions are selected from cell proliferation, cell viability, cytotoxicity, tumor infiltration, increased cytokine production, anti-tumor immune responses, and/or resistance to exhaustion.

BRIEF DESCRIPTION OF THE FIGURES

FIG. 1A-FIG. 1B illustrate combinations of endogenous target genes that can be modified by the methods described herein.

FIG. 2A-FIG. 2B illustrate combinations of endogenous target genes that can be modified by the methods described herein.

FIG. 3A-FIG. 3B illustrate combinations of endogenous target genes that can be modified by the methods described herein.

FIG. 4A-FIG. 4D illustrates editing of the TRAC and B2M genes using methods described herein.

FIG. 7A shows tumor growth in mice treated with Cblb-edited OT1 T cells compared to control-edited OT1 T cells. FIG. 7B shows tumor growth in mice treated with Socs1-edited OT1 T cells compared to control and Pd1-edited OT1 T cells.

FIG. 8A shows tumor growth in mice treated with Socs1-edited PMEL T cells compared to control-edited T cells. FIG. 8B shows tumor growth in mice treated with Ankrd11-edited PMEL T cells compared to control-edited T cells.

DETAILED DESCRIPTION

Figure 5A:
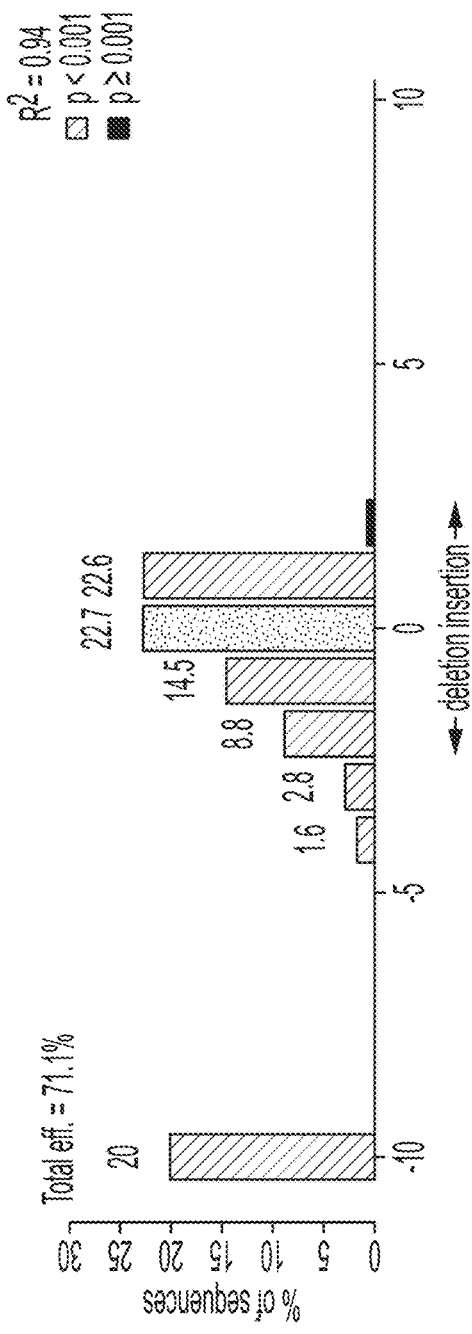
FIG. 5A-FIG. 5B illustrate TIDE analysis data for editing of CBLB in primary human T cells.

The present disclosure provides methods and compositions related to the modification of immune effector cells to increase their therapeutic efficacy in the context of immunotherapy. In some embodiments, immune effector cells are modified by the methods of the present disclosure to reduce expression of one or more endogenous target genes, or to reduce one or more functions of an endogenous protein such that one or more effector functions of the immune cells are enhanced. In some embodiments, the immune effector cells are further modified by introduction of transgenes conferring antigen specificity, such as introduction of T cell receptor (TCR) or chimeric antigen receptor (CAR) expression constructs. In some embodiments, the present disclosure provides compositions and methods for modifying immune effector cells, such as compositions of gene-regulating systems. In some embodiments, the present disclosure provides methods of treating a cell proliferative disorder, such as a cancer, comprising administration of the modified immune effector cells described herein to a subject in need thereof.

I. Definitions

As used in this specification and the appended claims, the singular forms "a," "an" and "the" include plural references unless the content clearly dictates otherwise.

As used in this specification, the term "and/or" is used in this disclosure to mean either "and" or "or" unless indicated otherwise.

Throughout this specification, unless the context requires otherwise, the words "comprise", or variations such as "comprises" or "comprising", will be understood to imply the inclusion of a stated element or integer or group of elements or integers but not the exclusion of any other element or integer or group of elements or integers.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Decrease" or "reduce" refers to a decrease or a reduction in a particular value of at least 5%, for example, a 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or 100% decrease as compared to a reference value. A decrease or reduction in a particular value may also be represented as a fold-change in the value compared to a reference value, for example, at least a 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold, or more, decrease as compared to a reference value.

"Increase" refers to an increase in a particular value of at least 5%, for example, a 5%, 6%, 7% 8%, 9%, 10%, 15%, 20%, 25%, 30%, 35%, 40%, 45%, 50%, 55%, 60%, 65%, 70%, 75%, 80%, 85%, 90%, 95%, 99%, 100%, 200%, 300%, 400%, 500%, or more increase as compared to a reference value. An increase in a particular value may also be represented as a fold-change in the value compared to a reference value, for example, at least a 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more, increase as compared to the level of a reference value.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

"Fragment" refers to a portion of a polypeptide or polynucleotide molecule containing less than the entire polypeptide or polynucleotide sequence. In some embodiments, a fragment of a polypeptide or polynucleotide comprises at least 10%, 20%, 30%, 40%, 50%, 60%, 70%, 80%, 90%, 95%, 96%, 97%, 98%, or 99% of the entire length of the reference polypeptide or polynucleotide. In some embodiments, a polypeptide or polynucleotide fragment may contain 5, 10, 15, 20, 25, 30, 35, 40, 45, 50, 60, 70, 80, 90, 100, 200, 300, 400, 500, 600, 700, 800, 900, 1000, or more nucleotides or amino acids.

The term "sequence identity" refers to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared.

"Complementary" refers to the capacity for pairing, through base stacking and specific hydrogen bonding, between two sequences comprising naturally or non-naturally occurring bases or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and SantaLucia, Nucl. Acids Research, 2005; 33 (19): 6258-6267.

As referred to herein, a "complementary nucleic acid sequence" is a nucleic acid sequence comprising a sequence of nucleotides that enables it to non-covalently bind to another nucleic acid in a sequence-specific, antiparallel, manner (i.e., a nucleic acid specifically binds to a complementary nucleic acid) under the appropriate in vitro and/or in vivo conditions of temperature and solution ionic strength.

Methods of sequence alignment for comparison and determination of percent sequence identity and percent complementarity are well known in the art. Optimal alignment of sequences for comparison can be conducted, e.g., by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), by manual alignment and visual inspection (see, e.g., Brent et al., (2003) Current Protocols in Molecular Biology), by use of algorithms know in the art including the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

Herein, the term "hybridize" refers to pairing between complementary nucleotide bases (e.g., adenine (A) forms a base pair with thymine (T) in a DNA molecule and with uracil (U) in an RNA molecule, and guanine (G) forms a base pair with cytosine (C) in both DNA and RNA molecules) to form a double-stranded nucleic acid molecule. (See, e.g., Wahl and Berger (1987) Methods Enzymol. 152:399; Kimmel, (1987) Methods Enzymol. 152:507). In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a guide RNA molecule is considered complementary to a uracil (U), and vice versa. As such, when a G/U base-pair can be made at a given nucleotide position a protein-binding segment (dsRNA duplex) of a guide RNA molecule, the position is not considered to be non-complementary, but is instead considered to be complementary. It is understood in the art that the sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted.

The term "modified" refers to a substance or compound (e.g., a cell, a polynucleotide sequence, and/or a polypeptide sequence) that has been altered or changed as compared to the corresponding unmodified substance or compound.

The term "naturally-occurring" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is naturally occurring.

"Isolated" refers to a material that is free to varying degrees from components which normally accompany it as found in its native state.

An "expression cassette" or "expression construct" refers to a DNA polynucleotide sequence operably linked to a promoter. "Operably linked" refers to a juxtaposition wherein the components so described are in a relationship permitting them to function in their intended manner. For instance, a promoter is operably linked to a polynucleotide sequence if the promoter affects the transcription or expression of the polynucleotide sequence.

The term "recombinant vector" as used herein refers to a polynucleotide molecule capable transferring or transporting another polynucleotide inserted into the vector. The inserted polynucleotide may be an expression cassette. In some embodiments, a recombinant vector may be viral vector or a non-viral vector (e.g., a plasmid).

The term "sample" refers to a biological composition (e.g., a cell or a portion of a tissue) that is subjected to analysis and/or genetic modification. In some embodiments, a sample is a "primary sample" in that it is obtained directly from a subject; in some embodiments, a "sample" is the result of processing of a primary sample, for example to remove certain components and/or to isolate or purify certain components of interest.

The term "subject" includes animals, such as e.g. mammals. In some embodiments, the mammal is a primate. In some embodiments, the mammal is a human. In some embodiments, subjects are livestock such as cattle, sheep, goats, cows, swine, and the like; or domesticated animals such as dogs and cats. In some embodiments (e.g., particularly in research contexts) subjects are rodents (e.g., mice, rats, hamsters), rabbits, primates, or swine such as inbred pigs and the like. The terms "subject" and "patient" are used interchangeably herein.

"Administration" refers herein to introducing an agent or composition into a subject.

"Treating" as used herein refers to delivering an agent or composition to a subject to affect a physiologic outcome.

As used herein, the term "effective amount" refers to the minimum amount of an agent or composition required to result in a particular physiological effect. The effective amount of a particular agent may be represented in a variety of ways based on the nature of the agent, such as mass/volume, # of cells/volume, particles/volume, (mass of the agent)/(mass of the subject), # of cells/(mass of subject), or particles/(mass of subject). The effective amount of a particular agent may also be expressed as the half-maximal effective concentration ($EC_{50}$), which refers to the concentration of an agent that results in a magnitude of a particular physiological response that is half-way between a reference level and a maximum response level.

"Population" of cells refers to any number of cells greater than 1, but is preferably at least $1 \times 10^3$ cells, at least $1 \times 10^4$ cells, at least $1 \times 10^5$ cells, at least $1 \times 10^6$ cells, at least $1 \times 10^7$ cells, at least $1 \times 10^8$ cells, at least $1 \times 10^9$ cells, at least $1 \times 10^{10}$ cells, or more cells. A population of cells may refer to an in vitro population (e.g., a population of cells in culture) or an in vivo population (e.g., a population of cells residing in a particular tissue).

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

IL Modified Immune Effector Cells

In some embodiments, the present disclosure provides modified immune effector cells. Herein, the term "modified immune effector cells" encompasses immune effector cells comprising one or more genomic modifications resulting in the reduced expression and/or function of one or more endogenous target genes as well as immune effector cells comprising a gene-regulating system capable of reducing the expression and/or function of one or more endogenous target genes. Herein, an "un-modified immune effector cell" or "control immune effector cell" refers to a cell or population of cells wherein the genomes have not been modified and that does not comprise a gene-regulating system or comprises a control gene-regulating system (e.g., an empty vector control, a non-targeting gRNA, a scrambled siRNA, etc.).

The term "immune effector cell" refers to cells involved in mounting innate and adaptive immune responses, including but not limited to lymphocytes (such as T-cells (including thymocytes) and B-cells), natural killer (NK) cells, NKT cells, macrophages, monocytes, eosinophils, basophils, neutrophils, dendritic cells, and mast cells. In some embodiments, the modified immune effector cell is a T cell, such as a CD4+ T cell, a CD8+ T cell (also referred to as a cytotoxic T cell or CTL), a regulatory T cell (Treg), a Th1 cell, a Th2 cell, or a Th17 cell.

In some embodiments, the immune effector cell is a T cell that has been isolated from a tumor sample (referred to herein as "tumor infiltrating lymphocytes" or "TILs"). Without wishing to be bound by theory, it is thought that TILs possess increase specificity to tumor antigens (Radvanyi et al., 2012 Clin Canc Res 18:6758-6770) and can therefore mediate tumor antigen-specific immune response (e.g., activation, proliferation, and cytotoxic activity against the cancer cell) leading to cancer cell destruction (Brudno et al., 2018 Nat Rev Clin Onc 15:31-46)) without the introduction of an exogenous engineered receptor. Therefore, in some embodiments, TILs are isolated from a tumor in a subject, expanded ex vivo, and re-infused into a subject. In some embodiments, TILs are modified to express one or more exogenous receptors specific for an autologous tumor antigen, expanded ex vivo, and re-infused into the subject. Such embodiments can be modeled using in vivo mouse models wherein mice have been transplanted with a cancer cell line expressing a cancer antigen (e.g., CD19) and are treated with modified T cells that express an exogenous receptor that is specific for the cancer antigen (See e.g., Examples 10 and 11).

In some embodiments, the immune effector cell is an animal cell or is derived from an animal cell, including invertebrate animals and vertebrate animals (e.g., fish, amphibian, reptile, bird, or mammal). In some embodiments, the immune effector cell is a mammalian cell or is derived from a mammalian cell (e.g., a pig, a cow, a goat, a sheep, a rodent, a non-human primate, a human, etc.). In some embodiments, the immune effector cell is a rodent cell or is derived from a rodent cell (e.g., a rat or a mouse). In some embodiments, the immune effector cell is a human cell or is derived from a human cell.

In some embodiments, the modified immune effector cells comprise one or more modifications (e.g., insertions, deletions, or mutations of one or more nucleic acids) in the genomic DNA sequence of an endogenous target gene resulting in the reduced expression and/or function the endogenous gene. Such modifications are referred to herein as "inactivating mutations" and endogenous genes comprising an inactivating mutation are referred to as "modified endogenous target genes." In some embodiments, the inactivating mutations reduce or inhibit mRNA transcription, thereby reducing the expression level of the encoded mRNA transcript and protein. In some embodiments, the inactivating mutations reduce or inhibit mRNA translation, thereby reducing the expression level of the encoded protein. In some embodiments, the inactivating mutations encode a modified endogenous protein with reduced or altered function compared to the unmodified (i.e., wild-type) version of the endogenous protein (e.g., a dominant-negative mutant, described infra).

In some embodiments, the modified immune effector cells comprise one or more genomic modifications at a genomic location other than an endogenous target gene that result in the reduced expression and/or function of the endogenous target gene or that result in the expression of a modified version of an endogenous protein. For example, in some embodiments, a polynucleotide sequence encoding a gene regulating system is inserted into one or more locations in the genome, thereby reducing the expression and/or function of an endogenous target gene upon the expression of the gene-regulating system. In some embodiments, a polynucleotide sequence encoding a modified version of an endogenous protein is inserted at one or more locations in the genome, wherein the function of the modified version of the protein is reduced compared to the un-modified or wild-type version of the protein (e.g., a dominant-negative mutant, described infra).

In some embodiments, the modified immune effector cells described herein comprise one or more modified endogenous target genes, wherein the one or more modifications result in a reduced expression and/or function of a gene product (i.e., an mRNA transcript or a protein) encoded by the endogenous target gene compared to an unmodified immune effector cell. For example, in some embodiments, a modified immune effector cell demonstrates reduced expression of an mRNA transcript and/or reduced expression of a protein. In some embodiments, the expression of the gene product in a modified immune effector cell is reduced by at least 5% compared to the expression of the gene product in an unmodified immune effector cell. In some embodiments, the expression of the gene product in a modified immune effector cell is reduced by at least 10%, 20%, 30%, 40%, 50%, 60%, 70%, 80%, 90%, or more compared to the expression of the gene product in an unmodified immune effector cell. In some embodiments, the modified immune effector cells described herein demonstrate reduced expression and/or function of gene products encoded by a plurality (e.g., two or more) of endogenous target genes compared to the expression of the gene products in an unmodified immune effector cell. For example, in some embodiments, a modified immune effector cell demonstrates reduced expression and/or function of gene products from 2, 3, 4, 5, 6, 7, 8, 9, 10, or more endogenous target genes compared to the expression of the gene products in an unmodified immune effector cell.

In some embodiments, the present disclosure provides a modified immune effector cell wherein one or more endogenous target genes, or a portion thereof, are deleted (i.e., "knocked-out") such that the modified immune effector cell does not express the mRNA transcript or protein. In some embodiments, a modified immune effector cell comprises deletion of a plurality of endogenous target genes, or portions thereof In some embodiments, a modified immune effector cell comprises deletion of 2, 3, 4, 5, 6, 7, 8, 9, 10, or more endogenous target genes.

In some embodiments, the modified immune effector cells described herein comprise one or more modified endogenous target genes, wherein the one or more modifications to the target DNA sequence result in expression of a protein with reduced or altered function (e.g., a "modified endogenous protein") compared to the function of the corresponding protein expressed in an unmodified immune effector cell (e.g., a "unmodified endogenous protein"). In some embodiments, the modified immune effector cells described herein comprise 2, 3, 4, 5, 6, 7, 8, 9, 10, or more modified endogenous target genes encoding 2, 3, 4, 5, 6, 7, 8, 9, 10, or more modified endogenous proteins. In some embodiments, the modified endogenous protein demonstrates reduced or altered binding affinity for another protein expressed by the modified immune effector cell or expressed by another cell; reduced or altered signaling capacity; reduced or altered enzymatic activity; reduced or altered DNA-binding activity; or reduced or altered ability to function as a scaffolding protein.

In some embodiments, the modified endogenous target gene comprises one or more dominant negative mutations. As used herein, a "dominant-negative mutation" refers to a substitution, deletion, or insertion of one or more nucleotides of a target gene such that the encoded protein acts antagonistically to the protein encoded by the unmodified target gene. The mutation is dominant-negative because the negative phenotype confers genic dominance over the positive phenotype of the corresponding unmodified gene. A gene comprising one or more dominant-negative mutations and the protein encoded thereby are referred to as a "dominant-negative mutants", e.g. dominant-negative genes and dominant-negative proteins. In some embodiments, the dominant negative mutant protein is encoded by an exogenous transgene inserted at one or more locations in the genome of the immune effector cell.

Various mechanisms for dominant negativity are known. Typically, the gene product of a dominant negative mutant retains some functions of the unmodified gene product but lacks one or more crucial other functions of the unmodified gene product. This causes the dominant-negative mutant to antagonize the unmodified gene product. For example, as an illustrative embodiment, a dominant-negative mutant of a transcription factor may lack a functional activation domain but retain a functional DNA binding domain. In this example, the dominant-negative transcription factor cannot activate transcription of the DNA as the unmodified transcription factor does, but the dominant-negative transcription factor can indirectly inhibit gene expression by preventing the unmodified transcription factor from binding to the transcription-factor binding site. As another illustrative embodiment, dominant-negative mutations of proteins that function as dimers are known. Dominant-negative mutants of such dimeric proteins may retain the ability to dimerize with unmodified protein but be unable to function otherwise. The dominant-negative monomers, by dimerizing with unmodified monomers to form heterodimers, prevent formation of functional homodimers of the unmodified monomers.

In some embodiments, the modified immune effector cells comprise a gene-regulating system capable of reducing the expression or function of one or more endogenous target genes. The gene-regulating system can reduce the expression and/or function of the endogenous target genes modifications by a variety of mechanisms including by modifying the genomic DNA sequence of the endogenous target gene (e.g., by insertion, deletion, or mutation of one or more nucleic acids in the genomic DNA sequence); by regulating transcription of the endogenous target gene (e.g., inhibition or repression of mRNA transcription); and/or by regulating translation of the endogenous target gene (e.g., by mRNA degradation).

In some embodiments, the modified immune effector cells described herein comprise a gene-regulating system (e.g., a nucleic acid-based gene-regulating system, a protein-based gene-regulating system, or a combination protein/nucleic acid-based gene-regulating system). In such embodiments, the gene-regulating system comprised in the modified immune effector cell is capable of modifying one or more endogenous target genes. In some embodiments, the modified immune effector cells described herein comprise a gene-regulating system comprising:

(a) one or more nucleic acid molecules capable of reducing the expression or modifying the function of a gene product encoded by one or more endogenous target genes; (b) one or more polynucleotides encoding a nucleic acid molecule that is capable of reducing the expression or modifying the function of a gene product encoded by one or more endogenous target genes;

(c) one or more proteins capable of reducing the expression or modifying the function of a gene product encoded by one or more endogenous target genes;

(d) one or more polynucleotides encoding a protein that is capable of reducing the expression or modifying the function of a gene product encoded by one or more endogenous target genes;

(e) one or more guide RNAs (gRNAs) capable of binding to a target DNA sequence in an endogenous gene;

(f) one or more polynucleotides encoding one or more gRNAs capable of binding to a target DNA sequence in an endogenous gene;

(g) one or more site-directed modifying polypeptides capable of interacting with a gRNA and modifying a target DNA sequence in an endogenous gene;

(h) one or more polynucleotides encoding a site-directed modifying polypeptide capable of interacting with a gRNA and modifying a target DNA sequence in an endogenous gene;

(i) one or more guide DNAs (gDNAs) capable of binding to a target DNA sequence in an endogenous gene;

(j) one or more polynucleotides encoding one or more gDNAs capable of binding to a target DNA sequence in an endogenous gene;

(k) one or more site-directed modifying polypeptides capable of interacting with a gDNA and modifying a target DNA sequence in an endogenous gene;

(l) one or more polynucleotides encoding a site-directed modifying polypeptide capable of interacting with a gDNA and modifying a target DNA sequence in an endogenous gene;

(m) one or more gRNAs capable of binding to a target mRNA sequence encoded by an endogenous gene;

(n) one or more polynucleotides encoding one or more gRNAs capable of binding to a target mRNA sequence encoded by an endogenous gene;

(o) one or more site-directed modifying polypeptides capable of interacting with a gRNA and modifying a target mRNA sequence encoded by an endogenous gene; (p) one or more polynucleotides encoding a site-directed modifying polypeptide capable of interacting with a gRNA and modifying a target mRNA sequence encoded by an endogenous gene; or (q) any combination of the above.

In some embodiments, one or more polynucleotides encoding the gene-regulating system are inserted into the genome of the immune effector cell. In some embodiments, one or more polynucleotides encoding the gene-regulating system are expressed episomaly and are not inserted into the genome of the immune effector cell.

In some embodiments, the modified immune effector cells described herein comprise reduced expression and/or function of one or more endogenous target genes and further comprise one or more exogenous transgenes inserted at one or more genomic loci (e.g., a genetic "knock-in"). In some embodiments, the one or more exogenous transgenes encode detectable tags, safety-switch systems, chimeric switch receptors, and/or engineered antigen-specific receptors.

In some embodiments, the modified immune effector cells described herein further comprise an exogenous transgene encoding a detectable tag. Examples of detectable tags include but are not limited to, FLAG tags, poly-histidine tags (e.g. 6×His), SNAP tags, Halo tags, cMyc tags, glutathione-S-transferase tags, avidin, enzymes, fluorescent proteins, luminescent proteins, chemiluminescent proteins, bioluminescent proteins, and phosphorescent proteins. In some embodiments the fluorescent protein is selected from the group consisting of blue/UV proteins (such as BFP, TagBFP, mTagBFP2, Azurite, EBFP2, mKalama1, Sirius, Sapphire, and T-Sapphire); cyan proteins (such as CFP, eCFP, Cerulean, SCFP3A, mTurquoise, mTurquoise2, monomeric Midoriishi-Cyan, TagCFP, and mTFP1); green proteins (such as: GFP, eGFP, meGFP (A208K mutation), Emerald, Superfolder GFP, Monomeric Azami Green, TagGFP2, mUKG, mWasabi, Clover, and mNeonGreen); yellow proteins (such as YFP, eYFP, Citrine, Venus, SYFP2, and TagYFP); orange proteins (such as Monomeric Kusabira-Orange, mKOx, mKO2, mOrange, and mOrange2); red proteins (such as RFP, mRaspberry, mCherry, mStrawberry, mTangerine, tdTomato, TagRFP, TagRFP-T, mApple, mRuby, and mRuby2); far-red proteins (such as mPlum, HcRed-Tandem, mKate2, mNeptune, and NirFP); near-infrared proteins (such as TagRFP657, IFP1.4, and iRFP); long stokes shift proteins (such as mKeima Red, LSS-mKate1, LSS-mKate2, and mBeRFP); photoactivatible proteins (such as PA-GFP, PAmCherry1, and PATagRFP); photoconvertible proteins (such as Kaede (green), Kaede (red), KikGR1 (green), KikGR1 (red), PS-CFP2, PS-CFP2, mEos2 (green), mEos2 (red), mEos3.2 (green), mEos3.2 (red), PSmOrange, and PSmOrange); and photoswitchable proteins (such as Dronpa). In some embodiments, the detectable tag can be selected from AmCyan, AsRed, DsRed2, DsRed Express, E2-Crimson, HcRed, ZsGreen, ZsYellow, mCherry, mStrawberry, mOrange, mBanana, mPlum, mRasberry, tdTomato, DsRed Monomer, and/or AcGFP, all of which are available from Clontech.

In some embodiments, the modified immune effector cells described herein further comprise an exogenous transgene encoding a safety-switch system. Safety-switch systems (also referred to in the art as suicide gene systems) comprise exogenous transgenes encoding for one or more proteins that enable the elimination of a modified immune effector cell after the cell has been administered to a subject. Examples of safety-switch systems are known in the art. For example, safety-switch systems include genes encoding for proteins that convert non-toxic pro-drugs into toxic compounds such as the Herpes simplex thymidine kinase (Hsv-tk) and ganciclovir (GCV) system (Hsv-tk/GCV). Hsv-tk converts non-toxic GCV into a cytotoxic compound that leads to cellular apoptosis. As such, administration of GCV to a subject that has been treated with modified immune effector cells comprising a transgene encoding the Hsv-tk protein can selectively eliminate the modified immune effector cells while sparing endogenous immune effector cells. (See e.g., Bonini et al., Science, 1997, 276(5319):1719-1724; Ciceri et al., Blood, 2007, 109(11):1828-1836; Bondanza et al., Blood 2006, 107(5):1828-1836).

Additional safety-switch systems include genes encoding for cell-surface markers, enabling elimination of modified immune effector cells by administration of a monoclonal antibody specific for the cell-surface marker via ADCC. In some embodiments, the cell-surface marker is CD20 and the modified immune effector cells can be eliminated by administration of an anti-CD20 monoclonal antibody such as Rituximab (See e.g., Introna et al., Hum Gene Ther, 2000, 11(4):611-620; Serafini et al., Hum Gene Ther, 2004, 14, 63-76; van Meerten et al., Gene Ther, 2006, 13, 789-797). Similar systems using EGF-R and Cetuximab or Panitumumab are described in International PCT Publication No. WO 2018006880. Additional safety-switch systems include transgenes encoding pro-apoptotic molecules comprising one or more binding sites for a chemical inducer of dimerization (CID), enabling elimination of modified immune effector cells by administration of a CID which induces oligomerization of the pro-apoptotic molecules and activation of the apoptosis pathway. In some embodiments, the pro-apoptotic molecule is Fas (also known as CD95) (Thomis et al., Blood, 2001, 97(5), 1249-1257). In some embodiments, the pro-apoptotic molecule is caspase-9 (Straathof et al., Blood, 2005, 105(11), 4247-4254).

In some embodiments, the modified immune effector cells described herein further comprise an exogenous transgene encoding a chimeric switch receptor. Chimeric switch receptors are engineered cell-surface receptors comprising an extracellular domain from an endogenous cell-surface receptor and a heterologous intracellular signaling domain, such that ligand recognition by the extracellular domain results in activation of a different signaling cascade than that activated by the wild type form of the cell-surface receptor. In some embodiments, the chimeric switch receptor comprises the extracellular domain of an inhibitory cell-surface receptor fused to an intracellular domain that leads to the transmission of an activating signal rather than the inhibitory signal normally transduced by the inhibitory cell-surface receptor. In particular embodiments, extracellular domains derived from cell-surface receptors known to inhibit immune effector cell activation can be fused to activating intracellular domains. Engagement of the corresponding ligand will then activate signaling cascades that increase, rather than inhibit, the activation of the immune effector cell. For example, in some embodiments, the modified immune effector cells described herein comprise a transgene encoding a PD1-CD28 switch receptor, wherein the extracellular domain of PD1 is fused to the intracellular signaling domain of CD28 (See e.g., Liu et al., Cancer Res 76:6 (2016), 1578-1590 and Moon et al., Molecular Therapy 22 (2014), S201). In some embodiments, the modified immune effector cells described herein comprise a transgene encoding the extracellular domain of CD200R and the intracellular signaling domain of CD28 (See Oda et al., Blood 130:22 (2017), 2410-2419).

In some embodiments, the modified immune effector cells described herein further comprise an engineered antigen-specific receptor recognizing a protein target expressed by a target cell, such as a tumor cell or an antigen presenting cell (APC), referred to herein as "modified receptor-engineered cells" or "modified RE-cells". The term "engineered antigen receptor" refers to a non-naturally occurring antigen-specific receptor such as a chimeric antigen receptor (CAR) or a recombinant T cell receptor (TCR). In some embodiments, the engineered antigen receptor is a CAR comprising an extracellular antigen binding domain fused via hinge and transmembrane domains to a cytoplasmic domain comprising a signaling domain. In some embodiments, the CAR extracellular domain binds to an antigen expressed by a target cell in an MHC-independent manner leading to activation and proliferation of the RE cell. In some embodiments, the extracellular domain of a CAR recognizes a tag fused to an antibody or antigen-binding fragment thereof In such embodiments, the antigen-specificity of the CAR is dependent on the antigen-specificity of the labeled antibody, such that a single CAR construct can be used to target multiple different antigens by substituting one antibody for another (See e.g., U.S. Pat. Nos. 9,233,125 and 9,624,279; US Patent Application Publication Nos. 20150238631 and 20180104354). In some embodiments, the extracellular domain of a CAR may comprise an antigen binding fragment derived from an antibody. Antigen binding domains that are useful in the present disclosure include, for example, scFvs; antibodies; antigen binding regions of antibodies; variable regions of the heavy/light chains; and single chain antibodies.

In some embodiments, the intracellular signaling domain of a CAR may be derived from the TCR complex zeta chain (such as CD3ξ signaling domains), FcγRIII, FcεRI, or the T-lymphocyte activation domain. In some embodiments, the intracellular signaling domain of a CAR further comprises a costimulatory domain, for example a 4-1BB, CD28, CD40, MyD88, or CD70 domain. In some embodiments, the intracellular signaling domain of a CAR comprises two costimulatory domains, for example any two of 4-1BB, CD28, CD40, MyD88, or CD70 domains. Exemplary CAR structures and intracellular signaling domains are known in the art (See e.g., WO 2009/091826; US 20130287748; WO 2015/142675; WO 2014/055657; and WO 2015/090229, incorporated herein by reference).

CARs specific for a variety of tumor antigens are known in the art, for example CD171-specific CARs (Park et al., Mol Ther (2007) 15(4):825-833), EGFRvIII-specific CARs (Morgan et al., Hum Gene Ther (2012) 23(10):1043-1053), EGF-R-specific CARs (Kobold et al., J Natl Cancer Inst (2014) 107(1):364), carbonic anhydrase K-specific CARs (Lamers et al., Biochem Soc Trans (2016) 44(3):951-959), FR-α-specific CARs (Kershaw et al., Clin Cancer Res (2006) 12(20):6106-6015), HER2-specific CARs (Ahmed et al., J Clin Oncol (2015) 33(15)1688-1696;Nakazawa et al., Mol Ther (2011) 19(12):2133-2143; Ahmed et al., Mol Ther (2009) 17(10):1779-1787; Luo et al., Cell Res (2016) 26(7): 850-853; Morgan et al., Mol Ther (2010) 18(4):843-851; Grada et al., Mol Ther Nucleic Acids (2013) 9(2):32), CEA-specific CARs (Katz et al., Clin Cancer Res (2015) 21(14):3149-3159), IL13Ra2-specific CARs (Brown et al., Clin Cancer Res (2015) 21(18):4062-4072), GD2-specific CARs (Louis et al., Blood (2011) 118(23):6050-6056; Caruana et al., Nat Med (2015) 21(5):524-529), ErbB2-specific CARs (Wilkie et al., J Clin Immunol (2012) 32(5): 1059-1070), VEGF-R-specific CARs (Chinnasamy et al., Cancer Res (2016) 22(2):436-447), FAP-specific CARs (Wang et al., Cancer Immunol Res (2014) 2(2):154-166), MSLN-specific CARs (Moon et al, Clin Cancer Res (2011) 17(14):4719-30), NKG2D-specific CARs (VanSeggelen et al., Mol Ther (2015) 23(10):1600-1610), CD19-specific CARs (Axicabtagene ciloleucel (Yescarta*) and Tisagenlecleucel (Kymriah©). See also, Li et al., J Hematol and Oncol (2018) 11(22), reviewing clinical trials of tumor-specific CARs.

In some embodiments, the engineered antigen receptor is an engineered TCR. Engineered TCRs comprise TCRα and/or TCRβ chains that have been isolated and cloned from T cell populations recognizing a particular target antigen. For example, TCRα and/or TCRβ genes (i.e., TRAC and TRBC) can be cloned from T cell populations isolated from individuals with particular malignancies or T cell populations that have been isolated from humanized mice immunized with specific tumor antigens or tumor cells. Engineered TCRs recognize antigen through the same mechanisms as their endogenous counterparts (e.g., by recognition of their cognate antigen presented in the context of major histocompatibility complex (MHC) proteins expressed on the surface of a target cell). This antigen engagement stimulates endogenous signal transduction pathways leading to activation and proliferation of the TCR-engineered cells.

Engineered TCRs specific for tumor antigens are known in the art, for example WT1-specific TCRs (JTCR016, Juno Therapeutics; WT1-TCRc4, described in US Patent Application Publication No. 20160083449), MART-1 specific TCRs (including the DMF4T clone, described in Morgan et al., Science 314 (2006) 126-129); the DMF5T clone, described in Johnson et al., Blood 114 (2009) 535-546); and the ID3T clone, described in van den Berg et al., Mol. Ther. 23 (2015) 1541-1550), gp100-specific TCRs (Johnson et al., Blood 114 (2009) 535-546), CEA-specific TCRs (Parkhurst et al., Mol Ther. 19 (2011) 620-626), NY-ESO and LAGE-1 specific TCRs (1G4T clone, described in Robbins et al., J Clin Oncol 26 (2011) 917-924; Robbins et al., Clin Cancer Res 21 (2015) 1019-1027; and Rapoport et al., Nature Medicine 21 (2015) 914-921), and MAGE-A3-specific TCRs (Morgan et al., J Immunother 36 (2013) 133-151) and Linette et al., Blood 122 (2013) 227-242). (See also, Debets et al., Seminars in Immunology 23 (2016) 10-21).

In some embodiments, the engineered antigen receptor is directed against a target antigen selected from a cluster of differentiation molecule, such as CD3, CD4, CD8, CD16, CD24, CD25, CD33, CD34, CD45, CD64, CD71, CD78, CD80 (also known as B7-1), CD86 (also known as B7-2), CD96, CD 116, CD 117, CD123, CD133, and CD138, CD371 (also known as CLL1); a tumor-associated surface antigen, such as 5T4, BCMA (also known as CD269 and TNFRSF17, UniProt #Q02223), carcinoembryonic antigen (CEA), carbonic anhydrase 9 (CAIX or MN/CAIX), CD19, CD20, CD22, CD30, CD40, disialogangliosides such as GD2, ELF2M, ductal-epithelial mucin, ephrin B2, epithelial cell adhesion molecule (EpCAM), ErbB2 (HER2/neu), FCRL5 (UniProt #Q68SN8), FKBP11 (UniProt #Q9NYL4), glioma-associated antigen, glycosphingolipids, gp36, GPRC5D (UniProt #Q9NZD1), mut hsp70-2, intestinal carboxyl esterase, IGF-I receptor, ITGA8 (UniProt #P53708), KAMP3, LAGE-la, MAGE, mesothelin, neutrophil elastase, NKG2D, Nkp30, NY-ESO-1, PAP, prostase, prostate-carcinoma tumor antigen-1 (PCTA-1), prostate specific antigen (PSA), PSMA, prostein, RAGE-1, ROR1, RU1 (SFMBT1), RU2 (DCDC2), SLAMF7 (UniProt #Q9NQ25), survivin, TAG-72, and telomerase; a major histocompatibility complex (MHC) molecule presenting a tumor-specific peptide epitope; tumor stromal antigens, such as the extra domain A (EDA) and extra domain B (EDB) of fibronectin; the A1 domain of tenascin-C(TnC A1) and fibroblast associated protein (FAP); cytokine receptors, such as epidermal growth factor receptor (EGFR), EGFR variant III (EGFRvIII), TFGβ-R or components thereof such as endoglin; a major histocompatibility complex (MHC) molecule; a virus-specific surface antigen such as an HIV-specific antigen (such as HIV gp120); an EBV-specific antigen, a CMV-specific antigen, a HPV-specific antigen, a Lassa virus-specific antigen, an Influenza virus-specific antigen as well as any derivate or variant of these surface antigens.

A. Effector Functions

In some embodiments, the modified immune effector cells described herein demonstrate an increase in one or more immune cell effector functions. Herein, the term "effector function" refers to functions of an immune cell related to the generation, maintenance, and/or enhancement of an immune response against a target cell or target antigen. In some embodiments, the modified immune effector cells described herein demonstrate one or more of the following characteristics compared to an unmodified immune effector cell: increased infiltration or migration in to a tumor, increased proliferation, increased or prolonged cell viability, increased resistance to inhibitory factors in the surrounding microenvironment such that the activation state of the cell is prolonged or increased, increased production of pro-inflammatory immune factors (e.g., pro-inflammatory cytokines, chemokines, and/or enzymes), increased cytotoxicity, and/or increased resistance to exhaustion.

In some embodiments, the modified immune effector cells described herein demonstrate increased infiltration into a tumor compared to an unmodified immune effector cell. In some embodiments, increased tumor infiltration by modified immune effector cells refers to an increase the number of modified immune effector cells infiltrating into a tumor during a given period of time compared to the number of unmodified immune effector cells that infiltrate into a tumor during the same period of time. In some embodiments, the modified immune effector cells demonstrate a 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20,25, 30, 35, 40, 45, 50, 60, 70, 80, 90, 100, or more fold increase in tumor filtration compared to an unmodified immune cell. Tumor infiltration can be measured by isolating one or more tumors from a subject and assessing the number of modified immune cells in the sample by flow cytometry, immunohistochemistry, and/or immunofluorescence.

In some embodiments, the modified immune effector cells described herein demonstrate an increase in cell proliferation compared to an unmodified immune effector cell. In these embodiments, the result is an increase in the number of modified immune effector cells present compared to unmodified immune effector cells after a given period of time. For example, in some embodiments, modified immune effector cells demonstrate increased rates of proliferation compared to unmodified immune effector cells, wherein the modified immune effector cells divide at a more rapid rate than unmodified immune effector cells. In some embodiments, the modified immune effector cells demonstrate a 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20,25, 30, 35, 40, 45, 50, 60, 70, 80, 90, 100, or more fold increase in the rate of proliferation compared to an unmodified immune cell. In some embodiments, modified immune effector cells demonstrate prolonged periods of proliferation compared to unmodified immune effector cells, wherein the modified immune effector cells and unmodified immune effector cells divide at similar rates, but wherein the modified immune effector cells maintain the proliferative state for a longer period of time. In some embodiments, the modified immune effector cells maintain a proliferative state for 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20,25, 30, 35, 40, 45, 50, 60, 70, 80, 90, 100, or more times longer than an unmodified immune cell.

In some embodiments, the modified immune effector cells described herein demonstrate increased or prolonged cell viability compared to an unmodified immune effector cell. In such embodiments, the result is an increase in the number of modified immune effector cells or present compared to unmodified immune effector cells after a given period of time. For example, in some embodiments, modified immune effector cells described herein remain viable and persist for 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20,25, 30, 35, 40, 45, 50, 60, 70, 80, 90, 100, or more times longer than an unmodified immune cell.

In some embodiments, the modified immune effector cells described herein demonstrate increased resistance to inhibitory factors compared to an unmodified immune effector cell. Exemplary inhibitory factors include signaling by immune checkpoint molecules (e.g., PD1, PDL1, CTLA4, LAG3, IDO) and/or inhibitory cytokines (e.g., IL-10, TGFβ).

In some embodiments, the modified T cells described herein demonstrate increased resistance to T cell exhaustion compared to an unmodified T cell. T cell exhaustion is a state of antigen-specific T cell dysfunction characterized by decreased effector function and leading to subsequent deletion of the antigen-specific T cells. In some embodiments, exhausted T cells lack the ability to proliferate in response to antigen, demonstrate decreased cytokine production, and/or demonstrate decreased cytotoxicity against target cells such as tumor cells. In some embodiments, exhausted T cells are identified by altered expression of cell surface markers and transcription factors, such as decreased cell surface expression of CD122 and CD127; increased expression of inhibitory cell surface markers such as PD1, LAG3, CD244, CD160, TIM3, and/or CTLA4; and/or increased expression of transcription factors such as Blimp1, NFAT, and/or BATF. In some embodiments, exhausted T cells demonstrate altered sensitivity cytokine signaling, such as increased sensitivity to TGFβ signaling and/or decreased sensitivity to IL-7 and IL-15 signaling. T cell exhaustion can be determined, for example, by co-culturing the T cells with a population of target cells and measuring T cell proliferation, cytokine production, and/or lysis of the target cells. In some embodiments, the modified immune effector cells described herein are co-cultured with a population of target cells (e.g., autologous tumor cells or cell lines that have been engineered to express a target tumor antigen) and effector cell proliferation, cytokine production, and/or target cell lysis is measured. These results are then compared to the results obtained from co-culture of target cells with a control population of immune cells (such as unmodified immune effector cells or immune effector cells that have a control modification).

In some embodiments, resistance to T cell exhaustion is demonstrated by increased production of one or more cytokines (e.g., IFNγ, TNFα, or IL-2) from the modified immune effector cells compared to the cytokine production observed from the control population of immune cells. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in cytokine production from the modified immune effector cells compared to the cytokine production from the control population of immune cells is indicative of an increased resistance to T cell exhaustion. In some embodiments, resistance to T cell exhaustion is demonstrated by increased proliferation of the modified immune effector cells compared to the proliferation observed from the control population of immune cells. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in proliferation of the modified immune effector cells compared to the proliferation of the control population of immune cells is indicative of an increased resistance to T cell exhaustion. In some embodiments, resistance to T cell exhaustion is demonstrated by increased target cell lysis by the modified immune effector cells compared to the target cell lysis observed by the control population of immune cells. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in target cell lysis by the modified immune effector cells compared to the target cell lysis by the control population of immune cells is indicative of an increased resistance to T cell exhaustion.

In some embodiments, exhaustion of the modified immune effector cells compared to control populations of immune cells is measured during the in vitro or ex vivo manufacturing process. For example, in some embodiments, TILs isolated from tumor fragments are modified according to the methods described herein and then expanded in one or more rounds of expansion to produce a population of modified TILs. In such embodiments, the exhaustion of the modified TILs can be determined immediately after harvest and prior to a first round of expansion, after the first round of expansion but prior to a second round of expansion, and/or after the first and the second round of expansion. In some embodiments, exhaustion of the modified immune effector cells compared to control populations of immune cells is measured at one or more time points after transfer of the modified immune effector cells into a subject. For example, in some embodiments, the modified cells are produced according to the methods described herein and administered to a subject. Samples can then be taken from the subject at various time points after the transfer to determine exhaustion of the modified immune effector cells in vivo over time.

In some embodiments, the modified immune effector cells described herein demonstrate increased expression or production of pro-inflammatory immune factors compared to an unmodified immune effector cell. Examples of pro-inflammatory immune factors include cytolytic factors, such as granzyme B, perforin, and granulysin; and pro-inflammatory cytokines such as interferons (IFNα, IFNβ, IFNγ), TNFα, IL-1β, IL-12, IL-2, IL-17, CXCL8, and/or IL-6.

In some embodiments, the modified immune effector cells described herein demonstrate increased cytotoxicity against a target cell compared to an unmodified immune effector cell. In some embodiments, the modified immune effector cells demonstrate a 1, 2, 3, 4, 5, 6, 7, 8, 9, 10, 20, 30, 40, 50, 60, 70, 80, 90, 100, or more fold increase in cytotoxicity against a target cell compared to an unmodified immune cell.

Assays for measuring immune effector function are known in the art. For example, tumor infiltration can be measured by isolating tumors from a subject and determining the total number and/or phenotype of the lymphocytes present in the tumor by flow cytometry, immunohistochemistry, and/or immunofluorescence. Cell-surface receptor expression can be determined by flow cytometry, immunohistochemistry, immunofluorescence, Western blot, and/or qPCR. Cytokine and chemokine expression and production can be measured by flow cytometry, immunohistochemistry, immunofluorescence, Western blot, ELISA, and/or qPCR. Responsiveness or sensitivity to extracellular stimuli (e.g., cytokines, inhibitory ligands, or antigen) can be measured by assaying cellular proliferation and/or activation of downstream signaling pathways (e.g., phosphorylation of downstream signaling intermediates) in response to the stimuli. Cytotoxicity can be measured by target-cell lysis assays known in the art, including in vitro or ex vivo co-culture of the modified immune effector cells with target cells and in vivo murine tumor models, such as those described throughout the Examples.

B. Regulation of Endogenous Pathways and Genes

In some embodiments, the modified immune effector cells described herein demonstrate a reduced expression or function of one or more endogenous target genes and/or comprise a gene-regulating system capable of reducing the expression and/or function of one or more endogenous target genes (described infra). In some embodiments, the one or more endogenous target genes are present in pathways related to the activation and regulation of effector cell responses. In such embodiments, the reduced expression or function of the one or more endogenous target genes enhances one or more effector functions of the immune cell.

Exemplary pathways suitable for regulation by the methods described herein are shown in Table 1. In some embodiments, the expression of an endogenous target gene in a particular pathway is reduced in the modified immune effector cells. In some embodiments, the expression of a plurality (e.g., two or more) of endogenous target genes in a particular pathway are reduced in the modified immune effector cells. For example, the expression of 2, 3, 4, 5, 6, 7, 8, 9, 10, or more endogenous target genes in a particular pathway may be reduced. In some embodiments, the expression of an endogenous target gene in one pathway and the expression of an endogenous target genes in another pathway is reduced in the modified immune effector cells. In some embodiments, the expression of a plurality of endogenous target genes in one pathway and the expression of a plurality of endogenous target genes in another pathway are reduced in the modified immune effector cells. For example, the expression of 2, 3, 4, 5, 6, 7, 8, 9, 10, or more endogenous target genes in one pathway may be reduced and the expression of 2, 3, 4, 5, 6, 7, 8, 9, 10, or more endogenous target genes in another particular pathway may be reduced.

In some embodiments, the expression of a plurality of endogenous target genes in a plurality of pathways is reduced. For example, one endogenous gene from each of a plurality of pathways (e.g., 2, 3, 4, 5, 6, 7, 8, 9, 10, or more pathways) may be reduced. In additional aspects, a plurality of endogenous genes (e.g., 2, 3, 4, 5, 6, 7, 8, 9, 10, or more genes) from each of a plurality of pathways (e.g., 2, 3, 4, 5, 6, 7, 8, 9, 10, or more pathways) may be reduced.

TABLE 1

Exemplary Endogenous Pathways

| Pathway | Description |
| --- | --- |
| Lymphocyte differentiation | Signaling pathway which controls stem cell differentiation from a common lymphoid progenitor to the distinctive lymphocyte type (T cell, B cell or NK cell) |
| NFκβ signaling | Signaling pathway that controls transcription of DNA, cytokine production and cell survival generally in response to harmful cell stimuli. |
| TGF-β signaling | Signaling pathway that regulates cell growth, cell differentiation, apoptosis, cellular homeostasis and other cellular functions. |
| T cell activation | Pathway that is initiated by binding of the T cell receptor (TCR) complex to a major histocompatibility complex molecule carrying a peptide antigen and by binding of the co-stimulatory receptor CD28 to proteins in the surface of the antigen presenting cell. Activation of a TCR initiates a signaling pathway which |

TABLE 1-continued

Exemplary Endogenous Pathways

| Pathway | Description |
| --- | --- |
| | triggers antibody production, activation of phagocytic cells and direct cell killing. |
| T cell growth | Signaling pathway that controls programmed cell death in response to either extrinsic signals or intrinsic cellular stresses |
| Pyrimidine biosynthesis | A de novo nucleotide biosynthesis pathway for components of RNA and DNA |
| Cytokine Signaling | Signaling pathways down stream of cytokine receptors, typically involve positive JAK/STAT signaling |
| Apoptosis initiation | Genes that initiate either the intrinsic or extrinsic apoptotic pathway, which drives programed cell death of the cell |
| Transcription initiation | Genes that directly bind the promoters of target genes and act as repressors or transcriptional activators of target gene transcription |
| Ca2++ binding | Ca2++ serves as a second messenger in response to stimuli and drives intracellular signaling in a number of processes, including inflammation and the immune response. In T cells, Ca2++ signaling is required for the activation of T cells in response to antigen |

Exemplary endogenous target genes are shown below in Tables 2 and 3.

In some embodiments, the modified effector cells comprise reduced expression and/or function of one or more of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., one or more endogenous target genes selected from Table 2). In some embodiments, the modified effector cells comprise reduced expression and/or function of one or more of TNFAIP3, CBLB, or BCOR.

In some embodiments, the modified immune effector cells comprise reduced expression and/or function of at least two genes selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR (e.g., at least two genes selected from Table 2). For example, in some embodiments, the modified immune effector cells comprise reduced expression and/or function of at least two genes selected from Combination Nos. 1-600, as illustrated in FIG. 1A-FIG. 1B. In some embodiments, the modified immune effector cells comprise reduced expression and/or function of BCOR and reduced expression and/or function of CBLB. While exemplary methods for modifying the expression of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and/or BCOR are described herein, the expression of these endogenous target genes may also be modified by methods known in the art. For example, inhibitory antibodies against PD1 (encoded by PDCD1), NRP1, HACR2, LAG3, TIGIT, and CTLA4 are known in the art and some are FDA approved for oncologic indications (e.g., nivolumab and pembrolizumab for PD1).

In some embodiments, the modified immune effector cells comprise reduced expression and/or function of one or more of BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 (e.g., one or more endogenous target genes selected from Table 3).

In some embodiments, the modified effector cells described herein comprise reduced expression and/or function of the Semaphorin 7A, (SEMA7A) gene, also known as CD108. In some embodiments, the modified effector cells described herein comprise an inactivating mutation in the SEMA7A gene.

In some embodiments, the modified effector cells described herein comprise reduced expression and/or function of the RNA-binding protein 39 (RBM39) gene. The RBM39 protein is found in the nucleus, where it colocalizes with core spliceosomal proteins. Studies of a mouse protein with high sequence similarity to this protein suggest that this protein may act as a transcriptional coactivator for JUN/AP-1 and estrogen receptors. In some embodiments, the modified effector cells described herein comprise an inactivating mutation in the RBM39 gene.

In some embodiments, the modified effector cells described herein comprise reduced expression and/or function of the Bcl-2-like protein 11 (BCL2L11) gene, also commonly called BIM. In some embodiments, the modified effector cells described herein comprise an inactivating mutation in the BCL2L11 gene In some embodiments, the modified effector cells described herein comprise reduced expression and/or function of the Friend leukemia integration 1 transcription factor (FL11) gene, also known as transcription factor ERGB. In some embodiments, the modified effector cells described herein comprise an inactivating mutation in the FL11 gene.

In some embodiments, the modified effector cells described herein comprise reduced expression and/or function of the Calmodulin 2 (CALM2) gene. In some embodiments, the modified effector cells described herein comprise an inactivating mutation in the CALM2 gene.

In some embodiments, the modified effector cells described herein comprise reduced expression and/or function of the Dihydroorotate dehydrogenase gene (DHODH) gene. The DHODH protein is a mitochondrial protein located on the outer surface of the inner mitochondrial membrane and catalyzes the ubiquinone-mediated oxidation of dihydroorotate to orotate in de novo pyrimidine biosynthesis. In some embodiments, the modified effector cells described herein comprise an inactivating mutation in the DHODH gene.

In some embodiments, the modified effector cells described herein comprise reduced expression and/or function of the uridine monophosphate synthase (UMPS) gene, also referred to as orotate phosphoribosyl transferase or orotidine-5'-decarboxylase. The UMPS protein catalyzes the formation of uridine monophosphate (UMP), an energy-carrying molecule in many important biosynthetic pathways. In some embodiments, the modified effector cells described herein comprise an inactivating mutation in the UMPS gene.

In some embodiments, the modified effector cells described herein comprise reduced expression and/or function of the cysteine rich hydrophobic domain 2 (CHIC2) gene. The encoded CHIC2 protein contains a cysteine-rich hydrophobic (CHIC) motif, and is localized to vesicular structures and the plasma membrane and is associated with some cases of acute myeloid leukemia. In some embodiments, the modified effector cells described herein comprise an inactivating mutation in the CHIC2 gene.

In some embodiments, the modified effector cells described herein comprise reduced expression and/or function of the Poly(rC)-binding protein 1(PCBP1) gene. In some embodiments, the modified effector cells described herein comprise an inactivating mutation in the PCBP1 gene.

In some embodiments, the modified effector cells described herein comprise reduced expression and/or function of the Protein polybromo-1 (PBRM1) gene, also known as BRG1-associated factor 180 (BAF180). PBRM1 is a component of the SWI/SNF-B chromatin-remodeling complex, and is a tumor suppressor gene in many cancer subtypes. Mutations are especially prevalent in clear cell renal cell carcinoma. In some embodiments, the modified effector cells described herein comprise an inactivating mutation in the PBRM1 gene.

In some embodiments, the modified effector cells described herein comprise reduced expression and/or function of the WD repeat-containing protein 6 (WDR6) gene, a member of the WD repeat protein family ubiquitously expressed in adult and fetal tissues. WD repeats are minimally conserved regions of approximately 40 amino acids typically bracketed by gly-his and trp-asp (GH-WD), which may facilitate formation of heterotrimeric or multiprotein complexes. Members of this family are involved in a variety of cellular processes, including cell cycle progression, signal transduction, apoptosis, and gene regulation. In some embodiments, the modified effector cells described herein comprise an inactivating mutation in the WDR6 gene.

In some embodiments, the modified effector cells described herein comprise reduced expression and/or function of the E2F transcription factor 8 (E2F8) gene. The encoded E2F8 protein regulates progression from G1 to S phase by ensuring the nucleus divides at the proper time. In some embodiments, the modified effector cells described herein comprise an inactivating mutation in the E2F8 gene.

In some embodiments, the modified effector cells described herein comprise reduced expression and/or function of the serpin family A member 3 (SERPINA3) gene. SERPINA3 encodes the Alpha 1-antichymotrypsin (α1AC, A1AC, or α1ACT) protein, which inhibits the activity of certain proteases, such as cathepsin G and chymases. In some embodiments, the modified effector cells described herein comprise an inactivating mutation in the SERPINA3 gene.

In some embodiments, the modified effector cells described herein comprise reduced expression and/or function of the GNAS complex locus (GNAS) gene. It is the stimulatory G-protein alpha subunit (Gs-α), a key component of many signal transduction pathways. In some embodiments, the modified effector cells described herein comprise an inactivating mutation in the GNAS gene.

In some embodiments, the modified effector cells described herein comprise reduced expression of the ANKRD11 gene. The ANKRD11 protein is an ankryin repeat domain containing protein thought to inhibit ligand-dependent activation of transcript by unknown mechanisms. The ANKRD11 protein is thought to be related to KBG syndrome.

In some embodiments, the modified effector cells described herein comprise reduced expression of the Suppressors of cytokine signaling SOCS 1 (SOCS1) gene. The SOCS1 protein comprises C-terminal SOCS box motifs, an SH2-domain, an ESS domain, and an N-terminal KIR domain. The 12 amino-acid residue called the kinase inhibitory region (KIR) has been found to be critical in the ability of SOCS1 to negatively regulate JAK1, TYK2 and JAK2 tyrosine kinase function.

In some embodiments, the modified immune effector cells comprise reduced expression and/or function of at least two genes selected from BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 (e.g., two or more genes selected from Table 3). For example, in some embodiments, the modified immune effector cells comprise reduced expression and/or function of at least two genes selected from Combination Nos. 1001-1240, as illustrated in FIG. 3A-FIG. 3B. In some embodiments, the modified immune effector cells comprise reduced expression and/or function of at least two genes selected from Combination Nos. 1001-1210, as illustrated in FIG. 3A. In some embodiments, the modified immune effector cells comprise reduced expression and/or function of at least two genes selected from Combination Nos. 1211-1240, as illustrated in FIG. 3B. In some embodiments, the modified immune effector cells comprise reduced expression and/or function of at least two genes selected from Combination Nos. 1211-1225, as illustrated in FIG. 3B. In some embodiments, the modified immune effector cells comprise reduced expression and/or function of at least two genes selected from Combination Nos. 1226-1240, as illustrated in FIG. 3B. In some embodiments, the modified immune effector cells comprise reduced expression and/or function of SOCS1, and ANKRD11.

In some embodiments, the modified effector cells comprise reduced expression and/or function of one or more of BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 (e.g., one or more gene selected from Table 3) and one or more of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., one or more gene selected from Table 2). For example, the modified immune effector cells may comprise reduced expression and/or function of a combination of endogenous target genes selected from Combination Nos. 601-1000. In some embodiments, the modified immune effector cells may comprise reduced expression and/or function of a combination of two endogenous target genes selected from Combination Nos. 601-950 (as illustrated in FIG. 2A). In some embodiments, the modified immune effector cells may comprise reduced expression and/or function of a combination of two endogenous target genes selected from Combination Nos. 951-1000 (as illustrated in FIG. 2B). In some embodiments, the modified immune effector cells may comprise reduced expression and/or function of a combination of two endogenous target genes selected from Combination Nos. 951-975 (as illustrated in FIG. 2B). In some embodiments, the modified immune effector cells may comprise reduced expression and/or function of a combination of two endogenous target genes selected from Combination Nos. 951-1000 (as illustrated in FIG. 2B).

In some embodiments, the modified effector cells comprise reduced expression and/or function of at least one gene selected from BCL2L11, FL11, CALM2, DHODH, UMPS, RBM39, SEMA7A, CHIC2, PCBP1, PBRM1, WDR6, E2F8, SERPINA3, and GNAS and reduced expression and/or function of at least one gene selected from TNFAIP3, CBLB, or BCOR. In some embodiments, the modified effector cells comprise reduced expression and/or function of SOCS1 and at least one gene selected from TNFAIP3, CBLB, or BCOR. In some embodiments, the modified effector cells comprise inactivating mutations in SOCS1 and at least one gene selected from TNFAIP3, CBLB, or BCOR. In some embodiments, the modified effector cells comprise reduced expression and/or function of ANKRD11 and at least one gene selected from TNFAIP3, CBLB, or BCOR. In some embodiments, the modified effector cells comprise inactivating mutations in ANKRD11 and at least one gene selected from TNFAIP3, CBLB, or BCOR.

In some embodiments, the modified effector cells comprise reduced expression and/or function of at least one gene selected from BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 and reduced expression and/or function of CBLB. In some embodiments, the modified effector cells comprise reduced expression and/or function of at least one gene selected from BCL2L11, FL11, CALM2, DHODH, UMPS, RBM39, SEMA7A, CHIC2, PCBP1, PBRM1, WDR6, E2F8, SERPINA3, and GNAS and reduced expression and/or function of CBLB. In some embodiments, the modified effector cells comprise reduced expression and/or function of SOCS1 and CBLB. In some embodiments, the modified effector cells comprise inactivating mutations in SOCS1 and CBLB. In some embodiments, the modified effector cells comprise reduced expression and/or function of ANKRD11 and CBLB. In some embodiments, the modified effector cells comprise inactivating mutations in ANKRD11 and CBLB.

In some embodiments, the modified immune effector cells comprise reduced expression and/or function of a gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., one or more gene selected from Table 2) and reduced expression and/or function of two genes selected from BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 (e.g., one or more gene selected from Table 3). For example, in some embodiments, the modified immune effector cells comprise reduced expression and/or function of a gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR in addition to reduced expression and/or function of two endogenous target gene combinations selected from Combination Nos. 1176-1681 (as illustrated in FIG. 3A-FIG. 3B).

In some embodiments, the modified immune effector cells comprise reduced expression and/or function of a gene selected from BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 (e.g., a gene selected from Table 3) and reduced expression and/or function of two genes selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., one or more gene selected from Table 2). For example, in some embodiments, the modified immune effector cells comprise reduced expression and/or function of any one of BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 in addition to reduced expression and/or function of two endogenous target gene combinations selected from Combination Nos. 1-600 illustrated in FIG. 1A-FIG. 1B. In some embodiments, the modified immune effector cells comprise reduced expression and/or function of a gene selected from BCL2L11, FL11, CALM2, DHODH, UMPS, RBM39, SEMA7A, CHIC2, PCBP1, PBRM1, WDR6, E2F8, SERPINA3, and GNAS in addition to reduced expression and/or function of two endogenous target gene combinations selected from Combination Nos. 1-600 illustrated in FIG. 1A FIG. 1B. In some embodiments, the modified immune effector cells comprise reduced expression and/or function of SOCS1 in addition to reduced expression and/or function of two endogenous target gene combinations selected from Combination Nos. 1-600 illustrated in FIG. 1A-FIG. 1B. n some embodiments, the modified immune effector cells comprise reduced expression and/or function of ANKRD11 in addition to reduced expression and/or function of two endogenous target gene combinations selected from Combination Nos. 1-600 illustrated in FIG. 1A-FIG. 1B.

In some embodiments, the modified immune effector cells comprise reduced expression and/or function of a plurality of genes selected from Table 2 and reduced expression and/or function of a plurality of genes selected from Table 3. In some embodiments, the modified immune effector cells comprise reduced expression and/or function of two genes selected from Table 2 and reduced expression and/or function of two genes selected from Table 3. For example, in some embodiments, the modified immune effector cells comprise reduced expression and/or function of a combination of two genes selected from Combination Nos. 1176-1681 as shown in FIG. 3A-FIG. 3B and a combination of two genes selected from Combination Nos. 1-600 as shown in FIG. 1A-FIG. 1B. In some embodiments, the modified immune effector cells may comprise reduced expression and/or function of three or more of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1 HAVCR2, LAG3, TIGIT, CTLA4, PTPN6, PDCD2, or BCOR and reduced expression and/or function of three or more of BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11.

TABLE 2

Exemplary Endogenous Genes

| Gene Symbol | Gene Name | Human UniProt Ref. | Human NCBI ID | Murine UniProt Ref. | Murine NCBI ID |
|---|---|---|---|---|---|
| IKZF1 | IKAROS family zinc finger 1 | Q13422 | 10320 | Q03267 | 22778 |
| IKZF2 | IKAROS family zinc finger 2 | Q9UKS7 | 22807 | P81183 | 22779 |
| IKZF3 | IKAROS family zinc finger 3 | Q9UKT9 | 22806 | O08900 | 22780 |
| NFKBIA | NFKB inhibitor alpha | P25963 | 4792 | Q9Z1E3 | 18035 |
| BCL3 | B cell CLL/lymphoma 3 | P20749 | 602 | Q9Z2F6 | 12051 |

TABLE 2-continued

Exemplary Endogenous Genes

| Gene Symbol | Gene Name | Human UniProt Ref. | Human NCBI ID | Murine UniProt Ref. | Murine NCBI ID |
|---|---|---|---|---|---|
| TNIP1 | TNFAIP3 interacting protein 1 | Q15025 | 10318 | Q9WUU8 | 57783 |
| TNFAIP3 | TNF alpha induced protein 3 | P21580 | 7128 | Q60769 | 21929 |
| SMAD2 | SMAD family member 2 | Q15796 | 4087 | Q919P9 | 17126 |
| TGFBR1 | transforming growth factor beta receptor 1 | P36897 | 7046 | Q64729 | 21812 |
| TGFBR2 | transforming growth factor beta receptor 2 | P37173 | 7048 | Q623212 | 21813 |
| TANK | TRAF family member associated NFKB activator | Q92844 | 10010 | P70347 | 21353 |
| FOXP3 | forkhead box P3 | Q9BZS1 | 50943 | Q99JB6 | 20371 |
| CBLB | Cbl proto-oncogene B | Q13191 | 868 | Q3TTA7 | 208650 |
| PPP2R2D | protein phosphatase 2 regulatory subunit Bdelta | Q66LE6 | 55844 | Q7ZX64 | 52432 |
| NRP1 | neuropilin 1 | Q14786 | 8829 | P97333 | 18186 |
| HAVCR2 | hepatitis A virus cellular receptor 2 | Q8TDQ0 | 84868 | Q8VIM0 | 171285 |
| LAG3 | lymphocyte activating 3 | P18627 | 3902 | Q61790 | 16768 |
| TIGIT | T cell immunoreceptor with Ig and ITIM domains | Q495A1 | 201633 | P86176 | 100043314 |
| CTLA4 | cytotoxic T-lymphocyte associated protein 4 | P16410 | 1493 | P09793 | 12477 |
| PTPN6 | protein tyrosine phosphatase, non-receptor type 6 | P29350 | 5777 | P29351 | 15170 |
| BCOR | BCL6 corepressor | Q6W2J9 | 54880 | Q8CGN4 | 71458 |
| GATA3 | GATA binding protein 3 | P23771 | 2625 | P23772 | 14462 |
| PDCD1 | Programmed cell death 1 protein | Q15116 | 5133 | Q02242 | 18566 |
| RC3H1 | Ring finger and CCCH-type domains 1 | Q5TC82 | 149041 | Q4VGL6 | 381305 |
| TRAF6 | TNF receptor associated factor 6 | Q9Y4K3 | 7186 | P70196 | 22034 |

TABLE 3

Exemplary Genes for Novel Regulation

| Gene Symbol | Gene Name | Human UniProt Ref. | Human NCBI ID | Murine UniProt Ref. | Murine NCBI ID |
|---|---|---|---|---|---|
| SEMA7A | semaphorin 7A | O75326 | 8482 | Q9QUR8 | 20361 |
| RBM39 | RNA binding motif protein 39 | Q14498 | 9584 | Q8VH51 | 170791 |
| BCL2L11 | BCL2 like 11 | O43521 | 10018 | O54918 | 12125 |
| FLI1 | Fli-1 proto-oncogene, ETS transcription factor | Q01543 | 2313 | P26323 | 14247 |
| CALM2 | calmodulin 2 | POP24 | 805 | P0DP30 | 12314 |
| DHODH | dihydroorotate dehydrogenase (quinone) | Q02127 | 1723 | O35435 | 56749 |
| UMPS | uridine monophosphate synthetase | P11172 | 7372 | P13439 | 22247 |
| CHIC2 | cysteine rich hydrophobic domain 2 | Q9UKJ5 | 26511 | Q9D9G3 | 74277 |
| PCBP1 | poly(rC) binding protein 1 | Q15365 | 5093 | P60335 | 23983 |
| PBRM1 | polybromo 1 | Q86U86 | 55193 | Q8BSQ9 | 66923 |
| WDR6 | WD repeat domain 6 | Q9NNW5 | 11180 | Q99ME2 | 83669 |
| E2F8 | E2F transcription factor 8 | A0AVK6 | 79733 | Q58FA4 | 108961 |
| SERPINA3 | serpin family A member 3 | P01011 | 12 | | |
| GNAS | guanine nucleotide binding protein, alpha stimulating | Q5JWF2 | 2778 | Q6R0H7 | 14683 |
| SOCS1 | suppressor of cytokine signaling 1 | O15524 | 8651 | O35716 | 12703 |
| ANKRD11 | ankyrin repeat domain 11 | Q15327 | 29123 | Q9CR42 | 77087 |

III. Gene-Regulating Systems

Herein, the term "gene-regulating system" refers to a protein, nucleic acid, or combination thereof that is capable of modifying an endogenous target DNA sequence when introduced into a cell, thereby regulating the expression or function of the encoded gene product. Numerous gene editing systems suitable for use in the methods of the present disclosure are known in the art including, but not limited to, shRNAs, siRNAs, zinc-finger nuclease systems, TALEN systems, and CRISPR/Cas systems.

As used herein, "regulate," when used in reference to the effect of a gene-regulating system on an endogenous target gene encompasses any change in the sequence of the endogenous target gene, any change in the epigenetic state of the endogenous target gene, and/or any change in the expression or function of the protein encoded by the endogenous target gene.

In some embodiments, the gene-regulating system may mediate a change in the sequence of the endogenous target gene, for example, by introducing one or more mutations into the endogenous target sequence, such as by insertion or deletion of one or more nucleic acids in the endogenous target sequence. Exemplary mechanisms that can mediate alterations of the endogenous target sequence include, but are not limited to, non-homologous end joining (NHEJ) (e.g., classical or alternative), microhomology-mediated end joining (MMEJ), homology-directed repair (e.g., endogenous donor template mediated), SDSA (synthesis dependent strand annealing), single strand annealing or single strand invasion.

In some embodiments, the gene-regulating system may mediate a change in the epigenetic state of the endogenous target sequence. For example, in some embodiments, the gene-regulating system may mediate covalent modifications of the endogenous target gene DNA (e.g., cytosine methylation and hydroxymethylation) or of associated histone proteins (e.g. lysine acetylation, lysine and arginine methylation, serine and threonine phosphorylation, and lysine ubiquitination and sumoylation).

In some embodiments, the gene-regulating system may mediate a change in the expression of the protein encoded by the endogenous target gene. In such embodiments, the gene-regulating system may regulate the expression of the encoded protein by modifications of the endogenous target DNA sequence, or by acting on the mRNA product encoded by the DNA sequence. In some embodiments, the gene-regulating system may result in the expression of a modified endogenous protein. In such embodiments, the modifications to the endogenous DNA sequence mediated by the gene-regulating system result in the expression of an endogenous protein demonstrating a reduced function as compared to the corresponding endogenous protein in an unmodified immune effector cell. In such embodiments, the expression level of the modified endogenous protein may be increased, decreased or may be the same, or substantially similar to, the expression level of the corresponding endogenous protein in an unmodified immune cell.

A. Nucleic Acid-Based Gene-Regulating Systems

As used herein, a nucleic acid-based gene-regulating system is a system comprising one or more nucleic acid molecules that is capable of regulating the expression of an endogenous target gene without the requirement for an exogenous protein. In some embodiments, the nucleic acid-based gene-regulating system comprises an RNA interference molecule or antisense RNA molecule that is complementary to a target nucleic acid sequence.

An "antisense RNA molecule" refers to an RNA molecule, regardless of length, that is complementary to an mRNA transcript. Antisense RNA molecules refer to single stranded RNA molecules that can be introduced to a cell, tissue, or subject and result in decreased expression of an endogenous target gene product through mechanisms that do not rely on endogenous gene silencing pathways, but rather rely on RNaseH-mediated degradation of the target mRNA transcript. In some embodiments, an antisense nucleic acid comprises a modified backbone, for example, phosphorothioate, phosphorodithioate, or others known in the art, or may comprise non-natural internucleoside linkages. In some embodiments, an antisense nucleic acid can comprise locked nucleic acids (LNA).

"RNA interference molecule" as used herein refers to an RNA polynucleotide that mediates the decreased the expression of an endogenous target gene product by degradation of a target mRNA through endogenous gene silencing pathways (e.g., Dicer and RNA-induced silencing complex (RISC)). Exemplary RNA interference agents include micro RNAs (also referred to herein as "miRNAs"), short hair-pin RNAs (shRNAs), small interfering RNAs (siRNAs), RNA aptamers, and morpholinos.

In some embodiments, the nucleic acid-based gene-regulating system comprises one or more miRNAs. miRNA refers to naturally occurring, small non-coding RNA molecules of about 21-25 nucleotides in length. miRNAs are at least partially complementary to one or more target mRNA molecules. miRNAs can downregulate (e.g., decrease) expression of an endogenous target gene product through translational repression, cleavage of the mRNA, and/or deadenylation.

In some embodiments, the nucleic acid-based gene-regulating system comprises one or more shRNAs. shRNAs are single stranded RNA molecules of about 50-70 nucleotides in length that form stem-loop structures and result in degradation of complementary mRNA sequences. shRNAs can be cloned in plasmids or in non-replicating recombinant viral vectors to be introduced intracellularly and result in the integration of the shRNA-encoding sequence into the genome. As such, an shRNA can provide stable and consistent repression of endogenous target gene translation and expression.

In some embodiments, nucleic acid-based gene-regulating system comprises one or more siRNAs. siRNAs refer to double stranded RNA molecules typically about 21-23 nucleotides in length. The siRNA associates with a multi protein complex called the RNA-induced silencing complex (RISC), during which the "passenger" sense strand is enzymatically cleaved. The antisense "guide" strand contained in the activated RISC then guides the RISC to the corresponding mRNA because of sequence homology and the same nuclease cuts the target mRNA, resulting in specific gene silencing. Optimally, an siRNA is 18, 19, 20, 21, 22, 23 or 24 nucleotides in length and has a 2 base overhang at its 3' end. siRNAs can be introduced to an individual cell and/or culture system and result in the degradation of target mRNA sequences. siRNAs and shRNAs are further described in Fire et al., Nature, 391:19, 1998 and U.S. Pat. Nos. 7,732, 417; 8,202,846; and 8,383,599.

In some embodiments, the nucleic acid-based gene-regulating system comprises one or more morpholinos. "Morpholino" as used herein refers to a modified nucleic acid oligomer wherein standard nucleic acid bases are bound to morpholine rings and are linked through phosphorodiamidate linkages. Similar to siRNA and shRNA, morpholinos bind to complementary mRNA sequences. However, morpholinos function through steric-inhibition of mRNA translation and alteration of mRNA splicing rather than targeting complementary mRNA sequences for degradation.

In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA encoded by a DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (i.e., those listed in Table 2). In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to a RNA sequence encoded by a DNA sequence defined by a set of genomic coordinates shown in Table 5A or Table 5B. Throughout this application, the referenced genomic coordinates are based on genomic annotations in the GRCh38 (also referred to as hg38) assembly of the human genome from the Genome Reference Consortium, available at the National Center for Biotechnology Information website. Tools and methods for converting genomic coordinates between one assembly and another are known in the art and can be used to convert the genomic coordinates provided herein to the corresponding coordinates in another assembly of the human genome, including conversion to an earlier assembly generated by the same institution or using the same algorithm (e.g., from GRCh38 to GRCh37), and conversion an assembly generated by a different institution or algorithm (e.g., from GRCh38 to NCBI33, generated by the International Human Genome Sequencing Consortium). Available methods and tools known in the art include, but are not limited to, NCBI Genome Remapping Service, available at the National Center for Biotechnology Information website, UCSC LiftOver, available at the UCSC Genome Brower website, and Assembly Converter, available at the Ensembl.org website.

In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 154-498 or SEQ ID NOs: 499-813. In some embodiments, the nucleic acid-based gene-regulating system is capable of reducing the expression and/or function of CBLB, and comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 499-524. In some embodiments, the nucleic acid-based gene-regulating system is capable of reducing the expression and/or function of BCOR, and comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 708-772 or SEQ ID NOs: 708-764. In some embodiments, the nucleic acid-based gene-regulating system is capable of reducing the expression and/or function of TNFAIP3, and comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 348-396 or SEQ ID NOs: 348-386. In some embodiments, the nucleic acid-based gene-regulating system comprises an siRNA molecule or an shRNA molecule selected from those known in the art, such as the siRNA and shRNA constructs available from commercial suppliers such as Sigma Aldrich, Dharmacon, ThermoFisher, and the like.

In some embodiments, the endogenous target gene is CBLB and the nucleic acid molecule is an shRNA encoded by a nucleic acid sequence selected from SEQ ID NOs: 41-44 (See International PCT Publication No. 2018156886) or selected from SEQ ID NOs: 45-53 (See International PCT Publication No. WO 2017120998). In some embodiments, the endogenous target gene is CBLB and the nucleic acid molecule is an siRNA comprising a nucleic acid sequence selected from SEQ ID NOs: 54-63 (See International PCT Publication No. WO 2018006880) or SEQ ID NOs: 64-73 (See International PCT Publication Nos. WO 2018120998 and WO 2018137293).

In some embodiments, the endogenous target gene is TNFAIP3 and the nucleic acid molecule is an shRNA encoded by a nucleic acid sequence selected from SEQ ID NOs: 74-95 (See U.S. Pat. No. 8,324,369). In some embodiments, the endogenous target gene is TNFAIP3 and the nucleic acid molecule is an siRNA comprising a nucleic acid sequence selected from SEQ ID NOs: 96-105 (See International PCT Publication No. WO 2018006880).

In some embodiments, the endogenous target gene is CTLA4 and the nucleic acid molecule is an shRNA encoded by a nucleic acid sequence selected from SEQ ID NOs: 128-133 (See International PCT Publication No. Nos. WO 2017120996). In some embodiments, the endogenous target gene is CTLA4 and the nucleic acid molecule is an siRNA comprising a nucleic acid sequence selected from SEQ ID NOs: 134-143 (See International PCT Publication Nos. WO2017120996, WO 201712098, WO 2018137295, and WO 2018137293) or SEQ ID NOs: 144-153 (See International PCT Publication No. WO 2018006880).

In some embodiments, the endogenous target gene is PDCD1 and the nucleic acid molecule is an shRNA encoded by a nucleic acid sequence selected from SEQ ID NOs: 106-107 (See International PCT Publication Nos. WO 2017120996). In some embodiments, the endogenous target gene is PDCD1 and the nucleic acid molecule is an siRNA comprising a nucleic acid sequence selected from SEQ ID NOs: 108-117 (See International PCT Publication Nos. WO2017120996, WO 201712998, WO 2018137295, and WO 2018137293) or SEQ ID NOs: 118-127 (See International PCT Publication No. WO 2018006880).

In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by a DNA sequence of a target gene selected from BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 (i.e., those listed in Table 3). In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99%, or is 100% identical to an RNA sequence encoded by a DNA sequence defined by a set of genomic coordinates shown in Table 6A-Table 6F. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% to identical to an RNA sequence encoded by one of SEQ ID NOs: 814-1232.

In some embodiments, the nucleic acid-based gene-regulating system is capable of reducing the expression and/or function of a target gene selected from BCL2L11, FL11, CALM2, DHODH, UMPS, RBM39, SEMA7A, CHIC2, PCBP1, PBRM1, WDR6, E2F8, SERPINA3, and GNAS. In some embodiments, the nucleic acid-based gene-regulating system comprises a nucleic acid molecule (e.g., an siRNA, an shRNA, an RNA aptamer, or a morpholino) that binds to a target RNA sequence that at least 90%, 95%, 96%, 97%, 98%, or 99% identical, or is 100% to identical to an RNA sequence encoded by a DNA sequence defined by a set of genomic coordinates shown in one of Table 6A or Table 6B. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% to identical an RNA sequence encoded by one of SEQ ID NOs: 814-1064.

In some embodiments, the nucleic acid-based gene-regulating system is capable of reducing the expression and/or function of SOCS1. In some embodiments, the nucleic acid-based gene-regulating system comprises a nucleic acid molecule (e.g., an siRNA, an shRNA, an RNA aptamer, or a morpholino) that binds to a target RNA sequence that is at least at least 90%, 95%, 96%, 97%, 98%, or 99% identical, or is 100% to identical to an RNA sequence encoded by a DNA sequence defined by a set of genomic coordinates shown in one of Table 6C or Table 6D. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 1088-1232. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 1088-1200. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 1088-1140. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 1088-1120. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 1088-1110. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 1102, 1103, 1105-1108, 1115. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 1106, 1110, 1115, 1116, 1118, 1126, 1129, 1141, 1157, 1174.

In some embodiments, the nucleic acid-based gene-regulating system is capable of reducing the expression and/or function of ANKRD11. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by a DNA sequence defined by a set of genomic coordinates shown in one of Table 6E or Table 6F. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 1065-1087.

In some embodiments, the endogenous target gene is SOCS1 and the nucleic acid molecule is an shRNA that binds to a target sequence selected from SEQ ID NOs: 1236-1255 (See U.S. Pat. No. 9,944,931). In some embodiments, the endogenous target gene is SOCS1 and the nucleic acid molecule is an shRNA encoded by a nucleic acid sequence selected from SEQ ID NOs: 1258-1260 (See U.S. Pat. No. 8,324,369). In some embodiments, the endogenous target gene is SOCS1 and the nucleic acid molecule is an siRNA comprising a nucleic acid sequence selected from SEQ ID NOs: 1261-1270 (See International PCT Publication Nos. WO 2017120996; WO 2018137295; WO 2017120998; and WO 2018137293).

In some embodiments, the endogenous target gene is ANKRD11 and the nucleic acid molecule is an shRNA that binds to a target sequence selected from SEQ ID NOs: 1233-1235 (See Gallagher et al., Developmental Cell (2015), 32(1); 31-42). In some embodiments, the endogenous target gene is ANKRD11 and the nucleic acid molecule is an shRNA encoded by a nucleic acid sequence selected from SEQ ID NOs: 1256-1257 (See Zhang et al., Biochem Biophys Res Commun (2007) 358(4): 1034-1040)

In some embodiments, the nucleic acid-based gene-regulating system comprises an siRNA molecule or an shRNA molecule selected from those known in the art, such as those available from commercial suppliers such as Sigma Aldrich, Dharmacon, ThermoFisher, and the like. Exemplary siRNA and shRNA constructs are described in Table 4A and Table 4B below. In some embodiments, the nucleic acid-based gene-regulating system comprises two or more siRNA molecules selected from those known in the art, such as the siRNA constructs described in Table 4A. In some embodiments, the nucleic acid-based gene-regulating system comprises two or more shRNA molecules selected from those known in the art, such as the shRNA constructs described in Table 4B.

TABLE 4A

Exemplary siRNA constructs

| Target Gene | siRNA construct |
| --- | --- |
| SEMA7A | MISSION ® esiRNA human SEMA7A (esiRNA1) (SigmaAldrich Product# EHU143161) |
| SEMA7A | MISSION ® esiRNA targeting mouse Sema7a (esiRNA1) (SigmaAldrich Product# EMU010311) |
| SEMA7A | human Rosetta Predictions (SigmaAldrich Product# NM_003612) |
| SEMA7A | murine Rosetta Predictions (SigmaAldrich Product# NM_011352) |
| RBM39 | MISSION ® esiRNA human RBM39 (esiRNA1) (SigmaAldrich Product# EHU070351) |
| RBM39 | human Rosetta Predictions (SigmaAldrich Product# NM_004902) |
| RBM39 | human Rosetta Predictions (SigmaAldrich Product# NM_184234) |
| RBM39 | human Rosetta Predictions (SigmaAldrich Product# NM_184237) |
| RBM39 | human Rosetta Predictions (SigmaAldrich Product# NM_184241) |
| RBM39 | human Rosetta Predictions (SigmaAldrich Product# NM_184244) |
| BCL2L11 | MISSION ® esiRNA targeting mouse Bcl2l11 (esiRNA1) (SigmaAldrich Product# |
| BCL2L11 | human Rosetta Predictions (SigmaAldrich Product# NM_006538) |
| BCL2L11 | human Rosetta Predictions (SigmaAldrich Product# NM_138621) |
| BCL2L11 | human Rosetta Predictions (SigmaAldrich Product# NM_138622) |
| BCL2L11 | human Rosetta Predictions (SigmaAldrich Product# NM_138623) |
| BCL2L11 | human Rosetta Predictions (SigmaAldrich Product# NM_138624) |

TABLE 4A-continued

Exemplary siRNA constructs

| Target Gene | siRNA construct |
|---|---|
| FLI1 | MISSION ® esiRNA human FLII (esiRNA1) (SigmaAldrich Product# EHU091961) |
| FLI1 | MISSION ® esiRNA targeting mouse Fli1 (esiRNA1) (SigmaAldrich Product# EMU090601) |
| FLI1 | human Rosetta Predictions (SigmaAldrich Product# NM_002017) |
| FLI1 | murine Rosetta Predictions (SigmaAldrich Product# NM_008026) |
| CALM2 | MISSION ® esiRNA human CALM2 (esiRNA1) (SigmaAldrich Product# EHU110161) |
| CALM2 | MISSION ® esiRNA targeting mouse Calm2 (SigmaAldrich Product# EMU176331) |
| CALM2 | human Rosetta Predictions (SigmaAldrich Product# NM_001743) |
| CALM2 | murine Rosetta Predictions (SigmaAldrich Product# NM_007589) |
| DHODH | MISSION ® esiRNA human DHODH (esiRNA1) (SigmaAldrich Product# EHU138421) |
| DHODH | MISSION ® esiRNA targeting mouse Dhodh (esiRNA1) (SigmaAldrich Product# EMU072221) |
| DHODH | human Rosetta Predictions (SigmaAldrich Product# NM_001025193) |
| DHODH | human Rosetta Predictions (SigmaAldrich Product# NM_001361) |
| DHODH | murine Rosetta Predictions (SigmaAldrich Product# NM_020046) |
| UMPS | MISSION ® esiRNA human UMPS (esiRNA1) (SigmaAldrich Product# EHU093891) |
| UMPS | MISSION ® esiRNA targeting mouse Umps (esiRNA1) (SigmaAldrich Product# EMU023181) |
| UMPS | human Rosetta Predictions (SigmaAldrich Product# NM_000373) |
| UMPS | murine Rosetta Predictions (SigmaAldrich Product# NM_009471) |
| CHIC2 | MISSION ® esiRNA human CHIC2 (esiRNA1) (SigmaAldrich Product# EHU137501) |
| CHIC2 | MISSION ® esiRNA targeting mouse Chic2 (esiRNA1) (SigmaAldrich Product# EMU019221 |
| CHIC2 | human Rosetta Predictions (SigmaAldrich Product# NM_012110) |
| CHIC2 | murine Rosetta Predictions (SigmaAldrich Product# NM_028850) |
| PCBP1 | MISSION ® esiRNA targeting mouse Pcbp1 (esiRNA1) (SigmaAldrich Product# EMU011551) |
| PCBP1 | human Rosetta Predictions (SigmaAldrich Product# NM_006196) |
| PCBP1 | murine Rosetta Predictions (SigmaAldrich Product# NM_011865) |
| PBRM1 | MISSION ® esiRNA human PBRM1 (esiRNA1) (SigmaAldrich Product# EHU075001) |
| PBRM1 | human Rosetta Predictions (SigmaAldrich Product# NM_018165) |
| PBRM1 | human Rosetta Predictions (SigmaAldrich Product# NM_018313) |
| PBRM1 | human Rosetta Predictions (SigmaAldrich Product# NM_181042) |
| WDR6 | MISSION ® esiRNA human WDR6 (esiRNA1) (SigmaAldrich Product# EHU065441) |
| WDR6 | MISSION ® esiRNA targeting mouse Wdr6 (esiRNA1) (SigmaAldrich Product# EMU038981) |
| WDR6 | human Rosetta Predictions (SigmaAldrich Product# NM_018031) |
| WDR6 | murine Rosetta Predictions (SigmaAldrich Product# NM_031392) |
| E2F8 | MISSION ® esiRNA human E2F8 (esiRNA1) (SigmaAldrich Product# EHU025641) |
| E2F8 | MISSION ® esiRNA targeting mouse E2f8 (SigmaAldrich Product# EMU206861) |
| E2F8 | human Rosetta Predictions (SigmaAldrich Product# NM_024680) |
| E2F8 | murine Rosetta Predictions (SigmaAldrich Product# NM_001013368) |
| SERPINA3 | MISSION ® esiRNA human SERPINA3 (esiRNA1) (SigmaAldrich Product# EHU150301) |
| SERPINA3 | human Rosetta Predictions (SigmaAldrich Product# NM_001085) |
| GNAS | MISSION ® esiRNA human GNAS (esiRNA1) (SigmaAldrich Product# EHU117321) |
| GNAS | MISSION ® esiRNA targeting mouse Gnas (esiRNA1) (SigmaAldrich Product# EMU074141) |
| GNAS | human Rosetta Predictions (SigmaAldrich Product# NM_000516) |
| GNAS | human Rosetta Predictions (SigmaAldrich Product# NM_001077488) |
| GNAS | human Rosetta Predictions (SigmaAldrich Product# NM_001077489) |
| GNAS | human Rosetta Predictions (SigmaAldrich Product# NM_001077490) |
| GNAS | human Rosetta Predictions (SigmaAldrich Product# NM_016592) |
| SOCS1 | MISSION ® esiRNA targeting mouse Socs1 (SigmaAlrich# EMU203261) |
| SOCS1 | Rosetta Predictions human (SigmaAlrich# NM_003745) |
| SOCS1 | Rosetta Predictions murine (SigmaAlrich# NM_009896) |
| ANKRD11 | MISSION ® esiRNA human ANKRD11 (esiRNA1) (SigmaAlrich#) |
| ANKRD11 | MISSION ® esiRNA targeting mouse Ankrd11 (esiRNA1) (SigmaAlrich# EMU078401) |
| ANKRD11 | Rosetta Predictions human (SigmaAlrich# NM_013275) |
| ANKRD11 | Rosetta Predictions murine (SigmaAlrich# NM_001081379) |
| ANKRD11 | Rosetta Predictions murine (SigmaAlrich# XM_134514) |
| ANKRD11 | Rosetta Predictions murine (SigmaAlrich# XM_902605) |

TABLE 4B

Exemplary shRNA constructs

| Target Gene | shRNA construct |
|---|---|
| SEMA7A | MISSION ® shRNA murine Plasmid DNA (SigmaAldrich Product# SHCLND-NM_011352) |
| SEMA7A | MISSION ® shRNA human Plasmid DNA (SigmaAldrich Product# SHCLND-NM_003612) |
| RBM39 | MISSION ® shRNA murine Plasmid DNA (SigmaAldrich Product# SHCLND-NM_133242) |
| RBM39 | MISSION ® shRNA human Plasmid DNA (SigmaAldrich Product# SHCLND-NM_004902) |
| BCL2L11 | MISSION ® shRNA murine Plasmid DNA (SigmaAldrich Product# SHCLND-NM_009754) |
| BCL2L11 | MISSION ® shRNA human Plasmid DNA (SigmaAldrich Product# SHCLND-NM_138621) |

TABLE 4B-continued

Exemplary shRNA constructs

| Target Gene | shRNA construct |
|---|---|
| FLI1 | MISSION ® shRNA human Plasmid DNA (SigmaAldrich Product# SHCLND-NM_002017) |
| FLI1 | MISSION ® shRNA murine Plasmid DNA (SigmaAldrich Product# SHCLND-NM_008026) |
| CALM2 | MISSION ® shRNA murine Plasmid DNA (SigmaAldrich Product# SHCLND-NM_007589) |
| CALM2 | MISSION ® shRNA human Plasmid DNA (SigmaAldrich Product# SHCLND-NM_001743) |
| DHODH | MISSION ® shRNA murine Plasmid DNA (SigmaAldrich Product# SHCLND-NM_020046) |
| DHODH | MISSION ® shRNA human Plasmid DNA (SigmaAldrich Product# SHCLND-NM_001361) |
| UMPS | MISSION ® shRNA murine Plasmid DNA (SigmaAldrich Product# SHCLND-NM_009471) |
| UMPS | MISSION ® shRNA human Plasmid DNA (SigmaAldrich Product# SHCLND-NM_000373) |
| CHIC2 | MISSION ® shRNA murine Plasmid DNA (SigmaAldrich Product# SHCLND-NM_028850) |
| CHIC2 | MISSION ® shRNA human Plasmid DNA (SigmaAldrich Product# SHCLND-NM_012110) |
| PCBP1 | MISSION ® shRNA murine Plasmid DNA (SigmaAldrich Product# SHCLND-NM_011865) |
| PCBP1 | MISSION ® shRNA human Plasmid DNA (SigmaAldrich Product# SHCLND-NM_006196) |
| PBRM1 | MISSION ® shRNA murine Plasmid DNA (SigmaAldrich Product# SHCLND-NM_001081251) |
| PBRM1 | MISSION ® shRNA human Plasmid DNA (SigmaAldrich Product# SHCLND-NM_018165) |
| WDR6 | MISSION ® shRNA murine Plasmid DNA (SigmaAldrich Product# SHCLND-NM_031392) |
| WDR6 | MISSION ® shRNA human Plasmid DNA (SigmaAldrich Product# SHCLND-NM_018031) |
| E2F8 | MISSION ® shRNA murine Plasmid DNA (SigmaAldrich Product# SHCLND-NM_001013368) |
| E2F8 | MISSION ® shRNA human Plasmid DNA (SigmaAldrich Product# SHCLND-NM_024680) |
| SERPINA3 | MISSION ® shRNA human Plasmid DNA (SigmaAldrich Product# SHCLND-NM_001085) |
| GNAS | MISSION ® shRNA murine Plasmid DNA (SigmaAldrich Product# SHCLND-NM_010309) |
| GNAS | MISSION ® shRNA human Plasmid DNA (SigmaAldrich Product# SHCLND-NM_000516) |
| SOCS1 | MISSION ® shRNA Plasmid DNA human (SigmaAlrich# SHCLND-NM_003745) MISSION ® shRNA Plasmid DNA murine (SigmaAlrich# SHCLND-NM_009896) |
| ANKRD11 | MISSION ® shRNA Plasmid DNA human (SigmaAlrich# SHCLND-NM_013275) MISSION ® shRNA Plasmid DNA murine (SigmaAlrich# SHCLND-NM_001081379) |

In some embodiments, the gene-regulating system comprises two or more nucleic acid molecules (e.g., two or more siRNAs, two or more shRNAs, two or more RNA aptamers, or two or more morpholinos), wherein at least one of the nucleic acid molecules binds to a target RNA sequence that is at least 90%, 95%, 96%, 97%, 98%, or 99% identical, or is 100% identical to an RNA sequence encoded by a DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., a gene selected from Table 2) and wherein at least one of the nucleic acid molecules binds to a target RNA sequence that is at least 90%, 95%, 96%, 97%, 98%, or 99% identical, or is 100% identical to an RNA sequence encoded by a DNA sequence of a target gene selected from BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 (e.g., a gene selected from Table 3).

In some embodiments, at least one of the two or more nucleic acid molecules to a target RNA sequence that is at least 90%, 95%, 96%, 97%, 98%, or 99% identical, or is 100% identical to an RNA sequence encoded by a DNA sequence defined by a set of genomic coordinates shown in Table 5A or Table 5B and at least one of the two or more nucleic acid molecules binds to a target RNA sequence that is at least 90%, 95%, 96%, 97%, 98%, or 99% identical, or is 100% identical to an RNA sequence encoded by a DNA sequence defined by a set of genomic coordinates shown in Table 6A-Table 6F. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 814-1232 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 154-498 or SEQ ID NOs: 499-813.

In some embodiments, the gene-regulating system comprises two or more nucleic acid molecules, wherein at least one of the nucleic acid molecules binds to a target RNA sequence encoded by a DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the nucleic acid molecules binds to a target RNA sequence encoded by a DNA sequence of a target gene selected from BCL2L11, FL11, CALM2, DHODH, UMPS, RBM39, SEMA7A, CHIC2, PCBP1, PBRM1, WDR6, E2F8, SERPINA3, and GNAS. In some embodiments, at least one of the two or more nucleic acid molecules to a target RNA sequence that is at least 90%, 95%, 96%, 97%, 98%, or 99% identical, or is 100% identical to an RNA sequence encoded by a DNA sequence defined by a set of genomic coordinates shown in Table 5A or Table 5B and at least one of the two or more nucleic acid molecules binds to a target RNA sequence that is at least 90%, 95%, 96%, 97%, 98%, or 99% identical, or is 100% identical to an RNA sequence encoded by a DNA sequence defined by a set of genomic coordinates shown in Table 6A or Table 6B. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 814-1064 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 154-498 or SEQ ID NOs: 499-813.

In some embodiments, the gene-regulating system comprises two or more nucleic acid molecules, wherein at least one of the nucleic acid molecules binds to a target RNA sequence encoded by a DNA sequence of CBLB and wherein at least one of the nucleic acid molecules binds to a target RNA sequence encoded by a DNA sequence of a target gene selected from BCL2L11, FL11, CALM2, DHODH, UMPS, RBM39, SEMA7A, CHIC2, PCBP1, PBRM1, WDR6, E2F8, SERPINA3, and GNAS. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 499-524 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 814-1064.

In some embodiments, the gene-regulating system comprises two or more nucleic acid molecules, wherein at least one of the nucleic acid molecules binds to a target RNA sequence encoded by a DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the nucleic acid molecules binds to a target RNA sequence encoded by a DNA sequence of the SOCS1 gene. In some embodiments, at least one of the two or more nucleic acid molecules to a target RNA sequence that is at least 90%, 95%, 96%, 97%, 98%, or 99% identical, or is 100% identical to an RNA sequence encoded by a DNA sequence defined by a set of genomic coordinates shown in Table 5A or Table 5B and at least one of the two or more nucleic acid molecules binds to a target RNA sequence that is at least 90%, 95%, 96%, 97%, 98%, or 99% identical, or is 100% identical to an RNA sequence encoded by a DNA sequence defined by a set of genomic coordinates shown in Table 6C or Table 6D. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 154-498 or SEQ ID NOs: 499-813 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1088-1232.

In some embodiments, the gene-regulating system comprises two or more nucleic acid molecules, wherein at least one of the nucleic acid molecules binds to a target RNA sequence encoded by the CBLB gene and wherein at least one of the nucleic acid molecules binds to a target RNA sequence encoded by a DNA sequence of the SOCS1 gene. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 499-524 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1088-1232, SEQ ID NOs: 1088-1200, SEQ ID NOs: 1088-1140, or SEQ ID NOs: 1088-1120. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 499-524 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1106, 1110, 1115, 1116, 1118, 1126, 1129, 1141, 1157, 1174. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 499-524 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1102, 1103, 1105-1108, 1115.

In some embodiments, the gene-regulating system comprises two or more nucleic acid molecules, wherein at least one of the nucleic acid molecules binds to a target RNA sequence encoded by a DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the nucleic acid molecules binds to a target RNA sequence encoded by a DNA sequence of the ANKRD11 gene. In some embodiments, at least one of the two or more nucleic acid molecules to a target RNA sequence that is at least 90%, 95%, 96%, 97%, 98%, or 99% identical, or is 100% identical to an RNA sequence encoded by a DNA sequence defined by a set of genomic coordinates shown in Table 5A or Table 5B and at least one of the two or more nucleic acid molecules binds to a target RNA sequence that is at least 90%, 95%, 96%, 97%, 98%, or 99% identical, or is 100% identical to an RNA sequence encoded by a DNA sequence defined by a set of genomic coordinates shown in Table 6E or Table 6F. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 154-498 or SEQ ID NOs: 499-813 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1065-1087.

In some embodiments, the gene-regulating system comprises two or more nucleic acid molecules, wherein at least one of the nucleic acid molecules binds to a target RNA sequence encoded by the CBLB gene and wherein at least one of the nucleic acid molecules binds to a target RNA sequence encoded by a DNA sequence of the ANKRD11 gene. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 499-524 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1065-1087.

In some embodiments, the gene-regulating system comprises two or more nucleic acid molecules, wherein at least one of the nucleic acid molecules binds to a target RNA sequence encoded by the ANKRD11 gene and wherein at least one of the nucleic acid molecules binds to a target RNA sequence encoded by a DNA sequence of the SOCS1 gene. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1065-1087 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1088-1232.

B. Protein-Based Gene-Regulating Systems

In some embodiments, a protein-based gene-regulating system is a system comprising one or more proteins capable of regulating the expression of an endogenous target gene in a sequence specific manner without the requirement for a nucleic acid guide molecule. In some embodiments, the protein-based gene-regulating system comprises a protein comprising one or more zinc-finger binding domains and an enzymatic domain. In some embodiments, the protein-based gene-regulating system comprises a protein comprising a Transcription activator-like effector nuclease (TALEN) domain and an enzymatic domain. Such embodiments are referred to herein as "TALENs".

1. Zinc Finger Systems

Zinc finger-based systems comprise a fusion protein comprising two protein domains: a zinc finger DNA binding domain and an enzymatic domain. A "zinc finger DNA binding domain", "zinc finger protein", or "ZFP" is a protein, or a domain within a larger protein, that binds DNA in a sequence-specific manner through one or more zinc fingers, which are regions of amino acid sequence within the binding domain whose structure is stabilized through coordination of a zinc ion. The zinc finger domain, by binding to a target DNA sequence, directs the activity of the enzymatic domain to the vicinity of the sequence and, hence, induces modification of the endogenous target gene in the vicinity of the target sequence. A zinc finger domain can be engineered to bind to virtually any desired sequence. Accordingly, after identifying a target genetic locus containing a target DNA sequence at which cleavage or recombination is desired (e.g., a target locus in a target gene referenced in Tables 2 or 3), one or more zinc finger binding domains can be engineered to bind to one or more target DNA sequences in the target genetic locus. Expression of a fusion protein comprising a zinc finger binding domain and an enzymatic domain in a cell, effects modification in the target genetic locus.

In some embodiments, a zinc finger binding domain comprises one or more zinc fingers. Miller et al. (1985) EMBO J. 4:1609-1614; Rhodes (1993) Scientific American Febuary:56-65; U.S. Pat. No. 6,453,242. Typically, a single zinc finger domain is about 30 amino acids in length. An individual zinc finger binds to a three-nucleotide (i.e., triplet) sequence (or a four-nucleotide sequence which can overlap, by one nucleotide, with the four-nucleotide binding site of an adjacent zinc finger). Therefore, the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. Binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain. In some embodiments, the DNA-binding domains of individual ZFNs comprise between three and six individual zinc finger repeats and can each recognize between 9 and 18 basepairs.

Zinc finger binding domains can be engineered to bind to a sequence of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal etal. (2001) Curr. Opin. Biotechnol. 12:632-637; Choo et al. (2000) Curr. Opin. Struct. Biol. 10:411-416. An engineered zinc finger binding domain can have a novel binding specificity, compared to a naturally-occurring zinc finger protein. Engineering methods include, but are not limited to, rational design and various types of selection.

Selection of a target DNA sequence for binding by a zinc finger domain can be accomplished, for example, according to the methods disclosed in U.S. Pat. No. 6,453,242. It will be clear to those skilled in the art that simple visual inspection of a nucleotide sequence can also be used for selection of a target DNA sequence. Accordingly, any means for target DNA sequence selection can be used in the methods described herein. A target site generally has a length of at least 9 nucleotides and, accordingly, is bound by a zinc finger binding domain comprising at least three zinc fingers. However, binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

In some embodiments, the zinc finger binding domains bind to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., a gene selected from Table 2). In some embodiments, the zinc finger binding domains bind to a target DNA sequence that is at least 90%, 95%, 96%, 97%, 98%, or 99% identical, or is 100% identical to a target DNA sequence defined by a set of genomic coordinates shown in Table 5A or Table 5B. In some embodiments, the zinc finger binding domains bind to a target DNA sequence that is at least 90%, 95%, 96%, 97%, 98%, or 99% identical, or is 100% identical to one of SEQ ID NOs: 154-498 or SEQ ID NOs: 499-813. In some embodiments, the zinc finger binding domains bind to a target DNA sequence that is at least 90%, 95%, 96%, 97%, 98%, or 99% identical, or is 100% identical to a target DNA sequence of CBLB. In some embodiments, the zinc finger binding domains bind to a target DNA sequence that is at least 90%, 95%, 96%, 97%, 98%, or 99% identical, or is 100% identical to one of SEQ ID NOs: 499-524. In some embodiments, the zinc finger binding domains bind to a target DNA sequence that is at least 90%, 95%, 96%, 97%, 98%, or 99% identical, or is 100% identical to a target DNA sequence of BCOR. In some embodiments, the zinc finger binding domains bind to a target DNA sequence that is at least 90%, 95%, 96%, 97%, 98%, or 99% identical, or is 100% identical to one of SEQ ID NOs: 708-772 or SEQ ID NOs: 708-764. In some embodiments, the zinc finger binding domains bind to a target DNA sequence that is at least 90%, 95%, 96%, 97%, 98%, or 99% identical, or is 100% identical to a target DNA sequence of TNFAIP3. In some embodiments, the zinc finger binding domains bind to a target DNA sequence that is at least 90%, 95%, 96%, 97%, 98%, or 99% identical, or is 100% identical to one of SEQ ID NOs: 348-396 or SEQ ID NOs: 348-386.

In some embodiments, the zinc finger binding domains bind to a target DNA sequence that is at least 90%, 95%, 96%, 97%, 98%, or 99% identical, or is 100% identical to a target DNA sequence of a target gene selected BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 (e.g., a gene selected from Table 3). In some embodiments, the zinc finger binding domains bind to a target DNA sequence that is at least 90%, 95%, 96%, 97%, 98%, or 99% identical, or is 100% identical to a target DNA sequence defined by a set of genomic coordinates shown in one of Table 6A-Table 6F. In some embodiments, the zinc finger binding domains bind to a target DNA sequence that is at least 90%, 95%, 96%, 97%, 98%, or 99% identical, or is 100% identical to one of SEQ ID NOs: 814-1232.

In some embodiments, the zinc finger binding domains bind to a target DNA sequence that is at least 90%, 95%, 96%, 97%, 98%, or 99% identical, or is 100% identical to a target DNA sequence of a target gene selected BCL2L11, FL11, CALM2, DHODH, UMPS, RBM39, SEMA7A, CHIC2, PCBP1, PBRM1, WDR6, E2F8, SERPINA3, and GNAS. In some embodiments, the zinc finger binding domains bind to a target DNA sequence that is at least 90%, 95%, 96%, 97%, 98%, or 99% identical, or is 100% identical to a target DNA sequence defined by a set of genomic coordinates shown in Table 6A or Table 6B. In some embodiments, the zinc finger binding domains bind to a target DNA sequence that is at least 90%, 95%, 96%, 97%, 98%, or 99% identical, or is 100% identical to one of SEQ ID NOs: 814-1064.

In some embodiments, the zinc finger binding domains bind to a target DNA sequence that is at least 90%, 95%, 96%, 97%, 98%, or 99% identical, or is 100% identical to a target DNA sequence of the SOCS1 gene. In some embodiments, the zinc finger binding domains bind to a target DNA sequence that is at least 90%, 95%, 96%, 97%, 98%, or 99% identical, or is 100% identical to a target DNA sequence defined by a set of genomic coordinates shown in Table 6C or Table 6D. In some embodiments, the zinc finger binding domains bind to a target DNA sequence that is at least 90%, 95%, 96%, 97%, 98%, or 99% identical, or is 100% identical to one of SEQ ID NOs: 1088-1232. In some embodiments, the zinc finger binding domains bind to a target DNA sequence that is at least $^9$00%, 95%, 96% o, 97%, 98% o, or 99% o identical, or is 100% o identical to a target DNA sequence of the ANKRD11 gene. In some embodiments, the zinc finger binding domains bind to a target DNA sequence that is at least 900%, 9500 960%, 9700 98% o, or 99% o identical, or is 100% o identical to a target DNA sequence defined by a set of genomic coordinates shown in Table 6E or Table 6F. In some embodiments, the zinc finger binding domains bind to a target DNA sequence that is at least 90% o, 9500 96% o, 9700 98% o, or 9900 identical, or is 100% o identical to one of SEQ ID NOs: 1065-1087. 002681 In some embodiments, the zinc finger system is selected from those known in the art, such as those available from commercial suppliers such as Sigma Aldrich. For example, in some embodiments, the zinc finger system is selected from those known in the art, such as those described in Table 7 below.

TABLE 7

Exemplary Zinc Finger Systems

| Target Gene | Zinc Finger System |
|---|---|
| SEMA7A | CompoZr ® Knockout ZFN plasmid human SEMA7A NM_003612 (SigmaAldrich Product # CKOZFND19082) |
| SEMA7A | CompoZr ® Knockout ZFN plasmid murine Sema7a NM_011352.2 (SigmaAldrich Product # CKOZFND19082) |
| RBM39 | CompoZr ® Knockout ZFN plasmid Human RBM39 (NM_004902) (SigmaAldrich Product # CKOZFND18044) |
| RBM39 | CompoZr ® Knockout ZFN plasmid Mouse Rbm39 (NM_133242.2) (SigmaAldrich Product # CKOZFND39983) |
| BCL2L11 | CompoZr ® Knockout ZFN plasmid Human BCL2L11 (NM_006538) (SigmaAldrich Product # CKOZFND3909) |
| BCL2L11 | CompoZr ® Knockout ZFN plasmid Mouse Bcl2l11 (NM_207680.2) (SigmaAldrich Product # CKOZFND27562) |
| FLI1 | CompoZr ® Knockout ZFN Kit Human FLI1 (NM_002017) (SigmaAldrich Product # CKOZFN8731) |
| FLI1 | CompoZr ® Knockout ZFN plasmid Mouse Fli1 (NM_008026.4) (SigmaAldrich Product # CKOZFND31430) |
| CALM2 | CompoZr ® Knockout ZFN Kit Human CALM2 (NM_001743) (SigmaAldrich Product # CKOZFN5301) |
| CALM2 | CompoZr ® Knockout ZFN plasmid Mouse Calm2 (NM_007589.5) (SigmaAldrich Product # CKOZFND27915) |
| DHODH | CompoZr ® Knockout ZFN plasmid Human DHODH (NM_001361) (SigmaAldrich Product # CKOZFND1982) |
| DHODH | CompoZr ® Knockout ZFN plasmid Mouse Dhodh (NM_020046.3) (SigmaAldrich Product # CKOZFND29960) |
| UMPS | CompoZr ® Knockout ZFN plasmid Human UMPS (NM_000373) (SigmaAldrich Product # CKOZFND1693) |
| UMPS | CompoZr ® Knockout ZFN plasmid Mouse Umps (NM_009471.2) (SigmaAldrich Product # CKOZFND43931) |
| CHIC2 | CompoZr ® Knockout ZFN Kit Human CHIC2 (NM_012110) (SigmaAldrich Product # CKOZFN6059) |
| CHIC2 | CompoZr ® Knockout ZFN plasmid Mouse Chic2 (NM_028850.4) (SigmaAldrich Product # CKOZFND28691) |
| PCBP1 | CompoZr ® Knockout ZFN plasmid Human PCBP1 (NM_006196) (SigmaAldrich Product # CKOZFND16392) |
| PCBP1 | CompoZr ® Knockout ZFN plasmid Mouse Pcbp1 (NM_011865.3) (SigmaAldrich Product # CKOZFND38313) |
| PBRM1 | CompoZr ® Knockout ZFN plasmid Human PBRM1 (NM_018165) (SigmaAldrich Product # CKOZFND2434) |
| PBRM1 | CompoZr ® Knockout ZFN plasmid Mouse Pbrm1 (NM_001081251.1) (SigmaAldrich Product # CKOZFND38304) |
| WDR6 | CompoZr ® Knockout ZFN plasmid Human WDR6 (NM_018031) (SigmaAldrich Product # CKOZFND22841) |
| WDR6 | CompoZr ® Knockout ZFN plasmid Mouse Wdr6 (NM_031392.2) (SigmaAldrich Product # CKOZFND44594) |
| E2F8 | CompoZr ® Knockout ZFN plasmid Human E2F8 (NM_024680) (SigmaAldrich Product # CKOZFND7610) |
| E2F8 | CompoZr ® Knockout ZFN plasmid Mouse E2f8 (NM_001013368.5) (SigmaAldrich Product # CKOZFND30371) |
| SERPINA3 | CompoZr ® Knockout ZFN plasmid Human SERPINA3 (NM_001085) (SigmaAldrich Product # CKOZFND1900) |

TABLE 7-continued

Exemplary Zinc Finger Systems

| Target Gene | Zinc Finger System |
|---|---|
| GNAS | CompoZr ® Knockout ZFN plasmid Human GNAS (NM_000516) (SigmaAldrich Product # CKOZFND1354) |
| GNAS | CompoZr ® Knockout ZFN plasmid Mouse Gnas (NM_001077510.2) (SigmaAldrich Product # CKOZFND32583) |
| SOCS1 | CompoZr ® Knockout ZFN plasmid Human SOCS1 (NM_003745) (SigmaAldrich# CKOZFND20320) |
| SOCS1 | CompoZr ® Knockout ZFN plasmid Mouse Socs1 (NM_009896.2) (SigmaAldrich# CKOZFND41801) |
| ANKRD11 | CompoZr ® Knockout ZFN plasmid Mouse Ankrd11 (NM_001081379.2) (SigmaAldrich# CKOZFND26692) |
| ANKRD11 | CompoZr ® Knockout ZFN plasmid Human ANKRD11 (NM_013275) (SigmaAldrich# CKOZFND3173) |

In some embodiments, the gene-regulating system comprises two or more ZFP-fusion proteins each comprising a zinc finger binding domain, wherein at least one of the zinc finger binding domains binds to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the zinc finger binding domains binds to a target DNA sequence that is at least 90%, 95%, 96%, 97%, 98%, or 99% identical, or is 100% to identical to a target DNA sequence of a target gene selected from BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11. In some embodiments, at least one of the zinc finger binding domains binds to a target DNA sequence that is at least 90%, 95%, 96%, 97%, 98%, or 99% identical, or is 100% to identical to a target DNA sequence defined by a set of genomic coordinates shown in Table 5A or Table 5B and at least one of the zinc finger binding domains binds to a target DNA sequence that is at least 90%, 95%, 96%, 97%, 98%, or 99% identical, or is 100% to identical to a target DNA sequence defined by a set of genomic coordinates shown in one of Tables 6A-Table 6F. In some embodiments, at least one of the zinc finger binding domains bind to a target DNA sequence that is at least 90%, 95%, 96%, 97%, 98%, or 99% identical, or is 100% to identical to one of SEQ ID NOs: 154-498 or SEQ ID NOs: 499-813 and at least one of the zinc finger binding domains binds to a target DNA sequence that is at least 90%, 95%, 96%, 97%, 98%, or 99% identical, or is 100% to identical to one of SEQ ID NOs: 814-1232.

In some embodiments, the gene-regulating system comprises two or more ZFP-fusion proteins each comprising a zinc finger binding domain, wherein at least one of the zinc finger binding domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the zinc finger binding domains binds to a target DNA sequence of a target gene selected from BCL2L11, FL11, CALM2, DHODH, UMPS, RBM39, SEMA7A, CHIC2, PCBP1, PBRM1, WDR6, E2F8, SERPINA3, and GNAS. In some embodiments, at least one of the two or more zinc finger binding domains binds to a target DNA sequence that is at least 90%, 95%, 96%, 97%, 98%, or 99% identical, or is 100% to identical to a target DNA sequence defined by a set of genomic coordinates shown in Table 5A or Table 5B and at least one of the two or more zinc finger binding domains binds to a target DNA sequence that is at least 90%, 95%, 96%, 97%, 98%, or 99% identical, or is 100% to identical to a target DNA sequence defined by a set of genomic coordinates shown in Table 6A or Table 6B. In some embodiments, at least one of the two or more zinc finger binding domains binds to a target DNA sequence that is at least 90%, 95%, 96%, 97%, 98%, or 99% identical, or is 100% to identical to one of SEQ ID NOs: 154-498 or SEQ ID NOs: 499-813 and at least one of the two or more zinc finger binding domains binds to a target DNA sequence that is at least 90%, 95%, 96%, 97%, 98%, or 99% identical, or is 100% to identical to one of SEQ ID NOs: 814-1064.

In some embodiments, the gene-regulating system comprises two or more ZFP-fusion proteins each comprising a zinc finger binding domain, wherein at least one of the zinc finger binding domains binds to a target DNA sequence of the CBLB gene and at least one of the zinc finger binding domains binds to a target DNA sequence of a target gene selected from BCL2L11, FL11, CALM2, DHODH, UMPS, RBM39, SEMA7A, CHIC2, PCBP1, PBRM1, WDR6, E2F8, SERPINA3, and GNAS. In some embodiments, at least one of the two or more zinc finger binding domains binds to a target DNA sequence that is at least 90%, 95%, 96%, 97%, 98%, or 99% identical, or is 100% identical to one of SEQ ID NOs: 499-524 and at least one of the two or more zinc finger binding domains binds to a target DNA sequence that is at least 90%, 95%, 96%, 97%, 98%, or 99% identical, or is 100% identical to one of SEQ ID NOs: 814-1064.

In some embodiments, the gene-regulating system comprises two or more ZFP-fusion proteins each comprising a zinc finger binding domain, wherein at least one of the zinc finger binding domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the zinc finger binding domains binds to a target DNA sequence of the SOCS1 gene. In some embodiments, at least one of the two or more zinc finger binding domains binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the two or more zinc finger binding domains binds to a target DNA sequence that is at least 90%, 95%, 96%, 97%, 98%, or 99% identical, or is 100% identical to a target DNA sequence defined by a set of genomic coordinates shown in Table 6C or Table 6D. In some embodiments, at least one of the two or more zinc finger binding domains binds to a target DNA sequence that is at least 90%, 95%, 96%, 97%, 98%, or 99% identical, or is 100% identical to one of SEQ ID NOs: 154-498 or SEQ ID NOs: 499-813 and at least one of the two or more zinc finger binding domains binds to a target DNA sequence that is at least 90%, 95%, 96%, 97%, 98%, or 99% identical, or is 100% identical to one of SEQ ID NOs: 1088-1232.

In some embodiments, the gene-regulating system comprises two or more ZFP-fusion proteins each comprising a zinc finger binding domain, wherein at least one of the zinc finger binding domains binds to a target DNA sequence a target gene of the CBLB gene and at least one of the zinc finger binding domains binds to a target DNA sequence of the SOCS1 gene. In some embodiments, at least one of the two or more zinc finger binding domains binds to a target DNA sequence that is at least 90%, 95%, 96%, 97%, 98%, or 99% identical, or is 100% identical to one of SEQ ID NOs: 499-524 and at least one of the two or more zinc finger binding domains binds to a target DNA sequence that is at least 90%, 95%, 96%, 97%, 98%, or 99% identical, or is 100% identical to one of SEQ ID NOs: 1088-1232.

In some embodiments, the gene-regulating system comprises two or more ZFP-fusion proteins each comprising a zinc finger binding domain, wherein at least one of the zinc finger binding domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the zinc finger binding domains binds to a target DNA sequence of the ANKRD11 gene. In some embodiments, at least one of the two or more zinc finger binding domains binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the two or more zinc finger binding domains binds to a target DNA sequence that is at least 90%, 95%, 96%, 97%, 98%, or 99% identical, or is 100% identical to a target DNA sequence defined by a set of genomic coordinates shown in Table 6D or Table 6E. In some embodiments, at least one of the two or more zinc finger binding domains binds to a target DNA sequence that is at least 90%, 95%, 96%, 97%, 98%, or 99% identical, or is 100% identical to one of SEQ ID NOs: 154-498 or SEQ ID NOs: 499-813 and at least one of the two or more zinc finger binding domains binds to a target DNA sequence that is at least 90%, 95%, 96%, 97%, 98%, or 99% identical, or is 100% identical to one of SEQ ID NOs: 1065-1087.

In some embodiments, the gene-regulating system comprises two or more ZFP-fusion proteins each comprising a zinc finger binding domain, wherein at least one of the zinc finger binding domains binds to a target DNA sequence the CBLB gene selected and at least one of the zinc finger binding domains binds to a target DNA sequence of the ANKRD11 gene. In some embodiments, at least one of the two or more zinc finger binding domains binds to a target DNA sequence that is at least 90%, 95%, 96%, 97%, 98%, or 99% identical, or is 100% identical to one of SEQ ID NOs: 499-524 and at least one of the two or more zinc finger binding domains binds to a target DNA sequence that is at least 90%, 95%, 96%, 97%, 98%, or 99% identical, or is 100% identical to one of SEQ ID NOs: 1065-1087.

The enzymatic domain portion of the zinc finger fusion proteins can be obtained from any endo- or exonuclease. Exemplary endonucleases from which an enzymatic domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., 51 Nuclease; mung bean nuclease; pancreatic DNaseI; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains.

In some embodiments, the gene-regulating system comprises two or more ZFP-fusion proteins each comprising a zinc finger binding domain, wherein at least one of the zinc finger binding domains binds to a target DNA sequence of SOCS1 and wherein at least one of the zinc finger binding domains binds to a target DNA sequence of ANKRD11. In some embodiments, at least one of the two or more zinc finger binding domains binds to a target DNA sequence that is at least 90%, 95%, 96%, 97%, 98%, or 99% identical, or is 100% identical to a target DNA sequence defined by a set of genomic coordinates shown in Table 6C or Table 6D and at least one of the two or more zinc finger binding domains binds to a target DNA sequence that is at least 90%, 95%, 96%, 97%, 98%, or 99% identical, or is 100% identical to a target DNA sequence defined by a set of genomic coordinates shown in Table 6E or Table 6F. In some embodiments, at least one of the two or more zinc finger binding domains binds to a target DNA sequence that is at least 90%, 95%, 96%, 97%, 98%, or 99% identical, or is 100% identical to one of SEQ ID NOs: 1088-1232 and at least one of the two or more zinc finger binding domains binds to a target DNA sequence that is at least 90%, 95%, 96%, 97%, 98%, or 99% identical, or is 100% identical to one of SEQ ID NOs: 1065-1087.

Exemplary restriction endonucleases (restriction enzymes) suitable for use as an enzymatic domain of the ZFPs described herein are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269: 31,978-31,982. Thus, in one embodiment, fusion proteins comprise the enzymatic domain from at least one Type IIS restriction enzyme and one or more zinc finger binding domains.

An exemplary Type IIS restriction enzyme, whose cleavage domain is separable from the binding domain, is FokI. This particular enzyme is active as a dimer. Bitinaite et al. (1998) Proc. Natl. Acad. Sci. USA 95: 10,570-10,575. Thus, for targeted double-stranded DNA cleavage using zinc finger-FokI fusions, two fusion proteins, each comprising a FokI enzymatic domain, can be used to reconstitute a catalytically active cleavage domain. Alternatively, a single polypeptide molecule containing a zinc finger binding domain and two FokI enzymatic domains can also be used. Exemplary ZFPs comprising FokI enzymatic domains are described in U.S. Pat. No. 9,782,437.

2. TALEN systems

TALEN-based systems comprise a protein comprising a TAL effector DNA binding domain and an enzymatic domain. They are made by fusing a TAL effector DNA-binding domain to a DNA cleavage domain (a nuclease which cuts DNA strands). The FokI restriction enzyme described above is an exemplary enzymatic domain suitable for use in TALEN-based gene-regulating systems.

TAL effectors are proteins that are secreted by *Xanthomonas* bacteria via their type III secretion system when they infect plants. The DNA binding domain contains a repeated, highly conserved, 33-34 amino acid sequence with divergent 12th and 13th amino acids. These two positions, referred to as the Repeat Variable Diresidue (RVD), are highly variable and strongly correlated with specific nucleotide recognition. Therefore, the TAL effector domains can be engineered to bind specific target DNA sequences by selecting a combination of repeat segments containing the appropriate RVDs. The nucleic acid specificity for RVD combinations is as follows: HD targets cytosine, NI targets adenine, NG targets thymine, and NN targets guanine (though, in some embodiments, NN can also bind adenine with lower specificity).

In some embodiments, the TAL effector domains bind to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., a gene selected from Table 2). In some embodiments, the TAL effector domains bind to a target DNA sequence that is at least 90%, 95%, 96%, 97%, 98%, or 99% identical, or is 100% identical to a target DNA sequence defined by a set of genomic coordinates shown in Table 5A or Table 5B. In some embodiments, the TAL effector domains bind to a target DNA sequence that is at least 90%, 95%, 96%, 97%, 98%, or 99% identical, or is 100% identical to one of SEQ ID NOs: 154-498 or SEQ ID NOs: 499-813. In some embodiments, the TAL effector domains bind to a target DNA sequence that is at least 90%, 95%, 96%, 97%, 98%, or 99% identical, or is 100% identical to a target DNA sequence of the CBLB gene. In some embodiments, the TAL effector domains bind to a target DNA sequence that is at least 90%, 95%, 96%, 97%, 98%, or 99% identical, or is 100% identical to one of SEQ ID NOs: 499-524. In some embodiments, the TAL effector domains bind to a target DNA sequence that is at least 90%, 95%, 96%, 97%, 98%, or 99% identical, or is 100% identical to a target DNA sequence of the BCOR gene, and bind to a target DNA sequence that is at least 90%, 95%, 96%, 97%, 98%, or 99% identical, or is 100% identical to one of SEQ ID NOs: 708-772 or SEQ ID NOs: 708-764. In some embodiments, the TAL effector domains bind to a target DNA sequence that is at least 90%, 95%, 96%, 97%, 98%, or 99% identical, or is 100% identical to a target DNA sequence of the TNFAIP3, bind to a target DNA sequence that is at least 90%, 95%, 96%, 97%, 98%, or 99% identical, or is 100% identical to one of SEQ ID NOs: 348-396 or SEQ ID NOs: 348-386.

In some embodiments, the TAL effector domains bind to a target DNA sequence that is at least 90%, 95%, 96%, 97%, 98%, or 99% identical, or is 100% identical to a target DNA sequence of a target gene selected from BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 (e.g., a gene selected from Table 3). In some embodiments, the TAL effector domains bind to a target DNA sequence that is at least 90%, 95%, 96%, 97%, 98%, or 99% identical, or is 100% identical to a target DNA sequence defined by a set of genomic coordinates shown in one of Tables 6A-Table 6F. In some embodiments, the TAL effector domains bind to a target DNA sequence that is at least 90%, 95%, 96%, 97%, 98%, or 99% identical, or is 100% identical to one of SEQ ID NOs: 814-1232.

In some embodiments, the TAL effector domains bind to a target DNA sequence that is at least 90%, 95%, 96%, 97%, 98%, or 99% identical, or is 100% identical to a target DNA sequence of a target gene selected from BCL2L11, FL11, CALM2, DHODH, UMPS, RBM39, SEMA7A, CHIC2, PCBP1, PBRM1, WDR6, E2F8, SERPINA3, and GNAS. In some embodiments, the TAL effector domains bind to a target DNA sequence that is at least 90%, 95%, 96%, 97%, 98%, or 99% identical, or is 100% identical to a target DNA sequence defined by a set of genomic coordinates shown in Table 6A or Table 6B. In some embodiments, the TAL effector domains bind to a target DNA sequence that is at least 90%, 95%, 96%, 97%, 98%, or 99% identical, or is 100% identical to one of SEQ ID NOs: 814-1064.

In some embodiments, the TAL effector domains bind to a target DNA sequence that is at least 90%, 95%, 96%, 97%, 98%, or 99% identical, or is 100% identical to a target DNA sequence of the SOCS1 gene. In some embodiments, the TAL effector domains bind to a target DNA sequence that is at least 90%, 95%, 96%, 97%, 98%, or 99% identical, or is 100% identical to a target DNA sequence defined by a set of genomic coordinates shown in Table 6C or Table 6D. In some embodiments, the TAL effector domains bind to a target DNA sequence that is at least 90%, 95%, 96%, 97%, 98%, or 99% identical, or is 100% identical to one of SEQ ID NOs: 1088-1232. In some embodiments, the TAL effector domains bind to a target DNA sequence that is at least 90%, 95%, 96%, 97%, 98%, or 99% identical, or is 100% identical to a target DNA sequence of the ANKRD11 gene. In some embodiments, the TAL effector domains bind to a target DNA sequence that is at least 90%, 95%, 96%, 97%, 98%, or 99% identical, or is 100% identical to a target DNA sequence defined by a set of genomic coordinates shown in Table 6E or Table 6F. In some embodiments, the TAL effector domains bind to a target DNA sequence that is at least 90%, 95%, 96%, 97%, 98%, or 99% identical, or is 100% identical to one of SEQ ID NOs: 1065-1087.

In some embodiments, the gene-regulating system comprises two or more TAL effector-fusion proteins each comprising a TAL effector domain, wherein at least one of the TAL effector domains binds to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the TAL effector domains binds to a target DNA sequence that is at least 90%, 95%, 96%, 97%, 98%, or 99% identical, or is 100% identical to a target DNA sequence of a target gene selected from BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11. In some embodiments, at least one of the TAL effector domains binds to a target DNA sequence that is at least 90%, 95%, 96%, 97%, 98%, or 99% identical, or 100% identical to a target DNA sequence defined by a set of genomic coordinates shown in Table 5A or Table 5B and at least one of the TAL effector domains binds to a target DNA sequence that is at least 90%, 95%, 96%, 97%, 98%, or 99% identical, or 100% identical to a target DNA sequence defined by a set of genomic coordinates shown in one of Tables 6A-Table 6F. In some embodiments, at least one of the TAL effector domains binds to a target DNA sequence that is at least 90%, 95%, 96%, 97%, 98%, or 99% identical, or is 100% identical to one of SEQ ID NOs: 154-498 or SEQ ID NOs: 499-813 and at least one of the TAL effector domains binds to a target DNA sequence that is at least 90%, 95%, 96%, 97%, 98%, or 99% identical, or is 100% identical to one of SEQ ID NOs: 814-1232.

In some embodiments, the gene-regulating system comprises two or more TAL effector-fusion proteins each comprising a TAL effector domain, wherein at least one of the TAL effector domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the TAL effector domains binds to a target DNA sequence of a target gene selected from BCL2L11, FL11, CALM2, DHODH, UMPS, RBM39, SEMA7A, CHIC2, PCBP1, PBRM1, WDR6, E2F8, SERPINA3, and GNAS. In some embodiments, at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the two or more TAL effector domains binds to a target DNA sequence that is at least 90% 95%, 96%, 97%, 98%, or 99% identical, or 100% identical to a target DNA sequence defined by a set of genomic coordinates shown in Table 6A or Table 6B. In some embodiments, at least one of the two or more TAL effector domains binds to a target DNA sequence that is at least 90%, 95%, 96%, 97%, 98%, or 99% identical, or is 100% identical to one of SEQ ID NOs: 154-498 or SEQ ID NOs: 499-813 and at least one of the two or more TAL effector domains binds to a target DNA sequence that is at least 90%, 95%, 96%, 97%, 98%, or 99% identical, or 100% identical to one of SEQ ID NOs: 814-1064.

In some embodiments, the gene-regulating system comprises two or more TAL effector-fusion proteins each comprising a TAL effector domain, wherein at least one of the TAL effector domains binds to a target DNA sequence of the CBLB gene and at least one of the TAL effector domains binds to a target DNA sequence of a target gene selected from BCL2L11, FL11, CALM2, DHODH, UMPS, RBM39, SEMA7A, CHIC2, PCBP1, PBRM1, WDR6, E2F8, SERPINA3, and GNAS. In some embodiments, at least one of the two or more TAL effector domains binds to a target DNA sequence that is at least 90%, 95%, 96%, 97%, 98%, or 99% identical, or is 100% identical to one of SEQ ID NOs: 499-524 and at least one of the two or more TAL effector domains binds to a target DNA sequence that is at least 90%, 95%, 96%, 97%, 98%, or 99% identical, or is 100% identical to one of SEQ ID NOs: 814-1064.

In some embodiments, the gene-regulating system comprises two or more TAL effector-fusion proteins each comprising a TAL effector domain, wherein at least one of the TAL effector domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the TAL effector domains binds to a target DNA sequence of the SOCS1 gene. In some embodiments, at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 6C or Table 6D. In some embodiments, at least one of the two or more TAL effector domains binds to a target DNA sequence that is at least 90%, 95%, 96%, 97%, 98%, or 99% identical, or is 100% identical to one of SEQ ID NOs: 154-498 or SEQ ID NOs: 499-813 and at least one of the two or more TAL effector domains binds to a target DNA sequence that is at least 90%, 95%, 96%, 97%, 98%, or 99% identical, or is 100% identical to one of SEQ ID NOs: 1088-1232.

In some embodiments, the gene-regulating system comprises two or more TAL effector-fusion proteins each comprising a TAL effector domain, wherein at least one of the TAL effector domains binds to a target DNA sequence of the CBLB and at least one of the TAL effector domains binds to a target DNA sequence of the SOCS1 gene. In some embodiments, at least one of the two or more TAL effector domains binds to a target DNA sequence that is at least 90%, 95%, 96%, 97%, 98%, or 99% identical, or is 100% identical to one of SEQ ID NOs: 499-524 and at least one of the two or more TAL effector domains binds to a target DNA sequence that is at least 90%, 95%, 96%, 97%, 98%, or 99% identical, or is 100% identical to one of SEQ ID NOs: 1088-1232.

In some embodiments, the gene-regulating system comprises two or more TAL effector-fusion proteins each comprising a TAL effector domain, wherein at least one of the TAL effector domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the TAL effector domains binds to a target DNA sequence of the ANKRD11 gene. In some embodiments, at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 6D or Table 6E. In some embodiments, at least one of the two or more TAL effector domains binds to a target DNA sequence that is at least 90%, 95%, 96%, 97%, 98%, or 99% identical, or is 100% identical to one of SEQ ID NOs: 154-498 or SEQ ID NOs: 499-813 and at least one of the two or more TAL effector domains binds to a target DNA sequence that is at least 90%, 95%, 96%, 97%, 98%, or 99% identical, or is 100% identical to one of SEQ ID NOs: 1065-1087.

In some embodiments, the gene-regulating system comprises two or more TAL effector-fusion proteins each comprising a TAL effector domain, wherein at least one of the TAL effector domains binds to a target DNA sequence of the CBLB gene selected and at least one of the TAL effector domains binds to a target DNA sequence of the ANKRD11 gene. In some embodiments, at least one of the two or more TAL effector domains binds to a target DNA sequence that is at least 90%, 95%, 96%, 97%, 98%, or 99% identical, or is 100% identical to one of SEQ ID NOs: 499-524 and at least one of the two or more TAL effector domains binds to a target DNA sequence that is at least 90%, 95%, 96%, 97%, 98%, or 99% identical, or is 100% identical to one of SEQ ID NOs: 1065-1087.

In some embodiments, the gene-regulating system comprises two or more TAL effector-fusion proteins each comprising a TAL effector domain, wherein at least one of the TAL effector domains binds to a target DNA sequence of the SOCS1 gene at least one of the TAL effector domains binds to a target DNA sequence of the ANKRD11 gene. In some embodiments, at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 6C or Table 6D and at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 6E or Table 6F. In some embodiments, at least one of the two or more TAL effector domains binds to a target DNA sequence that is at least 90%, 95%, 96%, 97%, 98%, or 99% identical, or is 100% identical to one of SEQ ID NOs: 1088-1232 and at least one of the two or more TAL effector domains binds to a target DNA sequence that is at least 90%, 95%, 96%, 97%, 98%, or 99% identical, or is 100% identical to one of SEQ ID NOs: 1065-1087.

Methods and compositions for assembling the TAL-effector repeats are known in the art. See e.g., Cermak et al, Nucleic Acids Research, 39:12, 2011, e82. Plasmids for constructions of the TAL-effector repeats are commercially available from Addgene.

C. Combination Nucleic Acid/Protein-Based Gene-Regulating Systems

Combination gene-regulating systems comprise a site-directed modifying polypeptide and a nucleic acid guide molecule. Herein, a "site-directed modifying polypeptide" refers to a polypeptide that binds to a nucleic acid guide molecule, is targeted to a target nucleic acid sequence, (for example, an endogenous target DNA or RNA sequence) by the nucleic acid guide molecule to which it is bound, and modifies the target nucleic acid sequence (e.g., by cleavage, mutation, or methylation of the target nucleic acid sequence).

A site-directed modifying polypeptide comprises two portions, a portion that binds the nucleic acid guide and an activity portion. In some embodiments, a site-directed modifying polypeptide comprises an activity portion that exhibits site-directed enzymatic activity (e.g., DNA methylation, DNA or RNA cleavage, histone acetylation, histone methylation, etc.), wherein the site of enzymatic activity is determined by the guide nucleic acid. In some cases, a site-directed modifying polypeptide comprises an activity portion that has enzymatic activity that modifies the endogenous target nucleic acid sequence(e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity). In other cases, a site-directed modifying polypeptide comprises an activity portion that has enzymatic activity that modifies a polypeptide (e.g., a histone) associated with the endogenous target nucleic acid sequence (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosy-lation activity, myristoylation activity or demyristoylation activity). In some embodiments, a site-directed modifying polypeptide comprises an activity portion that modulates transcription of a target DNA sequence (e.g., to increase or decrease transcription). In some embodiments, a site-directed modifying polypeptide comprises an activity portion that modulates expression or translation of a target RNA sequence (e.g., to increase or decrease transcription).

The nucleic acid guide comprises two portions: a first portion that is complementary to, and capable of binding with, an endogenous target nucleic sequence (referred to herein as a "nucleic acid-binding segment"), and a second portion that is capable of interacting with the site-directed modifying polypeptide (referred to herein as a "protein-binding segment"). In some embodiments, the nucleic acid-binding segment and protein-binding segment of a nucleic acid guide are comprised within a single polynucleotide molecule. In some embodiments, the nucleic acid-binding segment and protein-binding segment of a nucleic acid guide are each comprised within separate polynucleotide molecules, such that the nucleic acid guide comprises two polynucleotide molecules that associate with each other to form the functional guide.

The nucleic acid guide mediates the target specificity of the combined protein/nucleic acid gene-regulating systems by specifically hybridizing with a target nucleic acid sequence. In some embodiments, the target nucleic acid sequence is an RNA sequence, such as an RNA sequence comprised within an mRNA transcript of a target gene. In some embodiments, the target nucleic acid sequence is a DNA sequence comprised within the DNA sequence of a target gene. Reference herein to a target gene encompasses the full-length DNA sequence for that particular gene which comprises a plurality of target genetic loci (i.e., portions of a particular target gene sequence (e.g., an exon or an intron)). Within each target genetic loci are shorter stretches of DNA sequences referred to herein as "target DNA sequences" that can be modified by the gene-regulating systems described herein. Further, each target genetic loci comprises a "target modification site," which refers to the precise location of the modification induced by the gene-regulating system (e.g., the location of an insertion, a deletion, or mutation, the location of a DNA break, or the location of an epigenetic modification).

The gene-regulating systems described herein may comprise a single nucleic acid guide, or may comprise a plurality of nucleic acid guides (e.g., 2, 3, 4, 5, 6, 7, 8, 9, 10, or more nucleic acid guides).

In some embodiments, the combined protein/nucleic acid gene-regulating systems comprise site-directed modifying polypeptides derived from Argonaute (Ago) proteins (e.g., T thermophiles Ago or TtAgo). In such embodiments, the site-directed modifying polypeptide is a T. thermophiles Ago DNA endonuclease and the nucleic acid guide is a guide DNA (gDNA) (See, Swarts et al., Nature 507 (2014), 258-261). In some embodiments, the present disclosure provides a polynucleotide encoding a gDNA. In some embodiments, a gDNA-encoding nucleic acid is comprised in an expression vector, e.g., a recombinant expression vector. In some embodiments, the present disclosure provides a polynucleotide encoding a TtAgo site-directed modifying polypeptide or variant thereof In some embodiments, the polynucleotide encoding a TtAgo site-directed modifying polypeptide is comprised in an expression vector, e.g., a recombinant expression vector.

In some embodiments, the gene editing systems described herein are CRISPR (Clustered Regularly Interspaced Short Palindromic Repeats)/Cas (CRISPR Associated) nuclease systems. In some embodiments, the CRISPR/Cas system is a Class 2 system. Class 2 CRISPR/Cas systems are divided into three types: Type II, Type V, and Type VI systems. In some embodiments, the CRISPR/Cas system is a Class 2 Type II system, utilizing the Cas9 protein. In such embodiments, the site-directed modifying polypeptide is a Cas9 DNA endonuclease (or variant thereof) and the nucleic acid guide molecule is a guide RNA (gRNA). In some embodiments, the CRISPR/Cas system is a Class 2 Type V system, utilizing the Cas12 proteins (e.g., Cas12a (also known as Cpf1), Cas12b (also known as C2c1), Cas12c (also known as C2c3), Cas12d (also known as CasY), and Cas12e (also known as CasX)). In such embodiments, the site-directed modifying polypeptide is a Cas12 DNA endonuclease (or variant thereof) and the nucleic acid guide molecule is a gRNA. In some embodiments, the CRISPR/Cas system is a Class 2 and Type VI system, utilizing the Cas13 proteins (e.g., Cas13a (also known as C2c2), Cas13b, and Cas13c). (See, Pyzocha et al., ACS Chemical Biology, 13(2), 347-356). In such embodiments, the site-directed modifying polypeptide is a Cas13 RNA riboendonuclease and the nucleic acid guide molecule is a gRNA.

A Cas polypeptide refers to a polypeptide that can interact with a gRNA molecule and, in concert with the gRNA molecule, home or localize to a target DNA or target RNA sequence. Cas polypeptides include naturally occurring Cas proteins and engineered, altered, or otherwise modified Cas proteins that differ by one or more amino acid residues from a naturally-occurring Cas sequence.

A guide RNA (gRNA) comprises two segments, a DNA-binding segment and a protein-binding segment. In some embodiments, the protein-binding segment of a gRNA is comprised in one RNA molecule and the DNA-binding segment is comprised in another separate RNA molecule. Such embodiments are referred to herein as "double-molecule gRNAs" or "two-molecule gRNA" or "dual gRNAs." In some embodiments, the gRNA is a single RNA molecule and is referred to herein as a "single-guide RNA" or an "sgRNA." The term "guide RNA" or "gRNA" is inclusive, referring both to two-molecule guide RNAs and sgRNAs.

The protein-binding segment of a gRNA comprises, in part, two complementary stretches of nucleotides that hybridize to one another to form a double stranded RNA duplex (dsRNA duplex), which facilitates binding to the Cas protein. The nucleic acid-binding segment (or "nucleic acid-binding sequence") of a gRNA comprises a nucleotide sequence that is complementary to and capable of binding to a specific target nucleic acid sequence sequence. The protein-binding segment of the gRNA interacts with a Cas polypeptide and the interaction of the gRNA molecule and site-directed modifying polypeptide results in Cas binding to the endogenous nucleic acid sequence and produces one or more modifications within or around the target nucleic acid sequence. The precise location of the target modification site is determined by both (i) base-pairing complementarity between the gRNA and the target nucleic acid sequence; and (ii) the location of a short motif, referred to as the protospacer adjacent motif (PAM), in the target DNA sequence (referred to as a protospacer flanking sequence (PFS) in target RNA sequences). The PAM/PFS sequence is required for Cas binding to the target nucleic acid sequence. A variety of PAM/PFS sequences are known in the art and are suitable for use with a particular Cas endonuclease (e.g., a Cas9 endonuclease)(See e.g., Nat Methods. 2013 November; 10(11): 1116-1121 and Sci Rep. 2014; 4: 5405). In some embodiments, the PAM sequence is located within 50 base pairs of the target modification site in a target DNA sequence. In some embodiments, the PAM sequence is located within 10 base pairs of the target modification site in a target DNA sequence. The DNA sequences that can be targeted by this method are limited only by the relative distance of the PAM sequence to the target modification site and the presence of a unique 20 base pair sequence to mediate sequence-specific, gRNA-mediated Cas binding. In some embodiments, the PFS sequence is located at the 3' end of the target RNA sequence. In some embodiments, the target modification site is located at the 5' terminus of the target locus. In some embodiments, the target modification site is located at the 3' end of the target locus. In some embodiments, the target modification site is located within an intron or an exon of the target locus.

In some embodiments, the present disclosure provides a polynucleotide encoding a gRNA. In some embodiments, a gRNA-encoding nucleic acid is comprised in an expression vector, e.g., a recombinant expression vector. In some embodiments, the present disclosure provides a polynucleotide encoding a site-directed modifying polypeptide. In some embodiments, the polynucleotide encoding a site-directed modifying polypeptide is comprised in an expression vector, e.g., a recombinant expression vector. 1. Cas proteins In some embodiments, the site-directed modifying polypeptide is a Cas protein. Cas molecules of a variety of species can be used in the methods and compositions described herein, including Cas molecules derived from *S. pyogenes, S. aureus, N. meningitidis*, S. thermophiles, Acidovorax avenae, Actinobacillus pleuropneumoniae, Actinobacillus succinogenes, Actinobacillus suis, Actinomyces sp., Cycliphilusdenitrificans, Aminomonaspaucivorans, *Bacillus cereus, Bacillus smithii, Bacillus thuringiensis, Bacteroides* sp., Blastopirellula marina, *Bradyrhizobium* sp., *Brevibacillus* laterospoxus, *Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium* dolichum, Gammaproteobacterium, *Gluconacetobacter diazotrophicus, Haemophilus parainfluenzae, Haemophilus sputomm, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea*, Neisseriaflavescens, *Neisseria* lactamica, *Neisseria meningitidis, Neisseria* sp., *Neisseria* wadsworthii, *Nitrosomonas* sp., Parvibaculum lavamentivorans, *Pasteurella multocida, Phascolarctobacterium succinatutens, Ralstonia syzygii, Rhodopseudomonas palustris*, Rhodovulum sp., Simonsiella *muelleri, Sphingomonas* sp., Sporolactobacillus vineae, *Staphylococcus aureus, Staphylococcus lugdunensis, Streptococcus* sp., Subdoligranulum sp., *Tistrella mobilis, Treponema* sp., or Verminephrobacter eiseniae.

In some embodiments, the Cas protein is a naturally-occurring Cas protein. In some embodiments, the Cas endonuclease is selected from the group consisting of C2C1, C2C3, Cpf1 (also referred to as Cas12a), Cas12b, Cas12c, Cas12d, Cas12e, Cas13a, Cas13b, Cas13c, Cas13d, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

In some embodiments, the Cas protein is an endoribonuclease such as a Cas13 protein. In some embodiments, the Cas13 protein is a Cas13a (Abudayyeh et al., Nature 550 (2017), 280-284), Cas13b (Cox et al., Science (2017) 358: 6336, 1019-1027), Cas13c (Cox et al., Science (2017) 358:6336, 1019-1027), or Cas13d (Zhang et al., Cell 175 (2018), 212-223) protein.

In some embodiments, the Cas protein is a wild-type or naturally occurring Cas9 protein or a Cas9 ortholog. Wild-type Cas9 is a multi-domain enzyme that uses an HNH nuclease domain to cleave the target strand of DNA and a RuvC-like domain to cleave the non-target strand. Binding of WT Cas9 to DNA based on gRNA specificity results in double-stranded DNA breaks that can be repaired by non-homologous end joining (NHEJ) or homology-directed repair (HDR). Exemplary naturally occurring Cas9 molecules are described in Chylinski et al., RNA Biology 2013 10:5, 727-737 and additional Cas9 orthologs are described in International PCT Publication No. WO 2015/071474. Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 11 bacterial family, a cluster 12 bacterial family, a cluster 13 bacterial family, a cluster 14 bacterial family, a cluster 15 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

In some embodiments, the naturally occurring Cas9 polypeptide is selected from the group consisting of SpCas9, SpCas9-HF1, SpCas9-HF2, SpCas9-HF3, SpCas9-HF4, SaCas9, FnCpf, FnCas9, eSpCas9, and NmeCas9. In some embodiments, the Cas9 protein comprises an amino acid sequence having at least 60%, 65%, 70%, 75%, 80%, 85%, 90%, 95%, 96%, 97%, 98%, 99%, or 100% sequence identity to a Cas9 amino acid sequence described in Chylinski et al., RNA Biology 2013 10:5, 727-737; Hou et al., PNAS Early Edition 2013, 1-6).

In some embodiments, the Cas polypeptide comprises one or more of the following activities:
(a) a nickase activity, i.e., the ability to cleave a single strand, e.g., the non-complementary strand or the complementary strand, of a nucleic acid molecule;
(b) a double stranded nuclease activity, i.e., the ability to cleave both strands of a double stranded nucleic acid and create a double stranded break, which in an embodiment is the presence of two nickase activities;
(c) an endonuclease activity;
(d) an exonuclease activity; and/or
(e) a helicase activity, i.e., the ability to unwind the helical structure of a double stranded nucleic acid.

In some embodiments, the Cas polypeptide is fused to heterologous proteins that recruit DNA-damage signaling proteins, exonucleases, or phosphatases to further increase the likelihood or the rate of repair of the target sequence by one repair mechanism or another. In some embodiments, a WT Cas polypeptide is co-expressed with a nucleic acid repair template to facilitate the incorporation of an exogenous nucleic acid sequence by homology-directed repair.

In some embodiments, different Cas proteins (i.e., Cas9 proteins from various species) may be advantageous to use in the various provided methods in order to capitalize on various enzymatic characteristics of the different Cas proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.).

In some embodiments, the Cas protein is a Cas9 protein derived from *S. pyogenes* and recognizes the PAM sequence motif NGG, NAG, NGA (*Mali* et al, Science 2013; 339 (6121): 823-826). In some embodiments, the Cas protein is a Cas9 protein derived from S. thermophiles and recognizes the PAM sequence motif NGGNG and/or NNAGAAW (W=A or T) (See, e.g., Horvath et al, Science, 2010; 327 (5962): 167-170, and Deveau et al, J Bacteriol 2008; 190(4): 1390-1400). In some embodiments, the Cas protein is a Cas9 protein derived from *S. mutans* and recognizes the PAM sequence motif NGG and/or NAAR (R=A or G) (See, e.g., Deveau et al, J BACTERIOL 2008; 190(4): 1390-1400). In some embodiments, the Cas protein is a Cas9 protein derived from *S. aureus* and recognizes the PAM sequence motif NNGRR (R=A or G). In some embodiments, the Cas protein is a Cas9 protein derived from *S. aureus* and recognizes the PAM sequence motif N GRRT (R=A or G). In some embodiments, the Cas protein is a Cas9 protein derived from *S. aureus* and recognizes the PAM sequence motif N GRRV (R=A or G). In some embodiments, the Cas protein is a Cas9 protein derived from *N. meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the Cas protein is a Cas13a protein derived from Leptotrichia shahii and recognizes the PFS sequence motif of a single 3' A, U, or C.

In some embodiments, a polynucleotide encoding a Cas protein is provided. In some embodiments, the polynucleotide encodes a Cas protein that is at least 90% identical to a Cas protein described in International PCT Publication No. WO 2015/071474 or Chylinski et al., RNA Biology 2013

10:5, 727-737. In some embodiments, the polynucleotide encodes a Cas protein that is at least 95%, 96%, 97%, 98%, or 99% identical to a Cas protein described in International PCT Publication No. WO 2015/071474 or Chylinski et al., RNA Biology 2013 10:5, 727-737. In some embodiments, the polynucleotide encodes a Cas protein that is 100% identical to a Cas protein described in International PCT Publication No. WO 2015/071474 or Chylinski et al., RNA Biology 2013 10:5, 727-737.

2. Cas Mutants

In some embodiments, the Cas polypeptides are engineered to alter one or more properties of the Cas polypeptide. For example, in some embodiments, the Cas polypeptide comprises altered enzymatic properties, e.g., altered nuclease activity, (as compared with a naturally occurring or other reference Cas molecule) or altered helicase activity. In some embodiments, an engineered Cas polypeptide can have an alteration that alters its size, e.g., a deletion of amino acid sequence that reduces its size without significant effect on another property of the Cas polypeptide. In some embodiments, an engineered Cas polypeptide comprises an alteration that affects PAM recognition. For example, an engineered Cas polypeptide can be altered to recognize a PAM sequence other than the PAM sequence recognized by the corresponding wild-type Cas protein.

Cas polypeptides with desired properties can be made in a number of ways, including alteration of a naturally occurring Cas polypeptide or parental Cas polypeptide, to provide a mutant or altered Cas polypeptide having a desired property. For example, one or more mutations can be introduced into the sequence of a parental Cas polypeptide (e.g., a naturally occurring or engineered Cas polypeptide). Such mutations and differences may comprise substitutions (e.g., conservative substitutions or substitutions of non-essential amino acids); insertions; or deletions. In some embodiments, a mutant Cas polypeptide comprises one or more mutations (e.g., at least 1, 2, 3, 4, 5, 10, 15, 20, 30, 40 or 50 mutations) relative to a parental Cas polypeptide.

In an embodiment, a mutant Cas polypeptide comprises a cleavage property that differs from a naturally occurring Cas polypeptide. In some embodiments, the Cas is a deactivated Cas (dCas) mutant. In such embodiments, the Cas polypeptide does not comprise any intrinsic enzymatic activity and is unable to mediate target nucleic acid cleavage. In such embodiments, the dCas may be fused with a heterologous protein that is capable of modifying the target nucleic acid in a non-cleavage based manner. For example, in some embodiments, a dCas protein is fused to transcription activator or transcription repressor domains (e.g., the Kruppel associated box (KRAB or SKD); the Mad mSIN3 interaction domain (SID or SID4X); the ERF repressor domain (ERD); the MAX-interacting protein 1 (MX11); methyl-CpG binding protein 2 (MECP2); etc.). In some such cases, the dCas fusion protein is targeted by the ggRNA to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target DNA or modifies a polypeptide associated with the target DNA). In some cases, the changes are transient (e.g., transcription repression or activation). In some cases, the changes are inheritable (e.g., when epigenetic modifications are made to the target DNA or to proteins associated with the target DNA, e.g., nucleosomal histones).

In some embodiments, the dCas is a dCas13 mutant (Konermann et al., Cell 173 (2018), 665-676). These dCas13 mutants can then be fused to enzymes that modify RNA, including adenosine deaminases (e.g., ADAR1 and ADAR2). Adenosine deaminases convert adenine to inosine, which the translational machinery treats like guanine, thereby creating a functional A→G change in the RNA sequence. In some embodiments, the dCas is a dCas9 mutant.

In some embodiments, the mutant Cas9 is a Cas9 nickase mutant. Cas9 nickase mutants comprise only one catalytically active domain (either the HNH domain or the RuvC domain). The Cas9 nickase mutants retain DNA binding based on gRNA specificity, but are capable of cutting only one strand of DNA resulting in a single-strand break (e.g. a "nick"). In some embodiments, two complementary Cas9 nickase mutants (e.g., one Cas9 nickase mutant with an inactivated RuvC domain, and one Cas9 nickase mutant with an inactivated HNH domain) are expressed in the same cell with two gRNAs corresponding to two respective target sequences; one target sequence on the sense DNA strand, and one on the antisense DNA strand. This dual-nickase system results in staggered double stranded breaks and can increase target specificity, as it is unlikely that two off-target nicks will be generated close enough to generate a double stranded break. In some embodiments, a Cas9 nickase mutant is co-expressed with a nucleic acid repair template to facilitate the incorporation of an exogenous nucleic acid sequence by homology-directed repair.

In some embodiments, the Cas polypeptides described herein can be engineered to alter the PAM/PFS specificity of the Cas polypeptide. In some embodiments, a mutant Cas polypeptide has a PAM/PFS specificity that is different from the PAM/PFS specificity of the parental Cas polypeptide. For example, a naturally occurring Cas protein can be modified to alter the PAM/PFS sequence that the mutant Cas polypeptide recognizes to decrease off target sites, improve specificity, or eliminate a PAM/PFS recognition requirement. In some embodiments, a Cas protein can be modified to increase the length of the PAM/PFS recognition sequence. In some embodiments, the length of the PAM recognition sequence is at least 4, 5, 6, 7, 8, 9, 10 or 15 amino acids in length. Cas polypeptides that recognize different PAM/PFS sequences and/or have reduced off-target activity can be generated using directed evolution. Exemplary methods and systems that can be used for directed evolution of Cas polypeptides are described, e.g., in Esvelt et al. Nature 2011, 472(7344): 499-503.

Exemplary Cas mutants are described in International PCT Publication No. WO 2015/161276 and Konermann et al., Cell 173 (2018), 665-676which are incorporated herein by reference in their entireties.

3. gRNAs

The present disclosure provides guide RNAs (gRNAs) that direct a site-directed modifying polypeptide to a specific target nucleic acid sequence. A gRNA comprises a "nucleic acid-targeting domain" or "targeting domain" and protein-binding segment. The targeting domain may also be referred to as a "spacer" sequence and comprises a nucleotide sequence that is complementary to a target nucleic acid sequence. As such, the targeting domain segment of a gRNA interacts with a target nucleic acid in a sequence-specific manner via hybridization (i.e., base pairing) and determines the location within the target nucleic acid that the gRNA will bind. The targeting domain segment of a gRNA can be modified (e.g., by genetic engineering) to hybridize to a desired sequence within a target nucleic acid sequence. In some embodiments, the targeting domain sequence is between about 13 and about 22 nucleotides in length. In some embodiments, the targeting domain sequence is about 13, 14, 15, 16, 17, 18, 19, 20, 21, or 22 nucleotides in length. In some embodiments, the targeting domain sequence is about 20 nucleotides in length.

The protein-binding segment of a gRNA interacts with a site-directed modifying polypeptide (e.g. a Cas protein) to form a ribonucleoprotein (RNP) complex comprising the gRNA and the site-directed modifying polypeptide. The targeting domain segment of the gRNA then guides the bound site-directed modifying polypeptide to a specific nucleotide sequence within target nucleic acid via the above-described spacer sequence. The protein-binding segment of a gRNA comprises at least two stretches of nucleotides that are complementary to one another and which form a double stranded RNA duplex. The protein-binding segment of a gRNA may also be referred to as a "scaffold" segment or a "tracr RNA". In some embodiments, the tracr RNA sequence is between about 30 and about 180 nucleotides in length. In some embodiments, the tracr RNA sequence is between about 40 and about 90 nucleotides, about 50 and about 90 nucleotides, about 60 and about 90 nucleotides, about 65 and about 85 nucleotides, about 70 and about 80 nucleotides, about 65 and about 75 nucleotides, or about 75 and about 85 nucleotides in length. In some embodiments, the tracr RNA sequence is about 70, 71, 72, 73, 74, 75, 76, 77, 78, 79, 80, 81, 82, 83, 84, 85, 86, 87, 88, or about 90 nucleotides in length. In some embodiments, the tracr RNA comprises a nucleic acid sequence encoded by the DNA sequence of SEQ ID NO: 34 (See *Mali* et al., Science (2013) 339(6121):823-826), SEQ ID NOs: 35-36 (See PCT Publication No. WO 2016/106236), SEQ ID NOs: 37-39 (See Deltcheva et al., Nature. 2011 Mar. 31; 471(7340): 602-607), or SEQ ID NO: 40 (See Chen et al., Cell 2013, 155(7); 1479-1491). Any of the foregoing tracr sequences are suitable for use in combination with any of the gRNA targeting domain embodiments described herein.

In some embodiments, a gRNA comprises two separate RNA molecules (i.e., a "dual gRNA"). In some embodiments, a gRNA comprises a single RNA molecule (i.e. a "single guide RNA" or "sgRNA"). Herein, use of the term "guide RNA" or "gRNA" is inclusive of both dual gRNAs and sgRNAs. A dual gRNA comprises two separate RNA molecules: a "crispr RNA" (or "crRNA") and a "tracr RNA". A crRNA molecule comprises a spacer sequence covalently linked to a "tracr mate" sequence. The tracer mate sequence comprises a stretch of nucleotides that are complementary to a corresponding sequence in the tracr RNA molecule. The crRNA molecule and tracr RNA molecule hybridize to one another via the complementarity of the tracr and tracer mate sequences.

In some embodiments, the gRNA is an sgRNA. In such embodiments, the nucleic acid-targeting sequence and the protein-binding sequence are present in a single RNA molecule by fusion of the spacer sequence to the tracr RNA sequence. In some embodiments, the sgRNA is about 50 to about 200 nucleotides in length. In some embodiments, the sgRNA is about 75 to about 150 or about 100 to about 125 nucleotides in length. In some embodiments, the sgRNA is about 100 nucleotides in length.

In some embodiments, the gRNAs of the present disclosure comprise a targeting domain sequence that is least 90%, 95%, 96%, 97%, 98%, or 99% complementary, or is 100% complementary to a target nucleic acid sequence within a target locus. In some embodiments, the target nucleic acid sequence is an RNA target sequence. In some embodiments, the target nucleic acid sequence is a DNA target sequence.

In some embodiments, the gRNAs provided herein comprise a targeting domain sequence that binds to a target DNA sequence that is at least 90%, 95%, 96%, 97%, 98%, or 99% identical, or is 100% identical to a sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., a gene selected from Table 2). In some embodiments, the targeting domain sequence binds to a target DNA sequence that is at least 90%, 95%, 96%, 97%, 98%, or 99% identical, or is 100% identical to a target DNA sequence defined by a set of genomic coordinates shown in Table 5A or Table 5B. In some embodiments, the targeting domain sequence binds to a target DNA sequence that is at least 90%, 95%, 96%, 97%, 98%, or 99% identical, or is 100% identical to one of SEQ ID NOs: 154-498 or SEQ ID NOs: 499-813. In some embodiments, the targeting domain sequence is encoded by a DNA sequence that is at least 90%, 95%, 96%, 97%, 98%, or 99% identical, or is 100% identical to one of SEQ ID NOs: 154-498 or SEQ ID NOs: 499-813.

In some embodiments, the gRNAs provided herein comprise a targeting domain sequence that binds to a target DNA sequence that is at least 90%, 95%, 96%, 97%, 98%, or 99% identical, or is 100% identical to a target DNA sequence of the CBLB gene. In some embodiments, the nucleic acid-binding segments of the gRNA sequences bind to a target DNA sequence that is at least 90%, 95%, 96%, 97%, 98%, or 99% identical, or is 100% identical to one of SEQ ID NOs: 499-524. In some embodiments, the nucleic acid-binding segment of the gRNA sequence is encoded by a DNA sequence that is at least 90%, 95%, 96%, 97%, 98%, or 99% identical, or is 100% identical to one of SEQ ID NOs: 499-524. Additional gRNAs suitable for targeting CBLB are described in US Patent Application Publication No. 2017/0175128.

In some embodiments, the gRNAs provided herein comprise a targeting domain sequence that binds to a target DNA sequence that is at least 90%, 95%, 96%, 97%, 98%, or 99% identical, or is 100% identical to a target DNA sequence of the TNFAIP3 gene. In some embodiments, the nucleic acid-binding segments of the gRNA sequences bind to a target DNA sequence that is at least 90%, 95%, 96%, 97%, 98%, or 99% identical, or is 100% identical to one of SEQ ID NOs: 348-396 or SEQ ID NOs: 348-386. In some embodiments, the gRNAs provided herein comprise a targeting domain sequence that binds to a target DNA sequence that is at least 90%, 95%, 96%, 97%, 98%, or 99% identical, or is 100% identical to a target DNA sequence of the BCOR gene. In some embodiments, the nucleic acid-binding segments of the gRNA sequences bind to a target DNA sequence that is at least 90%, 95%, 96%, 97%, 98%, or 99% identical, or is 100% identical to one of SEQ ID NOs: 708-772 or SEQ ID NOs: 708-764.

In some embodiments, the gRNAs provided herein comprise a targeting domain sequence that binds to a target DNA sequence that is at least 90%, 95%, 96%, 97%, 98%, or 99% identical, or is 100% identical to a sequence of a target gene selected from BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 (e.g., a gene selected from Table 3). In some embodiments, the targeting domain sequence binds to a target DNA sequence that is at least 90%, 95%, 96%, 97%, 98%, or 99% identical, or is 100% identical to a target DNA sequence defined by a set of genomic coordinates shown in Tables 6A-Table 6F. In some embodiments, the targeting domain sequence binds to a target DNA sequence that is at least 90%, 95%, 96%, 97%, 98%, or 99% identical, or is 100% identical to one of SEQ ID NOs: 814-1232. In some embodiments, the targeting domain sequence is encoded by a DNA sequence that is at least 90%, 95%, 96%, 97%, 98%, or 99% identical, or is 100% identical to one of SEQ ID NOs: 814-1232.

In some embodiments, the gRNAs provided herein comprise a targeting domain sequence that binds to a target DNA sequence that is at least 90%, 95%, 96%, 97%, 98%, or 99% identical, or is 100% identical to a sequence of a target gene selected from BCL2L11, FL11, CALM2, DHODH, UMPS, RBM39, SEMA7A, CHIC2, PCBP1, PBRM1, WDR6, E2F8, SERPINA3, and GNAS. In some embodiments, the targeting domain sequence binds to a target DNA sequence that is at least 90%, 95%, 96%, 97%, 98%, or 99% identical, or is 100% identical to a target DNA sequence defined by a set of genomic coordinates shown in Table 6A or Table 6B. In some embodiments, the targeting domain sequence binds to a target DNA sequence that is at least 90%, 95%, 96%, 97%, 98%, or 99% identical, or is 100% identical to one of SEQ ID NOs: 814-1064. In some embodiments, the targeting domain sequence is encoded by a DNA sequence that is at least 90%, 95%, 96%, 97%, 98%, or 99% identical, or is 100% identical to one of SEQ ID NOs: 814-1064.

In some embodiments, the gRNAs provided herein comprise a targeting domain sequence that binds to a target DNA sequence that is at least 90%, 95%, 96%, 97%, 98%, or 99% identical, or is 100% identical to a sequence of the SOCS1 gene. In some embodiments, the targeting domain sequence binds to a target DNA sequence that is at least 90%, 95%, 96%, 97%, 98%, or 99% identical, or is 100% identical to a target DNA sequence defined by a set of genomic coordinates shown in Table 6C or Table 6D. In some embodiments, the targeting domain sequence binds to a target DNA sequence that is at least 90%, 95%, 96%, 97%, 98%, or 99% identical, or is 100% identical to one of SEQ ID NOs: 1088-1232. In some embodiments, the targeting domain sequence is encoded by a DNA sequence that is at least 90%, 95%, 96%, 97%, 98%, or 99% identical, or is 100% identical to one of SEQ ID NOs: 1088-1232. In some embodiments, the targeting domain sequence binds to a target DNA sequence that is at least 90%, 95%, 96%, 97%, 98%, or 99% identical, or is 100% identical to one of SEQ ID NOs: 1088-1200. In some embodiments, the targeting domain sequence is encoded by a DNA sequence that is at least 90%, 95%, 96%, 97%, 98%, or 99% identical, or is 100% identical to one of SEQ ID NOs: 1088-1200.

In some embodiments, the gRNAs provided herein comprise a targeting domain sequence that binds to a target DNA sequence in the SOCS1 gene, wherein the targeting domain sequence is at least 90%, 95%, 96%, 97%, 98%, or 99% identical, or is 100% identical to one of SEQ ID NOs: 1088-1140. In some embodiments, the targeting domain sequence is encoded by a DNA sequence that is at least 90%, 95%, 96%, 97%, 98%, or 99% identical, or is 100% identical to one of SEQ ID NOs: 1088-1140. In some embodiments, the targeting domain sequence binds to a target DNA sequence that is at least 90%, 95%, 96%, 97%, 98%, or 99% identical, or is 100% identical to one of SEQ ID NOs: 1088-1120. In some embodiments, the targeting domain sequence is encoded by a DNA sequence that is at least 90%, 95%, 96%, 97%, 98%, or 99% identical, or is 100% identical to one of SEQ ID NOs: 1088-1120. In some embodiments, the targeting domain sequence binds to a target DNA sequence that is at least 90%, 95%, 96%, 97%, 98%, or 99% identical, or is 100% identical to one of SEQ ID NOs: 1106, 1110, 1115, 1116, 1118, 1126, 1129, 1141, 1157, 1174. In some embodiments, the targeting domain sequence is encoded by a DNA sequence that is at least 90%, 95%, 96%, 97%, 98%, or 99% identical, or is 100% identical to one of SEQ ID NOs: 1106, 1110, 1115, 1116, 1118, 1126, 1129, 1141, 1157, 1174. In some embodiments, the targeting domain sequence binds to a target DNA sequence that is at least 90%, 95%, 96%, 97%, 98%, or 99% identical, or is 100% identical to one of SEQ ID NOs: 1102, 1103, 1105-1108, 1115. In some embodiments, the targeting domain sequence is encoded by a DNA sequence that is at least 90%, 95%, 96%, 97%, 98%, or 99% identical, or is 100% identical to one of SEQ ID NOs: 1102, 1103, 1105-1108, 1115.

In some embodiments, the gRNAs provided herein comprise a targeting domain sequence that binds to a target DNA sequence that is at least 90%, 95%, 96%, 97%, 98%, or 99% identical, or is 100% identical to a sequence of the ANKRD11 gene. In some embodiments, the targeting domain sequence binds to a target DNA sequence that is at least 90%, 95%, 96%, 97%, 98%, or 99% identical, or is 100% identical to a target DNA sequence defined by a set of genomic coordinates shown in Table 6E or Table 6F. In some embodiments, the targeting domain sequence binds to a target DNA sequence that is at least 90%, 95%, 96%, 97%, 98%, or 99% identical, or is 100% identical to one of SEQ ID NOs: 1065-1087. In some embodiments, the targeting domain sequence is encoded by DNA sequence that is at least 90%, 95%, 96%, 97%, 98%, or 99% identical, or is 100% identical to one of SEQ ID NOs: 1065-1087.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., a gene selected from Table 2) and wherein at least one of the gRNAs comprises a targeting domain that binds to a target DNA sequence that is at least 90%, 95%, 96%, 97%, 98%, or 99% identical, or is 100% identical to a target DNA sequence of a target gene selected from BCL2L11, FL11, CALM2, DHODH, UMPS, RBM39, SEMA7A, CHIC2, PCBP1, PBRM1, WDR6, E2F8, SERPINA3, GNAS, SOCS1, and ANKRD11 (e.g., a gene selected from Table 3).

In some embodiments, at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in one of Tables 6A-6F. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain that binds to a target DNA sequence that is at least 90%, 95%, 96%, 97%, 98%, or 99% identical, or is 100% identical to one of SEQ ID NOs: 814-1232. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain encoded by a nucleic acid sequence that is at least 90%, 95%, 96%, 97%, 98%, or 99% identical, or is 100% identical to one of SEQ ID NOs: 814-1232.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the gRNAs comprises a targeting domain that binds to a target DNA sequence that is at least 90%, 95%, 96%, 97%, 98%, or 99% identical, or is 100% identical to a target DNA sequence of a target gene selected from BCL2L11, FL11, CALM2, DHODH, UMPS, RBM39, SEMA7A, CHIC2, PCBP1, PBRM1, WDR6, E2F8, SERPINA3, and GNAS. In some embodiments, at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in one of Table 6A or Table 6B. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain that binds to a target DNA sequence that is at least 90%, 95%, 96%, 97%, 98%, or 99% identical, or is 100% identical to one of SEQ ID NOs: 814-1064. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain encoded by a nucleic acid sequence that is at least 90%, 95%, 96%, 97%, 98%, or 99% identical, or is 100% identical to one of SEQ ID NOs: 814-1064.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of the CBLB and wherein at least one of the gRNAs comprises a targeting domain that binds to a target DNA sequence that is at least 90%, 95%, 96%, 97%, 98%, or 99% identical, or is 100% identical to a target DNA sequence of a target gene selected from BCL2L11, FL11, CALM2, DHODH, UMPS, RBM39, SEMA7A, CHIC2, PCBP1, PBRM11, WDR6, E2F8, SERPINA3, and GNAS. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 499-524 and at least one of the gRNAs comprises a targeting domain that binds to a target DNA sequence that is at least 90%, 95%, 96%, 97%, 98%, or 99% identical, or is 100% identical to one of SEQ ID NOs: 814-1064. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 499-524 and at least one of the gRNAs comprises a targeting domain encoded by a nucleic acid sequence that is at least 90%, 95%, 96%, 97%, 98%, or 99% identical, or is 100% identical to one of SEQ ID NOs: 814-1064.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the gRNAs comprises a targeting domain that binds to a target DNA sequence that is at least 90%, 95%, 96%, 97%, 98%, or 99% identical, or is 100% identical to a target DNA sequence of the SOCS1 gene. In some embodiments, at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in one of Table 6C or Table 6D. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain that binds to a target DNA sequence that is at least 90%, 95%, 96%, 97%, 98%, or 99% identical, or is 100% identical to one of SEQ ID NOs: 1088-1232. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain encoded by a nucleic acid sequence that is at least 90%, 95%, 96%, 97%, 98%, or 99% identical, or is 100% identical to one of SEQ ID NOs: 1088-1232.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of the CBLB gene and wherein at least one of the gRNAs comprises a targeting domain that binds to a target DNA sequence that is at least 90%, 95%, 96%, 97%, 98%, or 99% identical, or is 100% identical to a target DNA sequence of the SOCS1 gene. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 499-524 and at least one of the gRNAs comprises a targeting domain that binds to a target DNA sequence that is at least 90%, 95%, 96%, 97%, 98%, or 99% identical, or is 100% identical to one of SEQ ID NOs: 1088-1232. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 499-524 and at least one of the gRNAs comprises a targeting domain encoded by a nucleic acid sequence that is at least 90%, 95%, 96%, 97%, 98%, or 99% identical, or is 100% identical to one of SEQ ID NOs: 1088-1232.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the gRNAs comprises a targeting domain that binds to a target DNA sequence that is at least 90%, 95%, 96%, 97%, 98%, or 99% identical, or is 100% identical to a target DNA sequence of the ANKRD11 gene. In some embodiments, at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in one of Table 6E or Table 6F. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain that binds to a target DNA sequence that is at least 90%, 95%, 96%, 97%, 98%, or 99% identical, or is 100% identical to one of SEQ ID NOs: 1065-1087. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain encoded by a nucleic acid sequence that is at least 90%, 95%, 96%, 97%, 98%, or 99% identical, or is 100% identical to one of SEQ ID NOs: 1065-1087.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of the CBLB gene and wherein at least one of the gRNAs comprises a targeting domain that binds to a target DNA sequence that is at least 90%, 95%, 96%, 97%, 98%, or 99% identical, or is 100% identical to a target DNA sequence of the ANKRD11 gene. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 499-524 and at least one of the gRNAs comprises a targeting domain that binds to a target DNA sequence that is at least 90%, 95%, 96%, 97%, 98%, or 99% identical, or is 100% identical to one of SEQ ID NOs: 1065-1087. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 499-524 and at least one of the gRNAs comprises a targeting domain encoded by a nucleic acid sequence that is at least 90%, 95%, 96%, 97%, 98%, or 99% identical, or is 100% identical to one of SEQ ID NOs: 1065-1087.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of the SOCS1 gene and at least one of the gRNAs comprises a targeting domain that binds to a target DNA sequence that is at least 90%, 95%, 96%, 97%, 98%, or 99% identical, or is 100% identical to a target DNA sequence of the ANKRD11 gene. In some embodiments, at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in Table 6C or Table 6D and at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in Table 6E or Table 6F. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 1088-1232 and at least one of the gRNAs comprises a targeting domain that binds to a target DNA sequence that is at least 90%, 95%, 96%, 97%, 98%, or 99% identical, or is 100% identical to one of SEQ ID NOs: 1065-1087.

In some embodiments, the nucleic acid-binding segments of the gRNA sequences described herein are designed to minimize off-target binding using algorithms known in the art (e.g., Cas-OFF finder) to identify target sequences that are unique to a particular target locus or target gene.

In some embodiments, the gRNAs described herein can comprise one or more modified nucleosides or nucleotides which introduce stability toward nucleases. In such embodiments, these modified gRNAs may elicit a reduced innate immune as compared to a non-modified gRNA. The term "innate immune response" includes a cellular response to exogenous nucleic acids, including single stranded nucleic acids, generally of viral or bacterial origin, which involves the induction of cytokine expression and release, particularly the interferons, and cell death.

In some embodiments, the gRNAs described herein are modified at or near the 5' end (e.g., within 1-10, 1-5, or 1-2 nucleotides of their 5' end). In some embodiments, the 5' end of a gRNA is modified by the inclusion of a eukaryotic mRNA cap structure or cap analog (e.g., a G(5')ppp(5')G cap analog, a m7G(5')ppp(5')G cap analog, or a 3'-O-Me-m7G (5')ppp(5')G anti reverse cap analog (ARCA)). In some embodiments, an in vitro transcribed gRNA is modified by treatment with a phosphatase (e.g., calf intestinal alkaline phosphatase) to remove the 5' triphosphate group. In some embodiments, a gRNA comprises a modification at or near its 3' end (e.g., within 1-10, 1-5, or 1-2 nucleotides of its 3' end). For example, in some embodiments, the 3' end of a gRNA is modified by the addition of one or more (e.g., 25-200) adenine (A) residues.

In some embodiments, modified nucleosides and modified nucleotides can be present in a gRNA, but also may be present in other gene-regulating systems, e.g., mRNA, RNAi, or siRNA-based systems. In some embodiments, modified nucleosides and nucleotides can include one or more of:

(a) alteration, e.g., replacement, of one or both of the non-linking phosphate oxygens and/or of one or more of the linking phosphate oxygens in the phosphodiester backbone linkage;
(b) alteration, e.g., replacement, of a constituent of the ribose sugar, e.g., of the 2' hydroxyl on the ribose sugar;
(c) wholesale replacement of the phosphate moiety with "dephospho" linkers;
(d) modification or replacement of a naturally occurring nucleobase;
(e) replacement or modification of the ribose-phosphate backbone;
(f) modification of the 3' end or 5' end of the oligonucleotide, e.g., removal, modification or replacement of a terminal phosphate group or conjugation of a moiety; and
(g) modification of the sugar.

In some embodiments, the modifications listed above can be combined to provide modified nucleosides and nucleotides that can have two, three, four, or more modifications. For example, in some embodiments, a modified nucleoside or nucleotide can have a modified sugar and a modified nucleobase. In some embodiments, every base of a gRNA is modified. In some embodiments, each of the phosphate groups of a gRNA molecule are replaced with phosphorothioate groups.

In some embodiments, a software tool can be used to optimize the choice of gRNA within a user's target sequence, e.g., to minimize total off-target activity across the genome. Off target activity may be other than cleavage. For example, for each possible gRNA choice using *S. pyogenes* Cas9, software tools can identify all potential off-target sequences (preceding either NAG or NGG PAMs) across the genome that contain up to a certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible gRNA can then be ranked according to its total predicted off-target cleavage; the top-ranked gRNAs represent those that are likely to have the greatest on-target and the least off-target cleavage. Other functions, e.g., automated reagent design for gRNA vector construction, primer design for the on-target Surveyor assay, and primer design for high-throughput detection and quantification of off-target cleavage via next-generation sequencing, can also be included in the tool.

IV. Polynucleotides

In some embodiments, the present disclosure provides polynucleotides or nucleic acid molecules encoding a gene-regulating system described herein. As used herein, the terms "nucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths, "in this context, means any length between the quoted values, such as 6, 7, 8, 9, etc., 101, 102, 103, etc.; 151, 152, 153, etc.; 201, 202, 203, etc.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, (xi) isolated removal of spurious translation initiation sites and/or (xii) elimination of fortuitous polyadenylation sites otherwise leading to truncated RNA transcripts.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

In particular embodiments, polynucleotides or variants have at least or about 50%, 55%, 60%, 65%, 70%, 71%, 72%, 73%, 74%, 75%,76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

Moreover, it will be appreciated by those of ordinary skill in the art that, as a result of the degeneracy of the genetic code, there are many nucleotide sequences that encode a polypeptide, or fragment of variant thereof, as described herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. Further, alleles of the genes comprising the polynucleotide sequences provided herein may also be used. Alleles are endogenous genes that are altered as a result of one or more mutations, such as deletions, additions and/or substitutions of nucleotides.

The polynucleotides contemplated herein, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed in particular embodiments, with the total length preferably being limited by the ease of preparation and use in the intended recombinant DNA protocol.

Polynucleotides can be prepared, manipulated and/or expressed using any of a variety of well-established techniques known and available in the art.

Vectors

In order to express a gene-regulating system described herein in a cell, an expression cassette encoding the gene-regulating system can be inserted into appropriate vector. The term "nucleic acid vector" is used herein to refer to a nucleic acid molecule capable transferring or transporting another nucleic acid molecule. The transferred nucleic acid is generally linked to, e.g., inserted into, the vector nucleic acid molecule. A nucleic acid vector may include sequences that direct autonomous replication in a cell, or may include sequences sufficient to allow integration into host cell DNA.

The term "expression cassette" as used herein refers to genetic sequences within a vector which can express an RNA, and subsequently a protein. The nucleic acid cassette contains the gene of interest, e.g., a gene-regulating system. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. The cassette can be removed and inserted into a plasmid or viral vector as a single unit.

In particular embodiments, vectors include, without limitation, plasmids, phagemids, cosmids, transposons, artificial chromosomes such as yeast artificial chromosome (YAC), bacterial artificial chromosome (BAC), or P1-derived artificial chromosome (PAC), bacteriophages such as lambda phage or M13 phage, and animal viruses. In particular embodiments, the coding sequences of the gene-regulating systems disclosed herein can be ligated into such vectors for the expression of the gene-regulating systems in mammalian cells.

In some embodiments, non-viral vectors are used to deliver one or more polynucleotides contemplated herein to an immune effector cell, e.g., a T cell. In some embodiments, the recombinant vector comprising a polynucleotide encoding one or more components of a gene-regulating system described herein is a plasmid. Numerous suitable plasmid expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other plasmid vector may be used so long as it is compatible with the host cell. Depending on the cell type and gene-regulating system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

In some embodiments, the recombinant vector comprising a polynucleotide encoding one or more components of a gene-regulating system described herein is a viral vector. Suitable viral vectors include, but are not limited to, viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., U.S. Pat. No. 7,078,387; Ali et al., Hum Gene Ther 9:81 86, 1998, Flannery et al, PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski etal., J. Vir. (1989) 63:3822-3828; Mendelson et al, Virol. (1988) 166: 154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. Examples of vectors are pClneo vectors (Promega) for expression in mammalian cells; pLenti4/V5-DEST™ pLenti6/V5-DEST™, and pLenti6.2/V5-GW/lacZ (Invitrogen) for lentivirus-mediated gene transfer and expression in mammalian cells.

In some embodiments, the vector is a non-integrating vector, including but not limited to, an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally. The vector is engineered to harbor the sequence coding for the origin of DNA replication or "ori" from a lymphotrophic herpes virus or a gamma herpesvirus, an adenovirus, SV40, a bovine papilloma virus, or a yeast, specifically a replication origin of a lymphotrophic herpes virus or a gamma herpesvirus corresponding to oriP of EBV. In a particular aspect, the lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gamma herpesvirus.

In some embodiments, a polynucleotide is introduced into a target or host cell using a transposon vector system. In certain embodiments, the transposon vector system comprises a vector comprising transposable elements and a polynucleotide contemplated herein; and a transposase. In one embodiment, the transposon vector system is a single transposase vector system, see, e.g., WO 2008/027384. Exemplary transposases include, but are not limited to: piggyBac, Sleeping Beauty, Mos1, Tc1/mariner, To12, mini-Tol2, Tc3, MuA, Himar I, Frog Prince, and derivatives thereof The piggyBac transposon and transposase are described, for example, in U.S. Pat. No. 6,962,810, which is incorporated herein by reference in its entirety. The Sleeping Beauty transposon and transposase are described, for example, in Izsvak et al., J. Mol. Biol. 302: 93-102 (2000), which is incorporated herein by reference in its entirety. The Tol2 transposon which was first isolated from the medaka fish Oryzias *latipes* and belongs to the hAT family of transposons is described in Kawakami et al. (2000). Mini-Tol2 is a variant of Tol2 and is described in Balciunas et al. (2006). The Tol2 and Mini-Tol2 transposons facilitate integration of a transgene into the genome of an organism when co-acting with the Tol2 transposase. The Frog Prince transposon and transposase are described, for example, in Miskey et al., Nucleic Acids Res. 31:6873-6881 (2003).

In some embodiments, a polynucleotide sequence encoding one or more components of a gene-regulating system described herein is operably linked to a control element, e.g., a transcriptional control element, such as a promoter. "Control elements" refer those non-translated regions of the vector (e.g., origin of replication, selection cassettes, promoters, enhancers, translation initiation signals (Shine Dalgarno sequence or Kozak sequence) introns, a polyadenylation sequence, 5' and 3' untranslated regions) which interact with host cellular proteins to carry out transcription and translation. Such elements may vary in their strength and specificity. The transcriptional control element may be functional in either a eukaryotic cell (e.g., a mammalian cell) or a prokaryotic cell (e.g., bacterial or archaeal cell). In some embodiments, a polynucleotide sequence encoding one or more components of a gene-regulating system described herein is operably linked to multiple control elements that allow expression of the polynucleotide in both prokaryotic and eukaryotic cells.

Depending on the cell type and gene-regulating system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544). The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide. The term "enhancer" refers to a segment of DNA which contains sequences capable of providing enhanced transcription and in some instances can function independent of their orientation relative to another control sequence. An enhancer can function cooperatively or additively with promoters and/or other enhancer elements.

In some embodiments, polynucleotides encoding one or more components of a gene-regulating system described herein are operably linked to a promoter. The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide encoding one or more components of a gene-regulating system, wherein the expression control sequence directs transcription of the nucleic acid corresponding to the second sequence.

Non-limiting examples of suitable eukaryotic promoters (promoters functional in a eukaryotic cell) include those from cytomegalovirus (CMV) immediate early, herpes simplex virus (HSV) thymidine kinase, a viral simian virus 40 (SV40) (e.g., early and late SV40), a spleen focus forming virus (SFFV) promoter, long terminal repeats (LTRs) from retrovirus (e.g., a Moloney murine leukemia virus (MoMLV) LTR promoter or a Rous sarcoma virus (RSV) LTR), a herpes simplex virus (HSV) (thymidine kinase) promoter, H5, P7.5, and P11 promoters from vaccinia virus, an elongation factor 1-alpha (EF1α) promoter, early growth response 1 (EGR1) promoter, a ferritin H (FerH) promoter, a ferritin L (FerL) promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90B1) promoter, a heat shock protein 70 kDa (HSP70) promoter, a 0-kinesin (0-KIN) promoter, the human ROSA 26 locus (Irions et al., Nature Biotechnology 25, 1477-1482 (2007)), a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter, and mouse metallothionein-1. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, green fluorescent protein, etc.) that are fused to the site-directed modifying polypeptide, thus resulting in a chimeric polypeptide.

In some embodiments, a polynucleotide sequence encoding one or more components of a gene-regulating system described herein is operably linked to a constitutive promoter. In such embodiments, the polynucleotides encoding one or more components of a gene-regulating system described herein are constitutively and/or ubiquitously expressed in a cell.

In some embodiments, a polynucleotide sequence encoding one or more components of a gene-regulating system described herein is operably linked to an inducible promoter. In such embodiments, polynucleotides encoding one or more components of a gene-regulating system described herein are conditionally expressed. As used herein, "conditional expression" may refer to any type of conditional expression including, but not limited to, inducible expression; repressible expression; expression in cells or tissues having a particular physiological, biological, or disease state (e.g., cell type or tissue specific expression) etc. Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

In some embodiments, the vectors described herein further comprise a transcription termination signal. Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rpgpA), variants thereof, or another suitable heterologous or endogenous polyA sequence known in the art.

In some embodiments, a vector may also comprise a sequence encoding a signal peptide (e.g., for nuclear localization, nucleolar localization, mitochondrial localization), fused to the polynucleotide encoding the one or more components of the system. For example, a vector may comprise a nuclear localization sequence (e.g., from SV40) fused to the polynucleotide encoding the one or more components of the system.

Methods of introducing polynucleotides and recombinant vectors into a host cell are known in the art, and any known method can be used to introduce components of a gene-regulating system into a cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al., Adv Drug Deliv Rev. 2012 Sep. 13. pii: 50169-409X (12)00283-9), microfluidics delivery methods (See e.g., International PCT Publication No. WO 2013/059343), and the like. In some embodiments, delivery via electroporation comprises mixing the cells with the components of a gene-regulating system in a cartridge, chamber, or cuvette and applying one or more electrical impulses of defined duration and amplitude. In some embodiments, cells are mixed with components of a gene-regulating system in a vessel connected to a device (e.g., a pump) which feeds the mixture into a cartridge, chamber, or cuvette wherein one or more electrical impulses of defined duration and amplitude are applied, after which the cells are delivered to a second vessel. Illustrative examples of polynucleotide delivery systems suitable for use in particular embodiments contemplated in particular embodiments include, but are not limited to, those provided by Amaxa Biosystems, Maxcyte, Inc., BTX Molecular Delivery Systems, Neon™ Transfection Systems, and Copernicus Therapeutics Inc. Lipofection reagents are sold commercially (e.g., Transfectam™ and Lipofectin™). Cationic and neutral lipids that are suitable for efficient lipofection of polynucleotides have been described in the literature. See e.g., Liu et al. (2003) *Gene Therapy.* 10:180-187; and Balazs et al. (2011) *Journal of Drug Delivery.* 2011:1-12.

In some embodiments, vectors comprising polynucleotides encoding one or more components of a gene-regulating system described herein are introduced to cells by viral delivery methods, e.g., by viral transduction. In some embodiments, vectors comprising polynucleotides encoding one or more components of a gene-regulating system described herein are introduced to cells by non-viral delivery methods. Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

In some embodiments, one or more components of a gene-regulating system, or polynucleotide sequence encoding one or more components of a gene-regulating system described herein are introduced to a cell in a non-viral delivery vehicle, such as a transposon, a nanoparticle (e.g., a lipid nanoparticle), a liposome, an exosome, an attenuated bacterium, or a virus-like particle. In some embodiments, the vehicle is an attenuated bacterium (e.g., naturally or artificially engineered to be invasive but attenuated to prevent pathogenesis including *Listeria monocytogenes*, certain *Salmonella* strains, *Bifidobacterium longum*, and modified *Escherichia coli*), bacteria having nutritional and tissue-specific tropism to target specific cells, and bacteria having modified surface proteins to alter target cell specificity. In some embodiments, the vehicle is a genetically modified bacteriophage (e.g., engineered phages having large packaging capacity, less immunogenicity, containing mammalian plasmid maintenance sequences and having incorporated targeting ligands). In some embodiments, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In some embodiments, the vehicle is a biological liposome. For example, the biological liposome is a phospholipid-based particle derived from human cells (e.g., erythrocyte ghosts, which are red blood cells broken down into spherical structures derived from the subject and wherein tissue targeting can be achieved by attachment of various tissue or cell-specific ligands), secretory exosomes, or subject derived membrane-bound nanovescicles (30-100 nm) of endocytic origin (e.g., can be produced from various cell types and can therefore be taken up by cells without the need for targeting ligands).

IV. Methods of Producing Modified Immune Effector Cells

In some embodiments, the present disclosure provides methods for producing modified immune effector cells. In some embodiments, the methods comprise introducing a gene-regulating system into a population of immune effector cells wherein the gene-regulating system is capable of reducing expression and/or function of one or more endogenous target genes.

The components of the gene-regulating systems described herein, e.g., a nucleic acid-, protein-, or nucleic acid/protein-based system can be introduced into target cells in a variety of forms using a variety of delivery methods and formulations. In some embodiments, a polynucleotide encoding one or more components of the system is delivered by a recombinant vector (e.g., a viral vector or plasmid, described supra). In some embodiments, where the system comprises more than a single component, a vector may comprise a plurality of polynucleotides, each encoding a component of the system. In some embodiments, where the system comprises more than a single component, a plurality of vectors may be used, wherein each vector comprises a polynucleotide encoding a particular component of the system. In some embodiments, the introduction of the gene-regulating system to the cell occurs in vitro. In some embodiments, the introduction of the gene-regulating system to the cell occurs in vivo. In some embodiments, the introduction of the gene-regulating system to the cell occurs ex vivo.

In particular embodiments, the introduction of the gene-regulating system to the cell occurs in vitro or ex vivo. In some embodiments, the immune effector cells are modified in vitro or ex vivo without further manipulation in culture. For example, in some embodiments, the methods of producing a modified immune effector cell described herein comprise introduction of a gene-regulating system in vitro or ex vivo without additional activation and/or expansion steps. In some embodiments, the immune effector cells are modified and are further manipulated in vitro or ex vivo. For example, in some embodiments, the immune effector cells are activated and/or expanded in vitro or ex vivo prior to introduction of a gene-regulating system. In some embodiments, a gene-regulating system is introduced to the immune effector cells and are then activated and/or expanded in vitro or ex vivo. In some embodiments, successfully modified cells can be sorted and/or isolated (e.g., by flow cytometry) from unsuccessfully modified cells to produce a purified population of modified immune effector cells. These successfully modified cells can then be further propagated to increase the number of the modified cells and/or cryopreserved for future use.

In some embodiments, the present disclosure provides methods for producing modified immune effector cells comprising obtaining a population of immune effector cells. The population of immune effector cells may be cultured in vitro under various culture conditions necessary to support growth, for example, at an appropriate temperature (e.g., 37° C.) and atmosphere (e.g., air plus 5% $CO_2$) and in an appropriate culture medium. Culture medium may be liquid or semi-solid, e.g. containing agar, methylcellulose, etc. Illustrative examples of cell culture media include Minimal Essential Media (MEM), Iscove's modified DMEM, RPMI 1640Clicks, AIM-V, F-12, X-Vivo 15, X-Vivo 20, and Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of the immune effector cells.

Culture media may be supplemented with one or more factors necessary for proliferation and viability including, but not limited to, growth factors such as serum (e.g., fetal bovine or human serum at about 5%-10%), interleukin-2 (IL-2), insulin, IFN-7, IL-4, IL-7, IL-21, GM-CSF, IL-10, IL-12, IL-15, TGFβ, and TNF-α. Illustrative examples of other additives for T cell expansion include, but are not limited to, surfactant, plasmanate, pH buffers such as HEPES, and reducing agents such as N-acetyl-cysteine and 2-mercaptoethanol, or any other additives suitable for the growth of cells known to the skilled artisan such as L-glutamine, a thiol, particularly 2-mercaptoethanol, and/or antibiotics, e.g. penicillin and streptomycin. Typically, antibiotics are included only in experimental cultures, not in cultures of cells that are to be infused into a subject.

In some embodiments, the population of immune effector cells is obtained from a sample derived from a subject. In some embodiments, a population of immune effector cells is obtained is obtained from a first subject and the population of modified immune effector cells produced by the methods described herein is administered to a second, different subject. In some embodiments, a population of immune effector cells is obtained from a subject and the population of modified immune effector cells produced by the methods described herein is administered to the same subject. In some embodiments, the sample is a tissue sample, a fluid sample, a cell sample, a protein sample, or a DNA or RNA sample. In some embodiments, a tissue sample may be derived from any tissue type including, but not limited to, skin, hair (including roots), bone marrow, bone, muscle, salivary gland, esophagus, stomach, small intestine (e.g., tissue from the duodenum, jejunum, or ileum), large intestine, liver, gallbladder, pancreas, lung, kidney, bladder, uterus, ovary, vagina, placenta, testes, thyroid, adrenal gland, cardiac tissue, thymus, spleen, lymph node, spinal cord, brain, eye, ear, tongue, cartilage, white adipose tissue, or brown adipose tissue. In some embodiments, a tissue sample may be derived from a cancerous, pre-cancerous, or non-cancerous tumor. In some embodiments, a fluid sample comprises buccal swabs, blood, plasma, oral mucous, vaginal mucous, peripheral blood, cord blood, saliva, semen, urine, ascites fluid, pleural fluid, spinal fluid, pulmonary lavage, tears, sweat, semen, seminal fluid, seminal plasma, prostatic fluid, pre-ejaculatory fluid (Cowper's fluid), excreta, cerebrospinal fluid, lymph, cell culture media comprising one or more populations of cells, buffered solutions comprising one or more populations of cells, and the like.

In some embodiments, the sample is processed to enrich or isolate a population of immune effector cells from the remainder of the sample. In certain embodiments, the sample is a peripheral blood sample which is then subject to leukapheresis to separate the red blood cells and platelets and to isolate lymphocytes. In some embodiments, the sample is a leukopak from which immune effector cells can be isolated or enriched. In some embodiments, the sample is a tumor sample that is further processed to isolate lymphocytes present in the tumor (i.e., by fragmentation and enzymatic digestion of the tumor to obtain a cell suspension of tumor infiltrating lymphocytes).

In some embodiments, a method for manufacturing modified immune effector cells contemplated herein comprises activation and/or expansion of a population of immune effector cells, as described, for example, in U.S. Pat. Nos.

6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In various embodiments, a method for manufacturing modified immune effector cells contemplated herein comprises activating a population of cells comprising immune effector cells. In particular embodiments, the immune effector cells are T cells. T cell activation can be accomplished by providing a primary stimulation signal (e.g., through the T cell TCR/CD3 complex or via stimulation of the CD2 surface protein) and by providing a secondary co-stimulation signal through an accessory molecule.

In some embodiments, the TCR/CD3 complex may be stimulated by contacting the T cell with a suitable CD3 binding agent, e.g., a CD3 ligand or an anti-CD3 monoclonal antibody. Illustrative examples of CD3 antibodies include, but are not limited to, OKT3, G19-4, BC3, CRIS-7 and 64.1. In some embodiments, a CD2 binding agent may be used to provide a primary stimulation signal to the T cells. Illustrative examples of CD2 binding agents include, but are not limited to, CD2 ligands and anti-CD2 antibodies, e.g., the T11.3 antibody in combination with the T11.1 or T11.2 antibody (Meuer, S. C. et al. (1984) *Cell* 36:897-906) and the 9.6 antibody (which recognizes the same epitope as TI 1.1) in combination with the 9-1 antibody (Yang, S. Y. et al. (1986) *J Immunol.* 137:1097-1100).

In addition to the stimulatory signal provided through the TCR/CD3 complex or CD2, induction of T cell responses typically requires a second, costimulatory signal provided by a ligand that specifically binds a costimulatory molecule on a T cell, thereby providing a costimulatory signal which, in addition to the primary signal provided by, for instance, binding of a TCR/CD3 complex, mediates a desired T cell response. Suitable costimulatory ligands include, but are not limited to, CD7, B7-1 (CD80), B7-2 (CD86), 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, ILT3, ILT4, an agonist or antibody that binds Toll ligand receptor, and a ligand that specifically binds with B7-H3.

In some embodiments, a costimulatory ligand comprises an antibody or antigen binding fragment thereof that specifically binds to a costimulatory molecule present on a T cell, including but not limited to, CD27, CD28, 4-1BB, OX40, CD30, CD40, ICOS, lymphocyte function-associated antigen-1 (LFA-1), CD7, LIGHT, NKG2C, B7-H3, and a ligand that specifically binds with CD83. In particular embodiments, a CD28 binding agent can be used to provide a costimulatory signal. Illustrative examples of CD28 binding agents include but are not limited to: natural CD28 ligands, e.g., a natural ligand for CD28 (e.g., a member of the B7 family of proteins, such as B7-1 (CD80) and B7-2 (CD86); and anti-CD28 monoclonal antibody or fragment thereof capable of crosslinking the CD28 molecule, e.g., monoclonal antibodies 9.3, B-T3, XR-CD28, KOLT-2, 15E8, 248.23.2, and EX5.3D10.

In certain embodiments, binding agents that provide stimulatory and costimulatory signals are localized on the surface of a cell. This can be accomplished by transfecting or transducing a cell with a nucleic acid encoding the binding agent in a form suitable for its expression on the cell surface or alternatively by coupling a binding agent to the cell surface. In some embodiments, the costimulatory signal is provided by a costimulatory ligand presented on an antigen presenting cell, such as an artificial APC (aAPC). Artificial APCs can be made by engineering K562, U937, 721.221, T2, or CIR cells to stably express and/or secrete of a variety of costimulatory molecules and cytokines to support ex vivo growth and long-term expansion of genetically modified T cells. In a particular embodiment, K32 or U32 aAPCs are used to direct the display of one or more antibody-based stimulatory molecules on the aAPC cell surface. Populations of T cells can be expanded by aAPCs expressing a variety of costimulatory molecules including, but not limited to, CD137L (4-1BBL), CD134L (OX40L), and/or CD80 or CD86. Exemplary aAPCs are provided in WO 03/057171 and US2003/0147869, incorporated by reference in their entireties.

In some embodiments, binding agents that provide activating and costimulatory signals are localized a solid surface (e.g., a bead or a plate). In some embodiments, the binding agents that provide activating and costimulatory signals are both provided in a soluble form (provided in solution).

In some embodiments, the population of immune effector cells is expanded in culture in one or more expansion phases. "Expansion" refers to culturing the population of immune effector cells for a pre-determined period of time in order to increase the number of immune effector cells. Expansion of immune effector cells may comprise addition of one or more of the activating factors described above and/or addition of one or more growth factors such as a cytokine (e.g., IL-2, IL-15, IL-21, and/or IL-7) to enhance or promote cell proliferation and/or survival. In some embodiments, combinations of IL-2, IL-15, and/or IL-21 can be added to the cultures during the one or more expansion phases. In some embodiments, the amount of IL-2 added during the one or more expansion phases is less than 6000 U/mL. In some embodiments, the amount of IL-2 added during the one or more expansion phases is about 5500 U/mL, about 5000 U/mL, about 4500 U/mL, about 4000 U/mL, about 3500 U/mL, about 3000 U/mL, about 2500 U/mL, about 2000 U/mL, about 1500 U/mL, about 1000 U/mL, or about 500 U/mL. In some embodiments, the amount of IL-2 added during the one or more expansion phases is between about 500 U/mL and about 5500 U/mL. In some embodiments, the population of immune effector cells may be co-cultured with feeder cells during the expansion process.

In some embodiments, the population of immune effector cells is expanded for a pre-determined period of time, wherein the pre-determined period of time is less than about 30 days. In some embodiments, the pre-determined period of time is less than 30 days, less than 25 days, less than 20 days, less than 18 days, less than 15 days, or less than 10 days. In some embodiments, the pre-determined period of time is less than 4 weeks, less than 3 weeks, less than 2 weeks, or less than 1 week. In some embodiments, the pre-determined period of time is about 7 days, 8 days, 9 days, 10 days, 11 days, 12 days, 13 days, 14 days, 15 days, 16 days, 17 days, 18 days, 19 days, 20 days, or 21 days. In some embodiments, the pre-determined period of time is about 5 days to about 25 days, about 10 to about 28 days, about 10 to about 25 days, about 10 to about 21 days, about 10 to about 20 days, about 10 to about 19 days, about 11 to about 28 days, about 11 to about 25 days, about 11 to about 21 days, about 11 to about 20 days, about 11 to about 19 days, about 12 to about 28 days, about 12 to about 25 days, about 12 to about 21 days, about 12 to about 20 days, about 12 to about 19 days, about 15 to about 28 days, about 15 to about 25 days, about 15 to about 21 days, about 15 to about 20 days, or about 15 to about 19 days. In some embodiments, the pre-determined period of time is about 5 days to about 10 days, about 10 days to about 15 days, about 15 days to about 20 days, or about 20 days to about 25 days.

In some embodiments, the population of immune effector cells is expanded until the number of cells reaches a predetermined threshold. For example, in some embodiments, the population of immune effector cells is expanded until the culture comprises at least $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, $1\times10^{13}$, or at least $5\times10^{13}$ total cells. In some embodiments, the population of immune effector cells is expanded until the culture comprises between about $1\times10^9$ total cells and about $1\times10^{11}$ total cells.

In some embodiments, the methods provided herein comprise at least two expansion phases. For example, in some embodiments, the population of immune effector cells can be expanded after isolation from a sample, allowed to rest, and then expanded again. In some embodiments, the immune effector cells can be expanded in one set of expansion conditions followed by a second round of expansion in a second, different, set of expansion conditions. Methods for ex vivo expansion of immune cells are known in the art, for example, as described in US Patent Application Publication Nos. 2018-0207201, 20180282694 and 20170152478 and U.S. Pat. Nos. 8,383,099 and 8,034,334, herein incorporated by reference.

At any point during the activation and/or expansion processes, the gene-regulating systems described herein can be introduced to the immune effector cells to produce a population of modified immune effector cells. In some embodiments, the gene-regulating system is introduced to the population of immune effector cells immediately after enrichment from a sample. In some embodiments, the gene-regulating system is introduced to the population of immune effector cells before, during, or after the one or more expansion process. In some embodiments, the gene-regulating system is introduced to the population of immune effector cells immediately after enrichment from a sample or harvest from a subject, and prior to any expansion rounds. In some embodiments, the gene-regulating system is introduced to the population of immune effector cells after a first round of expansion and prior to a second round of expansion. In some embodiments, the gene-regulating system is introduced to the population of immune effector cells after a first and a second round of expansion.

In some embodiments, the present disclosure provides methods of manufacturing populations of modified immune effector cells comprising obtaining a population of immune effector cells, introducing a gene-regulating system described herein to the population of immune effector cells, and expanding the population of immune effector cells in one or more round of expansion. In some aspects of this embodiment, the population of immune effector cells is expanded in a first round of expansion prior to the introduction of the gene-regulating system and is expanded in a second round of expansion after the introduction of the gene-regulating system. In some aspects of this embodiment, the population of immune effector cells is expanded in a first round of expansion and a second round of expansion prior to the introduction of the gene-regulating system. In some aspects of this embodiment, the gene-regulating system is introduced to the population of immune effector cells prior to the first and second rounds of expansion.

In some embodiments, the methods described herein comprise removal of a tumor from a subject and processing of the tumor sample to obtain a population of tumor infiltrating lymphocytes (e.g., by fragmentation and enzymatic digestion of the tumor to obtain a cell suspension) introducing a gene-regulating system described herein to the population of immune effector cells, and expanding the population of immune effector cells in one or more round of expansion. In some aspects of this embodiment, the population of tumor infiltrating lymphocytes is expanded in a first round of expansion prior to the introduction of the gene-regulating system and is expanded in a second round of expansion after the introduction of the gene-regulating system. In some aspects of this embodiment, the population of tumor infiltrating lymphocytes is expanded in a first round of expansion and a second round of expansion prior to the introduction of the gene-regulating system. In some aspects of this embodiment, the gene-regulating system is introduced to the population of tumor infiltrating lymphocytes prior to the first and second rounds of expansion.

In some embodiments, the modified immune effector cells produced by the methods described herein may be used immediately. In some embodiments, the manufacturing methods contemplated herein may further comprise cryopreservation of modified immune cells for storage and/or preparation for use in a subject. As used herein, "cryopreserving," refers to the preservation of cells by cooling to sub-zero temperatures, such as (typically) 77 K or −196° C. (the boiling point of liquid nitrogen). In some embodiments, a method of storing modified immune effector cells comprises cryopreserving the immune effector cells such that the cells remain viable upon thawing. When needed, the cryopreserved modified immune effector cells can be thawed, grown and expanded for more such cells. Cryoprotective agents are often used at sub-zero temperatures to prevent the cells being preserved from damage due to freezing at low temperatures or warming to room temperature. Cryopreservative agents and optimal cooling rates can protect against cell injury. Cryoprotective agents which can be used include but are not limited to dimethyl sulfoxide (DMSO) (Lovelock and Bishop, Nature, 1959; 183: 1394-1395; Ashwood-Smith, *Nature,* 1961; 190: 1204-1205), glycerol, polyvinylpyrrolidine (Rinfret, Ann. N.Y. *Acad. Sci.,* 1960; 85: 576), and polyethylene glycol (Sloviter and Ravdin, *Nature,* 1962; 196: 48). In some embodiments, the cells are frozen in 10% dimethylsulfoxide (DMSO), 50% serum, 40% buffered medium, or some other such solution as is commonly used in the art to preserve cells at such freezing temperatures, and thawed in a manner as commonly known in the art for thawing frozen cultured cells.

A. Producing Modified Immune Effector Cells Using CRISPR/Cas Systems

In some embodiments, a method of producing a modified immune effector cell involves contacting a target DNA sequence with a complex comprising a gRNA and a Cas polypeptide. As discussed above, a gRNA and Cas polypeptide form a complex, wherein the DNA-binding domain of the gRNA targets the complex to a target DNA sequence and wherein the Cas protein (or heterologous protein fused to an enzymatically inactive Cas protein) modifies target DNA sequence. In some embodiments, this complex is formed intracellularly after introduction of the gRNA and Cas protein (or polynucleotides encoding the gRNA and Cas proteins) to a cell. In some embodiments, the nucleic acid encoding the Cas protein is a DNA nucleic acid and is introduced to the cell by transduction. In some embodiments, the Cas9 and gRNA components of a CRISPR/Cas gene editing system are encoded by a single polynucleotide molecule. In some embodiments, the polynucleotide encoding the Cas protein and gRNA component are comprised in a viral vector and introduced to the cell by viral transduction. In some embodiments, the Cas9 and gRNA components of a CRISPR/Cas gene editing system are encoded by different polynucleotide molecules. In some embodiments, the polynucleotide encoding the Cas protein is comprised in a first viral vector and the polynucleotide encoding the gRNA is comprised in a second viral vector. In some aspects of this embodiment, the first viral vector is introduced to a cell prior to the second viral vector. In some aspects of this embodiment, the second viral vector is introduced to a cell prior to the first viral vector. In such embodiments, integration of the vectors results in sustained expression of the Cas9 and gRNA components. However, sustained expression of Cas9 may lead to increased off-target mutations and cutting in some cell types. Therefore, in some embodiments, an mRNA nucleic acid sequence encoding the Cas protein may be introduced to the population of cells by transfection. In such embodiments, the expression of Cas9 will decrease over time, and may reduce the number of off target mutations or cutting sites.

In some embodiments, this complex is formed in a cell-free system by mixing the gRNA molecules and Cas proteins together and incubating for a period of time sufficient to allow complex formation. This pre-formed complex, comprising the gRNA and Cas protein and referred to herein as a CRISPR-ribonucleoprotein (CRISPR-RNP) can then be introduced to a cell in order to modify a target DNA sequence. In some embodiments, the CRISPR-RNP is introduced to the cell by electroporation.

In any of the above described embodiments for producing a modified immune effect cell using the CRISPR/Cas system, the system may comprise one or more gRNAs targeting a single endogenous target gene, for example to produce a single-edited modified immune effector cell. Alternatively, in any of the above described embodiments for producing a modified immune effect cell using the CRISPR/Cas system, the system may comprise two or more gRNAs targeting two or more endogenous target genes, for example to produce a dual-edited modified immune effector cell.

B. Producing Modified Immune Effector Cells Using shRNA Systems

In some embodiments, the present disclosure provides a method of producing a modified immune effector cell by introducing into the cell one or more DNA polynucleotides encoding one or more shRNA molecules with sequence complementary to the mRNA transcript of a target gene. The immune effector cell can be modified to produce the shRNA by introducing specific DNA sequences into the cell nucleus via a small gene cassette. Both retroviruses and lentiviruses can be used to introduce shRNA-encoding DNAs into immune effector cells. The introduced DNA can either become part of the cell's own DNA or persist in the nucleus, and instructs the cell machinery to produce shRNAs. shRNAs may be processed by Dicer or AGO2-mediated slicer activity inside the cell to induce RNAi mediated gene knockdown.

C. Producing Modified Immune Effector Cells Using SOCS1 and/or CBLB Inhibitors

In some embodiments, the present disclosure provides methods of manufacturing modified immune effector cells comprising introducing a gene-regulating system described herein to a population of immune effector cells; introducing an inhibitor of SOCS1 and/or CBLB to the population of immune effector cells; and expanding the population of immune effector cells to produce the population of modified immune effector cells. In such embodiments, the introduction of the SOCS1 and/or CBLB inhibitor during the manufacturing process provides one or more improvements to methods in vitro or ex vivo manufacturing of lymphocytes, for example by increasing the number of cells obtained by the manufacturing methods (such as by decreasing the amount of time required to expand the population of lymphocytes to produce a sufficient number of cells for use in therapy), decreasing the amount of exogenous activation and/or growth factors required to produce a sufficient number of cells for use in therapy, and/or increasing the resistance of the lymphocytes to exhaustion during the manufacturing process. While exemplary methods of utilizing SOCS1 and/or CBLB inhibition in the manufacturing of the modified immune effector cells described herein are provided, these methods are applicable to the manufacturing of any lymphocyte population for therapeutic use.

In some embodiments, the addition of the SOCS1 and/or CBLB inhibitor reduces the length of expansion time required to produce a sufficient number of immune effector cells for use in downstream therapeutic applications. In some embodiments, the pre-determined period of time is less than 30 days, less than 25 days, less than 20 days, less than 18 days, less than 15 days, or less than 10 days. In some embodiments, the pre-determined period of time is less than 4 weeks, less than 3 weeks, less than 2 weeks, or less than 1 week. In some embodiments, the pre-determined period of time is about 7 days, 8 days, 9 days, 10 days, 11 days, 12 days, 13 days, 14 days, 15 days, 16 days, 17 days, 18 days, 19 days, 20 days, or 21 days. In some embodiments, the pre-determined period of time is about 5 days to about 25 days, about 10 to about 28 days, about 10 to about 25 days, about 10 to about 21 days, about 10 to about 20 days, about 10 to about 19 days, about 11 to about 28 days, about 11 to about 25 days, about 11 to about 21 days, about 11 to about 20 days, about 11 to about 19 days, about 12 to about 28 days, about 12 to about 25 days, about 12 to about 21 days, about 12 to about 20 days, about 12 to about 19 days, about 15 to about 28 days, about 15 to about 25 days, about 15 to about 21 days, about 15 to about 20 days, or about 15 to about 19 days. In some embodiments, the pre-determined period of time is about 5 days to about 10 days, about 10 days to about 15 days, about 15 days to about 20 days, or about 20 days to about 25 days.

In some embodiments, the total number of cells produced by the manufacturing methods comprising addition of a SOCS1 and/or CBLB inhibitor is at least about 1.2, 1.3, 1.4, 1.5, 1.6, 1.7, 1.8, 1.9, 2.0, 2.5, 3.0, 3.5, 4.0, 4.5, or 5 fold greater than the total number of cells produced by the manufacturing methods in the absence of a SOCS1 and/or CBLB inhibitor. In some embodiments, the total number of cells in the expanded population of lymphocytes is about 1.2, 1.3, 1.4, 1.5, 1.6, 1.7, 1.8, 1.9, 2.0, 2.5, 3.0, 3.5, 4.0, 4.5, or 5 fold greater than the total number of cells in an expanded population of lymphocytes produced in the absence of a SOCS1 and/or CBLB inhibitor. In some embodiments, the total number of cells produced by the manufacturing methods comprising addition of a SOCS1 and/or CBLB inhibitor is at least about 1.2, 1.3, 1.4, 1.5, 1.6, 1.7, 1.8, 1.9, 2.0, 2.5, 3.0, 3.5, 4.0, 4.5, or 5 fold greater than the total number of cells produced by the manufacturing methods in the presence of an inhibitor of an endogenous gene other than SOCS1 or CBLB. Without wishing to be bound by theory, the increased number of cells produced by manufacturing methods in the presence of a SOCS1 or CBLB inhibitor may occur by a variety of mechanisms, such as increased proliferation of the immune effector cells in the presence of the inhibitor (i.e., an increased growth rate) or increased survival of the immune effector cells in the presence of the inhibitor.

In some embodiments, introduction of the SOCS1 and/or CBLB inhibitor increases the resistance of the lymphocyte populations to exhaustion during and/or after the manufacturing process. In some embodiments, introduction of the SOCS1 and/or CBLB inhibitor during the manufacturing process increases the resistance of the T cell populations to T cell exhaustion compared to manufacturing in the absence of the SOCS1 and/or CBLB inhibitor. In some embodiments, resistance to T cell exhaustion is demonstrated by increased production of one or more cytokines (e.g., IFNγ, TNFα, or IL-2). In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in cytokine production from the lymphocyte populations produced in the presence of a SOCS1 and/or CBLB inhibitor compared to the cytokine production from lymphocyte populations produced in the absence of a SOCS1 and/or CBLB inhibitor is indicative of an increased resistance to T cell exhaustion. In some embodiments, resistance to T cell exhaustion is demonstrated by increased proliferation of the lymphocyte populations produced in the presence of a SOCS1 and/or CBLB inhibitor compared to the proliferation of the lymphocyte populations produced in the absence of a SOCS1 and/or CBLB inhibitor. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in proliferation of the lymphocyte populations produced in the presence of a SOCS1 and/or CBLB inhibitor compared to the proliferation of the lymphocyte populations produced in the absence of a SOCS1 and/or CBLB inhibitor is indicative of an increased resistance to T cell exhaustion. In some embodiments, resistance to T cell exhaustion is demonstrated by increased target cell lysis by the lymphocyte populations produced in the presence of a SOCS1 and/or CBLB inhibitor compared to the target cell lysis observed in the lymphocyte populations produced in the absence of a SOCS1 and/or CBLB inhibitor. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in target cell lysis by the lymphocyte populations produced in the presence of a SOCS1 and/or CBLB inhibitor compared to the target cell lysis by the lymphocyte populations produced in the absence of a SOCS1 and/or CBLB inhibitor is indicative of an increased resistance to T cell exhaustion.

In some embodiments, T cell exhaustion is measured at one or more time-points during the in vitro or ex vivo manufacturing process. For example, in some embodiments, lymphocytes are expanded in one or more rounds of expansion to produce a population of modified TILs. In such embodiments, the exhaustion of the modified TILs can be determined immediately after harvest and prior to a first round of expansion, after the first round of expansion but prior to a second round of expansion, and/or after the first and the second round of expansion. In some embodiments, T cell exhaustion is measured at one or more time points after completion of the in vitro or ex vivo manufacturing process.

In some embodiments, addition of the SOCS1 and/or CBLB inhibitor during the manufacturing process reduces the amount of cytokines and/or activation factors needed to produce the expanded population of lymphocytes. For example, in some embodiments, the addition of the SOCS1 and/or CBLB inhibitor at one or more steps of the manufacturing process reduces the amount of IL-2, 4-1BBL (CD137L), and/or anti-CD3 required in the culture in order to produce the population of expanded lymphocytes. In some embodiments, the amount of IL-2 needed to produce the population of expanded lymphocytes is less than 6000 U/mL when the SOCS1 and/or CBLB inhibitor is added at one or more steps of the manufacturing process. In some embodiments, the amount of IL-2 required to produce the populations of expanded lymphocytes according to the methods described herein is about 5500 U/mL, about 5000 U/mL, about 4500 U/mL, about 4000 U/mL, about 3500 U/mL, about 3000 U/mL, about 2500 U/mL, about 2000 U/mL, about 1500 U/mL, about 1000 U/mL, or about 500 U/mL. In some embodiments, the amount of IL-2 required to produce the populations of expanded lymphocytes according to the methods described herein is between about 500 U/mL and about 5500 U/mL. In some embodiments, addition of the SOCS1 and/or CBLB inhibitor during the manufacturing process eliminates the need for addition of one or more cytokines and/or activation factors in order to produce the expanded population of lymphocytes. For example, in some embodiments, addition of the SOCS1 and/or CBLB inhibitor during one or more steps of the manufacturing process eliminates the need for exogenous IL-2 and/or anti-CD3 antibodies in the culture. In some embodiments, the inhibition of SOCS1 and/or CBLB is temporary. In such embodiments, the SOCS1 and/or CBLB inhibitor is removed from or degraded during the culture of the population of lymphocytes, such that the expression of the SOCS1 and/or CBLB genes, or function of the SOCS1 and/or CBLB proteins, in the final population of lymphocytes is substantially the same as is observed in cells that have not been exposed to the SOCS1 and/or CBLB inhibitor.

The inhibitor of SOCS1 and/or CBLB can be added to the culture at any point throughout the manufacturing process. For example, in some embodiments, the inhibitor of SOCS1 and/or CBLB is added to the culture after processing of the tumor sample and prior to any expansion phases and remains present throughout the remainder of the manufacturing process. In some embodiments, the inhibitor of SOCS1 and/or CBLB is added to the culture before or during the first expansion phase and removed prior to the second expansion phase. In some embodiments, the inhibitor of SOCS1 and/or CBLB is added to the culture before or during the first expansion phase and remains present throughout the remainder of the manufacturing process. In some embodiments, the inhibitor of SOCS1 and/or CBLB is added to the culture after the first expansion phase and prior to or during the second expansion phase and remains present throughout the remainder of the manufacturing process. In some embodiments, the inhibitor of SOCS1 and/or CBLB is added to the culture prior to or during the second expansion phase and removed after the completion of the second expansion phase. In some embodiments, the inhibitor of SOCS1 and/or CBLB is added to the culture prior to the first expansion phase and remains present throughout the remainder of the manufacturing process. In some embodiments, the inhibitor of SOCS1 and/or CBLB is added to the culture during the second expansion phase and remains present after the completion of the manufacturing process. In some embodiments, the inhibitor of SOCS1 and/or CBLB is added to the culture before, during, or after any of the steps in the manufacturing process and is removed prior to infusion of the manufactured population into a patient.

V. Compositions and Kits

The term "composition" as used herein refers to a formulation of a gene-regulating system or a modified immune effector cell described herein that is capable of being administered or delivered to a subject or cell. Typically, formulations include all physiologically acceptable compositions including derivatives and/or prodrugs, solvates, stereoisomers, racemates, or tautomers thereof with any physiologically acceptable carriers, diluents, and/or excipients. A "therapeutic composition" or "pharmaceutical composition" (used interchangeably herein) is a composition of a gene-regulating system or a modified immune effector cell capable of being administered to a subject for the treatment of a particular disease or disorder or contacted with a cell for modification of one or more endogenous target genes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, and/or emulsifier which has been approved by the United States Food and Drug Administration as being acceptable for use in humans and/or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations. Except insofar as any conventional media and/or agent is incompatible with the agents of the present disclosure, its use in therapeutic compositions is contemplated. Supplementary active ingredients also can be incorporated into the compositions.

"Pharmaceutically acceptable salt" includes both acid and base addition salts. Pharmaceutically-acceptable salts include the acid addition salts (formed with the free amino groups of the protein) and which are formed with inorganic acids such as, for example, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-O-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, ptoluenesulfonic acid, trifluoroacetic acid, undecylenic acid, and the like. Salts formed with the free carboxyl groups can also be derived from inorganic bases such as, for example, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

In some embodiments, the present disclosure provides kits for carrying out a method described herein. In some embodiments, a kit can include:

(a) one or more nucleic acid molecules capable of reducing the expression or modifying the function of a gene product encoded by one or more endogenous target genes;

(b) one or more polynucleotides encoding a nucleic acid molecule that is capable of reducing the expression or modifying the function of a gene product encoded by one or more endogenous target genes;

(c) one or more proteins capable of reducing the expression or modifying the function of a gene product encoded by one or more endogenous target genes;

(d) one or more polynucleotides encoding a modifying protein that is capable of reducing the expression or modifying the function of a gene product encoded by one or more endogenous target genes;

(e) one or more gRNAs capable of binding to a target DNA sequence in an endogenous gene;

(f) one or more polynucleotides encoding one or more gRNAs capable of binding to a target DNA sequence in an endogenous gene;

(g) one or more site-directed modifying polypeptides capable of interacting with a gRNA and modifying a target DNA sequence in an endogenous gene;

(h) one or more polynucleotides encoding a site-directed modifying polypeptide capable of interacting with a gRNA and modifying a target DNA sequence in an endogenous gene;

(i) one or more guide DNAs (gDNAs) capable of binding to a target DNA sequence in an endogenous gene;

(j) one or more polynucleotides encoding one or more gDNAs capable of binding to a target DNA sequence in an endogenous gene;

(k) one or more site-directed modifying polypeptides capable of interacting with a gDNA and modifying a target DNA sequence in an endogenous gene;

(l) one or more polynucleotides encoding a site-directed modifying polypeptide capable of interacting with a gDNA and modifying a target DNA sequence in an endogenous gene;

(m) one or more gRNAs capable of binding to a target mRNA sequence encoded by an endogenous gene;

(n) one or more polynucleotides encoding one or more gRNAs capable of binding to a target mRNA sequence encoded by an endogenous gene;

(o) one or more site-directed modifying polypeptides capable of interacting with a gRNA and modifying a target mRNA sequence encoded by an endogenous gene;

(p) one or more polynucleotides encoding a site-directed modifying polypeptide capable of interacting with a gRNA and modifying a target mRNA sequence encoded by an endogenous gene;

(q) a modified immune effector cell described herein; or (r) any combination of the above.

In some embodiments, the kits described herein further comprise one or more immune checkpoint inhibitors. Several immune checkpoint inhibitors are known in the art and have received FDA approval for the treatment of one or more cancers. For example, FDA-approved PD-L1 inhibitors include Atezolizumab (Tecentriq®, Genentech), Avelumab (Bavencio®, Pfizer), and Durvalumab (Imfinzi®, AstraZeneca); FDA-approved PD-1 inhibitors include Pembrolizumab (Keytruda®, Merck) and Nivolumab (Opdivo®, Bristol-Myers Squibb); and FDA-approved CTLA4 inhibitors include Ipilimumab (Yervoy®, Bristol-Myers Squibb). Additional inhibitory immune checkpoint molecules that may be the target of future therapeutics include A2AR, B7-H3, B7-H4, BTLA, IDO, LAG3 (e.g., BMS-986016, under development by BSM), KIR (e.g., Lirilumab, under development by BSM), TIM3, TIGIT, and VISTA.

In some embodiments, the kits described herein comprise one or more components of a gene-regulating system (or one or more polynucleotides encoding the one or more components) and one or more immune checkpoint inhibitors known in the art (e.g., a PD1 inhibitor, a CTLA4 inhibitor, a PDL1 inhibitor, etc.). In some embodiments, the kits described herein comprise one or more components of a gene-regulating system (or one or more polynucleotides encoding the one or more components) and an anti-PD1 antibody (e.g., Pembrolizumab or Nivolumab). In some embodiments, the kits described herein comprise a modified immune effector cell described herein (or population thereof) and one or more immune checkpoint inhibitors known in the art (e.g., a PD1 inhibitor, a CTLA4 inhibitor, a PDL1 inhibitor, etc.). In some embodiments, the kits described herein comprise a modified immune effector cell described herein (or population thereof) and an anti-PD1 antibody (e.g., Pembrolizumab or Nivolumab).

In some embodiments, the kit comprises one or more components of a gene-regulating system (or one or more polynucleotides encoding the one or more components) and a reagent for reconstituting and/or diluting the components. In some embodiments, a kit comprising one or more components of a gene-regulating system (or one or more polynucleotides encoding the one or more components) and further comprises one or more additional reagents, where such additional reagents can be selected from: a buffer for introducing the gene-regulating system into a cell; a wash buffer; a control reagent; a control expression vector or RNA polynucleotide; a reagent for in vitro production of the gene-regulating system from DNA, and the like. Components of a kit can be in separate containers or can be combined in a single container.

In addition to above-mentioned components, in some embodiments a kit further comprises instructions for using the components of the kit to practice the methods of the present disclosure. The instructions for practicing the methods are generally recorded on a suitable recording medium. For example, the instructions may be printed on a substrate, such as paper or plastic, etc. As such, the instructions may be present in the kits as a package insert or in the labeling of the container of the kit or components thereof (i.e., associated with the packaging or sub-packaging). In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

VI. Therapeutic Methods and Applications

In some embodiments, the modified immune effector cells and gene-regulating systems described herein may be used in a variety of therapeutic applications. For example, in some embodiments the modified immune effector cells and/or gene-regulating systems described herein may be administered to a subject for purposes such as gene therapy, e.g. to treat a disease, for use as an antiviral, for use as an anti-pathogenic, for use as an anti-cancer therapeutic, or for biological research.

In some embodiments, the subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals (e.g. mice, rats, guinea pigs, hamsters, rabbits, etc.) may be used for experimental investigations.

Administration of the modified immune effector cells described herein, populations thereof, and compositions thereof can occur by injection, irrigation, inhalation, consumption, electro-osmosis, hemodialysis, iontophoresis, and other methods known in the art. In some embodiments, administration route is local or systemic. In some embodiments administration route is intraarterial, intracranial, intradermal, intraduodenal, intrammamary, intrameningeal, intraperitoneal, intrathecal, intratumoral, intravenous, intravitreal, ophthalmic, parenteral, spinal, subcutaneous, ureteral, urethral, vaginal, or intrauterine.

In some embodiments, the administration route is by infusion (e.g., continuous or bolus). Examples of methods for local administration, that is, delivery to the site of injury or disease, include through an Ommaya reservoir, e.g. for intrathecal delivery (See e.g., U.S. Pat. Nos. 5,222,982 and 5,385,582, incorporated herein by reference); by bolus injection, e.g. by a syringe, e.g. into a joint; by continuous infusion, e.g. by cannulation, such as with convection (See e.g., US Patent Application Publication No. 2007-0254842, incorporated herein by reference); or by implanting a device upon which the cells have been reversibly affixed (see e.g. US Patent Application Publication Nos. 2008-0081064 and 2009-0196903, incorporated herein by reference). In some embodiments, the administration route is by topical administration or direct injection. In some embodiments, the modified immune effector cells described herein may be provided to the subject alone or with a suitable substrate or matrix, e.g. to support their growth and/or organization in the tissue to which they are being transplanted.

In some embodiments, at least $1\times10^3$ cells are administered to a subject. In some embodiments, at least $5\times10^3$ cells, $1\times10^4$ cells, $5\times10^4$ cells, $1\times10^5$ cells, $5\times10^5$ cells, $1\times10^6$, $2\times10^6$, 3 4 5$\times10^6$ $5\times10^6 \times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more cells are administered to a subject. In some embodiments, between about $1\times10^7$ and about $1\times10^{12}$ cells are administered to a subject. In some embodiments, between about $1\times10^8$ and about $1\times10^{12}$ cells are administered to a subject. In some embodiments, between about $1\times10^9$ and about $1\times10^{12}$ cells are administered to a subject. In some embodiments, between about $1\times10^{10}$ and about $1\times10^{12}$ cells are administered to a subject. In some embodiments, between about $1\times10^{11}$ and about $1\times10^{12}$ cells are administered to a subject. In some embodiments, between about $1\times10^7$ and about $1\times10^{11}$ cells are administered to a subject. In some embodiments, between about $1\times10^7$ and about $1\times10^{10}$ cells are administered to a subject. In some embodiments, between about $1\times10^7$ and about $1\times10^9$ cells are administered to a subject. In some embodiments, between about $1\times10^7$ and about $1\times10^8$ cells are administered to a subject. The number of administrations of treatment to a subject may vary. In some embodiments, introducing the modified immune effector cells into the subject may be a one-time event. In some embodiments, such treatment may require an on-going series of repeated treatments. In some embodiments, multiple administrations of the modified immune effector cells may be required before an effect is observed. The exact protocols depend upon the disease or condition, the stage of the disease and parameters of the individual subject being treated.

In some embodiments, the gene-regulating systems described herein are employed to modify cellular DNA or RNA in vivo, such as for gene therapy or for biological research. In such embodiments, a gene-regulating system may be administered directly to the subject, such as by the methods described supra. In some embodiments, the gene-regulating systems described herein are employed for the ex vivo or in vitro modification of a population of immune effector cells. In such embodiments, the gene-regulating systems described herein are administered to a sample comprising immune effector cells.

In some embodiments, the modified immune effector cells described herein are administered to a subject. In some embodiments, the modified immune effector cells described herein administered to a subject are autologous immune effector cells. The term "autologous" in this context refers to cells that have been derived from the same subject to which they are administered. For example, immune effector cells may be obtained from a subject, modified ex vivo according to the methods described herein, and then administered to the same subject in order to treat a disease. In such embodiments, the cells administered to the subject are autologous immune effector cells. In some embodiments, the modified immune effector cells, or compositions thereof, administered to a subject are allogenic immune effector cells. The term "allogenic" in this context refers to cells that have been derived from one subject and are administered to another subject. For example, immune effector cells may be obtained from a first subject, modified ex vivo according to the methods described herein and then administered to a second subject in order to treat a disease. In such embodiments, the cells administered to the subject are allogenic immune effector cells.

In some embodiments, the modified immune effector cells described herein are administered to a subject in order to treat a disease. In some embodiments, treatment comprises delivering an effective amount of a population of cells (e.g., a population of modified immune effector cells) or composition thereof to a subject in need thereof. In some embodiments, treating refers to the treatment of a disease in a mammal, e.g., in a human, including (a) inhibiting the disease, i.e., arresting disease development or preventing disease progression; (b) relieving the disease, i.e., causing regression of the disease state or relieving one or more symptoms of the disease; and (c) curing the disease, i.e., remission of one or more disease symptoms. In some embodiments, treatment may refer to a short-term (e.g., temporary and/or acute) and/or a long-term (e.g., sustained) reduction in one or more disease symptoms. In some embodiments, treatment results in an improvement or remediation of the symptoms of the disease. The improvement is an observable or measurable improvement, or may be an improvement in the general feeling of well-being of the subject.

The effective amount of a modified immune effector cell administered to a particular subject will depend on a variety of factors, several of which will differ from patient to patient including the disorder being treated and the severity of the disorder; activity of the specific agent(s) employed; the age, body weight, general health, sex and diet of the patient; the timing of administration, route of administration; the duration of the treatment; drugs used in combination; the judgment of the prescribing physician; and like factors known in the medical arts.

In some embodiments, the effective amount of a modified immune effector cell may be the number of cells required to result in at least 1, 2, 3, 4, 5, 6, 7, 8, 9, 10, 20, 30, 40, 50, 60, 70, 80, 90, 100, or more fold decrease in tumor mass or volume, decrease in the number of tumor cells, or decrease in the number of metastases. In some embodiments, the effective amount of a modified immune effector cell may be the number of cells required to achieve an increase in life expectancy, an increase in progression-free or disease-free survival, or amelioration of various physiological symptoms associated with the disease being treated. In some embodiments, an effective amount of modified immune effector cells will be at least $1\times10^3$ cells, for example $5\times10^3$ cells, $1\times10^4$ cells, $5\times10^4$ cells, $1\times10^5$ cells, $5\times10^5$ cells, $1\times10^6$, $2\times10^6$, $3\times10^6$, $4\times10^6$, $5\times10^6$, $1\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more cells.

In some embodiments, the modified immune effector cells and gene-regulating systems described herein may be used in the treatment of a cell-proliferative disorder, such as a cancer. Cancers that may be treated using the compositions and methods disclosed herein include cancers of the blood and solid tumors. For example, cancers that may be treated using the compositions and methods disclosed herein include, but are not limited to, adenoma, carcinoma, sarcoma, leukemia or lymphoma. In some embodiments, the cancer is chronic lymphocytic leukemia (CLL), B cell acute lymphocytic leukemia (B-ALL), acute lymphoblastic leukemia (ALL), acute myeloid leukemia (AML), non-Hodgkin's lymphoma (NHL), diffuse large cell lymphoma (DLCL), diffuse large B cell lymphoma (DLBCL), Hodgkin's lymphoma, multiple myeloma, renal cell carcinoma (RCC), neuroblastoma, colorectal cancer, bladder cancer, breast cancer, colorectal cancer, ovarian cancer, melanoma, sarcoma, prostate cancer, lung cancer, esophageal cancer, hepatocellular carcinoma, pancreatic cancer, astrocytoma, mesothelioma, head and neck cancer, and medulloblastoma, and liver cancer. In some embodiments, the cancer is selected from a melanoma, head and neck cancer, bladder cancer, lung cancer, cervical cancer, pancreatic cancer, breast cancer, and colorectal cancer. In some embodiments, the cancer is insensitive, or resistant, to treatment with a PD1 inhibitor. In some embodiments, the cancer is insensitive, or resistant to treatment with a PD1 inhibitor and is selected from a melanoma, head and neck cancer, bladder cancer, lung cancer, cervical cancer, pancreatic cancer, breast cancer, and colorectal cancer.

As described above, several immune checkpoint inhibitors are currently approved for use in a variety of oncologic indications (e.g., CTLA4 inhibitors, PD1 inhibitors, PDL1 inhibitors, etc.). In some embodiments, administration of a modified immune effector cell comprising reduced expression and/or function of an endogenous target gene described herein results in an enhanced therapeutic effect (e.g., a more significant reduction in tumor growth, an increase in tumor infiltration by lymphocytes, an increase in the length of progression free survival, etc.) than is observed after treatment with an immune checkpoint inhibitor.

Further, some oncologic indications are non-responsive (i.e., are insensitive) to treatment with immune checkpoint inhibitors. Further still, some oncologic indications that are initially responsive (i.e., sensitive) to treatment with immune checkpoint inhibitors develop an inhibitor-resistant phenotype during the course of treatment. Therefore, in some embodiments, the modified immune effector cells described herein, or compositions thereof, are administered to treat a cancer that is resistant (or partially resistant) or insensitive (or partially insensitive) to treatment with one or more immune checkpoint inhibitors. In some embodiments, administration of the modified immune effector cells or compositions thereof to a subject suffering from a cancer that is resistant (or partially resistant) or insensitive (or partially insensitive) to treatment with one or more immune checkpoint inhibitors results in treatment of the cancer (e.g., reduction in tumor growth, an increase in the length of progression free survival, etc.). In some embodiments, the cancer is resistant (or partially resistant) or insensitive (or partially insensitive) to treatment with a PD1 inhibitor.

In some embodiments, the modified immune effector cells or compositions thereof are administered in combination with an immune checkpoint inhibitor. In some embodiments, administration of the modified immune effector cells in combination with the immune checkpoint inhibitor results in an enhanced therapeutic effect in a cancer that is resistant, refractory, or insensitive to treatment by an immune checkpoint inhibitor than is observed by treatment with either the modified immune effector cells or the immune checkpoint inhibitor alone. In some embodiments, administration of the modified immune effector cells in combination with the immune checkpoint inhibitor results in an enhanced therapeutic effect in a cancer that is partially resistant, partially refractory, or partially insensitive to treatment by an immune checkpoint inhibitor than is observed by treatment with either the modified immune effector cells or the immune checkpoint inhibitor alone. In some embodiments, the cancer is resistant (or partially resistant), refractory (or partially refractory), or insensitive (or partially insensitive) to treatment with a PD1 inhibitor.

In some embodiments, administration of a modified immune effector cell described herein or composition thereof in combination with an anti-PD1 antibody results in an enhanced therapeutic effect in a cancer that is resistant or insensitive to treatment by the anti-PD1 antibody alone. In some embodiments, administration of a modified immune effector cell described herein or composition thereof in combination with an anti-PD1 antibody results in an enhanced therapeutic effect in a cancer that is partially resistant or partially insensitive to treatment by the anti-PD1 antibody alone.

Cancers that demonstrate resistance or sensitivity to immune checkpoint inhibition are known in the art and can be tested in a variety of in vivo and in vitro models. For example, some melanomas are sensitive to treatment with an immune checkpoint inhibitor such as an anti-PD1 antibody and can be modeled in an in vivo B16-Ova tumor model (See Examples 6, 14, and 17). Further, some colorectal cancers are known to be resistant to treatment with an immune checkpoint inhibitor such as an anti-PD1 antibody and can be modeled in a PMEL/MC38-gp100 model (See Examples 7 and 15). Further still, some lymphomas are known to be insensitive to treatment with an immune checkpoint inhibitor such as an anti-PD1 antibody and can be modeled in a various models by adoptive transfer or subcutaneous administration of lymphoma cell lines, such as Raji cells (See Examples 10, 12, and 13).

In some embodiments, the modified immune effector cells and gene-regulating systems described herein may be used in the treatment of a viral infection. In some embodiments, the virus is selected from one of adenoviruses, herpesviruses (including, for example, herpes simplex virus and Epstein Barr virus, and herpes zoster virus), poxviruses, papovaviruses, hepatitis viruses, (including, for example, hepatitis B virus and hepatitis C virus), papilloma viruses, orthomyxoviruses (including, for example, influenza A, influenza B, and influenza C), paramyxoviruses, coronaviruses, picornaviruses, reoviruses, togaviruses, flaviviruses, bunyaviridae, rhabdoviruses, rotavirus, respiratory syncitial virus, human immunodeficiency virus, or retroviruses.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

EXAMPLES

Example 1: Materials and Methods

The experiments described herein utilize the CRISPR/Cas9 system to modulate expression of one or more endogenous target genes in different T cell populations.

I. Materials gRNAs: Unless otherwise indicated, all experiments use single-molecule gRNAs (sgRNAs). Dual gRNA molecules were used as indicated and were formed by duplexing 200 µM tracrRNA (IDT Cat #1072534) with 200 µM of target-specific crRNA (IDT) in nuclease free duplex buffer (IDT Cat #11-01-03-01) for 5 min at 950 C, to form 100 µM of tracrRNA:crRNA duplex, where the tracrRNA and crRNA are present at a 1:1 ratio. Targeting sequences of the gRNAs used in the following experiments are provided in Table 10 below.

TABLE 10

Targeting sequences of experimental gRNAs

| Target Gene | Guide ID | Sequence | SEQ ID |
|---|---|---|---|
| Pdcd1-murine | Nm.Pdcd1 | CGGAGGATCTTATGCTGAAC | 778 |
| Lag3-murine | Nm.Lag3 | GCCAAGTGGACTCCTCCTGG | 602 |
| Cblb-murine | Nm.Cblb | CCTTATCTTCAGTCACATGC | 502 |
| CBLB-human | Nm.CBLB | TAAACTTACCTGAAACAGCC | 521 |
| BCOR-human | Nm.BCOR | GTGCAGACTGGAGAATACAG | 715 |
| Socs1-murine | Nm.Socs1_1 | GCCGGCCGCTTCCACTTGGA | 1090 |
| Socs1-murine | Nm.Socs1_2 | CGAGCCCGTGGGCACCTTCT | 1098 |
| Ankrd11-murine | Nm.Ankrd11_1 | GTGAACCTCCTGTTAGGCAA | 1068 |
| Ankrd11-murine | Nm.Ankrd11_2 | GGCGAATTGGCTACTTTCAA | 1065 |

Cas9: Cas9 was expressed in target cells by introduction of either Cas9 mRNA or a Cas9 protein. Unless otherwise indicated, Cas9-encoding mRNA comprising a nuclear localization sequence (Cas9-NLS mRNA) derived from *S. pyogenes* (Trilink L-7206) or Cas9 protein derived from *S. pyogenes* (IDT Cat #1074182) was used in the following experiments.

RNPs: For human ribonucleoproteins (RNPs), gRNA-Cas9 RNPs were formed by combining 1.2 µL of 100 µM tracrRNA:crRNA duplex with 1 µL of 20 µM Cas9 protein and 0.8 L of PBS. Mixtures were incubated at RT for 20 minutes to form the RNP complexes. For murine RNPs, gRNA-Cas9 RNPs were formed by combining 1 Volume of 44 µM tracrRNA:crRNA duplex with 1 Volume of 36 µM Cas9. Mixtures were incubated at RT for 20 minutes to form the RNP complexes..

Mice: Wild type CD8+ T cells were derived from C57BL/6J mice (The Jackson Laboratory, Bar Harbor ME). Ovalbumin (Ova)-specific CD8+ T cells were derived from OT1 mice (C57BL/6-Tg(TcraTcrb) 1100Mjb/J; Jackson Laboratory). OT1 mice comprise a transgenic TCR that recognizes residues 257-264 of the ovalbumin (Ova) protein. gp100-specific CD8+ T cells were derived from PMEL mice (B6.Cg-Thy1<a>/CyTg(TcraTcrb) 8Rest/J; The Jackson Laboratory, Bar Harbor ME Cat #005023). Mice constitutively expressing the Cas9 protein were obtain from Jackson labs (B6J.129(Cg)-Gt(ROSA)26Sortml.1(CAG-cas9*,-EGFP)Fezh/J; The Jackson Laboratory, Bar Harbor ME Strain #026179), TCR-transgenic mice constitutively expressing Cas9 were obtained by breeding of OT1 and PMEL mice with Cas9 mice.

siRNAs: Self-delivering Accell siRNAs (Dharmacon) are used for gene silencing in murine CD8 T cells. Control (catalog #: K-005000-G1-02) or Socs1 (Catalog #E-043120-00-0005) or Ankrd11 (Catalog #E-061462-00-0005) gene targeting Accell siRNA are prepared according to the manufacturer's instructions. Purified murine CD8 T-cells are activated with anti-CD3/anti-CD28 beads (Dynabeads™ Mouse T-Activator CD3/CD28 for T-Cell Expansion and Activation Cat #11456D) in siRNA delivery media (Dharmacon Catalog #B-005000-500) containing 2.5% Heat Inactivated FBS supplemented with 10 ng/mL of Recombinant Mouse IL-2 (Biolegend Catalog #575406). Self-delivering Accell siRNAs are added at a final concentration of 1 µM. After 72h, activation beads are removed and cells are assessed for STAT phosphorylation by flow cytometry or pelleted for RNA isolation and gene expression analysis by qRT-PCR.

Zinc-fingers: Engineered zinc finger nuclease (ZFN) domains were generated by Sigma Aldrich in plasmid pairs (CSTZFN-1KT COMPOZR® Custom Zinc Finger Nuclease (ZFN) R-3257609). The domains were customized to recognize positions Chr8:122899675-122899667 and Chr8:122899614-122899608 of mouseAnkrd11 gene, positions Chr16:10784576-10784562 and Chr16:10784346-10784325 of mouse Socs1 gene and positions Chr6:42538446-42538447 of the control mouse gene 0fr455. Plasmids are prepared using the commercial NEB Monarch Miniprep system (Cat #T1010) following manufacturer's protocol. The DNA template is linearized using 10 µg total input and purified using the NEB Monarch PCR and DNA Cleanup kit (Cat #T1030). An in vitro transcription reaction to generate 5'-capped RNA transcripts is performed using 6 µg of purified DNA template and the Promega T7 RiboMAX Large Scale RNA Production System (P1300 and P1712) following the manufacture's conditions. Transcripts are purified using Qiagen RNeasy Mini purification kit (Cat #74104). The integrity and concentration of each ZFN domain transcript is confirmed using the Agilent 4200 TapeStation system. Purified transcripts are polyadenylated using the NEB *E. coli* Poly(A) Polymerase (M0276) using 10 units per reaction. The addition of polyadenylated tails is confirmed by a size shift using the Agilent 4200 TapeStation system. Each mature ZFN domain mRNA transcript is combined with its corresponding pair and 10 µg of each pair is mixed with 5 million mouse CD8 T cells and is electroporated according to the methods described below for murine T cell electroporation.

CAR Expression Constructs: CARs specific for human CD19, Her2/Erbb2, and EGFR proteins were generated. Briefly, the 22 amino acid signal peptide of the human granulocyte-macrophage colony stimulating factor receptor subunit alpha (GMSCF-Rα) was fused to an antigen-specific scFv domain specifically binding to one of CD19, Her2/Erbb2, or EGFR. The human CD8a stalk was used as a transmembrane domain. The intracellular signaling domains of the CD34 chain were fused to the cytoplasmic end of the CD8a stalk. For anti-CD19 CARs, the scFv was derived from the anti-human CD19 clone FMC63. To create a CAR specific for human HER2/ERBB2, the anti-human HER2 scFv derived from trastuzumab was used. Similarly, to generate a CAR specific for EGFR, the anti-EGFR scFv derived from cetuximab was used. A summary of exemplary CAR constructs is shown below and amino acid sequences of the full length CAR constructs are provided in SEQ ID NOs: 26, 28, and 30, and nucleic acid sequences of the full length CAR constructs are provided in SEQ ID NOs: 27, 29, and 31.

TABLE 11

Exemplary CAR constructs

| CAR Ref ID | Target | Ag-binding domain | Intracellular Domain | Transmembrane Domain | AA SEQ ID | NA SEQ ID |
|---|---|---|---|---|---|---|
| KSQCAR017 | human EGFR | Cetuximab H225 scFv | CD3 zeta | CD8a hinge | 26 | 27 |
| KSQCAR1909 | human CD19 | FMC63 scFv | CD3 zeta | CD8a hinge | 28 | 29 |
| KSQCAR010 | human HER2 | Herceptin scFv | CD3 zeta | CD8a hinge | 30 | 31 |

Engineered TCRs Expression Constructs: Recombinant TCRs specific for NY-ESO1, MART-1, and WT-1 were generated. Paired TCR-α:TCR-β variable region protein sequences encoding the 1G4 TCR specific for the NY-ESO-1 peptide SLLMWITQC (SEQ ID NO: 2), the DMF4 and DMF5 TCRs specific for the MART-1 peptide AAGIGILTV (SEQ ID NO: 3), and the DLT and high-affinity DLT TCRs specific for the WT-1 peptide, each presented by HLA-A*02:01, were identified from the literature (Robbins et al, Journal of Immunology 2008 180:6116-6131). TCRα chains were composed of V and J gene segments and CDR3α sequences and TCRβ chains were composed of V, D, and J gene segment and CDR3-β sequences. The native TRAC (SEQ ID NO: 22) and TRBC (SEQ ID NOs: 24) protein sequences were fused to the C-terminal ends of the α and β chain variable regions, respectively, to produce 1G4-TCR α/βchains (SEQ ID NOs: 11 and 10, respectively), 95:LY 1G4-TCR α/βchains (SEQ ID NOs: 14 and 13, respectively), DLT-TCR α/βchains (SEQ ID NOs: 5 and 4, respectively), high-affinity DLT-TCR α/βchains (SEQ ID NOs: 8 and 7, respectively), DMF4-TCR α/βchains (SEQ ID NOs: 17 and 16, respectively), and DMF5-TCR α/βchains (SEQ ID NOs: 20 and 19, respectively).

Codon-optimized DNA sequences encoding the engineered TCRα and TCRβ chain proteins were generated where the P2A sequence (SEQ ID NO: 1) was inserted between the DNA sequences encoding the TCRβ and the TCRα chain, such that expression of both TCR chains was driven off of a single promoter in a stoichiometric fashion. The expression cassettes encoding the engineered TCR chains therefore comprised the following format: TCRβ—P2A—TCRα. Final protein sequences for each TCR construct are provided in SEQ ID NO: 12 (1G4), SEQ ID NO: 15 (95:LY 1G4), SEQ ID NO: 6 (DLT), SEQ ID NO: 9 (high-affinity DLT), SEQ ID NO: 18 (DMF4),and SEQ ID NO: 21 (DMF5).

Lentiviral Expression Constructs: The CAR and engineered TCR expression constructs described above were then inserted into a plasmid comprising an SFFV promoter driving expression of the engineered receptor, a T2A sequence, and a puromycin resistance cassette. Unless otherwise indicated, these plasmids further comprised a human or a murine (depending on the species the T cells were derived from) U6 promoter driving expression of one or more sgRNAs. Lentivirus constructs comprising an engineered TCR expression construct may further comprise an sgRNA targeting the endogenous TRAC gene, which encodes the constant region of the α chain of the T cell receptor.

Lentiviruses encoding the engineered receptors described above were generated as follows. Briefly, 289×10$^6$ of LentiX-293T cells were plated out in a 5-layer CellSTACK 24 hours prior to transfection. Serum-free OptiMEM and TransIT-293 were combined and incubated for 5 minutes before combining helper plasmids (58 µg VSVG and 115 µg PAX2-Gag-Pol) with 231 µg of an engineered receptor- and sgRNA-expressing plasmid described above. After 20 minutes, this mixture was added to the LentiX-293T cells with fresh media. Media was replaced 18 hours after transfection and viral supernatants were collected 48 hours post-transfection. Supernatants were treated with Benzonase® nuclease and passed through a 0.45 µm filter to isolate the viral particles. Virus particles were then concentrated by Tangential Flow Filtration (TFF), aliquoted, tittered, and stored at −80° C.

II. Methods

Human T cell Isolation and Activation: Total human PBMCs were isolated from fresh leukopacks by Ficoll gradient centrifugation. CD8+ T-cells were then purified from total PBMCs using a CD8+ T-cell isolation kit (Stemcell Technologies Cat #17953). For T cell activation, CD8+ T cells were plated at 2×106 cells/mL in X-VIVO 15 T Cell Expansion Medium (Lonza, Cat #04-418Q) in a T175 flask, with 6.25 µL/mL of ImmunoCult T-cell activators (anti-CD3/CD28/CD2, StemCell Technologies, Vancouver BC, Canada) and 10 ng/mL human IL2. T-cells were activated for 18 hours prior to transduction with lentiviral constructs.

TIL Isolation and Activation: Tumor infiltrating lymphocytes can also be modified by the methods described herein. In such cases, tumors are surgically resected from human patients and diced with scalpel blades into 1 mm3 pieces, with a single piece of tumor placed into each well of a 24 plate. 2 mL of complete TIL media (RPMI+10% heat inactivated human male AB serum, 1 mM pyruvate, 20 µg/mL gentamycin, 1× glutamax) supplemented with 6000 U/mL of recombinant human IL-2 is added to each well of isolated TILs. 1 mL of media is removed from the well and replaced with fresh media and IL-2 up to 3 times a week as needed. As wells reach confluence, they are split 1:1 in new media+IL-2. After 4-5 weeks of culture, the cells are harvested for rapid expansion.

TIL RapidExpansion: TILs are rapidly expanded by activating 500,000 TILs with 26×106 allogeneic, irradiated (5000cGy) PBMC feeder cells in 20 mL TIL media+20 mL of Aim-V media (Invitrogen)+30 ng/mL OKT3 mAb. 48 hours later (Day 2), 6000 U/mL IL-2 is added to the cultures. On day 5, 20 mL of media is removed, and 20 mL fresh media (+30 ng/ml OKT3) is added. On Day 7, cells are counted, and reseeded at 60×106 cells/L in G-Rex6M well plates (Wilson Wolf, Cat #80660M) or G-Rex100M (Wilson Wolf, Cat #81100S), depending on the number of cells available. 6000 U/mL fresh IL-2 is added on Day 9 and 3000 U/mL fresh IL-2 is added on Day 12. TILs are harvested on Day 14. Expanded cells are then slow-frozen in Cryostor CS-10 (Stemcell Technologies Cat #07930) using Coolcell Freezing containers (Corning) and stored long term in liquid nitrogen.

Murine T cell Isolation and Activation: Spleens from WT or transgenic mice were harvested and reduced to a single cell suspension using the GentleMACS system, according to the manufacturer's recommendations. Purified CD8+ T cells were obtained using the EasySep Mouse CD8+ T Cell Isolation Kit (Catalog #19853). CD8 T-cells were cultured at $1 \times 10^6$ cells/mL in complete T cell media (RPMI+10% heat inactivated FBS, 20 mM HEPES, 100 U/mL Penicillin, 100 μg/mL Streptomycin, 50 μM Beta-Mercaptoethanol) supplemented with 2 ng/mL of Recombinant Mouse IL-2 (Biolegend Catalog #575406) and activated with anti-CD3/anti-CD28 beads (Dynabeads™ Mouse T-Activator CD3/CD28 for T-Cell Expansion and Activation Cat #11456D).

Lentiviral transduction of T cells: T-cells activated 18 hours prior were seeded at 5×106 cells per well in a 6 well plate, in 1.5 mL volume of X-VIVO 15 media, 10 ng/mL human IL-2 and 12.5 μL Immunocult Human CD3/CD28/CD2 T-cell Activator. Lentivirus expressing the engineered receptors was added at an MOI capable of infecting 80% of all cells. 25 μL of Retronectin (1 mg/mL) was added to each well. XVIVO-15 media was added to a final volume of 2.0 mL per well. Unless otherwise indicated, lentiviruses also expressed the sgRNAs. Plates were spun at 600×g for 1.5 hours at room temperature. After 18 hours (Day 2), cells were washed and seeded at 1×106 cells/mL in X-VIVO 15, 10 ng/mL IL2+ T-cell activators.

Electroporation of human T cells: 3 days after T cell activation, T cells were harvested and resuspended in nucleofection buffer (18% supplement 1, 82% P3 buffer from the Amaxa P3 primary cell 4D-Nucleofector X kit S) at a concentration of $100 \times 10^6$ cells/mL. 1.5 μL of sgRNA/Cas9 RNP complexes (containing 120 pmol of crRNA:tracrRNA duplex and 20 pmol of Cas9 nuclease) and 2. 1 μL (100 pmol) of electroporation enhancer were added per 20 μL of cell solution. 25 μL of the cell/RNP/enhancer mixture was then added to each electroporation well. Cells were electroporated using the Lonza electroporator with the "EO-115" program. After electroporation, 80 μL of warm X-VIVO 15 media was added to each well and cells were pooled into a culture flask at a density of $2 \times 10^6$ cells/mL in X-VIVO 15 media containing IL-2 (10 ng/mL). On Day 4, cells were washed, counted, and seeded at densities of 50-100×10⁶ cells/L in X-VIVO 15 media containing IL-2 (10 ng/mL) in G-Rex6M well plates or G-Rex100M, depending on the number of cells available. On Days 6 and 8, 10 ng/mL of fresh recombinant human IL-2 was added to the cultures.

Electroporation of mouse T cells: Murine T-cells activated 48 hours prior were harvested, activation beads were removed and cells were washed and resuspended in Neon nucleofection buffer T. Up to $2 \times 10^6$ cells resuspended in 9 μL Buffer T and 20×10⁶ cells resuspended in 90 μL Buffer T can be electroporated using Neon™ 10—L tip and Neon™ 100—L tip respectively. gRNA/Cas9 RNP complexes or ZFN mRNAs (1 μL per 10 μL tip or 10 μL per 100 μL tip) and 10.8 μM electroporation enhancer (2 μL per 10 μL Tip or 20 μL per 100 μL Tip) were added to the cells. T-cells mixed with gRNA/Cas9 RNP complexes or ZFN mRNAs were pipetted into the Neon™ tips and electroporated using the Neon Transfection System (1700 V/20 ms/1 pulses). Immediately after electroporation, cells were transferred into a culture flask at a density of $1.6 \times 10^6$ cells/mL in warm complete T cell media supplemented with 2 ng/mL of Recombinant Mouse IL-2. Edited murine CD8 T cells were further cultured at $1 \times 10^6$ cells/mL in complete T cell media supplemented with IL-2 for an additional 1-4 days.

Purification and characterization of engineered T cells: 10 days after T cell activation, cells were removed from the culture flasks, and edited, engineered receptor-expressing CD8+ T cells were purified. Expression of the engineered receptor can be determined by antibody staining, e.g., antibodies for V012 for DMF4 TCR or V013/13.1 for NY-ESO-1 or 1G4). Further determination of editing of target genes can be assessed by FACS analysis of surface proteins (e.g., CD3), western blot of the target protein, and/or TIDE/NGS analysis of the genomic cut-site. Purified cells can then be slow-frozen in Cryostor CS-10 (Stemcell Technologies Cat #07930) using Coolcell Freezing containers (Corning), and stored long term in liquid nitrogen for future use.

Example 2: Characterization of Edited, Receptor-Engineered T Cells

Experiments were performed in which edited receptor-expressing cells were purified based on cell surface expression of CD3. Prior to engineering, CD8+ T cells express CD3 molecules on the cell surface as part of a complex that includes the TCR α/β chains (FIG. 4A). The T cells were transduced with a lentivirus expressing a CAR, a guide RNA targeting the TRAC gene, and a guide RNA targeting the B2M gene, which was used to assess the editing of non-TCR genes as a proxy for target gene editing. Following lentiviral transduction and Cas9 mRNA electroporation, successfully transduced and edited T cells demonstrate a loss of surface CD3 expression due to editing of the TRAC gene and a loss of HLA-ABC expression due to the editing of the B2M gene (FIG. 4B). CD3-expressing cells were removed from the bulk population (FIG. 4B) using the EasySep human CD3-positive selection kit (StemCell Tech Cat #18051). Cells were then subjected to two rounds of negative magnetic selection for CD3. This process yielded highly purified CD3-negative T cells expressing (FIG. 4C). Staining with a recombinant CD19-Fc reagent (which binds CD19 CAR) demonstrated that edited cells show surface expression of the CD19 CAR, whereas unedited cells do not (FIG. 4D). Similar experiments were performed with CD45 and B2M targeting sgRNAs. Cas9 editing activity in T cells was confirmed by assessing CD45 and B2M expression by flow cytometry was assessed 96 hours later, and efficient Cas9 function is indicated by a loss of CD45 expression on the surface of the T cells as determined by FACS. Co-electroporation with Cas9 mRNA and Cas9 RNPs led to substantial editing at the CD45 and B2M loci, with 66.3% of the cells exhibiting dual editing.

Target editing was performed as described in the above examples and the editing of a single exemplary gene, CBLB, was confirmed using both the Tracking of Indels by Decomposition (TIDE) analysis method and western blot analysis. TIDE quantifies editing efficacy and identifies the predominant types of insertions and deletions (indels) in the DNA of a targeted cell pool.

Figure 5B:
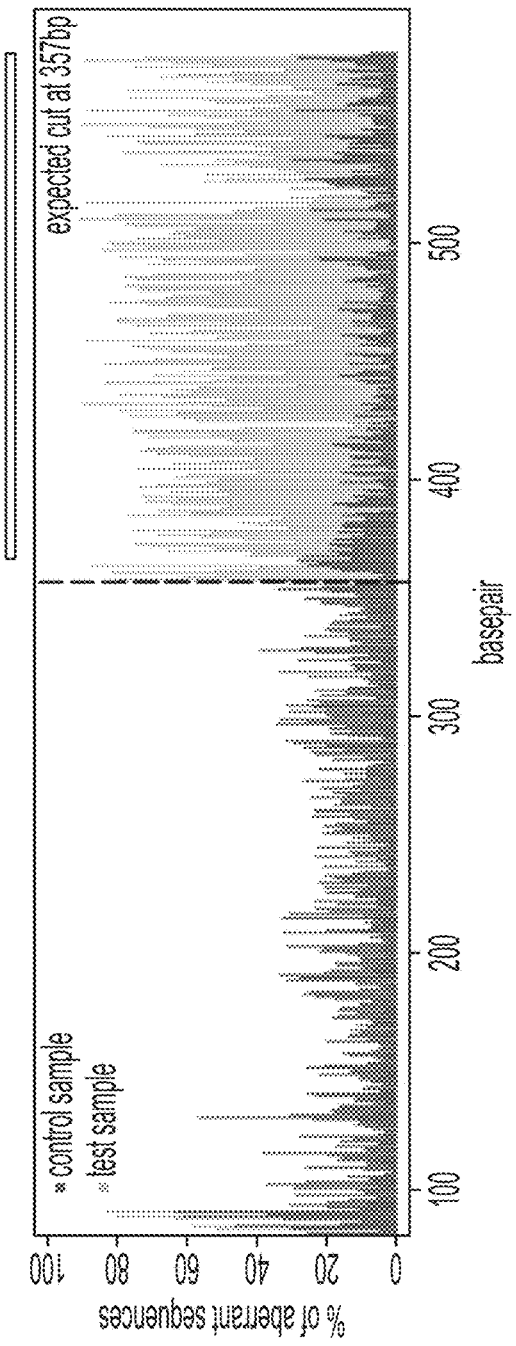
Figure 6:
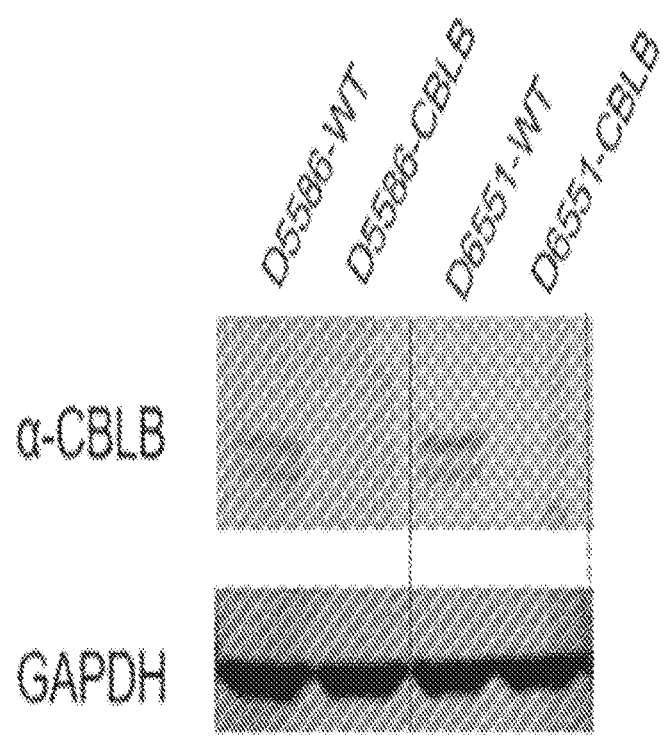
FIG. 6 illustrates a western blot for CBLB protein in primary human T cells edited with a CBLB sgRNA (D6551-CBLB) compared to unedited controls (D6551-WT).

Genomic DNA (gDNA) was isolated from edited T cells using the Qiagen Blood and Cell Culture DNA Mini Kit (Cat #: 13323) following the vendor recommended protocol and quantified. Following gDNA isolation, PCR was performed to amplify the region of edited DNA using locus-specific PCR primers (F: 5'-CCACCTCCAGTTGTTGCATT-3' (SEQ ID NO: 32); R: 5'—TGCTGCTTCAAAGG-GAGGTA-3' (SEQ ID NO: 33). The resulting PCR products were run on a 1% agarose gel, extracted, and purified using the QIAquick Gel Extraction Kit (Cat #: 28706). Extracted products were sequenced by Sanger sequencing and Sanger sequencing chromatogram sequence files were analyzed by TIDE. In CBLB-edited T cells edited by methods using either gRNA/Cas9 RNP complexes or Cas9 mRNA introduced with gRNA expressing lentivirus, the resulting TIDE analysis confirmed editing of the CBLB target gene. In addition to TIDE, depletion of CBLB protein levels were confirmed by western blot using an anti-CBLB antibody (SCT Cat #9498). The data is provided in FIGS. 5A and 5B and FIG. 6.

Another method by which editing of a gene is assessed is by next generation sequencing. For this method, genomic DNA (gDNA) was isolated from edited T cells using the Qiagen Blood and Cell Culture DNA Mini Kit (Cat #: 13323) following the vendor recommended protocol and quantified. Following gDNA isolation, PCR was performed to amplify the region of edited genomic DNA using locus-specific PCR primers containing overhangs required for the addition of Illumina Next Generation sequencing adapters. The resulting PCR product was run on a 1% agarose gel to ensure specific and adequate amplification of the genomic locus occurred before PCR cleanup was conducted according to the vendor recommended protocol using the Monarch PCR & DNA Cleanup Kit (Cat #: T1030S). Purified PCR product was then quantified, and a second PCR was performed to anneal the Illumina sequencing adapters and sample specific indexing sequences required for multiplexing. Following this, the PCR product was run on a 1% agarose gel to assess size before being purified using AMPure XP beads (produced internally). Purified PCR product was then quantified via qPCR using the Kapa Illumina Library Quantification Kit (Cat #: KK4923) and Kapa Illumina Library Quantification DNA Standards (Cat #: KK4903). Quantified product was then loaded on the Illumina NextSeq 500 system using the Illumina NextSeq 500/550 Mid Output Reagent Cartridge v2 (Cat #: FC-404-2003). Analysis of produced sequencing data was performed to assess insertions and deletions (indels) at the anticipated cut site in the DNA of the edited T cell pool.

Example 3: Identification of Adoptive T Cell Transfer Therapy Targets Through an Ot1/B16-Ova Crispr/Cas9 Functional Genomic Screen Experiments were performed to identify targets that regulate accumulation of T cells in tumors. A pooled CRISPR screen was performed in which a pool of sgRNAs, each of which target a single gene, were introduced into a population of tumor-specific T cells such that each cell in the population comprised a single sgRNA targeting a single gene. To determine the effect of a particular gene on the accumulation of T cells in tumor samples, the frequency of each sgRNA in the population of T cells was determined at the beginning of the experiment and compared to the frequency of the same sgRNA at a later time-point in the experiment. The frequency of sgRNAs targeting genes that positively regulate T cell accumulation in tumor samples (e.g., genes that positively-regulate T cell proliferation, viability, and/or tumor infiltration) is expected to increase over time, while the frequency of sgRNAs targeting genes that negatively regulate T cell accumulation in tumor samples (e.g., genes that negatively-regulate T cell proliferation, viability, and/or tumor infiltration) is expected to decrease over time.

Pooled CRISPR screens were performed with CD8+ T cells derived from Cas9 expressing OT1 mice according to methods described in Example 1. The pooled sgRNA library and Cas9 mRNA were introduced to purified OTI CD8+ T cells and cultured in vitro to generate a population of edited CD8+ T cells. After in vitro engineering, the edited OT1 CD8+ T cells were intravenously (iv) administered to B16-Ova tumor-bearing, C56BL/6 mice. After in vivo expansion, organs were harvested and CD45+ were enriched. Genomic DNA from the isolated CD45+ cells was isolated using Qiagen DNA extraction kits. The sgRNA library was then amplified by PCR and sequenced using Illumina next-generation sequencing (NGS).

The distribution and/or frequency of each sgRNA in samples harvested from tumor-bearing mice was analyzed and compared to the distribution and/or frequency of each sgRNA in the initial T cell population. Statistical analyses were performed for each individual sgRNA to identify guides that were significantly enriched in T cell populations harvested from tumor bearing mice and to assign an enrichment score to each of the guides. Enrichment scores for individual sgRNA targeting the same gene were aggregated to identify target genes that had a consistent and reproducible effect on T cell accumulation across multiple sgRNAs and across multiple OT1 donor mice. The results of these experiments are shown below in Table 12. Percentiles in Table 12 were calculated using the following equation: percentile score=1-(gene enrichment rank/total number of genes screened).

TABLE 12

| Target Gene Percentile Scores | |
| --- | --- |
| Target Name | Percentile Score |
| Ikzf1 | 0.995 |
| Nfkbia | 0.986 |
| Gata3 | 0.993 |
| Bcl3 | 0.698 |
| Ikzf3 | 0.995 |
| Smad2 | 0.978 |
| Tgfbr1 | 0.991 |
| Tgfbr2 | 0.987 |
| Tnip1 | 0.991 |
| Tnfaip3 | 0.998 |
| Ikzf2 | 0.622 |
| Tank | 0.83 |
| Ptpn6 | 0.782 |
| Bcor | 0.72 |
| Cblb | 0.999 |
| Nrp1 | 0.826 |
| Havcr2 | 0.86 |
| Lag3 | 0.82 |
| Bcl2l11 | 0.9928 |
| Chic2 | 0.997 |
| Fli1 | 0.999 |
| Pcbp1 | 0.997 |
| Pbrm | 0.944 |
| Wdr6 | 0.953 |
| E2f8 | 0.867 |
| Serpina3 | 0.822 |

TABLE 12-continued

Target Gene Percentile Scores

| Target Name | Percentile Score |
|---|---|
| Sema7a | 0.78 |
| Dhodh | 0.99 |
| Umps | 0.989 |
| Socs1 | 0.999 |
| Ankrd11 | 0.999 |

Example 4: Identification of Adoptive T Cell Transfer Therapy Targets Through in Vitro Car-T and Crispr/Cas9 Functional Genomic Screens Experiments were performed to identify targets that regulate accumulation of CAR-T cells tumor samples. A pooled, genome-wide CRISPR screen was performed in which a pool of sgRNAs, each of which target a single gene, was introduced into a population of tumor-specific human CAR-T cells, such that each cell in the population comprised a single sgRNA targeting a single gene. To determine the effect of a particular gene in CAR-T cell accumulation in tumor samples, the frequency of each sgRNA in the population of CAR-T cells was determined at the beginning of the experiment and compared to the frequency of the same sgRNA at a later time-point in the experiment. The frequency of sgRNAs targeting genes that positively regulate CAR-T cell accumulation in tumor samples (e.g., genes that positively-regulate T cell proliferation, viability, and/or tumor infiltration) is expected to increase over time, while the frequency of sgRNAs targeting genes that negatively regulate CAR-T cell accumulation in tumor samples (e.g., genes that negatively-regulate T cell proliferation, viability, and/or tumor infiltration) is expected to decrease over time.

In vitro screens were performed using CAR-T cells specific for human CD19. Pooled sgRNA libraries were introduced to the CD19 CARTs as described above and cells were electroporated with Cas9 mRNA as described in Example 1 to generate a population of Cas9-edited CD19 CARTs. The edited CD19 CARTs were then co-cultured with an adherent colorectal carcinoma (CRC) cell line engineered to express CD19 or a Burkitt's lymphoma cell line expressing endogenous CD19. CARTs were harvested at various time points throughout the co-culture period and cell pellets were frozen down. Genomic DNA (gDNA) was isolated from these cell pellets using Qiagen DNA extraction kits and sequenced using Illumina next-generation sequencing.

The distribution and/or frequency of each sgRNA in the aliquots taken from the CART/tumor cell co-culture was analyzed and compared to the distribution and/or frequency of each sgRNA in the initial edited CAR-T cell population. Statistical analyses were performed for each individual sgRNA to identify sgRNAs that were significantly enriched in CAR-T cell populations after tumor cell co-culture and to assign an enrichment score to each of the guides. Enrichment scores for individual sgRNA that target the same gene were aggregated to identify target genes that have a consistent and reproducible effect on CAR-T cell accumulation in tumor samples across multiple sgRNAs and CAR-T cell population. Targets were ranked and called for further investigation based on percentile. The results of these experiments are shown below in Table 13. Percentiles in Table 13 were calculated using the following equation: percentile score=1-(gene enrichment rank/total number of genes screened).

TABLE 13

Target Gene Percentile Scores

| Target Name | Percentile Score |
|---|---|
| IKZF1 | 0.999 |
| IKZF3 | 0.962 |
| TGFBR1 | 0.778 |
| TNIP1 | 0.64 |
| TNFAIP3 | 0.791 |
| FOXP3 | 0.866 |
| IKZF2 | 0.907 |
| TANK | 0.93 |
| PTPN6 | 0.707 |
| BCOR | 0.999 |
| CBLB | 0.989 |
| BCL2L11 | 0.93 |
| CHIC2 | 0.71 |
| WDR6 | 0.962 |
| E2F8 | 0.971 |
| DHODH | 0.763 |
| SOCS1 | 0.673 |
| ANKRD11 | 0.716 |

Example 5: Identification of Adoptive T Cell Transfer Therapy Targets Through an IN Vivo CAR-T/TUMOR CRISPR/CAS9 FUNCTIONAL GENOMIC SCREEN Experiments were performed to identify targets that regulate CAR-T cell accumulation in the presence of tumors. A pooled CRISPR screen was performed in which a pool of sgRNAs, each of which target a single gene, was introduced into a population of tumor-specific human CAR-T cells such that each cell in the population comprised a single sgRNA targeting a single gene. To determine the effect of a particular gene in CAR-T cell accumulation in tumor samples, the frequency of each sgRNA in the population of CAR-T cells was determined at the beginning of the experiment and compared to the frequency of the same sgRNA at a later time-point in the experiment. The frequency of sgRNAs targeting genes that positively regulate CAR-T cell accumulation in tumor samples (e.g., genes that positively-regulate T cell proliferation, viability, and/or tumor infiltration) is expected to increase over time, while the frequency of sgRNAs targeting genes that negatively regulate CAR-T cell accumulation in tumor samples (e.g., genes that negatively regulate T cell proliferation, viability, and/or tumor infiltration) is expected to decrease over time.

In vivo screens performed in two separate subcutaneous xenograft models: a Burkitt lymphoma model and a colorectal cancer (CRC) model. For the Burkitt model, $1 \times 10^6$ Burkitt lymphoma tumor cells in Matrigel were subcutaneously injected into the right flank of 6-8 week old NOD/SCID gamma (NSG) mice. Mice were monitored, randomized, and enrolled into the study 13 days post-inoculation, when tumors reached approximately 200 mm$^3$ in volume. For the CRC model, CRC cells were engineered to express CD19, and $5 \times 10^6$ tumor cells in Matrigel were subcutaneously injected into the right flank of 6-8 week old NSG mice. Mice were monitored, randomized, and enrolled into the study 12 days post-inoculation when tumors reached approximately 200 mm$^3$ in volume. Cas9-engineered CD19 CAR-T cells were administered iv via the tail vein at $3 \times 10^6$ and $10 \times 10^6$/mouse (3M and 10M). Tumors were collected 8 to 10 days post-CAR-T injection and frozen in liquid nitrogen. These tissues were later dissociated and processed for genomic DNA extraction.

The distribution and/or frequency of each sgRNA in the genomic DNA samples taken at study end was analyzed and compared to the distribution and/or frequency of each sgRNA in the initial edited-CAR-T cell population. Statistical analyses were performed for each individual sgRNA to identify sgRNAs that are significantly enriched in genomic DNA samples taken at study end and to assign an enrichment score to each of the guides. Enrichment scores for individual sgRNA that target the same gene were aggregated to identify target genes that have a consistent and reproducible effect on CAR-T cell abundance across multiple sgRNAs and CAR-T cell populations. Targets were ranked and called for further investigation based on percentile. The results of these experiments are shown below in Table 14. Percentiles in Table 14 were calculated using the following equation: percentile score=1-(gene enrichment rank/total number of genes screened).

TABLE 14

Target Gene Percentile Scores

| Target Name | Percentile Score |
| --- | --- |
| NFKBIA | 0.95 |
| SMAD2 | 0.816 |
| FOXP3 | 0.92 |
| IKZF2 | 0.895 |
| TANK | 0.923 |
| PTPN6 | 0.979 |
| CBLB | 0.958 |
| PPP2R2D | 0.926 |
| NRP1 | 0.795 |
| HAVCR2 | 0.992 |
| LAG3 | 0.97 |
| TIGIT | 0.916 |
| CTLA4 | 0.884 |
| BCL2L11 | 0.776 |
| RBM39 | 0.94 |
| E2F8 | 0.968 |
| CALM2 | 0.902 |
| SERPINA3 | 0.907 |
| SEMA7A | 0.918 |
| SOCS1 | 0.934 |

Example 6: Validation of Single-Edited Adoptively Transferred T Cells in a Murine Ot1/B16 Ova Syngeneic Tumor Model Targets with percentile scores of 0.6 or greater in Examples 3-5 were selected for further evaluation in a single-guide format to determine whether editing a target gene in tumor-specific T cells conferred an increase in anti-tumor efficacy. Evaluation of exemplary targets is described herein, however these methods can be used to evaluate any of the potential targets described above.

Anti-tumor efficacy of single-edited T cells was evaluated in mice using the B16-Ova subcutaneous syngeneic tumor model, which is sensitive to treatment with anti-PD1 antibodies. Briefly, 6-8 week old female C57BL/6J mice from Jackson labs were injected subcutaneously with $0.5 \times 10^6$ B16-Ova tumor cells. When tumors reached a volume of approximately 100 mm³ mice were randomized into groups of 10 and injected intravenously with edited mouse OT1 CD8+ T cells via tail vein. Prior to injection, the OT1 T cells were edited by electroporation with gRNA/Cas9 RNP complexes comprising (i) a control gRNA; (ii) a single PD1-targeting gRNA; (iii) a single Cblb-targeting gRNA; (iv) a single Socs1-targeting gRNA. To generate a population of tumor-specific CD8+ T cells with edited target genes, spleens from female OT1 mice were harvested and CD8 T cells were isolated as described in Example 1. The edited OT1 CD8+ T cells were then administered intravenously to B16-Ova tumor-bearing C56BL/6 mice. Body weight and tumor volume were measured at least twice per week. Tumor volume was calculated as mean and standard error of the mean for each treatment group. The percentage tumor growth inhibition (TGI) was calculated using mean tumor volumes (TV) according to the following formulas:

$$\% \text{ TGI}=(\text{TV-Target}_{final}-\text{TV-Target}_{initial})/(\text{TV-Control}_{final}-\text{TV-Control}_{initial}),$$

where TV=mean tumor volume, final for Cb1b TGI=Day 18 post-T cell transfer, final for Socs1 TGI=Day 17 post-T cell transfer, and initial=Day 0 (i.e., day of T cell transfer).

Figure 7A:
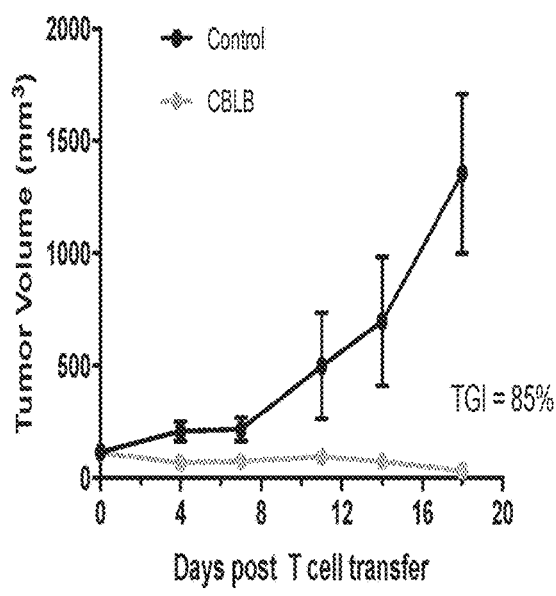
FIG. 7A-FIG. 7B show tumor growth over time in a murine B16/Ova syngeneic tumor model.
Figure 7B:
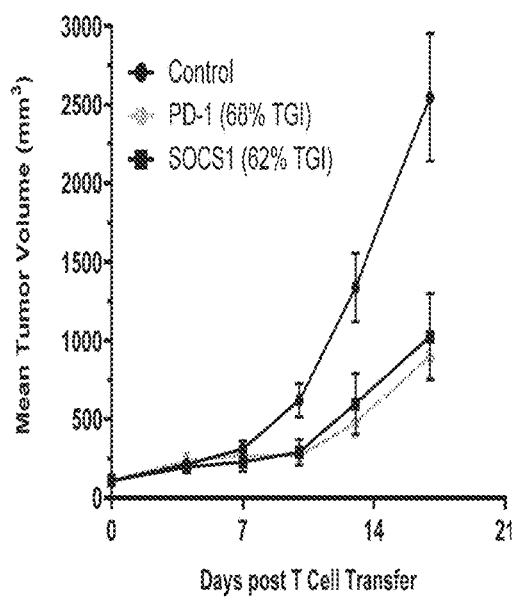

Results of Cblb-edited T cells are shown in FIG. 7A. These data demonstrate that editing of the Cb1b gene in T cells leads to anti-tumor efficacy with a TGI of 85% at day 18. Results of Socs1-edited T cells are shown in FIG. 7B. These data demonstrate that editing of the Socs1 gene in T cells enhances anti-tumor efficacy of the T cells with a TGI of 62% at day 17. Similar experiments can be performed to assess the anti-tumor efficacy of Ankrd11-edited T cells.

Example 7: Validation of Single-Edited Adoptively Transferred T Cells in a Murine Mc38/Gp100 Syngeneic Tumor Model Targets with percentile scores of 0.6 or greater in Examples 3-5 were selected for further evaluation in a single-guide format to determine whether editing a target gene in tumor-specific T cells conferred an increase in anti-tumor efficacy in a murine MC38gp100 subcutaneous syngeneic tumor model of colorectal cancer (which is insensitive to treatment with anti-PD1 antibodies). Evaluation of exemplary targets is described herein, however these methods can be used to evaluate any of the potential targets described above.

Briefly, 6-8 week old female C57BL/6J mice from Jackson labs were injected subcutaneously with $1 \times 10^6$ MC38gp100 tumor cells. Prior to injection, the T cells were edited by electroporation with gRNA/Cas9 RNP complexes comprising (i) a control gRNA; (ii) a single Socs1-targeting gRNA; or (iii) a single Ankrd11-targeting gRNA. When tumors reached a volume of approximately 100 mm³ mice were randomized into groups of 10 and injected intravenously with Socs1-edited or Ankrd11-edited mouse PMEL CD4+ T cells via tail vein. Body weight and tumor volume was measured at least twice per week. Tumor volume was calculated as mean and standard error of the mean for each treatment group.

Figure 8A:
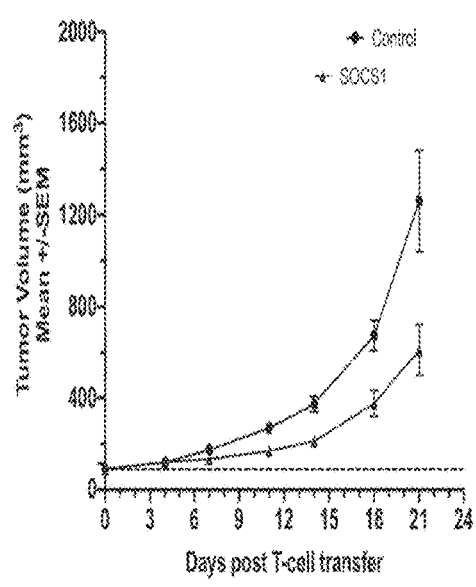
FIG. 8A-FIG. 8B shows tumor growth over time in a murine MC38/gp100 syngeneic tumor model.
Figure 8B:
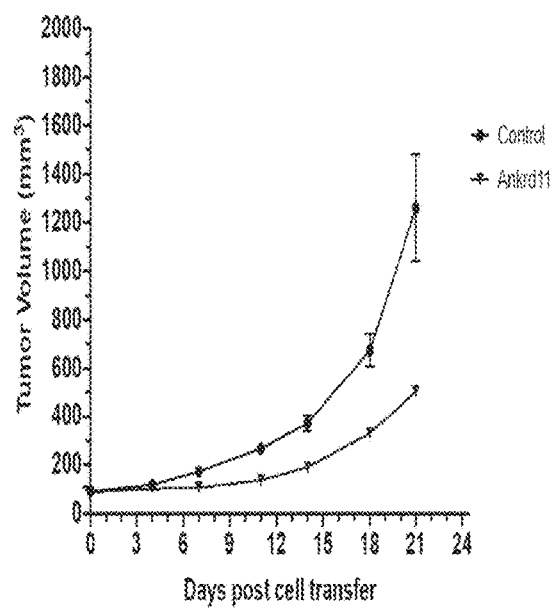
Figure 9:
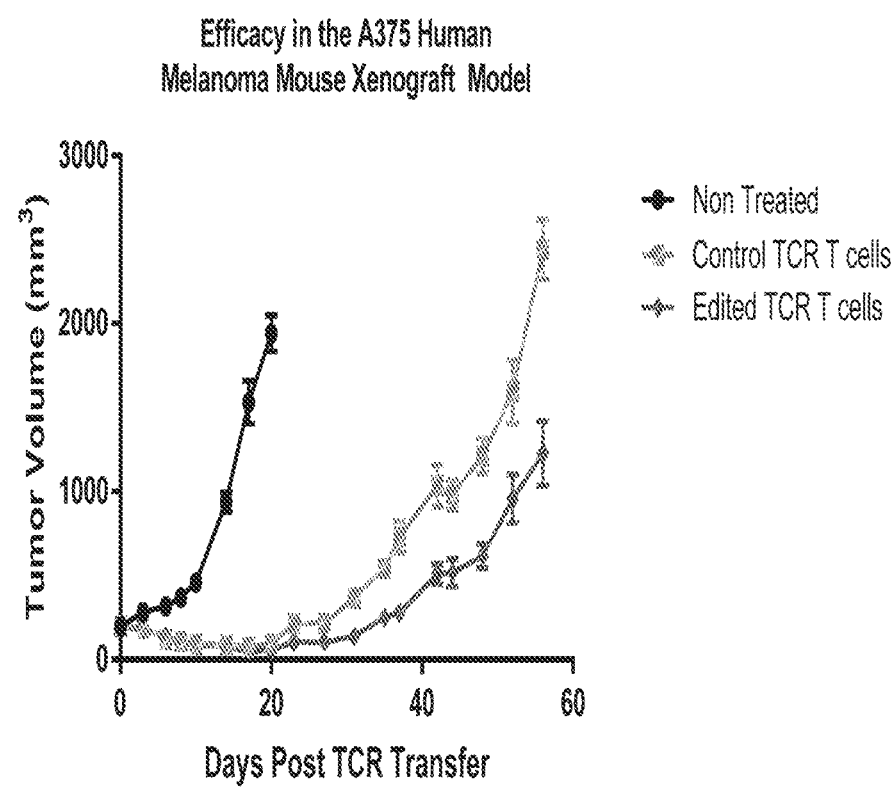
FIG. 9 shows tumor growth over time in a murine A375 xenograft model for mice treated with CBLB-edited T cells compared to control-edited T cells.

Results of Socs1-edited T cells are shown in FIG. 8A and show significant reduction in tumor growth at day Day 21 compared to controls. Results of Ankrd11-edited T cells are shown in FIG. 8B, and similarly show significant reduction in tumor growth at Day 21 compared to controls.

Example 8: Validation of Single-Edited Adoptively Transferred T Cells in a Murine Ot1/Eg70Va Subcutaneous Syngeneic Tumor Model Anti-tumor efficacy of Socs1, Ankrd11, and Cb1b are further evaluated in mice using the Eg7-Ova subcutaneous syngeneic tumor model. 6-8 week old female C57BL/6J mice from Jackson labs are injected subcutaneously with $1 \times 10^6$ Eg7-Ova tumor cells. When tumors reach a volume of approximately 100 mm³ mice are randomized into groups of 10 and injected intravenously with edited mouse OT1 CD8+ T cells via tail vein. Prior to injection these cells are edited with either a control guide or a single guide editing for the Socs1, Ankrd11, or Cb1b genes. Body weight and tumor volume are measured at least twice per week. Tumor volume is calculated as mean and standard error of the mean for each treatment group.

These data are expected to demonstrate that editing of the Socs1, Ankrd11, or Cblb genes in T cells enhances anti-tumor efficacy of the T cells compared to controls.

Example 9: Validation of Single-Edited Adoptively Transferred T Cells in the A375 Xenograft Tumor Model Targets with percentile scores of 0.6 or greater in Examples 3-5 were selected for further evaluation in a single-guide format to determine whether editing a target gene in tumor-specific T cells conferred an increase in anti-tumor efficacy in the A375 xenograft tumor model. Evaluation of exemplary targets is described herein, however these methods can be used to evaluate any of the potential targets described above.

Figure 10:
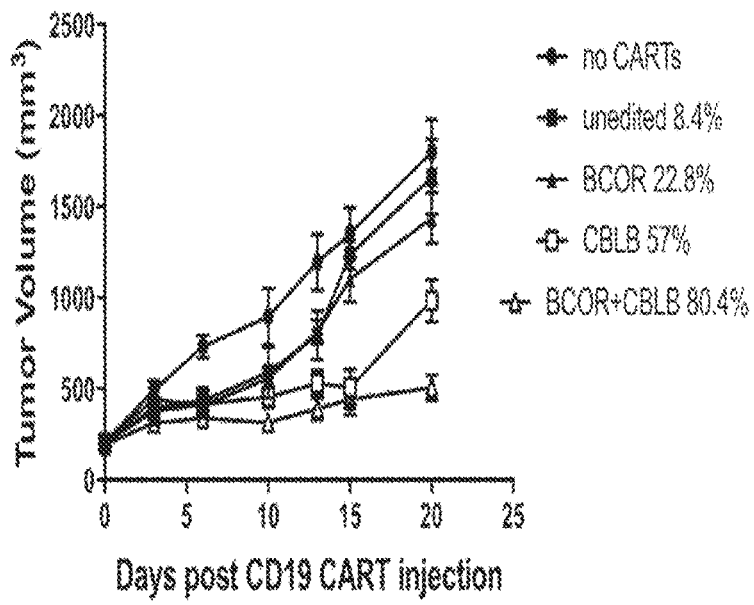
FIG. 10 shows tumor growth over time in mice treated with BCOR-edited, CBLB-edited, or BCOR CBLB dual-edited anti-CD19 CAR T cells. Tumor growth is compared to mice treated with no CAR T cells or unedited anti-CD19 CAR T cells.

Briefly, 6-8 week old NSG mice from Jackson labs were injected subcutaneously with $5 \times 10^6$ A375 cells. When tumors reached a volume of approximately 200 mm$^3$, mice are randomized into groups of 8 and injected intravenously with $18.87 \times 10^6$ edited Tg-TCR cells via tail vein. The CBLB gene in the isolated CD8+ T cells were edited according to methods described in Example 1. The edited Tg-TCR CD8+ T cells were then administered intravenously to A375 tumor-bearing mice. Body weight and tumor volume was measured at least twice per week. Tumor volume was calculated as mean and standard error of the mean for each treatment group (FIG. 10). Similar experiments are performed to assess the anti-tumor efficacy of SOCSI-edited and ANKRD11-edited T cells in the A375 xenograft model. These experiments are expected to show enhanced anti-tumor efficacy of the edited T cells compared to controls.

Example 10: Validation of Single-Edited Adoptively Transferred Cd19 Car-T Cells in a Raji Xenograft Model Experiments are performed to assess the anti-tumor efficacy of SOCSI-edited, ANKRD11-edited, and CBLB-edited 1$^{st}$ generation CD19 CAR-T cells (human) and in the Raji cell-derived xenograft subcutaneous tumor model. Raji cells are a human lymphoma cell line that are known to be insensitive to treatment with anti-PD1 antibodies. Briefly, 6-8 week old female NSG mice from Jackson labs are injected subcutaneously with $3 \times 10^6$ Raji tumor cells. When tumors reach a volume of approximately 200 mm$^3$, mice are randomized into groups of 5 and injected intravenously with edited human CD19 CART cells via tail vein. Prior to injection, the CAR-T cells are edited by electroporation with gRNA/Cas9 RNP complexes comprising (i) a control gRNA; (ii) a single gRNA targeting the SOCS1 gene; (iii) a single gRNA targeting the ANKRD11 gene; (iv) or a single gRNA targeting the CBLB gene. Body weight and tumor volume are measured at least twice per week. Tumor volume is calculated as mean and standard error of the mean for each treatment group. These experiments are expected to demonstrate enhanced anti-tumor efficacy of SOCSI-edited and ANKRD11-edited CAR-T cells compared to control cells as indicated by enhanced tumor growth inhibition and decreased tumor volume over time.

Example 11: Screen for Dual-Edit Combinations

A double sgRNA library was constructed in a retroviral backbone. The library consisted of two U6 promoters (one human and one mouse), each driving expression of a single guide RNA (guide+ tracr, sgRNA). The guides were cloned as pools to provide random pairings between guides, such that every sgRNA would be paired with every other sgRNA. The final double guide library was transfected into Phoenix-Eco 293T cells to generate murine ecotropic retrovirus. TCR transgenic OT1 cells expressing Cas9 were infected with the sgRNA-expressing virus to edit the two loci targeted by each of the sgRNAs. The edited transgenic T-cells were then transferred into mice bearing>400 mm$^3$ B16-Ova tumors allografts. After two weeks, the tumors were excised and the tumor-infiltrating T-cells were purified by digesting the tumors and enriching for CD45+ cells present in the tumors. Genomic DNA was extracted from CD45+ cells using a Qiagen QUIAamp DNA blood kit and the retroviral inserts were recovered by PCR using primers corresponding to the retroviral backbone sequences. The resulting PCR product were then sequenced to identify the sgRNAs present in the tumors two weeks after transfer. The representation of guide pairs in the final isolated cell populations was compared to the initial plasmid population and the population of infected transgenic T-cells before injection into the mouse. The frequency of sgRNA pairs that improved T-cells fitness and/or tumor infiltration were expected to increase over time, while combinations that impaired fitness were expected to decrease over time. Table 15 below shows the median fold change of sgRNA frequency in the final cell population compared to the sgRNA frequency in the initial cell population transferred in vivo.

TABLE 15

| sgRNA frequency in Combination Screen | | |
|---|---|---|
| GeneA | GeneB | Avg(Tmedian.Ifoldch.all) |
| CBLB | CBLB | 0.17 |
| CBLB | CTLA4 | 0.21 |
| CBLB | LAG3 | 0.08 |
| CBLB | Olfr1389 | 0.03 |
| CBLB | Olfr453 | 0.04 |
| CBLB | TGFBR1 | 0.15 |
| CBLB | TGFBR2 | 0.75 |
| CBLB | TIGIT | 0.31 |
| CBLB | ZAP70 | 0 |
| Havcr2 | Havcr2 | 0.02 |
| Havcr2 | LAG3 | 0.01 |
| Havcr2 | Olfr1389 | 0 |
| Havcr2 | Olfr453 | 0.01 |
| Havcr2 | PDCD1 | 0.02 |
| LAG3 | Olfr1389 | 0 |
| LAG3 | Olfr453 | 0.02 |
| LAG3 | PDCD1 | 0.02 |
| Olfr1389 | Olfr1389 | 0.01 |
| Olfr1389 | Olfr453 | 0 |
| Olfr1389 | PDCD1 | 0.02 |
| Olfr453 | Olfr453 | 0.01 |
| Olfr453 | PDCD1 | 0.01 |
| PDCD1 | CTLA4 | 0.59 |
| PDCD1 | LAG3 | 0.02 |
| PDCD1 | PDCD1 | 0.02 |
| PDCD1 | TGFBR1 | 0.02 |
| PDCD1 | TGFBR2 | 0.07 |
| PDCD1 | TIGIT | 0.02 |
| PDCD1 | ZAP70 | 0 |
| TGFBR1 | CTLA4 | 0.01 |

TABLE 15-continued sgRNA frequency in Combination Screen

| GeneA | GeneB | Avg(Tmedian.Ifoldch.all) |
|---|---|---|
| TGFBR1 | LAG3 | 0 |
| TGFBR1 | TGFBR1 | 0.06 |
| TGFBR1 | TGFBR2 | 0.07 |
| TGFBR1 | TIGIT | 0.03 |
| TGFBR1 | ZAP70 | 0 |

Example 12: Validation of Dual-Edited Cd19 Car-T Cells in Raji Xenograft Model

Targets were further evaluated in combination studies to determine combinations of edited genes that increased anti-tumor efficacy of T cells in xenograft tumor models. Evaluation of exemplary targets is described herein, however these methods can be used to evaluate any of the potential targets described above.

As an example of a combination effect for anti-tumor efficacy of editing, CBLB and BCOR were edited, either independently or together, in $1^{st}$ generation CD19 CAR-T cells and evaluated in mice using the Raji subcutaneous cell derived xenograft tumor model. Raji cells are a lymphoma cell line that are known to be insensitive to treatment with anti-PD1 antibodies. 6-8 week old female NSG mice from Jackson labs were injected subcutaneously with $3 \times 10^6$ Raji tumor cells. When tumors reached a volume of approximately 200 mm$^3$ mice were randomized into groups of 5 and injected intravenously with edited human CD19 CART cells via tail vein. Prior to injection the adoptively transferred cells were edited with either a control guide or a guide editing for CBLB and/or BCOR. Body weight and tumor volume was measured at least twice per week. Tumor volume was calculated as mean and standard error of the mean for each treatment group.

As shown in FIG. 10, when compared to a control guide, adoptive transfer of BCOR and CBLB edited human CD19 CART cells, with target genes edited either alone or together as indicated, resulted in an anti-tumor response in the subcutaneous Burkitt's Lymphoma Raji mouse model. The anti-tumor efficacy was greater when both targets were edited in combination as compared to either target alone or as compared to a control guide. Similar experiments are performed to assess the efficacy of Socs1/Ankrd11 dual-edited T cells in the CD19 CAR-T Raji cell xenograft model.

Figure 11:
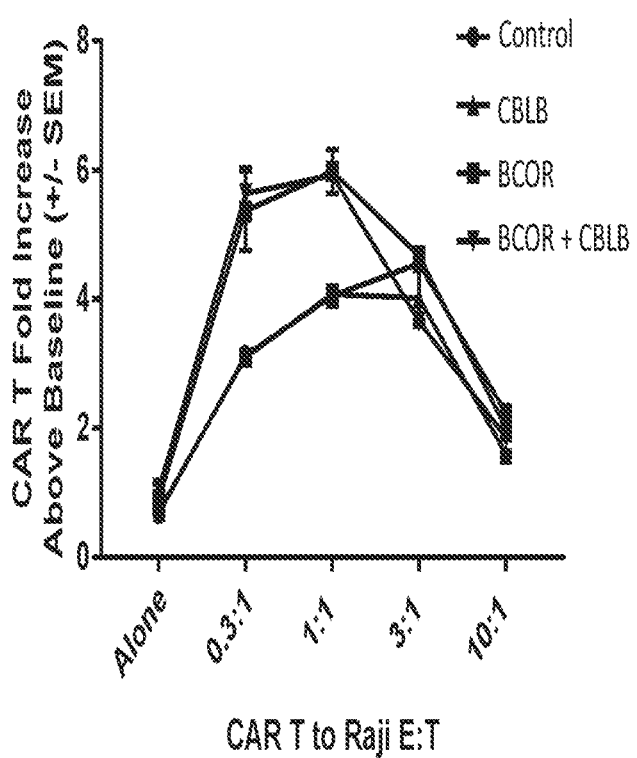
FIG. 11 shows accumulation of BCOR-edited or BCOR/CBLB-edited CD19 CAR T cells in an in vitro culture system.
Figure 12:
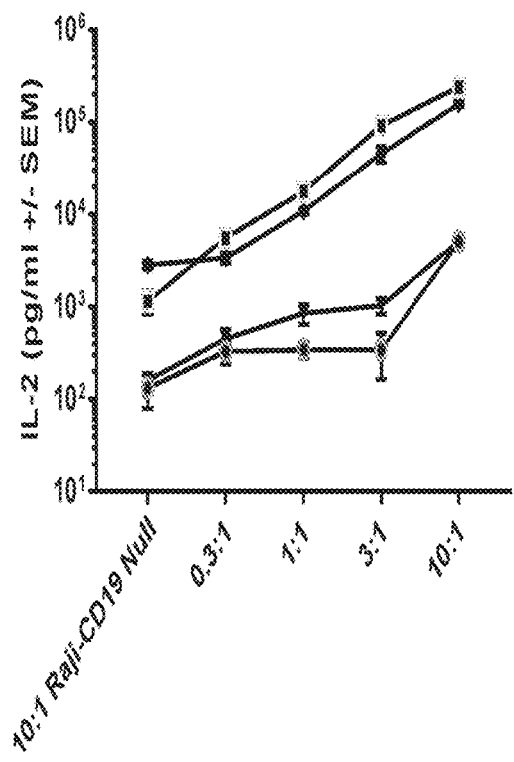
FIG. 12 shows IL-2 production by BCOR-edited or BCOR/CBLB-edited CD19 CAR T cells in an in vitro culture system.
Figure 13:
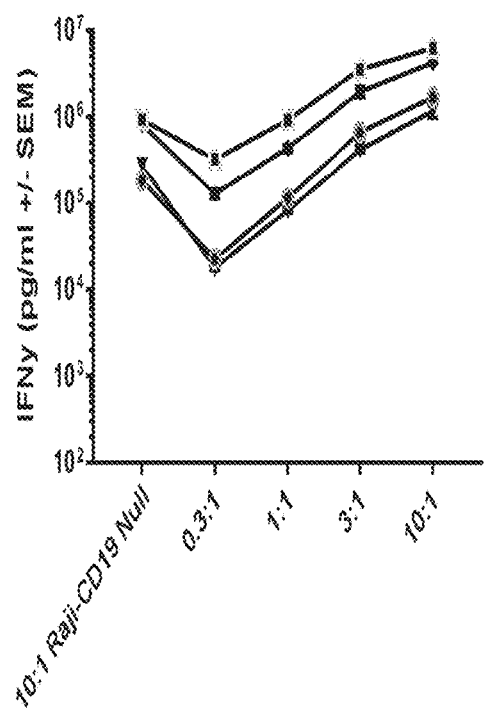
FIG. 13 shows IFNγ production by BCOR-edited or BCOR/CBLB-edited CD19 CAR T cells in an in vitro culture system.

Example 13: Double-Editing of Bcor and Cb1b in Car-Ts Leads to Enhanced Accumulation and Cytokine Production in the Presence of Tumor $1^{st}$ generation CD19 CAR-Ts were generated from human CD8 T cells, and a negative control gene, BCOR, CBLB, or both BCOR and CBLB were edited by electroporation using guide RNAs complexed to Cas9 in an RNP format. CD19 CAR-Ts were co-cultured with Raji Burkitt's Lymphoma cells in vitro at a 1:0, 0.3:1, 1:1, 3:1 and 10:1 ratio. After 24 hours, total cell counts of CAR-T cells were determined, and supernatants saved for cytokine analyses. As shown in FIG. 11, BCOR and BCOR+ CBLB-edited CARTs demonstrated 30% greater accumulation compared to either control or CBLB-edited CARTs, demonstrating that editing of the BCOR confers an enhanced ability of the CAR-T cells to accumulate in the presence of a tumor. Further, CBLB and CBLB+BCOR-edited CARTs produced 10-fold or more IL-2 (FIG. 12) and IFNγ (FIG. 13) compared to either control-edited CARTs, demonstrating that editing of CBLB resulted in enhanced CAR-T cell production of cytokines known to increase overall T cell fitness and functional ability. The increased production of IL-2 by CD8 T cells is surprising as these cells typically do not produce IL-2. These data demonstrate that, in some instances, production of CAR-T cells with enhanced effector functions requires editing of multiple genes. For example, in this example, the production of CAR-T cells that demonstrated both enhanced accumulation in the presence of a tumor and enhanced production of IL-2 and IFNγ cytokines required editing of both BCOR and CBLB genes.

Similar experiments are performed to assess the effect of SOCS1 CBLB dual-edited CAR-T cells and ANKRD11 CBLB dual-edited CAR-T cells on accumulation in the presence of tumor and cytokine production.

Example 14: Validation of Dual-Edited, Adoptively Transferred T Cells in a Murine Ot1/B16 Ova Syngeneic Tumor Model Targets were further evaluated in combination studies to determine combinations of edited genes that increased anti-tumor efficacy of T cells in syngeneic tumor models. Evaluation of exemplary targets is described herein, however these methods can be used to evaluate any of the potential targets described above.

Anti-tumor efficacy of Socs1/Cb1b dual-edited T cells was evaluated in mice using the B16Ova subcutaneous syngeneic tumor model. Briefly, 6-8 week old female C57BL/6J mice from Jackson labs were injected subcutaneously with $0.5 \times 10^6$ B16Ova tumor cells. When tumors in the entire cohort of mice reached an average volume of approximately 485 mm$^3$, the mice were randomized into groups of 10 and injected intravenously with edited murine OT1 CD8+ T cells via tail vein. Prior to injection, these cells were edited by electroporation with gRNA/Cas9 RNP complexes comprising (i) a control gRNA; (ii) a single gRNA targeting the PD-1 gene (SEQ ID NO: 531); (iii) a single gRNA targeting the Socs1 gene (SEQ ID NO: 738); or (iv) 2 gRNAs targeting the Cb1b (SEQ ID NO: 310) and Socs1 genes. Editing efficiency of the gRNA/Cas9 complex targeting the Cb1b and Socs1 genes was determined to be 94% and 92% respectively, assessed using the NGS method. Body weight and tumor volume were measured at least twice per week. Tumor volume was calculated as mean and standard error of the mean for each treatment group. The percentage tumor growth inhibition (TGI) was calculated using the mean tumor volume according to the following formula:

% TGI=(TV-Target$_{final}$−TV-Target$_{initial}$)/(TV-Control$_{final}$−TV-Control$_{initial}$)*100, where TV=mean tumor volume, final=Day 7 post-T cell transfer, and initial=Day 0 (i.e., day of T cell transfer).

Figure 14:
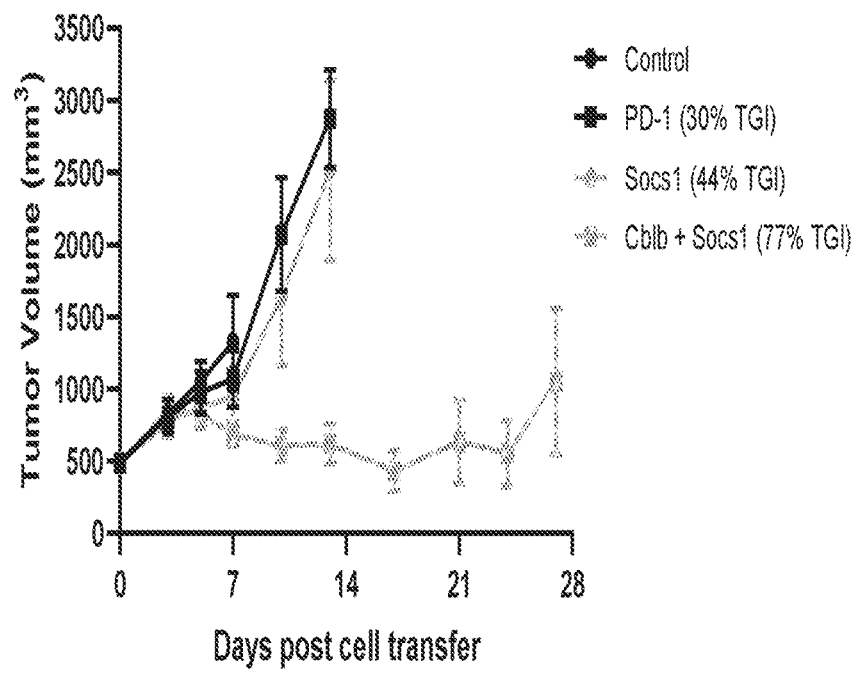
FIG. 14 shows tumor growth over time in mice treated with Cb1b/Socs1 dual-edited OT1 T cells in a murine B16/Ova syngeneic tumor model.

As shown in FIG. 14, transfer of Socs1/Cb1b dual-edited T cells resulted in an enhanced TGI compared to transfer of PD1 single-edited T cells or Socs1 single-edited T cells (Socs1/Cb1b TGI=77% compared to 30% and 44% for PD1 and Socs1 single edits, respectively). Similar experiments are performed to assess the anti-tumor effects of Ankrd11/Cb1b dual-edited T cells.

Example 15: Validation of Dual-Edited, Adoptively Transferred T Cells in a Murine PMEL/MC38-Gp100 Tumor Model Anti-tumor efficacy of Ankrd11/Socs1 dual-edited T cells is evaluated in mice using the MC38gp100 subcutaneous syngeneic tumor model. Briefly, 6-8 week old female C57BL/6J mice from Jackson labs are injected subcutaneously with 1×10⁶ MC38gp100 tumor cells. When tumors reached a volume of approximately 100 mm³ mice are randomized into groups of 10 and injected intravenously with edited murine PMEL CD8+ T cells via tail vein. Prior to injection, T cells are edited by electroporation with gRNA/Cas9 RNP complexes comprising (i) a control gRNA; (ii) a single gRNA targeting the PD1 gene; (iii) a single gRNA targeting the Ankrd11 gene; (iv) a single gRNA targeting the Socs1 gene; or (v) 2 gRNAs targeting both the Ankrd11 and Socs1 genes. Body weight and tumor volume are measured at least twice per week. Tumor volume is calculated as mean and standard error of the mean for each treatment group. The percentage tumor growth inhibition (TGI) is calculated using the mean tumor volume according to the following formula:

$$(TV\text{-}Target_{final} - TV\text{-}Target_{initial})/(TV\text{-}Control_{final} - TV\text{-}Control_{initial}),$$

where TV=mean tumor volume, final=Day 21 post-T cell transfer, and initial=Day 0 (i.e., day of T cell transfer)

These experiments are expected to show enhanced TGI after transfer of Ankrd11/Socs1 dual-edited T cells compared to transfer of PD1 single-edited T cells, Ankrd11 single-edited T cells, or Socs1 single-edited T cells.

Example 16: Validation of Dual-Edited, Adoptively Transferred T Cells in a Murine B16-F10 Syngeneic Tumor Model Anti-tumor efficacy of Socs1/Ankrd11 dual-edited T cells was evaluated in mice using the aggressive metastatic B16-F10 syngeneic tumor model with disease manifesting as lung metastasis. Briefly, 6-8 week old female C57BL/6J mice from Jackson labs were injected intravenously with 0.5×10⁶ B16-F10 tumor cells. Mice were weighed and assigned to treatment groups using a randomization procedure prior to inoculation. At Day 3 post tumor inoculation, mice were injected intravenously with edited murine PMEL CD8+ T cells via tail vein. Prior to injection these cells were edited by electroporation with gRNA/Cas9 RNP complexes comprising (i) a control gRNA; (ii) a single gRNA targeting the Socs1 gene; (iii) a single gRNA targeting the Ankrd11 gene; or (iv) 2 gRNAs targeting each of the Socs1 and Ankrd11 genes. Editing efficiency of the gRNA/Cas9 complex targeting the Ankrd11 and Socs1 genes was determined to be 70% and 72% respectively, assessed using the NGS method. Body weight was monitored at least twice per week. At Day 15 post tumor inoculation (Day 12 post edited PMEL transfer), mice lungs were perfused and fixed with 10% para-formaldehyde. After overnight fixation, lungs were transferred to 70% EtOH for further preservation. Tumor efficacy was evaluated by visually assessing the B16-F10 tumor burden which can be seen as black colonies of cancer cells on the lungs.

Large numbers of metastatic colonies were observed in all lungs from the untreated group or from mice treated with control-edited PMEL CD8+ T cells signifying significant disease progression. Partial efficacy was seen in mice treated with Socs1 single-edited cells and Ankrd11 single-edited cells demonstrated minimal efficacy. Dual editing of Socs1 and Ankrd11 resulted in similar anti-tumor efficacy as single editing of Socs1. The results of this experiment are summarized below in Table 16.

TABLE 16

Efficacy of Ankrd11 and Socs1 Single and Dual-Edited T cells in B16-F10 Tumor Model

| Target Gene | PD-1 resistant-B16F10 (lung) |
|---|---|
| Ankrd11 | − |
| Socs1 | ++ |
| Socs1/Ankrd11 | ++ |
| Control | − |

(−) = no efficacy observed;
(+) = modest responses in majority of animals;
(++) = strong responses in majority of animals;
(+++) = strong responses, including some complete responses, in all animals treated Similar experiments were performed to assess the anti-tumor efficacy of Socs1/Cblb dual-edited T cells in the B16-F10 metastatic model according to the method described above. Prior to injection, T cells were edited by electroporation with gRNA/Cas9 RNP complexes comprising (i) a control gRNA; (ii) a single gRNA targeting the Socs1 gene (SEQ ID NO: 738); (iii) a single gRNA targeting the Cblb gene (SEQ ID NO: 310); or (iv) 2 gRNAs targeting each of the Socs1 and Cblb genes. The dual editing efficiency of the gRNA/Cas9 complex targeting the Cblb and Socs1 genes was determined to be 74% and 72% respectively, assessed using the NGS method. Large numbers of metastatic colonies were observed in all lungs from the untreated group or from mice treated with control-edited PMEL CD8+ T cells signifying significant disease progression. Partial efficacy was seen in mice treated with Socs1 single-edited cells and Cblb single-edited cells demonstrated minimal efficacy. However, treatment with Socs1/Cblb dual-edited cells resulted in strong anti-tumor efficacy with a near complete inhibition of tumor formation. The results of this experiment are summarized below in Table 17.

TABLE 17

Efficacy of Socs1 and Cblb Single and Dual-Edited T cells in B16-F10 Tumor Model

| Target Gene | PD-1 resistant-B16F10 (lung) |
|---|---|
| Cblb | + |
| Socs1 | ++ |
| Socs1/Cblb | +++ |
| Control | − |

(−) = no efficacy observed;
(+) = modest responses in majority of animals;
(++) = strong responses in majority of animals;
(+++) = strong responses, including some complete responses, in all animals treated.

Example 17: Efficacy of PD1/Lag3 Dual-Edited Transgenic T Cells in a B16-Ova Murine Tumor Model Anti-tumor efficacy of PD-1/Lag3 dual-edited T cells was evaluated in mice using the B16Ova subcutaneous syngeneic tumor model. 6-8 week old female C57BL/6J mice from Jackson labs were injected subcutaneously with 0.5× 10⁶ B16Ova tumor cells. When tumors in the entire cohort of mice reached an average volume of approximately 485 mm³, the mice were randomized into groups of 10 and injected intravenously with edited mouse OT1 CD8+ T cells via tail vein. Prior to injection these cells were edited by electroporation with gRNA/Cas9 RNP complexes comprising (1) a non-targeting control gRNA; (2) a single gRNA targeting the PD1gene; (3) a single gRNA targeting the Lag3 gene; (4) 2 gRNAs, one targeting each of the PD1 and Lag3 genes. Body weight and tumor volume were measured at least twice per week. Tumor volume was calculated as mean and standard error of the mean for each treatment group. The percentage tumor growth inhibition (TGI) was calculated using the following formula:

% TGI=(PD1/Lag3TV$_{final}$−PD1/Lag3TV$_{initial}$)/(Control TV$_{final}$−Control TV$_{initial}$), where TV=mean tumor volume, final=Day 10 and initial=day of edited mouse OT1 CD8+ T cell transfer.

Figure 15:
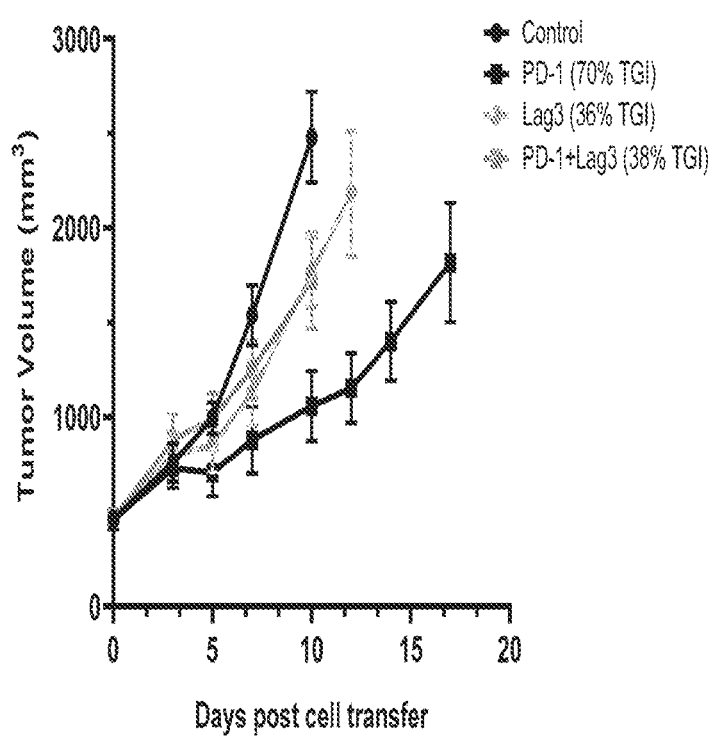
FIG. 15 shows the anti-tumor efficacy of PD1/Lag3 dual-edited transgenic T cells in a B16-Ova murine tumor model.

The data in FIG. 15 show adoptive transfer of PD1 single-edited T cells resulted in a TGI of 70% and adoptive transfer of Lag3 single-edited T cells resulted in a TGI of 36%. Surprisingly, combination edits of PD1 and Lag3 did not result in enhanced tumor growth inhibition and demonstrated a TGI of 38%.

Example 18: Validation of Targets for Adoptive T Cell Transfer of Tumor Infiltrating Lymphocytes Anti-tumor efficacy of Socs1, Ankrd11, and Cb1b single- and dual-edited tumor infiltrating lymphocytes (TILs) is evaluated in mice using the B16Ova subcutaneous syngeneic tumor model. Two mice cohorts are used in this experiment: a donor cohort of CD45.1 Pep Boy mice (B6.SJL-Ptprc$^a$ Pepc$^b$/BoyJ) and a recipient cohort of CD45.2 C57BL/6J mice (Jackson labs), each comprised of 6-8 week old female mice.

To generate TILs, donor CD45.1 Pep Boy mice (B6.SJL-Ptprc$^a$ Pepc$^b$/BoyJ) are injected subcutaneously with 0.5×10$^6$ B16-Ova cells. On Day 14 post-tumor cell inoculation, tumors are harvested to generate edited CD45.1 Tumor Infiltrating Lymphocytes (TILs) to infuse into the second cohort of mice. B16-OVA tumors (200-600 mm$^3$) are harvested, diced, and reduced to a single cell suspension using the GentleMACS system and mouse Tumor Dissociation Kit (Miltenyi Biotech Catalog #130-096-730), according to the manufacturer's recommendations. Tumor suspension are filtered over 70 m cell strainers and TILs are enriched using CD4/CD8 (TIL) Microbeads (Miltenyi Biotech Catalog #130-116-480). Isolated TILs are cultured in 6 well plates at 1.5×10$^6$ cells/mL in complete mTIL media (RPMI+10% heat inactivated FBS, 20 mM HEPES, 100 U/mL Penicillin, 100 μg/mL Streptomycin, 50 μM Beta-Mercaptoethanol, 1× Glutamax) supplemented with 3000 U/mL of recombinant human IL-2 (Peprotech Catalog #200-02). On Day 3 cells are harvested, washed and resuspended in nucleofection buffer T and electroporated with RNPs using the Neon Transfection System. After electroporation, TILs are cultured in 6 well plates at 1.5×10$^6$ cells/mL in complete mTIL media supplemented with 3000 U/mL of recombinant human IL-2. On Day 5 and 7, cells are resuspended in fresh complete mTIL media supplemented with 3000 U/mL of recombinant human IL-2 and plated in flasks at a density of 1×10$^6$ cells/mL. On Day 8, cells are harvested counted and resuspended in PBS for injection in vivo.

These TIL cells are edited by electroporation of gRNA/Cas9 complexes comprising (1) a non-targeting control gRNA; (2) a single gRNA targeting the Cb1b gene; (3) a single gRNA targeting the Socs1 gene; (4) a single gRNA targeting Ankrd11; (5) 2 gRNAs, one targeting each of the Cb1b and Socs1 genes; (6) 2 gRNAs, one targeting each of the Cb1b and Ankrd11 genes; or (7) 2 gRNAs, one targeting each of the Socs1 and Ankrd11 genes.

Recipient CD45.2 C57BL/6J mice are injected subcutaneously with 0.5×10$^6$ B16-Ova tumor cells. When tumors reached a volume of approximately 100 mm$^3$, mice are randomized into groups of 10 and injected intravenously with edited CD45.1 TILs via tail vein. Optionally, mice can be injected intraperitoneal with cyclophosphamide (200 mg/kg) to induce lymphodepletion prior to T cell transfer and the edited-TILs can be administered intravenously in combination with intraperitoneal treatment with recombinant human IL-2 (720,000 IU/Kg) twice daily for up to a maximum of 4 days.

Body weight and tumor volume are measured at least twice per week. Tumor volume is calculated as mean and standard error of the mean for each treatment group and the % TGI is calculated according to the following formula:

% TGI=(TV-target$_{final}$−TV-targe$_{initial}$)/(TV-Control$_{final}$−TV-Control$_{initial}$), where TV=mean tumor volume, final=Day 17 and initial=day of edited TIL transfer.

These results are expected to show that compared to a control guide, adoptive transfer of single-edited or dual-edited mouse TILs results in an enhanced anti-tumor response in the B16Ova subcutaneous mouse model compared to treatment with control-edited cells.

Example 19: Validation of Targets for Engineered T Cell Therapy

Experiments are performed to validate the effects of editing SOCS1, ANKRD11, BCL2L11, FL11, CALM2, DHODH, UMPS, RBM39, SEMA7A, CHIC2, PCBP1, PBRM1, WDR6, E2F8, SERPINA3, GNAS, and EGR2 on the anti-tumor efficacy of CAR T cells and T cells engineered to express an artificial TCR. The engineered T cells are edited as described in Example 1 to reduce expression of the target genes. These edited T cells are then evaluated in subcutaneous murine xenograft models using the indicated cell type. For example, T cells engineered with a CD19-specific CAR or artificial TCR can be evaluated as described above in Example 8 in a Raji cell model or any of the other cell lines shown in Table 18, below, T cells engineered with a MART1-specific CAR or artificial TCR can be evaluated in a SKMEL5, WM2664, or IGR1 cell model, etc.

TABLE 18

| Engineered Receptor Specificity and Target Cell Lines | |
|---|---|
| Receptor Specificity | Target Cell Line |
| CD19 | Raji, Daudi, Jeko, NALM-6, NALM-16, RAMOS, JeKo1 |
| BCMA | Multiple Myeloma cell lines NCI-H929, U266-B1, and RPMI-8226 |
| NYESO | A375 |
| MART1 | SKMEL5, WM2664, IGR1 |
| HER2+ | BT474 |

Briefly, 6-8 week old female NSG mice from Jackson labs are injected subcutaneously with 3×10$^6$ target cells. When tumors reached a volume of approximately 200 mm$^3$, mice are randomized into groups of 5 and injected intravenously with the edited engineered T cells via tail vein. Prior to injection the adoptively transferred cells are edited with either a control guide or a guide editing for SOCS1, ANKRD11, BCL2L11, FL11, CALM2, DHODH, UMPS, RBM39, SEMA7A, CHIC2, PCBP1, PBRM1, WDR6, E2F8, SERPINA3, GNAS, and EGR2. Body weight and tumor volume are measured at least twice per week. Tumor volume is calculated as mean and standard error of the mean for each treatment group. The results of these experiments are expected to show enhanced anti-tumor efficacy of SOCS1, ANKRD11, BCL2L11, FL11, CALM2, DHODH, UMPS, RBM39, SEMA7A, CHIC2, PCBP1, PBRM1, WDR6, E2F8, SERPINA3, GNAS, and EGR2-edited engineered T cells or as compared to a control guide, measured by survival and or reduction in tumor size.

Example 20: Validation of Target Editing on Receptor-Engineered T Function

Experiments are performed to validate the effects of editing SOCS1, ANKRD11, BCL2L11, FL11, CALM2, DHODH, UMPS, RBM39, SEMA7A, CHIC2, PCBP1, PBRM1, WDR6, E2F8, SERPINA3, GNAS, and EGR2 on engineered T cell cytokine production. Briefly, the engineered T cells described in Table 17 above are generated from human CD8 T cells, and one or more of SOCS1, ANKRD11, BCL2L11, FL11, CALM2, DHODH, UMPS, RBM39, SEMA7A, CHIC2, PCBP1, PBRM1, WDR6, E2F8, SERPINA3, GNAS, and EGR2 are edited by electroporation using guide RNAs complexed to Cas9 in an RNP format. CAR-Ts are co-cultured with the corresponding cell line indicated in Table 18 in vitro at a 1:0, 0.3:1, 1:1, 3:1 and 10:1 ratio. After 24 hours, total cell counts of engineered T cells are determined, and supernatants saved for cytokine analyses. The results of these experiments are expected to show enhanced accumulation of and increased levels of cytokine production from edited CAR T cells compared to control edited cells.

Example 21: Manufacturing of Dual-Edited Tumor Infiltrating Lymphocytes

Edited TILs are manufactured following established protocols used previously in FDA-approved clinical trials for the isolation and expansion of TIL's. Following removal of tumor tissue, the tumor is both fragmented into 2 mm$^3$ pieces and mechanically/enzymatically homogenized and cultured in 6,000 IU/mL recombinant human IL-2 for up to 6 weeks or until the cell numbers reach or exceed 1×10$^8$; this is defined as the pre-rapid expansion phase (pre-REP) of TIL manufacturing. Upon completion of the pre-REP stage TILs are electroporated with gRNA/Cas9 RNP complexes targeting SOCS1, ANKRD11, BCL2L11, FL11, CALM2, DHODH, UMPS, RBM39, SEMA7A, CHIC2, PCBP1, PBRM1, WDR6, E2F8, SERPINA3, GNAS, and EGR2 genes under cGMP conditions. Cells may be also electroporated prior to or during the pre-REP process. Following electroporation, 50×10$^6$ cells are transferred into a 1 L G-Rex™ culture flask with a 1:100 ratio of TIL:irradiated feeder cells for approximately 2 weeks. This portion of manufacturing is defined as the rapid expansion phase (REP). After the REP phase, TIL's are harvested, washed, and suspended in a solution for immediate infusion into the patient.

EXAMPLE 22: PHASE I STUDIES OF EDITED IMMUNE EFFECTOR CELLS

Phase 1, open-label, single-center studies will be performed, in which metastatic melanoma patients who are relapsed or refractory to anti PD-1 therapy will be treated with the modified cells described herein. Patients will receive a single infusion of cells and will remain on study until they experience progressive disease or therapy intolerance. Radiological PD will be determined by a local radiologist before discontinuation of study participation.

Study Objectives: The primary objectives of the study are (1) to determine the maximum tolerated dose (MTD), dose limiting toxicities (DLTs), and dose of cell compositions (and the associated concomitant medications required) recommended for future studies for patients with advanced solid tumors; and (2) to observe patients for any evidence of anti-cancer activity of the transferred edited cells. The secondary objectives of the study are: (1) to determine the pharmacokinetics of the cellular compositions; (2) to assess of on-target activity of the cellular compositions, as determined by changes in pharmacodynamic biomarkers in biologic samples; and (3) to assess of proliferation of the modified cells, as determined by engineered TIL persistence post treatment. The exploratory objectives of the study are (1) to correlate any underlying genetic mutation(s) with clinical response.

Study End-Points: The primary endpoints of this study are: Incidence and severity of adverse events (AEs), graded according the National Cancer Institute Common Terminology Criteria for Adverse Events (NCI CTCAE), version 4.3; Clinical laboratory abnormalities; Changes in 12-lead electrocardiogram (ECG) parameters; Objective response rate (ORR), per RECIST v1.1; CNS response (ORR and progression free survival [PFS], per RECIST v1.1, in patients who have active brain metastases). The secondary endpoints of this study are: Patient-reported symptoms and health-related quality of life (HRQoL) scores; Time to response; Duration of response; Disease control rate (the percentage of patients with best response of complete response [CR], PR, or SD), per RECIST v1.1; Time on treatment; Immunophenotyping; Persistence, trafficking and function of genetically engineered TIL; Pharmacodynamic biomarker in pre and post-dose samples. The exploratory endpoints of this study are: Assessment of cancer-associated mutations and/or genetic alterations utilizing FoundationOne® Cancer Gene Panel, or comparable alternative, in pre-dose tumor biopsy and/or peripheral blood.

Treatment Regimen: A summary of the treatment regimen is as follows:
(a) Day -7 & -6: cyclophosphamide 60 mg/kg, i.v.
(b) Days -5 to -1: fludarabine 25 mg/m$^2$, iv.
(c) Day 1: Cell infusion
(d) Day 1-Day 15: IL-2 (125,000 IU/kg/day) up to a maximum of 14 administrations The first dose of cells administered will not exceed a total dose of 1×10$^9$ cells. Should the patient experience dose limiting toxicity (DLT), two additional patients will be treated at this dose level. If the first patient completes the DLT monitoring period (21 days) without experiencing a DLT, subsequent patients will be treated at doses not to exceed 1×10$^{11}$ TILs.

Concomitant Treatment: Palliation and supportive care are permitted during the study for management of symptoms and underlying medical conditions that may develop during the study.

Efficacy Evaluation: Tumor response will be determined per RECIST v1.1 by the local radiologist and/or investigator. Tumor assessment will be performed every 6 weeks until disease progression and will continue for patients who have discontinued due to reasons other than disease progression, until disease progression, or to the start of another anticancer therapy. Survival will also be followed for up to 3 years after the last patient enrolled into the study.

Safety Evaluation: Safety assessments will include physical and laboratory examinations, vital signs, and ECGs.

Adverse events will be graded according to the NCI CTCAE v4.03. Adverse event incidence rates, as well as the frequency of occurrence of overall toxicity, categorized by toxicity grades (severity), will be described for each cohort of the study. Listings of laboratory test results will also be generated, and descriptive statistics summarizing the changes in laboratory tests over time will be presented.

Molecular Genetic Evaluations: The mutation status of genes implicated in tumor biology will be determined through molecular analysis of tumor tissue and plasma samples. Results of these tests will be provided to the investigator and the sponsor immediately after analysis, per the testing procedure. Molecular analysis methods include, but are not limited to, direct sequencing and/or digital polymerase chain reaction (PCR).

Patient-Reported Symptoms and Quality of Life Evaluations: Patient-reported symptoms and HRQoL will be collected by administering the validated European Organisation for Research and Treatment of Cancer (EORTC) Quality of Life Questionnaire (QLQ)-C30 (v.3.0), which has been studied extensively in global clinical studies. The EORTC QLQ-C30 will be scored for 5 functional scales (physical, role, cognitive, emotional, and social functioning); 3 symptom scales (fatigue, pain, and nausea/vomiting); and a global health status/QoL scale. Six single-item scales also are included (dyspnea, insomnia, appetite loss, constipation, diarrhea, and financial difficulties).

Study Assessments: Assessment parameters for these studies include radiological imaging of the tumor prior to dose administration and on Day 1 of every odd number cycle thereafter, blood sample collection for PK analysis (Day 1, 2, 3, weekly×4, monthly×6) and pharmacodynamics analysis, and cytokine panel analysis (Day 1, 2, 3, weekly×4, monthly×6).

Example 23: Assay Development for the Assessment of SOCS1-Edited T Cells

To assess for SOCSI-dependent pharmacology, assays are developed that quantify SOCSI-dependent biology. These assays are also intended to be used to assess target-dependent pharmacology in dual-edited TILs. The activity of sgRNAs targeting SOCS1 in TILs is assessed in these assays.

SOCS1 is a negative regulator of JAK/STAT signaling. Therefore, SOCSI-dependent pharmacology.

Figure 16:
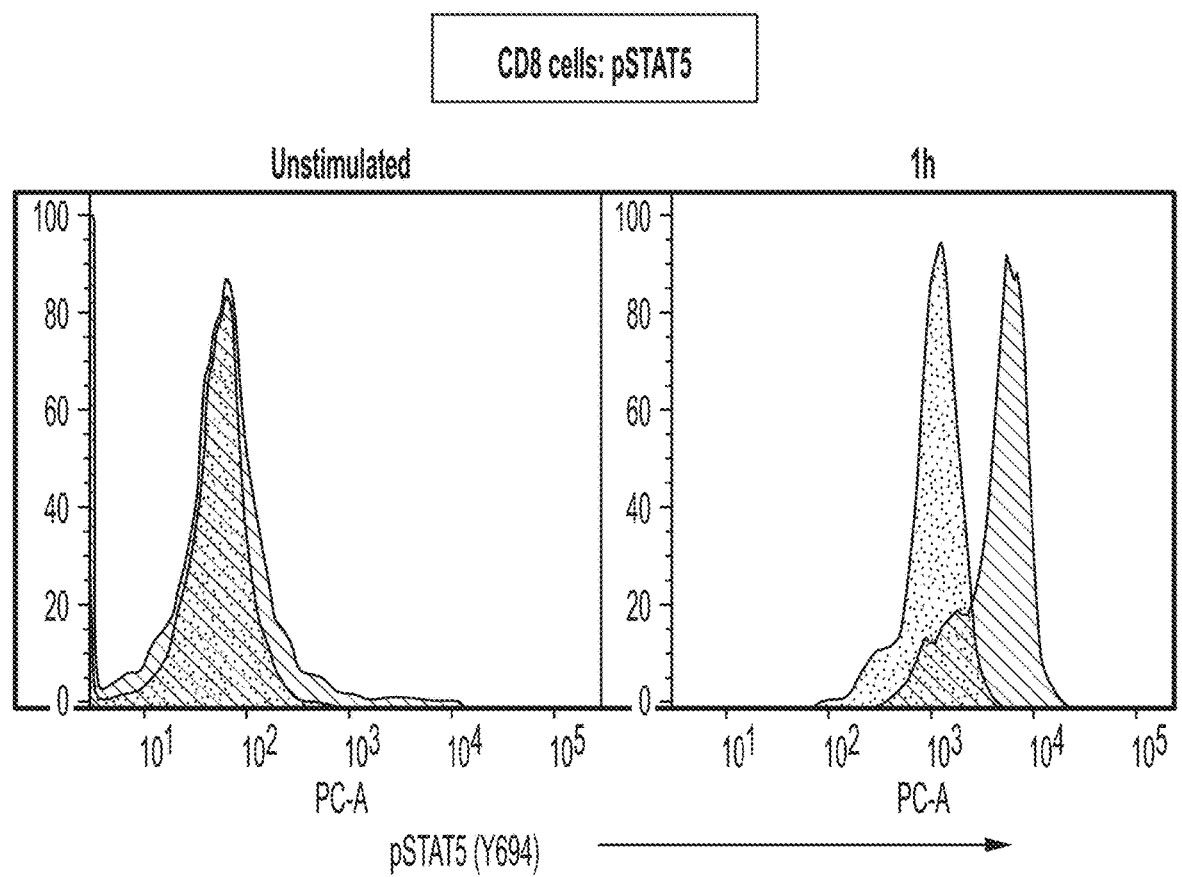
FIG. 16 shows the increase in pSTAT5 levels in primary human CD8 T cells in response to IL-2 signaling after deletion of SOCS1.

SOCS1 negatively regulates cytokine signaling in T cells, in part by inhibiting JAK1, a kinase involved in STAT5 phosphorylation and cytokine signal transduction. Upon IL-2 signaling through the IL-2 receptor complex, STAT5 is phosphorylated in a JAK1-dependent manner. Therefore, can be measured by increases in JAK/STAT signaling and levels of pSTAT5 and activation of downstream signaling pathways upon IL-2 stimulation. Indeed, deletion of SOCS1 lead to an increase in pSTAT5 levels in primary human CD8 T cells in response to IL-2 signaling (FIG. 16).

To determine the impact of genetic inactivation of SOCS1 on cell function in vitro, multiple parameters may be assessed that correlate with T cell function. These include cytokine production (e.g., IL-6 and IL-12), baseline cell surface phenotypes and activated cell surface phenotypes, T cell differentiation state, and tumor-killing ability.

Example 24: Socs1-Tiling Screen and Validation Assays

A CRISPR-Cas9 tiling screen was performed to determine candidate inhibitor target locations within a target locus spanning the SOCS1 gene. Primary human CD8+ T cells were isolated as described in Example 1 and transduced with a lentiviral library expressing sgRNAs designed to target genomic positions across the full length of the SOCS1 gene. Two days after transduction with the lentiviral library, the transduced CD8+ T cells were electroporated with Cas9 mRNA and cultured for an additional 10 days. After 10 days of culture subsequent to electroporation with Cas9 mRNA, the screen was divided into two arms: a proliferation read-out and a phosphoSTAT5 read-out. Additional assays were performed to validate gRNAs identified in the tiling screen. 104 distinct SOCSI-targeting gRNAs were assayed according to the following parameters.

Tiling Screen

Figure 17A:
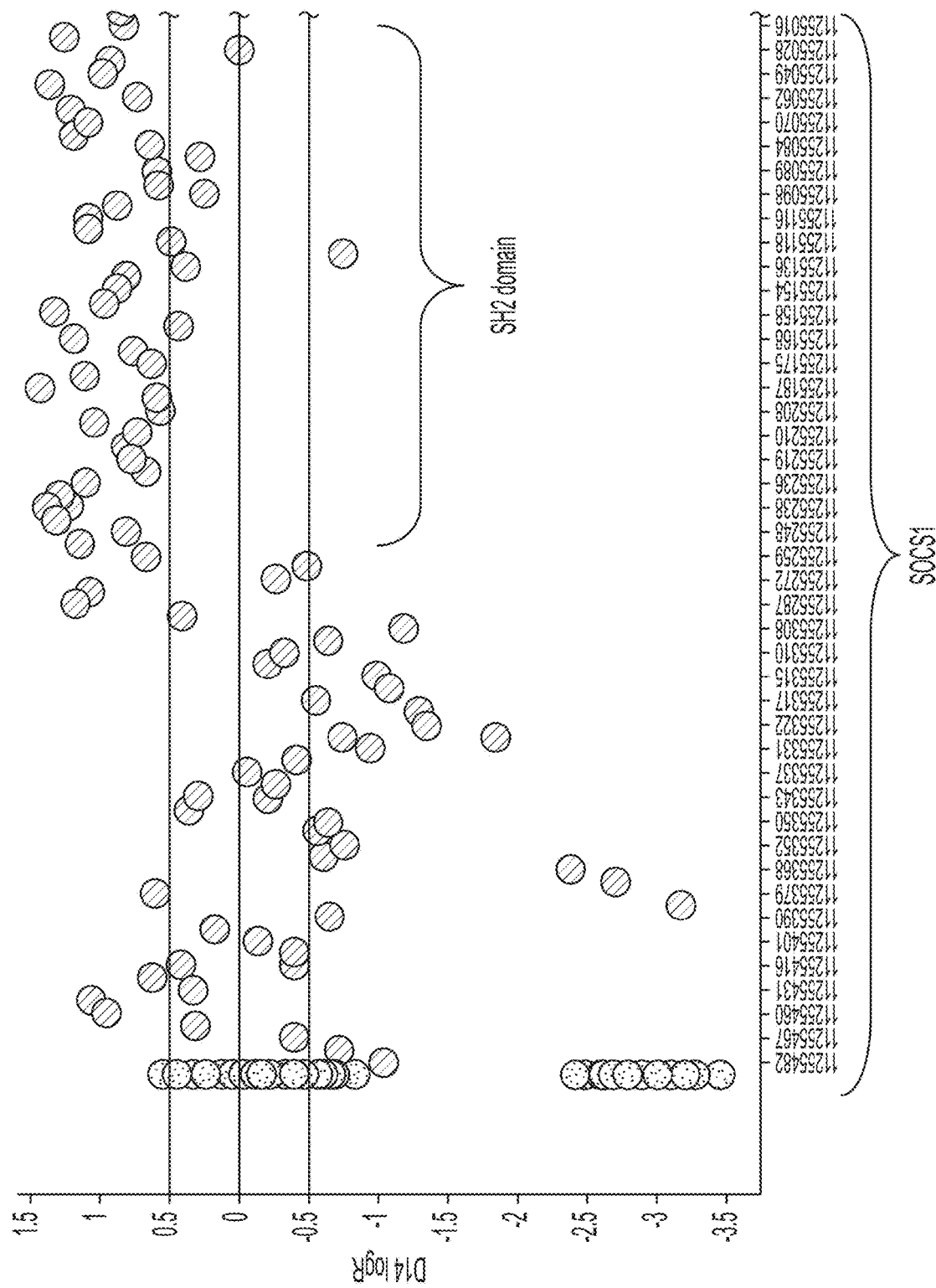
FIGS. 17A-17B shows gRNA enrichment from a SOCS1 tiling screen.
Figure 17B:
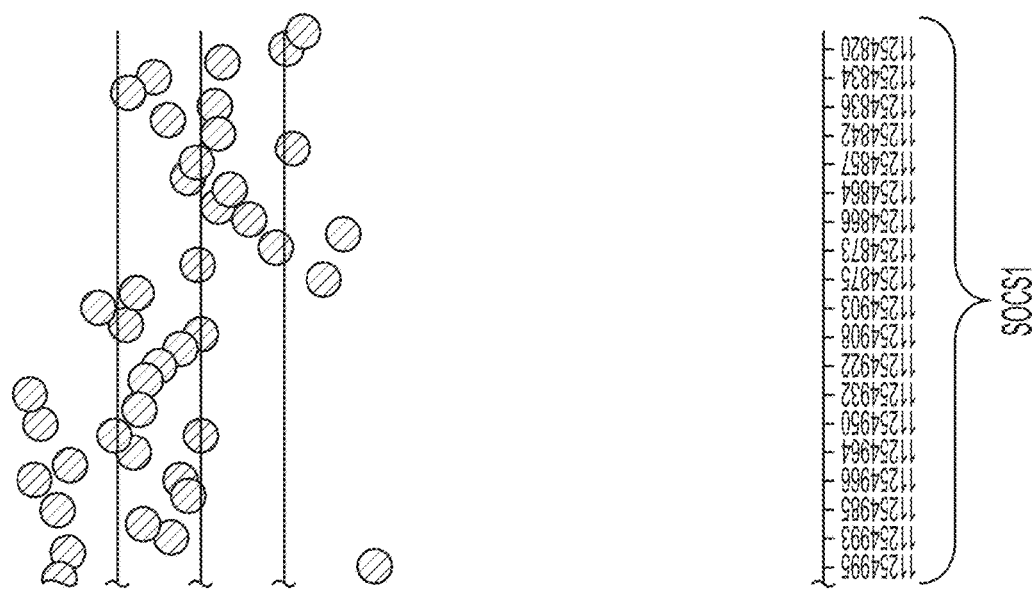

Proliferation Read-out: Cells were harvested on Day 10 after Cas9 mRNA electroporation. DNA was extracted and amplicons spanning the recognition sites for the various sgRNAs in the library were amplified by polymerase chain reaction (PCR) and sequenced by next-generation sequencing (NGS). Enrichment or depletion of each of the sgRNAs is shown in FIGS. 17A-17B and is represented as the log ratio of final counts divided by reference counts. Those sgRNAs causing the greatest enrichment of T cells were selected as top hits for further study.

Additional Assays for Guide Validation

Additional assays were developed to further characterize the efficacy and on-target activity of gRNAs identified in the tiling screen described above. Cells were isolated and electroporated with Cas9:gRNA RNPs containing SOCSI-specific gRNAs identified in tiling screens. Cells were cultured for approximately 10 days at which point the following assays were performed.

DNA Editing Assay: A DNA editing assay was developed to compare the ability of individual guides to direct editing of their respective target at the DNA level (See e.g., Tsai et al. 2015 Nature Biotechnology). After electroporation with Cas9:gRNA RNPs, cells were cultured for approximately 10 days, at which point pellets were harvested and DNA was extracted. Amplicons spanning the genomic target loci for the various sgRNAs were amplified by PCR using guide-specific primer sets and sequenced by NGS. Sequencing reads were aligned to the predicted guide cut site, and the percentage of reads displaying an edited DNA sequence was determined. The cutting percentage for each off-target site was calculated as the number of off-target site sequencing reads compared to the number of on-target sequencing reads for each Socs1 gRNA. Outcomes were evaluated based on two criteria: 1) the overall percentage of off target editing and 2) the identity of the off-target edited genes. Optimal guides were identified those having the lowest level percent off-target editing and/or most benign off target edited genes profile. For example, gene editing in intragenic regions was viewed as a benign effect while editing in known oncogenes or tumor suppressors was viewed as an undesirable off target profile.

Western Blot Assay: A Western Blot assay was used to compare the ability of individual guides to reduce protein expression of their respective targets. After electroporation with Cas9:gRNA RNPs, cells were cultured for approximately 10 days, cell pellets were then harvested, and lysed in RIPA buffer with protease and phosphatase inhibitors. Extracted protein was quantified by Bradford assay, and 1 µg was loaded onto an automated Western Blotting instrument (Wes Separation Module by Protein Simple) using the machine's standard 12-230 kD Wes Separation Module protocol. Commercially available target specific primary antibodies were employed, followed by incubation with HRP-conjugated secondary antibodies. The signal detected per target guide was normalized to the respective signal seen in the negative control guide sample.

Validation Results: 100 SOCSI-targeting gRNAs (SEQ ID NOs: 1101-1200) were identified as optimal guides based on DNA editing activity and protein outgrowth assays described above. Of these 100 guides, the top 40 (SEQ ID NOs: 1101-1140), the top 20 (SEQ ID NOs: 1101-1120), and the top 10 (SEQ ID NOs: 1101-1110) guides were identified. Within these subsets, 7 SOCSI-targeting guides were identified as particular candidates of interest (SEQ ID NOs: 1102, 1103, 1105-1108, 1115). Similar experiments were performed for BCOR and TNFAIP3, with 57 BCOR gRNAs (SEQ ID NOs: 708-764) and 39 TNFAIP3 gRNAs (SEQ ID NOs: 348-386) identified as potential optimal guides.

Example 25: SOCS1 SH2 Domain as a Specific Target of SOCS1 Inhibitors

A CRISPR-Cas9 tiling screen was performed to determine candidate inhibitor target locations within a target locus spanning the SOCS1 gene. Primary human CD8+ T cells were isolated as described in Example 2 and transduced with a lentiviral library expressing sgRNAs designed to target genomic positions across the full length of the SOCS1 gene. Two days after transduction with the lentiviral library, the transduced CD8+ T cells were electroporated with Cas9 mRNA and cultured for an additional 14 days. After 14 days of culture subsequent to electroporation with Cas9 mRNA, DNA was extracted from the cells and amplicons spanning the recognition sites for the various sgRNAs in the library were amplified by polymerase chain reaction (PCR) and sequenced by next-generation sequencing (NGS). Enrichment of each of the sgRNAs is shown in FIGS. 17A-17B and is represented as the log ratio of final counts divided by reference counts. As shown, guides that were enriched over time targeted the DNA encoding the SH2 domain (SEQ ID NOs: 1106, 1110, 1115, 1116, 1118, 1126, 1129, 1141, 1157, 1174). This result suggests that SOCS1 inhibitors targeting the SOCS1 gene generally, but particularly SOCS1 inhibitors targeting the SH2 domain of the SOCS1 gene, increase cell survival and/or proliferation of cells such as, for example, primary CD8+ T cells.

Example 27: Expression of T Cell Activation Markers in Edited Murine Cd8 T Cells Spleens from female PMEL mice were harvested and CD8 T cells were isolated as described in Example 1. CD8 T cells were electroporated with RNPs comprising Cas9 protein and sgRNAs targeting Ankrd11, Socs1, or a control gene. Across multiple guides, Ankrd11-editing efficiency was measured to be 54%, and Socs1-editing efficiency was measured to be 55-75%.

Expression of Ifng and Gzma was measured by RNA-seq. RNA extraction and sequencing (RNA-seq) from pellets of 3 million edited cells was performed by Wuxi NextCode. Gene expression levels were quantified as TPMs (Li et al., in Bioinformatics: The Impact of Accurate Quantification on Proteomic and Genetic Analysis and Research (2014)) using Salmon (version 0.11.2, Patro et al., Nat. Methods (2017) and Gencode mouse gene annotation (version M15). R package limma[3] (version 3.38.0, Ritchie et al., Nucleic Acids Res. (2015)) was used to analyze the differentially expressed genes (DEGs). When multiple guides were used to inhibit a target, the analysis incorporated the impact of each guide and only genes affected by all guides were considered significantly differentially expressed.

These experiments revealed that Ankrd11-edited and Socs1-edited mouse PMEL cells demonstrated significantly increased expression of Ifng mRNA (Ankrd11-edited: 2-fold relative to control gRNA, $p=4.7\times10^{27}$; Socs1-edited: 1.8-fold relative to control gRNA, $p=1.4\times10^{-18}$) and Gzma mRNA (Ankrd11-edited: 2.9-fold relative to control gRNA, $p=1.9\times10^{-141}$; Socs1-edited: 1.6-fold relative to control gRNA, $p=2.6\times10^{-29}$). Together these data demonstrate that Ankrd11 and Socs1 inhibition with gRNAs leads to robust activation of mouse T-cells. Together these data demonstrate that Ankrd11-edited and Socs1-edited PMEL cells demonstrate increased expression of the T cell activation markers Ifng and Gzma as measured by mRNA expression.

Example 28: Socs1 and CBL-B Inhibition Drive Increased Expansion of Human CD4+ and CD8+ T Cells In Vitro Experiments were performed to identify targets that regulate the in vitro accumulation of human CD4+ and CD8+ T cells. On Day 0, $400\times10^6$ human CD8+ T cells or $800\times10^6$ CD4 T cells were each purified from leukopaks from three independent human donors. T cells were plated into T-75 flasks (15 mL volume) at $1\times10^6$ cells/mL in expansion medium (ImmunoCult-XF T-cell Expansion Medium, Stem-Cell Tech #10981)+10 ng/mL human IL2 and activated for 24 hours by 25 µL/mL of anti-CD3/CD28/CD2 T-cell activator (ImmunoCult T-cell activator, StemCell Technologies, Vancouver BC, Canada). On Day 1, T cells were transduced with lentivirus expressing the genome-wide PrecisionOne guide-library. Cas9 mRNA was introduced by electroporation on Day 4. Following electroporation of Cas9, T cells were cultured in expansion medium with 10 ng/mL human IL2, monitored for viability, and counted every other day. On Day 10, T cells were washed and re-suspended in expansion mediums+10 ng/mL human IL2 and T-cell activators. On Day 14, cells were washed again to remove activators, and re-suspended in expansion medium+10 ng/mL human IL2. On Day 20, cells were removed from culture and genomic DNA was harvested from $50\times10^6$ cells for each sample. Library guide sequences were amplified by PCR from 100 µg of genomic DNA and sequenced on an Illumina NextSeq 500 instrument at a depth of approximately 500 reads per unique sgRNA in the library.

Figure 18:
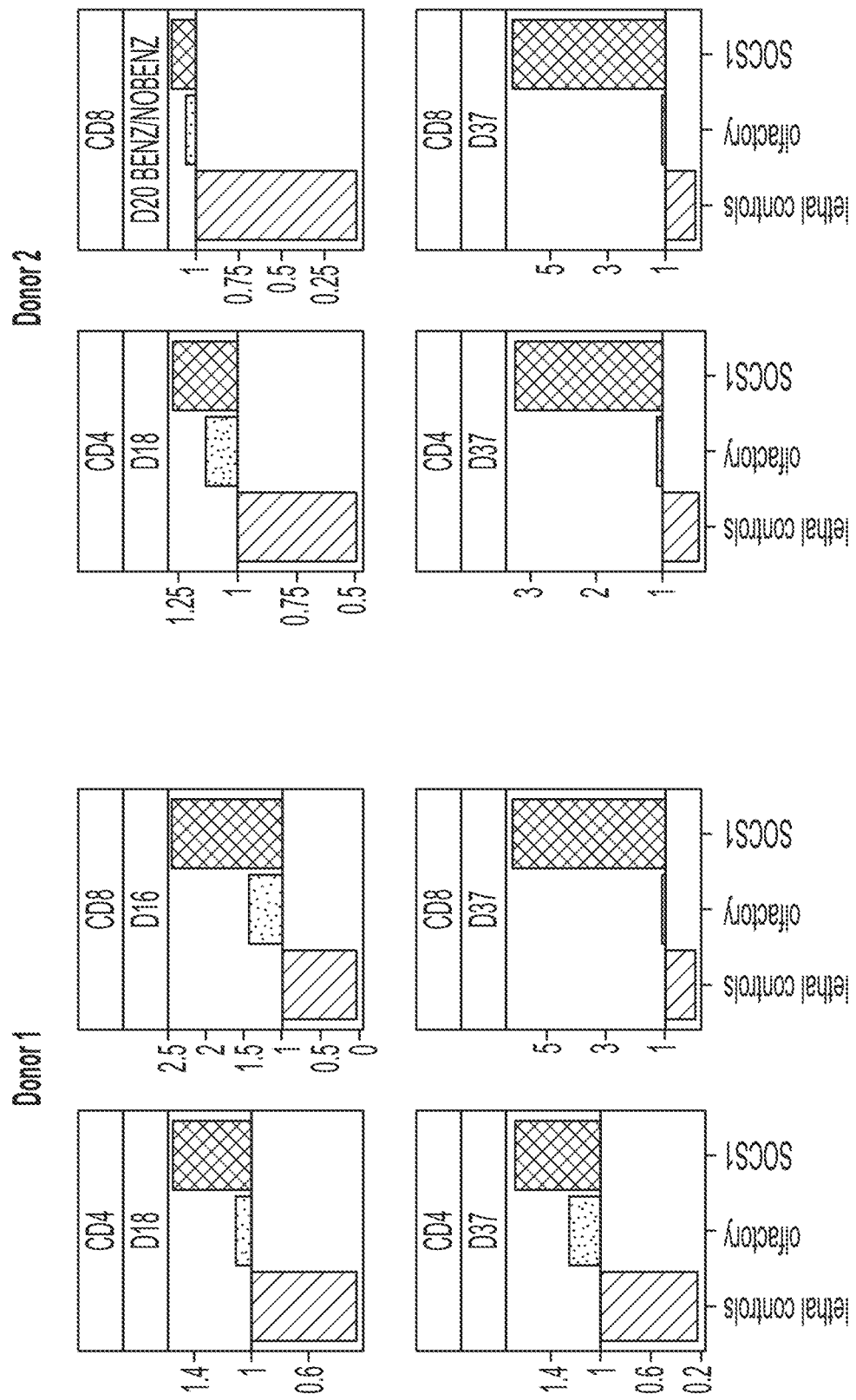
FIG. 18 shows in vitro accumulation of CD4+ and C8+ human T cell with SOCS1-targeting gRNAs.

As shown in FIG. 18, guides targeting the SOCS1 genes lead to enhanced accumulation of human CD4+ and CD8+ T cells in vitro at both early (day 18) and late (day 37) time points compared to the accumulation of guides targeting genes required for T cell survival (lethal controls) or guides targeting non-T cell olfactory genes (olfactory).

Figure 19:
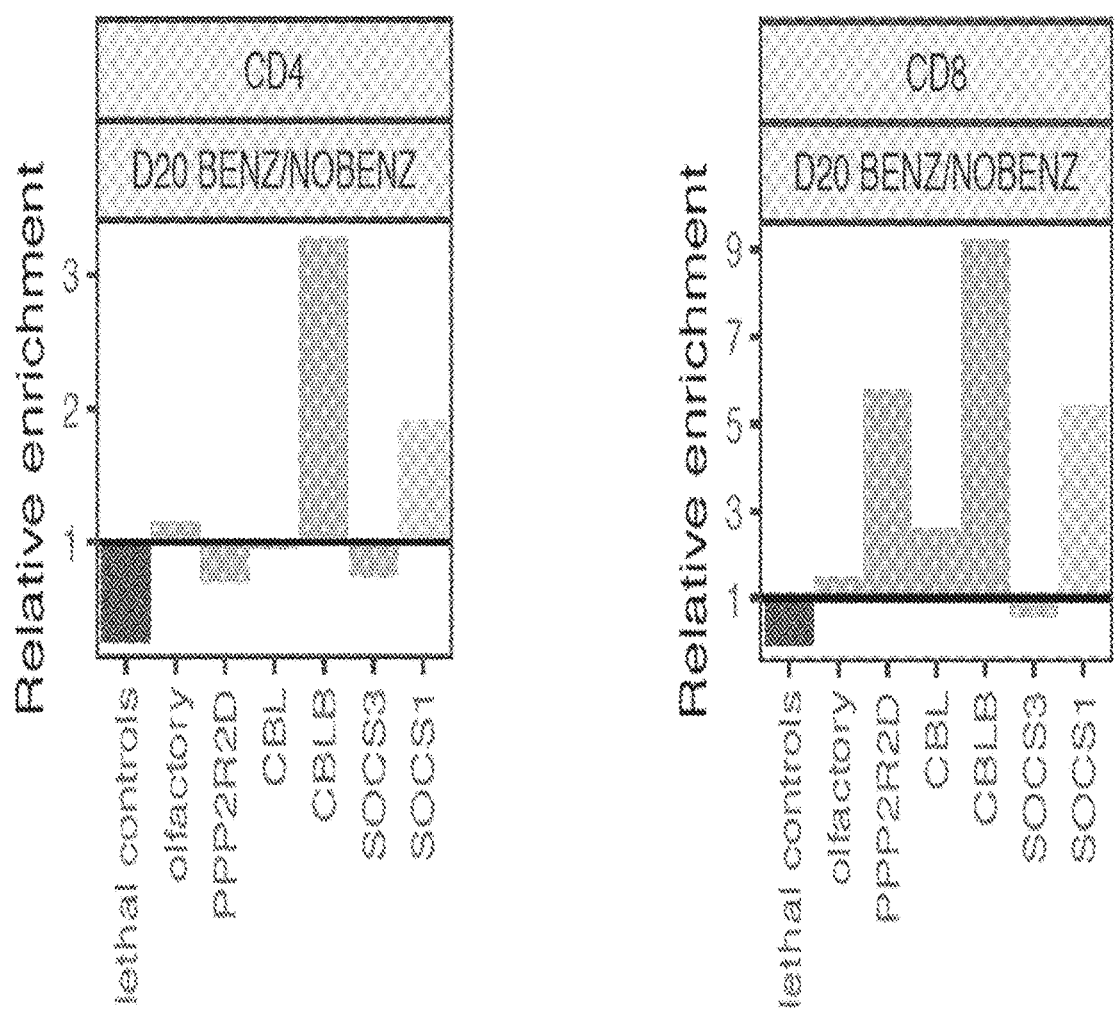
FIG. 19 shows in vitro accumulation of CD4+ and C8+ human T cell with SOCS1-targeting gRNAs or CBLB-targeting gRNAs compared to guides targeting known regulators of T cell function, PP2R2D, CBL, and SOCS3.

Similar experiments were performed with gRNAs targeting SOCS1 and CBLB, as well as known regulators of T cell function: PPP2R2D, SOCS3, and CBL. As shown in FIG. 19, targeting of the SOCS1 and CBLB genes resulted in increased accumulation of CD4+ and CD8+T cells. Surprisingly, targeting of PPP2R2D, SOCS3, and CBL genes did not lead to enrichment of CD4+ T cells and guides targeting the SOCS3 and CBL genes did not result in increased CD8+T cell accumulation under similar conditions (FIG. 19).

Example 29: Inhibition of Socs1 Drives Increased In Vitro Expansion of Murine CD8+T Cells Experiments were performed to identify targets that regulate the in vitro accumulation of murine CD8+ T cells.

Murine CD8 T cells were isolated from Cas9×OT1 transgenic mice spleens and activated as described in Example 1. 24 hours after activation, T cells were seeded at $3\times10^6$ cells per well in a 6 well plate coated with 5 g/mL RetroNectin (Takara Clontech Catalog #T100B) in 2 mL volume of complete RPMI with 5 g/mL Protamine Sulfate and 2 ng/mL of Recombinant Mouse IL-2. Lentivirus expressing a sgRNA library and Thy1.1 was added to each well. Plates were spun at 600×g for 1.5 hours at room temperature. 24 hours after infection, cells were washed and cultured at $1\times10^6$ cells/mL in complete T cell media supplemented with 2 ng/mL of Recombinant Mouse IL-2. On Day 3 activation beads were removed and cells were further cultured at $1\times10^6$ cells/mL in complete T cell media supplemented with Recombinant Mouse IL-2 for a total of 5 Days. Transduced cells were enriched by positive selection using EasySep Mouse CD90.1 Positive Selection Kit (StemCell Catalog #18958) and genomic DNA was harvested from $5\times10^6$ cells. Library guide sequences were amplified by PCR from 100 µg of genomic DNA and sequenced on an Illumina NextSeq 500 instrument.

Figure 20:
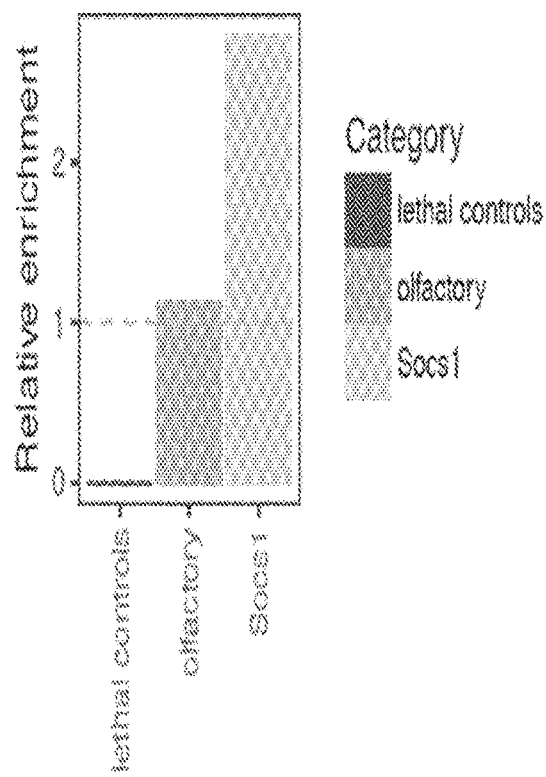
FIG. 20 shows in vitro accumulation of murine CD8+ T cells with SOCS1-targeting gRNAs.

The data in FIG. 20 demonstrate that editing the murine Socs1 gene leads to greater accumulation of murine CD8+ T cells in vitro in response to non-antigen specific activation (e.g., CD3/CD28+IL-2 stimulation) compared to the accumulation observed with lethal and olfactory control guides.

Example 30: Validation of SOCS1 as a Target Driving Increased In Vitro Expansion of Mouse CD8 T Cells Through Single Guide Editing Spleens from female PMEL mice were harvested and CD8 T cells were isolated as described in Example 1. CD8 T cells were electroporated with gRNA/Cas9 RNP complexes comprising gRNAs targeting Ankrd11, Socs1, PD1 or a control gene. PMEL T cells were expanded in vitro for a total of 5 days.

Figure 21:
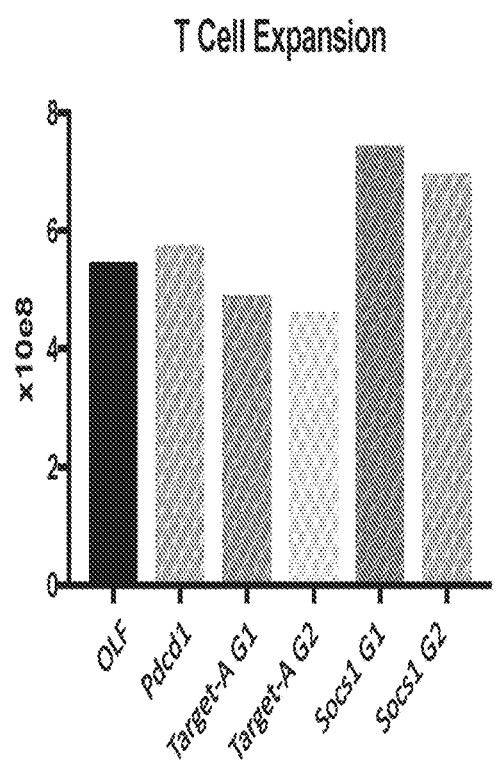
FIG. 21 shows in vitro accumulation of murine CD8+ T cells with SOCS1-targeting gRNAs compared to guides targeting other regulators of T cell function, PDCD1 and Target-A.

5 days after initial activation, the total number of viable cells present in culture was determined. The data in FIG. 21 demonstrate that Socs1 gene editing leads to greater expansion of CD8+ of T cells in comparison to guides targeting control, Pdcd1, and Ankrd11 genes.

Example 31: Identification of Socs1 as a Target Driving Increased Expansion of Human CAR-T Cells During Co-Culture with Tumor Cell Lines In vitro screens were performed using CAR-T cells specific for human CD19. Pooled sgRNA libraries were introduced to the CD19 CAR-Ts as described above in Example 4 and cells were electroporated with Cas9 mRNA to generate a population of Cas9-edited CD19 CAR-Ts. The edited CD19 CARTs were then co-cultured with DLD-1 cells expressing a truncated CD19, an adherent colorectal carcinoma (CRC) cell line engineered to express the transmembrane and extracellular domains of human CD19. On Day -1, edited CAR-Ts were thawed and re-suspended to $2\times10^6$ cells/mL in expansion medium (ImmunoCult-XF, StemCell Tech #10981)+10 ng/mL IL2 and 1× Pen/Strep and incubated for 18 hours at 370 C. In parallel, DLD-1 cells were treated with 50 µg/mL mitomycin (Sigma #M4287) for 20 minutes, washed, and then plated overnight. On Day 0, CAR-Ts were added at a 3:1 effector to target ratio (E:T) to the plated DLD-1 cells. On Day 3, CAR-Ts were washed and re-suspended to 1×106 cells/mL in expansion medium. On Day 6, DLD-1 cells were mitomycin treated as previously stated and plated overnight. CAR-Ts were added to DLD-1 cells on Day 7 for a total of two co-culture incubations. CAR-Ts were harvested at various time points throughout the co-culture period and cell pellets were frozen down. Genomic DNA (gDNA) was isolated from these cell pellets using Qiagen DNA extraction kits and sequenced using Illumina next-generation sequencing.

The distribution and/or frequency of each sgRNA in the aliquots taken from the CAR-T/feeder cell co-culture was analyzed and compared to the distribution and/or frequency of each sgRNA in the initial edited CAR-T cell population. Statistical analyses were performed for each individual sgRNA to identify sgRNAs that were significantly enriched in CAR-T cell populations following tumor cell co-culture. Enrichment scores for individual gRNAs that target the same gene were aggregated to identify target genes that have a consistent and reproducible effect on in vitro CAR-T cell accumulation.

Figure 22:
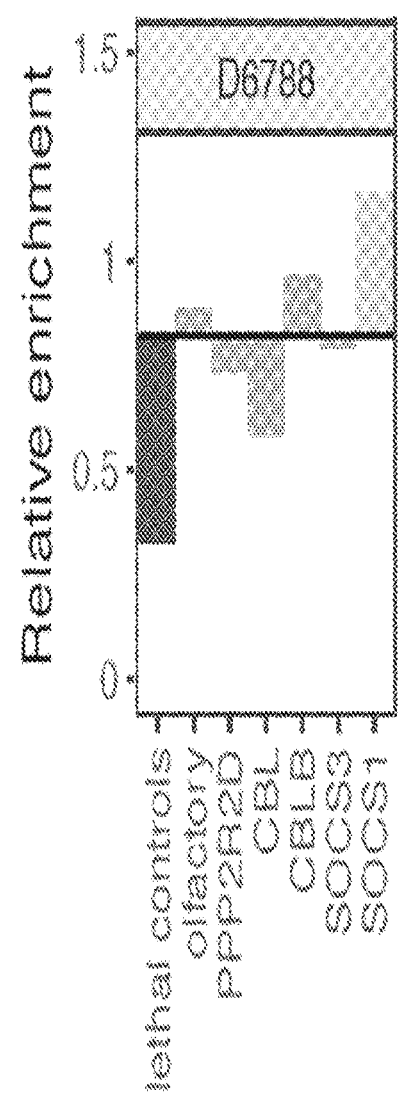
FIG. 22 shows in vitro accumulation of human CAR-T cells with guides targeting SOCS1 and CBLB in response to antigen-specific stimulation.

The results of this experiment demonstrated that guides targeting the SOCS1 and CBLB genes led to increased accumulation of CAR-Ts in vitro (FIG. 22). The results also demonstrate that guides targeting the PPP2R2D, CBL, and SOCS3 genes, which are known negative regulators of T cell proliferation, did not drive enhanced in vitro accumulation of CAR-Ts. Guides targeting the DGKA and DGKZ genes, which are known negative regulators of T cell proliferation, also did not convey enhanced accumulation (data not shown).

Example 32: Inhibition of SOCS1 Drives Increased In Vitro Expansion of Human Tils Tumor infiltrating lymphocytes are generated from surgically resected tumors from human patients and diced with scalpel blades into 1 mm³ pieces, with a single piece of tumor placed into each well of a 24-well plate. 2 mL of complete TIL media (RPMI+10% heat inactivated human male AB serum, 1 mM pyruvate, 20 µg/mL gentamycin, 1× glutamax) supplemented with 6000 U/mL of recombinant human IL-2 is added to each well of isolated TILs. 1 mL of media is removed from the well and replaced with fresh media and IL-2 up to 3 times a week as needed. As wells reach confluence, they are split 1:1 in new media+IL-2. After 4-5 weeks of culture, the cells are harvested for engineering and rapid expansion.

The activity of SOCS1 and/or CBLB are inhibited by a variety of methods, including the gRNA/Cas9 methods described, shRNA, shMIR, or expression of a dominant negative SOCS1 or CBLB construct. TILs are then rapidly expanded by co-culturing 500,000 TILs with $26\times10^6$ allogeneic, irradiated (5000 cGy) PBMC feeder cells in 20 mL TIL media+20 mL of Aim-V media (Invitrogen)+30 ng/mL OKT3 mAb. 48 hours later (Day 2), 6000 U/mL IL-2 is added to the cultures. On day 5, 20 mL of media is removed, and 20 mL fresh media (+30 ng/ml OKT3) is added. On Day 7, cells are counted, and reseeded at $60\times10^6$ cells/L in G-Rex6M well plates (Wilson Wolf, Cat #80660M) or G-Rex100M (Wilson Wolf, Cat #81100S), depending on the number of cells available. 6000 U/mL fresh IL-2 is added on Day 9 and 3000 U/mL fresh IL-2 is added on Day 12. TILs are harvested on Day 14. Expanded cells are then slow-frozen in Cryostor CS-10 (Stemcell Technologies Cat #07930) using Coolcell Freezing containers (Corning) and stored long term in liquid nitrogen. These experiments are expected to show that engineering of TILs to possess reduced SOCS1 and/or CBLB function leads to increased in vitro accumulation of TILs.

Example 33: Inhibition of Socs1 Increases Surface Expression of T Cell Activation Markers Experiments were performed to assess the effects of SOCS1 inhibition on the phenotype of tumor infiltrating lymphocytes. TILs from three patients were expanded ex vivo from a cell suspension of enzymatically digested melanoma tumors in high dose IL-2 as described above in Example 32. These were frozen, later thawed, and rested again in high dose IL-2 overnight. Approximately 200,000 to 500,000 TILs were then stimulated with plate-bound human anti--CD3 antibodies (clone OKT3) for 48 hours. After CD3 stimulation, cells were edited for SOCS or a negative control gene by electroporation of guide RNAs complexed to Cas9 in an RNP format. Edited TILs were allowed to recover overnight and then rapidly expanded as described in Example 32. This was done in the presence of irradiated peripheral blood mononuclear cells (PBMC) from five allogeneic, healthy donors and high dose IL-2 in a G-Rex flask. IL-2 was added every other day. Media was changed on day five. Cells were cultured for 14 days. On day 14, cells were stained with fluorescently labeled antibodies against CD3, CD8, CD25, CD137, and PD1 and analyzed by FACS to determine the cell-surface marker expression. Results from 2 of the 3 donors are shown in FIG. 23.

Figure 23A:
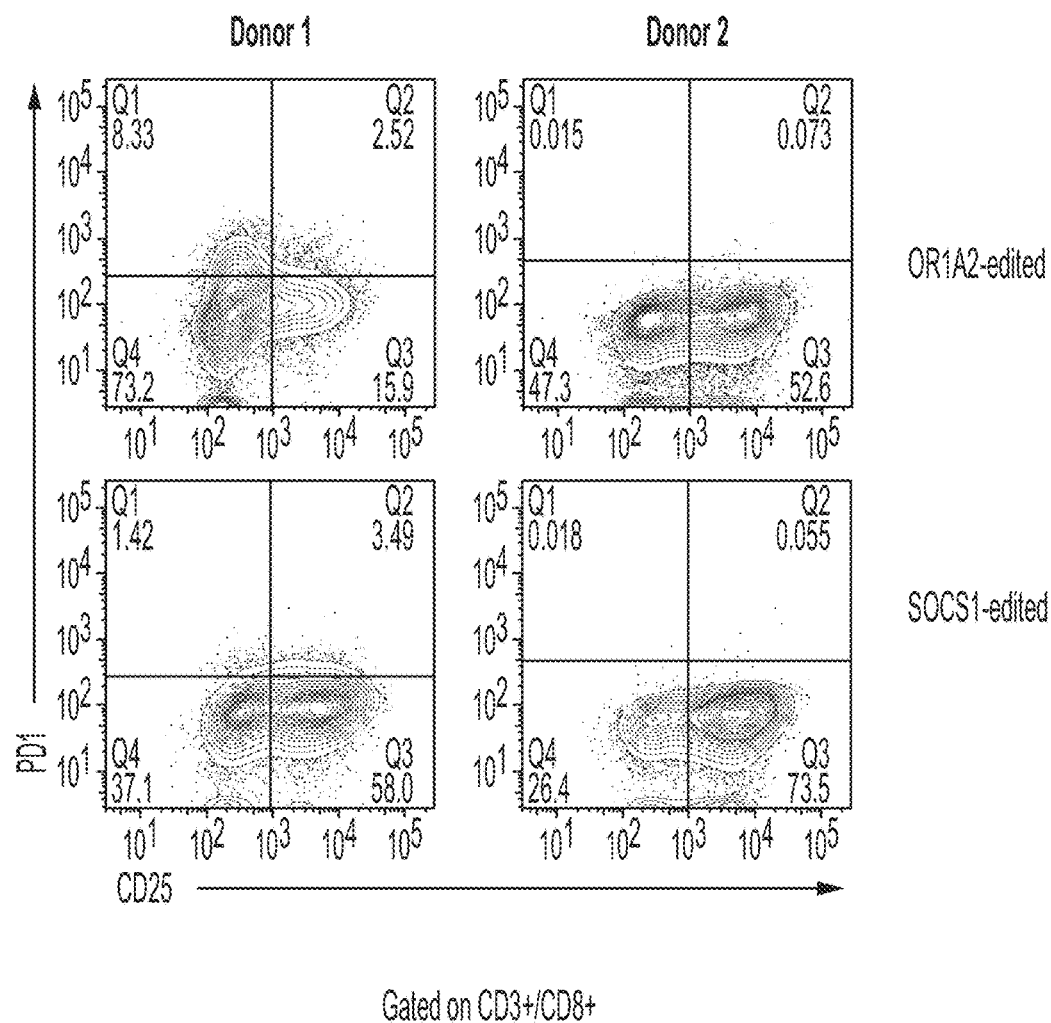
FIG. 23A-FIG. 23B shows surface expression of PD1 and CD25 (FIG. 23A) and 4-1BB (FIG. 23B) on SOCS1-edited and control-edited tumor infiltrating lymphocytes.
Figure 23B:
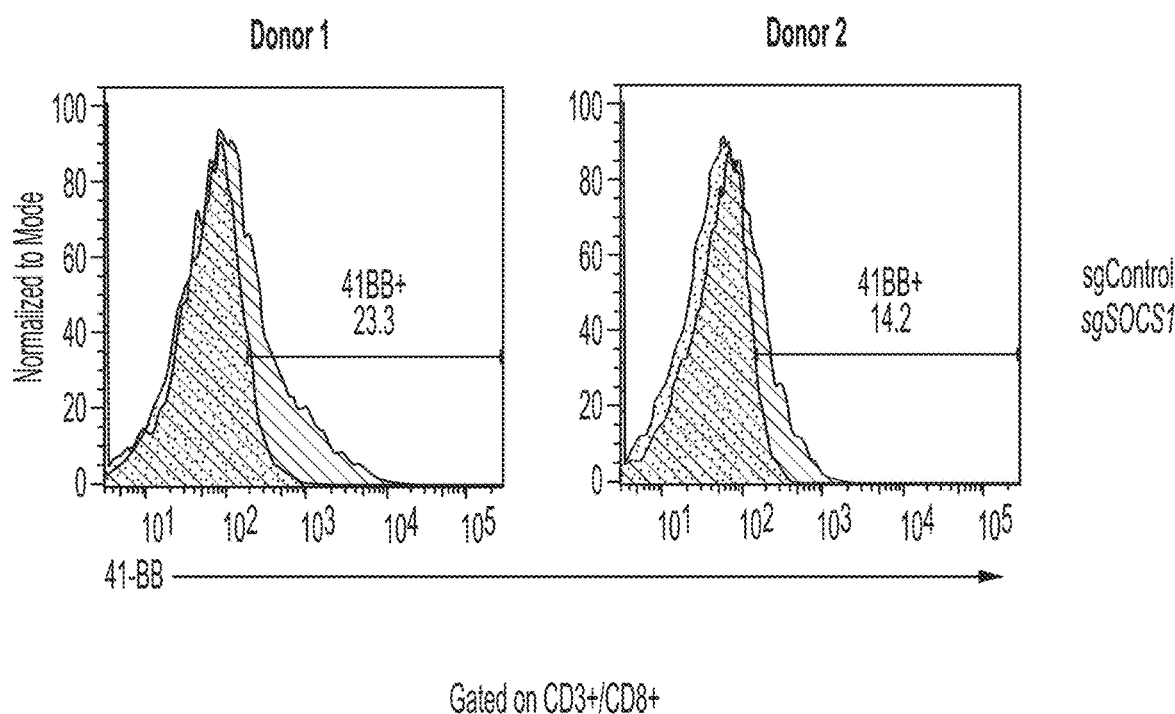

As shown in FIG. 23A and FIG. 23B, in two donors, SOCS1-edited cells demonstrated increased expression of CD25 (from 15.9% to 58% in Donor 1 and 52.6% to 75.3% in Donor 2) and increased expression of 4-1BB (from 1% to 23.3% in Donor 1 and 0 to $1^40.2\%$ in Donor 2) relative to control-edited cells. The editing efficiency of the SOCS1 gene in each donor was evaluated by NGS sequencing of PCR amplicons from the sgRNA cut site. The editing efficiency was 27% for Donor 1 and 67% for Donor 2. The third donor (not depicted) had an editing efficiency of 15% and had a less pronounced increase in CD25 expression, and no increase in 4-1BB expression. The increased expression of CD25 and 4-1BB in SOCSI-edited TILs suggests that inhibition of SOCS1 increases TIL activation and responsiveness to IL-2. These results also suggest that SOCS1 inhibition may reduce or prevent TIL exhaustion, as SOCS1-edited cells from Donor 1 also expressed less PD1, which is a known marker of TIL exhaustion.

TABLE 5A

Human Genome Coordinates

| Target | Coordinates | Target | Coordinates | Target | Coordinates |
|---|---|---|---|---|---|
| IKZF1 | chr7:50387344-50387363 | TNFAIP3 | chr6:137879270-137879289 | HAVCR2 | chr5:157106863-157106882 |
| IKZF1 | chr7:50400471-50400490 | TNFAIP3 | chr6:137878846-137878865 | HAVCR2 | chr5:157088943-157088962 |
| IKZF1 | chr7:50327652-50327671 | TNFAIP3 | chr6:137876140-137876159 | HAVCR2 | chr5:157106706-157106725 |
| IKZF1 | chr7:50400507-50400526 | TNFAIP3 | chr6:137878571-137878590 | HAVCR2 | chr5:157106886-157106905 |
| IKZF1 | chr7:50376576-50376595 | TNFAIP3 | chr6:137878573-137878592 | HAVCR2 | chr5:157106767-157106786 |
| IKZF1 | chr7:50400314-50400333 | TNFAIP3 | chr6:137878653-137878672 | HAVCR2 | chr5:157106825-157106844 |
| IKZF1 | chr7:50327681-50327700 | TNFAIP3 | chr6:137878827-137878846 | HAVCR2 | chr5:157106718-157106737 |
| IKZF1 | chr7:50391851-50391870 | TNFAIP3 | chr6:137878726-137878745 | HAVCR2 | chr5:157104727-157104746 |
| IKZF1 | chr7:50368009-50368028 | TNFAIP3 | chr6:137871457-137871476 | HAVCR2 | chr5:157087278-157087297 |
| IKZF1 | chr7:50382569-50382588 | TNFAIP3 | chr6:137876104-137876123 | LAG3 | chr12:6774679-6774698 |
| IKZF1 | chr7:50376631-50376650 | TNFAIP3 | chr6:137876762-137878781 | LAG3 | chr12:6773300-6773319 |
| IKZF1 | chr7:50400366-50400385 | TNFAIP3 | chr6:137876083-137876102 | LAG3 | chr12:6773939-6773958 |
| IKZF1 | chr7:50391772-50391791 | TNFAIP3 | chr6:137871402-137871421 | LAG3 | chr12:6775340-6775359 |
| IKZF1 | chr7:50399915-50399934 | TNFAIP3 | chr6:137871501-137871520 | LAG3 | chr12:6773781-6773800 |
| IKZF1 | chr7:50400414-50400433 | TNFAIP3 | chr6:137874861-137874880 | LAG3 | chr12:6773221-6773240 |
| IKZF1 | chr7:50368040-50368059 | TNFAIP3 | chr6:137871362-137871381 | LAG3 | chr12:6773335-6773354 |
| IKZF1 | chr7:50382550-50382569 | TNFAIP3 | chr6:137871249-137871268 | LAG3 | chr12:6774608-6774627 |
| IKZF1 | chr7:50387353-50387372 | TNFAIP3 | chr6:137874972-137874991 | LAG3 | chr12:6775514-6775533 |
| NFKBIA | chr14:35404635-35404654 | TNFAIP3 | chr6:137878495-137878514 | LAG3 | chr12:6773804-6773823 |
| NFKBIA | chr14:35402653-35402672 | TNFAIP3 | chr6:137874842-137874861 | LAG3 | chr12:6773283-6773302 |
| NFKBIA | chr14:35402494-35402513 | TNFAIP3 | chr6:137876139-137876158 | LAG3 | chr12:6774798-6774817 |
| NFKBIA | chr14:35404445-35404464 | TNFAIP3 | chr6:137871437-137871456 | TIGIT | chr3:114307905-114307924 |
| NFKBIA | chr14:35403152-35403171 | TANK | chr2:161232836-161232855 | TIGIT | chr3:114295774-114295793 |
| NFKBIA | chr14:35403258-35403277 | TANK | chr2:161179709-161179728 | TIGIT | chr3:114295717-114295736 |

TABLE 5A-continued

Human Genome Coordinates

| Target | Coordinates | Target | Coordinates | Target | Coordinates |
|---|---|---|---|---|---|
| NFKBIA | chr14:35404463-35404482 | TANK | chr2:161224725-161224744 | TIGIT | chr3:114295630-114295649 |
| NFKBIA | chr14:35403202-35403221 | TANK | chr2:161204665-161204684 | TIGIT | chr3:114295615-114295634 |
| NFKBIA | chr14:35404411-35404430 | TANK | chr2:161161386-161161405 | TIGIT | chr3:114295821-114295840 |
| NFKBIA | chr14:35402666-35402685 | TANK | chr2:161231124-161231143 | TIGIT | chr3:114295767-114295786 |
| NFKBIA | chr14:35403330-35403349 | TANK | chr2:161179740-161179759 | TIGIT | chr3:114299648-114299667 |
| NFKBIA | chr14:35403695-35403714 | TANK | chr2:161232788-161232807 | TIGIT | chr3:114295577-114295596 |
| BCL3 | chr19:44757097-44757116 | TANK | chr2:161232777-161232796 | TIGIT | chr3:114295650-114295669 |
| BCL3 | chr19:44757336-44757355 | TANK | chr2:161223970-161223989 | TIGIT | chr3:114294023-114294042 |
| BCL3 | chr19:44756280-44756299 | TANK | chr2:161203501-161203520 | TIGIT | chr3:114299682-114299701 |
| BCL3 | chr19:44748932-44748951 | TANK | chr2:161203590-161203609 | CTLA4 | chr2:203872820-203872839 |
| BCL3 | chr19:44756229-44756248 | TANK | chr2:161204749-161204768 | CTLA4 | chr2:203871417-203871436 |
| BCL3 | chr19:44751352-44751371 | TANK | chr2:161179691-161179710 | CTLA4 | chr2:203870885-203870904 |
| BCL3 | chr19:44756315-44756334 | TANK | chr2:161161378-161161397 | CTLA4 | chr2:203867944-203867963 |
| BCL3 | chr19:44757028-44757047 | FOXP3 | chrX:49258389-49258408 | CTLA4 | chr2:203871421-203871440 |
| BCL3 | chr19:44748876-44748895 | FOXP3 | chrX:49255792-49255811 | CTLA4 | chr2:203872759-203872778 |
| BCL3 | chr19:44758720-44758739 | FOXP3 | chrX:49253120-49253139 | CTLA4 | chr2:203867944-203867963 |
| BCL3 | chr19:44756334-44756353 | FOXP3 | chrX:49251742-49251761 | CTLA4 | chr2:203870640-203870659 |
| BCL3 | chr19:44751300-44751319 | FOXP3 | chrX:49256916-49256935 | CTLA4 | chr2:203870767-203870786 |
| BCL3 | chr19:44758258-44758277 | FOXP3 | chrX:49254054-49254073 | CTLA4 | chr2:203868001-203868020 |
| IKZF3 | chr17:39765927-39765946 | FOXP3 | chrX:49258314-49258333 | CTLA4 | chr2:203870606-203870625 |
| IKZF3 | chr17:39766306-39766325 | FOXP3 | chrX:49251666-49251685 | CTLA4 | chr2:203872716-203872735 |
| IKZF3 | chr17:39788315-39788334 | FOXP3 | chrX:49257496-49257515 | PTPN6 | chr12:6955147-6955166 |
| IKZF3 | chr17:39832082-39832101 | FOXP3 | chrX:49258351-49258370 | PTPN6 | chr12:6956188-6956207 |
| IKZF3 | chr17:39766366-39766385 | IKZF2 | chr2:213057056-213057075 | PTPN6 | chr12:6952101-6952120 |
| IKZF3 | chr17:39766410-39766429 | IKZF2 | chr2:213056895-213056914 | PTPN6 | chr12:6954832-6954851 |
| IKZF3 | chr17:39765981-39766000 | IKZF2 | chr2:213007992-213008011 | PTPN6 | chr12:6951504-6951523 |
| IKZF3 | chr17:39766262-39766281 | IKZF2 | chr2:213022029-213022048 | PTPN6 | chr12:6951637-6951656 |
| IKZF3 | chr17:39766122-39766141 | IKZF2 | chr2:213148620-213148639 | PTPN6 | chr12:6952004-6952023 |
| IKZF3 | chr17:39777926-39777945 | IKZF2 | chr2:213049845-213049864 | PTPN6 | chr12:6954960-6954979 |
| IKZF3 | chr17:39777960-39777979 | IKZF2 | chr2:213049749-213049768 | PTPN6 | chr12:6945764-6945783 |
| IKZF3 | chr17:39791548-39791567 | IKZF2 | chr2:213013838-213013857 | PTPN6 | chr12:6952156-6952175 |
| IKZF3 | chr17:39791554-39791573 | IKZF2 | chr2:213147704-213147723 | PTPN6 | chr12:6951688-6951707 |
| IKZF3 | chr17:39788306-39788325 | IKZF2 | chr2:213007950-213007969 | PTPN6 | chr12:6952055-6952074 |
| IKZF3 | chr17:39777690-39777709 | IKZF2 | chr2:213049803-213049822 | PTPN6 | chr12:6952004-6952023 |
| SMAD2 | chr18:47869428-47869447 | IKZF2 | chr2:213022103-213022122 | PTPN6 | chr12:6954869-6954888 |
| SMAD2 | chr18:47896710-47896729 | IKZF2 | chr2:213013910-213013929 | BCOR | chrX:40074116-40074135 |
| SMAD2 | chr18:47869333-47869352 | IKZF2 | chr2:213056913-213056932 | BCOR | chrX:40073790-40073809 |
| SMAD2 | chr18:47869252-47869271 | IKZF2 | chr2:213147790-213147809 | BCOR | chrX:40077875-40077894 |

TABLE 5A-continued

Human Genome Coordinates

| Target | Coordinates | Target | Coordinates | Target | Coordinates |
|---|---|---|---|---|---|
| SMAD2 | chr18:47869371-47869390 | IKZF2 | chr2:213049707-213049726 | BCOR | chrX:40052324-40052343 |
| SMAD2 | chr18:47870547-47870566 | GATA3 | chr10:8064032-8064051 | BCOR | chrX:40073729-40073748 |
| SMAD2 | chr18:47896523-47896542 | GATA3 | chr10:8064079-8064098 | BCOR | chrX:40054273-40054292 |
| SMAD2 | chr18:47845647-47845666 | GATA3 | chr10:8073748-8073767 | BCOR | chrX:40073193-40073212 |
| SMAD2 | chr18:47896640-47896659 | GATA3 | chr10:8058824-8058843 | BCOR | chrX:40074630-40074649 |
| TGFBR1 | chr9:99128854-99128873 | GATA3 | chr10:8058443-8058462 | BCOR | chrX:40062797-40062816 |
| TGFBR1 | chr9:99137867-99137886 | GATA3 | chr10:8069573-8069592 | BCOR | chrX:40072605-40072624 |
| TGFBR1 | chr9:99128995-99129014 | GATA3 | chr10:8069532-8069551 | BCOR | chrX:40073675-40073694 |
| TGFBR1 | chr9:99132565-99132584 | GATA3 | chr10:8055748-8055767 | BCOR | chrX:40073080-40073099 |
| TGFBRI | chr9:99137897-99137916 | GATA3 | chr10:8058395-8058414 | BCOR | chrX:40074432-40074451 |
| TGFBR1 | chr9:99137998-99138017 | GATA3 | chr10:8058737-8058756 | BCOR | chrX:40074150-40074169 |
| TGFBR1 | chr9:99137939-99137958 | GATA3 | chr10:8058349-8058368 | BCOR | chrX:40073363-40073382 |
| TGFBR1 | chr9:99132706-99132725 | GATA3 | chr10:8058824-8058843 | BCOR | chrX:40064581-40064600 |
| TGFBR1 | chr9:99128942-99128961 | RC3H1 | chr1:173946812-173946831 | BCOR | chrX:40062765-40062784 |
| TGFBR1 | chr9:99129014-99129033 | RC3H1 | chr1:173992926-173992945 | BCOR | chrX:40072562-40072581 |
| TGFBR2 | chr3:30650327-30650346 | RC3H1 | chr1:173980872-173980891 | BCOR | chrX:40072987-40073006 |
| TGFBR2 | chr3:30650394-30650413 | RC3H1 | chr1:173982779-173982798 | BCOR | chrX:40075168-40075187 |
| TGFBR2 | chr3:30671914-30671933 | RC3H1 | chr1:173980941-173980960 | BCOR | chrX:40073376-40073395 |
| TGFBR2 | chr3:30671753-30671772 | RC3H1 | chr1:173992844-173992863 | BCOR | chrX:40073489-40073508 |
| TGFBR2 | chr3:30672089-30672108 | RC3H1 | chr1:173992895-173992914 | BCOR | chrX:40072671-40072690 |
| TGFBR2 | chr3:30623239-30623258 | RC3H1 | chr1:173992882-173992901 | BCOR | chrX:40073707-40073726 |
| TGFBR2 | chr3:30650357-30650376 | RC3H1 | chr1:173961717-173961736 | BCOR | chrX:40072455-40072474 |
| TGFBR2 | chr3:30672412-30672431 | RC3H1 | chr1:173984495-173984514 | BCOR | chrX:40073856-40073875 |
| TGFBR2 | chr3:30671782-30671801 | RC3H1 | chr1:173980811-173980830 | BCOR | chrX:40073454-40073473 |
| TGFBR2 | chr3:30644886-30644905 | RC3H1 | chr1:173964926-173964945 | BCOR | chrX:40073223-40073242 |
| TGFBR2 | chr3:30671709-30671728 | RC3H1 | chr1:173982894-173982913 | BCOR | chrX:40057164-40057183 |
| TGFBR2 | chr3:30671765-30671784 | TRAF6 | chr11:36501306-36501325 | BCOR | chrX:40063694-40063713 |
| TGFBR2 | chr3:30623229-30623248 | TRAF6 | chr11:36490635-36490654 | BCOR | chrX:40073114-40073133 |
| TGFBR2 | chr3:30671933-30671952 | TRAF6 | chr11:36498527-36498546 | BCOR | chrX:40063765-40063784 |
| TGFBR2 | chr3:30644834-30644853 | TRAF6 | chr11:36492548-36492567 | BCOR | chrX:40074230-40074249 |
| TNIP1 | chr5:151039096-151039115 | TRAF6 | chr11:36501355-36501374 | BCOR | chrX:40063788-40063807 |
| TNIP1 | chr5:151039165-151039184 | TRAF6 | chr11:36501423-36501442 | BCOR | chrX:40073550-40073569 |
| TNIP1 | chr5:151033531-151033550 | TRAF6 | chr11:36501487-36501506 | BCOR | chrX:40072510-40072529 |
| TNIP1 | chr5:151052229-151052248 | TRAF6 | chr11:36490112-36490131 | BCOR | chrX:40074371-40074390 |
| TNIP1 | chr5:151056754-151056773 | TRAF6 | chr11:36498546-36498565 | BCOR | chrX:40062953-40062972 |
| TNIP1 | chr5:151063682-151063701 | TRAF6 | chr11:36490590-36490609 | BCOR | chrX:40071047-40071066 |
| TNIP1 | chr5:151033527-151033546 | TRAF6 | chr11:36501262-36501281 | BCOR | chrX:40073673-40073692 |
| TNIP1 | chr5:151056795-151056814 | TRAF6 | chr11:36497165-36497184 | BCOR | chrX:40074756-40074775 |

TABLE 5A-continued

| Target | Coordinates | Target | Coordinates | Target | Coordinates |
|---|---|---|---|---|---|
| TNIP1 | chr5:151033778-151033797 | CBLB | chr3:105853475-105853494 | BCOR | chrX:40074952-40074971 |
| TNIP1 | chr5:151045881-151045900 | CBLB | chr3:105853600-105853619 | BCOR | chrX:40063752-40063771 |
| TNIP1 | chr5:151063608-151063627 | CBLB | chr3:105720111-105720130 | BCOR | chrX:40062753-40062772 |
| TNIP1 | chr5:151035692-151035711 | CBLB | chr3:105867412-105867431 | BCOR | chrX:40073052-40073071 |
| TNIP1 | chr5:151056834-151056853 | CBLB | chr3:105867529-105867548 | BCOR | chrX:40075122-40075141 |
| TNIP1 | chr5:151064993-151065012 | CBLB | chr3:105720160-105720179 | BCOR | chrX:40063806-40063825 |
| TNIP1 | chr5:151033749-151033768 | CBLB | chr3:105853421-105853440 | BCOR | chrX:40074193-40074212 |
| TNFAIP3 | chr6:137878782-137878801 | CBLB | chr3:105751453-105751472 | BCOR | chrX:40074839-40074858 |
| TNFAIP3 | chr6:137874872-137874891 | CBLB | chr3:105693541-105693560 | BCOR | chrX:40074647-40074666 |
| TNFAIP3 | chr6:137878447-137878466 | CBLB | chr3:105867449-105867468 | BCOR | chrX:40070980-40070999 |
| TNFAIP3 | chr6:137878901-137878920 | CBLB | chr3:105853514-105853533 | BCOR | chrX:40074386-40074405 |
| TNFAIP3 | chr6:137880092-137880111 | PPP2R2D | chr10:131940160-131940179 | BCOR | chrX:40072494-40072513 |
| TNFAIP3 | chr6:137878710-137878729 | PPP2R2D | chr10:131934499-131934518 | BCOR | chrX:40074087-40074106 |
| TNFAIP3 | chr6:137877173-137877192 | PPP2R2D | chr10:131947775-131947794 | BCOR | chrX:40057291-40057310 |
| TNFAIP3 | chr6:137878510-137878529 | PPP2R2D | chr10:131945305-131945324 | BCOR | chrX:40073603-40073622 |
| TNFAIP3 | chr6:137879002-137879021 | PPP2R2D | chr10:131911562-131911581 | BCOR | chrX:40074157-40074176 |
| TNFAIP3 | chr6:137871467-137871486 | PPP2R2D | chr10:131944056-131944075 | BCOR | chrX:40075017-40075036 |
| TNFAIP3 | chr6:137879001-137879020 | PPP2R2D | chr10:131945382-131945401 | BCOR | chrX:40074903-40074922 |
| TNFAIP3 | chr6:137875731-137875750 | PPP2R2D | chr10:131947633-131947652 | BCOR | chrX:40074949-40074968 |
| TNFAIP3 | chr6:137875820-137875839 | PPP2R2D | chr10:131901284-131901303 | BCOR | chrX:40053888-40053907 |
| TNFAIP3 | chr6:137880133-137880152 | PPP2R2D | chr10:131911594-131911613 | BCOR | chrX:40074785-40074804 |
| TNFAIP3 | chr6:137878796-137878815 | NRP1 | chr10:33254103-33254122 | BCOR | chrX:40077894-40077913 |
| TNFAIP3 | chr6:137877195-137877214 | NRP1 | chr10:33263822-33263841 | BCOR | chrX:40076456-40076475 |
| TNFAIP3 | chr6:137880103-137880122 | NRP1 | chr10:33263660-33263679 | BCOR | chrX:40062904-40062923 |
| TNFAIP3 | chr6:137875750-137875769 | NRP1 | chr10:33256447-33256466 | PDCD1 | chr2:241852282-241852301 |
| TNFAIP3 | chr6:137878979-137878998 | NRP1 | chr10:33263677-33263696 | PDCD1 | chr2:241852278-241852297 |
| TNFAIP3 | chr6:137880119-137880138 | NRP1 | chr10:33263699-33263718 | PDCD1 | chr2:241852879-241852898 |
| TNFAIP3 | chr6:137878741-137878760 | NRP1 | chr10:33256400-33256419 | PDCD1 | chr2:241852752-241852771 |
| TNFAIP3 | chr6:137878795-137878814 | NRP1 | chr10:33254025-33254044 | PDCD1 | chr2:241852618-241852637 |
| TNFAIP3 | chr6:137878817-137878836 | NRP1 | chr10:33330718-33330737 | PDCD1 | chr2:241852729-241852748 |
| TNFAIP3 | chr6:137878974-137878993 | NRP1 | chr10:33254069-33254088 | PDCD1 | chr2:241852687-241852706 |
| TNFAIP3 | chr6:137874868-137874887 | NRP1 | chr10:33256432-33256451 | PDCD1 | chr2:241852796-241852815 |
| TNFAIP3 | chr6:137876091-137876110 | HAVCR2 | chr5:157106936-157106955 | PDCD1 | chr2:241852933-241852952 |
| TNFAIP3 | chr6:137877199-137877218 | HAVCR2 | chr5:157095368-157095387 | PDCD1 | chr2:241852831-241852850 |
|  |  | HAVCR2 | chr5:157106898-157106917 | PDCD1 | chr2:241851189-241851208 |

TABLE 5B

| | Murine Genome Coordinates | | | | |
|---|---|---|---|---|---|
| Target | Coordinates | Target | Coordinates | Target | Coordinates |
| Ikzf1 | chr11:11754053-11754072 | Gata3 | chr2:9874375-9874394 | Lag3 | chr6:124908392-124908411 |
| Ikzf1 | chr11:11707883-11707902 | Gata3 | chr2:9858592-9858611 | Lag3 | chr6:124909391-124909410 |
| Ikzf1 | chr11:11754068-11754087 | Gata3 | chr2:9877463-9877482 | Lag3 | chr6:124909410-124909429 |
| Ikzf1 | chr11:11754134-11754153 | Gata3 | chr2:9877514-9877533 | Tigit | chr16:43662107-43662126 |
| Ikzf1 | chr11:11754153-11754172 | Gata3 | chr2:9858607-9858626 | Tigit | chr16:43662060-43662079 |
| Ikzf1 | chr11:11754103-11754122 | Gata3 | chr2:9877338-9877357 | Tigit | chr16:43661976-43661995 |
| Ikzf1 | chr11:11754015-11754034 | Gata3 | chr2:9863114-9863133 | Tigit | chr16:43662254-43662273 |
| Ikzf1 | chr11:11754119-11754138 | Gata3 | chr2:9858626-9858645 | Tigit | chr16:43661994-43662013 |
| Nfkbia | chr12:55491236-55491255 | Rc3h1 | chr1:160930251-160930270 | Tigit | chr16:43662156-43662175 |
| Nfkbia | chr12:55491172-55491191 | Rc3h1 | chr1:160930280-160930299 | Tigit | chr16:43662277-43662296 |
| Nfkbia | chr12:55491206-55491225 | Rc3h1 | chr1:160930154-160930173 | Tigit | chr16:43662012-43662031 |
| Nfkbia | chr12:55490633-55490652 | Rc3h1 | chr1:160942614-160942633 | Tigit | chr16:43664036-43664055 |
| Nfkbia | chr12:55491112-55491131 | Rc3h1 | chr1:160930266-160930285 | Tigit | chr16:43664057-43664076 |
| Nfkbia | chr12:55490800-55490819 | Rc3h1 | chr1:160930185-160930204 | Tigit | chr16:43649030-43649049 |
| Nfkbia | chr12:55490821-55490840 | Rc3h1 | chr1:160938126-160938145 | Tigit | chr16:43662129-43662148 |
| Nfkbia | chr12:55490526-55490545 | Rc3h1 | chr1:160930198-160930217 | Tigit | chr16:43662059-43662078 |
| Nfkbia | chr12:55491657-55491676 | Traf6 | chr2:101688485-101688504 | Tigit | chr16:43662148-43662167 |
| Nfkbia | chr12:55491177-55491196 | Traf6 | chr2:101691455-101691474 | Tigit | chr16:43664021-43664040 |
| Nfkbia | chr12:55491675-55491694 | Traf6 | chr2:101688575-101688594 | Ctla4 | chr1:60914621-60914640 |
| Nfkbia | chr12:55490773-55490792 | Traf6 | chr2:101684742-101684761 | Ctla4 | chr1:60909166-60909185 |
| Nfkbia | chr12:55490809-55490828 | Traf6 | chr2:101688539-101688558 | Ctla4 | chr1:60914725-60914744 |
| Nfkbia | chr12:55491735-55491754 | Traf6 | chr2:101691482-101691501 | Ctla4 | chr1:60909219-60909238 |
| Nfkbia | chr12:55490571-55490590 | Traf6 | chr2:101688558-101688577 | Ctla4 | chr1:60914673-60914692 |
| Nfkbia | chr12:55490588-55490607 | Traf6 | chr2:101684510-101684529 | Ctla4 | chr1:60912501-60912520 |
| Nfkbia | chr12:55491715-55491734 | Cblb | chr16:52152499-52152518 | Ctla4 | chr1:60912446-60912465 |
| Nfkbia | chr12:55492316-55492335 | Cblb | chr16:52139574-52139593 | Ctla4 | chr1:60912725-60912744 |
| Nfkbia | chr12:55491207-55491226 | Cblb | chr16:52139603-52139622 | Ctla4 | chr1:60912516-60912535 |
| Bcl3 | chr3:19809245-19809264 | Cblb | chr16:52112122-52112141 | Ctla4 | chr1:60912664-60912683 |
| Bcl3 | chr3:19811059-19811078 | Cblb | chr16:52112134-52112153 | Ctla4 | chr1:60912477-60912496 |
| Bcl3 | chr3:19809632-19809651 | Cblb | chr16:52152535-52152554 | Ctla4 | chr1:60912618-60912637 |
| Bcl3 | chr3:19809634-19809653 | Cblb | chr16:52142891-52142910 | Ctla4 | chr1:60912682-60912701 |
| Bcl3 | chr3:19809551-19809570 | Cblb | chr16:52135797-52135816 | Ctla4 | chr1:60912697-60912716 |
| Bcl3 | chr3:19809516-19809535 | Cblb | chr16:52131105-52131124 | Ctla4 | chr1:60912605-60912624 |
| Bcl3 | chr3:19812411-19812430 | Cblb | chr16:52112169-52112188 | Ctla4 | chr1:60912433-60912452 |
| Bcl3 | chr3:19811610-19811629 | Cblb | chr16:52204542-52204561 | Ctla4 | chr1:60909202-60909221 |
| Ikzf3 | chr11:98516898-98516917 | Cblb | chr16:52131058-52131077 | Ctla4 | chr1:60909165-60909184 |
| Ikzf3 | chr11:98467268-98467287 | Cblb | chr16:52135876-52135895 | Ctla4 | chr1:60914619-60914638 |
| Ikzf3 | chr11:98467464-98467483 | Cblb | chr16:52135763-52135782 | Ctla4 | chr1:60909244-60909263 |

TABLE 5B-continued

| Murine Genome Coordinates | | | | | |
|---|---|---|---|---|---|
| Target | Coordinates | Target | Coordinates | Target | Coordinates |
| Ikzf3 | chr11:98467325-98467344 | Cblb | chr16:52139509-52139528 | Ptpn6 | chr6:124727399-124727418 |
| Ikzf3 | chr11:98467181-98467200 | Ppp2r2d | chr7:138876553-138876572 | Ptpn6 | chr6:124732470-124732489 |
| Ikzf3 | chr11:98477038-98477057 | Ppp2r2d | chr7:138882200-138882219 | Ptpn6 | chr6:124732484-124732503 |
| Ikzf3 | chr11:98466977-98466996 | Ppp2r2d | chr7:138876565-138876584 | Ptpn6 | chr6:124727385-124727404 |
| Ikzf3 | chr11:98467103-98467122 | Ppp2r2d | chr7:138882451-138882470 | Ptpn6 | chr6:124721816-124721835 |
| Tgfbr1 | chr4:47396418-47396437 | Ppp2r2d | chr7:138882404-138882423 | Ptpn6 | chr6:124725324-124725343 |
| Tgfbr1 | chr4:47396363-47396382 | Ppp2r2d | chr7:138869675-138869694 | Ptpn6 | chr6:124732430-124732449 |
| Tgfbr1 | chr4:47393272-47393291 | Ppp2r2d | chr7:138876686-138876705 | Ptpn6 | chr6:124732454-124732473 |
| Tgfbr1 | chr4:47393468-47393487 | Ppp2r2d | chr7:138874130-138874149 | Ptpn6 | chr6:124732329-124732348 |
| Tgfbr1 | chr4:47393456-47393475 | Nrp1 | chr8:128363358-128363377 | Ptpn6 | chr6:124725334-124725353 |
| Tgfbr1 | chr4:47396564-47396583 | Nrp1 | chr8:128363296-128363315 | Ptpn6 | chr6:124732349-124732368 |
| Tgfbr1 | chr4:47393315-47393334 | Nrp1 | chr8:128359628-128359647 | Ptpn6 | chr6:124732309-124732328 |
| Tgfbr1 | chr4:47396434-47396453 | Nrp1 | chr8:128476138-128476157 | Ptpn6 | chr6:124727402-124727421 |
| Tgfbr1 | chr4:47393288-47393307 | Nrp1 | chr8:128363272-128363291 | Ptpn6 | chr6:124732435-124732454 |
| Tgfbr1 | chr4:47396512-47396531 | Nrp1 | chr8:128359612-128359631 | Pdcd1 | chr1:94041239-94041258 |
| Tgfbr1 | chr4:47402873-47402892 | Nrp1 | chr8:128363336-128363355 | Pdcd1 | chr1:94041292-94041311 |
| Tgfbr1 | chr4:47396539-47396558 | Nrp1 | chr8:128363210-128363229 | Pdcd1 | chr1:94041357-94041376 |
| Tgfbr1 | chr4:47393266-47393285 | Nrp1 | chr8:128425932-128425951 | Pdcd1 | chr1:94041207-94041226 |
| Tgfbr1 | chr4:47396394-47396413 | Nrp1 | chr8:128497936-128497955 | Pdcd1 | chr1:94041223-94041242 |
| Tgfbr1 | chr4:47393462-47393481 | Nrp1 | chr8:128468551-128468570 | Pdcd1 | chr1:94041394-94041413 |
| Tgfbr2 | chr9:116129944-116129963 | Nrp1 | chr8:128363251-128363270 | Pdcd1 | chr1:94041165-94041184 |
| Tgfbr2 | chr9:116129900-116129919 | Nrp1 | chr8:128460693-128460712 | Pdcd1 | chr1:94041179-94041198 |
| Tgfbr2 | chr9:116129928-116129947 | Havcr2 | chr11:46456439-46456458 | Pdcd1 | chr1:94041468-94041487 |
| Tgfbr2 | chr9:116131548-116131567 | Havcr2 | chr11:46469515-46469534 | Pdcd1 | chr1:94041331-94041350 |
| Tgfbr2 | chr9:116131562-116131581 | Havcr2 | chr11:46466864-46466883 | Pdcd1 | chr1:94041421-94041440 |
| Tgfbr2 | chr9:116131610-116131629 | Havcr2 | chr11:46479374-46479393 | Pdcd1 | chr1:94041165-94041184 |
| Tgfbr2 | chr9:116131588-116131607 | Havcr2 | chr11:46456495-46456514 | Pdcd1 | chr1:94041421-94041440 |
| Tgfbr2 | chr9:116131529-116131548 | Havcr2 | chr11:46479356-46479375 | Pdcd1 | chr1:94041331-94041350 |
| Tgfbr2 | chr9:116110272-116110291 | Havcr2 | chr11:46455033-46455052 | Pdcd1 | chr1:94041468-94041487 |
| Tgfbr2 | chr9:116109969-116109988 | Havcr2 | chr11:46469534-46469553 | Pdcd1 | chr1:94041239-94041258 |
| Tgfbr2 | chr9:116129901-116129920 | Havcr2 | chr11:46456242-46456261 | Pdcd1 | chr1:94041292-94041311 |
| Tgfbr2 | chr9:116129988-116130007 | Havcr2 | chr11:46479302-46479321 | Pdcd1 | chr1:94041357-94041376 |
| Tgfbr2 | chr9:116110004-116110023 | Havcr2 | chr11:46456496-46456515 | Pdcd1 | chr1:94041207-94041226 |
| Tnip1 | chr11:54939673-54939692 | Havcr2 | chr11:46456355-46456374 | Pdcd1 | chr1:94041223-94041242 |
| Tnip1 | chr11:54930778-54930797 | Havcr2 | chr11:46469521-46469540 | Pdcd1 | chr1:94041394-94041413 |
| Tnip1 | chr11:54934036-54934055 | Havcr2 | chr11:46459111-46459130 | Pdcd1 | chr1:94041179-94041198 |
| Tnip1 | chr11:54934071-54934090 | Havcr2 | chr11:46456301-46456320 | Pdcd1 | chr1:94041412-94041431 |
| Tnip1 | chr11:54930799-54930818 | Lag3 | chr6:124908571-124908590 | Pdcd1 | chr1:94041268-94041287 |

TABLE 5B-continued

Murine Genome Coordinates

| Target | Coordinates | Target | Coordinates | Target | Coordinates |
|---|---|---|---|---|---|
| Tnip1 | chr11:54930820-54930839 | Lag3 | chr6:124909259-124909278 | Pdcd1 | chr1:94041309-94041328 |
| Tnip1 | chr11:54933977-54933996 | Lag3 | chr6:124909424-124909443 | Pdcd1 | chr1:94041469-94041488 |
| Tnip1 | chr11:54929117-54929136 | Lag3 | chr6:124908491-124908510 | Pdcd1 | chr1:94041189-94041208 |
| Tnfaip3 | chr10:19011464-19011483 | Lag3 | chr6:124909299-124909318 | Pdcd1 | chr1:94041331-94041350 |
| Tnfaip3 | chr10:19008246-19008265 | Lag3 | chr6:124909474-124909493 | Pdcd1 | chr1:94041239-94041258 |
| Tnfaip3 | chr10:19008332-19008351 | Lag3 | chr6:124909286-124909305 | Pdcd1 | chr1:94041292-94041311 |
| Tnfaip3 | chr10:19006919-19006938 | Lag3 | chr6:124908450-124908469 | | |
| Tnfaip3 | chr10:19008294-19008313 | Lag3 | chr6:124908529-124908548 | | |
| Tnfaip3 | chr10:19008234-19008253 | Lag3 | chr6:124909272-124909291 | | |
| Tnfaip3 | chr10:19002796-19002815 | Lag3 | chr6:124909399-124909418 | | |
| Tnfaip3 | chr10:19006981-19007000 | Lag3 | chr6:124909228-124909247 | | |

TABLE 6A

Human Genome Coordinates

| Target | Coordinates | Target | Coordinates | Target | Coordinates |
|---|---|---|---|---|---|
| BCL2L11 | chr2:111123809-111123828 | PBRM1 | chr3:52554752-52554771 | CALM2 | chr2:47167608-47167627 |
| BCL2L11 | chr2:111142346-111142365 | PBRM1 | chr3:52603635-52603654 | CALM2 | chr2:47162389-47162408 |
| BCL2L11 | chr2:111150125-111150144 | PBRM1 | chr3:52634703-52634722 | CALM2 | chr2:47162623-47162642 |
| BCL2L11 | chr2:111164161-111164180 | PBRM1 | chr3:52662232-52662251 | CALM2 | chr2:47161766-47161785 |
| BCL2L11 | chr2:111123880-111123899 | PBRM1 | chr3:52609796-52609815 | CALM2 | chr2:47161806-47161825 |
| BCL2L11 | chr2:111142303-111142322 | PBRM1 | chr3:52554720-52554739 | CALM2 | chr2:47162544-47162563 |
| BCL2L11 | chr2:111128637-111128656 | PBRM1 | chr3:52668623-52668642 | CALM2 | chr2:47167482-47167501 |
| BCL2L11 | chr2:111124067-111124086 | PBRM1 | chr3:52679663-52679682 | CALM2 | chr2:47162606-47162625 |
| BCL2L11 | chr2:111150032-111150051 | PBRM1 | chr3:52617272-52617291 | CALM2 | chr2:47162351-47162370 |
| BCL2L11 | chr2:111153772-111153791 | PBRM1 | chr3:52678502-52678521 | CALM2 | chr2:47162279-47162298 |
| BCL2L11 | chr2:111124106-111124125 | PBRM1 | chr3:52558272-52558291 | CALM2 | chr2:47172416-47172435 |
| BCL2L11 | chr2:111123866-111123885 | PBRM1 | chr3:52668512-52668531 | SERPINA3 | chr14:94614673-94614692 |
| BCL2L11 | chr2:111130128-111130147 | PBRM1 | chr3:52643284-52643303 | SERPINA3 | chr14:94619278-94619297 |
| BCL2L11 | chr2:111123761-111123780 | PBRM1 | chr3:52558266-52558285 | SERPINA3 | chr14:94614582-94614601 |
| BCL2L11 | chr2:111150081-111150100 | PBRM1 | chr3:52634800-52634819 | SERPINA3 | chr14:94619423-94619442 |
| BCL2L11 | chr2:111123790-111123809 | PBRM1 | chr3:52603596-52603615 | SERPINA3 | chr14:94614528-94614547 |
| BCL2L11 | chr2:111153779-111153798 | PBRM1 | chr3:52643330-52643349 | SERPINA3 | chr14:94614599-94614618 |
| BCL2L11 | chr2:111124008-111124027 | PBRM1 | chr3:52651751-52651770 | SERPINA3 | chr14:94614744-94614763 |
| BCL2L11 | chr2:111123848-111123867 | WDR6 | chr3:49008972-49008991 | SERPINA3 | chr14:94614944-94614963 |
| BCL2L11 | chr2:111123849-111123868 | WDR6 | chr3:49011963-49011982 | SERPINA3 | chr14:94614885-94614904 |
| CHIC2 | chr4:54064267-54064286 | WDR6 | chr3:49011741-49011760 | SERPINA3 | chr14:94614692-94614711 |
| CHIC2 | chr4:54049066-54049085 | WDR6 | chr3:49014895-49014914 | SEMA7A | chr15:74417586-74417605 |

TABLE 6A-continued

| Target | Coordinates | Target | Coordinates | Target | Coordinates |
|---|---|---|---|---|---|
| CHIC2 | chr4:54048982-54049001 | WDR6 | chr3:49012228-49012247 | SEMA7A | chr15:74416690-74416709 |
| CHIC2 | chr4:54064276-54064295 | WDR6 | chr3:49007462-49007481 | SEMA7A | chr15:74417405-74417424 |
| CHIC2 | chr4:54014101-54014120 | WDR6 | chr3:49012620-49012639 | SEMA7A | chr15:74416640-74416659 |
| CHIC2 | chr4:54013870-54013889 | WDR6 | chr3:49012948-49012967 | SEMA7A | chr15:74415947-74415966 |
| CHIC2 | chr4:54049029-54049048 | RBM39 | chr20:35729298-35729317 | SEMA7A | chr15:74411646-74411665 |
| CHIC2 | chr4:54049258-54049277 | RBM39 | chr20:35738973-35738992 | SEMA7A | chr15:74417429-74417448 |
| CHIC2 | chr4:54064203-54064222 | RBM39 | chr20:35725067-35725086 | SEMA7A | chr15:74414850-74414869 |
| CHIC2 | chr4:54064222-54064241 | RBM39 | chr20:35714187-35714206 | SEMA7A | chr15:74417393-74417412 |
| CHIC2 | chr4:54014065-54014084 | RBM39 | chr20:35716784-35716803 | DHODH | chr16:72014466-72014485 |
| CHIC2 | chr4:54064183-54064202 | RBM39 | chr20:35739528-35739547 | DHODH | chr16:72008782-72008801 |
| FLI1 | chr11:128772938-128772957 | RBM39 | chr20:35734223-35734242 | DHODH | chr16:72012120-72012139 |
| FLI1 | chr11:128810556-128810575 | RBM39 | chr20:35735042-35735061 | DHODH | chr16:72012061-72012080 |
| FLI1 | chr11:128768268-128768287 | RBM39 | chr20:35724711-35724730 | DHODH | chr16:72022430-72022449 |
| FLI1 | chr11:128772807-128772826 | RBM39 | chr20:35729482-35729501 | DHODH | chr16:72014503-72014522 |
| FLI1 | chr11:128807189-128807208 | RBM39 | chr20:35731997-35732016 | DHODH | chr16:72014529-72014548 |
| FLI1 | chr11:128768230-128768249 | RBM39 | chr20:35731969-35731988 | DHODH | chr16:72012094-72012113 |
| FLI1 | chr11:128807207-128807226 | RBM39 | chr20:35740826-35740845 | DHODH | chr16:72012147-72012166 |
| FLI1 | chr11:128810519-128810538 | RBM39 | chr20:35716771-35716790 | DHODH | chr16:72017036-72017055 |
| FLI1 | chr11:128810490-128810509 | RBM39 | chr20:35707976-35707995 | DHODH | chr16:72008781-72008800 |
| FLI1 | chr11:128810665-128810684 | RBM39 | chr20:35734220-35734239 | DHODH | chr16:72012216-72012235 |
| FLI1 | chr11:128772978-128772997 | RBM39 | chr20:35707942-35707961 | DHODH | chr16:72014491-72014510 |
| FLI1 | chr11:128772894-128772913 | RBM39 | chr20:35729478-35729497 | DHODH | chr16:72008781-72008800 |
| PCBP1 | chr2:70087872-70087891 | RBM39 | chr20:35740555-35740574 | DHODH | chr16:72014548-72014567 |
| PCBP1 | chr2:70087909-70087928 | RBM39 | chr20:35736543-35736562 | UMPS | chr3:124738139-124738158 |
| PCBP1 | chr2:70087790-70087809 | RBM39 | chr20:35739531-35739550 | UMPS | chr3:124730574-124730593 |
| PCBP1 | chr2:70087821-70087840 | RBM39 | chr20:35732003-35732022 | UMPS | chr3:124737663-124737682 |
| PCBP1 | chr2:70087998-70088017 | RBM39 | chr20:35714241-35714260 | UMPS | chr3:124737918-124737937 |
| PCBP1 | chr2:70088588-70088607 | RBM39 | chr20:35736551-35736570 | UMPS | chr3:124735177-124735196 |
| PCBP1 | chr2:70088106-70088125 | E2F8 | chr11:19234923-19234942 | GNAS | chr20:58895661-58895680 |
| PCBP1 | chr2:70087940-70087959 | E2F8 | chr11:19234390-19234409 | GNAS | chr20:58903685-58903704 |
| PCBP1 | chr2:70088307-70088326 | E2F8 | chr11:19237345-19237364 | GNAS | chr20:58905460-58905479 |
| PCBP1 | chr2:70088200-70088219 | E2F8 | chr11:19235005-19235024 | GNAS | chr20:58840352-58840371 |
| PCBP1 | chr2:70088063-70088082 | E2F8 | chr11:19225425-19225444 | GNAS | chr20:58840096-58840115 |
| PCBP1 | chr2:70087845-70087864 | E2F8 | chr11:19237329-19237348 | GNAS | chr20:58840253-58840272 |
| | | E2F8 | chr11:19234967-19234986 | GNAS | chr20:58891819-58891838 |
| | | E2F8 | chr11:19234422-19234441 | GNAS | chr20:58891756-58891775 |
| | | E2F8 | chr11:19237906-19237925 | GNAS | chr20:58891768-58891787 |
| | | E2F8 | chr11:19237980-19237999 | GNAS | chr20:58840195-58840214 |

TABLE 6A-continued

| Human Genome Coordinates | | | | | |
|---|---|---|---|---|---|
| Target | Coordinates | Target | Coordinates | Target | Coordinates |
| | | E2F8 | chr11:19232290-19232309 | GNAS | chr20:58891728-58891747 |
| | | E2F8 | chr11:19229509-19229528 | GNAS | chr20:58840198-58840217 |

TABLE 6B

| Murine Genome Coordinates | | | | | |
|---|---|---|---|---|---|
| Target | Coordinates | Target | Coordinates | Target | Coordinates |
| Bcl2l11 | chr2:128128713-128128732 | Fli1 | chr9:32461444-32461463 | Wdr6 | chr9:108578530-108578549 |
| Bcl2l11 | chr2:128147115-128147134 | Fli1 | chr9:32461386-32461405 | Wdr6 | chr9:108576565-108576584 |
| Bcl2l11 | chr2:128128731-128128750 | Fli1 | chr9:32461401-32461420 | Wdr6 | chr9:108578514-108578533 |
| Bcl2l11 | chr2:128147173-128147192 | Fli1 | chr9:32465687-32465706 | Wdr6 | chr9:108578497-108578516 |
| Bcl2l11 | chr2:128128648-128128667 | Fli1 | chr9:32461420-32461439 | Wdr6 | chr9:108576511-108576530 |
| Bcl2l11 | chr2:128128660-128128679 | Fli1 | chr9:32424186-32424205 | Dhodh | chr8:109596082-109596101 |
| Bcl2l11 | chr2:128147091-128147110 | Fli1 | chr9:32461239-32461258 | Dhodh | chr8:109601459-109601478 |
| Bcl2l11 | chr2:128128682-128128701 | Fli1 | chr9:32424232-32424251 | Dhodh | chr8:109603453-109603472 |
| Bcl2l11 | chr2:128128640-128128659 | Pcbp1 | chr6:86525508-86525527 | Dhodh | chr8:109603306-109603325 |
| Bcl2l11 | chr2:128147141-128147160 | Pcbp1 | chr6:86524927-86524946 | Dhodh | chr8:109603364-109603383 |
| Bcl2l11 | chr2:128158269-128158288 | Pcbp1 | chr6:86525842-86525861 | Dhodh | chr8:109603351-109603370 |
| Bcl2l11 | chr2:128158233-128158252 | Pcbp1 | chr6:86525525-86525544 | Dhodh | chr8:109596173-109596192 |
| Bcl2l11 | chr2:128147129-128147148 | Pcbp1 | chr6:86525608-86525627 | Dhodh | chr8:109601503-109601522 |
| Bcl2l11 | chr2:128128753-128128772 | Pcbp1 | chr6:86525731-86525750 | Gnas | chr2:174334196-174334215 |
| Bcl2l11 | chr2:128158301-128158320 | Pcbp1 | chr6:86525676-86525695 | Gnas | chr2:174345476-174345495 |
| Bcl2l11 | chr2:128147086-128147105 | Pcbp1 | chr6:86525148-86525167 | Gnas | chr2:174346023-174346042 |
| Bcl2l11 | chr2:128128730-128128749 | Pbrm1 | 14:31040494-31040513 | Gnas | chr2:174341872-174341891 |
| Bcl2l11 | chr2:128128992-128129011 | Pbrm1 | 14:31038941-31038960 | Gnas | chr2:174345749-174345768 |
| Chic2 | chr5:75027179-75027198 | Pbrm1 | 14:31061547-31061566 | Gnas | chr2:174345419-174345438 |
| Chic2 | chr5:75044295-75044314 | Pbrm1 | 14:31036055-31036074 | Gnas | chr2:174334251-174334270 |
| Chic2 | chr5:75044192-75044211 | Pbrm1 | 14:31067548-31067567 | Gnas | chr2:174345768-174345787 |
| Chic2 | chr5:75011480-75011499 | Pbrm1 | 14:31027510-31027529 | | |
| Chic2 | chr5:75044214-75044233 | Pbrm1 | 14:31067943-31067962 | | |
| Chic2 | chr5:75011437-75011456 | Pbrm1 | 14:31030854-31030873 | | |
| Chic2 | chr5:75027108-75027127 | | | | |
| Chic2 | chr5:75044244-75044263 | | | | |

TABLE 6C

Human Genome Coordinates

| Target | Coordinates | Target | Coordinates |
|---|---|---|---|
| SOCS1 | chr16:11255187-11255206 | SOCS1 | chr16:11254923-11254942 |
| SOCS1 | chr16:11255238-11255257 | SOCS1 | chr16:11255431-11255450 |
| SOCS1 | chr16:11255058-11255077 | SOCS1 | chr16:11255343-11255362 |
| SOCS1 | chr16:11255158-11255177 | SOCS1 | chr16:11255088-11255107 |
| SOCS1 | chr16:11255239-11255258 | SOCS1 | chr16:11254834-11254853 |
| SOCS1 | chr16:11255237-11255256 | SOCS1 | chr16:11254922-11254941 |
| SOCS1 | chr16:11255019-11255038 | SOCS1 | chr16:11255098-11255117 |
| SOCS1 | chr16:11255066-11255085 | SOCS1 | chr16:11254993-11255012 |
| SOCS1 | chr16:11255238-11255257 | SOCS1 | chr16:11254840-11254859 |
| SOCS1 | chr16:11255168-11255187 | SOCS1 | chr16:11255400-11255419 |
| SOCS1 | chr16:11255079-11255098 | SOCS1 | chr16:11254920-11254939 |
| SOCS1 | chr16:11255287-11255306 | SOCS1 | chr16:11254966-11254985 |
| SOCS1 | chr16:11255249-11255268 | SOCS1 | chr16:11254860-11254879 |
| SOCS1 | chr16:11255186-11255205 | SOCS1 | chr16:11254980-11254999 |
| SOCS1 | chr16:11255236-11255255 | SOCS1 | chr16:11254857-11254876 |
| SOCS1 | chr16:11255116-11255135 | SOCS1 | chr16:11254874-11254893 |
| SOCS1 | chr16:11255070-11255089 | SOCS1 | chr16:11255028-11255047 |
| SOCS1 | chr16:11255117-11255136 | SOCS1 | chr16:11254956-11254975 |
| SOCS1 | chr16:11255283-11255302 | SOCS1 | chr16:11254908-11254927 |
| SOCS1 | chr16:11255442-11255461 | SOCS1 | chr16:11255337-11255356 |
| SOCS1 | chr16:11255209-11255228 | SOCS1 | chr16:11254836-11254855 |
| SOCS1 | chr16:11254932-11254951 | SOCS1 | chr16:11254842-11254861 |
| SOCS1 | chr16:11254966-11254985 | SOCS1 | chr16:11254865-11254884 |
| SOCS1 | chr16:11254950-11254969 | SOCS1 | chr16:11254830-11254849 |
| SOCS1 | chr16:11255049-11255068 | SOCS1 | chr16:11255401-11255420 |
| SOCS1 | chr16:11255155-11255174 | SOCS1 | chr16:11254864-11254883 |
| SOCS1 | chr16:11255460-11255479 | SOCS1 | chr16:11255311-11255330 |
| SOCS1 | chr16:11255037-11255056 | SOCS1 | chr16:11255343-11255362 |
| SOCS1 | chr16:11255154-11255173 | SOCS1 | chr16:11255342-11255361 |
| SOCS1 | chr16:11255115-11255134 | SOCS1 | chr16:11255272-11255291 |
| SOCS1 | chr16:11254985-11255004 | SOCS1 | chr16:11254866-11254885 |
| SOCS1 | chr16:11255013-11255032 | SOCS1 | chr16:11255310-11255329 |
| SOCS1 | chr16:11255016-11255035 | SOCS1 | chr16:11255336-11255355 |
| SOCS1 | chr16:11255139-11255158 | SOCS1 | chr16:11255416-11255435 |
| SOCS1 | chr16:11255248-11255267 | SOCS1 | chr16:11255402-11255421 |
| SOCS1 | chr16:11255217-11255236 | SOCS1 | chr16:11255467-11255486 |
| SOCS1 | chr16:11254994-11255013 | SOCS1 | chr16:11254873-11254892 |
| SOCS1 | chr16:11254965-11254984 | SOCS1 | chr16:11255265-11255284 |
| SOCS1 | chr16:11255219-11255238 | SOCS1 | chr16:11254820-11254839 |
| SOCS1 | chr16:11255173-11255192 | SOCS1 | chr16:11254848-11254867 |
| SOCS1 | chr16:11255210-11255229 | SOCS1 | chr16:11255317-11255336 |
| SOCS1 | chr16:11255062-11255081 | SOCS1 | chr16:11255351-11255370 |
| SOCS1 | chr16:11255259-11255278 | SOCS1 | chr16:11254811-11254830 |
| SOCS1 | chr16:11255230-11255249 | SOCS1 | chr16:11255353-11255372 |
| SOCS1 | chr16:11255084-11255103 | SOCS1 | chr16:11255350-11255369 |
| SOCS1 | chr16:11255175-11255194 | SOCS1 | chr16:11255309-11255328 |
| SOCS1 | chr16:11255419-11255438 | SOCS1 | chr16:11255390-11255409 |
| SOCS1 | chr16:11254903-11254922 | SOCS1 | chr16:11255478-11255497 |
| SOCS1 | chr16:11255089-11255108 | SOCS1 | chr16:11255330-11255349 |
| SOCS1 | chr16:11255379-11255398 | SOCS1 | chr16:11254875-11254894 |
| SOCS1 | chr16:11255206-11255225 | SOCS1 | chr16:11255124-11255143 |
| SOCS1 | chr16:11255090-11255109 | SOCS1 | chr16:11255352-11255371 |
| SOCS1 | chr16:11255208-11255227 | SOCS1 | chr16:11254872-11254891 |
| SOCS1 | chr16:11254956-11254975 | SOCS1 | chr16:11255331-11255350 |
| SOCS1 | chr16:11255118-11255137 | SOCS1 | chr16:11255315-11255334 |
| SOCS1 | chr16:11254906-11254925 | SOCS1 | chr16:11255482-11255501 |
| SOCS1 | chr16:11255167-11255186 | SOCS1 | chr16:11254995-11255014 |
| SOCS1 | chr16:11254835-11254854 | SOCS1 | chr16:11255316-11255335 |
| SOCS1 | chr16:11255292-11255311 | SOCS1 | chr16:11255308-11255327 |
| SOCS1 | chr16:11255416-11255435 | SOCS1 | chr16:11255321-11255340 |
| SOCS1 | chr16:11255136-11255155 | SOCS1 | chr16:11255322-11255341 |
| SOCS1 | chr16:11254964-11254983 | SOCS1 | chr16:11255330-11255349 |
| SOCS1 | chr16:11254896-11254915 | SOCS1 | chr16:11255368-11255387 |
| SOCS1 | chr16:11254940-11254959 | | |

TABLE 6C-continued

Human Genome Coordinates

| Target | Coordinates | Target | Coordinates |
|---|---|---|---|
| SOCS1 | chr16:11255349-11255368 | SOCS1 | chr16:11255377-11255396 |
| SOCS1 | chr16:11254992-11255011 | SOCS1 | chr16:11255380-11255399 |

TABLE 6D

Murine Genome Coordinates

| Target | Coordinate |
|---|---|
| Socs1 | chr16:10784479-10784498 |
| Socs1 | chr16:10784409-10784428 |
| Socs1 | chr16:10784456-10784475 |
| Socs1 | chr16:10784322-10784341 |
| Socs1 | chr16:10784548-10784567 |
| Socs1 | chr16:10784596-10784615 |
| Socs1 | chr16:10784264-10784283 |
| Socs1 | chr16:10784628-10784647 |
| Socs1 | chr16:10784526-10784545 |
| Socs1 | chr16:10784508-10784527 |
| Socs1 | chr16:10784565-10784584 |
| Socs1 | chr16:10784474-10784493 |
| Socs1 | chr16:10784293-10784312 |

TABLE 6E

Human Genome Coordinates

| Target | Coordinate |
|---|---|
| ANKRD11 | chr16:89288541-89288560 |
| ANKRD11 | chr16:89290691-89290710 |
| ANKRD11 | chr16:89288526-89288545 |
| ANKRD11 | chr16:89313561-89313580 |
| ANKRD11 | chr16:89288584-89288603 |
| ANKRD11 | chr16:89288496-89288515 |
| ANKRD11 | chr16:89288665-89288684 |
| ANKRD11 | chr16:89317012-89317031 |
| ANKRD11 | chr16:89291739-89291758 |
| ANKRD11 | chr16:89284853-89284872 |
| ANKRD11 | chr16:89288497-89288516 |
| ANKRD11 | chr16:89288541-89288560 |
| ANKRD11 | chr16:89291754-89291773 |
| ANKRD11 | chr16:89305261-89305280 |
| ANKRD11 | chr16:89286074-89286093 |

TABLE 6F

Murine Genome Coordinates

| Target | Coordinate |
|---|---|
| Ankrd11 | chr8:122896622-122896641 |
| Ankrd11 | chr8:122899602-122899621 |
| Ankrd11 | chr8:122898650-122898669 |
| Ankrd11 | chr8:122896595-122896614 |
| Ankrd11 | chr8:122902337-122902356 |
| Ankrd11 | chr8:122896609-122896628 |
| Ankrd11 | chr8:122899616-122899635 |
| Ankrd11 | chr8:122900153-122900172 |

The invention claimed is:

1. A method of treating cancer in a subject in need thereof, the method comprising: administering to the subject a composition comprising a therapeutically effective amount of modified human tumor infiltrating lymphocytes (TILs) that have been modified in vitro to comprise an insertion, deletion, or mutation in an endogenous SOCS1 gene, wherein endogenous SOCS1 gene expression is reduced in the modified human TILs, relative to unmodified human TILs obtained from the subject, and the modified human TILs are autologous to the subject.

2. The method of claim 1, wherein the modified human TILs further comprise an exogenous transgene expressing an immune activating molecule, and the immune activating molecule is selected from the group consisting of a cytokine, a chemokine, a co-stimulatory molecule, an activating peptide, and an antibody or an antigen-binding fragment thereof.

3. The method of claim 1, wherein the cancer is selected from a leukemia, a lymphoma, and a solid tumor.

4. The method of claim 1, wherein the cancer is a melanoma.

5. The method of claim 1, wherein the cancer is a head and neck cancer.

6. The method of claim 1, wherein the cancer is a lung cancer.

7. The method of claim 1, wherein the modified human TILs further comprise an insertion, deletion, or mutation in an endogenous gene selected from ANKRD11, BCL2L11, BCOR, CALM2, CBLB, CHIC2, CTLA4, DHODH, E2F8, FL11, FOXP3, GATA3, GNAS, IKZF1, HAVCR2, IKZF2, IKZF3, LAG3, NFKBIA BCL3, NRP1, PBRM1, PCBP1, PDCD1, PPP2R2D, PTPN6, RBM39, RC3H1, SEMA7A, SERPINA3, SMAD2, TANK, TGFBR1, TGFBR2, TIGIT, TNFAIP3, TNIP1, TRAF6, UMPS, and WDR6.

* * * * *

SEQUENCE LISTING

```
Sequence total quantity: 1270
SEQ ID NO: 1       moltype = AA  length = 22
FEATURE            Location/Qualifiers
REGION             1..22
```

```
                        note = P2A linker sequence
source                  1..22
                        mol_type = protein
                        organism = synthetic construct
SEQUENCE: 1
GSGATNFSLL KQAGDVEENP GP                                                    22

SEQ ID NO: 2            moltype = AA  length = 8
FEATURE                 Location/Qualifiers
source                  1..8
                        mol_type = protein
                        organism = Homo sapiens
SEQUENCE: 2
SLLMWITQ                                                                     8

SEQ ID NO: 3            moltype = AA  length = 9
FEATURE                 Location/Qualifiers
source                  1..9
                        mol_type = protein
                        organism = Homo sapiens
SEQUENCE: 3
AAGIGILTV                                                                    9

SEQ ID NO: 4            moltype = AA  length = 310
FEATURE                 Location/Qualifiers
source                  1..310
                        mol_type = protein
                        organism = Homo sapiens
SEQUENCE: 4
MSNQVLCCVV LCFLGANTVD GGITQSPKYL FRKEGQNVTL SCEQNLNHDA MYWYRQDPGQ            60
GLRLIYYSQI VNDFQKGDIA EGYSVSREKK ESFPLTVTSA QKNPTAFYLC ASSPGALYEQ           120
YFGPGTRLTV TEDLKNVFPP EVAVFEPSEA EISHTQKATL VCLATGFYPD HVELSWWVNG           180
KEVHSGVCTD PQPLKEQPAL NDSRYCLSSR LRVSATFWQN PRNHFRCQVQ FYGLSENDEW           240
TQDRAKPVTQ IVSAEAWGRA DCGFTSESYQ QGVLSATILY EILLGKATLY AVLVSALVLM           300
AMVKRKDSRG                                                                 310

SEQ ID NO: 5            moltype = AA  length = 270
FEATURE                 Location/Qualifiers
source                  1..270
                        mol_type = protein
                        organism = Homo sapiens
SEQUENCE: 5
MTSIRAVFIF LWLQLDLVNG ENVEQHPSTL SVQEGDSAVI KCTYSDSASN YFPWYKQELG            60
KRPQLIIDIR SNVGEKKDQR IAVTLNKTAK HFSLHITETQ PEDSAVYFCA ATEDYQLIWG           120
AGTKLIIKPD IQNPDPAVYQ LRDSKSSDKS VCLFTDFDSQ TNVSQSKDSD VYITDKCVLD           180
MRSMDFKSNS AVAWSNKSDF ACANAFNNSI IPEDTFFPSP ESSCDVKLVE KSFETDTNLN           240
FQNLSVIGFR ILLLKVAGFN LLMTLRLWSS                                           270

SEQ ID NO: 6            moltype = AA  length = 602
FEATURE                 Location/Qualifiers
REGION                  1..602
                        note = DLT TCR
source                  1..602
                        mol_type = protein
                        organism = synthetic construct
SEQUENCE: 6
MSNQVLCCVV LCFLGANTVD GGITQSPKYL FRKEGQNVTL SCEQNLNHDA MYWYRQDPGQ            60
GLRLIYYSQI VNDFQKGDIA EGYSVSREKK ESFPLTVTSA QKNPTAFYLC ASSPGALYEQ           120
YFGPGTRLTV TEDLKNVFPP EVAVFEPSEA EISHTQKATL VCLATGFYPD HVELSWWVNG           180
KEVHSGVCTD PQPLKEQPAL NDSRYCLSSR LRVSATFWQN PRNHFRCQVQ FYGLSENDEW           240
TQDRAKPVTQ IVSAEAWGRA DCGFTSESYQ QGVLSATILY EILLGKATLY AVLVSALVLM           300
AMVKRKDSRG GSGATNFSLL KQAGDVEENP GPMTSIRAVF IFLWLQLDLV NGENVEQHPS           360
TLSVQEGDSA VIKCTYSDSA SNYFPWYKQE LGKRPQLIIR IRSNVGEKKD QRIAVTLNKT           420
AKHFSLHITE TQPEDSAVYF CAATEDYQLI WGAGTKLIIK PDIQNPDPAV YQLRDSKSSD           480
KSVCLFTDFD SQTNVSQSKD SDVYITDKCV LDMRSMDFKS NSAVAWSNKS DFACANAFNN           540
SIIPEDTFFP SPESSCDVKL VEKSFETDTN LNFQNLSVIG FRILLLKVAG FNLLMTLRLW           600
SS                                                                         602

SEQ ID NO: 7            moltype = AA  length = 310
FEATURE                 Location/Qualifiers
source                  1..310
                        mol_type = protein
                        organism = Homo sapiens
SEQUENCE: 7
MSNQVLCCVV LCFLGANTVD GGITQSPKYL FRKEGQNVTL SCEQNLNHDA MYWYRQDPGQ            60
GLRLIYYSQI VNDFQKGDIA EGYSVSREKK ESFPLTVTSA QKNPTAFYLC ASSPGALYEQ           120
YFGPGTRLTV TEDLKNVFPP EVAVFEPSEA EISHTQKATL VCLATGFYPD HVELSWWVNG           180
KEVHSGVCTD PQPLKEQPAL NDSRYCLSSR LRVSATFWQN PRNHFRCQVQ FYGLSENDEW           240
TQDRAKPVTQ IVSAEAWGRA DCGFTSESYQ QGVLSATILY EILLGKATLY AVLVSALVLM           300
```

```
AMVKRKDSRG                                                                   310

SEQ ID NO: 8            moltype = AA   length = 270
FEATURE                 Location/Qualifiers
source                  1..270
                        mol_type = protein
                        organism = Homo sapiens
SEQUENCE: 8
MTSIRAVFIF LWLQLDLVNG ENVEQHPSTL SVQEGDSAVI KCTYSDSASN YFPWYKQELG   60
KRPQLIIDIR SNVGEKKDQR IAVTLNKTAK HFSLHITETQ PEDSAVYFCA ATEDLTLIWG  120
AGTKLIIKPD IQNPDPAVYQ LRDSKSSDKS VCLFTDFDSQ TNVSQSKDSD VYITDKCVLD  180
MRSMDFKSNS AVAWSNKSDF ACANAFNNSI IPEDTFFPSP ESSCDVKLVE KSFETDTNLN  240
FQNLSVIGFR ILLLKVAGFN LLMTLRLWSS                                   270

SEQ ID NO: 9            moltype = AA   length = 602
FEATURE                 Location/Qualifiers
REGION                  1..602
                        note = High affinity DLT TCR
source                  1..602
                        mol_type = protein
                        organism = synthetic construct
SEQUENCE: 9
MSNQVLCCVV LCFLGANTVD GGITQSPKYL FRKEGQNVTL SCEQNLNHDA MYWYRQDPGQ   60
GLRLIYYSQI VNDFQKGDIA EGYSVSREKK ESFPLTVTSA QKNPTAFYLC ASSPGALYEQ  120
YFGPGTRLTV TEDLKNVFPP EVAVFEPSEA EISHTQKATL VCLATGFYPD HVELSWWVNG  180
KEVHSGVCTD PQPLKEQPAL NDSRYCLSSR LRVSATFWQN PRNHFRCQVQ FYGLSENDEW  240
TQDRAKPVTQ IVSAEAWGRA DCGFTSESYQ QGVLSATILY EILLGKATLY AVLVSALVLM  300
AMVKRKDSRG GSGATNFSLL KQAGDVEENP GPMTSIRAVF IFLWLQLDLV NGENVEQHPS  360
TLSVQEGDSA VIKCTYSDSA SNYFPWYKQE LGKRPQLIID IRSNVGEKKD QRIAVTLNKT  420
AKHFSLHITE TQPEDSAVYF CAATEDLTLI WGAGTKLIIK PDIQNPDPAV YQLRDSKSSD  480
KSVCLFTDFD SQTNVSQSKD SDVYITDKCV LDMRSMDFKS NSAVAWSNKS DFACANAFNN  540
SIIPEDTFFP SPESSCDVKL VEKSFETDTN LNFQNLSVIG FRILLLKVAG FNLLMTLRLW  600
SS                                                                 602

SEQ ID NO: 10           moltype = AA   length = 311
FEATURE                 Location/Qualifiers
source                  1..311
                        mol_type = protein
                        organism = Homo sapiens
SEQUENCE: 10
MSIGLLCCAA LSLLWAGPVN AGVTQTPKFQ VLKTGQSMTL QCAQDMNHEY MSWYRQDPGM   60
GLRLIHYSVG AGITDQGEVP NGYNVSRSTT EDFPLRLLSA APSQTSVYFC ASSYVGNTGE  120
LFFGEGSRLT VLEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR G                                                       311

SEQ ID NO: 11           moltype = AA   length = 274
FEATURE                 Location/Qualifiers
source                  1..274
                        mol_type = protein
                        organism = Homo sapiens
SEQUENCE: 11
METLLGLLIL WLQLQWVSSK QEVTQIPAAL SVPEGENLVL NCSFTDSAIY NLQWFRQDPG   60
KGLTSLLLIQ SSQREQTSGR LNASLDKSSG RSTLYIAASQ PGDSATYLCA VRPTSGGSYI  120
PTFGRGTSLI VHPYIQNPDP AVYQLRDSKS SDKSVCLFTD FDSQTNVSQS KDSDVYITDK  180
CVLDMRSMDF KSNSAVAWSN KSDFACANAF NNSIIPEDTF FPSPESSCDV KLVEKSFETD  240
TNLNFQNLSV IGFRILLLKV AGFNLLMTLR LWSS                              274

SEQ ID NO: 12           moltype = AA   length = 607
FEATURE                 Location/Qualifiers
REGION                  1..607
                        note = IG4 TCR
source                  1..607
                        mol_type = protein
                        organism = synthetic construct
SEQUENCE: 12
MSIGLLCCAA LSLLWAGPVN AGVTQTPKFQ VLKTGQSMTL QCAQDMNHEY MSWYRQDPGM   60
GLRLIHYSVG AGITDQGEVP NGYNVSRSTT EDFPLRLLSA APSQTSVYFC ASSYVGNTGE  120
LFFGEGSRLT VLEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR GGSGATNFSL LKQAGDVEEN PGPMETLLGL LILWLQLQWV SSKQEVTQIP  360
AALSVPEGEN LVLNCSFTDS AIYNLQWFRQ DPGKGLTSLL LIQSSQREQT SGRLNASLDK  420
SSGRSTLYIA ASQPGDSATY LCAVRPTSGG SYIPTFGRGT SLIVHPYIQN PDPAVYQLRD  480
SKSSDKSVCL FTDFDSQTNV SQSKDSDVYI TDKCVLDMRS MDFKSNSAVA WSNKSDFACA  540
NAFNNSIIPE DTFFPSPESS CDVKLVEKSF ETDTNLNFQN LSVIGFRILL LKVAGFNLLM  600
TLRLWSS                                                            607
```

| | | |
|---|---|---|
| SEQ ID NO: 13 | moltype = AA length = 311 | |
| FEATURE | Location/Qualifiers | |
| REGION | 1..311 | |
| | note = 95L TCRb | |
| source | 1..311 | |
| | mol_type = protein | |
| | organism = synthetic construct | |

SEQUENCE: 13
```
MSIGLLCCAA LSLLWAGPVN AGVTQTPKFQ VLKTGQSMTL QCAQDMNHEY MSWYRQDPGM   60
GLRLIHYSVG AGITDQGEVP NGYNVSRSTT EDFPLRLLSA APSQTSVYFC ASSYVGNTGE  120
LFFGEGSRLT VLEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR G                                                      311
```

| | | |
|---|---|---|
| SEQ ID NO: 14 | moltype = AA length = 274 | |
| FEATURE | Location/Qualifiers | |
| REGION | 1..274 | |
| | note = 95L TCRa | |
| source | 1..274 | |
| | mol_type = protein | |
| | organism = synthetic construct | |

SEQUENCE: 14
```
METLLGLLIL WLQLQWVSSK QEVTQIPAAL SVPEGENLVL NCSFTDSAIY NLQWFRQDPG   60
KGLTSLLLIQ SSQREQTSGR LNASLDKSSG RSTLYIAASQ PGDSATYLCA VRPLYGGSYI  120
PTFGRGTSLI VHPYIQNPDP AVYQLRDSKS SDKSVCLFTD FDSQTNVSQS KDSDVYITDK  180
CVLDMRSMDF KSNSAVAWSN KSDFACANAF NNSIIPEDTF FPSPESSCDV KLVEKSFETD  240
TNLNFQNLSV IGFRILLLKV AGFNLLMTLR LWSS                              274
```

| | | |
|---|---|---|
| SEQ ID NO: 15 | moltype = AA length = 607 | |
| FEATURE | Location/Qualifiers | |
| REGION | 1..607 | |
| | note = 95L IG4 TCR | |
| source | 1..607 | |
| | mol_type = protein | |
| | organism = synthetic construct | |

SEQUENCE: 15
```
MSIGLLCCAA LSLLWAGPVN AGVTQTPKFQ VLKTGQSMTL QCAQDMNHEY MSWYRQDPGM   60
GLRLIHYSVG AGITDQGEVP NGYNVSRSTT EDFPLRLLSA APSQTSVYFC ASSYVGNTGE  120
LFFGEGSRLT VLEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR GGSGATNFSL LKQAGDVEEN PGPMETLLGL LILWLQLQWV SSKQEVTQIP  360
AALSVPEGEN LVLNCSFTDS AIYNLQWFRQ DPGKGLTSLL LIQSSQREQT SGRLNASLDK  420
SSGRSTLYIA ASQPGDSATY LCAVRPLYGG SYIPTFGRGT SLIVHPYIQN PDPAVYQLRD  480
SKSSDKSVCL FTDFDSQTNV SQSKDSDVYI TDKCVLDMRS MDFKSNSAVA WSNKSDFACA  540
NAFNNSIIPE DTFFPSPESS CDVKLVEKSF ETDTNLNFQN LSVIGFRILL LKVAGFNLLM  600
TLRLWSS                                                           607
```

| | | |
|---|---|---|
| SEQ ID NO: 16 | moltype = AA length = 311 | |
| FEATURE | Location/Qualifiers | |
| source | 1..311 | |
| | mol_type = protein | |
| | organism = Homo sapiens | |

SEQUENCE: 16
```
MGTRLFFYVA LCLLWTGHMD AGITQSPRHK VTETGTPVTL RCHQTENHRY MYWYRQDPGH   60
GLRLIHYSYG VKDTDKGEVS DGYSVSRSKT EDFLLTLESA TSSQTSVYFC AISEVGVGQP  120
QHFGDGTRLS ILEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR G                                                      311
```

| | | |
|---|---|---|
| SEQ ID NO: 17 | moltype = AA length = 268 | |
| FEATURE | Location/Qualifiers | |
| source | 1..268 | |
| | mol_type = protein | |
| | organism = Homo sapiens | |

SEQUENCE: 17
```
MLLEHLLIIL WMQLTWVSGQ QLNQSPQSMF IQEGEDVSMN CTSSSIFNTW LWYKQEPGEG   60
PVLLIALYKA GELTSNGRLT AQFGITRKDS FLNISASIPS DVGIYFCAGG TGNQFYFGTG  120
TSLTVIPNIQ NPDPAVYQLR DSKSSDKSVC LFTDFDSQTN VSQSKDSDVY ITDKCVLDMR  180
SMDFKSNSAV AWSNKSDFAC ANAFNNSIIP EDTFFPSPES SCDVKLVEKS FETDTNLNFQ  240
NLSVIGFRIL LLKVAGFNLL MTLRLWSS                                     268
```

| | | |
|---|---|---|
| SEQ ID NO: 18 | moltype = AA length = 601 | |
| FEATURE | Location/Qualifiers | |
| REGION | 1..601 | |
| | note = DMF4 TCR | |
| source | 1..601 | |

```
                        mol_type = protein
                        organism = synthetic construct
SEQUENCE: 18
MGTRLFFYVA LCLLWTGHMD AGITQSPRHK VTETGTPVTL RCHQTENHRY MYWYRQDPGH   60
GLRLIHYSYG VKDTDKGEVS DGYSVSRSKT EDFLLTLESA TSSQTSVYFC AISEVGVGQP  120
QHFGDGTRLS ILEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR GGSGATNFSL LKQAGDVEEN PGPMLLEHLL IILWMQLTWV SGQQLNQSPQ  360
SMFIQEGEDV SMNCTSSSIF NTWLWYKQEP GEGPVLLIAL YKAGELTSNG RLTAQFGITR  420
KDSFLNISAS IPSDVGIYFC AGGTGNQFYF GTGTSLTVIP NIQNPDPAVY QLRDSKSSDK  480
SVCLFTDFDS QTNVSQSKDS DVYITDKCVL DMRSMDFKSN SAVAWSNKSD FACANAFNNS  540
IIPEDTFFPS PESSCDVKLV EKSFETDTNL NFQNLSVIGF RILLLKVAGF NLLMTLRLWS  600
S                                                                 601

SEQ ID NO: 19           moltype = AA  length = 310
FEATURE                 Location/Qualifiers
source                  1..310
                        mol_type = protein
                        organism = Homo sapiens
SEQUENCE: 19
MRIRLLCCVA FSLLWAGPVI AGITQAPTSQ ILAAGRRMTL RCTQDMRHNA MYWYRQDLGL   60
GLRLIHYSNT AGTTGKGEVP DGYSVSRANT DDFPLTLASA VPSQTSVYFC ASSLSFGTEA  120
FFGQGTRLTV VEDLKNVFPP EVAVFEPSEA EISHTQKATL VCLATGFYPD HVELSWWVNG  180
KEVHSGVCTD PQPLKEQPAL NDSRYCLSSR LRVSATFWQN PRNHFRCQVQ FYGLSENDEW  240
TQDRAKPVTQ IVSAEAWGRA DCGFTSESYQ QGVLSATILY EILLGKATLY AVLVSALVLM  300
AMVKRKDSRG                                                        310

SEQ ID NO: 20           moltype = AA  length = 272
FEATURE                 Location/Qualifiers
source                  1..272
                        mol_type = protein
                        organism = Homo sapiens
SEQUENCE: 20
MKSLRVLLVI LWLQLSWVWS QQKEVEQNSG PLSVPEGAIA SLNCTYSDRG SQSFFWYRQY   60
SGKSPELIMF IYSNGDKEDG RFTAQLNKAS QYVSLLIRDS QPSDSATYLC AVNFGGGKLI  120
FGQGTELSVK PNIQNPDPAV YQLRDSKSSD KSVCLFTDFD SQTNVSQSKD SDVYITDKCV  180
LDMRSMDFKS NSAVAWSNKS DFACANAFNN SIIPEDTFFP SPESSCDVKL VEKSFETDTN  240
LNFQNLSVIG FRILLLKVAG FNLLMTLRLW SS                                272

SEQ ID NO: 21           moltype = AA  length = 604
FEATURE                 Location/Qualifiers
REGION                  1..604
                        note = DMF5 TCR
source                  1..604
                        mol_type = protein
                        organism = synthetic construct
SEQUENCE: 21
MRIRLLCCVA FSLLWAGPVI AGITQAPTSQ ILAAGRRMTL RCTQDMRHNA MYWYRQDLGL   60
GLRLIHYSNT AGTTGKGEVP DGYSVSRANT DDFPLTLASA VPSQTSVYFC ASSLSFGTEA  120
FFGQGTRLTV VEDLKNVFPP EVAVFEPSEA EISHTQKATL VCLATGFYPD HVELSWWVNG  180
KEVHSGVCTD PQPLKEQPAL NDSRYCLSSR LRVSATFWQN PRNHFRCQVQ FYGLSENDEW  240
TQDRAKPVTQ IVSAEAWGRA DCGFTSESYQ QGVLSATILY EILLGKATLY AVLVSALVLM  300
AMVKRKDSRG GSGATNFSLL KQAGDVEENP GPMKSLRVLL VILWLQLSWV WSQQKEVEQN  360
SGPLSVPEGA IASLNCTYSD RGSQSFFWYR QYSGKSPELI MFIYSNGDKE DGRFTAQLNK  420
ASQYVSLLIR DSQPSDSATY LCAVNFGGGK LIFGQGTELS VKPNIQNPDP AVYQLRDSKS  480
SDKSVCLFTD FDSQTNVSQS KDSDVYITDK CVLDMRSMDF KSNSAVAWSN KSDFACANAF  540
NNSIIPEDTF FPSPESSCDV KLVEKSFETD TNLNFQNLSV IGFRILLLKV AGFNLLMTLR  600
LWSS                                                              604

SEQ ID NO: 22           moltype = AA  length = 142
FEATURE                 Location/Qualifiers
source                  1..142
                        mol_type = protein
                        organism = Homo sapiens
SEQUENCE: 22
PNIQNPDPAV YQLRDSKSSD KSVCLFTDFD SQTNVSQSKD SDVYITDKTV LDMRSMDFKS   60
NSAVAWSNKS DFACANAFNN SIIPEDTFFP SPESSCDVKL VEKSFETDTN LNFQNLSVIG  120
FRILLLKVAG FNLLMTLRLW SS                                           142

SEQ ID NO: 23           moltype = AA  length = 142
FEATURE                 Location/Qualifiers
REGION                  1..142
                        note = cys modified TRAC
source                  1..142
                        mol_type = protein
                        organism = synthetic construct
SEQUENCE: 23
PNIQNPDPAV YQLRDSKSSD KSVCLFTDFD SQTNVSQSKD SDVYITDKCV LDMRSMDFKS   60
```

```
NSAVAWSNKS DFACANAFNN SIIPEDTFFP SPESSCDVKL VEKSFETDTN LNFQNLSVIG    120
FRILLLKVAG FNLLMTLRLW SS                                            142

SEQ ID NO: 24           moltype = AA  length = 178
FEATURE                 Location/Qualifiers
source                  1..178
                        mol_type = protein
                        organism = Homo sapiens
SEQUENCE: 24
DLKNVFPPEV AVFEPSEAEI SHTQKATLVC LATGFYPDHV ELSWWVNGKE VHSGVSTDPQ    60
PLKEQPALND SRYCLSSRLR VSATFWQNPR NHFRCQVQFY GLSENDEWTQ DRAKPVTQIV    120
SAEAWGRADC GFTSESYQQG VLSATILYEI LLGKATLYAV LVSALVLMAM VKRKDSRG     178

SEQ ID NO: 25           moltype = AA  length = 178
FEATURE                 Location/Qualifiers
REGION                  1..178
                        note = cys modified TRBC
source                  1..178
                        mol_type = protein
                        organism = synthetic construct
SEQUENCE: 25
DLKNVFPPEV AVFEPSEAEI SHTQKATLVC LATGFYPDHV ELSWWVNGKE VHSGVCTDPQ    60
PLKEQPALND SRYCLSSRLR VSATFWQNPR NHFRCQVQFY GLSENDEWTQ DRAKPVTQIV    120
SAEAWGRADC GFTSESYQQG VLSATILYEI LLGKATLYAV LVSALVLMAM VKRKDSRG     178

SEQ ID NO: 26           moltype = AA  length = 444
FEATURE                 Location/Qualifiers
REGION                  1..444
                        note = KSQ CAR017
source                  1..444
                        mol_type = protein
                        organism = synthetic construct
SEQUENCE: 26
MLLLVTSLLL CELPHPAFLL IPDILLTQSP VILSVSPGER VSFSCRASQS IGTNIHWYQQ    60
RTNGSPRLLI KYASESISGI PSRFSGSGSG TDFTLSINSV ESEDIADYYC QQNNNWPTTF    120
GAGTKLELKG GGGSGGGGSG GGGSQVQLKQ SGPGLVQPSQ SLSITCTVSG FSLTNYGVHW    180
VRQSPGKGLE WLGVIWSGGN TDYNTPFTSR LSINKDNSKS QVFFKMNSLQ SNDTAIYYCA    240
RALTYYDYEF AYWGQGTLVT VSATTTPAPR PPTPAPTIAS QPLSLRPEAC RPAAGGAVHT    300
RGLDFACDIY IWAPLAGTCG VLLLSLVITL YCRVKFSRSA DAPAYQQGQN QLYNELNLGR    360
REEYDVLDKR RGRDPEMGGK PRRKNPQEGL YNELQKDKMA EAYSEIGMKG ERRRGKGHDG    420
LYQGLSTATK DTYDALHMQA LPPR                                          444

SEQ ID NO: 27           moltype = DNA  length = 1328
FEATURE                 Location/Qualifiers
misc_feature            1..1328
                        note = KSQ CAR017
source                  1..1328
                        mol_type = other DNA
                        organism = synthetic construct
SEQUENCE: 27
atgctcctcc tggttactag cttgcttttg tgcgaactgc cgcatcctgc cttccttctc    60
atcccagata tacttctgac acaatcctcg gtaatacttt ccgtctcacc ggggagcga    120
gtgtcatttt catgccgggc gagtcaatcc atcgggacga atattcactg tatcagcaa    180
aggactaacg gctcaccacg ccttctcatc aagtatgcca gtgagtccat aagtggcatt    240
ccctctagat tctcaggatc aggcagtggc acggacttca cattgtcaat taatagcgta    300
gaaagtgagg acatagcaga ttattattgc caacaaaaca ataactggcc taccacattc    360
ggtgcaggca ccaagcttga gttgaagggg ggtggtggtt ctggaggcgg tgggagcggt    420
ggtggtgggt cacaagtgca gcttaagcaa agcggaccag gtctggtcca acctagccag    480
tcactgtcaa tcacatgtac ggtatccggc tttagtctga caaattatgg cgtccactgg    540
gtaaggcaat ccccctggaaa gggcctcgag tggttggggg tgatttggag cggaggaaac    600
accgactata atacccctt cacctccaga ctgtccataa acaaggacaa ctctaaaagt    660
caggtattct tcaaaatgaa cagtctgcaa agtaatgaca cagcgatata ttattgcgcg    720
agagccctta catactacga ttcgagttc gcttattggg gacaaggaac gttggtacgg    780
gtgtctgcca caaccactcc tgctcccagg ccaccaacac cggcgcctac catagcgtca    840
cagccgctta gtctcaggcc ggaagcgtgt cgccccgcag ccggtggggc ggtccacaca    900
cgcgggctgg atttcgcatg cgatatatac atctgggcac ccttgccgg gacctgcggt    960
gttttgctct tgtctctcgt aatcacgctg tactgtcggg ttaagttttc aagatctgcg    1020
gatgccccgg cataccaaca aggcagaat cagttgtaca acgaactgaa cttgggcaga    1080
cgcgaggagt atgatgtctt ggacaagagg cggggcgcg acccggaaat ggttggcaaa    1140
ccacggcgca agaacccaca agaggggctt tacaacgaat tgcagaaaga caagatggcc    1200
gaggcataca gcgagattgg catgaaagga gagaggagga gggaaagggg gcatgatggc    1260
ctttatcagg gcctttctac tgccaccaag gacacatacg acgcactgca catgcaggca    1320
ttgccacc                                                            1328

SEQ ID NO: 28           moltype = AA  length = 446
FEATURE                 Location/Qualifiers
REGION                  1..446
                        note = KSQ CAR1909
source                  1..446
```

```
                         mol_type = protein
                         organism = synthetic construct
SEQUENCE: 28
MLLLVTSLLL CELPHPAFLL IPDIQMTQTT SSLSASLGDR VTISCRASQD ISKYLNWYQQ    60
KPDGTVKLLI YHTSRLHSGV PSRFSGSGSG TDYSLTISNL EQEDIATYFC QQGNTLPYTF   120
GGGTKLEITG GGGSGGGGSG GGGSEVKLQE SGPGLVAPSQ SLSVTCTVSG VSLPDYGVSW   180
IRQPPRKGLE WLGVIWGSET TYYNSALKSR LTIIKDNSKS QVFLKMNSLQ TDDTAIYYCA   240
KHYYYGGSYA MDYWGQGTSV TVSSTTTPAP RPPTPAPTIA SQPLSLRPEA CRPAAGGAVH   300
TRGLDFACDI YIWAPLAGTC GVLLLSLVIT LYCLRVKFSR SADAPAYQQG QNQLYNELNL   360
GRREEYDVLD KRRGRDPEMG GKPRRKNPQE GLYNELQKDK MAEAYSEIGM KGERRRGKGH   420
DGLYQGLSTA TKDTYDALHM QALPPR                                       446

SEQ ID NO: 29            moltype = DNA  length = 1338
FEATURE                  Location/Qualifiers
misc_feature             1..1338
                         note = KSQ CAR1909
source                   1..1338
                         mol_type = other DNA
                         organism = synthetic construct
SEQUENCE: 29
atgctccttc ttgtgacgtc actcctgctt tgtgagctgc cgcacccggc ctttctgctc     60
ataccgaca  tacaaatgac acagacgaca agttcccttc ccgcctcctt gggcgaccga    120
gtgacaatca gttgccgagc ttcccaggac atatctaaat atttgaattg gtatcagcaa    180
aagccagatg gtacggttaa acttcttatc taccacacct ccaggctcca ttctggggtt    240
ccgagccgat tctctggatc tggctcaggg accgattatt ctttgactat ttccaatttg    300
gagcaggaag acatcgcaac ctatttctgc caacaaggaa atacgctacc atacaccttc    360
ggcgggggca ccaaactcga gattactggg ggtgggggga gtggaggagg gggttccggt    420
ggaggtgggt cagaagtcaa gctgcaagag agtgggcccg gttggttgc tcctagccaa     480
tccttgagtg taacatgcac cgttagcgga gtttcacttc ctgactacgg tgttagctgg    540
ataagacgc  ccccgaggaa gggtctggaa tggctggggg tcatttgggg cagtgagacg    600
acatattaca acagtgcctt gaaatccagg cttacgatca taaaagacaa tagtaaaagc    660
caagtgttcc tcaagatgaa ctctcttcag accgacgaca cagccatcta ctattgcgca    720
aaacattatt attatggagg tagttacgct atggactatt ggggccaggg gacttcagtg    780
acggtgagta gtaccacgac tccggcaccg agaccaccaa caccagcccc aacaattgca    840
tcacagccct tgagccttag acccgaggcc tgtaggcccg ccgcaggagg ggcagttcat    900
acgcgaggat tggactttgc atgtgacatc tatatctggg cgccacttgc gggaacttgc    960
ggtgtccttt tgctctcatt ggtcattacc ctctatgtt  tgagagtaaa attttcccgc   1020
tccgctgatg cgcctgcata ccagcaaggt cagaaccaac tctacatga  gcttaacctc   1080
ggtagaagag aggaaatatga cgtccttgat aagaggagga gccgagaccc agaaatgggg   1140
ggaaagccgc gccgcaagaa tccacaagaa ggtctttaca atgaactgca gaaggacaaa   1200
atggccgaag cgtatagcga gataggaatg aaagccgaac ggagacgggg caaggggcat   1260
gacgggcttt accaaggact tagcacacg  acgaaggata catacgacgc actgcatatg   1320
caagcgctgc caccgcgc                                                 1338

SEQ ID NO: 30            moltype = AA  length = 496
FEATURE                  Location/Qualifiers
REGION                   1..496
                         note = KSQ CAR010
source                   1..496
                         mol_type = protein
                         organism = synthetic construct
SEQUENCE: 30
MDFQVQIFSF LLISASVIMS RGATGGATTT TCAGGTGCAG ATTTTCAGCT TCCTGCTAAT    60
CAGTGCCTCA DIQMTQSPSS LSASVGDRVT ITCRASQDVN TAVAWYQQKP GKAPKLLIYS   120
ASFLYSGVPS RFSGSRSGTD FTLTISSLQP EDFATYYCQQ HYTTPPTFGQ GTKVEIKRTG   180
STSGSGKPGS GEGSEVQLVE SGGGLVQPGG SLRLSCAASG FNIKDTYIHW VRQAPGKGLE   240
WVARIYPTNG YTRYADSVKG RFTISADTSK NTAYLQMNSL RAEDTAVYYC SRWGGDGFYA   300
MDVWGQGTLV TVSSTTTPAP RPPTPAPTIA SQPLSLRPEA CRPAAGGAVH TRGLDFACDI   360
YIWAPLAGTC GVLLLSLVIT LYCLRVKFSR SADAPAYQQG QNQLYNELNL GRREEYDVLD   420
KRRGRDPEMG GKPRRKNPQE GLYNELQKDK MAEAYSEIGM KGERRRGKGH DGLYQGLSTA   480
TKDTYDALHM QALPPR                                                   496

SEQ ID NO: 31            moltype = DNA  length = 1488
FEATURE                  Location/Qualifiers
misc_feature             1..1488
                         note = KSQ CAR010
source                   1..1488
                         mol_type = other DNA
                         organism = synthetic construct
SEQUENCE: 31
atggactttc aggtgcagat cttctcattc ctcctatca gtgcgagtgt aattatgtca      60
agaggtgcta caggcggtgc taccacgacg acatgcgcag gggtaccgg ttgtgcagga    120
gcgaccacga ctacctgcgc aggttgtacc acctgttgta ctggatgtac tgctgcgaca    180
tgtgcgggga cggttggttg cacttgtgcg gacatacaa tgaccaaag cccgtccagc    240
ctgtctgcat cagttgggga tagagtgacg attacatgta gagcaagcca ggatgttaac    300
accgccgtag cgtggtacca acaaaaacca ggtaaagccc cgaagctgct catatactcc    360
gccagctttc tgtattcagg cgttcccagt cggttcagcg gcagcagatc agggacggat    420
tttacgctca ctatctcttc ccttcagcct gaagattttg ctacctatta ttgtcagcag    480
cattacacga ctccccccaa cttttggtcag gggactaaag ttgaaatcaa acgaacgggc    540
```

```
tccacctcag gtagcggtaa gccaggcagc ggagaagggt ctgaagtcca gttggttgag    600
agtggaggcg gtcttgtgca acccggtggc agcttgcgac tgagctgtgc agcgtctggc    660
ttcaacataa aagatactta tattcattgg gtaagacagg ctcctggtaa agggctggaa    720
tgggtggcac gaatatatcc gactaacggt tataccagat acgccgattc tgttaagggc    780
aggttcacaa taagcgccga cacaagtaag aatacggcgt atctgcagat gaattcactt    840
cgagctgaag acacagcggt atactactgc tccaggtggg gtggggatgg tttttatgcg    900
atggacgttt ggggtcaagg aacactggta actgttagtt ctaccacgac acctgctcct    960
aggcccccca caccggcacc tacgatcgct tcccagccgc ttagcctccg cccggaggca   1020
tgccgcccg ctgcggggggg agcggtacat actcgcgggt tggacttcgc ttgcgacatc   1080
tacatttggg caccactggc aggcacatgt ggcgttctgt tgcttagtct ggttattaca   1140
ctgtattgcc tgcgagttaa attctcccgc agcgctgatg cgcccgccta tcagcaaggt   1200
caaaaccagc tgtataatga gcttaatttg gacgccgag aagagtatga cgtccttgac    1260
aagaggcgcg ggcgcgatcc ggagatgggt ggtaaaccgc gccggaaaaa ccccaggaa    1320
ggccttaca atgagctcca aaaagataaa atggcagagg catactctga aataggaatg   1380
aagggcgaga gacgccgggg taagggacac gatggccttt atcaagggct tagtacagcc   1440
acgaaggata cgtatgacgc tctgcacatg caggctcttc ccccgaga                1488

SEQ ID NO: 32            moltype = DNA   length = 20
FEATURE                  Location/Qualifiers
misc_feature             1..20
                         note = Primer
source                   1..20
                         mol_type = other DNA
                         organism = synthetic construct
SEQUENCE: 32
ccacctccag ttgttgcatt                                                20

SEQ ID NO: 33            moltype = DNA   length = 20
FEATURE                  Location/Qualifiers
misc_feature             1..20
                         note = Primer
source                   1..20
                         mol_type = other DNA
                         organism = synthetic construct
SEQUENCE: 33
tgctgcttca aagggaggta                                                20

SEQ ID NO: 34            moltype = DNA   length = 83
FEATURE                  Location/Qualifiers
misc_feature             1..83
                         note = tracrRNA
source                   1..83
                         mol_type = other DNA
                         organism = synthetic construct
SEQUENCE: 34
gttttagagc tagaaatagc aagttaaaat aaggctagtc cgttatcaac ttgaaaaagt    60
ggcaccgagt cggtgctttt ttt                                            83

SEQ ID NO: 35            moltype = DNA   length = 65
FEATURE                  Location/Qualifiers
misc_feature             1..65
                         note = tracrRNA
source                   1..65
                         mol_type = other DNA
                         organism = synthetic construct
SEQUENCE: 35
gggcttcatg ccgaaatcaa caccctgtca ttttatggca gggtgttttc gttatttaat    60
ttttt                                                                65

SEQ ID NO: 36            moltype = DNA   length = 39
FEATURE                  Location/Qualifiers
misc_feature             1..39
                         note = tracrRNA
source                   1..39
                         mol_type = other DNA
                         organism = synthetic construct
SEQUENCE: 36
aaatcaacac cctgtcattt tatggcaggg tgttttttt                            39

SEQ ID NO: 37            moltype = DNA   length = 170
FEATURE                  Location/Qualifiers
misc_feature             1..170
                         note = tracrRNA
source                   1..170
                         mol_type = other DNA
                         organism = synthetic construct
SEQUENCE: 37
gtattaagta ttgttttatg gctgataaat ttctttgaat ttctccttga ttatttgtta    60
taaaagttat aaaataatct tgttggaacc attcaaaaca gcatagcaag ttaaaataag   120
```

```
gctagtccgt tatcaacttg aaaaagtggc accgagtcgg tgcttttttt              170

SEQ ID NO: 38           moltype = DNA   length = 89
FEATURE                 Location/Qualifiers
misc_feature            1..89
                        note = tracrRNA
source                  1..89
                        mol_type = other DNA
                        organism = synthetic construct
SEQUENCE: 38
gttggaacca ttcaaaacag catagcaagt taaataagg ctagtccgtt atcaacttga    60
aaaagtggca ccgagtcggt gcttttttt                                    89

SEQ ID NO: 39           moltype = DNA   length = 76
FEATURE                 Location/Qualifiers
misc_feature            1..76
                        note = tracrRNA
source                  1..76
                        mol_type = other DNA
                        organism = synthetic construct
SEQUENCE: 39
aaaacagcat agcaagttaa aataaggcta gtccgttatc aacttgaaaa agtggcaccg   60
agtcggtgct tttttt                                                  76

SEQ ID NO: 40           moltype = DNA   length = 93
FEATURE                 Location/Qualifiers
misc_feature            1..93
                        note = tracrRNA
source                  1..93
                        mol_type = other DNA
                        organism = synthetic construct
SEQUENCE: 40
gtttaagagc tatgctggaa acagcatagc aagtttaaat aaggctagtc cgttatcaac   60
ttgaaaaagt ggcaccgagt cggtgctttt ttt                               93

SEQ ID NO: 41           moltype = DNA   length = 141
FEATURE                 Location/Qualifiers
misc_feature            1..141
                        note = CBLB shRNA
source                  1..141
                        mol_type = other DNA
                        organism = synthetic construct
SEQUENCE: 41
gaaggctcga aaggtatat tgctgttgac agtgagcgat cagtgagaat gagtacttta    60
tagtgaagcc acagatgtat aaagtactca ttctcactga gtgcctactg cctcggactt   120
caaggggcta gaattcgagc a                                            141

SEQ ID NO: 42           moltype = DNA   length = 141
FEATURE                 Location/Qualifiers
misc_feature            1..141
                        note = CBLB shRNA
source                  1..141
                        mol_type = other DNA
                        organism = synthetic construct
SEQUENCE: 42
gaaggctcga aaggtatat tgctgttgac agtgagcgaa ggtgaaaatg tcaaaactaa    60
tagtgaagcc acagatgtat tagttttgac attttcacct gtgcctactg cctcggactt   120
caaggggcta gaattcgagc a                                            141

SEQ ID NO: 43           moltype = DNA   length = 141
FEATURE                 Location/Qualifiers
misc_feature            1..141
                        note = CBLB shRNA
source                  1..141
                        mol_type = other DNA
                        organism = synthetic construct
SEQUENCE: 43
gaaggctcga aaggtatat tgctgttgac agtgagcgcc cagaaattca ccacagaaaa    60
tagtgaagcc acagatgtat tttctgtggt gaatttctgg ttgcctactg cctcggactt   120
caaggggcta gaattcgagc a                                            141

SEQ ID NO: 44           moltype = DNA   length = 141
FEATURE                 Location/Qualifiers
misc_feature            1..141
                        note = CBLB shRNA
source                  1..141
                        mol_type = other DNA
                        organism = synthetic construct
SEQUENCE: 44
```

-continued

```
gaaggctcga gaaggtatat tgctgttgac agtgagcgac cagaactgta gacaccaaaa    60
tagtgaagcc acagatgtat tttggtgtct acagttctgg ctgcctactg cctcggactt   120
caagggcta gaattcgagc a                                              141

SEQ ID NO: 45           moltype = DNA  length = 21
FEATURE                 Location/Qualifiers
misc_feature            1..21
                        note = CBLB shRNA
source                  1..21
                        mol_type = other DNA
                        organism = synthetic construct
SEQUENCE: 45
gtcaattcca gggagataac t                                              21

SEQ ID NO: 46           moltype = DNA  length = 21
FEATURE                 Location/Qualifiers
misc_feature            1..21
                        note = CBLB shRNA
source                  1..21
                        mol_type = other DNA
                        organism = synthetic construct
SEQUENCE: 46
gcctggaagc aatggctcta a                                              21

SEQ ID NO: 47           moltype = DNA  length = 21
FEATURE                 Location/Qualifiers
misc_feature            1..21
                        note = CBLB shRNA
source                  1..21
                        mol_type = other DNA
                        organism = synthetic construct
SEQUENCE: 47
gcaccaaacc cggaagctat a                                              21

SEQ ID NO: 48           moltype = DNA  length = 21
FEATURE                 Location/Qualifiers
misc_feature            1..21
                        note = CBLB shRNA
source                  1..21
                        mol_type = other DNA
                        organism = synthetic construct
SEQUENCE: 48
gttgcactcg attgggacag t                                              21

SEQ ID NO: 49           moltype = DNA  length = 21
FEATURE                 Location/Qualifiers
misc_feature            1..21
                        note = CBLB shRNA
source                  1..21
                        mol_type = other DNA
                        organism = synthetic construct
SEQUENCE: 49
ggattatgtg aacctacacc t                                              21

SEQ ID NO: 50           moltype = DNA  length = 21
FEATURE                 Location/Qualifiers
misc_feature            1..21
                        note = CBLB shRNA
source                  1..21
                        mol_type = other DNA
                        organism = synthetic construct
SEQUENCE: 50
ggaatcacag cgagttcaaa t                                              21

SEQ ID NO: 51           moltype = DNA  length = 21
FEATURE                 Location/Qualifiers
misc_feature            1..21
                        note = CBLB shRNA
source                  1..21
                        mol_type = other DNA
                        organism = synthetic construct
SEQUENCE: 51
gcaaggcata gtctcattga a                                              21

SEQ ID NO: 52           moltype = DNA  length = 21
FEATURE                 Location/Qualifiers
misc_feature            1..21
                        note = CBLB shRNA
source                  1..21
```

```
                            mol_type = other DNA
                            organism = synthetic construct
SEQUENCE: 52
ggtgaagaga gccttagaga t                                                21

SEQ ID NO: 53               moltype = DNA  length = 21
FEATURE                     Location/Qualifiers
misc_feature                1..21
                            note = CBLB shRNA
source                      1..21
                            mol_type = other DNA
                            organism = synthetic construct
SEQUENCE: 53
gtgaagagag ccttagagat a                                                21

SEQ ID NO: 54               moltype = RNA  length = 23
FEATURE                     Location/Qualifiers
misc_feature                1..23
                            note = CBLB siRNA
source                      1..23
                            mol_type = other RNA
                            organism = synthetic construct
SEQUENCE: 54
aggagctaag gtcttttcca atg                                              23

SEQ ID NO: 55               moltype = RNA  length = 23
FEATURE                     Location/Qualifiers
misc_feature                1..23
                            note = CBLB siRNA
source                      1..23
                            mol_type = other RNA
                            organism = synthetic construct
SEQUENCE: 55
atgtcgatgc aaaaattgca aaa                                              23

SEQ ID NO: 56               moltype = RNA  length = 23
FEATURE                     Location/Qualifiers
misc_feature                1..23
                            note = CBLB siRNA
source                      1..23
                            mol_type = other RNA
                            organism = synthetic construct
SEQUENCE: 56
gtcacatgct ggcagaaatc aaa                                              23

SEQ ID NO: 57               moltype = RNA  length = 23
FEATURE                     Location/Qualifiers
misc_feature                1..23
                            note = CBLB siRNA
source                      1..23
                            mol_type = other RNA
                            organism = synthetic construct
SEQUENCE: 57
tccaggttac atggcatttc tca                                              23

SEQ ID NO: 58               moltype = RNA  length = 23
FEATURE                     Location/Qualifiers
misc_feature                1..23
                            note = CBLB siRNA
source                      1..23
                            mol_type = other RNA
                            organism = synthetic construct
SEQUENCE: 58
ttgaactttg aacctgtgaa atg                                              23

SEQ ID NO: 59               moltype = RNA  length = 23
FEATURE                     Location/Qualifiers
misc_feature                1..23
                            note = CBLB siRNA
source                      1..23
                            mol_type = other RNA
                            organism = synthetic construct
SEQUENCE: 59
tccacatcaa cagctaaatc att                                              23

SEQ ID NO: 60               moltype = RNA  length = 23
FEATURE                     Location/Qualifiers
misc_feature                1..23
                            note = CBLB siRNA
```

```
source                     1..23
                           mol_type = other RNA
                           organism = synthetic construct
SEQUENCE: 60
atgctggcag aaatcaaagc aat                                              23

SEQ ID NO: 61              moltype = RNA   length = 23
FEATURE                    Location/Qualifiers
misc_feature               1..23
                           note = CBLB siRNA
source                     1..23
                           mol_type = other RNA
                           organism = synthetic construct
SEQUENCE: 61
tgcagagaat gacaaagatg tca                                              23

SEQ ID NO: 62              moltype = RNA   length = 23
FEATURE                    Location/Qualifiers
misc_feature               1..23
                           note = CBLB siRNA
source                     1..23
                           mol_type = other RNA
                           organism = synthetic construct
SEQUENCE: 62
ggcagaactc accagtcaca tca                                              23

SEQ ID NO: 63              moltype = RNA   length = 23
FEATURE                    Location/Qualifiers
misc_feature               1..23
                           note = CBLB siRNA
source                     1..23
                           mol_type = other RNA
                           organism = synthetic construct
SEQUENCE: 63
tcggtcctgt gataatggtc act                                              23

SEQ ID NO: 64              moltype = RNA   length = 23
FEATURE                    Location/Qualifiers
misc_feature               1..23
                           note = CBLB siRNA
source                     1..23
                           mol_type = other RNA
                           organism = synthetic construct
SEQUENCE: 64
aggagctaag gtcttttcca atg                                              23

SEQ ID NO: 65              moltype = RNA   length = 23
FEATURE                    Location/Qualifiers
misc_feature               1..23
                           note = CBLB siRNA
source                     1..23
                           mol_type = other RNA
                           organism = synthetic construct
SEQUENCE: 65
atgtcgatgc aaaaattgca aaa                                              23

SEQ ID NO: 66              moltype = RNA   length = 23
FEATURE                    Location/Qualifiers
misc_feature               1..23
                           note = CBLB siRNA
source                     1..23
                           mol_type = other RNA
                           organism = synthetic construct
SEQUENCE: 66
gtcacatgct ggcagaaatc aaa                                              23

SEQ ID NO: 67              moltype = RNA   length = 23
FEATURE                    Location/Qualifiers
misc_feature               1..23
                           note = CBLB siRNA
source                     1..23
                           mol_type = other RNA
                           organism = synthetic construct
SEQUENCE: 67
tccaggttac atggcatttc tca                                              23

SEQ ID NO: 68              moltype = RNA   length = 23
FEATURE                    Location/Qualifiers
misc_feature               1..23
```

```
                              note = CBLB siRNA
source                        1..23
                              mol_type = other RNA
                              organism = synthetic construct
SEQUENCE: 68
ttgaactttg aacctgtgaa atg                                            23

SEQ ID NO: 69                 moltype = RNA  length = 23
FEATURE                       Location/Qualifiers
misc_feature                  1..23
                              note = CBLB siRNA
source                        1..23
                              mol_type = other RNA
                              organism = synthetic construct
SEQUENCE: 69
tccacatcaa cagctaaatc att                                            23

SEQ ID NO: 70                 moltype = RNA  length = 23
FEATURE                       Location/Qualifiers
misc_feature                  1..23
                              note = CBLB siRNA
source                        1..23
                              mol_type = other RNA
                              organism = synthetic construct
SEQUENCE: 70
atgctggcag aaatcaaagc aat                                            23

SEQ ID NO: 71                 moltype = RNA  length = 23
FEATURE                       Location/Qualifiers
misc_feature                  1..23
                              note = CBLB siRNA
source                        1..23
                              mol_type = other RNA
                              organism = synthetic construct
SEQUENCE: 71
tgcagagaat gacaaagatg tca                                            23

SEQ ID NO: 72                 moltype = RNA  length = 23
FEATURE                       Location/Qualifiers
misc_feature                  1..23
                              note = CBLB siRNA
source                        1..23
                              mol_type = other RNA
                              organism = synthetic construct
SEQUENCE: 72
ggcagaactc accagtcaca tca                                            23

SEQ ID NO: 73                 moltype = RNA  length = 23
FEATURE                       Location/Qualifiers
misc_feature                  1..23
                              note = CBLB siRNA
source                        1..23
                              mol_type = other RNA
                              organism = synthetic construct
SEQUENCE: 73
tcggtcctgt gataatggtc act                                            23

SEQ ID NO: 74                 moltype = DNA  length = 19
FEATURE                       Location/Qualifiers
misc_feature                  1..19
                              note = TNFAIP3 shRNA
source                        1..19
                              mol_type = other DNA
                              organism = synthetic construct
SEQUENCE: 74
agacacacgc aactttaaa                                                 19

SEQ ID NO: 75                 moltype = DNA  length = 19
FEATURE                       Location/Qualifiers
misc_feature                  1..19
                              note = TNFAIP3 shRNA
source                        1..19
                              mol_type = other DNA
                              organism = synthetic construct
SEQUENCE: 75
cagacacacg caactttaa                                                 19

SEQ ID NO: 76                 moltype = DNA  length = 19
FEATURE                       Location/Qualifiers
```

```
misc_feature            1..19
                        note = TNFAIP3 shRNA
source                  1..19
                        mol_type = other DNA
                        organism = synthetic construct
SEQUENCE: 76
acacacgcaa ctttaaatt                                                    19

SEQ ID NO: 77           moltype = DNA  length = 19
FEATURE                 Location/Qualifiers
misc_feature            1..19
                        note = TNFAIP3 shRNA
source                  1..19
                        mol_type = other DNA
                        organism = synthetic construct
SEQUENCE: 77
acgaatgctt tcagttcaa                                                    19

SEQ ID NO: 78           moltype = DNA  length = 19
FEATURE                 Location/Qualifiers
misc_feature            1..19
                        note = TNFAIP3 shRNA
source                  1..19
                        mol_type = other DNA
                        organism = synthetic construct
SEQUENCE: 78
atactcggaa ctggaatga                                                    19

SEQ ID NO: 79           moltype = DNA  length = 19
FEATURE                 Location/Qualifiers
misc_feature            1..19
                        note = TNFAIP3 shRNA
source                  1..19
                        mol_type = other DNA
                        organism = synthetic construct
SEQUENCE: 79
gaagcttgtg gcgctgaaa                                                    19

SEQ ID NO: 80           moltype = DNA  length = 21
FEATURE                 Location/Qualifiers
misc_feature            1..21
                        note = TNFAIP3 shRNA
source                  1..21
                        mol_type = other DNA
                        organism = synthetic construct
SEQUENCE: 80
aaagccggct gcgtgtattt t                                                 21

SEQ ID NO: 81           moltype = DNA  length = 21
FEATURE                 Location/Qualifiers
misc_feature            1..21
                        note = TNFAIP3 shRNA
source                  1..21
                        mol_type = other DNA
                        organism = synthetic construct
SEQUENCE: 81
aaagggagct ctagtccttt t                                                 21

SEQ ID NO: 82           moltype = DNA  length = 21
FEATURE                 Location/Qualifiers
misc_feature            1..21
                        note = TNFAIP3 shRNA
source                  1..21
                        mol_type = other DNA
                        organism = synthetic construct
SEQUENCE: 82
aagggagctc tagtcctttt t                                                 21

SEQ ID NO: 83           moltype = DNA  length = 21
FEATURE                 Location/Qualifiers
misc_feature            1..21
                        note = TNFAIP3 shRNA
source                  1..21
                        mol_type = other DNA
                        organism = synthetic construct
SEQUENCE: 83
aagccctcat cgacagaaac a                                                 21

SEQ ID NO: 84           moltype = DNA  length = 21
```

```
FEATURE              Location/Qualifiers
misc_feature         1..21
                     note = TNFAIP3 shRNA
source               1..21
                     mol_type = other DNA
                     organism = synthetic construct
SEQUENCE: 84
aaacgaacgg tgacggcaat t                                              21

SEQ ID NO: 85        moltype = DNA  length = 21
FEATURE              Location/Qualifiers
misc_feature         1..21
                     note = TNFAIP3 shRNA
source               1..21
                     mol_type = other DNA
                     organism = synthetic construct
SEQUENCE: 85
aaacagacac acgcaacttt a                                              21

SEQ ID NO: 86        moltype = DNA  length = 21
FEATURE              Location/Qualifiers
misc_feature         1..21
                     note = TNFAIP3 shRNA
source               1..21
                     mol_type = other DNA
                     organism = synthetic construct
SEQUENCE: 86
aacagacaca cgcaaccttta a                                             21

SEQ ID NO: 87        moltype = DNA  length = 21
FEATURE              Location/Qualifiers
misc_feature         1..21
                     note = TNFAIP3 shRNA
source               1..21
                     mol_type = other DNA
                     organism = synthetic construct
SEQUENCE: 87
aatgtgcagc acaacggatt t                                              21

SEQ ID NO: 88        moltype = DNA  length = 21
FEATURE              Location/Qualifiers
misc_feature         1..21
                     note = TNFAIP3 shRNA
source               1..21
                     mol_type = other DNA
                     organism = synthetic construct
SEQUENCE: 88
aaaagccggc tgcgtgtatt t                                              21

SEQ ID NO: 89        moltype = DNA  length = 21
FEATURE              Location/Qualifiers
misc_feature         1..21
                     note = TNFAIP3 shRNA
source               1..21
                     mol_type = other DNA
                     organism = synthetic construct
SEQUENCE: 89
aaactcaacc agctgccttt t                                              21

SEQ ID NO: 90        moltype = DNA  length = 20
FEATURE              Location/Qualifiers
misc_feature         1..20
                     note = TNFAIP3 shRNA
source               1..20
                     mol_type = other DNA
                     organism = synthetic construct
SEQUENCE: 90
aaactcaacc agctgccttt                                                20

SEQ ID NO: 91        moltype = DNA  length = 21
FEATURE              Location/Qualifiers
misc_feature         1..21
                     note = TNFAIP3 shRNA
source               1..21
                     mol_type = other DNA
                     organism = synthetic construct
SEQUENCE: 91
aagtccttcc tcaggctttg t                                              21
```

```
SEQ ID NO: 92              moltype = DNA  length = 21
FEATURE                    Location/Qualifiers
misc_feature               1..21
                           note = TNFAIP3 shRNA
source                     1..21
                           mol_type = other DNA
                           organism = synthetic construct
SEQUENCE: 92
aaagccagaa gaaactcaac t                                                 21

SEQ ID NO: 93              moltype = DNA  length = 21
FEATURE                    Location/Qualifiers
misc_feature               1..21
                           note = TNFAIP3 shRNA
source                     1..21
                           mol_type = other DNA
                           organism = synthetic construct
SEQUENCE: 93
aatccgagct gttccacttg t                                                 21

SEQ ID NO: 94              moltype = DNA  length = 21
FEATURE                    Location/Qualifiers
misc_feature               1..21
                           note = TNFAIP3 shRNA
source                     1..21
                           mol_type = other DNA
                           organism = synthetic construct
SEQUENCE: 94
aaggctggga ccatggcaca a                                                 21

SEQ ID NO: 95              moltype = DNA  length = 21
FEATURE                    Location/Qualifiers
misc_feature               1..21
                           note = TNFAIP3 shRNA
source                     1..21
                           mol_type = other DNA
                           organism = synthetic construct
SEQUENCE: 95
aatgccgcaa agttggatga a                                                 21

SEQ ID NO: 96              moltype = RNA  length = 23
FEATURE                    Location/Qualifiers
misc_feature               1..23
                           note = TNFAIP3 siRNA
source                     1..23
                           mol_type = other RNA
                           organism = synthetic construct
SEQUENCE: 96
tcctcagttt cgggagatca tcc                                               23

SEQ ID NO: 97              moltype = RNA  length = 23
FEATURE                    Location/Qualifiers
misc_feature               1..23
                           note = TNFAIP3 siRNA
source                     1..23
                           mol_type = other RNA
                           organism = synthetic construct
SEQUENCE: 97
gagtctctca aatctcagga att                                               23

SEQ ID NO: 98              moltype = RNA  length = 23
FEATURE                    Location/Qualifiers
misc_feature               1..23
                           note = TNFAIP3 siRNA
source                     1..23
                           mol_type = other RNA
                           organism = synthetic construct
SEQUENCE: 98
agctctagtc cttttttgtgt aat                                              23

SEQ ID NO: 99              moltype = RNA  length = 23
FEATURE                    Location/Qualifiers
misc_feature               1..23
                           note = TNFAIP3 siRNA
source                     1..23
                           mol_type = other RNA
                           organism = synthetic construct
SEQUENCE: 99
cactggaaat gttcagaact tgc                                               23
```

```
SEQ ID NO: 100          moltype = RNA  length = 23
FEATURE                 Location/Qualifiers
misc_feature            1..23
                        note = TNFAIP3 siRNA
source                  1..23
                        mol_type = other RNA
                        organism = synthetic construct
SEQUENCE: 100
atgatgaatg ggacaatctt atc                                                23

SEQ ID NO: 101          moltype = RNA  length = 23
FEATURE                 Location/Qualifiers
misc_feature            1..23
                        note = TNFAIP3 siRNA
source                  1..23
                        mol_type = other RNA
                        organism = synthetic construct
SEQUENCE: 101
cacactgtgt ttcatcgagt aca                                                23

SEQ ID NO: 102          moltype = RNA  length = 23
FEATURE                 Location/Qualifiers
misc_feature            1..23
                        note = TNFAIP3 siRNA
source                  1..23
                        mol_type = other RNA
                        organism = synthetic construct
SEQUENCE: 102
gcagaaccat ccatggactg tga                                                23

SEQ ID NO: 103          moltype = RNA  length = 23
FEATURE                 Location/Qualifiers
misc_feature            1..23
                        note = TNFAIP3 siRNA
source                  1..23
                        mol_type = other RNA
                        organism = synthetic construct
SEQUENCE: 103
aaagatgtgg cctttgtga tgg                                                 23

SEQ ID NO: 104          moltype = RNA  length = 23
FEATURE                 Location/Qualifiers
misc_feature            1..23
                        note = TNFAIP3 siRNA
source                  1..23
                        mol_type = other RNA
                        organism = synthetic construct
SEQUENCE: 104
ttcagaactt gccagttttg tcc                                                23

SEQ ID NO: 105          moltype = RNA  length = 23
FEATURE                 Location/Qualifiers
misc_feature            1..23
                        note = TNFAIP3 siRNA
source                  1..23
                        mol_type = other RNA
                        organism = synthetic construct
SEQUENCE: 105
atgagactgg caatggtcac agg                                                23

SEQ ID NO: 106          moltype = DNA  length = 21
FEATURE                 Location/Qualifiers
misc_feature            1..21
                        note = PDCD1 shRNA
source                  1..21
                        mol_type = other DNA
                        organism = synthetic construct
SEQUENCE: 106
ggccaggatg gttcttagac t                                                  21

SEQ ID NO: 107          moltype = DNA  length = 21
FEATURE                 Location/Qualifiers
misc_feature            1..21
                        note = PDCD1 shRNA
source                  1..21
                        mol_type = other DNA
                        organism = synthetic construct
SEQUENCE: 107
```
ggatttccag tggcgagaga a                                                21

SEQ ID NO: 108          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 108
gcctgtgttc tctgtggact atg                                              23

SEQ ID NO: 109          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 109
ggtgctgcta gtctgggtcc tgg                                              23

SEQ ID NO: 110          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 110
gacagagaga agggcagaag tgc                                              23

SEQ ID NO: 111          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 111
cagcttctcc aacacatcgg aga                                              23

SEQ ID NO: 112          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 112
ccgtgtcaca caactgccca acg                                              23

SEQ ID NO: 113          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 113
tatgccacca ttgtctttcc tag                                              23

SEQ ID NO: 114          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 114
tgctaaactg gtaccgcatg agc                                              23

SEQ ID NO: 115          moltype = RNA   length = 23
FEATURE                 Location/Qualifiers
misc_feature            1..23
                        note = PDCD1 siRNA
source                  1..23
                        mol_type = other RNA
                        organism = synthetic construct

```
SEQUENCE: 115
gtgacagaga gaagggcaga agt                                              23

SEQ ID NO: 116          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 116
ctgaggatgg acactgctct tgg                                              23

SEQ ID NO: 117          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 117
atcggagagc ttcgtgctaa act                                              23

SEQ ID NO: 118          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 118
gcctgtgttc tctgtggact atg                                              23

SEQ ID NO: 119          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 119
ggtgctgcta gtctgggtcc tgg                                              23

SEQ ID NO: 120          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 120
gacagagaga agggcagaag tgc                                              23

SEQ ID NO: 121          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 121
cagcttctcc aacacatcgg aga                                              23

SEQ ID NO: 122          moltype = RNA   length = 23
FEATURE                 Location/Qualifiers
misc_feature            1..23
                        note = PDCD1 siRNA
source                  1..23
                        mol_type = other RNA
                        organism = synthetic construct
SEQUENCE: 122
ccgtgtcaca caactgccca acg                                              23

SEQ ID NO: 123          moltype = RNA   length = 23
FEATURE                 Location/Qualifiers
misc_feature            1..23
                        note = PDCD1 siRNA
source                  1..23
                        mol_type = other RNA
```

-continued

```
                        organism = synthetic construct
SEQUENCE: 123
tatgccacca ttgtctttcc tag                                              23

SEQ ID NO: 124          moltype = RNA  length = 23
FEATURE                 Location/Qualifiers
misc_feature            1..23
                        note = PDCD1 siRNA
source                  1..23
                        mol_type = other RNA
                        organism = synthetic construct
SEQUENCE: 124
tgctaaactg gtaccgcatg agc                                              23

SEQ ID NO: 125          moltype = RNA  length = 23
FEATURE                 Location/Qualifiers
misc_feature            1..23
                        note = PDCD1 siRNA
source                  1..23
                        mol_type = other RNA
                        organism = synthetic construct
SEQUENCE: 125
gtgacagaga gaagggcaga agt                                              23

SEQ ID NO: 126          moltype = RNA  length = 23
FEATURE                 Location/Qualifiers
misc_feature            1..23
                        note = PDCD1 siRNA
source                  1..23
                        mol_type = other RNA
                        organism = synthetic construct
SEQUENCE: 126
ctgaggatgg acactgctct tgg                                              23

SEQ ID NO: 127          moltype = RNA  length = 23
FEATURE                 Location/Qualifiers
misc_feature            1..23
                        note = PDCD1 siRNA
source                  1..23
                        mol_type = other RNA
                        organism = synthetic construct
SEQUENCE: 127
atcggagagc ttcgtgctaa act                                              23

SEQ ID NO: 128          moltype = DNA  length = 21
FEATURE                 Location/Qualifiers
misc_feature            1..21
                        note = CTLA4 shRNA
source                  1..21
                        mol_type = other DNA
                        organism = synthetic construct
SEQUENCE: 128
ggcaacggaa cccagattta t                                                21

SEQ ID NO: 129          moltype = DNA  length = 21
FEATURE                 Location/Qualifiers
misc_feature            1..21
                        note = CTLA4 shRNA
source                  1..21
                        mol_type = other DNA
                        organism = synthetic construct
SEQUENCE: 129
ggaacccaaa ttacgtgtac t                                                21

SEQ ID NO: 130          moltype = DNA  length = 21
FEATURE                 Location/Qualifiers
misc_feature            1..21
                        note = CTLA4 shRNA
source                  1..21
                        mol_type = other DNA
                        organism = synthetic construct
SEQUENCE: 130
gaacccaaat tacgtgtact a                                                21

SEQ ID NO: 131          moltype = DNA  length = 21
FEATURE                 Location/Qualifiers
misc_feature            1..21
                        note = CTLA4 shRNA
source                  1..21
```

-continued

```
                            mol_type = other DNA
                            organism = synthetic construct
SEQUENCE: 131
gggagaagac tatattgtac a                                                 21

SEQ ID NO: 132              moltype = DNA   length = 21
FEATURE                     Location/Qualifiers
misc_feature                1..21
                            note = CTLA4 shRNA
source                      1..21
                            mol_type = other DNA
                            organism = synthetic construct
SEQUENCE: 132
gacgtttata gccgaaatga t                                                 21

SEQ ID NO: 133              moltype = DNA   length = 21
FEATURE                     Location/Qualifiers
misc_feature                1..21
                            note = CTLA4 shRNA
source                      1..21
                            mol_type = other DNA
                            organism = synthetic construct
SEQUENCE: 133
gacactaata caccaggtag a                                                 21

SEQ ID NO: 134              moltype = RNA   length = 23
FEATURE                     Location/Qualifiers
misc_feature                1..23
                            note = CTLA4 siRNA
source                      1..23
                            mol_type = other RNA
                            organism = synthetic construct
SEQUENCE: 134
acctcactat ccaaggactg agg                                               23

SEQ ID NO: 135              moltype = RNA   length = 23
FEATURE                     Location/Qualifiers
misc_feature                1..23
                            note = CTLA4 siRNA
source                      1..23
                            mol_type = other RNA
                            organism = synthetic construct
SEQUENCE: 135
atgagttgac cttcctagat gat                                               23

SEQ ID NO: 136              moltype = RNA   length = 23
FEATURE                     Location/Qualifiers
misc_feature                1..23
                            note = CTLA4 siRNA
source                      1..23
                            mol_type = other RNA
                            organism = synthetic construct
SEQUENCE: 136
ggggaatgag ttgaccttcc tag                                               23

SEQ ID NO: 137              moltype = RNA   length = 23
FEATURE                     Location/Qualifiers
misc_feature                1..23
                            note = CTLA4 siRNA
source                      1..23
                            mol_type = other RNA
                            organism = synthetic construct
SEQUENCE: 137
ctctggatcc ttgcagcagt tag                                               23

SEQ ID NO: 138              moltype = RNA   length = 23
FEATURE                     Location/Qualifiers
misc_feature                1..23
                            note = CTLA4 siRNA
source                      1..23
                            mol_type = other RNA
                            organism = synthetic construct
SEQUENCE: 138
ctcctctgga tccttgcagc agt                                               23

SEQ ID NO: 139              moltype = RNA   length = 23
FEATURE                     Location/Qualifiers
misc_feature                1..23
                            note = CTLA4 siRNA
```

```
source                      1..23
                            mol_type = other RNA
                            organism = synthetic construct
SEQUENCE: 139
tttgtgtgtg agtatgcatc tcc                                              23

SEQ ID NO: 140              moltype = RNA   length = 23
FEATURE                     Location/Qualifiers
misc_feature                1..23
                            note = CTLA4 siRNA
source                      1..23
                            mol_type = other RNA
                            organism = synthetic construct
SEQUENCE: 140
cacctccagt ggaaatcaag tga                                              23

SEQ ID NO: 141              moltype = RNA   length = 23
FEATURE                     Location/Qualifiers
misc_feature                1..23
                            note = CTLA4 siRNA
source                      1..23
                            mol_type = other RNA
                            organism = synthetic construct
SEQUENCE: 141
cacgggactc tacatctgca agg                                              23

SEQ ID NO: 142              moltype = RNA   length = 23
FEATURE                     Location/Qualifiers
misc_feature                1..23
                            note = CTLA4 siRNA
source                      1..23
                            mol_type = other RNA
                            organism = synthetic construct
SEQUENCE: 142
ttctgacttc ctcctctgga tcc                                              23

SEQ ID NO: 143              moltype = RNA   length = 23
FEATURE                     Location/Qualifiers
misc_feature                1..23
                            note = CTLA4 siRNA
source                      1..23
                            mol_type = other RNA
                            organism = synthetic construct
SEQUENCE: 143
aagtctgtgc ggcaacctac atg                                              23

SEQ ID NO: 144              moltype = RNA   length = 23
FEATURE                     Location/Qualifiers
misc_feature                1..23
                            note = CTLA4 siRNA
source                      1..23
                            mol_type = other RNA
                            organism = synthetic construct
SEQUENCE: 144
acctcactat ccaaggactg agg                                              23

SEQ ID NO: 145              moltype = RNA   length = 23
FEATURE                     Location/Qualifiers
misc_feature                1..23
                            note = CTLA4 siRNA
source                      1..23
                            mol_type = other RNA
                            organism = synthetic construct
SEQUENCE: 145
atgagttgac cttcctagat gat                                              23

SEQ ID NO: 146              moltype = RNA   length = 23
FEATURE                     Location/Qualifiers
misc_feature                1..23
                            note = CTLA4 siRNA
source                      1..23
                            mol_type = other RNA
                            organism = synthetic construct
SEQUENCE: 146
ggggaatgag ttgaccttcc tag                                              23

SEQ ID NO: 147              moltype = RNA   length = 23
FEATURE                     Location/Qualifiers
misc_feature                1..23
```

```
                                note  = CTLA4 siRNA
source                          1..23
                                mol_type = other RNA
                                organism = synthetic construct
SEQUENCE: 147
ctctggatcc ttgcagcagt tag                                              23

SEQ ID NO: 148          moltype = RNA  length = 23
FEATURE                 Location/Qualifiers
misc_feature            1..23
                                note = CTLA4 siRNA
source                          1..23
                                mol_type = other RNA
                                organism = synthetic construct
SEQUENCE: 148
ctcctctgga tccttgcagc agt                                              23

SEQ ID NO: 149          moltype = RNA  length = 23
FEATURE                 Location/Qualifiers
misc_feature            1..23
                                note = CTLA4 siRNA
source                          1..23
                                mol_type = other RNA
                                organism = synthetic construct
SEQUENCE: 149
tttgtgtgtg agtatgcatc tcc                                              23

SEQ ID NO: 150          moltype = RNA  length = 23
FEATURE                 Location/Qualifiers
misc_feature            1..23
                                note = CTLA4 siRNA
source                          1..23
                                mol_type = other RNA
                                organism = synthetic construct
SEQUENCE: 150
cacctccagt ggaaatcaag tga                                              23

SEQ ID NO: 151          moltype = RNA  length = 23
FEATURE                 Location/Qualifiers
misc_feature            1..23
                                note = CTLA4 siRNA
source                          1..23
                                mol_type = other RNA
                                organism = synthetic construct
SEQUENCE: 151
cacgggactc tacatctgca agg                                              23

SEQ ID NO: 152          moltype = RNA  length = 23
FEATURE                 Location/Qualifiers
misc_feature            1..23
                                note = CTLA4 siRNA
source                          1..23
                                mol_type = other RNA
                                organism = synthetic construct
SEQUENCE: 152
ttctgacttc ctcctctgga tcc                                              23

SEQ ID NO: 153          moltype = RNA  length = 23
FEATURE                 Location/Qualifiers
misc_feature            1..23
                                note = CTLA4 siRNA
source                          1..23
                                mol_type = other RNA
                                organism = synthetic construct
SEQUENCE: 153
aagtctgtgc ggcaacctac atg                                              23

SEQ ID NO: 154          moltype = DNA  length = 20
FEATURE                 Location/Qualifiers
source                          1..20
                                mol_type = genomic DNA
                                organism = Mus musculus
SEQUENCE: 154
gccgcaggag gttgcctttc                                                  20

SEQ ID NO: 155          moltype = DNA  length = 20
FEATURE                 Location/Qualifiers
source                          1..20
                                mol_type = genomic DNA
```

```
                        organism = Mus musculus
SEQUENCE: 155
tccaagagtg atcgaggcat                                                   20

SEQ ID NO: 156          moltype = DNA  length = 20
FEATURE                 Location/Qualifiers
source                  1..20
                        mol_type = genomic DNA
                        organism = Mus musculus
SEQUENCE: 156
agtgcagctt gatgtgccgc                                                   20

SEQ ID NO: 157          moltype = DNA  length = 20
FEATURE                 Location/Qualifiers
source                  1..20
                        mol_type = genomic DNA
                        organism = Mus musculus
SEQUENCE: 157
cggtgagggc gtccctccgg                                                   20

SEQ ID NO: 158          moltype = DNA  length = 20
FEATURE                 Location/Qualifiers
source                  1..20
                        mol_type = genomic DNA
                        organism = Mus musculus
SEQUENCE: 158
ggccacctga ggacgcactc                                                   20

SEQ ID NO: 159          moltype = DNA  length = 20
FEATURE                 Location/Qualifiers
source                  1..20
                        mol_type = genomic DNA
                        organism = Mus musculus
SEQUENCE: 159
gttgcaaaga tggcatttga                                                   20

SEQ ID NO: 160          moltype = DNA  length = 20
FEATURE                 Location/Qualifiers
source                  1..20
                        mol_type = genomic DNA
                        organism = Mus musculus
SEQUENCE: 160
cctttccagt gcaaccagtg                                                   20

SEQ ID NO: 161          moltype = DNA  length = 20
FEATURE                 Location/Qualifiers
source                  1..20
                        mol_type = genomic DNA
                        organism = Mus musculus
SEQUENCE: 161
caactatgcc tgccgccgga                                                   20

SEQ ID NO: 162          moltype = DNA  length = 20
FEATURE                 Location/Qualifiers
source                  1..20
                        mol_type = genomic DNA
                        organism = Homo sapiens
SEQUENCE: 162
gttggtaaac ctcacaaatg                                                   20

SEQ ID NO: 163          moltype = DNA  length = 20
FEATURE                 Location/Qualifiers
source                  1..20
                        mol_type = genomic DNA
                        organism = Homo sapiens
SEQUENCE: 163
cgtgatccag gaagagcacc                                                   20

SEQ ID NO: 164          moltype = DNA  length = 20
FEATURE                 Location/Qualifiers
source                  1..20
                        mol_type = genomic DNA
                        organism = Homo sapiens
SEQUENCE: 164
tctggagtat cgcttacagg                                                   20

SEQ ID NO: 165          moltype = DNA  length = 20
FEATURE                 Location/Qualifiers
source                  1..20
```

-continued

```
                            mol_type = genomic DNA
                            organism = Homo sapiens
SEQUENCE: 165
ggaagccgtg gcagcccatg                                                    20

SEQ ID NO: 166              moltype = DNA   length = 20
FEATURE                     Location/Qualifiers
source                      1..20
                            mol_type = genomic DNA
                            organism = Homo sapiens
SEQUENCE: 166
gcgtgcctgt gaaatgaatg                                                    20

SEQ ID NO: 167              moltype = DNA   length = 20
FEATURE                     Location/Qualifiers
source                      1..20
                            mol_type = genomic DNA
                            organism = Homo sapiens
SEQUENCE: 167
cgcgtgcggg gcgatgtggt                                                    20

SEQ ID NO: 168              moltype = DNA   length = 20
FEATURE                     Location/Qualifiers
source                      1..20
                            mol_type = genomic DNA
                            organism = Homo sapiens
SEQUENCE: 168
tgagcccatg ccgatccccg                                                    20

SEQ ID NO: 169              moltype = DNA   length = 20
FEATURE                     Location/Qualifiers
source                      1..20
                            mol_type = genomic DNA
                            organism = Homo sapiens
SEQUENCE: 169
ctcttaccaa gaaatttctg                                                    20

SEQ ID NO: 170              moltype = DNA   length = 20
FEATURE                     Location/Qualifiers
source                      1..20
                            mol_type = genomic DNA
                            organism = Homo sapiens
SEQUENCE: 170
catatggggc tgatgacttt                                                    20

SEQ ID NO: 171              moltype = DNA   length = 20
FEATURE                     Location/Qualifiers
source                      1..20
                            mol_type = genomic DNA
                            organism = Homo sapiens
SEQUENCE: 171
ggggcctcat tcacccagaa                                                    20

SEQ ID NO: 172              moltype = DNA   length = 20
FEATURE                     Location/Qualifiers
source                      1..20
                            mol_type = genomic DNA
                            organism = Homo sapiens
SEQUENCE: 172
gcctcgggag agaaaatgaa                                                    20

SEQ ID NO: 173              moltype = DNA   length = 20
FEATURE                     Location/Qualifiers
source                      1..20
                            mol_type = genomic DNA
                            organism = Homo sapiens
SEQUENCE: 173
cgcgcagcag gtcgtaggcg                                                    20

SEQ ID NO: 174              moltype = DNA   length = 20
FEATURE                     Location/Qualifiers
source                      1..20
                            mol_type = genomic DNA
                            organism = Homo sapiens
SEQUENCE: 174
tctctgatcc tatcttgcac                                                    20

SEQ ID NO: 175              moltype = DNA   length = 20
FEATURE                     Location/Qualifiers
```

```
source                    1..20
                          mol_type = genomic DNA
                          organism = Homo sapiens
SEQUENCE: 175
ggacaggccc ttgtcccctg                                                    20

SEQ ID NO: 176            moltype = DNA   length = 20
FEATURE                   Location/Qualifiers
source                    1..20
                          mol_type = genomic DNA
                          organism = Homo sapiens
SEQUENCE: 176
ccgcgtggtc agcaccagcg                                                    20

SEQ ID NO: 177            moltype = DNA   length = 20
FEATURE                   Location/Qualifiers
source                    1..20
                          mol_type = genomic DNA
                          organism = Homo sapiens
SEQUENCE: 177
aagatttggg aattattgca                                                    20

SEQ ID NO: 178            moltype = DNA   length = 20
FEATURE                   Location/Qualifiers
source                    1..20
                          mol_type = genomic DNA
                          organism = Homo sapiens
SEQUENCE: 178
cttccagtgc aatcagtgcg                                                    20

SEQ ID NO: 179            moltype = DNA   length = 20
FEATURE                   Location/Qualifiers
source                    1..20
                          mol_type = genomic DNA
                          organism = Homo sapiens
SEQUENCE: 179
cctcacaaat gtggatattg                                                    20

SEQ ID NO: 180            moltype = DNA   length = 20
FEATURE                   Location/Qualifiers
source                    1..20
                          mol_type = genomic DNA
                          organism = Mus musculus
SEQUENCE: 180
cctcgaaagt ctcggagctc                                                    20

SEQ ID NO: 181            moltype = DNA   length = 20
FEATURE                   Location/Qualifiers
source                    1..20
                          mol_type = genomic DNA
                          organism = Mus musculus
SEQUENCE: 181
ctgcgtcaag actgctacac                                                    20

SEQ ID NO: 182            moltype = DNA   length = 20
FEATURE                   Location/Qualifiers
source                    1..20
                          mol_type = genomic DNA
                          organism = Mus musculus
SEQUENCE: 182
tgctcacagg caagatgtag                                                    20

SEQ ID NO: 183            moltype = DNA   length = 20
FEATURE                   Location/Qualifiers
source                    1..20
                          mol_type = genomic DNA
                          organism = Mus musculus
SEQUENCE: 183
ccggacagcc ctccaccttg                                                    20

SEQ ID NO: 184            moltype = DNA   length = 20
FEATURE                   Location/Qualifiers
source                    1..20
                          mol_type = genomic DNA
                          organism = Mus musculus
SEQUENCE: 184
agacctacca ttgtagttgg                                                    20

SEQ ID NO: 185            moltype = DNA   length = 20
```

```
FEATURE                 Location/Qualifiers
source                  1..20
                        mol_type = genomic DNA
                        organism = Mus musculus
SEQUENCE: 185
ccaagtgctc cacgatggcc                                                   20

SEQ ID NO: 186          moltype = DNA   length = 20
FEATURE                 Location/Qualifiers
source                  1..20
                        mol_type = genomic DNA
                        organism = Mus musculus
SEQUENCE: 186
agcctctatc cacggctacc                                                   20

SEQ ID NO: 187          moltype = DNA   length = 20
FEATURE                 Location/Qualifiers
source                  1..20
                        mol_type = genomic DNA
                        organism = Mus musculus
SEQUENCE: 187
gccccaggta agctggtagg                                                   20

SEQ ID NO: 188          moltype = DNA   length = 20
FEATURE                 Location/Qualifiers
source                  1..20
                        mol_type = genomic DNA
                        organism = Mus musculus
SEQUENCE: 188
gcaagcagcg cacctgctgc                                                   20

SEQ ID NO: 189          moltype = DNA   length = 20
FEATURE                 Location/Qualifiers
source                  1..20
                        mol_type = genomic DNA
                        organism = Mus musculus
SEQUENCE: 189
tcaagactgc tacactggcc                                                   20

SEQ ID NO: 190          moltype = DNA   length = 20
FEATURE                 Location/Qualifiers
source                  1..20
                        mol_type = genomic DNA
                        organism = Mus musculus
SEQUENCE: 190
gcaggttgtt ctggaagttg                                                   20

SEQ ID NO: 191          moltype = DNA   length = 20
FEATURE                 Location/Qualifiers
source                  1..20
                        mol_type = genomic DNA
                        organism = Mus musculus
SEQUENCE: 191
gggtgctgat gtcaacgctc                                                   20

SEQ ID NO: 192          moltype = DNA   length = 20
FEATURE                 Location/Qualifiers
source                  1..20
                        mol_type = genomic DNA
                        organism = Mus musculus
SEQUENCE: 192
ccacgatggc caggtagccg                                                   20

SEQ ID NO: 193          moltype = DNA   length = 20
FEATURE                 Location/Qualifiers
source                  1..20
                        mol_type = genomic DNA
                        organism = Mus musculus
SEQUENCE: 193
tggtcagcgg cttctcttcg                                                   20

SEQ ID NO: 194          moltype = DNA   length = 20
FEATURE                 Location/Qualifiers
source                  1..20
                        mol_type = genomic DNA
                        organism = Mus musculus
SEQUENCE: 194
aatgtggggc tgatgtcaac                                                   20
```

```
SEQ ID NO: 195          moltype = DNA   length = 20
FEATURE                 Location/Qualifiers
source                  1..20
                        mol_type = genomic DNA
                        organism = Mus musculus
SEQUENCE: 195
atttcaacaa gagcgaaacc                                                        20

SEQ ID NO: 196          moltype = DNA   length = 20
FEATURE                 Location/Qualifiers
source                  1..20
                        mol_type = genomic DNA
                        organism = Mus musculus
SEQUENCE: 196
cacctgacca atgacttcca                                                        20

SEQ ID NO: 197          moltype = DNA   length = 20
FEATURE                 Location/Qualifiers
source                  1..20
                        mol_type = genomic DNA
                        organism = Mus musculus
SEQUENCE: 197
gccctggaag cagcagctca                                                        20

SEQ ID NO: 198          moltype = DNA   length = 20
FEATURE                 Location/Qualifiers
source                  1..20
                        mol_type = genomic DNA
                        organism = Mus musculus
SEQUENCE: 198
gctcacaggc aagatgtaga                                                        20

SEQ ID NO: 199          moltype = DNA   length = 20
FEATURE                 Location/Qualifiers
source                  1..20
                        mol_type = genomic DNA
                        organism = Homo sapiens
SEQUENCE: 199
cgtccgcgcc atgttccagg                                                        20

SEQ ID NO: 200          moltype = DNA   length = 20
FEATURE                 Location/Qualifiers
source                  1..20
                        mol_type = genomic DNA
                        organism = Homo sapiens
SEQUENCE: 200
tggtttcagg agccctgtaa                                                        20

SEQ ID NO: 201          moltype = DNA   length = 20
FEATURE                 Location/Qualifiers
source                  1..20
                        mol_type = genomic DNA
                        organism = Homo sapiens
SEQUENCE: 201
acccggatac agcagcagct                                                        20

SEQ ID NO: 202          moltype = DNA   length = 20
FEATURE                 Location/Qualifiers
source                  1..20
                        mol_type = genomic DNA
                        organism = Homo sapiens
SEQUENCE: 202
ttccagggct ccgagccgcg                                                        20

SEQ ID NO: 203          moltype = DNA   length = 20
FEATURE                 Location/Qualifiers
source                  1..20
                        mol_type = genomic DNA
                        organism = Homo sapiens
SEQUENCE: 203
ctgaaggcta ccaactacaa                                                        20

SEQ ID NO: 204          moltype = DNA   length = 20
FEATURE                 Location/Qualifiers
source                  1..20
                        mol_type = genomic DNA
                        organism = Homo sapiens
SEQUENCE: 204
gggtatttcc tcgaaagtct                                                        20
```

| | | |
|---|---|---|
| SEQ ID NO: 205<br>FEATURE<br>source<br><br>SEQUENCE: 205<br>gagccgcagg aggtgccgcg | moltype = DNA   length = 20<br>Location/Qualifiers<br>1..20<br>mol_type = genomic DNA<br>organism = Homo sapiens | <br><br><br><br><br>20 |
| SEQ ID NO: 206<br>FEATURE<br>source<br><br>SEQUENCE: 206<br>ctgagtcagg actcccacgc | moltype = DNA   length = 20<br>Location/Qualifiers<br>1..20<br>mol_type = genomic DNA<br>organism = Homo sapiens | <br><br><br><br><br>20 |
| SEQ ID NO: 207<br>FEATURE<br>source<br><br>SEQUENCE: 207<br>cacttacgag tccccgtcct | moltype = DNA   length = 20<br>Location/Qualifiers<br>1..20<br>mol_type = genomic DNA<br>organism = Homo sapiens | <br><br><br><br><br>20 |
| SEQ ID NO: 208<br>FEATURE<br>source<br><br>SEQUENCE: 208<br>ctcaaattcc ttttggtttc | moltype = DNA   length = 20<br>Location/Qualifiers<br>1..20<br>mol_type = genomic DNA<br>organism = Homo sapiens | <br><br><br><br><br>20 |
| SEQ ID NO: 209<br>FEATURE<br>source<br><br>SEQUENCE: 209<br>ggttggtgat cacagccaag | moltype = DNA   length = 20<br>Location/Qualifiers<br>1..20<br>mol_type = genomic DNA<br>organism = Homo sapiens | <br><br><br><br><br>20 |
| SEQ ID NO: 210<br>FEATURE<br>source<br><br>SEQUENCE: 210<br>gcaggttgtt ctggaagttg | moltype = DNA   length = 20<br>Location/Qualifiers<br>1..20<br>mol_type = genomic DNA<br>organism = Homo sapiens | <br><br><br><br><br>20 |
| SEQ ID NO: 211<br>FEATURE<br>source<br><br>SEQUENCE: 211<br>cacaggtcat tgatatctta | moltype = DNA   length = 20<br>Location/Qualifiers<br>1..20<br>mol_type = genomic DNA<br>organism = Mus musculus | <br><br><br><br><br>20 |
| SEQ ID NO: 212<br>FEATURE<br>source<br><br>SEQUENCE: 212<br>catggtgcaa ctcctgctgc | moltype = DNA   length = 20<br>Location/Qualifiers<br>1..20<br>mol_type = genomic DNA<br>organism = Mus musculus | <br><br><br><br><br>20 |
| SEQ ID NO: 213<br>FEATURE<br>source<br><br>SEQUENCE: 213<br>gtgaacgctc agatgtattc | moltype = DNA   length = 20<br>Location/Qualifiers<br>1..20<br>mol_type = genomic DNA<br>organism = Mus musculus | <br><br><br><br><br>20 |
| SEQ ID NO: 214<br>FEATURE<br>source<br><br>SEQUENCE: 214 | moltype = DNA   length = 20<br>Location/Qualifiers<br>1..20<br>mol_type = genomic DNA<br>organism = Mus musculus | |

-continued

```
atacatctga gcgttcacgt                                          20

SEQ ID NO: 215       moltype = DNA   length = 20
FEATURE              Location/Qualifiers
source               1..20
                     mol_type = genomic DNA
                     organism = Mus musculus
SEQUENCE: 215
gtgcgcagcg gggctgacag                                          20

SEQ ID NO: 216       moltype = DNA   length = 20
FEATURE              Location/Qualifiers
source               1..20
                     mol_type = genomic DNA
                     organism = Mus musculus
SEQUENCE: 216
tcacaatgac acacctctca                                          20

SEQ ID NO: 217       moltype = DNA   length = 20
FEATURE              Location/Qualifiers
source               1..20
                     mol_type = genomic DNA
                     organism = Mus musculus
SEQUENCE: 217
tagacgtcca taacaacctg                                          20

SEQ ID NO: 218       moltype = DNA   length = 20
FEATURE              Location/Qualifiers
source               1..20
                     mol_type = genomic DNA
                     organism = Mus musculus
SEQUENCE: 218
acgatccagg gccatggggc                                          20

SEQ ID NO: 219       moltype = DNA   length = 20
FEATURE              Location/Qualifiers
source               1..20
                     mol_type = genomic DNA
                     organism = Homo sapiens
SEQUENCE: 219
gctggaccgc catggccaga                                          20

SEQ ID NO: 220       moltype = DNA   length = 20
FEATURE              Location/Qualifiers
source               1..20
                     mol_type = genomic DNA
                     organism = Homo sapiens
SEQUENCE: 220
gttcactgcc acgtgcaggg                                          20

SEQ ID NO: 221       moltype = DNA   length = 20
FEATURE              Location/Qualifiers
source               1..20
                     mol_type = genomic DNA
                     organism = Homo sapiens
SEQUENCE: 221
gctggtcaac ctcttccagc                                          20

SEQ ID NO: 222       moltype = DNA   length = 20
FEATURE              Location/Qualifiers
source               1..20
                     mol_type = genomic DNA
                     organism = Homo sapiens
SEQUENCE: 222
acaaggcccg cagcgccgcg                                          20

SEQ ID NO: 223       moltype = DNA   length = 20
FEATURE              Location/Qualifiers
source               1..20
                     mol_type = genomic DNA
                     organism = Homo sapiens
SEQUENCE: 223
caggcctctc catattgctg                                          20

SEQ ID NO: 224       moltype = DNA   length = 20
FEATURE              Location/Qualifiers
source               1..20
                     mol_type = genomic DNA
                     organism = Homo sapiens
```

```
SEQUENCE: 224
gccacccgtg cagatgagga                                               20

SEQ ID NO: 225         moltype = DNA  length = 20
FEATURE                Location/Qualifiers
source                 1..20
                       mol_type = genomic DNA
                       organism = Homo sapiens
SEQUENCE: 225
tcgacatcta caacaaccta                                               20

SEQ ID NO: 226         moltype = DNA  length = 20
FEATURE                Location/Qualifiers
source                 1..20
                       mol_type = genomic DNA
                       organism = Homo sapiens
SEQUENCE: 226
atgtggtgat cacagccagg                                               20

SEQ ID NO: 227         moltype = DNA  length = 20
FEATURE                Location/Qualifiers
source                 1..20
                       mol_type = genomic DNA
                       organism = Homo sapiens
SEQUENCE: 227
gcgcttgcgg agcggcagcg                                               20

SEQ ID NO: 228         moltype = DNA  length = 20
FEATURE                Location/Qualifiers
source                 1..20
                       mol_type = genomic DNA
                       organism = Homo sapiens
SEQUENCE: 228
acaggtcatc gacatcctga                                               20

SEQ ID NO: 229         moltype = DNA  length = 20
FEATURE                Location/Qualifiers
source                 1..20
                       mol_type = genomic DNA
                       organism = Homo sapiens
SEQUENCE: 229
gaccgagcct cacctgccgt                                               20

SEQ ID NO: 230         moltype = DNA  length = 20
FEATURE                Location/Qualifiers
source                 1..20
                       mol_type = genomic DNA
                       organism = Homo sapiens
SEQUENCE: 230
atacccatg atgtgcccca                                                20

SEQ ID NO: 231         moltype = DNA  length = 20
FEATURE                Location/Qualifiers
source                 1..20
                       mol_type = genomic DNA
                       organism = Homo sapiens
SEQUENCE: 231
gtgaacgcgc aaatgtactc                                               20

SEQ ID NO: 232         moltype = DNA  length = 20
FEATURE                Location/Qualifiers
source                 1..20
                       mol_type = genomic DNA
                       organism = Mus musculus
SEQUENCE: 232
ttttctatct catgaggttt                                               20

SEQ ID NO: 233         moltype = DNA  length = 20
FEATURE                Location/Qualifiers
source                 1..20
                       mol_type = genomic DNA
                       organism = Mus musculus
SEQUENCE: 233
aggcatccca ttgcgggcct                                               20

SEQ ID NO: 234         moltype = DNA  length = 20
FEATURE                Location/Qualifiers
source                 1..20
                       mol_type = genomic DNA
```

```
                              organism = Mus musculus
SEQUENCE: 234
tcggcccgag taagtgctat                                              20

SEQ ID NO: 235          moltype = DNA   length = 20
FEATURE                 Location/Qualifiers
source                  1..20
                        mol_type = genomic DNA
                        organism = Mus musculus
SEQUENCE: 235
gcgatcctcg tggttgctgt                                              20

SEQ ID NO: 236          moltype = DNA   length = 20
FEATURE                 Location/Qualifiers
source                  1..20
                        mol_type = genomic DNA
                        organism = Mus musculus
SEQUENCE: 236
ttctttgttg atcactttga                                              20

SEQ ID NO: 237          moltype = DNA   length = 20
FEATURE                 Location/Qualifiers
source                  1..20
                        mol_type = genomic DNA
                        organism = Mus musculus
SEQUENCE: 237
ttcttccaaa ccagcaagtg                                              20

SEQ ID NO: 238          moltype = DNA   length = 20
FEATURE                 Location/Qualifiers
source                  1..20
                        mol_type = genomic DNA
                        organism = Mus musculus
SEQUENCE: 238
gacagatgct cacttcaaca                                              20

SEQ ID NO: 239          moltype = DNA   length = 20
FEATURE                 Location/Qualifiers
source                  1..20
                        mol_type = genomic DNA
                        organism = Mus musculus
SEQUENCE: 239
tgatgttcac catccacatg                                              20

SEQ ID NO: 240          moltype = DNA   length = 20
FEATURE                 Location/Qualifiers
source                  1..20
                        mol_type = genomic DNA
                        organism = Homo sapiens
SEQUENCE: 240
catagtccag gaagaggacg                                              20

SEQ ID NO: 241          moltype = DNA   length = 20
FEATURE                 Location/Qualifiers
source                  1..20
                        mol_type = genomic DNA
                        organism = Homo sapiens
SEQUENCE: 241
gataactgga accatctccg                                              20

SEQ ID NO: 242          moltype = DNA   length = 20
FEATURE                 Location/Qualifiers
source                  1..20
                        mol_type = genomic DNA
                        organism = Homo sapiens
SEQUENCE: 242
caagcagaga agttcccttg                                              20

SEQ ID NO: 243          moltype = DNA   length = 20
FEATURE                 Location/Qualifiers
source                  1..20
                        mol_type = genomic DNA
                        organism = Homo sapiens
SEQUENCE: 243
aaagacctga tgttacctgc                                              20

SEQ ID NO: 244          moltype = DNA   length = 20
FEATURE                 Location/Qualifiers
source                  1..20
```

```
                            mol_type = genomic DNA
                            organism = Homo sapiens
SEQUENCE: 244
ttcggcgcca agatagctga                                          20

SEQ ID NO: 245              moltype = DNA   length = 20
FEATURE                     Location/Qualifiers
source                      1..20
                            mol_type = genomic DNA
                            organism = Homo sapiens
SEQUENCE: 245
gctcatacag acccgcatga                                          20

SEQ ID NO: 246              moltype = DNA   length = 20
FEATURE                     Location/Qualifiers
source                      1..20
                            mol_type = genomic DNA
                            organism = Homo sapiens
SEQUENCE: 246
agtgatcaac aaggaagggg                                          20

SEQ ID NO: 247              moltype = DNA   length = 20
FEATURE                     Location/Qualifiers
source                      1..20
                            mol_type = genomic DNA
                            organism = Homo sapiens
SEQUENCE: 247
acccgggctg agatgtcaaa                                          20

SEQ ID NO: 248              moltype = DNA   length = 20
FEATURE                     Location/Qualifiers
source                      1..20
                            mol_type = genomic DNA
                            organism = Homo sapiens
SEQUENCE: 248
tgtgattctg gcgttcttca                                          20

SEQ ID NO: 249              moltype = DNA   length = 20
FEATURE                     Location/Qualifiers
source                      1..20
                            mol_type = genomic DNA
                            organism = Homo sapiens
SEQUENCE: 249
ggtcagtgaa gccgacacca                                          20

SEQ ID NO: 250              moltype = DNA   length = 20
FEATURE                     Location/Qualifiers
source                      1..20
                            mol_type = genomic DNA
                            organism = Homo sapiens
SEQUENCE: 250
cttgcagtct tatgccgaga                                          20

SEQ ID NO: 251              moltype = DNA   length = 20
FEATURE                     Location/Qualifiers
source                      1..20
                            mol_type = genomic DNA
                            organism = Homo sapiens
SEQUENCE: 251
atgccccaca ctgattacac                                          20

SEQ ID NO: 252              moltype = DNA   length = 20
FEATURE                     Location/Qualifiers
source                      1..20
                            mol_type = genomic DNA
                            organism = Homo sapiens
SEQUENCE: 252
attccagtgt aatcagtgtg                                          20

SEQ ID NO: 253              moltype = DNA   length = 20
FEATURE                     Location/Qualifiers
source                      1..20
                            mol_type = genomic DNA
                            organism = Homo sapiens
SEQUENCE: 253
aagttccctt gaggagcaca                                          20

SEQ ID NO: 254              moltype = DNA   length = 20
FEATURE                     Location/Qualifiers
```

```
source                      1..20
                            mol_type = genomic DNA
                            organism = Homo sapiens
SEQUENCE: 254
ggacagatta gcaagcaatg                                                   20

SEQ ID NO: 255              moltype = DNA   length = 20
FEATURE                     Location/Qualifiers
source                      1..20
                            mol_type = genomic DNA
                            organism = Homo sapiens
SEQUENCE: 255
cttcccaaca ggtctcttga                                                   20

SEQ ID NO: 256              moltype = DNA   length = 20
FEATURE                     Location/Qualifiers
source                      1..20
                            mol_type = genomic DNA
                            organism = Homo sapiens
SEQUENCE: 256
agcagtctct tcacaactgg                                                   20

SEQ ID NO: 257              moltype = DNA   length = 20
FEATURE                     Location/Qualifiers
source                      1..20
                            mol_type = genomic DNA
                            organism = Homo sapiens
SEQUENCE: 257
tcacagtcat catgaactca                                                   20

SEQ ID NO: 258              moltype = DNA   length = 20
FEATURE                     Location/Qualifiers
source                      1..20
                            mol_type = genomic DNA
                            organism = Homo sapiens
SEQUENCE: 258
caactctctg atagtggtaa                                                   20

SEQ ID NO: 259              moltype = DNA   length = 20
FEATURE                     Location/Qualifiers
source                      1..20
                            mol_type = genomic DNA
                            organism = Homo sapiens
SEQUENCE: 259
aatcggcaat atataacatg                                                   20

SEQ ID NO: 260              moltype = DNA   length = 20
FEATURE                     Location/Qualifiers
source                      1..20
                            mol_type = genomic DNA
                            organism = Homo sapiens
SEQUENCE: 260
agcacttgct ctgaaatttg                                                   20

SEQ ID NO: 261              moltype = DNA   length = 20
FEATURE                     Location/Qualifiers
source                      1..20
                            mol_type = genomic DNA
                            organism = Homo sapiens
SEQUENCE: 261
ctaaatgtgt taccatacca                                                   20

SEQ ID NO: 262              moltype = DNA   length = 20
FEATURE                     Location/Qualifiers
source                      1..20
                            mol_type = genomic DNA
                            organism = Homo sapiens
SEQUENCE: 262
attattgaat ccatacctgg                                                   20

SEQ ID NO: 263              moltype = DNA   length = 20
FEATURE                     Location/Qualifiers
source                      1..20
                            mol_type = genomic DNA
                            organism = Homo sapiens
SEQUENCE: 263
agaatgggca ggaagaaaag                                                   20

SEQ ID NO: 264              moltype = DNA   length = 20
```

| | | |
|---|---|---|
| FEATURE | Location/Qualifiers | |
| source | 1..20<br>mol_type = genomic DNA<br>organism = Mus musculus | |
| SEQUENCE: 264<br>aaggtcggtt tggagaagtt | | 20 |
| SEQ ID NO: 265<br>FEATURE<br>source | moltype = DNA length = 20<br>Location/Qualifiers<br>1..20<br>mol_type = genomic DNA<br>organism = Mus musculus | |
| SEQUENCE: 265<br>attgttcttt gaacaagcag | | 20 |
| SEQ ID NO: 266<br>FEATURE<br>source | moltype = DNA length = 20<br>Location/Qualifiers<br>1..20<br>mol_type = genomic DNA<br>organism = Mus musculus | |
| SEQUENCE: 266<br>tggccttggt cctgtggagc | | 20 |
| SEQ ID NO: 267<br>FEATURE<br>source | moltype = DNA length = 20<br>Location/Qualifiers<br>1..20<br>mol_type = genomic DNA<br>organism = Mus musculus | |
| SEQUENCE: 267<br>acaacatcag ggtctggatc | | 20 |
| SEQ ID NO: 268<br>FEATURE<br>source | moltype = DNA length = 20<br>Location/Qualifiers<br>1..20<br>mol_type = genomic DNA<br>organism = Mus musculus | |
| SEQUENCE: 268<br>atttatgata tgacaacatc | | 20 |
| SEQ ID NO: 269<br>FEATURE<br>source | moltype = DNA length = 20<br>Location/Qualifiers<br>1..20<br>mol_type = genomic DNA<br>organism = Mus musculus | |
| SEQUENCE: 269<br>tttatagcag cagacaacaa | | 20 |
| SEQ ID NO: 270<br>FEATURE<br>source | moltype = DNA length = 20<br>Location/Qualifiers<br>1..20<br>mol_type = genomic DNA<br>organism = Mus musculus | |
| SEQUENCE: 270<br>gcaatgcaga cgaagcagac | | 20 |
| SEQ ID NO: 271<br>FEATURE<br>source | moltype = DNA length = 20<br>Location/Qualifiers<br>1..20<br>mol_type = genomic DNA<br>organism = Mus musculus | |
| SEQUENCE: 271<br>agtttggcga ggcaaatggc | | 20 |
| SEQ ID NO: 272<br>FEATURE<br>source | moltype = DNA length = 20<br>Location/Qualifiers<br>1..20<br>mol_type = genomic DNA<br>organism = Mus musculus | |
| SEQUENCE: 272<br>gagctggcag ctgtcattgc | | 20 |
| SEQ ID NO: 273<br>FEATURE<br>source | moltype = DNA length = 20<br>Location/Qualifiers<br>1..20<br>mol_type = genomic DNA<br>organism = Mus musculus | |
| SEQUENCE: 273<br>tctgataaat ctctgcctct | | 20 |

```
SEQ ID NO: 274           moltype = DNA   length = 20
FEATURE                  Location/Qualifiers
source                   1..20
                         mol_type = genomic DNA
                         organism = Mus musculus
SEQUENCE: 274
gaatagatac actgttactg                                                     20

SEQ ID NO: 275           moltype = DNA   length = 20
FEATURE                  Location/Qualifiers
source                   1..20
                         mol_type = genomic DNA
                         organism = Mus musculus
SEQUENCE: 275
gttacgccat gaaaatatcc                                                     20

SEQ ID NO: 276           moltype = DNA   length = 20
FEATURE                  Location/Qualifiers
source                   1..20
                         mol_type = genomic DNA
                         organism = Mus musculus
SEQUENCE: 276
gtcagctggc cttggtcctg                                                     20

SEQ ID NO: 277           moltype = DNA   length = 20
FEATURE                  Location/Qualifiers
source                   1..20
                         mol_type = genomic DNA
                         organism = Mus musculus
SEQUENCE: 277
aatgctttct tgtaacacaa                                                     20

SEQ ID NO: 278           moltype = DNA   length = 20
FEATURE                  Location/Qualifiers
source                   1..20
                         mol_type = genomic DNA
                         organism = Mus musculus
SEQUENCE: 278
gatatgacaa catcagggtc                                                     20

SEQ ID NO: 279           moltype = DNA   length = 20
FEATURE                  Location/Qualifiers
source                   1..20
                         mol_type = genomic DNA
                         organism = Homo sapiens
SEQUENCE: 279
tggcagaaac actgtaacgc                                                     20

SEQ ID NO: 280           moltype = DNA   length = 20
FEATURE                  Location/Qualifiers
source                   1..20
                         mol_type = genomic DNA
                         organism = Homo sapiens
SEQUENCE: 280
attgttctct gaacaagcaa                                                     20

SEQ ID NO: 281           moltype = DNA   length = 20
FEATURE                  Location/Qualifiers
source                   1..20
                         mol_type = genomic DNA
                         organism = Homo sapiens
SEQUENCE: 281
catacaaacg gcctatctcg                                                     20

SEQ ID NO: 282           moltype = DNA   length = 20
FEATURE                  Location/Qualifiers
source                   1..20
                         mol_type = genomic DNA
                         organism = Homo sapiens
SEQUENCE: 282
gagatgcaga cgaagcacac                                                     20

SEQ ID NO: 283           moltype = DNA   length = 20
FEATURE                  Location/Qualifiers
source                   1..20
                         mol_type = genomic DNA
                         organism = Homo sapiens
SEQUENCE: 283
attgtgttac aagaaagcat                                                     20
```

```
SEQ ID NO: 284            moltype = DNA   length = 20
FEATURE                   Location/Qualifiers
source                    1..20
                          mol_type = genomic DNA
                          organism = Homo sapiens
SEQUENCE: 284
agaacgttcg tggttccgtg                                                20

SEQ ID NO: 285            moltype = DNA   length = 20
FEATURE                   Location/Qualifiers
source                    1..20
                          mol_type = genomic DNA
                          organism = Homo sapiens
SEQUENCE: 285
gtttggagag gaaagtggcg                                                20

SEQ ID NO: 286            moltype = DNA   length = 20
FEATURE                   Location/Qualifiers
source                    1..20
                          mol_type = genomic DNA
                          organism = Homo sapiens
SEQUENCE: 286
atttatgata tgacaacgtc                                                20

SEQ ID NO: 287            moltype = DNA   length = 20
FEATURE                   Location/Qualifiers
source                    1..20
                          mol_type = genomic DNA
                          organism = Homo sapiens
SEQUENCE: 287
gttgtgtata actttgtctg                                                20

SEQ ID NO: 288            moltype = DNA   length = 20
FEATURE                   Location/Qualifiers
source                    1..20
                          mol_type = genomic DNA
                          organism = Homo sapiens
SEQUENCE: 288
gtgcaccctc ttcaaaaact                                                20

SEQ ID NO: 289            moltype = DNA   length = 20
FEATURE                   Location/Qualifiers
source                    1..20
                          mol_type = genomic DNA
                          organism = Mus musculus
SEQUENCE: 289
gaccccaagc tcacctacca                                                20

SEQ ID NO: 290            moltype = DNA   length = 20
FEATURE                   Location/Qualifiers
source                    1..20
                          mol_type = genomic DNA
                          organism = Mus musculus
SEQUENCE: 290
ttctcccaag tgtgtcatga                                                20

SEQ ID NO: 291            moltype = DNA   length = 20
FEATURE                   Location/Qualifiers
source                    1..20
                          mol_type = genomic DNA
                          organism = Mus musculus
SEQUENCE: 291
ttccagagtg aagccgtggt                                                20

SEQ ID NO: 292            moltype = DNA   length = 20
FEATURE                   Location/Qualifiers
source                    1..20
                          mol_type = genomic DNA
                          organism = Mus musculus
SEQUENCE: 292
acggccacgc agacttcatg                                                20

SEQ ID NO: 293            moltype = DNA   length = 20
FEATURE                   Location/Qualifiers
source                    1..20
                          mol_type = genomic DNA
                          organism = Mus musculus
SEQUENCE: 293
```

```
ttcatgcggc ttctcacaga                                               20

SEQ ID NO: 294          moltype = DNA   length = 20
FEATURE                 Location/Qualifiers
source                  1..20
                        mol_type = genomic DNA
                        organism = Mus musculus
SEQUENCE: 294
ggacttctgg ttgtcgcaag                                               20

SEQ ID NO: 295          moltype = DNA   length = 20
FEATURE                 Location/Qualifiers
source                  1..20
                        mol_type = genomic DNA
                        organism = Mus musculus
SEQUENCE: 295
catgagcaac tgcagcatca                                               20

SEQ ID NO: 296          moltype = DNA   length = 20
FEATURE                 Location/Qualifiers
source                  1..20
                        mol_type = genomic DNA
                        organism = Mus musculus
SEQUENCE: 296
ccagaggccc ccttaccaca                                               20

SEQ ID NO: 297          moltype = DNA   length = 20
FEATURE                 Location/Qualifiers
source                  1..20
                        mol_type = genomic DNA
                        organism = Mus musculus
SEQUENCE: 297
caacaacagg tcgggactgc                                               20

SEQ ID NO: 298          moltype = DNA   length = 20
FEATURE                 Location/Qualifiers
source                  1..20
                        mol_type = genomic DNA
                        organism = Mus musculus
SEQUENCE: 298
cagcttggcc ttgtagacct                                               20

SEQ ID NO: 299          moltype = DNA   length = 20
FEATURE                 Location/Qualifiers
source                  1..20
                        mol_type = genomic DNA
                        organism = Mus musculus
SEQUENCE: 299
catgacacac ttgggagaag                                               20

SEQ ID NO: 300          moltype = DNA   length = 20
FEATURE                 Location/Qualifiers
source                  1..20
                        mol_type = genomic DNA
                        organism = Mus musculus
SEQUENCE: 300
gttcttgtcg ttcttcctcc                                               20

SEQ ID NO: 301          moltype = DNA   length = 20
FEATURE                 Location/Qualifiers
source                  1..20
                        mol_type = genomic DNA
                        organism = Mus musculus
SEQUENCE: 301
gctggacacg ctggtgggga                                               20

SEQ ID NO: 302          moltype = DNA   length = 20
FEATURE                 Location/Qualifiers
source                  1..20
                        mol_type = genomic DNA
                        organism = Homo sapiens
SEQUENCE: 302
ccagaataaa gtcatggtag                                               20

SEQ ID NO: 303          moltype = DNA   length = 20
FEATURE                 Location/Qualifiers
source                  1..20
                        mol_type = genomic DNA
                        organism = Homo sapiens
```

```
SEQUENCE: 303
cacatgaaga aagtctcacc                                               20

SEQ ID NO: 304         moltype = DNA  length = 20
FEATURE                Location/Qualifiers
source                 1..20
                       mol_type = genomic DNA
                       organism = Homo sapiens
SEQUENCE: 304
ttgagctgga caccctggtg                                               20

SEQ ID NO: 305         moltype = DNA  length = 20
FEATURE                Location/Qualifiers
source                 1..20
                       mol_type = genomic DNA
                       organism = Homo sapiens
SEQUENCE: 305
gcttctgctg ccggttaacg                                               20

SEQ ID NO: 306         moltype = DNA  length = 20
FEATURE                Location/Qualifiers
source                 1..20
                       mol_type = genomic DNA
                       organism = Homo sapiens
SEQUENCE: 306
gaacatactc cagttcctga                                               20

SEQ ID NO: 307         moltype = DNA  length = 20
FEATURE                Location/Qualifiers
source                 1..20
                       mol_type = genomic DNA
                       organism = Homo sapiens
SEQUENCE: 307
gggcagtcct attacagctg                                               20

SEQ ID NO: 308         moltype = DNA  length = 20
FEATURE                Location/Qualifiers
source                 1..20
                       mol_type = genomic DNA
                       organism = Homo sapiens
SEQUENCE: 308
ttctccaaag tgcattatga                                               20

SEQ ID NO: 309         moltype = DNA  length = 20
FEATURE                Location/Qualifiers
source                 1..20
                       mol_type = genomic DNA
                       organism = Homo sapiens
SEQUENCE: 309
tggatgacct ggctaacagt                                               20

SEQ ID NO: 310         moltype = DNA  length = 20
FEATURE                Location/Qualifiers
source                 1..20
                       mol_type = genomic DNA
                       organism = Homo sapiens
SEQUENCE: 310
cctgggaaac cggcaagacg                                               20

SEQ ID NO: 311         moltype = DNA  length = 20
FEATURE                Location/Qualifiers
source                 1..20
                       mol_type = genomic DNA
                       organism = Homo sapiens
SEQUENCE: 311
gaagccacag gaagtctgtg                                               20

SEQ ID NO: 312         moltype = DNA  length = 20
FEATURE                Location/Qualifiers
source                 1..20
                       mol_type = genomic DNA
                       organism = Homo sapiens
SEQUENCE: 312
acagatatgg caactcccag                                               20

SEQ ID NO: 313         moltype = DNA  length = 20
FEATURE                Location/Qualifiers
source                 1..20
                       mol_type = genomic DNA
```

```
                        organism = Homo sapiens
SEQUENCE: 313
gcagaagctg agttcaacct                                                     20

SEQ ID NO: 314          moltype = DNA  length = 20
FEATURE                 Location/Qualifiers
source                  1..20
                        mol_type = genomic DNA
                        organism = Homo sapiens
SEQUENCE: 314
tcatctgccc cagctgtaat                                                     20

SEQ ID NO: 315          moltype = DNA  length = 20
FEATURE                 Location/Qualifiers
source                  1..20
                        mol_type = genomic DNA
                        organism = Homo sapiens
SEQUENCE: 315
ggggaaaggt cgctttgctg                                                     20

SEQ ID NO: 316          moltype = DNA  length = 20
FEATURE                 Location/Qualifiers
source                  1..20
                        mol_type = genomic DNA
                        organism = Homo sapiens
SEQUENCE: 316
gcaggatttc tggttgtcac                                                     20

SEQ ID NO: 317          moltype = DNA  length = 20
FEATURE                 Location/Qualifiers
source                  1..20
                        mol_type = genomic DNA
                        organism = Mus musculus
SEQUENCE: 317
ccagctcctc tgccttctgc                                                     20

SEQ ID NO: 318          moltype = DNA  length = 20
FEATURE                 Location/Qualifiers
source                  1..20
                        mol_type = genomic DNA
                        organism = Mus musculus
SEQUENCE: 318
cagccagatc ccgctgttcc                                                     20

SEQ ID NO: 319          moltype = DNA  length = 20
FEATURE                 Location/Qualifiers
source                  1..20
                        mol_type = genomic DNA
                        organism = Mus musculus
SEQUENCE: 319
ggccctcgag ttcaacaggt                                                     20

SEQ ID NO: 320          moltype = DNA  length = 20
FEATURE                 Location/Qualifiers
source                  1..20
                        mol_type = genomic DNA
                        organism = Mus musculus
SEQUENCE: 320
gtgaagagct ggctgtggtc                                                     20

SEQ ID NO: 321          moltype = DNA  length = 20
FEATURE                 Location/Qualifiers
source                  1..20
                        mol_type = genomic DNA
                        organism = Mus musculus
SEQUENCE: 321
ggccaagctg gacaagggcc                                                     20

SEQ ID NO: 322          moltype = DNA  length = 20
FEATURE                 Location/Qualifiers
source                  1..20
                        mol_type = genomic DNA
                        organism = Mus musculus
SEQUENCE: 322
ccaggagaat gaagccctga                                                     20

SEQ ID NO: 323          moltype = DNA  length = 20
FEATURE                 Location/Qualifiers
source                  1..20
```

```
                        mol_type = genomic DNA
                        organism = Mus musculus
SEQUENCE: 323
tgctggcctc acctgcagga                                               20

SEQ ID NO: 324          moltype = DNA   length = 20
FEATURE                 Location/Qualifiers
source                  1..20
                        mol_type = genomic DNA
                        organism = Mus musculus
SEQUENCE: 324
ccagagggtg ctggcaagaa                                               20

SEQ ID NO: 325          moltype = DNA   length = 20
FEATURE                 Location/Qualifiers
source                  1..20
                        mol_type = genomic DNA
                        organism = Homo sapiens
SEQUENCE: 325
gatccagcgg ctcaacaagg                                               20

SEQ ID NO: 326          moltype = DNA   length = 20
FEATURE                 Location/Qualifiers
source                  1..20
                        mol_type = genomic DNA
                        organism = Homo sapiens
SEQUENCE: 326
ccaaaaggtc aagtacctgc                                               20

SEQ ID NO: 327          moltype = DNA   length = 20
FEATURE                 Location/Qualifiers
source                  1..20
                        mol_type = genomic DNA
                        organism = Homo sapiens
SEQUENCE: 327
acttaacctt cctctctgga                                               20

SEQ ID NO: 328          moltype = DNA   length = 20
FEATURE                 Location/Qualifiers
source                  1..20
                        mol_type = genomic DNA
                        organism = Homo sapiens
SEQUENCE: 328
gcagcttcgg aaggagaacg                                               20

SEQ ID NO: 329          moltype = DNA   length = 20
FEATURE                 Location/Qualifiers
source                  1..20
                        mol_type = genomic DNA
                        organism = Homo sapiens
SEQUENCE: 329
cacgcgcctc acctgcagaa                                               20

SEQ ID NO: 330          moltype = DNA   length = 20
FEATURE                 Location/Qualifiers
source                  1..20
                        mol_type = genomic DNA
                        organism = Homo sapiens
SEQUENCE: 330
gaaggcagag gagctagtga                                               20

SEQ ID NO: 331          moltype = DNA   length = 20
FEATURE                 Location/Qualifiers
source                  1..20
                        mol_type = genomic DNA
                        organism = Homo sapiens
SEQUENCE: 331
cctcacttaa ccttcctctc                                               20

SEQ ID NO: 332          moltype = DNA   length = 20
FEATURE                 Location/Qualifiers
source                  1..20
                        mol_type = genomic DNA
                        organism = Homo sapiens
SEQUENCE: 332
tgtgcacctt ggatgccagt                                               20

SEQ ID NO: 333          moltype = DNA   length = 20
FEATURE                 Location/Qualifiers
```

```
source                  1..20
                        mol_type = genomic DNA
                        organism = Homo sapiens
SEQUENCE: 333
ctcaggagag cgttaccatg                                               20

SEQ ID NO: 334          moltype = DNA   length = 20
FEATURE                 Location/Qualifiers
source                  1..20
                        mol_type = genomic DNA
                        organism = Homo sapiens
SEQUENCE: 334
cgagaagaag gtgaagatgc                                               20

SEQ ID NO: 335          moltype = DNA   length = 20
FEATURE                 Location/Qualifiers
source                  1..20
                        mol_type = genomic DNA
                        organism = Homo sapiens
SEQUENCE: 335
tatacctgtg agctcagcca                                               20

SEQ ID NO: 336          moltype = DNA   length = 20
FEATURE                 Location/Qualifiers
source                  1..20
                        mol_type = genomic DNA
                        organism = Homo sapiens
SEQUENCE: 336
ccaggtgaag atcttcgagg                                               20

SEQ ID NO: 337          moltype = DNA   length = 20
FEATURE                 Location/Qualifiers
source                  1..20
                        mol_type = genomic DNA
                        organism = Homo sapiens
SEQUENCE: 337
cttcacccac ctgggccgca                                               20

SEQ ID NO: 338          moltype = DNA   length = 20
FEATURE                 Location/Qualifiers
source                  1..20
                        mol_type = genomic DNA
                        organism = Homo sapiens
SEQUENCE: 338
gccgggaatt ctccttcact                                               20

SEQ ID NO: 339          moltype = DNA   length = 20
FEATURE                 Location/Qualifiers
source                  1..20
                        mol_type = genomic DNA
                        organism = Homo sapiens
SEQUENCE: 339
cccgcagaga tgttctgggt                                               20

SEQ ID NO: 340          moltype = DNA   length = 20
FEATURE                 Location/Qualifiers
source                  1..20
                        mol_type = genomic DNA
                        organism = Mus musculus
SEQUENCE: 340
aaaagagcaa gccttaccat                                               20

SEQ ID NO: 341          moltype = DNA   length = 20
FEATURE                 Location/Qualifiers
source                  1..20
                        mol_type = genomic DNA
                        organism = Mus musculus
SEQUENCE: 341
tgctgcagag ggccttcctc                                               20

SEQ ID NO: 342          moltype = DNA   length = 20
FEATURE                 Location/Qualifiers
source                  1..20
                        mol_type = genomic DNA
                        organism = Mus musculus
SEQUENCE: 342
ctccttctgt cctcaggtga                                               20

SEQ ID NO: 343          moltype = DNA   length = 20
```

```
FEATURE                 Location/Qualifiers
source                  1..20
                        mol_type = genomic DNA
                        organism = Mus musculus
SEQUENCE: 343
tacagatatc ccatcgtcct                                                   20

SEQ ID NO: 344          moltype = DNA  length = 20
FEATURE                 Location/Qualifiers
source                  1..20
                        mol_type = genomic DNA
                        organism = Mus musculus
SEQUENCE: 344
tgcagcttgt cagtacatgt                                                   20

SEQ ID NO: 345          moltype = DNA  length = 20
FEATURE                 Location/Qualifiers
source                  1..20
                        mol_type = genomic DNA
                        organism = Mus musculus
SEQUENCE: 345
tctccttaag ggtgctgcag                                                   20

SEQ ID NO: 346          moltype = DNA  length = 20
FEATURE                 Location/Qualifiers
source                  1..20
                        mol_type = genomic DNA
                        organism = Mus musculus
SEQUENCE: 346
agtgatcaca agcaggggcc                                                   20

SEQ ID NO: 347          moltype = DNA  length = 20
FEATURE                 Location/Qualifiers
source                  1..20
                        mol_type = genomic DNA
                        organism = Mus musculus
SEQUENCE: 347
cactttcaaa ggagcaaaat                                                   20

SEQ ID NO: 348          moltype = DNA  length = 20
FEATURE                 Location/Qualifiers
source                  1..20
                        mol_type = genomic DNA
                        organism = Homo sapiens
SEQUENCE: 348
ctcctcaggg ttccacgcca                                                   20

SEQ ID NO: 349          moltype = DNA  length = 20
FEATURE                 Location/Qualifiers
source                  1..20
                        mol_type = genomic DNA
                        organism = Homo sapiens
SEQUENCE: 349
gccccacatg tactgagaag                                                   20

SEQ ID NO: 350          moltype = DNA  length = 20
FEATURE                 Location/Qualifiers
source                  1..20
                        mol_type = genomic DNA
                        organism = Homo sapiens
SEQUENCE: 350
cttaccaaaa gaaatcaatc                                                   20

SEQ ID NO: 351          moltype = DNA  length = 20
FEATURE                 Location/Qualifiers
source                  1..20
                        mol_type = genomic DNA
                        organism = Homo sapiens
SEQUENCE: 351
acactgaatg tgcagcacaa                                                   20

SEQ ID NO: 352          moltype = DNA  length = 20
FEATURE                 Location/Qualifiers
source                  1..20
                        mol_type = genomic DNA
                        organism = Homo sapiens
SEQUENCE: 352
aagtcagtcc cacagcgtcc                                                   20
```

| | | |
|---|---|---|
| SEQ ID NO: 353<br>FEATURE<br>source | moltype = DNA   length = 20<br>Location/Qualifiers<br>1..20<br>mol_type = genomic DNA<br>organism = Homo sapiens | |
| SEQUENCE: 353<br>actccaagcc gggccctgag | | 20 |
| SEQ ID NO: 354<br>FEATURE<br>source | moltype = DNA   length = 20<br>Location/Qualifiers<br>1..20<br>mol_type = genomic DNA<br>organism = Homo sapiens | |
| SEQUENCE: 354<br>gctcttaaaa gagtacttaa | | 20 |
| SEQ ID NO: 355<br>FEATURE<br>source | moltype = DNA   length = 20<br>Location/Qualifiers<br>1..20<br>mol_type = genomic DNA<br>organism = Homo sapiens | |
| SEQUENCE: 355<br>atggcaggaa aacagcgagc | | 20 |
| SEQ ID NO: 356<br>FEATURE<br>source | moltype = DNA   length = 20<br>Location/Qualifiers<br>1..20<br>mol_type = genomic DNA<br>organism = Homo sapiens | |
| SEQUENCE: 356<br>gaagtgccaa gcctgcctcc | | 20 |
| SEQ ID NO: 357<br>FEATURE<br>source | moltype = DNA   length = 20<br>Location/Qualifiers<br>1..20<br>mol_type = genomic DNA<br>organism = Homo sapiens | |
| SEQUENCE: 357<br>gacaccagtt gagtttcttc | | 20 |
| SEQ ID NO: 358<br>FEATURE<br>source | moltype = DNA   length = 20<br>Location/Qualifiers<br>1..20<br>mol_type = genomic DNA<br>organism = Homo sapiens | |
| SEQUENCE: 358<br>gaggcaggct tggcacttcc | | 20 |
| SEQ ID NO: 359<br>FEATURE<br>source | moltype = DNA   length = 20<br>Location/Qualifiers<br>1..20<br>mol_type = genomic DNA<br>organism = Homo sapiens | |
| SEQUENCE: 359<br>tcgggccatg ggtgtgtctg | | 20 |
| SEQ ID NO: 360<br>FEATURE<br>source | moltype = DNA   length = 20<br>Location/Qualifiers<br>1..20<br>mol_type = genomic DNA<br>organism = Homo sapiens | |
| SEQUENCE: 360<br>tcacctgaaa tgacaatgat | | 20 |
| SEQ ID NO: 361<br>FEATURE<br>source | moltype = DNA   length = 20<br>Location/Qualifiers<br>1..20<br>mol_type = genomic DNA<br>organism = Homo sapiens | |
| SEQUENCE: 361<br>ccgcattccc tccccaggca | | 20 |
| SEQ ID NO: 362<br>FEATURE<br>source | moltype = DNA   length = 20<br>Location/Qualifiers<br>1..20<br>mol_type = genomic DNA<br>organism = Homo sapiens | |
| SEQUENCE: 362<br>ggcccccag tggactcctc | | 20 |

| | | |
|---|---|---|
| SEQ ID NO: 363<br>FEATURE<br>source | moltype = DNA   length = 20<br>Location/Qualifiers<br>1..20<br>mol_type = genomic DNA<br>organism = Homo sapiens | |
| SEQUENCE: 363<br>gtgatagaaa tccccgtcca | | 20 |
| SEQ ID NO: 364<br>FEATURE<br>source | moltype = DNA   length = 20<br>Location/Qualifiers<br>1..20<br>mol_type = genomic DNA<br>organism = Homo sapiens | |
| SEQUENCE: 364<br>ttctggaacc tggacgctgt | | 20 |
| SEQ ID NO: 365<br>FEATURE<br>source | moltype = DNA   length = 20<br>Location/Qualifiers<br>1..20<br>mol_type = genomic DNA<br>organism = Homo sapiens | |
| SEQUENCE: 365<br>agttgtactg aagtccactt | | 20 |
| SEQ ID NO: 366<br>FEATURE<br>source | moltype = DNA   length = 20<br>Location/Qualifiers<br>1..20<br>mol_type = genomic DNA<br>organism = Homo sapiens | |
| SEQUENCE: 366<br>cacacaaggc acttggatcc | | 20 |
| SEQ ID NO: 367<br>FEATURE<br>source | moltype = DNA   length = 20<br>Location/Qualifiers<br>1..20<br>mol_type = genomic DNA<br>organism = Homo sapiens | |
| SEQUENCE: 367<br>agaacaccat tccgtgcctg | | 20 |
| SEQ ID NO: 368<br>FEATURE<br>source | moltype = DNA   length = 20<br>Location/Qualifiers<br>1..20<br>mol_type = genomic DNA<br>organism = Homo sapiens | |
| SEQUENCE: 368<br>catggcgctc ggggcctctc | | 20 |
| SEQ ID NO: 369<br>FEATURE<br>source | moltype = DNA   length = 20<br>Location/Qualifiers<br>1..20<br>mol_type = genomic DNA<br>organism = Homo sapiens | |
| SEQUENCE: 369<br>gccccccagt ggactcctca | | 20 |
| SEQ ID NO: 370<br>FEATURE<br>source | moltype = DNA   length = 20<br>Location/Qualifiers<br>1..20<br>mol_type = genomic DNA<br>organism = Homo sapiens | |
| SEQUENCE: 370<br>gctgtcggtg gggccgaatg | | 20 |
| SEQ ID NO: 371<br>FEATURE<br>source | moltype = DNA   length = 20<br>Location/Qualifiers<br>1..20<br>mol_type = genomic DNA<br>organism = Homo sapiens | |
| SEQUENCE: 371<br>caagtgcctt gtgtggtctg | | 20 |
| SEQ ID NO: 372<br>FEATURE<br>source | moltype = DNA   length = 20<br>Location/Qualifiers<br>1..20<br>mol_type = genomic DNA<br>organism = Homo sapiens | |
| SEQUENCE: 372 | | |

```
gccacttctc agtacatgtg                                            20

SEQ ID NO: 373           moltype = DNA  length = 20
FEATURE                  Location/Qualifiers
source                   1..20
                         mol_type = genomic DNA
                         organism = Homo sapiens
SEQUENCE: 373
tacagatacc ccattgttct                                            20

SEQ ID NO: 374           moltype = DNA  length = 20
FEATURE                  Location/Qualifiers
source                   1..20
                         mol_type = genomic DNA
                         organism = Homo sapiens
SEQUENCE: 374
tagaaatccc cgtccaaggc                                            20

SEQ ID NO: 375           moltype = DNA  length = 20
FEATURE                  Location/Qualifiers
source                   1..20
                         mol_type = genomic DNA
                         organism = Homo sapiens
SEQUENCE: 375
aaagccggct gcgtgtattt                                            20

SEQ ID NO: 376           moltype = DNA  length = 20
FEATURE                  Location/Qualifiers
source                   1..20
                         mol_type = genomic DNA
                         organism = Homo sapiens
SEQUENCE: 376
tggtctcact gaacagaaaa                                            20

SEQ ID NO: 377           moltype = DNA  length = 20
FEATURE                  Location/Qualifiers
source                   1..20
                         mol_type = genomic DNA
                         organism = Homo sapiens
SEQUENCE: 377
tggtgaccct gaaggacagt                                            20

SEQ ID NO: 378           moltype = DNA  length = 20
FEATURE                  Location/Qualifiers
source                   1..20
                         mol_type = genomic DNA
                         organism = Homo sapiens
SEQUENCE: 378
agagaaagct ggggcacgga                                            20

SEQ ID NO: 379           moltype = DNA  length = 20
FEATURE                  Location/Qualifiers
source                   1..20
                         mol_type = genomic DNA
                         organism = Homo sapiens
SEQUENCE: 379
cgtgccccag ctttctctca                                            20

SEQ ID NO: 380           moltype = DNA  length = 20
FEATURE                  Location/Qualifiers
source                   1..20
                         mol_type = genomic DNA
                         organism = Homo sapiens
SEQUENCE: 380
tatgccatga gtgctcagag                                            20

SEQ ID NO: 381           moltype = DNA  length = 20
FEATURE                  Location/Qualifiers
source                   1..20
                         mol_type = genomic DNA
                         organism = Homo sapiens
SEQUENCE: 381
agggctgggt gctgtcggtg                                            20

SEQ ID NO: 382           moltype = DNA  length = 20
FEATURE                  Location/Qualifiers
source                   1..20
                         mol_type = genomic DNA
                         organism = Homo sapiens
```

```
SEQUENCE: 382
ccatgccagg gagcccctca                                                    20

SEQ ID NO: 383         moltype = DNA  length = 20
FEATURE                Location/Qualifiers
source                 1..20
                       mol_type = genomic DNA
                       organism = Homo sapiens
SEQUENCE: 383
gagtttcttc tggctttcca                                                    20

SEQ ID NO: 384         moltype = DNA  length = 20
FEATURE                Location/Qualifiers
source                 1..20
                       mol_type = genomic DNA
                       organism = Homo sapiens
SEQUENCE: 384
gctgtcatag ccgagaacaa                                                    20

SEQ ID NO: 385         moltype = DNA  length = 20
FEATURE                Location/Qualifiers
source                 1..20
                       mol_type = genomic DNA
                       organism = Homo sapiens
SEQUENCE: 385
gggagaagcc tatgagccct                                                    20

SEQ ID NO: 386         moltype = DNA  length = 20
FEATURE                Location/Qualifiers
source                 1..20
                       mol_type = genomic DNA
                       organism = Homo sapiens
SEQUENCE: 386
ggggtatctg tagcattcct                                                    20

SEQ ID NO: 387         moltype = DNA  length = 20
FEATURE                Location/Qualifiers
source                 1..20
                       mol_type = genomic DNA
                       organism = Homo sapiens
SEQUENCE: 387
tggatgatct cccgaaactg                                                    20

SEQ ID NO: 388         moltype = DNA  length = 20
FEATURE                Location/Qualifiers
source                 1..20
                       mol_type = genomic DNA
                       organism = Homo sapiens
SEQUENCE: 388
cttgtggcgc tgaaaacgaa                                                    20

SEQ ID NO: 389         moltype = DNA  length = 20
FEATURE                Location/Qualifiers
source                 1..20
                       mol_type = genomic DNA
                       organism = Homo sapiens
SEQUENCE: 389
actgagaagt ggcatgcatg                                                    20

SEQ ID NO: 390         moltype = DNA  length = 20
FEATURE                Location/Qualifiers
source                 1..20
                       mol_type = genomic DNA
                       organism = Homo sapiens
SEQUENCE: 390
tgaacatttc cagtgtgtat                                                    20

SEQ ID NO: 391         moltype = DNA  length = 20
FEATURE                Location/Qualifiers
source                 1..20
                       mol_type = genomic DNA
                       organism = Homo sapiens
SEQUENCE: 391
ttgctcaaat acaaagcctg                                                    20

SEQ ID NO: 392         moltype = DNA  length = 20
FEATURE                Location/Qualifiers
source                 1..20
                       mol_type = genomic DNA
```

```
                            organism = Homo sapiens
SEQUENCE: 392
tgagagactc cagttgccag                                               20

SEQ ID NO: 393           moltype = DNA  length = 20
FEATURE                  Location/Qualifiers
source                   1..20
                         mol_type = genomic DNA
                         organism = Homo sapiens
SEQUENCE: 393
gcatgagtac aagaaatggc                                               20

SEQ ID NO: 394           moltype = DNA  length = 20
FEATURE                  Location/Qualifiers
source                   1..20
                         mol_type = genomic DNA
                         organism = Homo sapiens
SEQUENCE: 394
gaggcaattg ccgtcacctg                                               20

SEQ ID NO: 395           moltype = DNA  length = 20
FEATURE                  Location/Qualifiers
source                   1..20
                         mol_type = genomic DNA
                         organism = Homo sapiens
SEQUENCE: 395
ctgtccttca gggtcaccaa                                               20

SEQ ID NO: 396           moltype = DNA  length = 20
FEATURE                  Location/Qualifiers
source                   1..20
                         mol_type = genomic DNA
                         organism = Homo sapiens
SEQUENCE: 396
cagaaacatc caggccaccc                                               20

SEQ ID NO: 397           moltype = DNA  length = 20
FEATURE                  Location/Qualifiers
source                   1..20
                         mol_type = genomic DNA
                         organism = Homo sapiens
SEQUENCE: 397
gtattcagct taaaaaattc                                               20

SEQ ID NO: 398           moltype = DNA  length = 20
FEATURE                  Location/Qualifiers
source                   1..20
                         mol_type = genomic DNA
                         organism = Homo sapiens
SEQUENCE: 398
atccatgcat gcctgccgga                                               20

SEQ ID NO: 399           moltype = DNA  length = 20
FEATURE                  Location/Qualifiers
source                   1..20
                         mol_type = genomic DNA
                         organism = Homo sapiens
SEQUENCE: 399
aatataccag acactgcaac                                               20

SEQ ID NO: 400           moltype = DNA  length = 20
FEATURE                  Location/Qualifiers
source                   1..20
                         mol_type = genomic DNA
                         organism = Homo sapiens
SEQUENCE: 400
tgtcttgcag ataacaatta                                               20

SEQ ID NO: 401           moltype = DNA  length = 20
FEATURE                  Location/Qualifiers
source                   1..20
                         mol_type = genomic DNA
                         organism = Homo sapiens
SEQUENCE: 401
ttgggtgtgt attccaaccg                                               20

SEQ ID NO: 402           moltype = DNA  length = 20
FEATURE                  Location/Qualifiers
source                   1..20
```

```
                            mol_type = genomic DNA
                            organism = Homo sapiens
SEQUENCE: 402
tttagaaagt gattcaaaag                                                   20

SEQ ID NO: 403              moltype = DNA   length = 20
FEATURE                     Location/Qualifiers
source                      1..20
                            mol_type = genomic DNA
                            organism = Homo sapiens
SEQUENCE: 403
agtaaaagaa ttacagcaaa                                                   20

SEQ ID NO: 404              moltype = DNA   length = 20
FEATURE                     Location/Qualifiers
source                      1..20
                            mol_type = genomic DNA
                            organism = Homo sapiens
SEQUENCE: 404
actacagcaa gggaaacagc                                                   20

SEQ ID NO: 405              moltype = DNA   length = 20
FEATURE                     Location/Qualifiers
source                      1..20
                            mol_type = genomic DNA
                            organism = Homo sapiens
SEQUENCE: 405
ttgctttcta tactacagca                                                   20

SEQ ID NO: 406              moltype = DNA   length = 20
FEATURE                     Location/Qualifiers
source                      1..20
                            mol_type = genomic DNA
                            organism = Homo sapiens
SEQUENCE: 406
gcagtccttt gctccatgaa                                                   20

SEQ ID NO: 407              moltype = DNA   length = 20
FEATURE                     Location/Qualifiers
source                      1..20
                            mol_type = genomic DNA
                            organism = Homo sapiens
SEQUENCE: 407
gcagagaata cgtgaacaac                                                   20

SEQ ID NO: 408              moltype = DNA   length = 20
FEATURE                     Location/Qualifiers
source                      1..20
                            mol_type = genomic DNA
                            organism = Homo sapiens
SEQUENCE: 408
taacatgaac ataccttgag                                                   20

SEQ ID NO: 409              moltype = DNA   length = 20
FEATURE                     Location/Qualifiers
source                      1..20
                            mol_type = genomic DNA
                            organism = Homo sapiens
SEQUENCE: 409
cctgaaatca ctttatcttg                                                   20

SEQ ID NO: 410              moltype = DNA   length = 20
FEATURE                     Location/Qualifiers
source                      1..20
                            mol_type = genomic DNA
                            organism = Homo sapiens
SEQUENCE: 410
ataaagcgta tgaagccttc                                                   20

SEQ ID NO: 411              moltype = DNA   length = 20
FEATURE                     Location/Qualifiers
source                      1..20
                            mol_type = genomic DNA
                            organism = Homo sapiens
SEQUENCE: 411
gtattccaac cgcggtaaga                                                   20

SEQ ID NO: 412              moltype = DNA   length = 20
FEATURE                     Location/Qualifiers
```

```
source                     1..20
                           mol_type = genomic DNA
                           organism = Homo sapiens
SEQUENCE: 412
ccgggccccc agcaggtctg                                               20

SEQ ID NO: 413             moltype = DNA   length = 20
FEATURE                    Location/Qualifiers
source                     1..20
                           mol_type = genomic DNA
                           organism = Homo sapiens
SEQUENCE: 413
cctacttagg cactgccagg                                               20

SEQ ID NO: 414             moltype = DNA   length = 20
FEATURE                    Location/Qualifiers
source                     1..20
                           mol_type = genomic DNA
                           organism = Homo sapiens
SEQUENCE: 414
gcttacccag cggatgagcg                                               20

SEQ ID NO: 415             moltype = DNA   length = 20
FEATURE                    Location/Qualifiers
source                     1..20
                           mol_type = genomic DNA
                           organism = Homo sapiens
SEQUENCE: 415
cttctctgga gcctccagga                                               20

SEQ ID NO: 416             moltype = DNA   length = 20
FEATURE                    Location/Qualifiers
source                     1..20
                           mol_type = genomic DNA
                           organism = Homo sapiens
SEQUENCE: 416
tccactgacc tgtccttcct                                               20

SEQ ID NO: 417             moltype = DNA   length = 20
FEATURE                    Location/Qualifiers
source                     1..20
                           mol_type = genomic DNA
                           organism = Homo sapiens
SEQUENCE: 417
acccaggcat catccgacaa                                               20

SEQ ID NO: 418             moltype = DNA   length = 20
FEATURE                    Location/Qualifiers
source                     1..20
                           mol_type = genomic DNA
                           organism = Homo sapiens
SEQUENCE: 418
catggggttc aaggaagaag                                               20

SEQ ID NO: 419             moltype = DNA   length = 20
FEATURE                    Location/Qualifiers
source                     1..20
                           mol_type = genomic DNA
                           organism = Homo sapiens
SEQUENCE: 419
aaaccatcct gccacctgga                                               20

SEQ ID NO: 420             moltype = DNA   length = 20
FEATURE                    Location/Qualifiers
source                     1..20
                           mol_type = genomic DNA
                           organism = Homo sapiens
SEQUENCE: 420
tcatggctgg gctctccagg                                               20

SEQ ID NO: 421             moltype = DNA   length = 20
FEATURE                    Location/Qualifiers
source                     1..20
                           mol_type = genomic DNA
                           organism = Homo sapiens
SEQUENCE: 421
cagggccgag atcttcgagg                                               20

SEQ ID NO: 422             moltype = DNA   length = 20
```

```
FEATURE               Location/Qualifiers
source                1..20
                      mol_type = genomic DNA
                      organism = Homo sapiens
SEQUENCE: 422
agagtgatga agagtgtgac                                                  20

SEQ ID NO: 423        moltype = DNA   length = 20
FEATURE               Location/Qualifiers
source                1..20
                      mol_type = genomic DNA
                      organism = Homo sapiens
SEQUENCE: 423
tcacatttca gtttaccatt                                                  20

SEQ ID NO: 424        moltype = DNA   length = 20
FEATURE               Location/Qualifiers
source                1..20
                      mol_type = genomic DNA
                      organism = Homo sapiens
SEQUENCE: 424
gctgatgcag tctcatatga                                                  20

SEQ ID NO: 425        moltype = DNA   length = 20
FEATURE               Location/Qualifiers
source                1..20
                      mol_type = genomic DNA
                      organism = Homo sapiens
SEQUENCE: 425
tgacattctg gagatagttg                                                  20

SEQ ID NO: 426        moltype = DNA   length = 20
FEATURE               Location/Qualifiers
source                1..20
                      mol_type = genomic DNA
                      organism = Homo sapiens
SEQUENCE: 426
cactttgact atggaaacag                                                  20

SEQ ID NO: 427        moltype = DNA   length = 20
FEATURE               Location/Qualifiers
source                1..20
                      mol_type = genomic DNA
                      organism = Homo sapiens
SEQUENCE: 427
aagctccaca ctggttacag                                                  20

SEQ ID NO: 428        moltype = DNA   length = 20
FEATURE               Location/Qualifiers
source                1..20
                      mol_type = genomic DNA
                      organism = Homo sapiens
SEQUENCE: 428
tagctacgcc tgtagaagaa                                                  20

SEQ ID NO: 429        moltype = DNA   length = 20
FEATURE               Location/Qualifiers
source                1..20
                      mol_type = genomic DNA
                      organism = Homo sapiens
SEQUENCE: 429
gctgtcatag agaagctcac                                                  20

SEQ ID NO: 430        moltype = DNA   length = 20
FEATURE               Location/Qualifiers
source                1..20
                      mol_type = genomic DNA
                      organism = Homo sapiens
SEQUENCE: 430
ttactgcttg tcatgtgact                                                  20

SEQ ID NO: 431        moltype = DNA   length = 20
FEATURE               Location/Qualifiers
source                1..20
                      mol_type = genomic DNA
                      organism = Homo sapiens
SEQUENCE: 431
aatcacctac cttggagctg                                                  20
```

-continued

| | | |
|---|---|---|
| SEQ ID NO: 432<br>FEATURE<br>source | moltype = DNA   length = 20<br>Location/Qualifiers<br>1..20<br>mol_type = genomic DNA<br>organism = Homo sapiens | |
| SEQUENCE: 432<br>gtaactttat gtgtctcaga | | 20 |
| SEQ ID NO: 433<br>FEATURE<br>source | moltype = DNA   length = 20<br>Location/Qualifiers<br>1..20<br>mol_type = genomic DNA<br>organism = Homo sapiens | |
| SEQUENCE: 433<br>cctcacaagt gcaactactg | | 20 |
| SEQ ID NO: 434<br>FEATURE<br>source | moltype = DNA   length = 20<br>Location/Qualifiers<br>1..20<br>mol_type = genomic DNA<br>organism = Homo sapiens | |
| SEQUENCE: 434<br>tccttacaat cttccatagg | | 20 |
| SEQ ID NO: 435<br>FEATURE<br>source | moltype = DNA   length = 20<br>Location/Qualifiers<br>1..20<br>mol_type = genomic DNA<br>organism = Homo sapiens | |
| SEQUENCE: 435<br>ggaggaatcc ggcttccgaa | | 20 |
| SEQ ID NO: 436<br>FEATURE<br>source | moltype = DNA   length = 20<br>Location/Qualifiers<br>1..20<br>mol_type = genomic DNA<br>organism = Homo sapiens | |
| SEQUENCE: 436<br>acaatgagct ttcacccgaa | | 20 |
| SEQ ID NO: 437<br>FEATURE<br>source | moltype = DNA   length = 20<br>Location/Qualifiers<br>1..20<br>mol_type = genomic DNA<br>organism = Homo sapiens | |
| SEQUENCE: 437<br>acttaccaga atgggtcctg | | 20 |
| SEQ ID NO: 438<br>FEATURE<br>source | moltype = DNA   length = 20<br>Location/Qualifiers<br>1..20<br>mol_type = genomic DNA<br>organism = Homo sapiens | |
| SEQUENCE: 438<br>gccatctcgc cgccacagtg | | 20 |
| SEQ ID NO: 439<br>FEATURE<br>source | moltype = DNA   length = 20<br>Location/Qualifiers<br>1..20<br>mol_type = genomic DNA<br>organism = Homo sapiens | |
| SEQUENCE: 439<br>gggctctatc acaaaatgaa | | 20 |
| SEQ ID NO: 440<br>FEATURE<br>source | moltype = DNA   length = 20<br>Location/Qualifiers<br>1..20<br>mol_type = genomic DNA<br>organism = Homo sapiens | |
| SEQUENCE: 440<br>cccctgacta tgaagaagga | | 20 |
| SEQ ID NO: 441<br>FEATURE<br>source | moltype = DNA   length = 20<br>Location/Qualifiers<br>1..20<br>mol_type = genomic DNA<br>organism = Homo sapiens | |
| SEQUENCE: 441<br>acctgtgctg gaccgggcct | | 20 |

| | | |
|---|---|---|
| SEQ ID NO: 442<br>FEATURE<br>source | moltype = DNA   length = 20<br>Location/Qualifiers<br>1..20<br>mol_type = genomic DNA<br>organism = Homo sapiens | |
| SEQUENCE: 442<br>gtagacggag aggggccccg | | 20 |
| SEQ ID NO: 443<br>FEATURE<br>source | moltype = DNA   length = 20<br>Location/Qualifiers<br>1..20<br>mol_type = genomic DNA<br>organism = Homo sapiens | |
| SEQUENCE: 443<br>aagcttgtag tagagcccac | | 20 |
| SEQ ID NO: 444<br>FEATURE<br>source | moltype = DNA   length = 20<br>Location/Qualifiers<br>1..20<br>mol_type = genomic DNA<br>organism = Homo sapiens | |
| SEQUENCE: 444<br>ctggaggagg aatgccaatg | | 20 |
| SEQ ID NO: 445<br>FEATURE<br>source | moltype = DNA   length = 20<br>Location/Qualifiers<br>1..20<br>mol_type = genomic DNA<br>organism = Homo sapiens | |
| SEQUENCE: 445<br>cagccactcc tacatggacg | | 20 |
| SEQ ID NO: 446<br>FEATURE<br>source | moltype = DNA   length = 20<br>Location/Qualifiers<br>1..20<br>mol_type = genomic DNA<br>organism = Homo sapiens | |
| SEQUENCE: 446<br>gaagggctg agattccagg | | 20 |
| SEQ ID NO: 447<br>FEATURE<br>source | moltype = DNA   length = 20<br>Location/Qualifiers<br>1..20<br>mol_type = genomic DNA<br>organism = Homo sapiens | |
| SEQUENCE: 447<br>ggagctgtac tcgggcacgt | | 20 |
| SEQ ID NO: 448<br>FEATURE<br>source | moltype = DNA   length = 20<br>Location/Qualifiers<br>1..20<br>mol_type = genomic DNA<br>organism = Homo sapiens | |
| SEQUENCE: 448<br>gctttgccgc cgtccagcca | | 20 |
| SEQ ID NO: 449<br>FEATURE<br>source | moltype = DNA   length = 20<br>Location/Qualifiers<br>1..20<br>mol_type = genomic DNA<br>organism = Homo sapiens | |
| SEQUENCE: 449<br>aggcccggtc cagcacaggt | | 20 |
| SEQ ID NO: 450<br>FEATURE<br>source | moltype = DNA   length = 20<br>Location/Qualifiers<br>1..20<br>mol_type = genomic DNA<br>organism = Mus musculus | |
| SEQUENCE: 450<br>gaggtggcgc ttacctgtgc | | 20 |
| SEQ ID NO: 451<br>FEATURE<br>source | moltype = DNA   length = 20<br>Location/Qualifiers<br>1..20<br>mol_type = genomic DNA<br>organism = Mus musculus | |
| SEQUENCE: 451 | | |

```
gctagacatc ttccggtttc                                              20

SEQ ID NO: 452           moltype = DNA  length = 20
FEATURE                  Location/Qualifiers
source                   1..20
                         mol_type = genomic DNA
                         organism = Mus musculus
SEQUENCE: 452
ggaagctcag tatccgctga                                              20

SEQ ID NO: 453           moltype = DNA  length = 20
FEATURE                  Location/Qualifiers
source                   1..20
                         mol_type = genomic DNA
                         organism = Mus musculus
SEQUENCE: 453
tgtctgggtg ctgaccgttg                                              20

SEQ ID NO: 454           moltype = DNA  length = 20
FEATURE                  Location/Qualifiers
source                   1..20
                         mol_type = genomic DNA
                         organism = Mus musculus
SEQUENCE: 454
aaggcatcca gacccgaaac                                              20

SEQ ID NO: 455           moltype = DNA  length = 20
FEATURE                  Location/Qualifiers
source                   1..20
                         mol_type = genomic DNA
                         organism = Mus musculus
SEQUENCE: 455
caaggtggac tcaccgtggt                                              20

SEQ ID NO: 456           moltype = DNA  length = 20
FEATURE                  Location/Qualifiers
source                   1..20
                         mol_type = genomic DNA
                         organism = Mus musculus
SEQUENCE: 456
agcccacagg cattgcagac                                              20

SEQ ID NO: 457           moltype = DNA  length = 20
FEATURE                  Location/Qualifiers
source                   1..20
                         mol_type = genomic DNA
                         organism = Mus musculus
SEQUENCE: 457
cccctgacta tgaagaaaga                                              20

SEQ ID NO: 458           moltype = DNA  length = 20
FEATURE                  Location/Qualifiers
source                   1..20
                         mol_type = genomic DNA
                         organism = Homo sapiens
SEQUENCE: 458
agtccatatg gaacccacgg                                              20

SEQ ID NO: 459           moltype = DNA  length = 20
FEATURE                  Location/Qualifiers
source                   1..20
                         mol_type = genomic DNA
                         organism = Homo sapiens
SEQUENCE: 459
agtctgagtg caaattgggc                                              20

SEQ ID NO: 460           moltype = DNA  length = 20
FEATURE                  Location/Qualifiers
source                   1..20
                         mol_type = genomic DNA
                         organism = Homo sapiens
SEQUENCE: 460
tacgaattgc accggaccag                                              20

SEQ ID NO: 461           moltype = DNA  length = 20
FEATURE                  Location/Qualifiers
source                   1..20
                         mol_type = genomic DNA
                         organism = Homo sapiens
```

-continued

| | | |
|---|---|---|
| SEQUENCE: 461<br>ttagaggctt gaggaaaccg | | 20 |
| SEQ ID NO: 462<br>FEATURE<br>source | moltype = DNA   length = 20<br>Location/Qualifiers<br>1..20<br>mol_type = genomic DNA<br>organism = Homo sapiens | |
| SEQUENCE: 462<br>ttagaaccta tgaagctctg | | 20 |
| SEQ ID NO: 463<br>FEATURE<br>source | moltype = DNA   length = 20<br>Location/Qualifiers<br>1..20<br>mol_type = genomic DNA<br>organism = Homo sapiens | |
| SEQUENCE: 463<br>cctgaataaa ctccaccgca | | 20 |
| SEQ ID NO: 464<br>FEATURE<br>source | moltype = DNA   length = 20<br>Location/Qualifiers<br>1..20<br>mol_type = genomic DNA<br>organism = Homo sapiens | |
| SEQUENCE: 464<br>aattcgaaag cccatcagtt | | 20 |
| SEQ ID NO: 465<br>FEATURE<br>source | moltype = DNA   length = 20<br>Location/Qualifiers<br>1..20<br>mol_type = genomic DNA<br>organism = Homo sapiens | |
| SEQUENCE: 465<br>tggccacaac ccaaactgat | | 20 |
| SEQ ID NO: 466<br>FEATURE<br>source | moltype = DNA   length = 20<br>Location/Qualifiers<br>1..20<br>mol_type = genomic DNA<br>organism = Homo sapiens | |
| SEQUENCE: 466<br>cagcatactc tgaggtacga | | 20 |
| SEQ ID NO: 467<br>FEATURE<br>source | moltype = DNA   length = 20<br>Location/Qualifiers<br>1..20<br>mol_type = genomic DNA<br>organism = Homo sapiens | |
| SEQUENCE: 467<br>ttacctctag cactgctgag | | 20 |
| SEQ ID NO: 468<br>FEATURE<br>source | moltype = DNA   length = 20<br>Location/Qualifiers<br>1..20<br>mol_type = genomic DNA<br>organism = Homo sapiens | |
| SEQUENCE: 468<br>tatgcagtcc attattgaca | | 20 |
| SEQ ID NO: 469<br>FEATURE<br>source | moltype = DNA   length = 20<br>Location/Qualifiers<br>1..20<br>mol_type = genomic DNA<br>organism = Homo sapiens | |
| SEQUENCE: 469<br>gtaacacagc ttattccgcg | | 20 |
| SEQ ID NO: 470<br>FEATURE<br>source | moltype = DNA   length = 20<br>Location/Qualifiers<br>1..20<br>mol_type = genomic DNA<br>organism = Homo sapiens | |
| SEQUENCE: 470<br>actttcccta gcaatgcagg | | 20 |
| SEQ ID NO: 471<br>FEATURE<br>source | moltype = DNA   length = 20<br>Location/Qualifiers<br>1..20<br>mol_type = genomic DNA | |

```
                                                organism = Mus musculus
SEQUENCE: 471
caaatgggca agccttacgg                                                              20

SEQ ID NO: 472           moltype = DNA  length = 20
FEATURE                  Location/Qualifiers
source                   1..20
                         mol_type = genomic DNA
                         organism = Mus musculus
SEQUENCE: 472
ctcaatgtcc gtattgatag                                                              20

SEQ ID NO: 473           moltype = DNA  length = 20
FEATURE                  Location/Qualifiers
source                   1..20
                         mol_type = genomic DNA
                         organism = Mus musculus
SEQUENCE: 473
agtctgagtg caaattgggc                                                              20

SEQ ID NO: 474           moltype = DNA  length = 20
FEATURE                  Location/Qualifiers
source                   1..20
                         mol_type = genomic DNA
                         organism = Mus musculus
SEQUENCE: 474
ccagatagtg caaattgcta                                                              20

SEQ ID NO: 475           moltype = DNA  length = 20
FEATURE                  Location/Qualifiers
source                   1..20
                         mol_type = genomic DNA
                         organism = Mus musculus
SEQUENCE: 475
tgatagtggt ctggtcaaat                                                              20

SEQ ID NO: 476           moltype = DNA  length = 20
FEATURE                  Location/Qualifiers
source                   1..20
                         mol_type = genomic DNA
                         organism = Mus musculus
SEQUENCE: 476
aattcgaaag cccatcagtt                                                              20

SEQ ID NO: 477           moltype = DNA  length = 20
FEATURE                  Location/Qualifiers
source                   1..20
                         mol_type = genomic DNA
                         organism = Mus musculus
SEQUENCE: 477
gcccattact ttgtgtagtg                                                              20

SEQ ID NO: 478           moltype = DNA  length = 20
FEATURE                  Location/Qualifiers
source                   1..20
                         mol_type = genomic DNA
                         organism = Mus musculus
SEQUENCE: 478
tggccacagc ccaaactgat                                                              20

SEQ ID NO: 479           moltype = DNA  length = 20
FEATURE                  Location/Qualifiers
source                   1..20
                         mol_type = genomic DNA
                         organism = Homo sapiens
SEQUENCE: 479
gcattcatac ttgctttcca                                                              20

SEQ ID NO: 480           moltype = DNA  length = 20
FEATURE                  Location/Qualifiers
source                   1..20
                         mol_type = genomic DNA
                         organism = Homo sapiens
SEQUENCE: 480
ttagatgcag aggaatcact                                                              20

SEQ ID NO: 481           moltype = DNA  length = 20
FEATURE                  Location/Qualifiers
source                   1..20
```

```
                        mol_type = genomic DNA
                        organism = Homo sapiens
SEQUENCE: 481
atggtgaaat gtccaaatga                                               20

SEQ ID NO: 482          moltype = DNA   length = 20
FEATURE                 Location/Qualifiers
source                  1..20
                        mol_type = genomic DNA
                        organism = Homo sapiens
SEQUENCE: 482
ttggttgcca tgaaaaggta                                               20

SEQ ID NO: 483          moltype = DNA   length = 20
FEATURE                 Location/Qualifiers
source                  1..20
                        mol_type = genomic DNA
                        organism = Homo sapiens
SEQUENCE: 483
tcatttatgg aggagatcca                                               20

SEQ ID NO: 484          moltype = DNA   length = 20
FEATURE                 Location/Qualifiers
source                  1..20
                        mol_type = genomic DNA
                        organism = Homo sapiens
SEQUENCE: 484
tgttacagcg ctacaggagc                                               20

SEQ ID NO: 485          moltype = DNA   length = 20
FEATURE                 Location/Qualifiers
source                  1..20
                        mol_type = genomic DNA
                        organism = Homo sapiens
SEQUENCE: 485
ctaaactgtg aaaacagctg                                               20

SEQ ID NO: 486          moltype = DNA   length = 20
FEATURE                 Location/Qualifiers
source                  1..20
                        mol_type = genomic DNA
                        organism = Homo sapiens
SEQUENCE: 486
aggcgtattg taccctggaa                                               20

SEQ ID NO: 487          moltype = DNA   length = 20
FEATURE                 Location/Qualifiers
source                  1..20
                        mol_type = genomic DNA
                        organism = Homo sapiens
SEQUENCE: 487
acgtgagatt ctttctctga                                               20

SEQ ID NO: 488          moltype = DNA   length = 20
FEATURE                 Location/Qualifiers
source                  1..20
                        mol_type = genomic DNA
                        organism = Homo sapiens
SEQUENCE: 488
ccagtcacac atgagaatgt                                               20

SEQ ID NO: 489          moltype = DNA   length = 20
FEATURE                 Location/Qualifiers
source                  1..20
                        mol_type = genomic DNA
                        organism = Homo sapiens
SEQUENCE: 489
gaagcagtgc aaacgccatg                                               20

SEQ ID NO: 490          moltype = DNA   length = 20
FEATURE                 Location/Qualifiers
source                  1..20
                        mol_type = genomic DNA
                        organism = Homo sapiens
SEQUENCE: 490
acattctgaa ggattgtcca                                               20

SEQ ID NO: 491          moltype = DNA   length = 20
FEATURE                 Location/Qualifiers
```

| | | |
|---|---|---|
| source | 1..20<br>mol_type = genomic DNA<br>organism = Mus musculus | |
| SEQUENCE: 491<br>agttgacaat gaaatactgc | | 20 |
| SEQ ID NO: 492<br>FEATURE<br>source | moltype = DNA   length = 20<br>Location/Qualifiers<br>1..20<br>mol_type = genomic DNA<br>organism = Mus musculus | |
| SEQUENCE: 492<br>aatatcatct gtgaatactg | | 20 |
| SEQ ID NO: 493<br>FEATURE<br>source | moltype = DNA   length = 20<br>Location/Qualifiers<br>1..20<br>mol_type = genomic DNA<br>organism = Mus musculus | |
| SEQUENCE: 493<br>taaaggctgt ttgcaaaaga | | 20 |
| SEQ ID NO: 494<br>FEATURE<br>source | moltype = DNA   length = 20<br>Location/Qualifiers<br>1..20<br>mol_type = genomic DNA<br>organism = Mus musculus | |
| SEQUENCE: 494<br>tgcaaacacc atgtggccac | | 20 |
| SEQ ID NO: 495<br>FEATURE<br>source | moltype = DNA   length = 20<br>Location/Qualifiers<br>1..20<br>mol_type = genomic DNA<br>organism = Mus musculus | |
| SEQUENCE: 495<br>gcgagagatt ctttccctga | | 20 |
| SEQ ID NO: 496<br>FEATURE<br>source | moltype = DNA   length = 20<br>Location/Qualifiers<br>1..20<br>mol_type = genomic DNA<br>organism = Mus musculus | |
| SEQUENCE: 496<br>atcctcatca gagaacaggt | | 20 |
| SEQ ID NO: 497<br>FEATURE<br>source | moltype = DNA   length = 20<br>Location/Qualifiers<br>1..20<br>mol_type = genomic DNA<br>organism = Mus musculus | |
| SEQUENCE: 497<br>acggtaaagt gcccaaataa | | 20 |
| SEQ ID NO: 498<br>FEATURE<br>source | moltype = DNA   length = 20<br>Location/Qualifiers<br>1..20<br>mol_type = genomic DNA<br>organism = Mus musculus | |
| SEQUENCE: 498<br>ttaaactgtg agaacagctg | | 20 |
| SEQ ID NO: 499<br>FEATURE<br>source | moltype = DNA   length = 20<br>Location/Qualifiers<br>1..20<br>mol_type = genomic DNA<br>organism = Mus musculus | |
| SEQUENCE: 499<br>tctttgttgc aggagtctga | | 20 |
| SEQ ID NO: 500<br>FEATURE<br>source | moltype = DNA   length = 20<br>Location/Qualifiers<br>1..20<br>mol_type = genomic DNA<br>organism = Mus musculus | |
| SEQUENCE: 500<br>caggggcttg ttatgaggta | | 20 |
| SEQ ID NO: 501 | moltype = DNA   length = 20 | |

| | | |
|---|---|---|
| FEATURE | Location/Qualifiers | |
| source | 1..20 mol_type = genomic DNA organism = Mus musculus | |
| SEQUENCE: 501 ctgattgatg gtagcaggga | | 20 |
| SEQ ID NO: 502 FEATURE source | moltype = DNA length = 20 Location/Qualifiers 1..20 mol_type = genomic DNA organism = Mus musculus | |
| SEQUENCE: 502 ccttatcttc agtcacatgc | | 20 |
| SEQ ID NO: 503 FEATURE source | moltype = DNA length = 20 Location/Qualifiers 1..20 mol_type = genomic DNA organism = Mus musculus | |
| SEQUENCE: 503 tcacatgctg gcagaaatca | | 20 |
| SEQ ID NO: 504 FEATURE source | moltype = DNA length = 20 Location/Qualifiers 1..20 mol_type = genomic DNA organism = Mus musculus | |
| SEQUENCE: 504 ttctgtcgct gtgagataaa | | 20 |
| SEQ ID NO: 505 FEATURE source | moltype = DNA length = 20 Location/Qualifiers 1..20 mol_type = genomic DNA organism = Mus musculus | |
| SEQUENCE: 505 acaaggcagt acctgccacg | | 20 |
| SEQ ID NO: 506 FEATURE source | moltype = DNA length = 20 Location/Qualifiers 1..20 mol_type = genomic DNA organism = Mus musculus | |
| SEQUENCE: 506 tgtgactcac ccgggataca | | 20 |
| SEQ ID NO: 507 FEATURE source | moltype = DNA length = 20 Location/Qualifiers 1..20 mol_type = genomic DNA organism = Mus musculus | |
| SEQUENCE: 507 gaggtccatc agatcagctc | | 20 |
| SEQ ID NO: 508 FEATURE source | moltype = DNA length = 20 Location/Qualifiers 1..20 mol_type = genomic DNA organism = Mus musculus | |
| SEQUENCE: 508 atctccctgg aactggccat | | 20 |
| SEQ ID NO: 509 FEATURE source | moltype = DNA length = 20 Location/Qualifiers 1..20 mol_type = genomic DNA organism = Mus musculus | |
| SEQUENCE: 509 tgcaaaaatt gcaaaactca | | 20 |
| SEQ ID NO: 510 FEATURE source | moltype = DNA length = 20 Location/Qualifiers 1..20 mol_type = genomic DNA organism = Mus musculus | |
| SEQUENCE: 510 tgcacagaac tattgtacca | | 20 |

```
SEQ ID NO: 511          moltype = DNA    length = 20
FEATURE                 Location/Qualifiers
source                  1..20
                        mol_type = genomic DNA
                        organism = Mus musculus
SEQUENCE: 511
cagattagtg cttaccttcc                                                   20

SEQ ID NO: 512          moltype = DNA    length = 20
FEATURE                 Location/Qualifiers
source                  1..20
                        mol_type = genomic DNA
                        organism = Mus musculus
SEQUENCE: 512
attccgtaaa atagagcccc                                                   20

SEQ ID NO: 513          moltype = DNA    length = 20
FEATURE                 Location/Qualifiers
source                  1..20
                        mol_type = genomic DNA
                        organism = Mus musculus
SEQUENCE: 513
ctgcactcgg ctgggacaat                                                   20

SEQ ID NO: 514          moltype = DNA    length = 20
FEATURE                 Location/Qualifiers
source                  1..20
                        mol_type = genomic DNA
                        organism = Homo sapiens
SEQUENCE: 514
ccttatgaaa aagtcaaaac                                                   20

SEQ ID NO: 515          moltype = DNA    length = 20
FEATURE                 Location/Qualifiers
source                  1..20
                        mol_type = genomic DNA
                        organism = Homo sapiens
SEQUENCE: 515
aaaatatcaa gtatatatgg                                                   20

SEQ ID NO: 516          moltype = DNA    length = 20
FEATURE                 Location/Qualifiers
source                  1..20
                        mol_type = genomic DNA
                        organism = Homo sapiens
SEQUENCE: 516
tctagcatcg gcatgccaaa                                                   20

SEQ ID NO: 517          moltype = DNA    length = 20
FEATURE                 Location/Qualifiers
source                  1..20
                        mol_type = genomic DNA
                        organism = Homo sapiens
SEQUENCE: 517
ttggaagctc atggacaaag                                                   20

SEQ ID NO: 518          moltype = DNA    length = 20
FEATURE                 Location/Qualifiers
source                  1..20
                        mol_type = genomic DNA
                        organism = Homo sapiens
SEQUENCE: 518
gatttcctcc tcgaccacca                                                   20

SEQ ID NO: 519          moltype = DNA    length = 20
FEATURE                 Location/Qualifiers
source                  1..20
                        mol_type = genomic DNA
                        organism = Homo sapiens
SEQUENCE: 519
cttcatctct tggatcaaag                                                   20

SEQ ID NO: 520          moltype = DNA    length = 20
FEATURE                 Location/Qualifiers
source                  1..20
                        mol_type = genomic DNA
                        organism = Homo sapiens
SEQUENCE: 520
aatgtatgaa gaacagtcac                                                   20
```

```
SEQ ID NO: 521          moltype = DNA   length = 20
FEATURE                 Location/Qualifiers
source                  1..20
                        mol_type = genomic DNA
                        organism = Homo sapiens
SEQUENCE: 521
taaacttacc tgaaacagcc                                                    20

SEQ ID NO: 522          moltype = DNA   length = 20
FEATURE                 Location/Qualifiers
source                  1..20
                        mol_type = genomic DNA
                        organism = Homo sapiens
SEQUENCE: 522
aagaatatga tgttcctccc                                                    20

SEQ ID NO: 523          moltype = DNA   length = 20
FEATURE                 Location/Qualifiers
source                  1..20
                        mol_type = genomic DNA
                        organism = Homo sapiens
SEQUENCE: 523
agcaagctgc cgcagatcgc                                                    20

SEQ ID NO: 524          moltype = DNA   length = 20
FEATURE                 Location/Qualifiers
source                  1..20
                        mol_type = genomic DNA
                        organism = Homo sapiens
SEQUENCE: 524
agtactcatt ctcactgagt                                                    20

SEQ ID NO: 525          moltype = DNA   length = 20
FEATURE                 Location/Qualifiers
source                  1..20
                        mol_type = genomic DNA
                        organism = Mus musculus
SEQUENCE: 525
gatgaccaga gactatctgt                                                    20

SEQ ID NO: 526          moltype = DNA   length = 20
FEATURE                 Location/Qualifiers
source                  1..20
                        mol_type = genomic DNA
                        organism = Mus musculus
SEQUENCE: 526
cctaaacagt gccattatga                                                    20

SEQ ID NO: 527          moltype = DNA   length = 20
FEATURE                 Location/Qualifiers
source                  1..20
                        mol_type = genomic DNA
                        organism = Mus musculus
SEQUENCE: 527
ctatctgtcg gtgaaggtct                                                    20

SEQ ID NO: 528          moltype = DNA   length = 20
FEATURE                 Location/Qualifiers
source                  1..20
                        mol_type = genomic DNA
                        organism = Mus musculus
SEQUENCE: 528
gaatatatac aagttattgg                                                    20

SEQ ID NO: 529          moltype = DNA   length = 20
FEATURE                 Location/Qualifiers
source                  1..20
                        mol_type = genomic DNA
                        organism = Mus musculus
SEQUENCE: 529
tggggtgcca ggctgtgtgg                                                    20

SEQ ID NO: 530          moltype = DNA   length = 20
FEATURE                 Location/Qualifiers
source                  1..20
                        mol_type = genomic DNA
                        organism = Mus musculus
SEQUENCE: 530
```

| | |
|---|---|
| catgtttcct tgcagaataa | 20 |

SEQ ID NO: 531  moltype = DNA  length = 20
FEATURE  Location/Qualifiers
source  1..20
  mol_type = genomic DNA
  organism = Mus musculus SEQUENCE: 531
aagttcgagt gctgctggaa                                                   20

SEQ ID NO: 532  moltype = DNA  length = 20
FEATURE  Location/Qualifiers
source  1..20
  mol_type = genomic DNA
  organism = Mus musculus SEQUENCE: 532
catcaagcca gctaatatgg                                                   20

SEQ ID NO: 533  moltype = DNA  length = 20
FEATURE  Location/Qualifiers
source  1..20
  mol_type = genomic DNA
  organism = Homo sapiens SEQUENCE: 533
aaatgagcag cattctgttg                                                   20

SEQ ID NO: 534  moltype = DNA  length = 20
FEATURE  Location/Qualifiers
source  1..20
  mol_type = genomic DNA
  organism = Homo sapiens SEQUENCE: 534
cttcttgcaa caggagacaa                                                   20

SEQ ID NO: 535  moltype = DNA  length = 20
FEATURE  Location/Qualifiers
source  1..20
  mol_type = genomic DNA
  organism = Homo sapiens SEQUENCE: 535
tggaacggtt cggataggta                                                   20

SEQ ID NO: 536  moltype = DNA  length = 20
FEATURE  Location/Qualifiers
source  1..20
  mol_type = genomic DNA
  organism = Homo sapiens SEQUENCE: 536
catcaagcct gctaacatgg                                                   20

SEQ ID NO: 537  moltype = DNA  length = 20
FEATURE  Location/Qualifiers
source  1..20
  mol_type = genomic DNA
  organism = Homo sapiens SEQUENCE: 537
ggcgtggaga ggagagctcg                                                   20

SEQ ID NO: 538  moltype = DNA  length = 20
FEATURE  Location/Qualifiers
source  1..20
  mol_type = genomic DNA
  organism = Homo sapiens SEQUENCE: 538
atgatcacta tttactgaaa                                                   20

SEQ ID NO: 539  moltype = DNA  length = 20
FEATURE  Location/Qualifiers
source  1..20
  mol_type = genomic DNA
  organism = Homo sapiens SEQUENCE: 539
tcgtctacag cagtagcaaa                                                   20

SEQ ID NO: 540  moltype = DNA  length = 20
FEATURE  Location/Qualifiers
source  1..20
  mol_type = genomic DNA
  organism = Homo sapiens

```
SEQUENCE: 540
cagagactac ctgtcggtga                                               20

SEQ ID NO: 541          moltype = DNA  length = 20
FEATURE                 Location/Qualifiers
source                  1..20
                        mol_type = genomic DNA
                        organism = Homo sapiens
SEQUENCE: 541
gtgcttctcg caggtcaagg                                               20

SEQ ID NO: 542          moltype = DNA  length = 20
FEATURE                 Location/Qualifiers
source                  1..20
                        mol_type = genomic DNA
                        organism = Homo sapiens
SEQUENCE: 542
tggcggctca gcatgatctg                                               20

SEQ ID NO: 543          moltype = DNA  length = 20
FEATURE                 Location/Qualifiers
source                  1..20
                        mol_type = genomic DNA
                        organism = Mus musculus
SEQUENCE: 543
caacccacat ttcgatttgg                                               20

SEQ ID NO: 544          moltype = DNA  length = 20
FEATURE                 Location/Qualifiers
source                  1..20
                        mol_type = genomic DNA
                        organism = Mus musculus
SEQUENCE: 544
agccattcac acttctcact                                               20

SEQ ID NO: 545          moltype = DNA  length = 20
FEATURE                 Location/Qualifiers
source                  1..20
                        mol_type = genomic DNA
                        organism = Mus musculus
SEQUENCE: 545
ccggctgtca cttaccgctg                                               20

SEQ ID NO: 546          moltype = DNA  length = 20
FEATURE                 Location/Qualifiers
source                  1..20
                        mol_type = genomic DNA
                        organism = Mus musculus
SEQUENCE: 546
tttgtttcac agtcgttcga                                               20

SEQ ID NO: 547          moltype = DNA  length = 20
FEATURE                 Location/Qualifiers
source                  1..20
                        mol_type = genomic DNA
                        organism = Mus musculus
SEQUENCE: 547
tggtaagaat gagggtaacc                                               20

SEQ ID NO: 548          moltype = DNA  length = 20
FEATURE                 Location/Qualifiers
source                  1..20
                        mol_type = genomic DNA
                        organism = Mus musculus
SEQUENCE: 548
gctgcggaaa gcgcccgcca                                               20

SEQ ID NO: 549          moltype = DNA  length = 20
FEATURE                 Location/Qualifiers
source                  1..20
                        mol_type = genomic DNA
                        organism = Mus musculus
SEQUENCE: 549
gttgatcatg attctctggt                                               20

SEQ ID NO: 550          moltype = DNA  length = 20
FEATURE                 Location/Qualifiers
source                  1..20
                        mol_type = genomic DNA
```

```
                              organism = Mus musculus
SEQUENCE: 550
ttgttgcaga caaatgtggc                                                      20

SEQ ID NO: 551           moltype = DNA  length = 20
FEATURE                  Location/Qualifiers
source                   1..20
                         mol_type = genomic DNA
                         organism = Mus musculus
SEQUENCE: 551
ctatgaccgg ctggagatct                                                      20

SEQ ID NO: 552           moltype = DNA  length = 20
FEATURE                  Location/Qualifiers
source                   1..20
                         mol_type = genomic DNA
                         organism = Mus musculus
SEQUENCE: 552
cacatgtccg gctctcatgt                                                      20

SEQ ID NO: 553           moltype = DNA  length = 20
FEATURE                  Location/Qualifiers
source                   1..20
                         mol_type = genomic DNA
                         organism = Mus musculus
SEQUENCE: 553
gaggtgtcat cattcagggt                                                      20

SEQ ID NO: 554           moltype = DNA  length = 20
FEATURE                  Location/Qualifiers
source                   1..20
                         mol_type = genomic DNA
                         organism = Mus musculus
SEQUENCE: 554
ccagggtacc tcacatctcc                                                      20

SEQ ID NO: 555           moltype = DNA  length = 20
FEATURE                  Location/Qualifiers
source                   1..20
                         mol_type = genomic DNA
                         organism = Mus musculus
SEQUENCE: 555
aaacctgtat cctgggaaac                                                      20

SEQ ID NO: 556           moltype = DNA  length = 20
FEATURE                  Location/Qualifiers
source                   1..20
                         mol_type = genomic DNA
                         organism = Homo sapiens
SEQUENCE: 556
agaccagttg gtgctatact                                                      20

SEQ ID NO: 557           moltype = DNA  length = 20
FEATURE                  Location/Qualifiers
source                   1..20
                         mol_type = genomic DNA
                         organism = Homo sapiens
SEQUENCE: 557
agtggagtga taaagtcccc                                                      20

SEQ ID NO: 558           moltype = DNA  length = 20
FEATURE                  Location/Qualifiers
source                   1..20
                         mol_type = genomic DNA
                         organism = Homo sapiens
SEQUENCE: 558
gaccggctag aaatctggga                                                      20

SEQ ID NO: 559           moltype = DNA  length = 20
FEATURE                  Location/Qualifiers
source                   1..20
                         mol_type = genomic DNA
                         organism = Homo sapiens
SEQUENCE: 559
cctcacattg ggcgttactg                                                      20

SEQ ID NO: 560           moltype = DNA  length = 20
FEATURE                  Location/Qualifiers
source                   1..20
```

```
                        mol_type = genomic DNA
                        organism = Homo sapiens
SEQUENCE: 560
ggatgttctg tcgctacgac                                              20

SEQ ID NO: 561          moltype = DNA  length = 20
FEATURE                 Location/Qualifiers
source                  1..20
                        mol_type = genomic DNA
                        organism = Homo sapiens
SEQUENCE: 561
cctgactcaa atcctccagg                                              20

SEQ ID NO: 562          moltype = DNA  length = 20
FEATURE                 Location/Qualifiers
source                  1..20
                        mol_type = genomic DNA
                        organism = Homo sapiens
SEQUENCE: 562
agagaatgcc cgatgaggat                                              20

SEQ ID NO: 563          moltype = DNA  length = 20
FEATURE                 Location/Qualifiers
source                  1..20
                        mol_type = genomic DNA
                        organism = Homo sapiens
SEQUENCE: 563
tacctgtatc cactctcggt                                              20

SEQ ID NO: 564          moltype = DNA  length = 20
FEATURE                 Location/Qualifiers
source                  1..20
                        mol_type = genomic DNA
                        organism = Homo sapiens
SEQUENCE: 564
tgtcctccaa atcgaagtga                                              20

SEQ ID NO: 565          moltype = DNA  length = 20
FEATURE                 Location/Qualifiers
source                  1..20
                        mol_type = genomic DNA
                        organism = Homo sapiens
SEQUENCE: 565
cattctcagg gtagttcagg                                              20

SEQ ID NO: 566          moltype = DNA  length = 20
FEATURE                 Location/Qualifiers
source                  1..20
                        mol_type = genomic DNA
                        organism = Homo sapiens
SEQUENCE: 566
tactgtggac agaaaacacc                                              20

SEQ ID NO: 567          moltype = DNA  length = 20
FEATURE                 Location/Qualifiers
source                  1..20
                        mol_type = genomic DNA
                        organism = Mus musculus
SEQUENCE: 567
gcccttagc tggtatctgc                                               20

SEQ ID NO: 568          moltype = DNA  length = 20
FEATURE                 Location/Qualifiers
source                  1..20
                        mol_type = genomic DNA
                        organism = Mus musculus
SEQUENCE: 568
atcagaactg ctatccacat                                              20

SEQ ID NO: 569          moltype = DNA  length = 20
FEATURE                 Location/Qualifiers
source                  1..20
                        mol_type = genomic DNA
                        organism = Mus musculus
SEQUENCE: 569
catggcagag acacagacac                                              20

SEQ ID NO: 570          moltype = DNA  length = 20
FEATURE                 Location/Qualifiers
```

```
source                      1..20
                            mol_type = genomic DNA
                            organism = Mus musculus
SEQUENCE: 570
cgaggagaac gtatatgaag                                                    20

SEQ ID NO: 571              moltype = DNA   length = 20
FEATURE                     Location/Qualifiers
source                      1..20
                            mol_type = genomic DNA
                            organism = Mus musculus
SEQUENCE: 571
aatgtgactc tggatgacca                                                    20

SEQ ID NO: 572              moltype = DNA   length = 20
FEATURE                     Location/Qualifiers
source                      1..20
                            mol_type = genomic DNA
                            organism = Mus musculus
SEQUENCE: 572
ggaaatatc tacaccatcg                                                     20

SEQ ID NO: 573              moltype = DNA   length = 20
FEATURE                     Location/Qualifiers
source                      1..20
                            mol_type = genomic DNA
                            organism = Mus musculus
SEQUENCE: 573
gtagtagttg cagcagcagc                                                    20

SEQ ID NO: 574              moltype = DNA   length = 20
FEATURE                     Location/Qualifiers
source                      1..20
                            mol_type = genomic DNA
                            organism = Mus musculus
SEQUENCE: 574
ttggagtggg agtctctgct                                                    20

SEQ ID NO: 575              moltype = DNA   length = 20
FEATURE                     Location/Qualifiers
source                      1..20
                            mol_type = genomic DNA
                            organism = Mus musculus
SEQUENCE: 575
tccttacttt atagggtcat                                                    20

SEQ ID NO: 576              moltype = DNA   length = 20
FEATURE                     Location/Qualifiers
source                      1..20
                            mol_type = genomic DNA
                            organism = Mus musculus
SEQUENCE: 576
caacttgcct ccaggagggt                                                    20

SEQ ID NO: 577              moltype = DNA   length = 20
FEATURE                     Location/Qualifiers
source                      1..20
                            mol_type = genomic DNA
                            organism = Mus musculus
SEQUENCE: 577
atgtgactct ggatgaccat                                                    20

SEQ ID NO: 578              moltype = DNA   length = 20
FEATURE                     Location/Qualifiers
source                      1..20
                            mol_type = genomic DNA
                            organism = Mus musculus
SEQUENCE: 578
ggggcaaggg attctgtcct                                                    20

SEQ ID NO: 579              moltype = DNA   length = 20
FEATURE                     Location/Qualifiers
source                      1..20
                            mol_type = genomic DNA
                            organism = Mus musculus
SEQUENCE: 579
actgctatcc acattggagt                                                    20

SEQ ID NO: 580              moltype = DNA   length = 20
```

-continued

| | | |
|---|---|---|
| FEATURE | Location/Qualifiers | |
| source | 1..20<br>mol_type = genomic DNA<br>organism = Mus musculus | |
| SEQUENCE: 580 | | |
| aaccatttct ctccgtggtt | | 20 |
| SEQ ID NO: 581 | moltype = DNA length = 20 | |
| FEATURE | Location/Qualifiers | |
| source | 1..20<br>mol_type = genomic DNA<br>organism = Mus musculus | |
| SEQUENCE: 581 | | |
| agtgtaactg cagggcagat | | 20 |
| SEQ ID NO: 582 | moltype = DNA length = 20 | |
| FEATURE | Location/Qualifiers | |
| source | 1..20<br>mol_type = genomic DNA<br>organism = Homo sapiens | |
| SEQUENCE: 582 | | |
| agaagtggaa tacagagcgg | | 20 |
| SEQ ID NO: 583 | moltype = DNA length = 20 | |
| FEATURE | Location/Qualifiers | |
| source | 1..20<br>mol_type = genomic DNA<br>organism = Homo sapiens | |
| SEQUENCE: 583 | | |
| atcagaatag gcatctacat | | 20 |
| SEQ ID NO: 584 | moltype = DNA length = 20 | |
| FEATURE | Location/Qualifiers | |
| source | 1..20<br>mol_type = genomic DNA<br>organism = Homo sapiens | |
| SEQUENCE: 584 | | |
| ggtgtagaag cagggcagat | | 20 |
| SEQ ID NO: 585 | moltype = DNA length = 20 | |
| FEATURE | Location/Qualifiers | |
| source | 1..20<br>mol_type = genomic DNA<br>organism = Homo sapiens | |
| SEQUENCE: 585 | | |
| aacctcgtgc ccgtctgctg | | 20 |
| SEQ ID NO: 586 | moltype = DNA length = 20 | |
| FEATURE | Location/Qualifiers | |
| source | 1..20<br>mol_type = genomic DNA<br>organism = Homo sapiens | |
| SEQUENCE: 586 | | |
| aagagaagat acagaattta | | 20 |
| SEQ ID NO: 587 | moltype = DNA length = 20 | |
| FEATURE | Location/Qualifiers | |
| source | 1..20<br>mol_type = genomic DNA<br>organism = Homo sapiens | |
| SEQUENCE: 587 | | |
| atgtgactct agcagacagt | | 20 |
| SEQ ID NO: 588 | moltype = DNA length = 20 | |
| FEATURE | Location/Qualifiers | |
| source | 1..20<br>mol_type = genomic DNA<br>organism = Homo sapiens | |
| SEQUENCE: 588 | | |
| tctacacccc agccgcccca | | 20 |
| SEQ ID NO: 589 | moltype = DNA length = 20 | |
| FEATURE | Location/Qualifiers | |
| source | 1..20<br>mol_type = genomic DNA<br>organism = Homo sapiens | |
| SEQUENCE: 589 | | |
| acatccagat actggctaaa | | 20 |

```
SEQ ID NO: 590          moltype = DNA   length = 20
FEATURE                 Location/Qualifiers
source                  1..20
                        mol_type = genomic DNA
                        organism = Homo sapiens
SEQUENCE: 590
tgtgtttgaa tgtggcaacg                                                     20

SEQ ID NO: 591          moltype = DNA   length = 20
FEATURE                 Location/Qualifiers
source                  1..20
                        mol_type = genomic DNA
                        organism = Homo sapiens
SEQUENCE: 591
agtcacattc tctatggtca                                                     20

SEQ ID NO: 592          moltype = DNA   length = 20
FEATURE                 Location/Qualifiers
source                  1..20
                        mol_type = genomic DNA
                        organism = Homo sapiens
SEQUENCE: 592
agtcggtgca ggggtgacct                                                     20

SEQ ID NO: 593          moltype = DNA   length = 20
FEATURE                 Location/Qualifiers
source                  1..20
                        mol_type = genomic DNA
                        organism = Homo sapiens
SEQUENCE: 593
tggccaaaga gatgaggctg                                                     20

SEQ ID NO: 594          moltype = DNA   length = 20
FEATURE                 Location/Qualifiers
source                  1..20
                        mol_type = genomic DNA
                        organism = Mus musculus
SEQUENCE: 594
actcctgggg gcaaatgaca                                                     20

SEQ ID NO: 595          moltype = DNA   length = 20
FEATURE                 Location/Qualifiers
source                  1..20
                        mol_type = genomic DNA
                        organism = Mus musculus
SEQUENCE: 595
tgaagccatc tctgtaggtg                                                     20

SEQ ID NO: 596          moltype = DNA   length = 20
FEATURE                 Location/Qualifiers
source                  1..20
                        mol_type = genomic DNA
                        organism = Mus musculus
SEQUENCE: 596
ggctgaagga gcagttcaaa                                                     20

SEQ ID NO: 597          moltype = DNA   length = 20
FEATURE                 Location/Qualifiers
source                  1..20
                        mol_type = genomic DNA
                        organism = Mus musculus
SEQUENCE: 597
tgccactctt tccagccacg                                                     20

SEQ ID NO: 598          moltype = DNA   length = 20
FEATURE                 Location/Qualifiers
source                  1..20
                        mol_type = genomic DNA
                        organism = Mus musculus
SEQUENCE: 598
aagtcagccc cctggactct                                                     20

SEQ ID NO: 599          moltype = DNA   length = 20
FEATURE                 Location/Qualifiers
source                  1..20
                        mol_type = genomic DNA
                        organism = Mus musculus
SEQUENCE: 599
acagtgattg ctagtccctc                                                     20
```

```
SEQ ID NO: 600           moltype = DNA   length = 20
FEATURE                  Location/Qualifiers
source                   1..20
                         mol_type = genomic DNA
                         organism = Mus musculus
SEQUENCE: 600
agccccaggt cccagagtcc                                                    20

SEQ ID NO: 601           moltype = DNA   length = 20
FEATURE                  Location/Qualifiers
source                   1..20
                         mol_type = genomic DNA
                         organism = Mus musculus
SEQUENCE: 601
ctgtgggtct ggcacaggct                                                    20

SEQ ID NO: 602           moltype = DNA   length = 20
FEATURE                  Location/Qualifiers
source                   1..20
                         mol_type = genomic DNA
                         organism = Mus musculus
SEQUENCE: 602
gccaagtgga ctcctcctgg                                                    20

SEQ ID NO: 603           moltype = DNA   length = 20
FEATURE                  Location/Qualifiers
source                   1..20
                         mol_type = genomic DNA
                         organism = Mus musculus
SEQUENCE: 603
gtaggtgagg acacagcccc                                                    20

SEQ ID NO: 604           moltype = DNA   length = 20
FEATURE                  Location/Qualifiers
source                   1..20
                         mol_type = genomic DNA
                         organism = Mus musculus
SEQUENCE: 604
tgcacagaga ctgggcggtc                                                    20

SEQ ID NO: 605           moltype = DNA   length = 20
FEATURE                  Location/Qualifiers
source                   1..20
                         mol_type = genomic DNA
                         organism = Mus musculus
SEQUENCE: 605
acgtacaacc tcaaggttct                                                    20

SEQ ID NO: 606           moltype = DNA   length = 20
FEATURE                  Location/Qualifiers
source                   1..20
                         mol_type = genomic DNA
                         organism = Mus musculus
SEQUENCE: 606
gctcaatgcc actgtcacgt                                                    20

SEQ ID NO: 607           moltype = DNA   length = 20
FEATURE                  Location/Qualifiers
source                   1..20
                         mol_type = genomic DNA
                         organism = Mus musculus
SEQUENCE: 607
agtctctgtg cactggttcc                                                    20

SEQ ID NO: 608           moltype = DNA   length = 20
FEATURE                  Location/Qualifiers
source                   1..20
                         mol_type = genomic DNA
                         organism = Mus musculus
SEQUENCE: 608
tgggcggtca ggacggctga                                                    20

SEQ ID NO: 609           moltype = DNA   length = 20
FEATURE                  Location/Qualifiers
source                   1..20
                         mol_type = genomic DNA
                         organism = Homo sapiens
SEQUENCE: 609
```

```
gttccggaac caatgcacag                                                    20

SEQ ID NO: 610          moltype = DNA   length = 20
FEATURE                 Location/Qualifiers
source                  1..20
                        mol_type = genomic DNA
                        organism = Homo sapiens
SEQUENCE: 610
tgcgaagagc aggggtcact                                                    20

SEQ ID NO: 611          moltype = DNA   length = 20
FEATURE                 Location/Qualifiers
source                  1..20
                        mol_type = genomic DNA
                        organism = Homo sapiens
SEQUENCE: 611
gcggtccctg aggtgcaccg                                                    20

SEQ ID NO: 612          moltype = DNA   length = 20
FEATURE                 Location/Qualifiers
source                  1..20
                        mol_type = genomic DNA
                        organism = Homo sapiens
SEQUENCE: 612
tccccacacc agcaggcagg                                                    20

SEQ ID NO: 613          moltype = DNA   length = 20
FEATURE                 Location/Qualifiers
source                  1..20
                        mol_type = genomic DNA
                        organism = Homo sapiens
SEQUENCE: 613
ccgctacacg gtgctgagcg                                                    20

SEQ ID NO: 614          moltype = DNA   length = 20
FEATURE                 Location/Qualifiers
source                  1..20
                        mol_type = genomic DNA
                        organism = Homo sapiens
SEQUENCE: 614
ccggtggtgt gggcccagga                                                    20

SEQ ID NO: 615          moltype = DNA   length = 20
FEATURE                 Location/Qualifiers
source                  1..20
                        mol_type = genomic DNA
                        organism = Homo sapiens
SEQUENCE: 615
gtttggggtg catacctgtc                                                    20

SEQ ID NO: 616          moltype = DNA   length = 20
FEATURE                 Location/Qualifiers
source                  1..20
                        mol_type = genomic DNA
                        organism = Homo sapiens
SEQUENCE: 616
aggctctgag agatcctggg                                                    20

SEQ ID NO: 617          moltype = DNA   length = 20
FEATURE                 Location/Qualifiers
source                  1..20
                        mol_type = genomic DNA
                        organism = Homo sapiens
SEQUENCE: 617
gctcaatgcc actgtcacat                                                    20

SEQ ID NO: 618          moltype = DNA   length = 20
FEATURE                 Location/Qualifiers
source                  1..20
                        mol_type = genomic DNA
                        organism = Homo sapiens
SEQUENCE: 618
gtcccggagg cctgcgcagc                                                    20

SEQ ID NO: 619          moltype = DNA   length = 20
FEATURE                 Location/Qualifiers
source                  1..20
                        mol_type = genomic DNA
                        organism = Homo sapiens
```

| | | |
|---|---|---|
| SEQUENCE: 619 gcagaaggct gagatcctgg | | 20 |
| SEQ ID NO: 620<br>FEATURE<br>source<br><br>SEQUENCE: 620<br>taggtgagga tgcagcccca | moltype = DNA  length = 20<br>Location/Qualifiers<br>1..20<br>mol_type = genomic DNA<br>organism = Homo sapiens | <br><br><br><br><br>20 |
| SEQ ID NO: 621<br>FEATURE<br>source<br><br>SEQUENCE: 621<br>ttcagtgatc gggtggtccc | moltype = DNA  length = 20<br>Location/Qualifiers<br>1..20<br>mol_type = genomic DNA<br>organism = Mus musculus | <br><br><br><br><br>20 |
| SEQ ID NO: 622<br>FEATURE<br>source<br><br>SEQUENCE: 622<br>gtctctgaca atgaatgaca | moltype = DNA  length = 20<br>Location/Qualifiers<br>1..20<br>mol_type = genomic DNA<br>organism = Mus musculus | <br><br><br><br><br>20 |
| SEQ ID NO: 623<br>FEATURE<br>source<br><br>SEQUENCE: 623<br>ctgagctttc ttggaccttc | moltype = DNA  length = 20<br>Location/Qualifiers<br>1..20<br>mol_type = genomic DNA<br>organism = Mus musculus | <br><br><br><br><br>20 |
| SEQ ID NO: 624<br>FEATURE<br>source<br><br>SEQUENCE: 624<br>aacatctctg cagaggaagg | moltype = DNA  length = 20<br>Location/Qualifiers<br>1..20<br>mol_type = genomic DNA<br>organism = Mus musculus | <br><br><br><br><br>20 |
| SEQ ID NO: 625<br>FEATURE<br>source<br><br>SEQUENCE: 625<br>caagggaga atattcctga | moltype = DNA  length = 20<br>Location/Qualifiers<br>1..20<br>mol_type = genomic DNA<br>organism = Mus musculus | <br><br><br><br><br>20 |
| SEQ ID NO: 626<br>FEATURE<br>source<br><br>SEQUENCE: 626<br>cactataaat ggccagaagc | moltype = DNA  length = 20<br>Location/Qualifiers<br>1..20<br>mol_type = genomic DNA<br>organism = Mus musculus | <br><br><br><br><br>20 |
| SEQ ID NO: 627<br>FEATURE<br>source<br><br>SEQUENCE: 627<br>caggcacgat agatacaaag | moltype = DNA  length = 20<br>Location/Qualifiers<br>1..20<br>mol_type = genomic DNA<br>organism = Mus musculus | <br><br><br><br><br>20 |
| SEQ ID NO: 628<br>FEATURE<br>source<br><br>SEQUENCE: 628<br>gtatcctggt gggatttaca | moltype = DNA  length = 20<br>Location/Qualifiers<br>1..20<br>mol_type = genomic DNA<br>organism = Mus musculus | <br><br><br><br><br>20 |
| SEQ ID NO: 629<br>FEATURE<br>source<br> | moltype = DNA  length = 20<br>Location/Qualifiers<br>1..20<br>mol_type = genomic DNA | |

```
                              organism = Mus musculus
SEQUENCE: 629
aggcagcctg tatcagcccc                                               20

SEQ ID NO: 631          moltype = DNA  length = 20
FEATURE                 Location/Qualifiers
source                  1..20
                        mol_type = genomic DNA
                        organism = Mus musculus
SEQUENCE: 630
gctgctcctg gtctgggtcc                                               20

SEQ ID NO: 631          moltype = DNA  length = 20
FEATURE                 Location/Qualifiers
source                  1..20
                        mol_type = genomic DNA
                        organism = Mus musculus
SEQUENCE: 631
tctctaggct tctgtagctc                                               20

SEQ ID NO: 632          moltype = DNA  length = 20
FEATURE                 Location/Qualifiers
source                  1..20
                        mol_type = genomic DNA
                        organism = Mus musculus
SEQUENCE: 632
ctgaagcgac atgccacccc                                               20

SEQ ID NO: 633          moltype = DNA  length = 20
FEATURE                 Location/Qualifiers
source                  1..20
                        mol_type = genomic DNA
                        organism = Mus musculus
SEQUENCE: 633
tctctgacaa tgaatgacac                                               20

SEQ ID NO: 634          moltype = DNA  length = 20
FEATURE                 Location/Qualifiers
source                  1..20
                        mol_type = genomic DNA
                        organism = Mus musculus
SEQUENCE: 634
ccatttatag tgttgacctg                                               20

SEQ ID NO: 635          moltype = DNA  length = 20
FEATURE                 Location/Qualifiers
source                  1..20
                        mol_type = genomic DNA
                        organism = Mus musculus
SEQUENCE: 635
tgccttcctc gctacaggta                                               20

SEQ ID NO: 636          moltype = DNA  length = 20
FEATURE                 Location/Qualifiers
source                  1..20
                        mol_type = genomic DNA
                        organism = Homo sapiens
SEQUENCE: 636
ttccacagaa tggattctga                                               20

SEQ ID NO: 637          moltype = DNA  length = 20
FEATURE                 Location/Qualifiers
source                  1..20
                        mol_type = genomic DNA
                        organism = Homo sapiens
SEQUENCE: 637
gctgaccgtg aacgatacag                                               20

SEQ ID NO: 638          moltype = DNA  length = 20
FEATURE                 Location/Qualifiers
source                  1..20
                        mol_type = genomic DNA
                        organism = Homo sapiens
SEQUENCE: 638
cccatccttc aaggatcgag                                               20

SEQ ID NO: 639          moltype = DNA  length = 20
FEATURE                 Location/Qualifiers
source                  1..20
```

```
                        mol_type = genomic DNA
                        organism = Homo sapiens
SEQUENCE: 639
caccacggca caagtgaccc                                               20

SEQ ID NO: 641          moltype = DNA   length = 20
FEATURE                 Location/Qualifiers
source                  1..20
                        mol_type = genomic DNA
                        organism = Homo sapiens
SEQUENCE: 640
atgtcacctc tcctccacca                                               20

SEQ ID NO: 641          moltype = DNA   length = 20
FEATURE                 Location/Qualifiers
source                  1..20
                        mol_type = genomic DNA
                        organism = Homo sapiens
SEQUENCE: 641
agtgtacgtc ccatcagggt                                               20

SEQ ID NO: 642          moltype = DNA   length = 20
FEATURE                 Location/Qualifiers
source                  1..20
                        mol_type = genomic DNA
                        organism = Homo sapiens
SEQUENCE: 642
gttcacggtc agcgactgga                                               20

SEQ ID NO: 643          moltype = DNA   length = 20
FEATURE                 Location/Qualifiers
source                  1..20
                        mol_type = genomic DNA
                        organism = Homo sapiens
SEQUENCE: 643
gcagatgacc accagcgtcg                                               20

SEQ ID NO: 644          moltype = DNA   length = 20
FEATURE                 Location/Qualifiers
source                  1..20
                        mol_type = genomic DNA
                        organism = Homo sapiens
SEQUENCE: 644
aacatttctg cagagaaagg                                               20

SEQ ID NO: 645          moltype = DNA   length = 20
FEATURE                 Location/Qualifiers
source                  1..20
                        mol_type = genomic DNA
                        organism = Homo sapiens
SEQUENCE: 645
ctgctgctcc cagttgacct                                               20

SEQ ID NO: 646          moltype = DNA   length = 20
FEATURE                 Location/Qualifiers
source                  1..20
                        mol_type = genomic DNA
                        organism = Homo sapiens
SEQUENCE: 646
aggccacatc tgcttcctgt                                               20

SEQ ID NO: 647          moltype = DNA   length = 20
FEATURE                 Location/Qualifiers
source                  1..20
                        mol_type = genomic DNA
                        organism = Homo sapiens
SEQUENCE: 647
ggtggtcgcg ttgactagaa                                               20

SEQ ID NO: 648          moltype = DNA   length = 20
FEATURE                 Location/Qualifiers
source                  1..20
                        mol_type = genomic DNA
                        organism = Mus musculus
SEQUENCE: 648
aagaagtcct cttacaacag                                               20

SEQ ID NO: 649          moltype = DNA   length = 20
FEATURE                 Location/Qualifiers
```

```
source                       1..20
                             mol_type = genomic DNA
                             organism = Mus musculus
SEQUENCE: 649
tccaagacaa gccatggctg                                                     20

SEQ ID NO: 650               moltype = DNA   length = 20
FEATURE                      Location/Qualifiers
source                       1..20
                             mol_type = genomic DNA
                             organism = Mus musculus
SEQUENCE: 650
tgctccttct tcttcataaa                                                     20

SEQ ID NO: 651               moltype = DNA   length = 20
FEATURE                      Location/Qualifiers
source                       1..20
                             mol_type = genomic DNA
                             organism = Mus musculus
SEQUENCE: 651
acaaaaggcc aagtcctaga                                                     20

SEQ ID NO: 652               moltype = DNA   length = 20
FEATURE                      Location/Qualifiers
source                       1..20
                             mol_type = genomic DNA
                             organism = Mus musculus
SEQUENCE: 652
tgaaattgct tttcacattc                                                     20

SEQ ID NO: 653               moltype = DNA   length = 20
FEATURE                      Location/Qualifiers
source                       1..20
                             mol_type = genomic DNA
                             organism = Mus musculus
SEQUENCE: 653
cacacaaacac tgatgaggtc                                                    20

SEQ ID NO: 654               moltype = DNA   length = 20
FEATURE                      Location/Qualifiers
source                       1..20
                             mol_type = genomic DNA
                             organism = Mus musculus
SEQUENCE: 654
gtggtgttgg ctagcagcca                                                     20

SEQ ID NO: 655               moltype = DNA   length = 20
FEATURE                      Location/Qualifiers
source                       1..20
                             mol_type = genomic DNA
                             organism = Mus musculus
SEQUENCE: 655
cccatgccca caaagtatgg                                                     20

SEQ ID NO: 656               moltype = DNA   length = 20
FEATURE                      Location/Qualifiers
source                       1..20
                             mol_type = genomic DNA
                             organism = Mus musculus
SEQUENCE: 656
aggtccgggt gactgtgctg                                                     20

SEQ ID NO: 657               moltype = DNA   length = 20
FEATURE                      Location/Qualifiers
source                       1..20
                             mol_type = genomic DNA
                             organism = Mus musculus
SEQUENCE: 657
aggactgaga gctgttgaca                                                     20

SEQ ID NO: 658               moltype = DNA   length = 20
FEATURE                      Location/Qualifiers
source                       1..20
                             mol_type = genomic DNA
                             organism = Mus musculus
SEQUENCE: 658
tgaatattca catggaaagc                                                     20

SEQ ID NO: 659               moltype = DNA   length = 20
```

```
FEATURE                 Location/Qualifiers
source                  1..20
                        mol_type = genomic DNA
                        organism = Mus musculus
SEQUENCE: 659
attaaaggta ccactgcaga                                                    20

SEQ ID NO: 660          moltype = DNA  length = 20
FEATURE                 Location/Qualifiers
source                  1..20
                        mol_type = genomic DNA
                        organism = Mus musculus
SEQUENCE: 660
cacgggactg tacctctgca                                                    20

SEQ ID NO: 661          moltype = DNA  length = 20
FEATURE                 Location/Qualifiers
source                  1..20
                        mol_type = genomic DNA
                        organism = Mus musculus
SEQUENCE: 661
acatgagttc caccttgcag                                                    20

SEQ ID NO: 662          moltype = DNA  length = 20
FEATURE                 Location/Qualifiers
source                  1..20
                        mol_type = genomic DNA
                        organism = Mus musculus
SEQUENCE: 662
ctagattacc ccttctgcag                                                    20

SEQ ID NO: 663          moltype = DNA  length = 20
FEATURE                 Location/Qualifiers
source                  1..20
                        mol_type = genomic DNA
                        organism = Mus musculus
SEQUENCE: 663
gacccaacct tcagtggtgt                                                    20

SEQ ID NO: 664          moltype = DNA  length = 20
FEATURE                 Location/Qualifiers
source                  1..20
                        mol_type = genomic DNA
                        organism = Mus musculus
SEQUENCE: 664
ctcaactgca gctgccttct                                                    20

SEQ ID NO: 665          moltype = DNA  length = 20
FEATURE                 Location/Qualifiers
source                  1..20
                        mol_type = genomic DNA
                        organism = Mus musculus
SEQUENCE: 665
ccaagacaag ccatggctgg                                                    20

SEQ ID NO: 666          moltype = DNA  length = 20
FEATURE                 Location/Qualifiers
source                  1..20
                        mol_type = genomic DNA
                        organism = Mus musculus
SEQUENCE: 666
aaaagaagtc ctcttacaac                                                    20

SEQ ID NO: 667          moltype = DNA  length = 20
FEATURE                 Location/Qualifiers
source                  1..20
                        mol_type = genomic DNA
                        organism = Mus musculus
SEQUENCE: 667
gatgaaaaga agagtgagca                                                    20

SEQ ID NO: 668          moltype = DNA  length = 20
FEATURE                 Location/Qualifiers
source                  1..20
                        mol_type = genomic DNA
                        organism = Homo sapiens
SEQUENCE: 668
atggactctc ttcttcataa                                                    20
```

| | | |
|---|---|---|
| SEQ ID NO: 669<br>FEATURE<br>source<br><br>SEQUENCE: 669<br>tccttgcagc agttagttcg | moltype = DNA  length = 20<br>Location/Qualifiers<br>1..20<br>mol_type = genomic DNA<br>organism = Homo sapiens | <br><br><br><br><br>20 |
| SEQ ID NO: 670<br>FEATURE<br>source<br><br>SEQUENCE: 670<br>ccgccatact acctgggcat | moltype = DNA  length = 20<br>Location/Qualifiers<br>1..20<br>mol_type = genomic DNA<br>organism = Homo sapiens | <br><br><br><br><br>20 |
| SEQ ID NO: 671<br>FEATURE<br>source<br><br>SEQUENCE: 671<br>ctgaaatcca aggcaagcca | moltype = DNA  length = 20<br>Location/Qualifiers<br>1..20<br>mol_type = genomic DNA<br>organism = Homo sapiens | <br><br><br><br><br>20 |
| SEQ ID NO: 672<br>FEATURE<br>source<br><br>SEQUENCE: 672<br>accccgaact aactgctgca | moltype = DNA  length = 20<br>Location/Qualifiers<br>1..20<br>mol_type = genomic DNA<br>organism = Homo sapiens | <br><br><br><br><br>20 |
| SEQ ID NO: 673<br>FEATURE<br>source<br><br>SEQUENCE: 673<br>ttttcacatt ctggctctgt | moltype = DNA  length = 20<br>Location/Qualifiers<br>1..20<br>mol_type = genomic DNA<br>organism = Homo sapiens | <br><br><br><br><br>20 |
| SEQ ID NO: 674<br>FEATURE<br>source<br><br>SEQUENCE: 674<br>tggcttgcct tggatttcag | moltype = DNA  length = 20<br>Location/Qualifiers<br>1..20<br>mol_type = genomic DNA<br>organism = Homo sapiens | <br><br><br><br><br>20 |
| SEQ ID NO: 675<br>FEATURE<br>source<br><br>SEQUENCE: 675<br>tgcatactca cacacaaagc | moltype = DNA  length = 20<br>Location/Qualifiers<br>1..20<br>mol_type = genomic DNA<br>organism = Homo sapiens | <br><br><br><br><br>20 |
| SEQ ID NO: 676<br>FEATURE<br>source<br><br>SEQUENCE: 676<br>cctagatgat tccatctgca | moltype = DNA  length = 20<br>Location/Qualifiers<br>1..20<br>mol_type = genomic DNA<br>organism = Homo sapiens | <br><br><br><br><br>20 |
| SEQ ID NO: 677<br>FEATURE<br>source<br><br>SEQUENCE: 677<br>aaacaggaga gtgcagggcc | moltype = DNA  length = 20<br>Location/Qualifiers<br>1..20<br>mol_type = genomic DNA<br>organism = Homo sapiens | <br><br><br><br><br>20 |
| SEQ ID NO: 678<br>FEATURE<br>source<br><br>SEQUENCE: 678<br>ctgctggcca gtaccacagc | moltype = DNA  length = 20<br>Location/Qualifiers<br>1..20<br>mol_type = genomic DNA<br>organism = Homo sapiens | <br><br><br><br><br>20 |

| | | |
|---|---|---|
| SEQ ID NO: 679<br>FEATURE<br>source<br><br>SEQUENCE: 679<br>aagaagccct cttacaacag | moltype = DNA length = 20<br>Location/Qualifiers<br>1..20<br>mol_type = genomic DNA<br>organism = Homo sapiens | <br><br><br><br><br>20 |
| SEQ ID NO: 680<br>FEATURE<br>source<br><br>SEQUENCE: 680<br>cgtcatgact accagagagg | moltype = DNA length = 20<br>Location/Qualifiers<br>1..20<br>mol_type = genomic DNA<br>organism = Mus musculus | <br><br><br><br><br>20 |
| SEQ ID NO: 681<br>FEATURE<br>source<br><br>SEQUENCE: 681<br>atgatcaggt gactcatatt | moltype = DNA length = 20<br>Location/Qualifiers<br>1..20<br>mol_type = genomic DNA<br>organism = Mus musculus | <br><br><br><br><br>20 |
| SEQ ID NO: 682<br>FEATURE<br>source<br><br>SEQUENCE: 682<br>gcctcgcagg gtggatgatc | moltype = DNA length = 20<br>Location/Qualifiers<br>1..20<br>mol_type = genomic DNA<br>organism = Mus musculus | <br><br><br><br><br>20 |
| SEQ ID NO: 683<br>FEATURE<br>source<br><br>SEQUENCE: 683<br>ccggcctttc tccacctctc | moltype = DNA length = 20<br>Location/Qualifiers<br>1..20<br>mol_type = genomic DNA<br>organism = Mus musculus | <br><br><br><br><br>20 |
| SEQ ID NO: 684<br>FEATURE<br>source<br><br>SEQUENCE: 684<br>ccagtacaag tttatttacg | moltype = DNA length = 20<br>Location/Qualifiers<br>1..20<br>mol_type = genomic DNA<br>organism = Mus musculus | <br><br><br><br><br>20 |
| SEQ ID NO: 685<br>FEATURE<br>source<br><br>SEQUENCE: 685<br>gtgcccacct cgggccagta | moltype = DNA length = 20<br>Location/Qualifiers<br>1..20<br>mol_type = genomic DNA<br>organism = Mus musculus | <br><br><br><br><br>20 |
| SEQ ID NO: 686<br>FEATURE<br>source<br><br>SEQUENCE: 686<br>cttctatgac ctgtacggag | moltype = DNA length = 20<br>Location/Qualifiers<br>1..20<br>mol_type = genomic DNA<br>organism = Mus musculus | <br><br><br><br><br>20 |
| SEQ ID NO: 687<br>FEATURE<br>source<br><br>SEQUENCE: 687<br>tattcggatc cagaactcag | moltype = DNA length = 20<br>Location/Qualifiers<br>1..20<br>mol_type = genomic DNA<br>organism = Mus musculus | <br><br><br><br><br>20 |
| SEQ ID NO: 688<br>FEATURE<br>source<br><br>SEQUENCE: 688 | moltype = DNA length = 20<br>Location/Qualifiers<br>1..20<br>mol_type = genomic DNA<br>organism = Mus musculus | |

-continued

```
tgggtactta aggtggatga                                               20

SEQ ID NO: 689          moltype = DNA  length = 20
FEATURE                 Location/Qualifiers
source                  1..20
                        mol_type = genomic DNA
                        organism = Mus musculus
SEQUENCE: 689
atgtgtccca tactggcccg                                               20

SEQ ID NO: 690          moltype = DNA  length = 20
FEATURE                 Location/Qualifiers
source                  1..20
                        mol_type = genomic DNA
                        organism = Mus musculus
SEQUENCE: 690
tggtgccatc tcggtcctgc                                               20

SEQ ID NO: 691          moltype = DNA  length = 20
FEATURE                 Location/Qualifiers
source                  1..20
                        mol_type = genomic DNA
                        organism = Mus musculus
SEQUENCE: 691
gtggggtccg agcagttcag                                               20

SEQ ID NO: 692          moltype = DNA  length = 20
FEATURE                 Location/Qualifiers
source                  1..20
                        mol_type = genomic DNA
                        organism = Mus musculus
SEQUENCE: 692
catcgtcatg actaccagag                                               20

SEQ ID NO: 693          moltype = DNA  length = 20
FEATURE                 Location/Qualifiers
source                  1..20
                        mol_type = genomic DNA
                        organism = Mus musculus
SEQUENCE: 693
ggggacttct atgacctgta                                               20

SEQ ID NO: 694          moltype = DNA  length = 20
FEATURE                 Location/Qualifiers
source                  1..20
                        mol_type = genomic DNA
                        organism = Homo sapiens
SEQUENCE: 694
ccagggtgga cgctacacag                                               20

SEQ ID NO: 695          moltype = DNA  length = 20
FEATURE                 Location/Qualifiers
source                  1..20
                        mol_type = genomic DNA
                        organism = Homo sapiens
SEQUENCE: 695
cattgatgta gtcggacccg                                               20

SEQ ID NO: 696          moltype = DNA  length = 20
FEATURE                 Location/Qualifiers
source                  1..20
                        mol_type = genomic DNA
                        organism = Homo sapiens
SEQUENCE: 696
ggtgtcctgc aggaccgcga                                               20

SEQ ID NO: 697          moltype = DNA  length = 20
FEATURE                 Location/Qualifiers
source                  1..20
                        mol_type = genomic DNA
                        organism = Homo sapiens
SEQUENCE: 697
gcaggcagag acgctgctgc                                               20

SEQ ID NO: 698          moltype = DNA  length = 20
FEATURE                 Location/Qualifiers
source                  1..20
                        mol_type = genomic DNA
                        organism = Homo sapiens
```

```
SEQUENCE: 698
gcccccagga tggtgaggta                                              20

SEQ ID NO: 699          moltype = DNA   length = 20
FEATURE                 Location/Qualifiers
source                  1..20
                        mol_type = genomic DNA
                        organism = Homo sapiens
SEQUENCE: 699
gatgcagaga ccctgctcaa                                              20

SEQ ID NO: 700          moltype = DNA   length = 20
FEATURE                 Location/Qualifiers
source                  1..20
                        mol_type = genomic DNA
                        organism = Homo sapiens
SEQUENCE: 700
ctgagttctg gatccgaata                                              20

SEQ ID NO: 701          moltype = DNA   length = 20
FEATURE                 Location/Qualifiers
source                  1..20
                        mol_type = genomic DNA
                        organism = Homo sapiens
SEQUENCE: 701
gatgtgggtg accctgagcg                                              20

SEQ ID NO: 702          moltype = DNA   length = 20
FEATURE                 Location/Qualifiers
source                  1..20
                        mol_type = genomic DNA
                        organism = Homo sapiens
SEQUENCE: 702
aacttaagga cacctgcaag                                              20

SEQ ID NO: 703          moltype = DNA   length = 20
FEATURE                 Location/Qualifiers
source                  1..20
                        mol_type = genomic DNA
                        organism = Homo sapiens
SEQUENCE: 703
gctccgatcc cactagtgag                                              20

SEQ ID NO: 704          moltype = DNA   length = 20
FEATURE                 Location/Qualifiers
source                  1..20
                        mol_type = genomic DNA
                        organism = Homo sapiens
SEQUENCE: 704
cggcccagtc gcaagaacca                                              20

SEQ ID NO: 705          moltype = DNA   length = 20
FEATURE                 Location/Qualifiers
source                  1..20
                        mol_type = genomic DNA
                        organism = Homo sapiens
SEQUENCE: 705
gtttgcgact ctgacagagc                                              20

SEQ ID NO: 706          moltype = DNA   length = 20
FEATURE                 Location/Qualifiers
source                  1..20
                        mol_type = genomic DNA
                        organism = Homo sapiens
SEQUENCE: 706
tattcggatc cagaactcag                                              20

SEQ ID NO: 707          moltype = DNA   length = 20
FEATURE                 Location/Qualifiers
source                  1..20
                        mol_type = genomic DNA
                        organism = Homo sapiens
SEQUENCE: 707
tcacgcacaa gaaacgtcca                                              20

SEQ ID NO: 708          moltype = DNA   length = 20
FEATURE                 Location/Qualifiers
source                  1..20
                        mol_type = genomic DNA
```

```
                            -continued organism = Homo sapiens
SEQUENCE: 708
agccagtgcc cgggcatgcc                                           20

SEQ ID NO: 709          moltype = DNA   length = 20
FEATURE                 Location/Qualifiers
source                  1..20
                        mol_type = genomic DNA
                        organism = Homo sapiens
SEQUENCE: 709
tcttcgttag gacttggccc                                           20

SEQ ID NO: 710          moltype = DNA   length = 20
FEATURE                 Location/Qualifiers
source                  1..20
                        mol_type = genomic DNA
                        organism = Homo sapiens
SEQUENCE: 710
cagctggatg aacagcgaga                                           20

SEQ ID NO: 711          moltype = DNA   length = 20
FEATURE                 Location/Qualifiers
source                  1..20
                        mol_type = genomic DNA
                        organism = Homo sapiens
SEQUENCE: 711
gaaaattgca gcgaaatatg                                           20

SEQ ID NO: 712          moltype = DNA   length = 20
FEATURE                 Location/Qualifiers
source                  1..20
                        mol_type = genomic DNA
                        organism = Homo sapiens
SEQUENCE: 712
actgggcgat accacagcag                                           20

SEQ ID NO: 713          moltype = DNA   length = 20
FEATURE                 Location/Qualifiers
source                  1..20
                        mol_type = genomic DNA
                        organism = Homo sapiens
SEQUENCE: 713
agtggcactt gggacttcta                                           20

SEQ ID NO: 714          moltype = DNA   length = 20
FEATURE                 Location/Qualifiers
source                  1..20
                        mol_type = genomic DNA
                        organism = Homo sapiens
SEQUENCE: 714
tcttggtagg tcacaaactc                                           20

SEQ ID NO: 715          moltype = DNA   length = 20
FEATURE                 Location/Qualifiers
source                  1..20
                        mol_type = genomic DNA
                        organism = Homo sapiens
SEQUENCE: 715
gtgcagactg gagaatacag                                           20

SEQ ID NO: 716          moltype = DNA   length = 20
FEATURE                 Location/Qualifiers
source                  1..20
                        mol_type = genomic DNA
                        organism = Homo sapiens
SEQUENCE: 716
tgatccctca ggagtccagg                                           20

SEQ ID NO: 717          moltype = DNA   length = 20
FEATURE                 Location/Qualifiers
source                  1..20
                        mol_type = genomic DNA
                        organism = Homo sapiens
SEQUENCE: 717
gatggccctg ctgtaacttt                                           20

SEQ ID NO: 718          moltype = DNA   length = 20
FEATURE                 Location/Qualifiers
source                  1..20
```

```
                        mol_type = genomic DNA
                        organism = Homo sapiens
SEQUENCE: 718
aacgttagtg atgacagcat                                                   20

SEQ ID NO: 719          moltype = DNA  length = 20
FEATURE                 Location/Qualifiers
source                  1..20
                        mol_type = genomic DNA
                        organism = Homo sapiens
SEQUENCE: 719
ccatgagaga gcccgttacg                                                   20

SEQ ID NO: 720          moltype = DNA  length = 20
FEATURE                 Location/Qualifiers
source                  1..20
                        mol_type = genomic DNA
                        organism = Homo sapiens
SEQUENCE: 720
ggataggcgt gggaatcaac                                                   20

SEQ ID NO: 721          moltype = DNA  length = 20
FEATURE                 Location/Qualifiers
source                  1..20
                        mol_type = genomic DNA
                        organism = Homo sapiens
SEQUENCE: 721
tatcccaagg ctccggaagg                                                   20

SEQ ID NO: 722          moltype = DNA  length = 20
FEATURE                 Location/Qualifiers
source                  1..20
                        mol_type = genomic DNA
                        organism = Homo sapiens
SEQUENCE: 722
tgggtaaggg aggtaactcc                                                   20

SEQ ID NO: 723          moltype = DNA  length = 20
FEATURE                 Location/Qualifiers
source                  1..20
                        mol_type = genomic DNA
                        organism = Homo sapiens
SEQUENCE: 723
tttccaacac tatactcgcc                                                   20

SEQ ID NO: 724          moltype = DNA  length = 20
FEATURE                 Location/Qualifiers
source                  1..20
                        mol_type = genomic DNA
                        organism = Homo sapiens
SEQUENCE: 724
acgtagtatt cccctgtcag                                                   20

SEQ ID NO: 725          moltype = DNA  length = 20
FEATURE                 Location/Qualifiers
source                  1..20
                        mol_type = genomic DNA
                        organism = Homo sapiens
SEQUENCE: 725
actgcccaca caaaatggtt                                                   20

SEQ ID NO: 726          moltype = DNA  length = 20
FEATURE                 Location/Qualifiers
source                  1..20
                        mol_type = genomic DNA
                        organism = Homo sapiens
SEQUENCE: 726
gctttaggtt cttgtcggtg                                                   20

SEQ ID NO: 727          moltype = DNA  length = 20
FEATURE                 Location/Qualifiers
source                  1..20
                        mol_type = genomic DNA
                        organism = Homo sapiens
SEQUENCE: 727
tgcaaaggtg gatgcgagca                                                   20

SEQ ID NO: 728          moltype = DNA  length = 20
FEATURE                 Location/Qualifiers
```

```
source                    1..20
                          mol_type = genomic DNA
                          organism = Homo sapiens
SEQUENCE: 728
taactcctgg ggtagggaat                                                     20

SEQ ID NO: 729            moltype = DNA   length = 20
FEATURE                   Location/Qualifiers
source                    1..20
                          mol_type = genomic DNA
                          organism = Homo sapiens
SEQUENCE: 729
ggctttggcg cccttgctgc                                                     20

SEQ ID NO: 730            moltype = DNA   length = 20
FEATURE                   Location/Qualifiers
source                    1..20
                          mol_type = genomic DNA
                          organism = Homo sapiens
SEQUENCE: 730
ggtaccaaca aagagaacct                                                     20

SEQ ID NO: 731            moltype = DNA   length = 20
FEATURE                   Location/Qualifiers
source                    1..20
                          mol_type = genomic DNA
                          organism = Homo sapiens
SEQUENCE: 731
gagttcatca tgcccgcgca                                                     20

SEQ ID NO: 732            moltype = DNA   length = 20
FEATURE                   Location/Qualifiers
source                    1..20
                          mol_type = genomic DNA
                          organism = Homo sapiens
SEQUENCE: 732
tttgccagct tagatggctt                                                     20

SEQ ID NO: 733            moltype = DNA   length = 20
FEATURE                   Location/Qualifiers
source                    1..20
                          mol_type = genomic DNA
                          organism = Homo sapiens
SEQUENCE: 733
tagatagcac aaccatttcc                                                     20

SEQ ID NO: 734            moltype = DNA   length = 20
FEATURE                   Location/Qualifiers
source                    1..20
                          mol_type = genomic DNA
                          organism = Homo sapiens
SEQUENCE: 734
agtttcaaag caaacgagaa                                                     20

SEQ ID NO: 735            moltype = DNA   length = 20
FEATURE                   Location/Qualifiers
source                    1..20
                          mol_type = genomic DNA
                          organism = Homo sapiens
SEQUENCE: 735
ctgccctatg ggcttccac                                                      20

SEQ ID NO: 736            moltype = DNA   length = 20
FEATURE                   Location/Qualifiers
source                    1..20
                          mol_type = genomic DNA
                          organism = Homo sapiens
SEQUENCE: 736
gtcaactgta gtgcccagga                                                     20

SEQ ID NO: 737            moltype = DNA   length = 20
FEATURE                   Location/Qualifiers
source                    1..20
                          mol_type = genomic DNA
                          organism = Homo sapiens
SEQUENCE: 737
tcagtgatgt tagtcccctg                                                     20

SEQ ID NO: 738            moltype = DNA   length = 20
```

-continued

```
FEATURE                 Location/Qualifiers
source                  1..20
                        mol_type = genomic DNA
                        organism = Homo sapiens
SEQUENCE: 738
ctaaagagga gaaaccagag                                              20

SEQ ID NO: 739          moltype = DNA   length = 20
FEATURE                 Location/Qualifiers
source                  1..20
                        mol_type = genomic DNA
                        organism = Homo sapiens
SEQUENCE: 739
cagcagatgg caaacctggc                                              20

SEQ ID NO: 740          moltype = DNA   length = 20
FEATURE                 Location/Qualifiers
source                  1..20
                        mol_type = genomic DNA
                        organism = Homo sapiens
SEQUENCE: 740
cagggcaact gaaggagagg                                              20

SEQ ID NO: 741          moltype = DNA   length = 20
FEATURE                 Location/Qualifiers
source                  1..20
                        mol_type = genomic DNA
                        organism = Homo sapiens
SEQUENCE: 741
acgatgggag cagcaggtgt                                              20

SEQ ID NO: 742          moltype = DNA   length = 20
FEATURE                 Location/Qualifiers
source                  1..20
                        mol_type = genomic DNA
                        organism = Homo sapiens
SEQUENCE: 742
cccacgtgct gaataacgga                                              20

SEQ ID NO: 743          moltype = DNA   length = 20
FEATURE                 Location/Qualifiers
source                  1..20
                        mol_type = genomic DNA
                        organism = Homo sapiens
SEQUENCE: 743
taccaaagat ggagctgatg                                              20

SEQ ID NO: 744          moltype = DNA   length = 20
FEATURE                 Location/Qualifiers
source                  1..20
                        mol_type = genomic DNA
                        organism = Homo sapiens
SEQUENCE: 744
caggccactg gtgaccgcct                                              20

SEQ ID NO: 745          moltype = DNA   length = 20
FEATURE                 Location/Qualifiers
source                  1..20
                        mol_type = genomic DNA
                        organism = Homo sapiens
SEQUENCE: 745
ctgctgtttg gcaggcggcc                                              20

SEQ ID NO: 746          moltype = DNA   length = 20
FEATURE                 Location/Qualifiers
source                  1..20
                        mol_type = genomic DNA
                        organism = Homo sapiens
SEQUENCE: 746
gccgactggg aaaggttgaa                                              20

SEQ ID NO: 747          moltype = DNA   length = 20
FEATURE                 Location/Qualifiers
source                  1..20
                        mol_type = genomic DNA
                        organism = Homo sapiens
SEQUENCE: 747
gctgtcatca ctaacgtttc                                              20
```

| | | |
|---|---|---|
| SEQ ID NO: 748<br>FEATURE<br>source | moltype = DNA  length = 20<br>Location/Qualifiers<br>1..20<br>mol_type = genomic DNA<br>organism = Homo sapiens | |
| SEQUENCE: 748<br>tccatgtaag gattgaccca | | 20 |
| SEQ ID NO: 749<br>FEATURE<br>source | moltype = DNA  length = 20<br>Location/Qualifiers<br>1..20<br>mol_type = genomic DNA<br>organism = Homo sapiens | |
| SEQUENCE: 749<br>accgaataca cccgagacag | | 20 |
| SEQ ID NO: 750<br>FEATURE<br>source | moltype = DNA  length = 20<br>Location/Qualifiers<br>1..20<br>mol_type = genomic DNA<br>organism = Homo sapiens | |
| SEQUENCE: 750<br>acctggccgg caaagcagga | | 20 |
| SEQ ID NO: 751<br>FEATURE<br>source | moltype = DNA  length = 20<br>Location/Qualifiers<br>1..20<br>mol_type = genomic DNA<br>organism = Homo sapiens | |
| SEQUENCE: 751<br>tactacgtgg agaatgccga | | 20 |
| SEQ ID NO: 752<br>FEATURE<br>source | moltype = DNA  length = 20<br>Location/Qualifiers<br>1..20<br>mol_type = genomic DNA<br>organism = Homo sapiens | |
| SEQUENCE: 752<br>gaaaaccgat tccggagggt | | 20 |
| SEQ ID NO: 753<br>FEATURE<br>source | moltype = DNA  length = 20<br>Location/Qualifiers<br>1..20<br>mol_type = genomic DNA<br>organism = Homo sapiens | |
| SEQUENCE: 753<br>gcactgagca tggaccgcac | | 20 |
| SEQ ID NO: 754<br>FEATURE<br>source | moltype = DNA  length = 20<br>Location/Qualifiers<br>1..20<br>mol_type = genomic DNA<br>organism = Homo sapiens | |
| SEQUENCE: 754<br>gttctctaag gtgcagcaag | | 20 |
| SEQ ID NO: 755<br>FEATURE<br>source | moltype = DNA  length = 20<br>Location/Qualifiers<br>1..20<br>mol_type = genomic DNA<br>organism = Homo sapiens | |
| SEQUENCE: 755<br>agttagcagc gagttccccg | | 20 |
| SEQ ID NO: 756<br>FEATURE<br>source | moltype = DNA  length = 20<br>Location/Qualifiers<br>1..20<br>mol_type = genomic DNA<br>organism = Homo sapiens | |
| SEQUENCE: 756<br>cagaagcgct gggcttggac | | 20 |
| SEQ ID NO: 757<br>FEATURE<br>source | moltype = DNA  length = 20<br>Location/Qualifiers<br>1..20<br>mol_type = genomic DNA<br>organism = Homo sapiens | |
| SEQUENCE: 757<br>cagcggctgg gccaagctgt | | 20 |

| | | |
|---|---|---|
| SEQ ID NO: 758<br>FEATURE<br>source | moltype = DNA  length = 20<br>Location/Qualifiers<br>1..20<br>mol_type = genomic DNA<br>organism = Homo sapiens | |
| SEQUENCE: 758<br>actttcgttc tgttctgcaa | | 20 |
| SEQ ID NO: 759<br>FEATURE<br>source | moltype = DNA  length = 20<br>Location/Qualifiers<br>1..20<br>mol_type = genomic DNA<br>organism = Homo sapiens | |
| SEQUENCE: 759<br>cgccttggca gagggaaccc | | 20 |
| SEQ ID NO: 760<br>FEATURE<br>source | moltype = DNA  length = 20<br>Location/Qualifiers<br>1..20<br>mol_type = genomic DNA<br>organism = Homo sapiens | |
| SEQUENCE: 760<br>gatgaggctg aatcaaatga | | 20 |
| SEQ ID NO: 761<br>FEATURE<br>source | moltype = DNA  length = 20<br>Location/Qualifiers<br>1..20<br>mol_type = genomic DNA<br>organism = Homo sapiens | |
| SEQUENCE: 761<br>gcggttcaag acagaaaaga | | 20 |
| SEQ ID NO: 762<br>FEATURE<br>source | moltype = DNA  length = 20<br>Location/Qualifiers<br>1..20<br>mol_type = genomic DNA<br>organism = Homo sapiens | |
| SEQUENCE: 762<br>tcttgttctc taagcagtac | | 20 |
| SEQ ID NO: 763<br>FEATURE<br>source | moltype = DNA  length = 20<br>Location/Qualifiers<br>1..20<br>mol_type = genomic DNA<br>organism = Homo sapiens | |
| SEQUENCE: 763<br>ggtgccatct gcattggcat | | 20 |
| SEQ ID NO: 764<br>FEATURE<br>source | moltype = DNA  length = 20<br>Location/Qualifiers<br>1..20<br>mol_type = genomic DNA<br>organism = Homo sapiens | |
| SEQUENCE: 764<br>tggcaagtat cccaaggctc | | 20 |
| SEQ ID NO: 765<br>FEATURE<br>source | moltype = DNA  length = 20<br>Location/Qualifiers<br>1..20<br>mol_type = genomic DNA<br>organism = Homo sapiens | |
| SEQUENCE: 765<br>gctgccacaa gcactctagg | | 20 |
| SEQ ID NO: 766<br>FEATURE<br>source | moltype = DNA  length = 20<br>Location/Qualifiers<br>1..20<br>mol_type = genomic DNA<br>organism = Homo sapiens | |
| SEQUENCE: 766<br>atagcactga agccatttgg | | 20 |
| SEQ ID NO: 767<br>FEATURE<br>source | moltype = DNA  length = 20<br>Location/Qualifiers<br>1..20<br>mol_type = genomic DNA<br>organism = Homo sapiens | |
| SEQUENCE: 767 | | |

```
gaatacaccc gagacagtgg                                              20

SEQ ID NO: 768           moltype = DNA   length = 20
FEATURE                  Location/Qualifiers
source                   1..20
                         mol_type = genomic DNA
                         organism = Homo sapiens
SEQUENCE: 768
tccaagtatc tgtggctcag                                              20

SEQ ID NO: 769           moltype = DNA   length = 20
FEATURE                  Location/Qualifiers
source                   1..20
                         mol_type = genomic DNA
                         organism = Homo sapiens
SEQUENCE: 769
tcaatggtgc tagttatctg                                              20

SEQ ID NO: 770           moltype = DNA   length = 20
FEATURE                  Location/Qualifiers
source                   1..20
                         mol_type = genomic DNA
                         organism = Homo sapiens
SEQUENCE: 770
gtgaacgttc ccatacaggg                                              20

SEQ ID NO: 771           moltype = DNA   length = 20
FEATURE                  Location/Qualifiers
source                   1..20
                         mol_type = genomic DNA
                         organism = Homo sapiens
SEQUENCE: 771
gaatcccttg aaccacaacg                                              20

SEQ ID NO: 772           moltype = DNA   length = 20
FEATURE                  Location/Qualifiers
source                   1..20
                         mol_type = genomic DNA
                         organism = Homo sapiens
SEQUENCE: 772
gctgtgtgca gacgaagaag                                              20

SEQ ID NO: 773           moltype = DNA   length = 20
FEATURE                  Location/Qualifiers
source                   1..20
                         mol_type = genomic DNA
                         organism = Mus musculus
SEQUENCE: 773
gacacacggc gcaatgacag                                              20

SEQ ID NO: 774           moltype = DNA   length = 20
FEATURE                  Location/Qualifiers
source                   1..20
                         mol_type = genomic DNA
                         organism = Mus musculus
SEQUENCE: 774
cagctgtatg atctggaagc                                              20

SEQ ID NO: 775           moltype = DNA   length = 20
FEATURE                  Location/Qualifiers
source                   1..20
                         mol_type = genomic DNA
                         organism = Mus musculus
SEQUENCE: 775
cagcaaccag actgaaaaac                                              20

SEQ ID NO: 776           moltype = DNA   length = 20
FEATURE                  Location/Qualifiers
source                   1..20
                         mol_type = genomic DNA
                         organism = Mus musculus
SEQUENCE: 776
gcagggagat ggccccacag                                              20

SEQ ID NO: 777           moltype = DNA   length = 20
FEATURE                  Location/Qualifiers
source                   1..20
                         mol_type = genomic DNA
                         organism = Mus musculus
```

| | | |
|---|---|---|
| SEQUENCE: 777 acagtggcat ctacctctgt | | 20 |
| SEQ ID NO: 778 FEATURE source | moltype = DNA length = 20 Location/Qualifiers 1..20 mol_type = genomic DNA organism = Mus musculus | |
| SEQUENCE: 778 cggaggatct tatgctgaac | | 20 |
| SEQ ID NO: 779 FEATURE source | moltype = DNA length = 20 Location/Qualifiers 1..20 mol_type = genomic DNA organism = Mus musculus | |
| SEQUENCE: 779 gagccctgga gcagagctcg | | 20 |
| SEQ ID NO: 780 FEATURE source | moltype = DNA length = 20 Location/Qualifiers 1..20 mol_type = genomic DNA organism = Mus musculus | |
| SEQUENCE: 780 gcaaaaatcg aggagagccc | | 20 |
| SEQ ID NO: 781 FEATURE source | moltype = DNA length = 20 Location/Qualifiers 1..20 mol_type = genomic DNA organism = Mus musculus | |
| SEQUENCE: 781 gccaggctgg gtagaaggtg | | 20 |
| SEQ ID NO: 782 FEATURE source | moltype = DNA length = 20 Location/Qualifiers 1..20 mol_type = genomic DNA organism = Mus musculus | |
| SEQUENCE: 782 gctcaaacca ttacagaagg | | 20 |
| SEQ ID NO: 783 FEATURE source | moltype = DNA length = 20 Location/Qualifiers 1..20 mol_type = genomic DNA organism = Mus musculus | |
| SEQUENCE: 783 ggacaagctg caggtgaagg | | 20 |
| SEQ ID NO: 784 FEATURE source | moltype = DNA length = 20 Location/Qualifiers 1..20 mol_type = genomic DNA organism = Mus musculus | |
| SEQUENCE: 784 gagccctgga gcagagctcg | | 20 |
| SEQ ID NO: 785 FEATURE source | moltype = DNA length = 20 Location/Qualifiers 1..20 mol_type = genomic DNA organism = Mus musculus | |
| SEQUENCE: 785 ggacaagctg caggtgaagg | | 20 |
| SEQ ID NO: 786 FEATURE source | moltype = DNA length = 20 Location/Qualifiers 1..20 mol_type = genomic DNA organism = Mus musculus | |
| SEQUENCE: 786 gctcaaacca ttacagaagg | | 20 |
| SEQ ID NO: 787 FEATURE source | moltype = DNA length = 20 Location/Qualifiers 1..20 mol_type = genomic DNA | |

```
                              organism = Mus musculus
SEQUENCE: 787
gccaggctgg gtagaaggtg                                                    20

SEQ ID NO: 788        moltype = DNA  length = 20
FEATURE               Location/Qualifiers
source                1..20
                      mol_type = genomic DNA
                      organism = Mus musculus
SEQUENCE: 788
gacacacggc gcaatgacag                                                    20

SEQ ID NO: 789        moltype = DNA  length = 20
FEATURE               Location/Qualifiers
source                1..20
                      mol_type = genomic DNA
                      organism = Mus musculus
SEQUENCE: 789
cagctgtatg atctggaagc                                                    20

SEQ ID NO: 790        moltype = DNA  length = 20
FEATURE               Location/Qualifiers
source                1..20
                      mol_type = genomic DNA
                      organism = Mus musculus
SEQUENCE: 790
cagcaaccag actgaaaaac                                                    20

SEQ ID NO: 791        moltype = DNA  length = 20
FEATURE               Location/Qualifiers
source                1..20
                      mol_type = genomic DNA
                      organism = Mus musculus
SEQUENCE: 791
gcagggagat ggccccacag                                                    20

SEQ ID NO: 792        moltype = DNA  length = 20
FEATURE               Location/Qualifiers
source                1..20
                      mol_type = genomic DNA
                      organism = Mus musculus
SEQUENCE: 792
acagtggcat ctacctctgt                                                    20

SEQ ID NO: 793        moltype = DNA  length = 20
FEATURE               Location/Qualifiers
source                1..20
                      mol_type = genomic DNA
                      organism = Mus musculus
SEQUENCE: 793
cggaggatct tatgctgaac                                                    20

SEQ ID NO: 794        moltype = DNA  length = 20
FEATURE               Location/Qualifiers
source                1..20
                      mol_type = genomic DNA
                      organism = Mus musculus
SEQUENCE: 794
gcaaaaatcg aggagagccc                                                    20

SEQ ID NO: 795        moltype = DNA  length = 20
FEATURE               Location/Qualifiers
source                1..20
                      mol_type = genomic DNA
                      organism = Mus musculus
SEQUENCE: 795
cgaccagttg acaagctgc                                                     20

SEQ ID NO: 796        moltype = DNA  length = 20
FEATURE               Location/Qualifiers
source                1..20
                      mol_type = genomic DNA
                      organism = Mus musculus
SEQUENCE: 796
catgtggaag tcatgcctgt                                                    20

SEQ ID NO: 797        moltype = DNA  length = 20
FEATURE               Location/Qualifiers
source                1..20
```

```
                        mol_type = genomic DNA
                        organism = Mus musculus
SEQUENCE: 797
agcgggcatc ctggacgggt                                                        20

SEQ ID NO: 798          moltype = DNA   length = 20
FEATURE                 Location/Qualifiers
source                  1..20
                        mol_type = genomic DNA
                        organism = Mus musculus
SEQUENCE: 798
ccaggctggg tagaaggtga                                                        20

SEQ ID NO: 799          moltype = DNA   length = 20
FEATURE                 Location/Qualifiers
source                  1..20
                        mol_type = genomic DNA
                        organism = Mus musculus
SEQUENCE: 799
gcacccaag gcaaaaatcg                                                         20

SEQ ID NO: 800          moltype = DNA   length = 20
FEATURE                 Location/Qualifiers
source                  1..20
                        mol_type = genomic DNA
                        organism = Mus musculus
SEQUENCE: 800
gctcaaacca ttacagaagg                                                        20

SEQ ID NO: 801          moltype = DNA   length = 20
FEATURE                 Location/Qualifiers
source                  1..20
                        mol_type = genomic DNA
                        organism = Mus musculus
SEQUENCE: 801
gacacacggc gcaatgacag                                                        20

SEQ ID NO: 802          moltype = DNA   length = 20
FEATURE                 Location/Qualifiers
source                  1..20
                        mol_type = genomic DNA
                        organism = Mus musculus
SEQUENCE: 802
cagctgtatg atctggaagc                                                        20

SEQ ID NO: 803          moltype = DNA   length = 20
FEATURE                 Location/Qualifiers
source                  1..20
                        mol_type = genomic DNA
                        organism = Homo sapiens
SEQUENCE: 803
cggccagttc caaaccctgg                                                        20

SEQ ID NO: 804          moltype = DNA   length = 20
FEATURE                 Location/Qualifiers
source                  1..20
                        mol_type = genomic DNA
                        organism = Homo sapiens
SEQUENCE: 804
cagttccaaa ccctggtggt                                                        20

SEQ ID NO: 805          moltype = DNA   length = 20
FEATURE                 Location/Qualifiers
source                  1..20
                        mol_type = genomic DNA
                        organism = Homo sapiens
SEQUENCE: 805
ctgcagcttc tccaacacat                                                        20

SEQ ID NO: 806          moltype = DNA   length = 20
FEATURE                 Location/Qualifiers
source                  1..20
                        mol_type = genomic DNA
                        organism = Homo sapiens
SEQUENCE: 806
cgtgtcacac aactgcccaa                                                        20

SEQ ID NO: 807          moltype = DNA   length = 20
FEATURE                 Location/Qualifiers
```

```
source                  1..20
                        mol_type = genomic DNA
                        organism = Homo sapiens
SEQUENCE: 807
agagctcagg gtgacaggtg                                                      20

SEQ ID NO: 808          moltype = DNA   length = 20
FEATURE                 Location/Qualifiers
source                  1..20
                        mol_type = genomic DNA
                        organism = Homo sapiens
SEQUENCE: 808
gcgtgacttc cacatgagcg                                                      20

SEQ ID NO: 809          moltype = DNA   length = 20
FEATURE                 Location/Qualifiers
source                  1..20
                        mol_type = genomic DNA
                        organism = Homo sapiens
SEQUENCE: 809
cagcggcacc tacctctgtg                                                      20

SEQ ID NO: 810          moltype = DNA   length = 20
FEATURE                 Location/Qualifiers
source                  1..20
                        mol_type = genomic DNA
                        organism = Homo sapiens
SEQUENCE: 810
gctgcggtcc tcgggaagg                                                       20

SEQ ID NO: 811          moltype = DNA   length = 20
FEATURE                 Location/Qualifiers
source                  1..20
                        mol_type = genomic DNA
                        organism = Homo sapiens
SEQUENCE: 811
gcagggctgg ggagaaggtg                                                      20

SEQ ID NO: 812          moltype = DNA   length = 20
FEATURE                 Location/Qualifiers
source                  1..20
                        mol_type = genomic DNA
                        organism = Homo sapiens
SEQUENCE: 812
catgagcccc agcaaccaga                                                      20

SEQ ID NO: 813          moltype = DNA   length = 20
FEATURE                 Location/Qualifiers
source                  1..20
                        mol_type = genomic DNA
                        organism = Homo sapiens
SEQUENCE: 813
gccctgtgtc cctgagcaga                                                      20

SEQ ID NO: 814          moltype = DNA   length = 20
FEATURE                 Location/Qualifiers
source                  1..20
                        mol_type = genomic DNA
                        organism = Mus musculus
SEQUENCE: 814
tagggcccc aggcctgagc                                                       20

SEQ ID NO: 815          moltype = DNA   length = 20
FEATURE                 Location/Qualifiers
source                  1..20
                        mol_type = genomic DNA
                        organism = Mus musculus
SEQUENCE: 815
aagatctgcg cccggagata                                                      20

SEQ ID NO: 816          moltype = DNA   length = 20
FEATURE                 Location/Qualifiers
source                  1..20
                        mol_type = genomic DNA
                        organism = Mus musculus
SEQUENCE: 816
gttctgtctg tagggaggta                                                      20

SEQ ID NO: 817          moltype = DNA   length = 20
```

| | | |
|---|---|---|
| FEATURE | Location/Qualifiers | |
| source | 1..20<br>mol_type = genomic DNA<br>organism = Mus musculus | |
| SEQUENCE: 817<br>caacgaaact tacacaagga | | 20 |
| SEQ ID NO: 818<br>FEATURE<br>source | moltype = DNA   length = 20<br>Location/Qualifiers<br>1..20<br>mol_type = genomic DNA<br>organism = Mus musculus | |
| SEQUENCE: 818<br>cactcagaac ttacatcaga | | 20 |
| SEQ ID NO: 819<br>FEATURE<br>source | moltype = DNA   length = 20<br>Location/Qualifiers<br>1..20<br>mol_type = genomic DNA<br>organism = Mus musculus | |
| SEQUENCE: 819<br>tctgagtgtg acagagaagg | | 20 |
| SEQ ID NO: 820<br>FEATURE<br>source | moltype = DNA   length = 20<br>Location/Qualifiers<br>1..20<br>mol_type = genomic DNA<br>organism = Mus musculus | |
| SEQUENCE: 820<br>ttcctcctga gactgtcgta | | 20 |
| SEQ ID NO: 821<br>FEATURE<br>source | moltype = DNA   length = 20<br>Location/Qualifiers<br>1..20<br>mol_type = genomic DNA<br>organism = Mus musculus | |
| SEQUENCE: 821<br>gacaattgca gcctgctgag | | 20 |
| SEQ ID NO: 822<br>FEATURE<br>source | moltype = DNA   length = 20<br>Location/Qualifiers<br>1..20<br>mol_type = genomic DNA<br>organism = Mus musculus | |
| SEQUENCE: 822<br>acttacatca gaaggttgct | | 20 |
| SEQ ID NO: 823<br>FEATURE<br>source | moltype = DNA   length = 20<br>Location/Qualifiers<br>1..20<br>mol_type = genomic DNA<br>organism = Mus musculus | |
| SEQUENCE: 823<br>gcacaggagc tgcggcggat | | 20 |
| SEQ ID NO: 824<br>FEATURE<br>source | moltype = DNA   length = 20<br>Location/Qualifiers<br>1..20<br>mol_type = genomic DNA<br>organism = Mus musculus | |
| SEQUENCE: 824<br>gttgtaagat aaccatttga | | 20 |
| SEQ ID NO: 825<br>FEATURE<br>source | moltype = DNA   length = 20<br>Location/Qualifiers<br>1..20<br>mol_type = genomic DNA<br>organism = Mus musculus | |
| SEQUENCE: 825<br>gtttgcaaat gattaccgcg | | 20 |
| SEQ ID NO: 826<br>FEATURE<br>source | moltype = DNA   length = 20<br>Location/Qualifiers<br>1..20<br>mol_type = genomic DNA<br>organism = Mus musculus | |
| SEQUENCE: 826<br>tcctgtgcaa tccgtatctc | | 20 |

```
SEQ ID NO: 827            moltype = DNA   length = 20
FEATURE                   Location/Qualifiers
source                    1..20
                          mol_type = genomic DNA
                          organism = Mus musculus
SEQUENCE: 827
tcgccgtcgg gattaccttg                                                    20

SEQ ID NO: 828            moltype = DNA   length = 20
FEATURE                   Location/Qualifiers
source                    1..20
                          mol_type = genomic DNA
                          organism = Mus musculus
SEQUENCE: 828
tcttccgtct ggtatggaga                                                    20

SEQ ID NO: 829            moltype = DNA   length = 20
FEATURE                   Location/Qualifiers
source                    1..20
                          mol_type = genomic DNA
                          organism = Mus musculus
SEQUENCE: 829
ttccatacga cagtctcagg                                                    20

SEQ ID NO: 830            moltype = DNA   length = 20
FEATURE                   Location/Qualifiers
source                    1..20
                          mol_type = genomic DNA
                          organism = Mus musculus
SEQUENCE: 830
ttctgtctgt agggaggtag                                                    20

SEQ ID NO: 831            moltype = DNA   length = 20
FEATURE                   Location/Qualifiers
source                    1..20
                          mol_type = genomic DNA
                          organism = Mus musculus
SEQUENCE: 831
caaccactat ctcagtgcaa                                                    20

SEQ ID NO: 832            moltype = DNA   length = 20
FEATURE                   Location/Qualifiers
source                    1..20
                          mol_type = genomic DNA
                          organism = Homo sapiens
SEQUENCE: 832
agctggggag gcctctccgc                                                    20

SEQ ID NO: 833            moltype = DNA   length = 20
FEATURE                   Location/Qualifiers
source                    1..20
                          mol_type = genomic DNA
                          organism = Homo sapiens
SEQUENCE: 833
ccactgaact tccctatgaa                                                    20

SEQ ID NO: 834            moltype = DNA   length = 20
FEATURE                   Location/Qualifiers
source                    1..20
                          mol_type = genomic DNA
                          organism = Homo sapiens
SEQUENCE: 834
ttaacgctta ctatgcaagg                                                    20

SEQ ID NO: 835            moltype = DNA   length = 20
FEATURE                   Location/Qualifiers
source                    1..20
                          mol_type = genomic DNA
                          organism = Homo sapiens
SEQUENCE: 835
aaccattcgt gggtggtctt                                                    20

SEQ ID NO: 836            moltype = DNA   length = 20
FEATURE                   Location/Qualifiers
source                    1..20
                          mol_type = genomic DNA
                          organism = Homo sapiens
SEQUENCE: 836
aggcaatcac ggaggtgaag                                                    20
```

```
SEQ ID NO: 837              moltype = DNA  length = 20
FEATURE                     Location/Qualifiers
source                      1..20
                            mol_type = genomic DNA
                            organism = Homo sapiens
SEQUENCE: 837
tggcttgcag atgactccgc                                                20

SEQ ID NO: 838              moltype = DNA  length = 20
FEATURE                     Location/Qualifiers
source                      1..20
                            mol_type = genomic DNA
                            organism = Homo sapiens
SEQUENCE: 838
aaagatcacc tatatcctct                                                20

SEQ ID NO: 839              moltype = DNA  length = 20
FEATURE                     Location/Qualifiers
source                      1..20
                            mol_type = genomic DNA
                            organism = Homo sapiens
SEQUENCE: 839
gttgatttgt cacaactcat                                                20

SEQ ID NO: 840              moltype = DNA  length = 20
FEATURE                     Location/Qualifiers
source                      1..20
                            mol_type = genomic DNA
                            organism = Homo sapiens
SEQUENCE: 840
gttctgatgc agcttccatg                                                20

SEQ ID NO: 841              moltype = DNA  length = 20
FEATURE                     Location/Qualifiers
source                      1..20
                            mol_type = genomic DNA
                            organism = Homo sapiens
SEQUENCE: 841
ttttccagtt agagaaatag                                                20

SEQ ID NO: 842              moltype = DNA  length = 20
FEATURE                     Location/Qualifiers
source                      1..20
                            mol_type = genomic DNA
                            organism = Homo sapiens
SEQUENCE: 842
tagtggttga aggcctggca                                                20

SEQ ID NO: 843              moltype = DNA  length = 20
FEATURE                     Location/Qualifiers
source                      1..20
                            mol_type = genomic DNA
                            organism = Homo sapiens
SEQUENCE: 843
ttgccttcag gattaccttg                                                20

SEQ ID NO: 844              moltype = DNA  length = 20
FEATURE                     Location/Qualifiers
source                      1..20
                            mol_type = genomic DNA
                            organism = Homo sapiens
SEQUENCE: 844
acagtctcac tctgtcaccc                                                20

SEQ ID NO: 845              moltype = DNA  length = 20
FEATURE                     Location/Qualifiers
source                      1..20
                            mol_type = genomic DNA
                            organism = Homo sapiens
SEQUENCE: 845
cactcagaac ttacatcaga                                                20

SEQ ID NO: 846              moltype = DNA  length = 20
FEATURE                     Location/Qualifiers
source                      1..20
                            mol_type = genomic DNA
                            organism = Homo sapiens
SEQUENCE: 846
```

```
cttgggcgat ccatatctct                                                  20

SEQ ID NO: 847         moltype = DNA   length = 20
FEATURE                Location/Qualifiers
source                 1..20
                       mol_type = genomic DNA
                       organism = Homo sapiens
SEQUENCE: 847
aggtagacaa ttgcagcctg                                                  20

SEQ ID NO: 848         moltype = DNA   length = 20
FEATURE                Location/Qualifiers
source                 1..20
                       mol_type = genomic DNA
                       organism = Homo sapiens
SEQUENCE: 848
acttcctcta tttctctaac                                                  20

SEQ ID NO: 849         moltype = DNA   length = 20
FEATURE                Location/Qualifiers
source                 1..20
                       mol_type = genomic DNA
                       organism = Homo sapiens
SEQUENCE: 849
actggaggat cgagacagca                                                  20

SEQ ID NO: 850         moltype = DNA   length = 20
FEATURE                Location/Qualifiers
source                 1..20
                       mol_type = genomic DNA
                       organism = Homo sapiens
SEQUENCE: 850
tccctacaga cagagccaca                                                  20

SEQ ID NO: 851         moltype = DNA   length = 20
FEATURE                Location/Qualifiers
source                 1..20
                       mol_type = genomic DNA
                       organism = Homo sapiens
SEQUENCE: 851
ttgtggctct gtctgtaggg                                                  20

SEQ ID NO: 852         moltype = DNA   length = 20
FEATURE                Location/Qualifiers
source                 1..20
                       mol_type = genomic DNA
                       organism = Mus musculus
SEQUENCE: 852
gctgttaact ctgttgatgc                                                  20

SEQ ID NO: 853         moltype = DNA   length = 20
FEATURE                Location/Qualifiers
source                 1..20
                       mol_type = genomic DNA
                       organism = Mus musculus
SEQUENCE: 853
ggctcgccgg ctcgggatgg                                                  20

SEQ ID NO: 854         moltype = DNA   length = 20
FEATURE                Location/Qualifiers
source                 1..20
                       mol_type = genomic DNA
                       organism = Mus musculus
SEQUENCE: 854
ccggagccgc ggaccaccac                                                  20

SEQ ID NO: 855         moltype = DNA   length = 20
FEATURE                Location/Qualifiers
source                 1..20
                       mol_type = genomic DNA
                       organism = Mus musculus
SEQUENCE: 855
cgattgagaa gttattagaa                                                  20

SEQ ID NO: 856         moltype = DNA   length = 20
FEATURE                Location/Qualifiers
source                 1..20
                       mol_type = genomic DNA
                       organism = Mus musculus
```

| | | |
|---|---|---|
| SEQUENCE: 856 gctcaagtac tcgcccgacc | | 20 |
| SEQ ID NO: 857 FEATURE source | moltype = DNA length = 20 Location/Qualifiers 1..20 mol_type = genomic DNA organism = Mus musculus | |
| SEQUENCE: 857 tccccgcagg actcaccttg | | 20 |
| SEQ ID NO: 858 FEATURE source | moltype = DNA length = 20 Location/Qualifiers 1..20 mol_type = genomic DNA organism = Mus musculus | |
| SEQUENCE: 858 ctgtgctgct gctgcacgtt | | 20 |
| SEQ ID NO: 859 FEATURE source | moltype = DNA length = 20 Location/Qualifiers 1..20 mol_type = genomic DNA organism = Mus musculus | |
| SEQUENCE: 859 ggacgaggag cgggccctgg | | 20 |
| SEQ ID NO: 860 FEATURE source | moltype = DNA length = 20 Location/Qualifiers 1..20 mol_type = genomic DNA organism = Homo sapiens | |
| SEQUENCE: 860 cgaaatctat gaggaagagg | | 20 |
| SEQ ID NO: 861 FEATURE source | moltype = DNA length = 20 Location/Qualifiers 1..20 mol_type = genomic DNA organism = Homo sapiens | |
| SEQUENCE: 861 actgttaact ctgttgatgc | | 20 |
| SEQ ID NO: 862 FEATURE source | moltype = DNA length = 20 Location/Qualifiers 1..20 mol_type = genomic DNA organism = Homo sapiens | |
| SEQUENCE: 862 gcacattagg ttgcagtatg | | 20 |
| SEQ ID NO: 863 FEATURE source | moltype = DNA length = 20 Location/Qualifiers 1..20 mol_type = genomic DNA organism = Homo sapiens | |
| SEQUENCE: 863 ggatttcgac gaaatctatg | | 20 |
| SEQ ID NO: 864 FEATURE source | moltype = DNA length = 20 Location/Qualifiers 1..20 mol_type = genomic DNA organism = Homo sapiens | |
| SEQUENCE: 864 tctcaatcga tcttcgtgtc | | 20 |
| SEQ ID NO: 865 FEATURE source | moltype = DNA length = 20 Location/Qualifiers 1..20 mol_type = genomic DNA organism = Homo sapiens | |
| SEQUENCE: 865 tgcattggag actgagcaaa | | 20 |
| SEQ ID NO: 866 FEATURE source | moltype = DNA length = 20 Location/Qualifiers 1..20 mol_type = genomic DNA | |

```
                              organism = Homo sapiens
SEQUENCE: 866
gccaacgtac attaacagga                                                      20

SEQ ID NO: 867        moltype = DNA  length = 20
FEATURE               Location/Qualifiers
source                1..20
                      mol_type = genomic DNA
                      organism = Homo sapiens
SEQUENCE: 867
gaattccctt cttcattaac                                                      20

SEQ ID NO: 868        moltype = DNA  length = 20
FEATURE               Location/Qualifiers
source                1..20
                      mol_type = genomic DNA
                      organism = Homo sapiens
SEQUENCE: 868
ccggacccgg tggtcgtccg                                                      20

SEQ ID NO: 869        moltype = DNA  length = 20
FEATURE               Location/Qualifiers
source                1..20
                      mol_type = genomic DNA
                      organism = Homo sapiens
SEQUENCE: 869
gcagctgctc aagtactcgc                                                      20

SEQ ID NO: 870        moltype = DNA  length = 20
FEATURE               Location/Qualifiers
source                1..20
                      mol_type = genomic DNA
                      organism = Homo sapiens
SEQUENCE: 870
aaacaatagg ttataccaca                                                      20

SEQ ID NO: 871        moltype = DNA  length = 20
FEATURE               Location/Qualifiers
source                1..20
                      mol_type = genomic DNA
                      organism = Homo sapiens
SEQUENCE: 871
cggtgacgtg accggagccg                                                      20

SEQ ID NO: 872        moltype = DNA  length = 20
FEATURE               Location/Qualifiers
source                1..20
                      mol_type = genomic DNA
                      organism = Mus musculus
SEQUENCE: 872
ccactgcaga ccccacactg                                                      20

SEQ ID NO: 873        moltype = DNA  length = 20
FEATURE               Location/Qualifiers
source                1..20
                      mol_type = genomic DNA
                      organism = Mus musculus
SEQUENCE: 873
tataaggaa tacggattga                                                       20

SEQ ID NO: 874        moltype = DNA  length = 20
FEATURE               Location/Qualifiers
source                1..20
                      mol_type = genomic DNA
                      organism = Mus musculus
SEQUENCE: 874
gtggctggag tgggctataa                                                      20

SEQ ID NO: 875        moltype = DNA  length = 20
FEATURE               Location/Qualifiers
source                1..20
                      mol_type = genomic DNA
                      organism = Mus musculus
SEQUENCE: 875
cggagagtca ttgtgcctgc                                                      20

SEQ ID NO: 876        moltype = DNA  length = 20
FEATURE               Location/Qualifiers
source                1..20
```

```
                              mol_type = genomic DNA
                              organism = Mus musculus
SEQUENCE: 876
cacaggagca cgttcgacag                                                 20

SEQ ID NO: 877                moltype = DNA  length = 20
FEATURE                       Location/Qualifiers
source                        1..20
                              mol_type = genomic DNA
                              organism = Mus musculus
SEQUENCE: 877
aatgacggac cctgatgagg                                                 20

SEQ ID NO: 878                moltype = DNA  length = 20
FEATURE                       Location/Qualifiers
source                        1..20
                              mol_type = genomic DNA
                              organism = Mus musculus
SEQUENCE: 878
catggtactt actttccctg                                                 20

SEQ ID NO: 879                moltype = DNA  length = 20
FEATURE                       Location/Qualifiers
source                        1..20
                              mol_type = genomic DNA
                              organism = Mus musculus
SEQUENCE: 879
ccaacgccag ctgtatcacc                                                 20

SEQ ID NO: 880                moltype = DNA  length = 20
FEATURE                       Location/Qualifiers
source                        1..20
                              mol_type = genomic DNA
                              organism = Homo sapiens
SEQUENCE: 880
cagcacttcc gtgttgtaga                                                 20

SEQ ID NO: 881                moltype = DNA  length = 20
FEATURE                       Location/Qualifiers
source                        1..20
                              mol_type = genomic DNA
                              organism = Homo sapiens
SEQUENCE: 881
caaaatgacg gaccccgatg                                                 20

SEQ ID NO: 882                moltype = DNA  length = 20
FEATURE                       Location/Qualifiers
source                        1..20
                              mol_type = genomic DNA
                              organism = Homo sapiens
SEQUENCE: 882
tggttctcga attacctgcg                                                 20

SEQ ID NO: 883                moltype = DNA  length = 20
FEATURE                       Location/Qualifiers
source                        1..20
                              mol_type = genomic DNA
                              organism = Homo sapiens
SEQUENCE: 883
tgtgaggcaa tggctggagt                                                 20

SEQ ID NO: 884                moltype = DNA  length = 20
FEATURE                       Location/Qualifiers
source                        1..20
                              mol_type = genomic DNA
                              organism = Homo sapiens
SEQUENCE: 884
gatcgtttgt gccctccaa                                                  20

SEQ ID NO: 885                moltype = DNA  length = 20
FEATURE                       Location/Qualifiers
source                        1..20
                              mol_type = genomic DNA
                              organism = Homo sapiens
SEQUENCE: 885
tcgttggtgg tcatgttggg                                                 20

SEQ ID NO: 886                moltype = DNA  length = 20
FEATURE                       Location/Qualifiers
```

```
source                        1..20
                              mol_type = genomic DNA
                              organism = Homo sapiens
SEQUENCE: 886
tcagtaagaa tacagagcaa                                                    20

SEQ ID NO: 887                moltype = DNA  length = 20
FEATURE                       Location/Qualifiers
source                        1..20
                              mol_type = genomic DNA
                              organism = Homo sapiens
SEQUENCE: 887
ccagctgtat cacctgggag                                                    20

SEQ ID NO: 888                moltype = DNA  length = 20
FEATURE                       Location/Qualifiers
source                        1..20
                              mol_type = genomic DNA
                              organism = Homo sapiens
SEQUENCE: 888
tgtcggagag cagctccagg                                                    20

SEQ ID NO: 889                moltype = DNA  length = 20
FEATURE                       Location/Qualifiers
source                        1..20
                              mol_type = genomic DNA
                              organism = Homo sapiens
SEQUENCE: 889
aacattatga ccaaagtgca                                                    20

SEQ ID NO: 890                moltype = DNA  length = 20
FEATURE                       Location/Qualifiers
source                        1..20
                              mol_type = genomic DNA
                              organism = Homo sapiens
SEQUENCE: 890
ggcggcactt actttccctg                                                    20

SEQ ID NO: 891                moltype = DNA  length = 20
FEATURE                       Location/Qualifiers
source                        1..20
                              mol_type = genomic DNA
                              organism = Homo sapiens
SEQUENCE: 891
actgtgtaaa atgaacaagg                                                    20

SEQ ID NO: 892                moltype = DNA  length = 20
FEATURE                       Location/Qualifiers
source                        1..20
                              mol_type = genomic DNA
                              organism = Mus musculus
SEQUENCE: 892
atcccccgcc acctggacct                                                    20

SEQ ID NO: 893                moltype = DNA  length = 20
FEATURE                       Location/Qualifiers
source                        1..20
                              mol_type = genomic DNA
                              organism = Mus musculus
SEQUENCE: 893
ggaaggcagg tcactattac                                                    20

SEQ ID NO: 894                moltype = DNA  length = 20
FEATURE                       Location/Qualifiers
source                        1..20
                              mol_type = genomic DNA
                              organism = Mus musculus
SEQUENCE: 894
ctgatgcacg gaaaggaagt                                                    20

SEQ ID NO: 895                moltype = DNA  length = 20
FEATURE                       Location/Qualifiers
source                        1..20
                              mol_type = genomic DNA
                              organism = Mus musculus
SEQUENCE: 895
cctgggcccc ggtgctctcg                                                    20

SEQ ID NO: 896                moltype = DNA  length = 20
```

```
FEATURE              Location/Qualifiers
source               1..20
                     mol_type = genomic DNA
                     organism = Mus musculus
SEQUENCE: 896
accagccgaa gtgtgaccgg                                                20

SEQ ID NO: 897       moltype = DNA   length = 20
FEATURE              Location/Qualifiers
source               1..20
                     mol_type = genomic DNA
                     organism = Mus musculus
SEQUENCE: 897
gtcagcgtga tgatcctctc                                                20

SEQ ID NO: 898       moltype = DNA   length = 20
FEATURE              Location/Qualifiers
source               1..20
                     mol_type = genomic DNA
                     organism = Mus musculus
SEQUENCE: 898
ctccagcttg tcgatgatca                                                20

SEQ ID NO: 899       moltype = DNA   length = 20
FEATURE              Location/Qualifiers
source               1..20
                     mol_type = genomic DNA
                     organism = Mus musculus
SEQUENCE: 899
tcccgtcccg ccgtgcatca                                                20

SEQ ID NO: 900       moltype = DNA   length = 20
FEATURE              Location/Qualifiers
source               1..20
                     mol_type = genomic DNA
                     organism = Homo sapiens
SEQUENCE: 900
tggcgcgcgg atcaacatct                                                20

SEQ ID NO: 901       moltype = DNA   length = 20
FEATURE              Location/Qualifiers
source               1..20
                     mol_type = genomic DNA
                     organism = Homo sapiens
SEQUENCE: 901
gagagaatca tcactctgac                                                20

SEQ ID NO: 902       moltype = DNA   length = 20
FEATURE              Location/Qualifiers
source               1..20
                     mol_type = genomic DNA
                     organism = Homo sapiens
SEQUENCE: 902
tccgtgcata agaagccgaa                                                20

SEQ ID NO: 903       moltype = DNA   length = 20
FEATURE              Location/Qualifiers
source               1..20
                     mol_type = genomic DNA
                     organism = Homo sapiens
SEQUENCE: 903
aagcatcatt gggaagaaag                                                20

SEQ ID NO: 904       moltype = DNA   length = 20
FEATURE              Location/Qualifiers
source               1..20
                     mol_type = genomic DNA
                     organism = Homo sapiens
SEQUENCE: 904
ctccatgacc aacagtaccg                                                20

SEQ ID NO: 905       moltype = DNA   length = 20
FEATURE              Location/Qualifiers
source               1..20
                     mol_type = genomic DNA
                     organism = Homo sapiens
SEQUENCE: 905
atttggaatg gtgagttcat                                                20
```

| | | |
|---|---|---|
| SEQ ID NO: 906<br>FEATURE<br>source | moltype = DNA  length = 20<br>Location/Qualifiers<br>1..20<br>mol_type = genomic DNA<br>organism = Homo sapiens | |
| SEQUENCE: 906<br>agagatccgc gagagtacgg | | 20 |
| SEQ ID NO: 907<br>FEATURE<br>source | moltype = DNA  length = 20<br>Location/Qualifiers<br>1..20<br>mol_type = genomic DNA<br>organism = Homo sapiens | |
| SEQUENCE: 907<br>gaaagcctta aagatggcat | | 20 |
| SEQ ID NO: 908<br>FEATURE<br>source | moltype = DNA  length = 20<br>Location/Qualifiers<br>1..20<br>mol_type = genomic DNA<br>organism = Homo sapiens | |
| SEQUENCE: 908<br>cagctcccca gtcatctgcg | | 20 |
| SEQ ID NO: 909<br>FEATURE<br>source | moltype = DNA  length = 20<br>Location/Qualifiers<br>1..20<br>mol_type = genomic DNA<br>organism = Homo sapiens | |
| SEQUENCE: 909<br>acacactcgg tgacagactg | | 20 |
| SEQ ID NO: 910<br>FEATURE<br>source | moltype = DNA  length = 20<br>Location/Qualifiers<br>1..20<br>mol_type = genomic DNA<br>organism = Homo sapiens | |
| SEQUENCE: 910<br>aatcagggag ccgcactggg | | 20 |
| SEQ ID NO: 911<br>FEATURE<br>source | moltype = DNA  length = 20<br>Location/Qualifiers<br>1..20<br>mol_type = genomic DNA<br>organism = Homo sapiens | |
| SEQUENCE: 911<br>gtcggttaag aggatccgcg | | 20 |
| SEQ ID NO: 912<br>FEATURE<br>source | moltype = DNA  length = 20<br>Location/Qualifiers<br>1..20<br>mol_type = genomic DNA<br>organism = Mus musculus | |
| SEQUENCE: 912<br>ccaaaacata caatgagcct | | 20 |
| SEQ ID NO: 913<br>FEATURE<br>source | moltype = DNA  length = 20<br>Location/Qualifiers<br>1..20<br>mol_type = genomic DNA<br>organism = Mus musculus | |
| SEQUENCE: 913<br>agactattat gcaataatta | | 20 |
| SEQ ID NO: 914<br>FEATURE<br>source | moltype = DNA  length = 20<br>Location/Qualifiers<br>1..20<br>mol_type = genomic DNA<br>organism = Mus musculus | |
| SEQUENCE: 914<br>aagactttgc gatctattta | | 20 |
| SEQ ID NO: 915<br>FEATURE<br>source | moltype = DNA  length = 20<br>Location/Qualifiers<br>1..20<br>mol_type = genomic DNA<br>organism = Mus musculus | |
| SEQUENCE: 915<br>gagcacatca cttaccactt | | 20 |

| | | |
|---|---|---|
| SEQ ID NO: 916<br>FEATURE<br>source | moltype = DNA   length = 20<br>Location/Qualifiers<br>1..20<br>mol_type = genomic DNA<br>organism = Mus musculus | |
| SEQUENCE: 916<br>gtaccaagac atagattcta | | 20 |
| SEQ ID NO: 917<br>FEATURE<br>source | moltype = DNA   length = 20<br>Location/Qualifiers<br>1..20<br>mol_type = genomic DNA<br>organism = Mus musculus | |
| SEQUENCE: 917<br>cctctgtgag ctgttcatta | | 20 |
| SEQ ID NO: 918<br>FEATURE<br>source | moltype = DNA   length = 20<br>Location/Qualifiers<br>1..20<br>mol_type = genomic DNA<br>organism = Mus musculus | |
| SEQUENCE: 918<br>aacgggcaag aaggatgaac | | 20 |
| SEQ ID NO: 919<br>FEATURE<br>source | moltype = DNA   length = 20<br>Location/Qualifiers<br>1..20<br>mol_type = genomic DNA<br>organism = Mus musculus | |
| SEQUENCE: 919<br>gaaaccactt cataatagtc | | 20 |
| SEQ ID NO: 920<br>FEATURE<br>source | moltype = DNA   length = 20<br>Location/Qualifiers<br>1..20<br>mol_type = genomic DNA<br>organism = Homo sapiens | |
| SEQUENCE: 920<br>cacacctggc ggaagatggt | | 20 |
| SEQ ID NO: 921<br>FEATURE<br>source | moltype = DNA   length = 20<br>Location/Qualifiers<br>1..20<br>mol_type = genomic DNA<br>organism = Homo sapiens | |
| SEQUENCE: 921<br>tggagagatt cttctttcac | | 20 |
| SEQ ID NO: 922<br>FEATURE<br>source | moltype = DNA   length = 20<br>Location/Qualifiers<br>1..20<br>mol_type = genomic DNA<br>organism = Homo sapiens | |
| SEQUENCE: 922<br>ggagttgtcg gaataaccaa | | 20 |
| SEQ ID NO: 923<br>FEATURE<br>source | moltype = DNA   length = 20<br>Location/Qualifiers<br>1..20<br>mol_type = genomic DNA<br>organism = Homo sapiens | |
| SEQUENCE: 923<br>caaatcccag agtttgcaag | | 20 |
| SEQ ID NO: 924<br>FEATURE<br>source | moltype = DNA   length = 20<br>Location/Qualifiers<br>1..20<br>mol_type = genomic DNA<br>organism = Homo sapiens | |
| SEQUENCE: 924<br>tcaggcaact cagatctaga | | 20 |
| SEQ ID NO: 925<br>FEATURE<br>source | moltype = DNA   length = 20<br>Location/Qualifiers<br>1..20<br>mol_type = genomic DNA<br>organism = Homo sapiens | |
| SEQUENCE: 925 | | | ttacccggtg gtgggatgcc                              20

SEQ ID NO: 926          moltype = DNA   length = 20
FEATURE                 Location/Qualifiers
source                  1..20
                        mol_type = genomic DNA
                        organism = Homo sapiens
SEQUENCE: 926
tcaaccagac tattatgaag                              20

SEQ ID NO: 927          moltype = DNA   length = 20
FEATURE                 Location/Qualifiers
source                  1..20
                        mol_type = genomic DNA
                        organism = Homo sapiens
SEQUENCE: 927
cccttccagc agtgtcagcg                              20

SEQ ID NO: 928          moltype = DNA   length = 20
FEATURE                 Location/Qualifiers
source                  1..20
                        mol_type = genomic DNA
                        organism = Homo sapiens
SEQUENCE: 928
gccaggcact ataatgagga                              20

SEQ ID NO: 929          moltype = DNA   length = 20
FEATURE                 Location/Qualifiers
source                  1..20
                        mol_type = genomic DNA
                        organism = Homo sapiens
SEQUENCE: 929
tcattagggc accaaagcga                              20

SEQ ID NO: 930          moltype = DNA   length = 20
FEATURE                 Location/Qualifiers
source                  1..20
                        mol_type = genomic DNA
                        organism = Homo sapiens
SEQUENCE: 930
ttgagcatcc ccattggtgt                              20

SEQ ID NO: 931          moltype = DNA   length = 20
FEATURE                 Location/Qualifiers
source                  1..20
                        mol_type = genomic DNA
                        organism = Homo sapiens
SEQUENCE: 931
ttgcattgtt aaaaagaagc                              20

SEQ ID NO: 932          moltype = DNA   length = 20
FEATURE                 Location/Qualifiers
source                  1..20
                        mol_type = genomic DNA
                        organism = Homo sapiens
SEQUENCE: 932
aggctgcctt tactgtgtga                              20

SEQ ID NO: 933          moltype = DNA   length = 20
FEATURE                 Location/Qualifiers
source                  1..20
                        mol_type = genomic DNA
                        organism = Homo sapiens
SEQUENCE: 933
tgctgattga gcatccccat                              20

SEQ ID NO: 934          moltype = DNA   length = 20
FEATURE                 Location/Qualifiers
source                  1..20
                        mol_type = genomic DNA
                        organism = Homo sapiens
SEQUENCE: 934
ccagctgcac gctatgaaga                              20

SEQ ID NO: 935          moltype = DNA   length = 20
FEATURE                 Location/Qualifiers
source                  1..20
                        mol_type = genomic DNA
                        organism = Homo sapiens

```
SEQUENCE: 935
aaaacatttg cataatgatg                                                    20

SEQ ID NO: 936           moltype = DNA   length = 20
FEATURE                  Location/Qualifiers
source                   1..20
                         mol_type = genomic DNA
                         organism = Homo sapiens
SEQUENCE: 936
ggataggact ccatccaact                                                    20

SEQ ID NO: 937           moltype = DNA   length = 20
FEATURE                  Location/Qualifiers
source                   1..20
                         mol_type = genomic DNA
                         organism = Homo sapiens
SEQUENCE: 937
atctcaagac cattgcccag                                                    20

SEQ ID NO: 938           moltype = DNA   length = 20
FEATURE                  Location/Qualifiers
source                   1..20
                         mol_type = genomic DNA
                         organism = Mus musculus
SEQUENCE: 938
gctcatactc ctcccggtta                                                    20

SEQ ID NO: 939           moltype = DNA   length = 20
FEATURE                  Location/Qualifiers
source                   1..20
                         mol_type = genomic DNA
                         organism = Mus musculus
SEQUENCE: 939
aggcgagggg cctgatttac                                                    20

SEQ ID NO: 940           moltype = DNA   length = 20
FEATURE                  Location/Qualifiers
source                   1..20
                         mol_type = genomic DNA
                         organism = Mus musculus
SEQUENCE: 940
gttacgggtc tggagtgtgt                                                    20

SEQ ID NO: 941           moltype = DNA   length = 20
FEATURE                  Location/Qualifiers
source                   1..20
                         mol_type = genomic DNA
                         organism = Mus musculus
SEQUENCE: 941
tgttggggac aggctgctgg                                                    20

SEQ ID NO: 942           moltype = DNA   length = 20
FEATURE                  Location/Qualifiers
source                   1..20
                         mol_type = genomic DNA
                         organism = Mus musculus
SEQUENCE: 942
tctggactct cttcaccatt                                                    20

SEQ ID NO: 943           moltype = DNA   length = 20
FEATURE                  Location/Qualifiers
source                   1..20
                         mol_type = genomic DNA
                         organism = Homo sapiens
SEQUENCE: 943
gagaatcact tgaacctggg                                                    20

SEQ ID NO: 944           moltype = DNA   length = 20
FEATURE                  Location/Qualifiers
source                   1..20
                         mol_type = genomic DNA
                         organism = Homo sapiens
SEQUENCE: 944
gcaggatgca ccctactaca                                                    20

SEQ ID NO: 945           moltype = DNA   length = 20
FEATURE                  Location/Qualifiers
source                   1..20
                         mol_type = genomic DNA
```

```
                            organism = Homo sapiens
SEQUENCE: 945
cattaggctc tggccgtacc                                                    20

SEQ ID NO: 946          moltype = DNA  length = 20
FEATURE                 Location/Qualifiers
source                  1..20
                        mol_type = genomic DNA
                        organism = Homo sapiens
SEQUENCE: 946
ccgtgagggc caccatctcg                                                    20

SEQ ID NO: 947          moltype = DNA  length = 20
FEATURE                 Location/Qualifiers
source                  1..20
                        mol_type = genomic DNA
                        organism = Homo sapiens
SEQUENCE: 947
agcgttcgta tctggaaggt                                                    20

SEQ ID NO: 948          moltype = DNA  length = 20
FEATURE                 Location/Qualifiers
source                  1..20
                        mol_type = genomic DNA
                        organism = Homo sapiens
SEQUENCE: 948
ataagctccg aggttgcccg                                                    20

SEQ ID NO: 949          moltype = DNA  length = 20
FEATURE                 Location/Qualifiers
source                  1..20
                        mol_type = genomic DNA
                        organism = Homo sapiens
SEQUENCE: 949
gctggcagtg actgatacag                                                    20

SEQ ID NO: 950          moltype = DNA  length = 20
FEATURE                 Location/Qualifiers
source                  1..20
                        mol_type = genomic DNA
                        organism = Homo sapiens
SEQUENCE: 950
acaaagatgg ccttgccaga                                                    20

SEQ ID NO: 951          moltype = DNA  length = 20
FEATURE                 Location/Qualifiers
source                  1..20
                        mol_type = genomic DNA
                        organism = Homo sapiens
SEQUENCE: 951
aagaagtaaa ctacctcaca                                                    20

SEQ ID NO: 952          moltype = DNA  length = 20
FEATURE                 Location/Qualifiers
source                  1..20
                        mol_type = genomic DNA
                        organism = Homo sapiens
SEQUENCE: 952
gctacgttct tcatggccgt                                                    20

SEQ ID NO: 953          moltype = DNA  length = 20
FEATURE                 Location/Qualifiers
source                  1..20
                        mol_type = genomic DNA
                        organism = Homo sapiens
SEQUENCE: 953
aagaattcga ccaagggatt                                                    20

SEQ ID NO: 954          moltype = DNA  length = 20
FEATURE                 Location/Qualifiers
source                  1..20
                        mol_type = genomic DNA
                        organism = Homo sapiens
SEQUENCE: 954
ttaatggcaa gacttgcaga                                                    20

SEQ ID NO: 955          moltype = DNA  length = 20
FEATURE                 Location/Qualifiers
source                  1..20
```

```
                                    mol_type = genomic DNA
                                    organism = Homo sapiens
SEQUENCE: 955
tgaaagtatc cagctgatga                                                        20

SEQ ID NO: 956           moltype = DNA   length = 20
FEATURE                  Location/Qualifiers
source                   1..20
                         mol_type = genomic DNA
                         organism = Homo sapiens
SEQUENCE: 956
ggcgagatgt gtgacagagg                                                        20

SEQ ID NO: 957           moltype = DNA   length = 20
FEATURE                  Location/Qualifiers
source                   1..20
                         mol_type = genomic DNA
                         organism = Homo sapiens
SEQUENCE: 957
agatgtagag ctttccaagg                                                        20

SEQ ID NO: 958           moltype = DNA   length = 20
FEATURE                  Location/Qualifiers
source                   1..20
                         mol_type = genomic DNA
                         organism = Homo sapiens
SEQUENCE: 958
tagatcttct tacatggaag                                                        20

SEQ ID NO: 959           moltype = DNA   length = 20
FEATURE                  Location/Qualifiers
source                   1..20
                         mol_type = genomic DNA
                         organism = Homo sapiens
SEQUENCE: 959
ctttctaggt tcgagatgtg                                                        20

SEQ ID NO: 960           moltype = DNA   length = 20
FEATURE                  Location/Qualifiers
source                   1..20
                         mol_type = genomic DNA
                         organism = Homo sapiens
SEQUENCE: 960
caacccaatc tttcctcgga                                                        20

SEQ ID NO: 961           moltype = DNA   length = 20
FEATURE                  Location/Qualifiers
source                   1..20
                         mol_type = genomic DNA
                         organism = Homo sapiens
SEQUENCE: 961
gtagaagcaa agagaggcga                                                        20

SEQ ID NO: 962           moltype = DNA   length = 20
FEATURE                  Location/Qualifiers
source                   1..20
                         mol_type = genomic DNA
                         organism = Homo sapiens
SEQUENCE: 962
ttcgatctcg acttcttgag                                                        20

SEQ ID NO: 963           moltype = DNA   length = 20
FEATURE                  Location/Qualifiers
source                   1..20
                         mol_type = genomic DNA
                         organism = Homo sapiens
SEQUENCE: 963
gcttgaggct ccttacaaga                                                        20

SEQ ID NO: 964           moltype = DNA   length = 20
FEATURE                  Location/Qualifiers
source                   1..20
                         mol_type = genomic DNA
                         organism = Homo sapiens
SEQUENCE: 964
ctgatgatgg acagtgaaac                                                        20

SEQ ID NO: 965           moltype = DNA   length = 20
FEATURE                  Location/Qualifiers
```

```
source                  1..20
                        mol_type = genomic DNA
                        organism = Homo sapiens
SEQUENCE: 965
cataataaca aacaaagcta                                                         20

SEQ ID NO: 966          moltype = DNA  length = 20
FEATURE                 Location/Qualifiers
source                  1..20
                        mol_type = genomic DNA
                        organism = Homo sapiens
SEQUENCE: 966
aggagatgta gagctttcca                                                         20

SEQ ID NO: 967          moltype = DNA  length = 20
FEATURE                 Location/Qualifiers
source                  1..20
                        mol_type = genomic DNA
                        organism = Homo sapiens
SEQUENCE: 967
ttggtcagat aatatgatta                                                         20

SEQ ID NO: 968          moltype = DNA  length = 20
FEATURE                 Location/Qualifiers
source                  1..20
                        mol_type = genomic DNA
                        organism = Homo sapiens
SEQUENCE: 968
gaggcaaccc aatctttcct                                                         20

SEQ ID NO: 969          moltype = DNA  length = 20
FEATURE                 Location/Qualifiers
source                  1..20
                        mol_type = genomic DNA
                        organism = Homo sapiens
SEQUENCE: 969
aggtgaattc atgggagtag                                                         20

SEQ ID NO: 970          moltype = DNA  length = 20
FEATURE                 Location/Qualifiers
source                  1..20
                        mol_type = genomic DNA
                        organism = Homo sapiens
SEQUENCE: 970
tacttactat gaagcattta                                                         20

SEQ ID NO: 971          moltype = DNA  length = 20
FEATURE                 Location/Qualifiers
source                  1..20
                        mol_type = genomic DNA
                        organism = Homo sapiens
SEQUENCE: 971
cagggcgaga tgtgtgacag                                                         20

SEQ ID NO: 972          moltype = DNA  length = 20
FEATURE                 Location/Qualifiers
source                  1..20
                        mol_type = genomic DNA
                        organism = Homo sapiens
SEQUENCE: 972
agcgaagtag aagcaaagag                                                         20

SEQ ID NO: 973          moltype = DNA  length = 20
FEATURE                 Location/Qualifiers
source                  1..20
                        mol_type = genomic DNA
                        organism = Homo sapiens
SEQUENCE: 973
agtgatgaac tggaaaggac                                                         20

SEQ ID NO: 974          moltype = DNA  length = 20
FEATURE                 Location/Qualifiers
source                  1..20
                        mol_type = genomic DNA
                        organism = Homo sapiens
SEQUENCE: 974
atgaagcatt tagggatctt                                                         20

SEQ ID NO: 975          moltype = DNA  length = 20
```

```
FEATURE                 Location/Qualifiers
source                  1..20
                        mol_type = genomic DNA
                        organism = Homo sapiens
SEQUENCE: 975
cttggcacct tgaagagcat                                               20

SEQ ID NO: 976          moltype = DNA   length = 20
FEATURE                 Location/Qualifiers
source                  1..20
                        mol_type = genomic DNA
                        organism = Homo sapiens
SEQUENCE: 976
tttaattggg gaggaccatg                                               20

SEQ ID NO: 977          moltype = DNA   length = 20
FEATURE                 Location/Qualifiers
source                  1..20
                        mol_type = genomic DNA
                        organism = Homo sapiens
SEQUENCE: 977
gtcattattc acagcagggt                                               20

SEQ ID NO: 978          moltype = DNA   length = 20
FEATURE                 Location/Qualifiers
source                  1..20
                        mol_type = genomic DNA
                        organism = Homo sapiens
SEQUENCE: 978
cgtcctagag agtttacata                                               20

SEQ ID NO: 979          moltype = DNA   length = 20
FEATURE                 Location/Qualifiers
source                  1..20
                        mol_type = genomic DNA
                        organism = Homo sapiens
SEQUENCE: 979
ctgcagggtg aagtttacaa                                               20

SEQ ID NO: 980          moltype = DNA   length = 20
FEATURE                 Location/Qualifiers
source                  1..20
                        mol_type = genomic DNA
                        organism = Homo sapiens
SEQUENCE: 980
tgacatctgc cttgacgaag                                               20

SEQ ID NO: 981          moltype = DNA   length = 20
FEATURE                 Location/Qualifiers
source                  1..20
                        mol_type = genomic DNA
                        organism = Homo sapiens
SEQUENCE: 981
aaaacaggta cacttggcac                                               20

SEQ ID NO: 982          moltype = DNA   length = 20
FEATURE                 Location/Qualifiers
source                  1..20
                        mol_type = genomic DNA
                        organism = Homo sapiens
SEQUENCE: 982
acttctaggc ttactatctg                                               20

SEQ ID NO: 983          moltype = DNA   length = 20
FEATURE                 Location/Qualifiers
source                  1..20
                        mol_type = genomic DNA
                        organism = Homo sapiens
SEQUENCE: 983
cgcaacagag atcagaaaag                                               20

SEQ ID NO: 984          moltype = DNA   length = 20
FEATURE                 Location/Qualifiers
source                  1..20
                        mol_type = genomic DNA
                        organism = Homo sapiens
SEQUENCE: 984
aaggctctca gggagagccg                                               20
```

```
SEQ ID NO: 985          moltype = DNA   length = 20
FEATURE                 Location/Qualifiers
source                  1..20
                        mol_type = genomic DNA
                        organism = Homo sapiens
SEQUENCE: 985
gttcatgtta cagaggaaag                                               20

SEQ ID NO: 986          moltype = DNA   length = 20
FEATURE                 Location/Qualifiers
source                  1..20
                        mol_type = genomic DNA
                        organism = Homo sapiens
SEQUENCE: 986
gcaagcatgc tcgaggacag                                               20

SEQ ID NO: 987          moltype = DNA   length = 20
FEATURE                 Location/Qualifiers
source                  1..20
                        mol_type = genomic DNA
                        organism = Homo sapiens
SEQUENCE: 987
tgcttgaagt tggacagcaa                                               20

SEQ ID NO: 988          moltype = DNA   length = 20
FEATURE                 Location/Qualifiers
source                  1..20
                        mol_type = genomic DNA
                        organism = Homo sapiens
SEQUENCE: 988
cactaaacca tttcaggtaa                                               20

SEQ ID NO: 989          moltype = DNA   length = 20
FEATURE                 Location/Qualifiers
source                  1..20
                        mol_type = genomic DNA
                        organism = Homo sapiens
SEQUENCE: 989
ctatttgaca aagatggtga                                               20

SEQ ID NO: 990          moltype = DNA   length = 20
FEATURE                 Location/Qualifiers
source                  1..20
                        mol_type = genomic DNA
                        organism = Homo sapiens
SEQUENCE: 990
aagaagttga tgaaatgatc                                               20

SEQ ID NO: 991          moltype = DNA   length = 20
FEATURE                 Location/Qualifiers
source                  1..20
                        mol_type = genomic DNA
                        organism = Homo sapiens
SEQUENCE: 991
cgccatgtga tgacaaacct                                               20

SEQ ID NO: 992          moltype = DNA   length = 20
FEATURE                 Location/Qualifiers
source                  1..20
                        mol_type = genomic DNA
                        organism = Homo sapiens
SEQUENCE: 992
gtcctgtaac tctgcttctg                                               20

SEQ ID NO: 993          moltype = DNA   length = 20
FEATURE                 Location/Qualifiers
source                  1..20
                        mol_type = genomic DNA
                        organism = Homo sapiens
SEQUENCE: 993
tcagcagttc aagaccagcc                                               20

SEQ ID NO: 994          moltype = DNA   length = 20
FEATURE                 Location/Qualifiers
source                  1..20
                        mol_type = genomic DNA
                        organism = Homo sapiens
SEQUENCE: 994
tgatggaact ataacaacaa                                               20
```

```
SEQ ID NO: 995              moltype = DNA   length = 20
FEATURE                     Location/Qualifiers
source                      1..20
                            mol_type = genomic DNA
                            organism = Homo sapiens
SEQUENCE: 995
ccatcattgt cagaaattca                                                     20

SEQ ID NO: 996              moltype = DNA   length = 20
FEATURE                     Location/Qualifiers
source                      1..20
                            mol_type = genomic DNA
                            organism = Homo sapiens
SEQUENCE: 996
gacgtacctt atcaaacaca                                                     20

SEQ ID NO: 997              moltype = DNA   length = 20
FEATURE                     Location/Qualifiers
source                      1..20
                            mol_type = genomic DNA
                            organism = Homo sapiens
SEQUENCE: 997
ctttgcacaa caaccctgca                                                     20

SEQ ID NO: 998              moltype = DNA   length = 20
FEATURE                     Location/Qualifiers
source                      1..20
                            mol_type = genomic DNA
                            organism = Homo sapiens
SEQUENCE: 998
aaggcggtgg agatgctcag                                                     20

SEQ ID NO: 999              moltype = DNA   length = 20
FEATURE                     Location/Qualifiers
source                      1..20
                            mol_type = genomic DNA
                            organism = Homo sapiens
SEQUENCE: 999
aggtgatgca aactcatcat                                                     20

SEQ ID NO: 1000             moltype = DNA   length = 20
FEATURE                     Location/Qualifiers
source                      1..20
                            mol_type = genomic DNA
                            organism = Homo sapiens
SEQUENCE: 1000
cggattagcc tccgccaacg                                                     20

SEQ ID NO: 1001             moltype = DNA   length = 20
FEATURE                     Location/Qualifiers
source                      1..20
                            mol_type = genomic DNA
                            organism = Homo sapiens
SEQUENCE: 1001
tgctcccaga gaccctgaag                                                     20

SEQ ID NO: 1002             moltype = DNA   length = 20
FEATURE                     Location/Qualifiers
source                      1..20
                            mol_type = genomic DNA
                            organism = Homo sapiens
SEQUENCE: 1002
tgacgaggag aatctgaccc                                                     20

SEQ ID NO: 1003             moltype = DNA   length = 20
FEATURE                     Location/Qualifiers
source                      1..20
                            mol_type = genomic DNA
                            organism = Homo sapiens
SEQUENCE: 1003
gctgaaagcg aagtccacgt                                                     20

SEQ ID NO: 1004             moltype = DNA   length = 20
FEATURE                     Location/Qualifiers
source                      1..20
                            mol_type = genomic DNA
                            organism = Homo sapiens
SEQUENCE: 1004
```

-continued

```
aggcctcaag ttcaacctca                                              20

SEQ ID NO: 1005          moltype = DNA   length = 20
FEATURE                  Location/Qualifiers
source                   1..20
                         mol_type = genomic DNA
                         organism = Homo sapiens SEQUENCE: 1005
agctgagtcc tgaaagtcag                                              20

SEQ ID NO: 1006          moltype = DNA   length = 20
FEATURE                  Location/Qualifiers
source                   1..20
                         mol_type = genomic DNA
                         organism = Homo sapiens SEQUENCE: 1006
tctgctggac aggttcacgg                                              20

SEQ ID NO: 1007          moltype = DNA   length = 20
FEATURE                  Location/Qualifiers
source                   1..20
                         mol_type = genomic DNA
                         organism = Homo sapiens SEQUENCE: 1007
ccccagagac aggaaggcca                                              20

SEQ ID NO: 1008          moltype = DNA   length = 20
FEATURE                  Location/Qualifiers
source                   1..20
                         mol_type = genomic DNA
                         organism = Homo sapiens SEQUENCE: 1008
cctaccttca aacagaacca                                              20

SEQ ID NO: 1009          moltype = DNA   length = 20
FEATURE                  Location/Qualifiers
source                   1..20
                         mol_type = genomic DNA
                         organism = Homo sapiens SEQUENCE: 1009
atggtggctt tgatgaactg                                              20

SEQ ID NO: 1010          moltype = DNA   length = 20
FEATURE                  Location/Qualifiers
source                   1..20
                         mol_type = genomic DNA
                         organism = Homo sapiens SEQUENCE: 1010
attgtattcc tgcttccgga                                              20

SEQ ID NO: 1011          moltype = DNA   length = 20
FEATURE                  Location/Qualifiers
source                   1..20
                         mol_type = genomic DNA
                         organism = Homo sapiens SEQUENCE: 1011
gatctactac ttcttccgag                                              20

SEQ ID NO: 1012          moltype = DNA   length = 20
FEATURE                  Location/Qualifiers
source                   1..20
                         mol_type = genomic DNA
                         organism = Homo sapiens SEQUENCE: 1012
gttcactgtc agtctccaag                                              20

SEQ ID NO: 1013          moltype = DNA   length = 20
FEATURE                  Location/Qualifiers
source                   1..20
                         mol_type = genomic DNA
                         organism = Homo sapiens SEQUENCE: 1013
tagacctcac acaggtccag                                              20

SEQ ID NO: 1014          moltype = DNA   length = 20
FEATURE                  Location/Qualifiers
source                   1..20
                         mol_type = genomic DNA
                         organism = Homo sapiens
```

-continued

```
SEQUENCE: 1014
ggaatacacc tcgtcccctg                                              20

SEQ ID NO: 1015           moltype = DNA   length = 20
FEATURE                   Location/Qualifiers
source                    1..20
                          mol_type = genomic DNA
                          organism = Homo sapiens
SEQUENCE: 1015
actcaagcct tcccaacccg                                              20

SEQ ID NO: 1016           moltype = DNA   length = 20
FEATURE                   Location/Qualifiers
source                    1..20
                          mol_type = genomic DNA
                          organism = Homo sapiens
SEQUENCE: 1016
aatacaatgg gaagatccct                                              20

SEQ ID NO: 1017           moltype = DNA   length = 20
FEATURE                   Location/Qualifiers
source                    1..20
                          mol_type = genomic DNA
                          organism = Mus musculus
SEQUENCE: 1017
gtgtccagtc ccaacactgc                                              20

SEQ ID NO: 1018           moltype = DNA   length = 20
FEATURE                   Location/Qualifiers
source                    1..20
                          mol_type = genomic DNA
                          organism = Mus musculus
SEQUENCE: 1018
agcggtggaa cacaggctac                                              20

SEQ ID NO: 1019           moltype = DNA   length = 20
FEATURE                   Location/Qualifiers
source                    1..20
                          mol_type = genomic DNA
                          organism = Mus musculus
SEQUENCE: 1019
aatccagtag ggattgctgc                                              20

SEQ ID NO: 1020           moltype = DNA   length = 20
FEATURE                   Location/Qualifiers
source                    1..20
                          mol_type = genomic DNA
                          organism = Mus musculus
SEQUENCE: 1020
ttaataacag cttggtcctc                                              20

SEQ ID NO: 1021           moltype = DNA   length = 20
FEATURE                   Location/Qualifiers
source                    1..20
                          mol_type = genomic DNA
                          organism = Mus musculus
SEQUENCE: 1021
aagtgtgact ccccagcctc                                              20

SEQ ID NO: 1022           moltype = DNA   length = 20
FEATURE                   Location/Qualifiers
source                    1..20
                          mol_type = genomic DNA
                          organism = Mus musculus
SEQUENCE: 1022
gggtttcctt cctgaggctg                                              20

SEQ ID NO: 1023           moltype = DNA   length = 20
FEATURE                   Location/Qualifiers
source                    1..20
                          mol_type = genomic DNA
                          organism = Mus musculus
SEQUENCE: 1023
ggggaagaat aagacttcgg                                              20

SEQ ID NO: 1024           moltype = DNA   length = 20
FEATURE                   Location/Qualifiers
source                    1..20
                          mol_type = genomic DNA
```

```
                              organism = Mus musculus
SEQUENCE: 1024
gggtttatgt gcaccaggta                                                20

SEQ ID NO: 1025          moltype = DNA  length = 20
FEATURE                  Location/Qualifiers
source                   1..20
                         mol_type = genomic DNA
                         organism = Homo sapiens
SEQUENCE: 1025
ttcccaggaa gtgagagttc                                                20

SEQ ID NO: 1026          moltype = DNA  length = 20
FEATURE                  Location/Qualifiers
source                   1..20
                         mol_type = genomic DNA
                         organism = Homo sapiens
SEQUENCE: 1026
cactcgcggg actcactttc                                                20

SEQ ID NO: 1027          moltype = DNA  length = 20
FEATURE                  Location/Qualifiers
source                   1..20
                         mol_type = genomic DNA
                         organism = Homo sapiens
SEQUENCE: 1027
atagaaacgc tcatctcccg                                                20

SEQ ID NO: 1028          moltype = DNA  length = 20
FEATURE                  Location/Qualifiers
source                   1..20
                         mol_type = genomic DNA
                         organism = Homo sapiens
SEQUENCE: 1028
ggatgctgtg atcatcctgg                                                20

SEQ ID NO: 1029          moltype = DNA  length = 20
FEATURE                  Location/Qualifiers
source                   1..20
                         mol_type = genomic DNA
                         organism = Homo sapiens
SEQUENCE: 1029
cctcaccagc caggataagg                                                20

SEQ ID NO: 1030          moltype = DNA  length = 20
FEATURE                  Location/Qualifiers
source                   1..20
                         mol_type = genomic DNA
                         organism = Homo sapiens
SEQUENCE: 1030
aatccagtag gaattgctgc                                                20

SEQ ID NO: 1031          moltype = DNA  length = 20
FEATURE                  Location/Qualifiers
source                   1..20
                         mol_type = genomic DNA
                         organism = Homo sapiens
SEQUENCE: 1031
tgacaagcat ggggaagccg                                                20

SEQ ID NO: 1032          moltype = DNA  length = 20
FEATURE                  Location/Qualifiers
source                   1..20
                         mol_type = genomic DNA
                         organism = Homo sapiens
SEQUENCE: 1032
tctcttcgcc tcctacctga                                                20

SEQ ID NO: 1033          moltype = DNA  length = 20
FEATURE                  Location/Qualifiers
source                   1..20
                         mol_type = genomic DNA
                         organism = Homo sapiens
SEQUENCE: 1033
acctgatgcc gactctgcag                                                20

SEQ ID NO: 1034          moltype = DNA  length = 20
FEATURE                  Location/Qualifiers
source                   1..20
```

```
                                       -continued
                                 mol_type = genomic DNA
                                 organism = Homo sapiens
SEQUENCE: 1034
cagtcacggg ctttcagtgg                                                     20

SEQ ID NO: 1035                  moltype = DNA   length = 20
FEATURE                          Location/Qualifiers
source                           1..20
                                 mol_type = genomic DNA
                                 organism = Homo sapiens
SEQUENCE: 1035
cactcgcggg actcacttgc                                                     20

SEQ ID NO: 1036                  moltype = DNA   length = 20
FEATURE                          Location/Qualifiers
source                           1..20
                                 mol_type = genomic DNA
                                 organism = Homo sapiens
SEQUENCE: 1036
ccgtggaagg agccccaggg                                                     20

SEQ ID NO: 1037                  moltype = DNA   length = 20
FEATURE                          Location/Qualifiers
source                           1..20
                                 mol_type = genomic DNA
                                 organism = Homo sapiens
SEQUENCE: 1037
cataaattcc gaaatccagt                                                     20

SEQ ID NO: 1038                  moltype = DNA   length = 20
FEATURE                          Location/Qualifiers
source                           1..20
                                 mol_type = genomic DNA
                                 organism = Homo sapiens
SEQUENCE: 1038
cactcgcggg actcactttc                                                     20

SEQ ID NO: 1039                  moltype = DNA   length = 20
FEATURE                          Location/Qualifiers
source                           1..20
                                 mol_type = genomic DNA
                                 organism = Homo sapiens
SEQUENCE: 1039
gtggacggac tttataagat                                                     20

SEQ ID NO: 1040                  moltype = DNA   length = 20
FEATURE                          Location/Qualifiers
source                           1..20
                                 mol_type = genomic DNA
                                 organism = Homo sapiens
SEQUENCE: 1040
gatgaaggag ttgataactc                                                     20

SEQ ID NO: 1041                  moltype = DNA   length = 20
FEATURE                          Location/Qualifiers
source                           1..20
                                 mol_type = genomic DNA
                                 organism = Homo sapiens
SEQUENCE: 1041
cccatctaca tcgatctgcg                                                     20

SEQ ID NO: 1042                  moltype = DNA   length = 20
FEATURE                          Location/Qualifiers
source                           1..20
                                 mol_type = genomic DNA
                                 organism = Homo sapiens
SEQUENCE: 1042
gttgaggttc ttcagaagga                                                     20

SEQ ID NO: 1043                  moltype = DNA   length = 20
FEATURE                          Location/Qualifiers
source                           1..20
                                 mol_type = genomic DNA
                                 organism = Homo sapiens
SEQUENCE: 1043
gcacccaaag aactcagctt                                                     20

SEQ ID NO: 1044                  moltype = DNA   length = 20
FEATURE                          Location/Qualifiers
```

| | | |
|---|---|---|
| source | 1..20<br>mol_type = genomic DNA<br>organism = Homo sapiens | |
| SEQUENCE: 1044<br>gaacagataa ctgtagccaa | | 20 |
| SEQ ID NO: 1045<br>FEATURE<br>source | moltype = DNA   length = 20<br>Location/Qualifiers<br>1..20<br>mol_type = genomic DNA<br>organism = Mus musculus | |
| SEQUENCE: 1045<br>cactttcctt tctcaggtgc | | 20 |
| SEQ ID NO: 1046<br>FEATURE<br>source | moltype = DNA   length = 20<br>Location/Qualifiers<br>1..20<br>mol_type = genomic DNA<br>organism = Mus musculus | |
| SEQUENCE: 1046<br>cagctacaac atggtcattc | | 20 |
| SEQ ID NO: 1047<br>FEATURE<br>source | moltype = DNA   length = 20<br>Location/Qualifiers<br>1..20<br>mol_type = genomic DNA<br>organism = Mus musculus | |
| SEQUENCE: 1047<br>cccgggccaa gtacttcatt | | 20 |
| SEQ ID NO: 1048<br>FEATURE<br>source | moltype = DNA   length = 20<br>Location/Qualifiers<br>1..20<br>mol_type = genomic DNA<br>organism = Mus musculus | |
| SEQUENCE: 1048<br>gaatgtagtc cactctgaac | | 20 |
| SEQ ID NO: 1049<br>FEATURE<br>source | moltype = DNA   length = 20<br>Location/Qualifiers<br>1..20<br>mol_type = genomic DNA<br>organism = Mus musculus | |
| SEQUENCE: 1049<br>gaccgtacca tcctcaggag | | 20 |
| SEQ ID NO: 1050<br>FEATURE<br>source | moltype = DNA   length = 20<br>Location/Qualifiers<br>1..20<br>mol_type = genomic DNA<br>organism = Mus musculus | |
| SEQUENCE: 1050<br>gtggtgtagc gagcgaactc | | 20 |
| SEQ ID NO: 1051<br>FEATURE<br>source | moltype = DNA   length = 20<br>Location/Qualifiers<br>1..20<br>mol_type = genomic DNA<br>organism = Mus musculus | |
| SEQUENCE: 1051<br>tgaagcactg gatccacttg | | 20 |
| SEQ ID NO: 1052<br>FEATURE<br>source | moltype = DNA   length = 20<br>Location/Qualifiers<br>1..20<br>mol_type = genomic DNA<br>organism = Mus musculus | |
| SEQUENCE: 1052<br>tgaggatcct gcatgttaat | | 20 |
| SEQ ID NO: 1053<br>FEATURE<br>source | moltype = DNA   length = 20<br>Location/Qualifiers<br>1..20<br>mol_type = genomic DNA<br>organism = Homo sapiens | |
| SEQUENCE: 1053<br>cattaaaccc attaacatgc | | 20 |
| SEQ ID NO: 1054 | moltype = DNA   length = 20 | |

```
                         -continued

FEATURE              Location/Qualifiers
source               1..20
                     mol_type = genomic DNA
                     organism = Homo sapiens
SEQUENCE: 1054
gggcaccagg ttgctcatgg                                                    20

SEQ ID NO: 1055      moltype = DNA   length = 20
FEATURE              Location/Qualifiers
source               1..20
                     mol_type = genomic DNA
                     organism = Homo sapiens
SEQUENCE: 1055
actgggcaca gtcaatcagc                                                    20

SEQ ID NO: 1056      moltype = DNA   length = 20
FEATURE              Location/Qualifiers
source               1..20
                     mol_type = genomic DNA
                     organism = Homo sapiens
SEQUENCE: 1056
ggaatctgac cacgagcacg                                                    20

SEQ ID NO: 1057      moltype = DNA   length = 20
FEATURE              Location/Qualifiers
source               1..20
                     mol_type = genomic DNA
                     organism = Homo sapiens
SEQUENCE: 1057
tgcctaagag gatggatcgg                                                    20

SEQ ID NO: 1058      moltype = DNA   length = 20
FEATURE              Location/Qualifiers
source               1..20
                     mol_type = genomic DNA
                     organism = Homo sapiens
SEQUENCE: 1058
cgcccgtgcc cagcagcgcg                                                    20

SEQ ID NO: 1059      moltype = DNA   length = 20
FEATURE              Location/Qualifiers
source               1..20
                     mol_type = genomic DNA
                     organism = Homo sapiens
SEQUENCE: 1059
gaaggacaag caggtctacc                                                    20

SEQ ID NO: 1060      moltype = DNA   length = 20
FEATURE              Location/Qualifiers
source               1..20
                     mol_type = genomic DNA
                     organism = Homo sapiens
SEQUENCE: 1060
ggaccagcgc aacgaggaga                                                    20

SEQ ID NO: 1061      moltype = DNA   length = 20
FEATURE              Location/Qualifiers
source               1..20
                     mol_type = genomic DNA
                     organism = Homo sapiens
SEQUENCE: 1061
cgaggagaag gcgcagcgtg                                                    20

SEQ ID NO: 1062      moltype = DNA   length = 20
FEATURE              Location/Qualifiers
source               1..20
                     mol_type = genomic DNA
                     organism = Homo sapiens
SEQUENCE: 1062
ggagagccag aggagcgcgg                                                    20

SEQ ID NO: 1063      moltype = DNA   length = 20
FEATURE              Location/Qualifiers
source               1..20
                     mol_type = genomic DNA
                     organism = Homo sapiens
SEQUENCE: 1063
actgttcccg aggcagccca                                                    20
```

```
SEQ ID NO: 1064          moltype = DNA   length = 20
FEATURE                  Location/Qualifiers
source                   1..20
                         mol_type = genomic DNA
                         organism = Homo sapiens
SEQUENCE: 1064
gcaggagagc cagaggagcg                                                      20

SEQ ID NO: 1065          moltype = DNA   length = 20
FEATURE                  Location/Qualifiers
source                   1..20
                         mol_type = genomic DNA
                         organism = Mus musculus
SEQUENCE: 1065
ggcgaattgg ctactttcaa                                                      20

SEQ ID NO: 1066          moltype = DNA   length = 20
FEATURE                  Location/Qualifiers
source                   1..20
                         mol_type = genomic DNA
                         organism = Mus musculus
SEQUENCE: 1066
acgtcaagga ctttgcaggt                                                      20

SEQ ID NO: 1067          moltype = DNA   length = 20
FEATURE                  Location/Qualifiers
source                   1..20
                         mol_type = genomic DNA
                         organism = Mus musculus
SEQUENCE: 1067
gccaagcaac tgttagccgc                                                      20

SEQ ID NO: 1068          moltype = DNA   length = 20
FEATURE                  Location/Qualifiers
source                   1..20
                         mol_type = genomic DNA
                         organism = Mus musculus
SEQUENCE: 1068
gtgaacctcc tgttaggcaa                                                      20

SEQ ID NO: 1069          moltype = DNA   length = 20
FEATURE                  Location/Qualifiers
source                   1..20
                         mol_type = genomic DNA
                         organism = Mus musculus
SEQUENCE: 1069
tttgccggac tttgagactg                                                      20

SEQ ID NO: 1070          moltype = DNA   length = 20
FEATURE                  Location/Qualifiers
source                   1..20
                         mol_type = genomic DNA
                         organism = Mus musculus
SEQUENCE: 1070
gttcaccatc gttggcgaat                                                      20

SEQ ID NO: 1071          moltype = DNA   length = 20
FEATURE                  Location/Qualifiers
source                   1..20
                         mol_type = genomic DNA
                         organism = Mus musculus
SEQUENCE: 1071
gggcgcggac gtgaacgtca                                                      20

SEQ ID NO: 1072          moltype = DNA   length = 20
FEATURE                  Location/Qualifiers
source                   1..20
                         mol_type = genomic DNA
                         organism = Mus musculus
SEQUENCE: 1072
tgtggcaggt gagggagaaa                                                      20

SEQ ID NO: 1073          moltype = DNA   length = 20
FEATURE                  Location/Qualifiers
source                   1..20
                         mol_type = genomic DNA
                         organism = Homo sapiens
SEQUENCE: 1073
ttgttggcag cgtcgtgcaa                                                      20
```

```
SEQ ID NO: 1074          moltype = DNA   length = 20
FEATURE                  Location/Qualifiers
source                   1..20
                         mol_type = genomic DNA
                         organism = Homo sapiens
SEQUENCE: 1074
gcaccgagcc gccatccgcg                                                     20

SEQ ID NO: 1075          moltype = DNA   length = 20
FEATURE                  Location/Qualifiers
source                   1..20
                         mol_type = genomic DNA
                         organism = Homo sapiens
SEQUENCE: 1075
aacaacgggc actacaaggt                                                     20

SEQ ID NO: 1076          moltype = DNA   length = 20
FEATURE                  Location/Qualifiers
source                   1..20
                         mol_type = genomic DNA
                         organism = Homo sapiens
SEQUENCE: 1076
cactgagatc acgattcttt                                                     20

SEQ ID NO: 1077          moltype = DNA   length = 20
FEATURE                  Location/Qualifiers
source                   1..20
                         mol_type = genomic DNA
                         organism = Homo sapiens
SEQUENCE: 1077
aggtgcggag gtgaacacca                                                     20

SEQ ID NO: 1078          moltype = DNA   length = 20
FEATURE                  Location/Qualifiers
source                   1..20
                         mol_type = genomic DNA
                         organism = Homo sapiens
SEQUENCE: 1078
gccggatgtg tgaagaacgg                                                     20

SEQ ID NO: 1079          moltype = DNA   length = 20
FEATURE                  Location/Qualifiers
source                   1..20
                         mol_type = genomic DNA
                         organism = Homo sapiens
SEQUENCE: 1079
gtgtctgttt ccaggctgga                                                     20

SEQ ID NO: 1080          moltype = DNA   length = 20
FEATURE                  Location/Qualifiers
source                   1..20
                         mol_type = genomic DNA
                         organism = Homo sapiens
SEQUENCE: 1080
aggagcagga cgatgcccaa                                                     20

SEQ ID NO: 1081          moltype = DNA   length = 20
FEATURE                  Location/Qualifiers
source                   1..20
                         mol_type = genomic DNA
                         organism = Homo sapiens
SEQUENCE: 1081
agccttgcag caccacaaca                                                     20

SEQ ID NO: 1082          moltype = DNA   length = 20
FEATURE                  Location/Qualifiers
source                   1..20
                         mol_type = genomic DNA
                         organism = Homo sapiens
SEQUENCE: 1082
actgacctct gaccaagccg                                                     20

SEQ ID NO: 1083          moltype = DNA   length = 20
FEATURE                  Location/Qualifiers
source                   1..20
                         mol_type = genomic DNA
                         organism = Homo sapiens
SEQUENCE: 1083
```

```
ccggatgtgt gaagaacggg                                                    20

SEQ ID NO: 1084         moltype = DNA   length = 20
FEATURE                 Location/Qualifiers
source                  1..20
                        mol_type = genomic DNA
                        organism = Homo sapiens
SEQUENCE: 1084
ttgcacgacg ctgccaacaa                                                    20

SEQ ID NO: 1085         moltype = DNA   length = 20
FEATURE                 Location/Qualifiers
source                  1..20
                        mol_type = genomic DNA
                        organism = Homo sapiens
SEQUENCE: 1085
ctccagccca gtccctgttg                                                    20

SEQ ID NO: 1086         moltype = DNA   length = 20
FEATURE                 Location/Qualifiers
source                  1..20
                        mol_type = genomic DNA
                        organism = Homo sapiens
SEQUENCE: 1086
tgagggagcg agccagcaag                                                    20

SEQ ID NO: 1087         moltype = DNA   length = 20
FEATURE                 Location/Qualifiers
source                  1..20
                        mol_type = genomic DNA
                        organism = Homo sapiens
SEQUENCE: 1087
gtgaacctcc tgttaggcaa                                                    20

SEQ ID NO: 1088         moltype = DNA   length = 20
FEATURE                 Location/Qualifiers
source                  1..20
                        mol_type = genomic DNA
                        organism = Mus musculus
SEQUENCE: 1088
gaagtgcacg cggatgctcg                                                    20

SEQ ID NO: 1089         moltype = DNA   length = 20
FEATURE                 Location/Qualifiers
source                  1..20
                        mol_type = genomic DNA
                        organism = Mus musculus
SEQUENCE: 1089
agtgctccag cagctcgaaa                                                    20

SEQ ID NO: 1090         moltype = DNA   length = 20
FEATURE                 Location/Qualifiers
source                  1..20
                        mol_type = genomic DNA
                        organism = Mus musculus
SEQUENCE: 1090
gccggccgct tccacttgga                                                    20

SEQ ID NO: 1091         moltype = DNA   length = 20
FEATURE                 Location/Qualifiers
source                  1..20
                        mol_type = genomic DNA
                        organism = Mus musculus
SEQUENCE: 1091
gctgtgtcgc cagcgcatcg                                                    20

SEQ ID NO: 1092         moltype = DNA   length = 20
FEATURE                 Location/Qualifiers
source                  1..20
                        mol_type = genomic DNA
                        organism = Mus musculus
SEQUENCE: 1092
gcgactgtcg cgcaccaaga                                                    20

SEQ ID NO: 1093         moltype = DNA   length = 20
FEATURE                 Location/Qualifiers
source                  1..20
                        mol_type = genomic DNA
                        organism = Mus musculus
```

```
SEQUENCE: 1093
gcgtgcacgg ggcgcacgag                                                    20

SEQ ID NO: 1094         moltype = DNA  length = 20
FEATURE                 Location/Qualifiers
source                  1..20
                        mol_type = genomic DNA
                        organism = Mus musculus
SEQUENCE: 1094
tcacggagta ccgggttaag                                                    20

SEQ ID NO: 1095         moltype = DNA  length = 20
FEATURE                 Location/Qualifiers
source                  1..20
                        mol_type = genomic DNA
                        organism = Mus musculus
SEQUENCE: 1095
ggacgcctgc ggcttctatt                                                    20

SEQ ID NO: 1096         moltype = DNA  length = 20
FEATURE                 Location/Qualifiers
source                  1..20
                        mol_type = genomic DNA
                        organism = Mus musculus
SEQUENCE: 1096
gcgcgaagaa gcagttccgt                                                    20

SEQ ID NO: 1097         moltype = DNA  length = 20
FEATURE                 Location/Qualifiers
source                  1..20
                        mol_type = genomic DNA
                        organism = Mus musculus
SEQUENCE: 1097
gctcagcgtg aagatggctt                                                    20

SEQ ID NO: 1098         moltype = DNA  length = 20
FEATURE                 Location/Qualifiers
source                  1..20
                        mol_type = genomic DNA
                        organism = Mus musculus
SEQUENCE: 1098
cgagcccgtg ggcaccttct                                                    20

SEQ ID NO: 1099         moltype = DNA  length = 20
FEATURE                 Location/Qualifiers
source                  1..20
                        mol_type = genomic DNA
                        organism = Mus musculus
SEQUENCE: 1099
atccgcgtgc acttccaggc                                                    20

SEQ ID NO: 1100         moltype = DNA  length = 20
FEATURE                 Location/Qualifiers
source                  1..20
                        mol_type = genomic DNA
                        organism = Mus musculus
SEQUENCE: 1100
cgccaggttc tcgcgaccca                                                    20

SEQ ID NO: 1101         moltype = DNA  length = 20
FEATURE                 Location/Qualifiers
source                  1..20
                        mol_type = genomic DNA
                        organism = Homo sapiens
SEQUENCE: 1101
gcggctgcgc gccgagcccg                                                    20

SEQ ID NO: 1102         moltype = DNA  length = 20
FEATURE                 Location/Qualifiers
source                  1..20
                        mol_type = genomic DNA
                        organism = Homo sapiens
SEQUENCE: 1102
ggacgcctgc ggattctact                                                    20

SEQ ID NO: 1103         moltype = DNA  length = 20
FEATURE                 Location/Qualifiers
source                  1..20
                        mol_type = genomic DNA
```

```
                        organism = Homo sapiens
SEQUENCE: 1103
ggctgccatc caggtgaaag                                            20

SEQ ID NO: 1104         moltype = DNA  length = 20
FEATURE                 Location/Qualifiers
source                  1..20
                        mol_type = genomic DNA
                        organism = Homo sapiens
SEQUENCE: 1104
gcggctgtcg cgcaccagga                                            20

SEQ ID NO: 1105         moltype = DNA  length = 20
FEATURE                 Location/Qualifiers
source                  1..20
                        mol_type = genomic DNA
                        organism = Homo sapiens
SEQUENCE: 1105
tggacgcctg cggattctac                                            20

SEQ ID NO: 1106         moltype = DNA  length = 20
FEATURE                 Location/Qualifiers
source                  1..20
                        mol_type = genomic DNA
                        organism = Homo sapiens
SEQUENCE: 1106
gacgcctgcg gattctactg                                            20

SEQ ID NO: 1107         moltype = DNA  length = 20
FEATURE                 Location/Qualifiers
source                  1..20
                        mol_type = genomic DNA
                        organism = Homo sapiens
SEQUENCE: 1107
agtgctccag cagctcgaag                                            20

SEQ ID NO: 1108         moltype = DNA  length = 20
FEATURE                 Location/Qualifiers
source                  1..20
                        mol_type = genomic DNA
                        organism = Homo sapiens
SEQUENCE: 1108
gccggccgct ttcacctgga                                            20

SEQ ID NO: 1109         moltype = DNA  length = 20
FEATURE                 Location/Qualifiers
source                  1..20
                        mol_type = genomic DNA
                        organism = Homo sapiens
SEQUENCE: 1109
agtagaatcc gcaggcgtcc                                            20

SEQ ID NO: 1110         moltype = DNA  length = 20
FEATURE                 Location/Qualifiers
source                  1..20
                        mol_type = genomic DNA
                        organism = Homo sapiens
SEQUENCE: 1110
cgcaccagga aggtgcccac                                            20

SEQ ID NO: 1111         moltype = DNA  length = 20
FEATURE                 Location/Qualifiers
source                  1..20
                        mol_type = genomic DNA
                        organism = Homo sapiens
SEQUENCE: 1111
ggccggcctg aaagtgcacg                                            20

SEQ ID NO: 1112         moltype = DNA  length = 20
FEATURE                 Location/Qualifiers
source                  1..20
                        mol_type = genomic DNA
                        organism = Homo sapiens
SEQUENCE: 1112
tccgttcgca cgccgattac                                            20

SEQ ID NO: 1113         moltype = DNA  length = 20
FEATURE                 Location/Qualifiers
source                  1..20
```

```
                             -continued mol_type = genomic DNA
                          organism = Homo sapiens
SEQUENCE: 1113
agcgcgctcc tggacgcctg                                                20

SEQ ID NO: 1114           moltype = DNA   length = 20
FEATURE                   Location/Qualifiers
source                    1..20
                          mol_type = genomic DNA
                          organism = Homo sapiens
SEQUENCE: 1114
cggctgcgcg ccgagcccgt                                                20

SEQ ID NO: 1115           moltype = DNA   length = 20
FEATURE                   Location/Qualifiers
source                    1..20
                          mol_type = genomic DNA
                          organism = Homo sapiens
SEQUENCE: 1115
acgcctgcgg attctactgg                                                20

SEQ ID NO: 1116           moltype = DNA   length = 20
FEATURE                   Location/Qualifiers
source                    1..20
                          mol_type = genomic DNA
                          organism = Homo sapiens
SEQUENCE: 1116
cgaggccatc ttcacgctaa                                                20

SEQ ID NO: 1117           moltype = DNA   length = 20
FEATURE                   Location/Qualifiers
source                    1..20
                          mol_type = genomic DNA
                          organism = Homo sapiens
SEQUENCE: 1117
tcaggccggc cgctttcacc                                                20

SEQ ID NO: 1118           moltype = DNA   length = 20
FEATURE                   Location/Qualifiers
source                    1..20
                          mol_type = genomic DNA
                          organism = Homo sapiens
SEQUENCE: 1118
cttagcgtga agatggcctc                                                20

SEQ ID NO: 1119           moltype = DNA   length = 20
FEATURE                   Location/Qualifiers
source                    1..20
                          mol_type = genomic DNA
                          organism = Homo sapiens
SEQUENCE: 1119
gccggtaatc ggcgtgcgaa                                                20

SEQ ID NO: 1120           moltype = DNA   length = 20
FEATURE                   Location/Qualifiers
source                    1..20
                          mol_type = genomic DNA
                          organism = Homo sapiens
SEQUENCE: 1120
ctgcattgtc ggctgccacc                                                20

SEQ ID NO: 1121           moltype = DNA   length = 20
FEATURE                   Location/Qualifiers
source                    1..20
                          mol_type = genomic DNA
                          organism = Homo sapiens
SEQUENCE: 1121
gtgcgccccg tgcacgctca                                                20

SEQ ID NO: 1122           moltype = DNA   length = 20
FEATURE                   Location/Qualifiers
source                    1..20
                          mol_type = genomic DNA
                          organism = Homo sapiens
SEQUENCE: 1122
gctgtgccgc cagcgcatcg                                                20

SEQ ID NO: 1123           moltype = DNA   length = 20
FEATURE                   Location/Qualifiers
```

| | | |
|---|---|---|
| source | 1..20<br>mol_type = genomic DNA<br>organism = Homo sapiens | |
| SEQUENCE: 1123<br>cacgcggcgc tggcgcagcg | | 20 |
| SEQ ID NO: 1124<br>FEATURE<br>source | moltype = DNA   length = 20<br>Location/Qualifiers<br>1..20<br>mol_type = genomic DNA<br>organism = Homo sapiens | |
| SEQUENCE: 1124<br>gctcctgcag cggccgcacg | | 20 |
| SEQ ID NO: 1125<br>FEATURE<br>source | moltype = DNA   length = 20<br>Location/Qualifiers<br>1..20<br>mol_type = genomic DNA<br>organism = Homo sapiens | |
| SEQUENCE: 1125<br>agctctcgcg gctgccatcc | | 20 |
| SEQ ID NO: 1126<br>FEATURE<br>source | moltype = DNA   length = 20<br>Location/Qualifiers<br>1..20<br>mol_type = genomic DNA<br>organism = Homo sapiens | |
| SEQUENCE: 1126<br>tggtgcgcga cagccgccag | | 20 |
| SEQ ID NO: 1127<br>FEATURE<br>source | moltype = DNA   length = 20<br>Location/Qualifiers<br>1..20<br>mol_type = genomic DNA<br>organism = Homo sapiens | |
| SEQUENCE: 1127<br>gatggtagca cacaaccagg | | 20 |
| SEQ ID NO: 1128<br>FEATURE<br>source | moltype = DNA   length = 20<br>Location/Qualifiers<br>1..20<br>mol_type = genomic DNA<br>organism = Homo sapiens | |
| SEQUENCE: 1128<br>agaggcagtc gaagctctcg | | 20 |
| SEQ ID NO: 1129<br>FEATURE<br>source | moltype = DNA   length = 20<br>Location/Qualifiers<br>1..20<br>mol_type = genomic DNA<br>organism = Homo sapiens | |
| SEQUENCE: 1129<br>gctggcggct gtcgcgcacc | | 20 |
| SEQ ID NO: 1130<br>FEATURE<br>source | moltype = DNA   length = 20<br>Location/Qualifiers<br>1..20<br>mol_type = genomic DNA<br>organism = Homo sapiens | |
| SEQUENCE: 1130<br>ccgaggccat cttcacgcta | | 20 |
| SEQ ID NO: 1131<br>FEATURE<br>source | moltype = DNA   length = 20<br>Location/Qualifiers<br>1..20<br>mol_type = genomic DNA<br>organism = Homo sapiens | |
| SEQUENCE: 1131<br>ggggccccca gcatgcggcg | | 20 |
| SEQ ID NO: 1132<br>FEATURE<br>source | moltype = DNA   length = 20<br>Location/Qualifiers<br>1..20<br>mol_type = genomic DNA<br>organism = Homo sapiens | |
| SEQUENCE: 1132<br>gctgctggag cactacgtgg | | 20 |
| SEQ ID NO: 1133 | moltype = DNA   length = 20 | |

-continued

```
FEATURE                 Location/Qualifiers
source                  1..20
                        mol_type = genomic DNA
                        organism = Homo sapiens
SEQUENCE: 1133
cgagctgctg gagcactacg                                                     20

SEQ ID NO: 1134         moltype = DNA   length = 20
FEATURE                 Location/Qualifiers
source                  1..20
                        mol_type = genomic DNA
                        organism = Homo sapiens
SEQUENCE: 1134
cgaaaaagca gttccgctgg                                                     20

SEQ ID NO: 1135         moltype = DNA   length = 20
FEATURE                 Location/Qualifiers
source                  1..20
                        mol_type = genomic DNA
                        organism = Homo sapiens
SEQUENCE: 1135
gcaggcgtcc aggagcgcgc                                                     20

SEQ ID NO: 1136         moltype = DNA   length = 20
FEATURE                 Location/Qualifiers
source                  1..20
                        mol_type = genomic DNA
                        organism = Homo sapiens
SEQUENCE: 1136
ggggcccctg agcgtgcacg                                                     20

SEQ ID NO: 1137         moltype = DNA   length = 20
FEATURE                 Location/Qualifiers
source                  1..20
                        mol_type = genomic DNA
                        organism = Homo sapiens
SEQUENCE: 1137
gcggcgccgc gccgcatgct                                                     20

SEQ ID NO: 1138         moltype = DNA   length = 20
FEATURE                 Location/Qualifiers
source                  1..20
                        mol_type = genomic DNA
                        organism = Homo sapiens
SEQUENCE: 1138
gcacgcggcg ctggcgcagc                                                     20

SEQ ID NO: 1139         moltype = DNA   length = 20
FEATURE                 Location/Qualifiers
source                  1..20
                        mol_type = genomic DNA
                        organism = Homo sapiens
SEQUENCE: 1139
tgggggcccc tgagcgtgca                                                     20

SEQ ID NO: 1140         moltype = DNA   length = 20
FEATURE                 Location/Qualifiers
source                  1..20
                        mol_type = genomic DNA
                        organism = Homo sapiens
SEQUENCE: 1140
caggaaggtg cccacgggct                                                     20

SEQ ID NO: 1141         moltype = DNA   length = 20
FEATURE                 Location/Qualifiers
source                  1..20
                        mol_type = genomic DNA
                        organism = Homo sapiens
SEQUENCE: 1141
tgcgccccgt gcacgctcag                                                     20

SEQ ID NO: 1142         moltype = DNA   length = 20
FEATURE                 Location/Qualifiers
source                  1..20
                        mol_type = genomic DNA
                        organism = Homo sapiens
SEQUENCE: 1142
gccatccagg tgaaagcggc                                                     20
```

| | | |
|---|---|---|
| SEQ ID NO: 1143 FEATURE source | moltype = DNA  length = 20 Location/Qualifiers 1..20 mol_type = genomic DNA organism = Homo sapiens | |
| SEQUENCE: 1143 cacgcgcgcc agcgcgctcc | | 20 |
| SEQ ID NO: 1144 FEATURE source | moltype = DNA  length = 20 Location/Qualifiers 1..20 mol_type = genomic DNA organism = Homo sapiens | |
| SEQUENCE: 1144 gggcccccag tagaatccgc | | 20 |
| SEQ ID NO: 1145 FEATURE source | moltype = DNA  length = 20 Location/Qualifiers 1..20 mol_type = genomic DNA organism = Homo sapiens | |
| SEQUENCE: 1145 atccgcgtgc actttcaggc | | 20 |
| SEQ ID NO: 1146 FEATURE source | moltype = DNA  length = 20 Location/Qualifiers 1..20 mol_type = genomic DNA organism = Homo sapiens | |
| SEQUENCE: 1146 cgagcccgtg ggcaccttcc | | 20 |
| SEQ ID NO: 1147 FEATURE source | moltype = DNA  length = 20 Location/Qualifiers 1..20 mol_type = genomic DNA organism = Homo sapiens | |
| SEQUENCE: 1147 ccacagcagc agagccccga | | 20 |
| SEQ ID NO: 1148 FEATURE source | moltype = DNA  length = 20 Location/Qualifiers 1..20 mol_type = genomic DNA organism = Homo sapiens | |
| SEQUENCE: 1148 agccaggttc tcgcggccca | | 20 |
| SEQ ID NO: 1149 FEATURE source | moltype = DNA  length = 20 Location/Qualifiers 1..20 mol_type = genomic DNA organism = Homo sapiens | |
| SEQUENCE: 1149 aaagtgcacg cggatgctcg | | 20 |
| SEQ ID NO: 1150 FEATURE source | moltype = DNA  length = 20 Location/Qualifiers 1..20 mol_type = genomic DNA organism = Homo sapiens | |
| SEQUENCE: 1150 ctcttcctcc tcctcgcccg | | 20 |
| SEQ ID NO: 1151 FEATURE source | moltype = DNA  length = 20 Location/Qualifiers 1..20 mol_type = genomic DNA organism = Homo sapiens | |
| SEQUENCE: 1151 gcgtgcacgg ggcgcacgag | | 20 |
| SEQ ID NO: 1152 FEATURE source | moltype = DNA  length = 20 Location/Qualifiers 1..20 mol_type = genomic DNA organism = Homo sapiens | |
| SEQUENCE: 1152 aagtgcacgc ggatgctcgt | | 20 |

| SEQ ID NO: 1153 | moltype = DNA   length = 20 | |
| --- | --- | --- |
| FEATURE | Location/Qualifiers | |
| source | 1..20 | |
| | mol_type = genomic DNA | |
| | organism = Homo sapiens | |
| SEQUENCE: 1153 | | |
| cgtgcgcccc gtgcacgctc | | 20 |
| SEQ ID NO: 1154 | moltype = DNA   length = 20 | |
| FEATURE | Location/Qualifiers | |
| source | 1..20 | |
| | mol_type = genomic DNA | |
| | organism = Homo sapiens | |
| SEQUENCE: 1154 | | |
| gcagcggccg cacgcggcgc | | 20 |
| SEQ ID NO: 1155 | moltype = DNA   length = 20 | |
| FEATURE | Location/Qualifiers | |
| source | 1..20 | |
| | mol_type = genomic DNA | |
| | organism = Homo sapiens | |
| SEQUENCE: 1155 | | |
| ccttagcgtg aagatggcct | | 20 |
| SEQ ID NO: 1156 | moltype = DNA   length = 20 | |
| FEATURE | Location/Qualifiers | |
| source | 1..20 | |
| | mol_type = genomic DNA | |
| | organism = Homo sapiens | |
| SEQUENCE: 1156 | | |
| caggttctcg cggcccacgg | | 20 |
| SEQ ID NO: 1157 | moltype = DNA   length = 20 | |
| FEATURE | Location/Qualifiers | |
| source | 1..20 | |
| | mol_type = genomic DNA | |
| | organism = Homo sapiens | |
| SEQUENCE: 1157 | | |
| gcgcaccagg aaggtgccca | | 20 |
| SEQ ID NO: 1158 | moltype = DNA   length = 20 | |
| FEATURE | Location/Qualifiers | |
| source | 1..20 | |
| | mol_type = genomic DNA | |
| | organism = Homo sapiens | |
| SEQUENCE: 1158 | | |
| gctgccggtc aaatctggaa | | 20 |
| SEQ ID NO: 1159 | moltype = DNA   length = 20 | |
| FEATURE | Location/Qualifiers | |
| source | 1..20 | |
| | mol_type = genomic DNA | |
| | organism = Homo sapiens | |
| SEQUENCE: 1159 | | |
| cggcgtgcga acggaatgtg | | 20 |
| SEQ ID NO: 1160 | moltype = DNA   length = 20 | |
| FEATURE | Location/Qualifiers | |
| source | 1..20 | |
| | mol_type = genomic DNA | |
| | organism = Homo sapiens | |
| SEQUENCE: 1160 | | |
| cagcagcaga gccccgacgg | | 20 |
| SEQ ID NO: 1161 | moltype = DNA   length = 20 | |
| FEATURE | Location/Qualifiers | |
| source | 1..20 | |
| | mol_type = genomic DNA | |
| | organism = Homo sapiens | |
| SEQUENCE: 1161 | | |
| gggcgaaaaa gcagttccgc | | 20 |
| SEQ ID NO: 1162 | moltype = DNA   length = 20 | |
| FEATURE | Location/Qualifiers | |
| source | 1..20 | |
| | mol_type = genomic DNA | |
| | organism = Homo sapiens | |
| SEQUENCE: 1162 | | |

-continued

```
cgcacgcggc gctggcgcag                                         20

SEQ ID NO: 1163          moltype = DNA   length = 20
FEATURE                  Location/Qualifiers
source                   1..20
                         mol_type = genomic DNA
                         organism = Homo sapiens
SEQUENCE: 1163
ggatgcgagc caggttctcg                                         20

SEQ ID NO: 1164          moltype = DNA   length = 20
FEATURE                  Location/Qualifiers
source                   1..20
                         mol_type = genomic DNA
                         organism = Homo sapiens
SEQUENCE: 1164
tggcggcaca gctcctgcag                                         20

SEQ ID NO: 1165          moltype = DNA   length = 20
FEATURE                  Location/Qualifiers
source                   1..20
                         mol_type = genomic DNA
                         organism = Homo sapiens
SEQUENCE: 1165
gcgcccgcgg ccgtgccccg                                         20

SEQ ID NO: 1166          moltype = DNA   length = 20
FEATURE                  Location/Qualifiers
source                   1..20
                         mol_type = genomic DNA
                         organism = Homo sapiens
SEQUENCE: 1166
ggcgccgcgc cgcatgctgg                                         20

SEQ ID NO: 1167          moltype = DNA   length = 20
FEATURE                  Location/Qualifiers
source                   1..20
                         mol_type = genomic DNA
                         organism = Homo sapiens
SEQUENCE: 1167
cggtggccac gatgcgctgg                                         20

SEQ ID NO: 1168          moltype = DNA   length = 20
FEATURE                  Location/Qualifiers
source                   1..20
                         mol_type = genomic DNA
                         organism = Homo sapiens
SEQUENCE: 1168
tgctgtggag actgcattgt                                         20

SEQ ID NO: 1169          moltype = DNA   length = 20
FEATURE                  Location/Qualifiers
source                   1..20
                         mol_type = genomic DNA
                         organism = Homo sapiens
SEQUENCE: 1169
taggatggta gcacacaacc                                         20

SEQ ID NO: 1170          moltype = DNA   length = 20
FEATURE                  Location/Qualifiers
source                   1..20
                         mol_type = genomic DNA
                         organism = Homo sapiens
SEQUENCE: 1170
gcggccgtgc cccgcggtcc                                         20

SEQ ID NO: 1171          moltype = DNA   length = 20
FEATURE                  Location/Qualifiers
source                   1..20
                         mol_type = genomic DNA
                         organism = Homo sapiens
SEQUENCE: 1171
gagcatccgc gtgcactttc                                         20

SEQ ID NO: 1172          moltype = DNA   length = 20
FEATURE                  Location/Qualifiers
source                   1..20
                         mol_type = genomic DNA
                         organism = Homo sapiens
```

| | | |
|---|---|---|
| SEQUENCE: 1172<br>cgctgccggt caaatctgga | | 20 |
| SEQ ID NO: 1173<br>FEATURE<br>source<br>SEQUENCE: 1173<br>cagcgcatcg tggccaccgt | moltype = DNA  length = 20<br>Location/Qualifiers<br>1..20<br>mol_type = genomic DNA<br>organism = Homo sapiens | 20 |
| SEQ ID NO: 1174<br>FEATURE<br>source<br>SEQUENCE: 1174<br>gcggatgctc gtgggtcccg | moltype = DNA  length = 20<br>Location/Qualifiers<br>1..20<br>mol_type = genomic DNA<br>organism = Homo sapiens | 20 |
| SEQ ID NO: 1175<br>FEATURE<br>source<br>SEQUENCE: 1175<br>cggcgccgcg ccgcatgctg | moltype = DNA  length = 20<br>Location/Qualifiers<br>1..20<br>mol_type = genomic DNA<br>organism = Homo sapiens | 20 |
| SEQ ID NO: 1176<br>FEATURE<br>source<br>SEQUENCE: 1176<br>cggtcaaatc tggaagggga | moltype = DNA  length = 20<br>Location/Qualifiers<br>1..20<br>mol_type = genomic DNA<br>organism = Homo sapiens | 20 |
| SEQ ID NO: 1177<br>FEATURE<br>source<br>SEQUENCE: 1177<br>aggaaggttc tggccgccgt | moltype = DNA  length = 20<br>Location/Qualifiers<br>1..20<br>mol_type = genomic DNA<br>organism = Homo sapiens | 20 |
| SEQ ID NO: 1178<br>FEATURE<br>source<br>SEQUENCE: 1178<br>ccacggtggc cacgatgcgc | moltype = DNA  length = 20<br>Location/Qualifiers<br>1..20<br>mol_type = genomic DNA<br>organism = Homo sapiens | 20 |
| SEQ ID NO: 1179<br>FEATURE<br>source<br>SEQUENCE: 1179<br>cgctgcgcca gcgccgcgtg | moltype = DNA  length = 20<br>Location/Qualifiers<br>1..20<br>mol_type = genomic DNA<br>organism = Homo sapiens | 20 |
| SEQ ID NO: 1180<br>FEATURE<br>source<br>SEQUENCE: 1180<br>aggagctcag gtagtcgcgg | moltype = DNA  length = 20<br>Location/Qualifiers<br>1..20<br>mol_type = genomic DNA<br>organism = Homo sapiens | 20 |
| SEQ ID NO: 1181<br>FEATURE<br>source<br>SEQUENCE: 1181<br>gcagcggggc ccccagcatg | moltype = DNA  length = 20<br>Location/Qualifiers<br>1..20<br>mol_type = genomic DNA<br>organism = Homo sapiens | 20 |
| SEQ ID NO: 1182<br>FEATURE<br>source | moltype = DNA  length = 20<br>Location/Qualifiers<br>1..20<br>mol_type = genomic DNA | |

```
                                    organism = Homo sapiens
SEQUENCE: 1182
ggaaggagct caggtagtcg                                                       20

SEQ ID NO: 1183         moltype = DNA  length = 20
FEATURE                 Location/Qualifiers
source                  1..20
                        mol_type = genomic DNA
                        organism = Homo sapiens
SEQUENCE: 1183
tcgcggagga cggggttgag                                                       20

SEQ ID NO: 1184         moltype = DNA  length = 20
FEATURE                 Location/Qualifiers
source                  1..20
                        mol_type = genomic DNA
                        organism = Homo sapiens
SEQUENCE: 1184
cgactgcctc ttcgagctgc                                                       20

SEQ ID NO: 1185         moltype = DNA  length = 20
FEATURE                 Location/Qualifiers
source                  1..20
                        mol_type = genomic DNA
                        organism = Homo sapiens
SEQUENCE: 1185
gcgccgcgtg cggccgctgc                                                       20

SEQ ID NO: 1186         moltype = DNA  length = 20
FEATURE                 Location/Qualifiers
source                  1..20
                        mol_type = genomic DNA
                        organism = Homo sapiens
SEQUENCE: 1186
caccgtgggc cgcgagaacc                                                       20

SEQ ID NO: 1187         moltype = DNA  length = 20
FEATURE                 Location/Qualifiers
source                  1..20
                        mol_type = genomic DNA
                        organism = Homo sapiens
SEQUENCE: 1187
gtgccccgcg gtcccggccc                                                       20

SEQ ID NO: 1188         moltype = DNA  length = 20
FEATURE                 Location/Qualifiers
source                  1..20
                        mol_type = genomic DNA
                        organism = Homo sapiens
SEQUENCE: 1188
ctgccggtca aatctggaag                                                       20

SEQ ID NO: 1189         moltype = DNA  length = 20
FEATURE                 Location/Qualifiers
source                  1..20
                        mol_type = genomic DNA
                        organism = Homo sapiens
SEQUENCE: 1189
cttcccette cagatttgac                                                       20

SEQ ID NO: 1190         moltype = DNA  length = 20
FEATURE                 Location/Qualifiers
source                  1..20
                        mol_type = genomic DNA
                        organism = Homo sapiens
SEQUENCE: 1190
ctcaggtagt cgcggaggac                                                       20

SEQ ID NO: 1191         moltype = DNA  length = 20
FEATURE                 Location/Qualifiers
source                  1..20
                        mol_type = genomic DNA
                        organism = Homo sapiens
SEQUENCE: 1191
cgggcgctgc cggtcaaatc                                                       20

SEQ ID NO: 1192         moltype = DNA  length = 20
FEATURE                 Location/Qualifiers
source                  1..20
```

```
                        mol_type = genomic DNA
                        organism = Homo sapiens
SEQUENCE: 1192
ggaaggttct ggccgccgtc                                                   20

SEQ ID NO: 1193         moltype = DNA   length = 20
FEATURE                 Location/Qualifiers
source                  1..20
                        mol_type = genomic DNA
                        organism = Homo sapiens
SEQUENCE: 1193
gctcaggtag tcgcggagga                                                   20

SEQ ID NO: 1194         moltype = DNA   length = 20
FEATURE                 Location/Qualifiers
source                  1..20
                        mol_type = genomic DNA
                        organism = Homo sapiens
SEQUENCE: 1194
gcggaagtgc gtgtcgccgg                                                   20

SEQ ID NO: 1195         moltype = DNA   length = 20
FEATURE                 Location/Qualifiers
source                  1..20
                        mol_type = genomic DNA
                        organism = Homo sapiens
SEQUENCE: 1195
ggaccgcggg gcacggccgc                                                   20

SEQ ID NO: 1196         moltype = DNA   length = 20
FEATURE                 Location/Qualifiers
source                  1..20
                        mol_type = genomic DNA
                        organism = Homo sapiens
SEQUENCE: 1196
gggaccgcgg ggcacggccg                                                   20

SEQ ID NO: 1197         moltype = DNA   length = 20
FEATURE                 Location/Qualifiers
source                  1..20
                        mol_type = genomic DNA
                        organism = Homo sapiens
SEQUENCE: 1197
gcgcgtgatg cgccggtaat                                                   20

SEQ ID NO: 1198         moltype = DNA   length = 20
FEATURE                 Location/Qualifiers
source                  1..20
                        mol_type = genomic DNA
                        organism = Homo sapiens
SEQUENCE: 1198
tcaggtagtc gcggaggacg                                                   20

SEQ ID NO: 1199         moltype = DNA   length = 20
FEATURE                 Location/Qualifiers
source                  1..20
                        mol_type = genomic DNA
                        organism = Homo sapiens
SEQUENCE: 1199
tgcggaagtg cgtgtcgccg                                                   20

SEQ ID NO: 1200         moltype = DNA   length = 20
FEATURE                 Location/Qualifiers
source                  1..20
                        mol_type = genomic DNA
                        organism = Homo sapiens
SEQUENCE: 1200
ggggccggga ccgcggggca                                                   20

SEQ ID NO: 1201         moltype = DNA   length = 20
FEATURE                 Location/Qualifiers
source                  1..20
                        mol_type = genomic DNA
                        organism = Homo sapiens
SEQUENCE: 1201
ccgtcggggc tctgctgctg                                                   20

SEQ ID NO: 1202         moltype = DNA   length = 20
FEATURE                 Location/Qualifiers
```

```
source                      1..20
                            mol_type = genomic DNA
                            organism = Homo sapiens
SEQUENCE: 1202
gaaggttctg gccgccgtcg                                                   20

SEQ ID NO: 1203             moltype = DNA   length = 20
FEATURE                     Location/Qualifiers
source                      1..20
                            mol_type = genomic DNA
                            organism = Homo sapiens
SEQUENCE: 1203
gtgtgctacc atcctacaga                                                   20

SEQ ID NO: 1204             moltype = DNA   length = 20
FEATURE                     Location/Qualifiers
source                      1..20
                            mol_type = genomic DNA
                            organism = Homo sapiens
SEQUENCE: 1204
gtcgcggagg acggggttga                                                   20

SEQ ID NO: 1205             moltype = DNA   length = 20
FEATURE                     Location/Qualifiers
source                      1..20
                            mol_type = genomic DNA
                            organism = Homo sapiens
SEQUENCE: 1205
cgctggcgcg cgtgatgcgc                                                   20

SEQ ID NO: 1206             moltype = DNA   length = 20
FEATURE                     Location/Qualifiers
source                      1..20
                            mol_type = genomic DNA
                            organism = Homo sapiens
SEQUENCE: 1206
gcgtgcacgg cgggcgctgc                                                   20

SEQ ID NO: 1207             moltype = DNA   length = 20
FEATURE                     Location/Qualifiers
source                      1..20
                            mol_type = genomic DNA
                            organism = Homo sapiens
SEQUENCE: 1207
tctggaaggg gaaggagctc                                                   20

SEQ ID NO: 1208             moltype = DNA   length = 20
FEATURE                     Location/Qualifiers
source                      1..20
                            mol_type = genomic DNA
                            organism = Homo sapiens
SEQUENCE: 1208
gtgcgtgtcg ccgggggccg                                                   20

SEQ ID NO: 1209             moltype = DNA   length = 20
FEATURE                     Location/Qualifiers
source                      1..20
                            mol_type = genomic DNA
                            organism = Homo sapiens
SEQUENCE: 1209
gggcacggcc gcgggcgcgc                                                   20

SEQ ID NO: 1210             moltype = DNA   length = 20
FEATURE                     Location/Qualifiers
source                      1..20
                            mol_type = genomic DNA
                            organism = Homo sapiens
SEQUENCE: 1210
gttaatgctg cgtgcacggc                                                   20

SEQ ID NO: 1211             moltype = DNA   length = 20
FEATURE                     Location/Qualifiers
source                      1..20
                            mol_type = genomic DNA
                            organism = Homo sapiens
SEQUENCE: 1211
gcacggccgc gggcgcgcgg                                                   20

SEQ ID NO: 1212             moltype = DNA   length = 20
```

```
FEATURE             Location/Qualifiers
source              1..20
                    mol_type = genomic DNA
                    organism = Homo sapiens
SEQUENCE: 1212
ggggcacggc cgcgggcgcg                                                   20

SEQ ID NO: 1213     moltype = DNA   length = 20
FEATURE             Location/Qualifiers
source              1..20
                    mol_type = genomic DNA
                    organism = Homo sapiens
SEQUENCE: 1213
gtgcggaagt gcgtgtcgcc                                                   20

SEQ ID NO: 1214     moltype = DNA   length = 20
FEATURE             Location/Qualifiers
source              1..20
                    mol_type = genomic DNA
                    organism = Homo sapiens
SEQUENCE: 1214
gaggaagagg aggaaggttc                                                   20

SEQ ID NO: 1215     moltype = DNA   length = 20
FEATURE             Location/Qualifiers
source              1..20
                    mol_type = genomic DNA
                    organism = Homo sapiens
SEQUENCE: 1215
ggctggcccc ttctgtagga                                                   20

SEQ ID NO: 1216     moltype = DNA   length = 20
FEATURE             Location/Qualifiers
source              1..20
                    mol_type = genomic DNA
                    organism = Homo sapiens
SEQUENCE: 1216
ggggccgggg ccgggaccgc                                                   20

SEQ ID NO: 1217     moltype = DNA   length = 20
FEATURE             Location/Qualifiers
source              1..20
                    mol_type = genomic DNA
                    organism = Homo sapiens
SEQUENCE: 1217
cgcggaggac ggggttgagg                                                   20

SEQ ID NO: 1218     moltype = DNA   length = 20
FEATURE             Location/Qualifiers
source              1..20
                    mol_type = genomic DNA
                    organism = Homo sapiens
SEQUENCE: 1218
tttcgccctt agcgtgaaga                                                   20

SEQ ID NO: 1219     moltype = DNA   length = 20
FEATURE             Location/Qualifiers
source              1..20
                    mol_type = genomic DNA
                    organism = Homo sapiens
SEQUENCE: 1219
ggcacggccg cgggcgcgcg                                                   20

SEQ ID NO: 1220     moltype = DNA   length = 20
FEATURE             Location/Qualifiers
source              1..20
                    mol_type = genomic DNA
                    organism = Homo sapiens
SEQUENCE: 1220
agtcgcggag gacggggttg                                                   20

SEQ ID NO: 1221     moltype = DNA   length = 20
FEATURE             Location/Qualifiers
source              1..20
                    mol_type = genomic DNA
                    organism = Homo sapiens
SEQUENCE: 1221
gggccggggc cgggaccgcg                                                   20
```

```
SEQ ID NO: 1222         moltype = DNA   length = 20
FEATURE                 Location/Qualifiers
source                  1..20
                        mol_type = genomic DNA
                        organism = Homo sapiens
SEQUENCE: 1222
aagtgcgtgt cgccgggggc                                                    20

SEQ ID NO: 1223         moltype = DNA   length = 20
FEATURE                 Location/Qualifiers
source                  1..20
                        mol_type = genomic DNA
                        organism = Homo sapiens
SEQUENCE: 1223
ctccggctgg cccttctgt                                                     20

SEQ ID NO: 1224         moltype = DNA   length = 20
FEATURE                 Location/Qualifiers
source                  1..20
                        mol_type = genomic DNA
                        organism = Homo sapiens
SEQUENCE: 1224
ggcggcgccg cgccgcatgc                                                    20

SEQ ID NO: 1225         moltype = DNA   length = 20
FEATURE                 Location/Qualifiers
source                  1..20
                        mol_type = genomic DNA
                        organism = Homo sapiens
SEQUENCE: 1225
agtgcgtgtc gccggggcc                                                     20

SEQ ID NO: 1226         moltype = DNA   length = 20
FEATURE                 Location/Qualifiers
source                  1..20
                        mol_type = genomic DNA
                        organism = Homo sapiens
SEQUENCE: 1226
tgtgcggaag tgcgtgtcgc                                                    20

SEQ ID NO: 1227         moltype = DNA   length = 20
FEATURE                 Location/Qualifiers
source                  1..20
                        mol_type = genomic DNA
                        organism = Homo sapiens
SEQUENCE: 1227
gtgtcgccgg gggccggggc                                                    20

SEQ ID NO: 1228         moltype = DNA   length = 20
FEATURE                 Location/Qualifiers
source                  1..20
                        mol_type = genomic DNA
                        organism = Homo sapiens
SEQUENCE: 1228
tgtcgccggg ggccggggcc                                                    20

SEQ ID NO: 1229         moltype = DNA   length = 20
FEATURE                 Location/Qualifiers
source                  1..20
                        mol_type = genomic DNA
                        organism = Homo sapiens
SEQUENCE: 1229
gcggtcccgg ccccggcccc                                                    20

SEQ ID NO: 1230         moltype = DNA   length = 20
FEATURE                 Location/Qualifiers
source                  1..20
                        mol_type = genomic DNA
                        organism = Homo sapiens
SEQUENCE: 1230
cgcgggggcc gcgggcgagg                                                    20

SEQ ID NO: 1231         moltype = DNA   length = 20
FEATURE                 Location/Qualifiers
source                  1..20
                        mol_type = genomic DNA
                        organism = Homo sapiens
SEQUENCE: 1231
cgcgggcgag gaggaggaag                                                    20
```

```
SEQ ID NO: 1232          moltype = DNA   length = 20
FEATURE                  Location/Qualifiers
source                   1..20
                         mol_type = genomic DNA
                         organism = Homo sapiens
SEQUENCE: 1232
gggcgaggag gaggaagagg                                                     20

SEQ ID NO: 1233          moltype = DNA   length = 21
FEATURE                  Location/Qualifiers
source                   1..21
                         mol_type = genomic DNA
                         organism = Homo sapiens
SEQUENCE: 1233
ccgtattgaa atggagtcaa a                                                   21

SEQ ID NO: 1234          moltype = DNA   length = 19
FEATURE                  Location/Qualifiers
source                   1..19
                         mol_type = genomic DNA
                         organism = Mus musculus
SEQUENCE: 1234
ggacgtgagt gtttccata                                                      19

SEQ ID NO: 1235          moltype = DNA   length = 19
FEATURE                  Location/Qualifiers
source                   1..19
                         mol_type = genomic DNA
                         organism = Mus musculus
SEQUENCE: 1235
ggaagcagga acaccgaaa                                                      19

SEQ ID NO: 1236          moltype = DNA   length = 21
FEATURE                  Location/Qualifiers
source                   1..21
                         mol_type = genomic DNA
                         organism = Mus musculus
SEQUENCE: 1236
tttcgagctg ctggagcact a                                                   21

SEQ ID NO: 1237          moltype = DNA   length = 21
FEATURE                  Location/Qualifiers
source                   1..21
                         mol_type = genomic DNA
                         organism = Mus musculus
SEQUENCE: 1237
tcgagctgct ggagcactac g                                                   21

SEQ ID NO: 1238          moltype = DNA   length = 21
FEATURE                  Location/Qualifiers
source                   1..21
                         mol_type = genomic DNA
                         organism = Mus musculus
SEQUENCE: 1238
tcgccaacgg aactgcttct t                                                   21

SEQ ID NO: 1239          moltype = DNA   length = 21
FEATURE                  Location/Qualifiers
source                   1..21
                         mol_type = genomic DNA
                         organism = Mus musculus
SEQUENCE: 1239
acttctggct ggagacctca t                                                   21

SEQ ID NO: 1240          moltype = DNA   length = 21
FEATURE                  Location/Qualifiers
source                   1..21
                         mol_type = genomic DNA
                         organism = Mus musculus
SEQUENCE: 1240
gcgagacctt cgactgcctt t                                                   21

SEQ ID NO: 1241          moltype = DNA   length = 21
FEATURE                  Location/Qualifiers
source                   1..21
                         mol_type = genomic DNA
                         organism = Mus musculus
SEQUENCE: 1241
```

```
cgacactcac ttccgcacct t                                              21

SEQ ID NO: 1242        moltype = DNA   length = 21
FEATURE                Location/Qualifiers
source                 1..21
                       mol_type = genomic DNA
                       organism = Mus musculus
SEQUENCE: 1242
ctacctgagt tccttcccct t                                              21

SEQ ID NO: 1243        moltype = DNA   length = 21
FEATURE                Location/Qualifiers
source                 1..21
                       mol_type = genomic DNA
                       organism = Mus musculus
SEQUENCE: 1243
ttccgctccc actccgatta c                                              21

SEQ ID NO: 1244        moltype = DNA   length = 21
FEATURE                Location/Qualifiers
source                 1..21
                       mol_type = genomic DNA
                       organism = Mus musculus
SEQUENCE: 1244
taacccggta ctccgtgact a                                              21

SEQ ID NO: 1245        moltype = DNA   length = 21
FEATURE                Location/Qualifiers
source                 1..21
                       mol_type = genomic DNA
                       organism = Mus musculus
SEQUENCE: 1245
tactccgtga ctacctgagt t                                              21

SEQ ID NO: 1246        moltype = DNA   length = 21
FEATURE                Location/Qualifiers
source                 1..21
                       mol_type = genomic DNA
                       organism = Mus musculus
SEQUENCE: 1246
cttccgctcc cactccgatt a                                              21

SEQ ID NO: 1247        moltype = DNA   length = 21
FEATURE                Location/Qualifiers
source                 1..21
                       mol_type = genomic DNA
                       organism = Mus musculus
SEQUENCE: 1247
gcgcgacagt cgccaacgga a                                              21

SEQ ID NO: 1248        moltype = DNA   length = 21
FEATURE                Location/Qualifiers
source                 1..21
                       mol_type = genomic DNA
                       organism = Mus musculus
SEQUENCE: 1248
tggacgcctg cggcttctat t                                              21

SEQ ID NO: 1249        moltype = DNA   length = 21
FEATURE                Location/Qualifiers
source                 1..21
                       mol_type = genomic DNA
                       organism = Mus musculus
SEQUENCE: 1249
cgcatccctc ttaacccggt a                                              21

SEQ ID NO: 1250        moltype = DNA   length = 21
FEATURE                Location/Qualifiers
source                 1..21
                       mol_type = genomic DNA
                       organism = Mus musculus
SEQUENCE: 1250
tacatattcc cagtatcttt g                                              21

SEQ ID NO: 1251        moltype = DNA   length = 21
FEATURE                Location/Qualifiers
source                 1..21
                       mol_type = genomic DNA
                       organism = Mus musculus
```

```
SEQUENCE: 1251
gcgccttatt atttcttatt a                                               21

SEQ ID NO: 1252         moltype = DNA  length = 21
FEATURE                 Location/Qualifiers
source                  1..21
                        mol_type = genomic DNA
                        organism = Mus musculus
SEQUENCE: 1252
ccgtgactac ctgagttcct t                                               21

SEQ ID NO: 1253         moltype = DNA  length = 21
FEATURE                 Location/Qualifiers
source                  1..21
                        mol_type = genomic DNA
                        organism = Mus musculus
SEQUENCE: 1253
ggagggtctc tggcttcatt t                                               21

SEQ ID NO: 1254         moltype = DNA  length = 21
FEATURE                 Location/Qualifiers
source                  1..21
                        mol_type = genomic DNA
                        organism = Mus musculus
SEQUENCE: 1254
ttcgcgctca gcgtgaagat g                                               21

SEQ ID NO: 1255         moltype = DNA  length = 21
FEATURE                 Location/Qualifiers
source                  1..21
                        mol_type = genomic DNA
                        organism = Mus musculus
SEQUENCE: 1255
atccctctta acccggtact c                                               21

SEQ ID NO: 1256         moltype = DNA  length = 64
FEATURE                 Location/Qualifiers
misc_feature            1..64
                        note = Ankrd11 shRNA
source                  1..64
                        mol_type = other DNA
                        organism = synthetic construct
SEQUENCE: 1256
gatccccgcg gaagctgccc ttcaccttca agagaggtga agggcagctt ccgcttttg      60
gaaa                                                                  64

SEQ ID NO: 1257         moltype = DNA  length = 64
FEATURE                 Location/Qualifiers
misc_feature            1..64
                        note = Ankrd11 shRNA
source                  1..64
                        mol_type = other DNA
                        organism = synthetic construct
SEQUENCE: 1257
agcttttcca aaaagcggaa gctgcccttc acctctcttg aaggtgaagg gcagcttccg     60
cggg                                                                  64

SEQ ID NO: 1258         moltype = DNA  length = 19
FEATURE                 Location/Qualifiers
misc_feature            1..19
                        note = Socs shRNA
source                  1..19
                        mol_type = other DNA
                        organism = synthetic construct
SEQUENCE: 1258
cacgcacttc cgcacattc                                                  19

SEQ ID NO: 1259         moltype = DNA  length = 19
FEATURE                 Location/Qualifiers
misc_feature            1..19
                        note = Socs shRNA
source                  1..19
                        mol_type = other DNA
                        organism = synthetic construct
SEQUENCE: 1259
ttccgttcgc acgccgatt                                                  19

SEQ ID NO: 1260         moltype = DNA  length = 19
FEATURE                 Location/Qualifiers
```

```
misc_feature            1..19
                        note = Socs shRNA
source                  1..19
                        mol_type = other DNA
                        organism = synthetic construct
SEQUENCE: 1260
gagcttcgac tgcctcttc                                                   19

SEQ ID NO: 1261         moltype = RNA  length = 23
FEATURE                 Location/Qualifiers
misc_feature            1..23
                        note = Socs siRNA
source                  1..23
                        mol_type = other RNA
                        organism = synthetic construct
SEQUENCE: 1261
cgcacttccg cacattccgt tcg                                              23

SEQ ID NO: 1262         moltype = RNA  length = 23
FEATURE                 Location/Qualifiers
misc_feature            1..23
                        note = Socs siRNA
source                  1..23
                        mol_type = other RNA
                        organism = synthetic construct
SEQUENCE: 1262
ggggagggtc tctggcttta ttt                                              23

SEQ ID NO: 1263         moltype = RNA  length = 23
FEATURE                 Location/Qualifiers
misc_feature            1..23
                        note = Socs siRNA
source                  1..23
                        mol_type = other RNA
                        organism = synthetic construct
SEQUENCE: 1263
cagcattaac tgggatgccg tgt                                              23

SEQ ID NO: 1264         moltype = RNA  length = 23
FEATURE                 Location/Qualifiers
misc_feature            1..23
                        note = Socs siRNA
source                  1..23
                        mol_type = other RNA
                        organism = synthetic construct
SEQUENCE: 1264
ccaggacctg aactcgcacc tcc                                              23

SEQ ID NO: 1265         moltype = RNA  length = 23
FEATURE                 Location/Qualifiers
misc_feature            1..23
                        note = Socs siRNA
source                  1..23
                        mol_type = other RNA
                        organism = synthetic construct
SEQUENCE: 1265
tacatatacc cagtatcttt gca                                              23

SEQ ID NO: 1266         moltype = RNA  length = 23
FEATURE                 Location/Qualifiers
misc_feature            1..23
                        note = Socs siRNA
source                  1..23
                        mol_type = other RNA
                        organism = synthetic construct
SEQUENCE: 1266
gccgacaatg cagtctccac agc                                              23

SEQ ID NO: 1267         moltype = RNA  length = 23
FEATURE                 Location/Qualifiers
misc_feature            1..23
                        note = Socs siRNA
source                  1..23
                        mol_type = other RNA
                        organism = synthetic construct
SEQUENCE: 1267
cccctggttg ttgtagcagc tta                                              23

SEQ ID NO: 1268         moltype = RNA  length = 23
```

```
FEATURE                 Location/Qualifiers
misc_feature            1..23
                        note = Socs siRNA
source                  1..23
                        mol_type = other RNA
                        organism = synthetic construct
SEQUENCE: 1268
ctgctgtgca gaatcctatt tta                                              23

SEQ ID NO: 1269         moltype = RNA  length = 23
FEATURE                 Location/Qualifiers
misc_feature            1..23
                        note = Socs siRNA
source                  1..23
                        mol_type = other RNA
                        organism = synthetic construct
SEQUENCE: 1269
tgggatgccg tgttattttg tta                                              23

SEQ ID NO: 1270         moltype = RNA  length = 23
FEATURE                 Location/Qualifiers
misc_feature            1..23
                        note = Socs siRNA
source                  1..23
                        mol_type = other RNA
                        organism = synthetic construct
SEQUENCE: 1270
tcgcacctcc tacctcttca tgt                                              23
```